US008309323B2

(12) United States Patent
Martin et al.

(10) Patent No.: US 8,309,323 B2

(45) Date of Patent: Nov. 13, 2012

(54) DIMETHYLOCTANE AS AN ADVANCED BIOFUEL

(75) Inventors: Kevin V. Martin, Solana Beach, CA (US); Stephen Picataggio, Rancho Santa Fe, CA (US); Paul Roessler, San Diego, CA (US); John Verruto, San Diego, CA (US); Kevin Watts, Scandia, MN (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 12/742,906

(22) PCT Filed: Nov. 13, 2008

(86) PCT No.: PCT/US2008/083436

§ 371 (c)(1), (2), (4) Date: Mar. 16, 2011

(87) PCT Pub. No.: WO2009/064910

PCT Pub. Date: May 22, 2009

(65) Prior Publication Data

US 2011/0160501 A1 Jun. 30, 2011

Related U.S. Application Data

(60) Provisional application No. 60/987,683, filed on Nov. 13, 2007.

(51) Int. Cl.

*C12P 1/00* (2006.01)
*C10L 1/04* (2006.01)

(52) U.S. Cl. ........................................... 435/41; 208/16

(58) Field of Classification Search ........................ None
See application file for complete search history.

(56) References Cited

U.S. PATENT DOCUMENTS

| | | | | |
|---|---|---|---|---|
| 5,186,722 | A * | 2/1993 | Cantrell et al. | 44/605 |
| 7,172,886 | B2 | 2/2007 | Keasling et al. | |
| 7,183,089 | B2 | 2/2007 | Keasling et al. | |
| 7,659,097 | B2 | 2/2010 | Renninger et al. | |
| 2007/0141574 | A1 | 6/2007 | Keasling et al. | |
| 2009/0155873 | A1 * | 6/2009 | Kashiyama et al. | 435/165 |
| 2010/0178679 | A1 | 7/2010 | Anthony et al. | |

FOREIGN PATENT DOCUMENTS

| | | | |
|---|---|---|---|
| WO | WO 05/60553 | * | 7/2005 |
| WO | WO2009/036067 | | 3/2009 |
| WO | WO2009/042070 | | 4/2009 |

OTHER PUBLICATIONS

Enklaar, C.J., JACS Abstracts of Papers on Organic Chemistry, 1908, vol. XCIV, Part I, ed. Gurney & Jackson, London—p. 664.*

Burke et al., "Geranyl Diphosphate Synthase: Cloning, Expression, and Characterization of this Prenyltransferase as a Heterodimer," *Proc. Natl. Acad. Sci. USA* (1999), 96(23)13062-13067.

Iijima et al., "Characterization of Geraniol Synthase from the Peltate Glands of Sweet Basil," *Plant Physiol.* (2004), 134:370-379, American Society of Plant Biologists.

Shalit et al., "Volatile Ester Formation in Roses. Identification of an Acetyl-Coenzyme A. Geraniol/Citronellol Acetyltransferase in Developing Rose Petals," *Plant Physiol.* (2003), 131:1868-1876, American Society of Plant Biologists.

Shimada et al., "Molecular Cloning and Functional Characterization of Four Monoterpene Synthase Genes from *Citrus unshiu Marc,*" *Plant Sci.* (2004), 166:49-58, Elsevier Ireland Ltd.

Chambon et al., "Isolation and properties of yeast mutants affected in farnesyl diphosphate dynthetase", *Curr Genet* 18:41-46, 1990.

Oswald et al., "Monoterpenoid biosynthesis in *Saccharomyces cerevisiae", FEMS Yeast Res* 7:413-421, 2007.

Withers et al., "Identification of Isopentenol Biosynthetic Genes from *Bacillus subtilis* by a Screening Method Based on Isoprenoid Precursor Toxicity", *Applied and Environmental Microbiology* 73(19):6277-6283, 2007.

Yang et al., "A geraniol-synthase gene from *Cinnamomum tenuipilum", Phytochemistry* 66:285-293, 2005.

* cited by examiner

*Primary Examiner* — Suzanne M Noakes

(74) *Attorney, Agent, or Firm* — DLA Piper LLP (US)

(57) ABSTRACT

This invention describes genes, metabolic pathways, microbial strains and methods to produce 2,6-dimethyloctane as an advanced biofuel from renewable feedstocks.

14 Claims, 7 Drawing Sheets pyruvate
D-glyceraldehyde-3-phosphate
DOXP
MEP
CDP-ME
CDP-MEP
MEcPP
HMB-PP
IPP
DMAPP L-leucine 4-methyl-2-oxopentanoate isovaleryl-CoA 3-methylcrotonyl-CoA 3-methyglutaconyl-CoA HMG-CoA

SEQUENCE LISTING

<160> NUMBER OF SEQ ID NOS: 161

<210> SEQ ID NO 1
<211> LENGTH: 1863
<212> TYPE: DNA
<213> ORGANISM: Escherichia coli

<400> SEQUENCE: 1
atgagttttg atattgccaa atacccgacc ctggcactgg tcgactccac ccaggagtta 60

-continued

```
cgactgttgc cgaaagagag tttaccgaaa ctctgcgacg aactgcgccg ctatttactc    120
gacagcgtga gccgttccag cgggcacttc gcctccgggc tgggcacggt cgaactgacc    180
gtggcgctgc actatgtcta caacaccccg tttgaccaat tgatttggga tgtggggcat    240
caggcttatc cgcataaaat tttgaccgga cgccgcgaca aaatcggcac catccgtcag    300
aaaggcggtc tgcacccgtt cccgtggcgc ggcgaaagcg aatatgacgt attaagcgtc    360
gggcattcat caacctccat cagtgccgga attggtattg cggttgctgc cgaaaaagaa    420
ggcaaaaatc gccgcaccgt ctgtgtcatt ggcgatggcg cgattaccgc aggcatggcg    480
tttgaagcga tgaatcacgc gggcgatatc cgtcctgata tgctggtgat tctcaacgac    540
aatgaaatgt cgatttccga aaatgtcggc gcgctcaaca accatctggc acagctgctt    600
tccggtaagc tttactcttc actgcgcgaa ggcgggaaaa aagttttctc tggcgtgccg    660
ccaattaaag agctgctcaa acgcaccgaa gaacatatta aaggcatggt agtgcctggc    720
acgttgtttg aagagctggg ctttaactac atcggcccgg tggacggtca cgatgtgctg    780
gggcttatca ccacgctaaa gaacatgcgc gacctgaaag gcccgcagtt cctgcatatc    840
atgaccaaaa aaggtcgtgg ttatgaaccg gcagaaaaag acccgatcac tttccacgcc    900
gtgcctaaat ttgatccctc cagcggttgt ttgccgaaaa gtagcggcgg tttgccgagc    960
tattcaaaaa tctttggcga ctggttgtgc gaaacggcag cgaaagacaa caagctgatg   1020
gcgattactc cggcgatgcg tgaaggttcc ggcatggtcg agttttcacg taaattcccg   1080
gatcgctact tcgacgtggc aattgccgag caacacgcgg tgacctttgc tgcgggtctg   1140
gcgattggtg ggtacaaacc cattgtcgcg atttactcca ctttcctgca acgcgcctat   1200
gatcaggtgc tgcatgacgt ggcgattcaa aagcttccgg tcctgttcgc catcgaccgc   1260
gcgggcattg ttggtgctga cggtcaaacc catcagggtg cttttgatct ctcttacctg   1320
cgctgcatac cggaaatggt cattatgacc ccgagcgatg aaaacgaatg tcgccagatg   1380
ctctataccg gctatcacta taacgatggc ccgtcagcgg tgcgctaccc gcgtggcaac   1440
gcggtcggcg tggaactgac gccgctggaa aaactaccaa ttggcaaagg cattgtgaag   1500
cgtcgtggcg agaaactggc gatccttaac tttggtacgc tgatgccaga agcggcgaaa   1560
gtcgccgaat cgctgaacgc cacgctggtc gatatgcgtt ttgtgaaacc gcttgatgaa   1620
gcgttaattc tggaaatggc cgccagccat gaagcgctgg tcaccgtaga agaaaacgcc   1680
attatgggcg gcgcaggcag cggcgtgaac gaagtgctga tggcccatcg taaaccagta   1740
cccgtgctga acattggcct gccggacttc tttattccgc aaggaactca ggaagaaatg   1800
cgcgccgaac tcggcctcga tgccgctggt atggaagcca aaatcaaggc ctggctggca   1860
taa                                                                 1863
```

<210> SEQ ID NO 2
<211> LENGTH: 620
<212> TYPE: PRT
<213> ORGANISM: Escherichia coli

<400> SEQUENCE: 2

```
Met Ser Phe Asp Ile Ala Lys Tyr Pro Thr Leu Ala Leu Val Asp Ser
 1               5                  10                  15

Thr Gln Glu Leu Arg Leu Leu Pro Lys Glu Ser Leu Pro Lys Leu Cys
            20                  25                  30

Asp Glu Leu Arg Arg Tyr Leu Leu Asp Ser Val Ser Arg Ser Ser Gly
        35                  40                  45
```

-continued

```
His Phe Ala Ser Gly Leu Gly Thr Val Glu Leu Thr Val Ala Leu His
    50                  55                  60

Tyr Val Tyr Asn Thr Pro Phe Asp Gln Leu Ile Trp Asp Val Gly His
65                  70                  75                  80

Gln Ala Tyr Pro His Lys Ile Leu Thr Gly Arg Arg Asp Lys Ile Gly
                85                  90                  95

Thr Ile Arg Gln Lys Gly Gly Leu His Pro Phe Pro Trp Arg Gly Glu
            100                 105                 110

Ser Glu Tyr Asp Val Leu Ser Val Gly His Ser Ser Thr Ser Ile Ser
        115                 120                 125

Ala Gly Ile Gly Ile Ala Val Ala Ala Glu Lys Glu Gly Lys Asn Arg
    130                 135                 140

Arg Thr Val Cys Val Ile Gly Asp Gly Ala Ile Thr Ala Gly Met Ala
145                 150                 155                 160

Phe Glu Ala Met Asn His Ala Gly Asp Ile Arg Pro Asp Met Leu Val
                165                 170                 175

Ile Leu Asn Asp Asn Glu Met Ser Ile Ser Glu Asn Val Gly Ala Leu
            180                 185                 190

Asn Asn His Leu Ala Gln Leu Leu Ser Gly Lys Leu Tyr Ser Ser Leu
        195                 200                 205

Arg Glu Gly Gly Lys Lys Val Phe Ser Gly Val Pro Pro Ile Lys Glu
    210                 215                 220

Leu Leu Lys Arg Thr Glu Glu His Ile Lys Gly Met Val Val Pro Gly
225                 230                 235                 240

Thr Leu Phe Glu Glu Leu Gly Phe Asn Tyr Ile Gly Pro Val Asp Gly
                245                 250                 255

His Asp Val Leu Gly Leu Ile Thr Thr Leu Lys Asn Met Arg Asp Leu
            260                 265                 270

Lys Gly Pro Gln Phe Leu His Ile Met Thr Lys Lys Gly Arg Gly Tyr
        275                 280                 285

Glu Pro Ala Glu Lys Asp Pro Ile Thr Phe His Ala Val Pro Lys Phe
    290                 295                 300

Asp Pro Ser Ser Gly Cys Leu Pro Lys Ser Ser Gly Gly Leu Pro Ser
305                 310                 315                 320

Tyr Ser Lys Ile Phe Gly Asp Trp Leu Cys Glu Thr Ala Ala Lys Asp
                325                 330                 335

Asn Lys Leu Met Ala Ile Thr Pro Ala Met Arg Glu Gly Ser Gly Met
            340                 345                 350

Val Glu Phe Ser Arg Lys Phe Pro Asp Arg Tyr Phe Asp Val Ala Ile
        355                 360                 365

Ala Glu Gln His Ala Val Thr Phe Ala Ala Gly Leu Ala Ile Gly Gly
    370                 375                 380

Tyr Lys Pro Ile Val Ala Ile Tyr Ser Thr Phe Leu Gln Arg Ala Tyr
385                 390                 395                 400

Asp Gln Val Leu His Asp Val Ala Ile Gln Lys Leu Pro Val Leu Phe
                405                 410                 415

Ala Ile Asp Arg Ala Gly Ile Val Gly Ala Asp Gly Gln Thr His Gln
            420                 425                 430

Gly Ala Phe Asp Leu Ser Tyr Leu Arg Cys Ile Pro Glu Met Val Ile
        435                 440                 445

Met Thr Pro Ser Asp Glu Asn Glu Cys Arg Gln Met Leu Tyr Thr Gly
    450                 455                 460

Tyr His Tyr Asn Asp Gly Pro Ser Ala Val Arg Tyr Pro Arg Gly Asn
465                 470                 475                 480
```

-continued

```
Ala Val Gly Val Glu Leu Thr Pro Leu Glu Lys Leu Pro Ile Gly Lys
                485                 490                 495

Gly Ile Val Lys Arg Arg Gly Glu Lys Leu Ala Ile Leu Asn Phe Gly
            500                 505                 510

Thr Leu Met Pro Glu Ala Ala Lys Val Ala Glu Ser Leu Asn Ala Thr
        515                 520                 525

Leu Val Asp Met Arg Phe Val Lys Pro Leu Asp Glu Ala Leu Ile Leu
    530                 535                 540

Glu Met Ala Ala Ser His Glu Ala Leu Val Thr Val Glu Glu Asn Ala
545                 550                 555                 560

Ile Met Gly Gly Ala Gly Ser Gly Val Asn Glu Val Leu Met Ala His
                565                 570                 575

Arg Lys Pro Val Pro Val Leu Asn Ile Gly Leu Pro Asp Phe Phe Ile
            580                 585                 590

Pro Gln Gly Thr Gln Glu Glu Met Arg Ala Glu Leu Gly Leu Asp Ala
        595                 600                 605

Ala Gly Met Glu Ala Lys Ile Lys Ala Trp Leu Ala
    610                 615                 620


<210> SEQ ID NO 3
<211> LENGTH: 1923
<212> TYPE: DNA
<213> ORGANISM: Arabidopsis thaliana

<400> SEQUENCE: 3

atgtcatatc aaacacagat taacaaattc tctcaaatgg ctctctccgt atttgccttt     60

ccttcttaca taaataggaa tccttcacta aaatatctta aaccttcttc tatgtcttct    120

acaaaatatt caaaagtaag agcaacaaca ttttcagaga aaggtgaata ttattcaaac    180

agaccaccaa ctcctttatt ggacacaatc aaccatccaa tgcacatgaa aatctctcc    240

atcaaagaac tcaaagttct ttcggacgag ttgagatctg atgttatttt taatgtttcg    300

aaaactggag gacacttggg ttcgaatctt ggtgttgttg agctcaccgt ggcccttcat    360

tacatcttca atactcctca tgataagatc ctttgggatg ttggtcatca gtcttatcct    420

cacaagattc taacgggaag aagaggaaag atgaagacaa taaggcagac caatggcctc    480

tccggctaca ccaagcgaag agagagtgag catgactctt ttggcaccgg gcacagttcg    540

accacactat ctgcaggctt agggatggct gtagggaggg atttgaaggg gatgaacaac    600

agcgtggttt cggttatagg cgatggtgct atgacagctg gacaagctta tgaagcaatg    660

aacaatgctg gctacttaca ctccaacatg attgtgattc tcaacgacaa caaacaagta    720

tctttgccta ctgctaactt ggatggacca actcaacctg ttggagctct gagctgtgct    780

cttagtaggc tgcaatctaa ttgtggaatg attagagaga ctagttcaac actgtttgaa    840

gaacttggtt ttcactatgt tggtccagtt gatggacaca acatagatga tctggtctcc    900

attcttgaaa cattaaagag caccaaaacc ataggaccgg ttcttatcca tgtcgtgact    960

gagaaaggtc gtggatatcc ttacgcagag agagctgatg acaagtatca tgttttaaaa   1020

tttgatccag aaacaggtaa acagttcaaa aatatttcca agactcagtc ttacacttcc   1080

tgttttgtgg aggccttgat tgcagaagca gaggcagaca aagatattgt tgccattcat   1140

gcagccatgg gaggtggaac catgttgaat ctcttcgaaa gccgctttcc tacaaggtgt   1200

ttcgatgtcg gcatagcaga acaacatgca gttaccttcg ctgctggtct tgcttgcgaa   1260

ggacttaagc ccttttgtac aatctactca tctttcatgc aacgggcata tgatcaagtt   1320
```

```
gtacatgatg ttgatctaca gaaactgcct gtgagatttg caatagatag agcaggactt   1380

atgggagcag atggtccaac acattgtgga gcatttgatg tgacgtttat ggcatgtcta   1440

ccaaacatga tagtaatggc tccatctgat gaagcagagc tttttaacat ggttgcaacc   1500

gctgcagcta ttgatgaccg tccttcttgc tttcgatatc atagaggaaa tggtattggt   1560

gtttcacttc ctcctggtaa caaaggtgtc cctcttcaga ttgggagagg taggatacta   1620

agggacggcg agagggttgc gcttttgggc tatggatcag cggtgcaaag atgtttagag   1680

gctgcatcta tgctaagcga acgcggatta aagataacag tagcggatgc aagattctgt   1740

aagccgttag atgttgctct cattcgtagc ttagctaaat cacacgaggt tttgatcacg   1800

gttgaagaag gttccattgg aggatttgga tcgcatgtgg tacaatttct tgcacttgat   1860

ggccttcttg atggaaagct caaggtatat cgaacatgga tcaccaatgg atcaactagc   1920

tga                                                                 1923
```

<210> SEQ ID NO 4
<211> LENGTH: 640
<212> TYPE: PRT
<213> ORGANISM: Arabidopsis thaliana

<400> SEQUENCE: 4

```
Met Ser Tyr Gln Thr Gln Ile Asn Lys Phe Ser Gln Met Ala Leu Ser
 1               5                  10                  15

Val Phe Ala Phe Pro Ser Tyr Ile Asn Arg Asn Pro Ser Leu Lys Tyr
            20                  25                  30

Leu Lys Pro Ser Ser Met Ser Ser Thr Lys Tyr Ser Lys Val Arg Ala
        35                  40                  45

Thr Thr Phe Ser Glu Lys Gly Glu Tyr Tyr Ser Asn Arg Pro Pro Thr
    50                  55                  60

Pro Leu Leu Asp Thr Ile Asn His Pro Met His Met Lys Asn Leu Ser
65                  70                  75                  80

Ile Lys Glu Leu Lys Val Leu Ser Asp Glu Leu Arg Ser Asp Val Ile
                85                  90                  95

Phe Asn Val Ser Lys Thr Gly Gly His Leu Gly Ser Asn Leu Gly Val
            100                 105                 110

Val Glu Leu Thr Val Ala Leu His Tyr Ile Phe Asn Thr Pro His Asp
        115                 120                 125

Lys Ile Leu Trp Asp Val Gly His Gln Ser Tyr Pro His Lys Ile Leu
    130                 135                 140

Thr Gly Arg Arg Gly Lys Met Lys Thr Ile Arg Gln Thr Asn Gly Leu
145                 150                 155                 160

Ser Gly Tyr Thr Lys Arg Arg Glu Ser Glu His Asp Ser Phe Gly Thr
                165                 170                 175

Gly His Ser Ser Thr Thr Leu Ser Ala Gly Leu Gly Met Ala Val Gly
            180                 185                 190

Arg Asp Leu Lys Gly Met Asn Asn Ser Val Val Ser Val Ile Gly Asp
        195                 200                 205

Gly Ala Met Thr Ala Gly Gln Ala Tyr Glu Ala Met Asn Asn Ala Gly
    210                 215                 220

Tyr Leu His Ser Asn Met Ile Val Ile Leu Asn Asp Asn Lys Gln Val
225                 230                 235                 240

Ser Leu Pro Thr Ala Asn Leu Asp Gly Pro Thr Gln Pro Val Gly Ala
                245                 250                 255

Leu Ser Cys Ala Leu Ser Arg Leu Gln Ser Asn Cys Gly Met Ile Arg
            260                 265                 270
```

-continued

```
Glu Thr Ser Ser Thr Leu Phe Glu Glu Leu Gly Phe His Tyr Val Gly
        275                 280                 285

Pro Val Asp Gly His Asn Ile Asp Asp Leu Val Ser Ile Leu Glu Thr
    290                 295                 300

Leu Lys Ser Thr Lys Thr Ile Gly Pro Val Leu Ile His Val Val Thr
305                 310                 315                 320

Glu Lys Gly Arg Gly Tyr Pro Tyr Ala Glu Arg Ala Asp Asp Lys Tyr
                325                 330                 335

His Val Leu Lys Phe Asp Pro Glu Thr Gly Lys Gln Phe Lys Asn Ile
            340                 345                 350

Ser Lys Thr Gln Ser Tyr Thr Ser Cys Phe Val Glu Ala Leu Ile Ala
        355                 360                 365

Glu Ala Glu Ala Asp Lys Asp Ile Val Ala Ile His Ala Ala Met Gly
    370                 375                 380

Gly Gly Thr Met Leu Asn Leu Phe Glu Ser Arg Phe Pro Thr Arg Cys
385                 390                 395                 400

Phe Asp Val Gly Ile Ala Glu Gln His Ala Val Thr Phe Ala Ala Gly
                405                 410                 415

Leu Ala Cys Glu Gly Leu Lys Pro Phe Cys Thr Ile Tyr Ser Ser Phe
            420                 425                 430

Met Gln Arg Ala Tyr Asp Gln Val Val His Asp Val Asp Leu Gln Lys
        435                 440                 445

Leu Pro Val Arg Phe Ala Ile Asp Arg Ala Gly Leu Met Gly Ala Asp
    450                 455                 460

Gly Pro Thr His Cys Gly Ala Phe Asp Val Thr Phe Met Ala Cys Leu
465                 470                 475                 480

Pro Asn Met Ile Val Met Ala Pro Ser Asp Glu Ala Glu Leu Phe Asn
                485                 490                 495

Met Val Ala Thr Ala Ala Ala Ile Asp Asp Arg Pro Ser Cys Phe Arg
            500                 505                 510

Tyr His Arg Gly Asn Gly Ile Gly Val Ser Leu Pro Pro Gly Asn Lys
        515                 520                 525

Gly Val Pro Leu Gln Ile Gly Arg Gly Arg Ile Leu Arg Asp Gly Glu
    530                 535                 540

Arg Val Ala Leu Leu Gly Tyr Gly Ser Ala Val Gln Arg Cys Leu Glu
545                 550                 555                 560

Ala Ala Ser Met Leu Ser Glu Arg Gly Leu Lys Ile Thr Val Ala Asp
                565                 570                 575

Ala Arg Phe Cys Lys Pro Leu Asp Val Ala Leu Ile Arg Ser Leu Ala
            580                 585                 590

Lys Ser His Glu Val Leu Ile Thr Val Glu Glu Gly Ser Ile Gly Gly
        595                 600                 605

Phe Gly Ser His Val Val Gln Phe Leu Ala Leu Asp Gly Leu Leu Asp
    610                 615                 620

Gly Lys Leu Lys Val Tyr Arg Thr Trp Ile Thr Asn Gly Ser Thr Ser
625                 630                 635                 640
```

<210> SEQ ID NO 5
<211> LENGTH: 1197
<212> TYPE: DNA
<213> ORGANISM: Escherichia coli

<400> SEQUENCE: 5
atgaagcaac tcaccattct gggctcgacc ggctcgattg gttgcagcac gctggacgtg 60

-continued

```
gtgcgccata atcccgaaca cttccgcgta gttgcgctgg tggcaggcaa aaatgtcact    120

cgcatggtag aacagtgcct ggaattctct ccccgctatg ccgtaatgga cgatgaagcg    180

agtgcgaaac ttcttaaaac gatgctacag caacagggta gccgcaccga agtcttaagt    240

gggcaacaag ccgcttgcga tatggcagcg cttgaggatg ttgatcaggt gatggcagcc    300

attgttggcg ctgctgggct gttacctacg cttgctgcga tccgcgcggg taaaaccatt    360

ttgctggcca ataaagaatc actggttacc tgcggacgtc tgtttatgga cgccgtaaag    420

cagagcaaag cgcaattgtt accggtcgat agcgaacata acgccatttt tcagagttta    480

ccgcaaccta tccagcataa tctgggatac gctgaccttg agcaaaatgg cgtggtgtcc    540

attttactta ccgggtctgg tggccctttc cgtgagacgc cattgcgcga tttggcaaca    600

atgacgccgg atcaagcctg ccgtcatccg aactggtcga tggggcgtaa aatttctgtc    660

gattcggcta ccatgatgaa caaaggtctg gaatacattg aagcgcgttg gctgtttaac    720

gccagcgcca gccagatgga agtgctgatt cacccgcagt cagtgattca ctcaatggtg    780

cgctatcagg acggcagtgt tctggcgcag ctgggggaac cggatatgcg tacgccaatt    840

gcccacacca tggcatggcc gaatcgcgtg aactctggcg tgaagccgct cgatttttgc    900

aaactaagtg cgttgacatt tgccgcaccg gattatgatc gttatccatg cctgaaactg    960

gcgatggagg cgttcgaaca aggccaggca gcgacgacag cattgaatgc cgcaaacgaa   1020

atcaccgttg ctgcttttct tgcgcaacaa atccgcttta cggatatcgc tgcgttgaat   1080

ttatccgtac tggaaaaaat ggatatgcgc gaaccacaat gtgtggacga tgtgttatct   1140

gttgatgcga acgcgcgtga agtcgccaga aaagaggtga tgcgtctcgc aagctga      1197


<210> SEQ ID NO 6
<211> LENGTH: 398
<212> TYPE: PRT
<213> ORGANISM: Escherichia coli

<400> SEQUENCE: 6

Met Lys Gln Leu Thr Ile Leu Gly Ser Thr Gly Ser Ile Gly Cys Ser
1               5                   10                  15

Thr Leu Asp Val Val Arg His Asn Pro Glu His Phe Arg Val Val Ala
            20                  25                  30

Leu Val Ala Gly Lys Asn Val Thr Arg Met Val Glu Gln Cys Leu Glu
        35                  40                  45

Phe Ser Pro Arg Tyr Ala Val Met Asp Asp Glu Ala Ser Ala Lys Leu
    50                  55                  60

Leu Lys Thr Met Leu Gln Gln Gln Gly Ser Arg Thr Glu Val Leu Ser
65                  70                  75                  80

Gly Gln Gln Ala Ala Cys Asp Met Ala Ala Leu Glu Asp Val Asp Gln
                85                  90                  95

Val Met Ala Ala Ile Val Gly Ala Ala Gly Leu Leu Pro Thr Leu Ala
            100                 105                 110

Ala Ile Arg Ala Gly Lys Thr Ile Leu Leu Ala Asn Lys Glu Ser Leu
        115                 120                 125

Val Thr Cys Gly Arg Leu Phe Met Asp Ala Val Lys Gln Ser Lys Ala
    130                 135                 140

Gln Leu Leu Pro Val Asp Ser Glu His Asn Ala Ile Phe Gln Ser Leu
145                 150                 155                 160

Pro Gln Pro Ile Gln His Asn Leu Gly Tyr Ala Asp Leu Glu Gln Asn
                165                 170                 175

Gly Val Val Ser Ile Leu Leu Thr Gly Ser Gly Gly Pro Phe Arg Glu
```

-continued

```
            180                 185                 190

Thr Pro Leu Arg Asp Leu Ala Thr Met Thr Pro Asp Gln Ala Cys Arg
        195                 200                 205

His Pro Asn Trp Ser Met Gly Arg Lys Ile Ser Val Asp Ser Ala Thr
    210                 215                 220

Met Met Asn Lys Gly Leu Glu Tyr Ile Glu Ala Arg Trp Leu Phe Asn
225                 230                 235                 240

Ala Ser Ala Ser Gln Met Glu Val Leu Ile His Pro Gln Ser Val Ile
                245                 250                 255

His Ser Met Val Arg Tyr Gln Asp Gly Ser Val Leu Ala Gln Leu Gly
            260                 265                 270

Glu Pro Asp Met Arg Thr Pro Ile Ala His Thr Met Ala Trp Pro Asn
        275                 280                 285

Arg Val Asn Ser Gly Val Lys Pro Leu Asp Phe Cys Lys Leu Ser Ala
    290                 295                 300

Leu Thr Phe Ala Ala Pro Asp Tyr Asp Arg Tyr Pro Cys Leu Lys Leu
305                 310                 315                 320

Ala Met Glu Ala Phe Glu Gln Gly Gln Ala Ala Thr Thr Ala Leu Asn
                325                 330                 335

Ala Ala Asn Glu Ile Thr Val Ala Ala Phe Leu Ala Gln Gln Ile Arg
            340                 345                 350

Phe Thr Asp Ile Ala Ala Leu Asn Leu Ser Val Leu Glu Lys Met Asp
        355                 360                 365

Met Arg Glu Pro Gln Cys Val Asp Asp Val Leu Ser Val Asp Ala Asn
    370                 375                 380

Ala Arg Glu Val Ala Arg Lys Glu Val Met Arg Leu Ala Ser
385                 390                 395
```

<210> SEQ ID NO 7
<211> LENGTH: 1434
<212> TYPE: DNA
<213> ORGANISM: Arabidopsis thaliana

<400> SEQUENCE: 7

```
atgatgacat taaactcact atctccagct gaatccaaag ctatttcttt cttggatacc      60

tccaggttca atccaatccc taaactctca ggtgggttta gtttgaggag gaggaatcaa     120

gggagaggtt ttggaaaagg tgttaagtgt tcagtgaaag tgcagcagca acaacaacct     180

cctccagcat ggcctgggag agctgtccct gaggcgcctc gtcaatcttg ggatggacca     240

aaacccatct ctatcgttgg atctactggt tctattggca ctcagacatt ggatattgtg     300

gctgagaatc ctgacaaatt cagagttgtg gctctagctg ctggttcgaa tgttactcta     360

cttgctgatc aggtaaggag atttaagcct gcattggttg ctgttagaaa cgagtcactg     420

attaatgagc ttaaagaggc tttagctgat ttggactata aactcgagat tattccagga     480

gagcaaggag tgattgaggt tgcccgacat cctgaagctg taaccgttgt taccggaata     540

gtaggttgtg cgggactaaa gcctacggtt gctgcaattg aagcaggaaa ggacattgct     600

cttgcaaaca aagagacatt aatcgcaggt ggtcctttcg tgcttccgct tgccaacaaa     660

cataatgtaa agattcttcc ggcagattca gaacattctg ccatatttca gtgtattcaa     720

ggtttgcctg aaggcgctct gcgcaagata atcttgactg catctggtgg agcttttagg     780

gattggcctg tcgaaaagct aaaggaagtt aaagtagcgg atgcgttgaa gcatccaaac     840

tggaacatgg gaaagaaaat cactgtggac tctgctacgc ttttcaacaa gggtcttgag     900

gtcattgaag cgcattattt gtttggagct gagtatgacg atatagagat tgtcattcat     960
```

```
ccgcaaagta tcatacattc catgattgaa acacaggatt catctgtgct tgctcaattg   1020

ggttggcctg atatgcgttt accgattctc tacaccatgt catggcccga tagagttcct   1080

tgttctgaag taacttggcc aagacttgac ctttgcaaac tcggttcatt gactttcaag   1140

aaaccagaca atgtgaaata cccatccatg gatcttgctt atgctgctgg acgagctgga   1200

ggcacaatga ctggagttct cagcgccgcc aatgagaaag ctgttgaaat gttcattgat   1260

gaaaagataa gctatttgga tatcttcaag gttgtggaat taacatgcga taaacatcga   1320

aacgagttgg taacatcacc gtctcttgaa gagattgttc actatgactt gtgggcacgt   1380

gaatatgccg cgaatgtgca gctttcttct ggtgctaggc cagttcatgc atga         1434
```

<210> SEQ ID NO 8
<211> LENGTH: 477
<212> TYPE: PRT
<213> ORGANISM: Arabidopsis thaliana

<400> SEQUENCE: 8

```
Met Met Thr Leu Asn Ser Leu Ser Pro Ala Glu Ser Lys Ala Ile Ser
 1               5                  10                  15

Phe Leu Asp Thr Ser Arg Phe Asn Pro Ile Pro Lys Leu Ser Gly Gly
            20                  25                  30

Phe Ser Leu Arg Arg Arg Asn Gln Gly Arg Gly Phe Gly Lys Gly Val
        35                  40                  45

Lys Cys Ser Val Lys Val Gln Gln Gln Gln Gln Pro Pro Pro Ala Trp
    50                  55                  60

Pro Gly Arg Ala Val Pro Glu Ala Pro Arg Gln Ser Trp Asp Gly Pro
65                  70                  75                  80

Lys Pro Ile Ser Ile Val Gly Ser Thr Gly Ser Ile Gly Thr Gln Thr
                85                  90                  95

Leu Asp Ile Val Ala Glu Asn Pro Asp Lys Phe Arg Val Val Ala Leu
            100                 105                 110

Ala Ala Gly Ser Asn Val Thr Leu Leu Ala Asp Gln Val Arg Arg Phe
        115                 120                 125

Lys Pro Ala Leu Val Ala Val Arg Asn Glu Ser Leu Ile Asn Glu Leu
    130                 135                 140

Lys Glu Ala Leu Ala Asp Leu Asp Tyr Lys Leu Glu Ile Ile Pro Gly
145                 150                 155                 160

Glu Gln Gly Val Ile Glu Val Ala Arg His Pro Glu Ala Val Thr Val
                165                 170                 175

Val Thr Gly Ile Val Gly Cys Ala Gly Leu Lys Pro Thr Val Ala Ala
            180                 185                 190

Ile Glu Ala Gly Lys Asp Ile Ala Leu Ala Asn Lys Glu Thr Leu Ile
        195                 200                 205

Ala Gly Gly Pro Phe Val Leu Pro Leu Ala Asn Lys His Asn Val Lys
    210                 215                 220

Ile Leu Pro Ala Asp Ser Glu His Ser Ala Ile Phe Gln Cys Ile Gln
225                 230                 235                 240

Gly Leu Pro Glu Gly Ala Leu Arg Lys Ile Ile Leu Thr Ala Ser Gly
                245                 250                 255

Gly Ala Phe Arg Asp Trp Pro Val Glu Lys Leu Lys Glu Val Lys Val
            260                 265                 270

Ala Asp Ala Leu Lys His Pro Asn Trp Asn Met Gly Lys Lys Ile Thr
        275                 280                 285

Val Asp Ser Ala Thr Leu Phe Asn Lys Gly Leu Glu Val Ile Glu Ala
```

-continued

```
    290                 295                 300

His Tyr Leu Phe Gly Ala Glu Tyr Asp Asp Ile Glu Ile Val Ile His
305                 310                 315                 320

Pro Gln Ser Ile Ile His Ser Met Ile Glu Thr Gln Asp Ser Ser Val
                325                 330                 335

Leu Ala Gln Leu Gly Trp Pro Asp Met Arg Leu Pro Ile Leu Tyr Thr
            340                 345                 350

Met Ser Trp Pro Asp Arg Val Pro Cys Ser Glu Val Thr Trp Pro Arg
        355                 360                 365

Leu Asp Leu Cys Lys Leu Gly Ser Leu Thr Phe Lys Lys Pro Asp Asn
    370                 375                 380

Val Lys Tyr Pro Ser Met Asp Leu Ala Tyr Ala Ala Gly Arg Ala Gly
385                 390                 395                 400

Gly Thr Met Thr Gly Val Leu Ser Ala Ala Asn Glu Lys Ala Val Glu
                405                 410                 415

Met Phe Ile Asp Glu Lys Ile Ser Tyr Leu Asp Ile Phe Lys Val Val
            420                 425                 430

Glu Leu Thr Cys Asp Lys His Arg Asn Glu Leu Val Thr Ser Pro Ser
        435                 440                 445

Leu Glu Glu Ile Val His Tyr Asp Leu Trp Ala Arg Glu Tyr Ala Ala
    450                 455                 460

Asn Val Gln Leu Ser Ser Gly Ala Arg Pro Val His Ala
465                 470                 475


<210> SEQ ID NO 9
<211> LENGTH: 711
<212> TYPE: DNA
<213> ORGANISM: Escherichia coli

<400> SEQUENCE: 9

atggcaacca ctcatttgga tgtttgcgcc gtggttccgg cggccggatt tggccgtcga      60

atgcaaacgg aatgtcctaa gcaatatctc tcaatcggta atcaaaccat tcttgaacac     120

tcggtgcatg cgctgctggc gcatccccgg gtgaaacgtg tcgtcattgc cataagtcct     180

ggcgatagcc gttttgcaca acttcctctg gcgaatcatc cgcaaatcac cgttgtagat     240

ggcggtgatg agcgtgccga ttccgtgctg gcaggtctga aagccgctgg cgacgcgcag     300

tgggtattgg tgcatgacgc cgctcgtcct tgtttgcatc aggatgacct cgcgcgattg     360

ttggcgttga gcgaaaccag ccgcacgggg gggatcctcg ccgcaccagt gcgcgatact     420

atgaaacgtg ccgaaccggg caaaaatgcc attgctcata ccgttgatcg caacggctta     480

tggcacgcgc tgacgccgca atttttccct cgtgagctgt tacatgactg tctgacgcgc     540

gctctaaatg aaggcgcgac tattaccgac gaagcctcgg cgctggaata ttgcggattc     600

catcctcagt tggtcgaagg ccgtgcggat aacattaaag tcacgcgccc ggaagatttg     660

gcactggccg agttttacct cacccgaacc atccatcagg agaatacata a              711


<210> SEQ ID NO 10
<211> LENGTH: 236
<212> TYPE: PRT
<213> ORGANISM: Escherichia coli

<400> SEQUENCE: 10

Met Ala Thr Thr His Leu Asp Val Cys Ala Val Val Pro Ala Ala Gly
 1               5                  10                  15

Phe Gly Arg Arg Met Gln Thr Glu Cys Pro Lys Gln Tyr Leu Ser Ile
            20                  25                  30
```

```
Gly Asn Gln Thr Ile Leu Glu His Ser Val His Ala Leu Leu Ala His
        35                  40                  45

Pro Arg Val Lys Arg Val Val Ile Ala Ile Ser Pro Gly Asp Ser Arg
    50                  55                  60

Phe Ala Gln Leu Pro Leu Ala Asn His Pro Gln Ile Thr Val Val Asp
65                  70                  75                  80

Gly Gly Asp Glu Arg Ala Asp Ser Val Leu Ala Gly Leu Lys Ala Ala
                85                  90                  95

Gly Asp Ala Gln Trp Val Leu Val His Asp Ala Ala Arg Pro Cys Leu
            100                 105                 110

His Gln Asp Asp Leu Ala Arg Leu Leu Ala Leu Ser Glu Thr Ser Arg
        115                 120                 125

Thr Gly Gly Ile Leu Ala Ala Pro Val Arg Asp Thr Met Lys Arg Ala
    130                 135                 140

Glu Pro Gly Lys Asn Ala Ile Ala His Thr Val Asp Arg Asn Gly Leu
145                 150                 155                 160

Trp His Ala Leu Thr Pro Gln Phe Phe Pro Arg Glu Leu Leu His Asp
                165                 170                 175

Cys Leu Thr Arg Ala Leu Asn Glu Gly Ala Thr Ile Thr Asp Glu Ala
            180                 185                 190

Ser Ala Leu Glu Tyr Cys Gly Phe His Pro Gln Leu Val Glu Gly Arg
        195                 200                 205

Ala Asp Asn Ile Lys Val Thr Arg Pro Glu Asp Leu Ala Leu Ala Glu
    210                 215                 220

Phe Tyr Leu Thr Arg Thr Ile His Gln Glu Asn Thr
225                 230                 235
```

<210> SEQ ID NO 11
<211> LENGTH: 909
<212> TYPE: DNA
<213> ORGANISM: Arabidopsis thaliana

<400> SEQUENCE: 11

```
atggcgatgc ttcagacgaa tcttggcttc attacttctc cgacatttct gtgtccgaag     60

cttaaagtca aattgaactc ttatctgtgg tttagctatc gttctcaagt tcaaaaactg    120

gatttttcga aaagggttaa tagaagctac aaaagagatg ctttattatt gtcaatcaag    180

tgttcttcat cgactggatt tgataatagc aatgttgttg tgaaggagaa gagtgtatct    240

gtgattcttt tagctggagg tcaaggcaag agaatgaaaa tgagtatgcc aaagcagtac    300

ataccacttc ttggtcagcc aattgctttg tatagctttt tcacgttttc acgtatgcct    360

gaagtgaagg aaattgtagt tgtatgtgat cctttttttca gagacatttt tgaagaatac    420

gaagaatcaa ttgatgttga tcttagattc gctattcctg gcaaagaaag acaagattct    480

gtttacagtg gacttcagga aatcgatgtg aactctgagc ttgtttgtat ccacgactct    540

gcccgaccat tggtgaatac tgaagatgtc gagaaggtcc ttaaagatgg ttccgcggtt    600

ggagcagctg tacttggtgt tcctgctaaa gctacaatca aagaggtcaa ttctgattcg    660

cttgtggtga aaactctcga cagaaaaacc ctatgggaaa tgcagacacc acaggtgatc    720

aaaccagagc tattgaaaaa gggtttcgag cttgtaaaaa gtgaaggtct agaggtaaca    780

gatgacgttt cgattgttga atacctcaag catccagttt atgtctctca aggatcttat    840

acaaacatca aggttacaac acctgatgat ttactgcttg ctgagagaat cttgagcgag    900

gactcatga                                                            909
```

<210> SEQ ID NO 12
<211> LENGTH: 302
<212> TYPE: PRT
<213> ORGANISM: Arabidopsis thaliana

<400> SEQUENCE: 12

```
Met Ala Met Leu Gln Thr Asn Leu Gly Phe Ile Thr Ser Pro Thr Phe
 1               5                  10                  15

Leu Cys Pro Lys Leu Lys Val Lys Leu Asn Ser Tyr Leu Trp Phe Ser
            20                  25                  30

Tyr Arg Ser Gln Val Gln Lys Leu Asp Phe Ser Lys Arg Val Asn Arg
        35                  40                  45

Ser Tyr Lys Arg Asp Ala Leu Leu Leu Ser Ile Lys Cys Ser Ser Ser
    50                  55                  60

Thr Gly Phe Asp Asn Ser Asn Val Val Val Lys Glu Lys Ser Val Ser
65                  70                  75                  80

Val Ile Leu Leu Ala Gly Gly Gln Gly Lys Arg Met Lys Met Ser Met
                85                  90                  95

Pro Lys Gln Tyr Ile Pro Leu Leu Gly Gln Pro Ile Ala Leu Tyr Ser
            100                 105                 110

Phe Phe Thr Phe Ser Arg Met Pro Glu Val Lys Glu Ile Val Val Val
        115                 120                 125

Cys Asp Pro Phe Phe Arg Asp Ile Phe Glu Glu Tyr Glu Glu Ser Ile
    130                 135                 140

Asp Val Asp Leu Arg Phe Ala Ile Pro Gly Lys Glu Arg Gln Asp Ser
145                 150                 155                 160

Val Tyr Ser Gly Leu Gln Glu Ile Asp Val Asn Ser Glu Leu Val Cys
                165                 170                 175

Ile His Asp Ser Ala Arg Pro Leu Val Asn Thr Glu Asp Val Glu Lys
            180                 185                 190

Val Leu Lys Asp Gly Ser Ala Val Gly Ala Ala Val Leu Gly Val Pro
        195                 200                 205

Ala Lys Ala Thr Ile Lys Glu Val Asn Ser Asp Ser Leu Val Val Lys
    210                 215                 220

Thr Leu Asp Arg Lys Thr Leu Trp Glu Met Gln Thr Pro Gln Val Ile
225                 230                 235                 240

Lys Pro Glu Leu Leu Lys Lys Gly Phe Glu Leu Val Lys Ser Glu Gly
                245                 250                 255

Leu Glu Val Thr Asp Asp Val Ser Ile Val Glu Tyr Leu Lys His Pro
            260                 265                 270

Val Tyr Val Ser Gln Gly Ser Tyr Thr Asn Ile Lys Val Thr Thr Pro
        275                 280                 285

Asp Asp Leu Leu Leu Ala Glu Arg Ile Leu Ser Glu Asp Ser
    290                 295                 300
```

<210> SEQ ID NO 13
<211> LENGTH: 852
<212> TYPE: DNA
<213> ORGANISM: Escherichia coli

<400> SEQUENCE: 13

```
atgcggacac agtggccctc tccggcaaaa cttaatctgt ttttatacat taccggtcag      60

cgtgcggatg gttaccacac gctgcaaacg ctgtttcagt ttcttgatta cggcgacacc     120

atcagcattg agcttcgtga cgatggggat attcgtctgt taacgcccgt tgaaggcgtg     180

gaacatgaag ataacctgat cgttcgcgca gcgcgattgt tgatgaaaac tgcggcagac     240
```

```
agcgggcgtc ttccgacggg aagcggtgcg aatatcagca ttgacaagcg tttgccgatg    300

ggcggcggtc tcggcggtgg ttcatccaat gccgcgacgg tcctggtggc attaaatcat    360

ctctggcaat gcgggctaag catggatgag ctggcggaaa tggggctgac gctgggcgca    420

gatgttcctg tctttgttcg ggggcatgcc gcgtttgccg aaggcgttgg tgaaatacta    480

acgccggtgg atccgccaga gaagtggtat ctggtggcgc accctggtgt aagtattccg    540

actccggtga tttttaaaga tcctgaactc ccgcgcaata cgccaaaaag gtcaatagaa    600

acgttgctaa aatgtgaatt cagcaatgat tgcgaggtta tcgcaagaaa acgttttcgc    660

gaggttgatg cggtgctttc ctggctgtta gaatacgccc cgtcgcgcct gactgggaca    720

ggggcctgtg tctttgctga atttgataca gagtctgaag cccgccaggt gctagagcaa    780

gccccggaat ggctcaatgg ctttgtggcg aaaggcgcta atctttcccc attgcacaga    840

gccatgcttt aa                                                        852


<210> SEQ ID NO 14
<211> LENGTH: 283
<212> TYPE: PRT
<213> ORGANISM: Escherichia coli

<400> SEQUENCE: 14

Met Arg Thr Gln Trp Pro Ser Pro Ala Lys Leu Asn Leu Phe Leu Tyr
 1               5                   10                  15

Ile Thr Gly Gln Arg Ala Asp Gly Tyr His Thr Leu Gln Thr Leu Phe
            20                  25                  30

Gln Phe Leu Asp Tyr Gly Asp Thr Ile Ser Ile Glu Leu Arg Asp Asp
        35                  40                  45

Gly Asp Ile Arg Leu Leu Thr Pro Val Glu Gly Val Glu His Glu Asp
    50                  55                  60

Asn Leu Ile Val Arg Ala Ala Arg Leu Leu Met Lys Thr Ala Ala Asp
65                  70                  75                  80

Ser Gly Arg Leu Pro Thr Gly Ser Gly Ala Asn Ile Ser Ile Asp Lys
                85                  90                  95

Arg Leu Pro Met Gly Gly Gly Leu Gly Gly Gly Ser Ser Asn Ala Ala
            100                 105                 110

Thr Val Leu Val Ala Leu Asn His Leu Trp Gln Cys Gly Leu Ser Met
        115                 120                 125

Asp Glu Leu Ala Glu Met Gly Leu Thr Leu Gly Ala Asp Val Pro Val
    130                 135                 140

Phe Val Arg Gly His Ala Ala Phe Ala Glu Gly Val Gly Glu Ile Leu
145                 150                 155                 160

Thr Pro Val Asp Pro Pro Glu Lys Trp Tyr Leu Val Ala His Pro Gly
                165                 170                 175

Val Ser Ile Pro Thr Pro Val Ile Phe Lys Asp Pro Glu Leu Pro Arg
            180                 185                 190

Asn Thr Pro Lys Arg Ser Ile Glu Thr Leu Leu Lys Cys Glu Phe Ser
        195                 200                 205

Asn Asp Cys Glu Val Ile Ala Arg Lys Arg Phe Arg Glu Val Asp Ala
    210                 215                 220

Val Leu Ser Trp Leu Leu Glu Tyr Ala Pro Ser Arg Leu Thr Gly Thr
225                 230                 235                 240

Gly Ala Cys Val Phe Ala Glu Phe Asp Thr Glu Ser Glu Ala Arg Gln
                245                 250                 255

Val Leu Glu Gln Ala Pro Glu Trp Leu Asn Gly Phe Val Ala Lys Gly
```

```
            260                 265                 270

Ala Asn Leu Ser Pro Leu His Arg Ala Met Leu
        275                 280


<210> SEQ ID NO 15
<211> LENGTH: 1152
<212> TYPE: DNA
<213> ORGANISM: Arabidopsis thaliana

<400> SEQUENCE: 15

atggcaacgg cttctcctcc atttatctca actctcagct tcactcactc ttctttcaaa      60

acttcttctt cttcttcatt ttctccgaag cttcttcgac ccctcttaag cttttccgtc     120

aaagcttcca gaaagcaagt agagatagtg tttgatcctg atgagaggct taataagata     180

ggtgatgatg ttgacaaaga agctcctttg tccaggctta agctcttctc accttgcaag     240

atcaatgttt tcttgaggat caccggaaag cgagaagatg ggtttcatga tttagcctct     300

ttgtttcatg tgattagctt aggagacact attaaattct cattgtcacc atcaaagtct     360

aaagatcgtt tgtctactaa cgttcaagga gtccctgttg atgggagaaa tctgattata     420

aaagcactta acctttacag gaagaaaact ggtagtaaca gattcttctg gattcattta     480

gataagaagg tgcctaccgg ggctggactc ggtggtggaa gtagtaatgc tgcaactgca     540

ctctgggcgg caaatgagct caatggaggt cttgtcactg agaacgaact ccaggattgg     600

tcaagtgaaa ttgggtcaga tattcctttc ttcttctcgc atggagctgc ctattgtacc     660

gggagaggtg agattgtcca agaccttcct ccacctttc ctcttgatct tccgatggtg      720

ctcataaagc cccgagaagc atgttccact gctgaagttt acaaacgtct tcgtttagat     780

cagacgagca atattaatcc cttgacatta ctagagaatg tgaccagcaa tggtgtgtct     840

caaagcatat gcgtaaacga tttggaaccg ccagcgtttt cagttcttcc atctctaaaa     900

cgcttgaagc aacggataat agcatctgga cgtggggaat acgatgctgt gtttatgtct     960

gggagtggaa gcactattat cggtattggt tcaccagatc ctcctcaatt tatatatgat    1020

gatgaagaat acaagaacgt gttcttgtct gaagcaaact ttatgacgcg tgaggctaat    1080

gaatggtaca aagaacctgc ttctgcaaat gctactacct catccgccga atctcgcatg    1140

gatttccaat ga                                                        1152


<210> SEQ ID NO 16
<211> LENGTH: 383
<212> TYPE: PRT
<213> ORGANISM: Arabidopsis thaliana

<400> SEQUENCE: 16

Met Ala Thr Ala Ser Pro Pro Phe Ile Ser Thr Leu Ser Phe Thr His
 1               5                  10                  15

Ser Ser Phe Lys Thr Ser Ser Ser Ser Ser Phe Ser Pro Lys Leu Leu
            20                  25                  30

Arg Pro Leu Leu Ser Phe Ser Val Lys Ala Ser Arg Lys Gln Val Glu
        35                  40                  45

Ile Val Phe Asp Pro Asp Glu Arg Leu Asn Lys Ile Gly Asp Asp Val
    50                  55                  60

Asp Lys Glu Ala Pro Leu Ser Arg Leu Lys Leu Phe Ser Pro Cys Lys
65                  70                  75                  80

Ile Asn Val Phe Leu Arg Ile Thr Gly Lys Arg Glu Asp Gly Phe His
                85                  90                  95

Asp Leu Ala Ser Leu Phe His Val Ile Ser Leu Gly Asp Thr Ile Lys
```

-continued

```
            100                 105                 110

Phe Ser Leu Ser Pro Ser Lys Ser Lys Asp Arg Leu Ser Thr Asn Val
        115                 120                 125

Gln Gly Val Pro Val Asp Gly Arg Asn Leu Ile Ile Lys Ala Leu Asn
    130                 135                 140

Leu Tyr Arg Lys Lys Thr Gly Ser Asn Arg Phe Phe Trp Ile His Leu
145                 150                 155                 160

Asp Lys Lys Val Pro Thr Gly Ala Gly Leu Gly Gly Gly Ser Ser Asn
                165                 170                 175

Ala Ala Thr Ala Leu Trp Ala Ala Asn Glu Leu Asn Gly Gly Leu Val
            180                 185                 190

Thr Glu Asn Glu Leu Gln Asp Trp Ser Ser Glu Ile Gly Ser Asp Ile
        195                 200                 205

Pro Phe Phe Phe Ser His Gly Ala Ala Tyr Cys Thr Gly Arg Gly Glu
    210                 215                 220

Ile Val Gln Asp Leu Pro Pro Pro Phe Pro Leu Asp Leu Pro Met Val
225                 230                 235                 240

Leu Ile Lys Pro Arg Glu Ala Cys Ser Thr Ala Glu Val Tyr Lys Arg
                245                 250                 255

Leu Arg Leu Asp Gln Thr Ser Asn Ile Asn Pro Leu Thr Leu Leu Glu
            260                 265                 270

Asn Val Thr Ser Asn Gly Val Ser Gln Ser Ile Cys Val Asn Asp Leu
        275                 280                 285

Glu Pro Pro Ala Phe Ser Val Leu Pro Ser Leu Lys Arg Leu Lys Gln
    290                 295                 300

Arg Ile Ile Ala Ser Gly Arg Gly Glu Tyr Asp Ala Val Phe Met Ser
305                 310                 315                 320

Gly Ser Gly Ser Thr Ile Ile Gly Ile Gly Ser Pro Asp Pro Pro Gln
                325                 330                 335

Phe Ile Tyr Asp Asp Glu Glu Tyr Lys Asn Val Phe Leu Ser Glu Ala
            340                 345                 350

Asn Phe Met Thr Arg Glu Ala Asn Glu Trp Tyr Lys Glu Pro Ala Ser
        355                 360                 365

Ala Asn Ala Thr Thr Ser Ser Ala Glu Ser Arg Met Asp Phe Gln
    370                 375                 380
```

```
<210> SEQ ID NO 17
<211> LENGTH: 480
<212> TYPE: DNA
<213> ORGANISM: Escherichia coli

<400> SEQUENCE: 17

atgcgaattg gacacggttt tgacgtacat gcctttggcg gtgaaggccc aattatcatt      60

ggtggcgtac gcattcctta cgaaaaagga ttgctggcgc attctgatgg cgacgtggcg     120

ctccatgcgt tgaccgatgc attgcttggc gcggcggcgc tgggggatat cggcaagctg     180

ttcccggata ccgatccggc atttaaaggt gccgatagcc gcgagctgct acgcgaagcc     240

tggcgtcgta ttcaggcgaa gggttatacc cttggcaacg tcgatgtcac tatcatcgct     300

caggcaccga agatgttgcc gcacattcca caaatgcgcg tgtttattgc cgaagatctc     360

ggctgccata tggatgatgt taacgtgaaa gccactacta cggaaaaact gggatttacc     420

ggacgtgggg aagggattgc ctgtgaagcg gtggcgctac tcattaaggc aacaaaatga     480

<210> SEQ ID NO 18
<211> LENGTH: 159
```

<212> TYPE: PRT
<213> ORGANISM: Escherichia coli

<400> SEQUENCE: 18

```
Met Arg Ile Gly His Gly Phe Asp Val His Ala Phe Gly Gly Glu Gly
 1               5                  10                  15

Pro Ile Ile Ile Gly Gly Val Arg Ile Pro Tyr Glu Lys Gly Leu Leu
            20                  25                  30

Ala His Ser Asp Gly Asp Val Ala Leu His Ala Leu Thr Asp Ala Leu
        35                  40                  45

Leu Gly Ala Ala Ala Leu Gly Asp Ile Gly Lys Leu Phe Pro Asp Thr
    50                  55                  60

Asp Pro Ala Phe Lys Gly Ala Asp Ser Arg Glu Leu Leu Arg Glu Ala
65                  70                  75                  80

Trp Arg Arg Ile Gln Ala Lys Gly Tyr Thr Leu Gly Asn Val Asp Val
                85                  90                  95

Thr Ile Ile Ala Gln Ala Pro Lys Met Leu Pro His Ile Pro Gln Met
            100                 105                 110

Arg Val Phe Ile Ala Glu Asp Leu Gly Cys His Met Asp Asp Val Asn
        115                 120                 125

Val Lys Ala Thr Thr Thr Glu Lys Leu Gly Phe Thr Gly Arg Gly Glu
    130                 135                 140

Gly Ile Ala Cys Glu Ala Val Ala Leu Leu Ile Lys Ala Thr Lys
145                 150                 155
```

<210> SEQ ID NO 19
<211> LENGTH: 672
<212> TYPE: DNA
<213> ORGANISM: Arabidopsis thaliana

<400> SEQUENCE: 19

```
atggctactt cttctactca gcttctactg tcttcttctt ctttgtttca ctctcaaatt     60

accaaaaagc cattccttct cccggcgacg aagatcggcg tttggagacc gaagaagtct    120

ctctcgttat catgtcgtcc ttcagcctcg gtttcagctg cttcttccgc cgtcgacgtc    180

aatgaatctg tgacttcaga gaaaccaacc aaaacgcttc cgtttcgaat cggtcatggt    240

ttcgatctac atcgtttaga gccagggtat cctctgatca tcggtgggat tgttattcct    300

catgatagag gctgcgaagc tcactccgat gtggatgcaa ttttgggagc actaggcctt    360

ccagatatag gtcagatttt ccctgactct gatcctaaat ggaaaggagc tgcttcttct    420

gtattcatca aagaagctgt gagactcatg gacgaggcag ggtatgagat aggaaaccta    480

gacgcgacgt tgattctcca gagaccaaaa attagtccac acaaagagac aatccgatcc    540

aatctgtcca agcttcttgg agcagatcct tctgtagtga acttgaaagc caaaacacat    600

gagaaagttg atagcctcgg agaaaacaga agcatagcag ctcacactgt tattctcctc    660

atgaagaaat ag                                                        672
```

<210> SEQ ID NO 20
<211> LENGTH: 223
<212> TYPE: PRT
<213> ORGANISM: Arabidopsis thaliana

<400> SEQUENCE: 20

```
Met Ala Thr Ser Ser Thr Gln Leu Leu Leu Ser Ser Ser Ser Leu Phe
 1               5                  10                  15

His Ser Gln Ile Thr Lys Lys Pro Phe Leu Leu Pro Ala Thr Lys Ile
            20                  25                  30
```

-continued

```
Gly Val Trp Arg Pro Lys Lys Ser Leu Ser Leu Ser Cys Arg Pro Ser
        35                  40                  45

Ala Ser Val Ser Ala Ala Ser Ser Ala Val Asp Val Asn Glu Ser Val
    50                  55                  60

Thr Ser Glu Lys Pro Thr Lys Thr Leu Pro Phe Arg Ile Gly His Gly
65                  70                  75                  80

Phe Asp Leu His Arg Leu Glu Pro Gly Tyr Pro Leu Ile Ile Gly Gly
                85                  90                  95

Ile Val Ile Pro His Asp Arg Gly Cys Glu Ala His Ser Asp Val Asp
            100                 105                 110

Ala Ile Leu Gly Ala Leu Gly Leu Pro Asp Ile Gly Gln Ile Phe Pro
        115                 120                 125

Asp Ser Asp Pro Lys Trp Lys Gly Ala Ala Ser Ser Val Phe Ile Lys
    130                 135                 140

Glu Ala Val Arg Leu Met Asp Glu Ala Gly Tyr Glu Ile Gly Asn Leu
145                 150                 155                 160

Asp Ala Thr Leu Ile Leu Gln Arg Pro Lys Ile Ser Pro His Lys Glu
                165                 170                 175

Thr Ile Arg Ser Asn Leu Ser Lys Leu Leu Gly Ala Asp Pro Ser Val
            180                 185                 190

Val Asn Leu Lys Ala Lys Thr His Glu Lys Val Asp Ser Leu Gly Glu
        195                 200                 205

Asn Arg Ser Ile Ala Ala His Thr Val Ile Leu Leu Met Lys Lys
    210                 215                 220
```

<210> SEQ ID NO 21
<211> LENGTH: 1119
<212> TYPE: DNA
<213> ORGANISM: Escherichia coli

<400> SEQUENCE: 21

```
atgcataacc aggctccaat tcaacgtaga aaatcaacac gtatttacgt tgggaatgtg      60

ccgattggcg atggtgctcc catcgccgta cagtccatga ccaatacgcg tacgacagac     120

gtcgaagcaa cggtcaatca aatcaaggcg ctggaacgcg ttggcgctga tatcgtccgt     180

gtatccgtac cgacgatgga cgcggcagaa gcgttcaaac tcatcaaaca gcaggttaac     240

gtgccgctgg tggctgacat ccacttcgac tatcgcattg cgctgaaagt agcggaatac     300

ggcgtcgatt gtctgcgtat taaccctggc aatatcggta atgaagagcg tattcgcatg     360

gtggttgact gtgcgcgcga taaaaacatt ccgatccgta ttggcgttaa cgccggatcg     420

ctggaaaaag atctgcaaga aaagtatggc gaaccgacgc cgcaggcgtt gctggaatct     480

gccatgcgtc atgttgatca tctcgatcgc ctgaacttcg atcagttcaa agtcagcgtg     540

aaagcgtctg acgtcttcct cgctgttgag tcttatcgtt tgctggcaaa acagatcgat     600

cagccgttgc atctggggat caccgaagcc ggtggtgcgc gcagcggggc agtaaaatcc     660

gccattggtt taggtctgct gctgtctgaa ggcatcggcg acacgctgcg cgtatcgctg     720

gcggccgatc cggtcgaaga gatcaaagtc ggtttcgata ttttgaaatc gctgcgtatc     780

cgttcgcgag ggatcaactt catcgcctgc ccgacctgtt cgcgtcagga atttgatgtt     840

atcggtacgg ttaacgcgct ggagcaacgc ctggaagata tcatcactcc gatggacgtt     900

tcgattatcg gctgcgtggt gaatggccca ggtgaggcgc tggtttctac actcggcgtc     960

accggcggca acaagaaaag cggcctctat gaagatggcg tgcgcaaaga ccgtctggac    1020

aacaacgata tgatcgacca gctggaagca cgcattcgtg cgaaagccag tcagctggac    1080
```

```
gaagcgcgtc gaattgacgt tcagcaggtt gaaaaataa                        1119


<210> SEQ ID NO 22
<211> LENGTH: 372
<212> TYPE: PRT
<213> ORGANISM: Escherichia coli

<400> SEQUENCE: 22

Met His Asn Gln Ala Pro Ile Gln Arg Arg Lys Ser Thr Arg Ile Tyr
 1               5                  10                  15

Val Gly Asn Val Pro Ile Gly Asp Gly Ala Pro Ile Ala Val Gln Ser
            20                  25                  30

Met Thr Asn Thr Arg Thr Thr Asp Val Glu Ala Thr Val Asn Gln Ile
        35                  40                  45

Lys Ala Leu Glu Arg Val Gly Ala Asp Ile Val Arg Val Ser Val Pro
    50                  55                  60

Thr Met Asp Ala Ala Glu Ala Phe Lys Leu Ile Lys Gln Gln Val Asn
65                  70                  75                  80

Val Pro Leu Val Ala Asp Ile His Phe Asp Tyr Arg Ile Ala Leu Lys
                85                  90                  95

Val Ala Glu Tyr Gly Val Asp Cys Leu Arg Ile Asn Pro Gly Asn Ile
            100                 105                 110

Gly Asn Glu Glu Arg Ile Arg Met Val Val Asp Cys Ala Arg Asp Lys
        115                 120                 125

Asn Ile Pro Ile Arg Ile Gly Val Asn Ala Gly Ser Leu Glu Lys Asp
    130                 135                 140

Leu Gln Glu Lys Tyr Gly Glu Pro Thr Pro Gln Ala Leu Leu Glu Ser
145                 150                 155                 160

Ala Met Arg His Val Asp His Leu Asp Arg Leu Asn Phe Asp Gln Phe
                165                 170                 175

Lys Val Ser Val Lys Ala Ser Asp Val Phe Leu Ala Val Glu Ser Tyr
            180                 185                 190

Arg Leu Leu Ala Lys Gln Ile Asp Gln Pro Leu His Leu Gly Ile Thr
        195                 200                 205

Glu Ala Gly Gly Ala Arg Ser Gly Ala Val Lys Ser Ala Ile Gly Leu
    210                 215                 220

Gly Leu Leu Leu Ser Glu Gly Ile Gly Asp Thr Leu Arg Val Ser Leu
225                 230                 235                 240

Ala Ala Asp Pro Val Glu Glu Ile Lys Val Gly Phe Asp Ile Leu Lys
                245                 250                 255

Ser Leu Arg Ile Arg Ser Arg Gly Ile Asn Phe Ile Ala Cys Pro Thr
            260                 265                 270

Cys Ser Arg Gln Glu Phe Asp Val Ile Gly Thr Val Asn Ala Leu Glu
        275                 280                 285

Gln Arg Leu Glu Asp Ile Ile Thr Pro Met Asp Val Ser Ile Ile Gly
    290                 295                 300

Cys Val Val Asn Gly Pro Gly Glu Ala Leu Val Ser Thr Leu Gly Val
305                 310                 315                 320

Thr Gly Gly Asn Lys Lys Ser Gly Leu Tyr Glu Asp Gly Val Arg Lys
                325                 330                 335

Asp Arg Leu Asp Asn Asn Asp Met Ile Asp Gln Leu Glu Ala Arg Ile
            340                 345                 350

Arg Ala Lys Ala Ser Gln Leu Asp Glu Ala Arg Arg Ile Asp Val Gln
        355                 360                 365
```

Gln Val Glu Lys
370

<210> SEQ ID NO 23
<211> LENGTH: 2154
<212> TYPE: DNA
<213> ORGANISM: Arabidopsis thaliana

<400> SEQUENCE: 23
atggcgactg gagtattgcc agctccggtt tctgggatca agataccgga ttcgaaagtc 60
gggtttggta aaagcatgaa tcttgtgaga atttgtgatg ttaggagtct aagatctgct 120
aggagaagag tttcggttat ccggaattca aaccaaggct ctgatttagc tgagcttcaa 180
cctgcatccg aaggaagccc tctcttagtg ccaagacaga aatattgtga atcattgcat 240
aagacggtga gaaggaagac tcgtactgtt atggttggaa atgtcgccct tggaagcgaa 300
catccgataa ggattcaaac gatgactact tcggatacaa aagatattac tggaactgtt 360
gatgaggtta tgagaatagc ggataaagga gctgatattg taaggataac tgttcaaggg 420
aagaaagagg cggatgcgtg ctttgaaata aaagataaac tcgttcagct taattacaat 480
ataccgctgg ttgcagatat tcattttgcc cctactgtag ccttacgagt cgctgaatgc 540
tttgacaaga tccgtgtcaa cccaggaaat tttgcggaca ggcgggccca gtttgagacg 600
atagattata cagaagatga atatcagaaa gaactccagc atatcgagca ggtcttcact 660
cctttggttg agaaatgcaa aaagtacggg agagcaatgc gtattgggac aaatcatgga 720
agtctttctg accgtatcat gagctattac ggggattctc cccgaggaat ggttgaatct 780
gcgtttgagt ttgcaagaat atgtcggaaa ttagactatc acaactttgt tttctcaatg 840
aaagcgagca acccagtgat catggtccag gcgtaccgtt tacttgtggc tgagatgtat 900
gttcatggat gggattatcc tttgcatttg ggagttactg aggcaggaga aggcgaagat 960
ggacggatga aatctgcgat tggaattggg acgcttcttc aggacgggct cggtgacaca 1020
ataagagttt cactgacgga gccaccagaa gaggagatag atccctgcag gcgattggct 1080
aacctcggga caaaagctgc caaacttcaa caaggcgttg caccgtttga agaaaagcat 1140
aggcattact ttgattttca gcgtcggacg ggtgatctac ctgtacaaaa agagggagaa 1200
gaggttgatt acagaaatgt ccttcaccgt gatggttctg ttctgatgtc gatttctctg 1260
gatcaactaa aggcacctga actcctctac agatcactcg ctacaaagct tgtcgtgggt 1320
atgccattca aggatctggc aactgttgat tcaatcttat taagagagct accgcctgta 1380
gatgatcaag tggctcgttt ggctctaaaa cggttgattg atgtcagtat gggagttata 1440
gcacctttat cagagcaact aacaaagcca ttgcccaatg ccatggttct tgtcaacctc 1500
aaggaactat ctggtggcgc ttacaagctt ctccctgaag gtacacgctt ggttgtctct 1560
ctacgaggcg atgagcctta cgaggagctt gaaatactca aaaacattga tgctactatg 1620
attctccatg atgtaccttt cactgaagac aaagttagca gagtacatgc agctcggagg 1680
ctattcgagt tcttatccga gaattcagtt aactttcctg ttattcatca cataaacttc 1740
ccaaccggaa tccacagaga cgaattggtg attcatgcag ggacatatgc tggaggcctt 1800
cttgtggatg gactaggtga tggcgtaatg ctcgaagcac ctgaccaaga ttttgatttt 1860
cttaggaata cttccttcaa cttattacaa ggatgcagaa tgcgtaacac taagacggaa 1920
tatgtatcgt gcccgtcttg tggaagaacg cttttcgact tgcaagaaat cagcgccgag 1980
atccgagaaa agacttccca tttacctggc gtttcggtta aaactcaaga ctttcataca 2040
tgtttttcaa gaaaaagttt tcttctgttt ttgaatgtaa acaaattgaa taatggcgca 2100
gatcgcaatc atgggatgca ttgtgaatgg accaggagaa atggcagatg ctga 2154

<210> SEQ ID NO 24
<211> LENGTH: 717
<212> TYPE: PRT
<213> ORGANISM: Arabidopsis thaliana

<400> SEQUENCE: 24

Met Ala Thr Gly Val Leu Pro Ala Pro Val Ser Gly Ile Lys Ile Pro
1 5 10 15

Asp Ser Lys Val Gly Phe Gly Lys Ser Met Asn Leu Val Arg Ile Cys
20 25 30

Asp Val Arg Ser Leu Arg Ser Ala Arg Arg Arg Val Ser Val Ile Arg
35 40 45

Asn Ser Asn Gln Gly Ser Asp Leu Ala Glu Leu Gln Pro Ala Ser Glu
50 55 60

Gly Ser Pro Leu Leu Val Pro Arg Gln Lys Tyr Cys Glu Ser Leu His
65 70 75 80

Lys Thr Val Arg Arg Lys Thr Arg Thr Val Met Val Gly Asn Val Ala
85 90 95

Leu Gly Ser Glu His Pro Ile Arg Ile Gln Thr Met Thr Thr Ser Asp
100 105 110

Thr Lys Asp Ile Thr Gly Thr Val Asp Glu Val Met Arg Ile Ala Asp
115 120 125

Lys Gly Ala Asp Ile Val Arg Ile Thr Val Gln Gly Lys Lys Glu Ala
130 135 140

Asp Ala Cys Phe Glu Ile Lys Asp Lys Leu Val Gln Leu Asn Tyr Asn
145 150 155 160

Ile Pro Leu Val Ala Asp Ile His Phe Ala Pro Thr Val Ala Leu Arg
165 170 175

Val Ala Glu Cys Phe Asp Lys Ile Arg Val Asn Pro Gly Asn Phe Ala
180 185 190

Asp Arg Arg Ala Gln Phe Glu Thr Ile Asp Tyr Thr Glu Asp Glu Tyr
195 200 205

Gln Lys Glu Leu Gln His Ile Glu Gln Val Phe Thr Pro Leu Val Glu
210 215 220

Lys Cys Lys Lys Tyr Gly Arg Ala Met Arg Ile Gly Thr Asn His Gly
225 230 235 240

Ser Leu Ser Asp Arg Ile Met Ser Tyr Tyr Gly Asp Ser Pro Arg Gly
245 250 255

Met Val Glu Ser Ala Phe Glu Phe Ala Arg Ile Cys Arg Lys Leu Asp
260 265 270

Tyr His Asn Phe Val Phe Ser Met Lys Ala Ser Asn Pro Val Ile Met
275 280 285

Val Gln Ala Tyr Arg Leu Leu Val Ala Glu Met Tyr Val His Gly Trp
290 295 300

Asp Tyr Pro Leu His Leu Gly Val Thr Glu Ala Gly Glu Gly Glu Asp
305 310 315 320

Gly Arg Met Lys Ser Ala Ile Gly Ile Gly Thr Leu Leu Gln Asp Gly
325 330 335

Leu Gly Asp Thr Ile Arg Val Ser Leu Thr Glu Pro Pro Glu Glu Glu
340 345 350

Ile Asp Pro Cys Arg Arg Leu Ala Asn Leu Gly Thr Lys Ala Ala Lys
355 360 365

-continued

```
Leu Gln Gln Gly Val Ala Pro Phe Glu Glu Lys His Arg His Tyr Phe
    370                 375                 380

Asp Phe Gln Arg Arg Thr Gly Asp Leu Pro Val Gln Lys Glu Gly Glu
385                 390                 395                 400

Glu Val Asp Tyr Arg Asn Val Leu His Arg Asp Gly Ser Val Leu Met
                405                 410                 415

Ser Ile Ser Leu Asp Gln Leu Lys Ala Pro Glu Leu Leu Tyr Arg Ser
            420                 425                 430

Leu Ala Thr Lys Leu Val Val Gly Met Pro Phe Lys Asp Leu Ala Thr
        435                 440                 445

Val Asp Ser Ile Leu Leu Arg Glu Leu Pro Pro Val Asp Asp Gln Val
    450                 455                 460

Ala Arg Leu Ala Leu Lys Arg Leu Ile Asp Val Ser Met Gly Val Ile
465                 470                 475                 480

Ala Pro Leu Ser Glu Gln Leu Thr Lys Pro Leu Pro Asn Ala Met Val
                485                 490                 495

Leu Val Asn Leu Lys Glu Leu Ser Gly Gly Ala Tyr Lys Leu Leu Pro
            500                 505                 510

Glu Gly Thr Arg Leu Val Val Ser Leu Arg Gly Asp Glu Pro Tyr Glu
        515                 520                 525

Glu Leu Glu Ile Leu Lys Asn Ile Asp Ala Thr Met Ile Leu His Asp
    530                 535                 540

Val Pro Phe Thr Glu Asp Lys Val Ser Arg Val His Ala Ala Arg Arg
545                 550                 555                 560

Leu Phe Glu Phe Leu Ser Glu Asn Ser Val Asn Phe Pro Val Ile His
                565                 570                 575

His Ile Asn Phe Pro Thr Gly Ile His Arg Asp Glu Leu Val Ile His
            580                 585                 590

Ala Gly Thr Tyr Ala Gly Gly Leu Leu Val Asp Gly Leu Gly Asp Gly
        595                 600                 605

Val Met Leu Glu Ala Pro Asp Gln Asp Phe Asp Phe Leu Arg Asn Thr
    610                 615                 620

Ser Phe Asn Leu Leu Gln Gly Cys Arg Met Arg Asn Thr Lys Thr Glu
625                 630                 635                 640

Tyr Val Ser Cys Pro Ser Cys Gly Arg Thr Leu Phe Asp Leu Gln Glu
                645                 650                 655

Ile Ser Ala Glu Ile Arg Glu Lys Thr Ser His Leu Pro Gly Val Ser
            660                 665                 670

Val Lys Thr Gln Asp Phe His Thr Cys Phe Ser Arg Lys Ser Phe Leu
        675                 680                 685

Leu Phe Leu Asn Val Asn Lys Leu Asn Asn Gly Ala Asp Arg Asn His
    690                 695                 700

Gly Met His Cys Glu Trp Thr Arg Arg Asn Gly Arg Cys
705                 710                 715
```

```
<210> SEQ ID NO 25
<211> LENGTH: 951
<212> TYPE: DNA
<213> ORGANISM: Escherichia coli

<400> SEQUENCE: 25

atgcagatcc tgttggccaa cccgcgtggt ttttgtgccg gggtagaccg cgctatcagc      60

attgttgaaa acgcgctggc catttacggc gcaccgatat atgtccgtca cgaagtggta     120

cataaccgct atgtggtcga tagcttgcgt gagcgtgggg ctatctttat tgagcagatt     180
```

```
agcgaagtac cggacggcgc gatcctgatt ttctccgcac acggtgtttc tcaggcggta    240

cgtaacgaag caaaaagtcg cgatttgacg gtgtttgatg ccacctgtcc gctggtgacc    300

aaagtgcata tggaagtcgc ccgcgccagt cgccgtggcg aagaatctat tctcatcggt    360

cacgccgggc acccggaagt ggaagggaca atgggccagt acagtaaccc ggaaggggga    420

atgtatctgg tcgaatcgcc ggacgatgtg tggaaactga cggtcaaaaa cgaagagaag    480

ctctccttta tgacccagac cacgctgtcg gtggatgaca cgtctgatgt gatcgacgcg    540

ctgcgtaaac gcttcccgaa aattgtcggt ccgcgcaaag atgacatctg ctacgccacg    600

actaaccgtc aggaagcggt acgcgccctg gcagaacagg cggaagttgt gttggtggtc    660

ggttcgaaaa actcctccaa ctccaaccgt ctggcggagc tggcccagcg tatgggcaaa    720

cgcgcgtttt tgattgacga tgcgaaagac atccaggaag agtgggtgaa agaggttaaa    780

tgcgtcggcg tgactgcggg cgcatcggct ccggatattc tggtgcagaa tgtggtggca    840

cgtttgcagc agctgggcgg tggtgaagcc attccgctgg aaggccgtga agaaaacatt    900

gttttcgaag tgccgaaaga gctgcgtgtc gatattcgtg aagtcgatta a             951
```

<210> SEQ ID NO 26
<211> LENGTH: 316
<212> TYPE: PRT
<213> ORGANISM: Escherichia coli

<400> SEQUENCE: 26

```
Met Gln Ile Leu Leu Ala Asn Pro Arg Gly Phe Cys Ala Gly Val Asp
 1               5                  10                  15

Arg Ala Ile Ser Ile Val Glu Asn Ala Leu Ala Ile Tyr Gly Ala Pro
            20                  25                  30

Ile Tyr Val Arg His Glu Val Val His Asn Arg Tyr Val Val Asp Ser
        35                  40                  45

Leu Arg Glu Arg Gly Ala Ile Phe Ile Glu Gln Ile Ser Glu Val Pro
    50                  55                  60

Asp Gly Ala Ile Leu Ile Phe Ser Ala His Gly Val Ser Gln Ala Val
65                  70                  75                  80

Arg Asn Glu Ala Lys Ser Arg Asp Leu Thr Val Phe Asp Ala Thr Cys
                85                  90                  95

Pro Leu Val Thr Lys Val His Met Glu Val Ala Arg Ala Ser Arg Arg
            100                 105                 110

Gly Glu Glu Ser Ile Leu Ile Gly His Ala Gly His Pro Glu Val Glu
        115                 120                 125

Gly Thr Met Gly Gln Tyr Ser Asn Pro Glu Gly Gly Met Tyr Leu Val
    130                 135                 140

Glu Ser Pro Asp Asp Val Trp Lys Leu Thr Val Lys Asn Glu Glu Lys
145                 150                 155                 160

Leu Ser Phe Met Thr Gln Thr Thr Leu Ser Val Asp Asp Thr Ser Asp
                165                 170                 175

Val Ile Asp Ala Leu Arg Lys Arg Phe Pro Lys Ile Val Gly Pro Arg
            180                 185                 190

Lys Asp Asp Ile Cys Tyr Ala Thr Thr Asn Arg Gln Glu Ala Val Arg
        195                 200                 205

Ala Leu Ala Glu Gln Ala Glu Val Val Leu Val Val Gly Ser Lys Asn
    210                 215                 220

Ser Ser Asn Ser Asn Arg Leu Ala Glu Leu Ala Gln Arg Met Gly Lys
225                 230                 235                 240

Arg Ala Phe Leu Ile Asp Asp Ala Lys Asp Ile Gln Glu Glu Trp Val
```

-continued

```
            245                 250                 255

Lys Glu Val Lys Cys Val Gly Val Thr Ala Gly Ala Ser Ala Pro Asp
        260                 265                 270

Ile Leu Val Gln Asn Val Val Ala Arg Leu Gln Gln Leu Gly Gly Gly
    275                 280                 285

Glu Ala Ile Pro Leu Glu Gly Arg Glu Glu Asn Ile Val Phe Glu Val
  290                 295                 300

Pro Lys Glu Leu Arg Val Asp Ile Arg Glu Val Asp
305                 310                 315


<210> SEQ ID NO 27
<211> LENGTH: 1401
<212> TYPE: DNA
<213> ORGANISM: Arabidopsis thaliana

<400> SEQUENCE: 27

atggctgttg cgctccaatt cagccgatta tgcgttcgac cggatacttt cgtgcgggag      60

aatcatctct ctggatccgg atctctccgc cgccggaaag ctttatcagt ccggtgctcg     120

tctggcgatg agaacgctcc ttcgccatcg gtggtgatgg actccgattt cgacgccaag     180

gtgttccgta agaacttgac gagaagcgat aattacaatc gtaaagggtt cggtcataag     240

gaggagacac tcaagctcat gaatcgagag tacaccagtg atatattgga gacactgaaa     300

acaaatgggt atacttattc ttggggagat gttactgtga aactcgctaa agcatatggt     360

ttttgctggg gtgttgagcg tgctgttcag attgcatatg aagcacgaaa gcagtttcca     420

gaggagaggc tttggattac taacgaaatc attcataacc cgaccgtcaa taagaggttg     480

gaagatatgg atgttaaaat tattccggtt gaggattcaa agaaacagtt tgatgtagta     540

gagaaagatg atgtggttat ccttcctgcg tttggagctg gtgttgacga gatgtatgtt     600

cttaatgata aaaaggtgca aattgttgac acgacttgtc cttgggtgac aaaggtctgg     660

aacacggttg agaagcacaa gaagggggaa tacacatcag taatccatgg taaatataat     720

catgaagaga cgattgcaac tgcgtctttt gcaggaaagt acatcattgt aaagaacatg     780

aaagaggcaa attacgtttg tgattacatt ctcggtggcc aatacgatgg atctagctcc     840

acaaaagagg agttcatgga gaaattcaaa tacgcaattt cgaagggttt cgatcccgac     900

aatgaccttg tcaaagttgg tattgcaaac caaacaacga tgctaaaggg agaaacagag     960

gagataggaa gattactcga gacaacaatg atgcgcaagt atggagtgga aaatgtaagc    1020

ggacatttca tcagcttcaa cacaatatgc gacgctactc aagagcgaca agacgcaatc    1080

tatgagctag tggaagagaa gattgacctc atgctagtgg ttggcggatg gaattcaagt    1140

aacacctctc accttcagga aatctcagag gcacggggaa tcccatctta ctggatcgat    1200

agtgagaaac ggataggacc tgggaataaa atagcctata agctccacta tggagaactg    1260

gtcgagaagg aaaactttct cccaaaggga ccaataacaa tcggtgtgac atcaggtgca    1320

tcaaccccgg ataaggtcgt ggaagatgct ttggtgaagg tgttcgacat taaacgtgaa    1380

gagttattgc agctggcttg a                                              1401


<210> SEQ ID NO 28
<211> LENGTH: 466
<212> TYPE: PRT
<213> ORGANISM: Arabidopsis thaliana

<400> SEQUENCE: 28

Met Ala Val Ala Leu Gln Phe Ser Arg Leu Cys Val Arg Pro Asp Thr
 1               5                  10                  15
```

-continued

```
Phe Val Arg Glu Asn His Leu Ser Gly Ser Gly Ser Leu Arg Arg Arg
            20                  25                  30

Lys Ala Leu Ser Val Arg Cys Ser Ser Gly Asp Glu Asn Ala Pro Ser
        35                  40                  45

Pro Ser Val Val Met Asp Ser Asp Phe Asp Ala Lys Val Phe Arg Lys
    50                  55                  60

Asn Leu Thr Arg Ser Asp Asn Tyr Asn Arg Lys Gly Phe Gly His Lys
65                  70                  75                  80

Glu Glu Thr Leu Lys Leu Met Asn Arg Glu Tyr Thr Ser Asp Ile Leu
                85                  90                  95

Glu Thr Leu Lys Thr Asn Gly Tyr Thr Tyr Ser Trp Gly Asp Val Thr
            100                 105                 110

Val Lys Leu Ala Lys Ala Tyr Gly Phe Cys Trp Gly Val Glu Arg Ala
        115                 120                 125

Val Gln Ile Ala Tyr Glu Ala Arg Lys Gln Phe Pro Glu Glu Arg Leu
    130                 135                 140

Trp Ile Thr Asn Glu Ile Ile His Asn Pro Thr Val Asn Lys Arg Leu
145                 150                 155                 160

Glu Asp Met Asp Val Lys Ile Ile Pro Val Glu Asp Ser Lys Lys Gln
                165                 170                 175

Phe Asp Val Val Glu Lys Asp Asp Val Val Ile Leu Pro Ala Phe Gly
            180                 185                 190

Ala Gly Val Asp Glu Met Tyr Val Leu Asn Asp Lys Lys Val Gln Ile
        195                 200                 205

Val Asp Thr Thr Cys Pro Trp Val Thr Lys Val Trp Asn Thr Val Glu
    210                 215                 220

Lys His Lys Lys Gly Glu Tyr Thr Ser Val Ile His Gly Lys Tyr Asn
225                 230                 235                 240

His Glu Glu Thr Ile Ala Thr Ala Ser Phe Ala Gly Lys Tyr Ile Ile
                245                 250                 255

Val Lys Asn Met Lys Glu Ala Asn Tyr Val Cys Asp Tyr Ile Leu Gly
            260                 265                 270

Gly Gln Tyr Asp Gly Ser Ser Ser Thr Lys Glu Glu Phe Met Glu Lys
        275                 280                 285

Phe Lys Tyr Ala Ile Ser Lys Gly Phe Asp Pro Asp Asn Asp Leu Val
    290                 295                 300

Lys Val Gly Ile Ala Asn Gln Thr Thr Met Leu Lys Gly Glu Thr Glu
305                 310                 315                 320

Glu Ile Gly Arg Leu Leu Glu Thr Thr Met Met Arg Lys Tyr Gly Val
                325                 330                 335

Glu Asn Val Ser Gly His Phe Ile Ser Phe Asn Thr Ile Cys Asp Ala
            340                 345                 350

Thr Gln Glu Arg Gln Asp Ala Ile Tyr Glu Leu Val Glu Glu Lys Ile
        355                 360                 365

Asp Leu Met Leu Val Val Gly Gly Trp Asn Ser Ser Asn Thr Ser His
    370                 375                 380

Leu Gln Glu Ile Ser Glu Ala Arg Gly Ile Pro Ser Tyr Trp Ile Asp
385                 390                 395                 400

Ser Glu Lys Arg Ile Gly Pro Gly Asn Lys Ile Ala Tyr Lys Leu His
                405                 410                 415

Tyr Gly Glu Leu Val Glu Lys Glu Asn Phe Leu Pro Lys Gly Pro Ile
            420                 425                 430

Thr Ile Gly Val Thr Ser Gly Ala Ser Thr Pro Asp Lys Val Val Glu
```

-continued

```
        435                 440                 445

Asp Ala Leu Val Lys Val Phe Asp Ile Lys Arg Glu Glu Leu Leu Gln
    450                 455                 460

Leu Ala
465


<210> SEQ ID NO 29
<211> LENGTH: 549
<212> TYPE: DNA
<213> ORGANISM: Escherichia coli

<400> SEQUENCE: 29

atgcaaacgg aacacgtcat tttattgaat gcacagggag ttcccacggg tacgctggaa     60

aagtatgccg cacacacggc agacacccgc ttacatctcg cgttctccag ttggctgttt    120

aatgccaaag gacaattatt agttacccgc cgcgcactga gcaaaaaagc atggcctggc    180

gtgtggacta actcggtttg tgggcaccca caactgggag aaagcaacga agacgcagtg    240

atccgccgtt gccgttatga gcttggcgtg gaaattacgc ctcctgaatc tatctatcct    300

gactttcgct accgcgccac cgatccgagt ggcattgtgg aaaatgaagt gtgtccggta    360

tttgccgcac gcaccactag tgcgttacag atcaatgatg atgaagtgat ggattatcaa    420

tggtgtgatt tagcagatgt attacacggt attgatgcca cgccgtgggc gttcagtccg    480

tggatggtga tgcaggcgac aaatcgcgaa gccagaaaac gattatctgc atttacccag    540

cttaaataa                                                            549


<210> SEQ ID NO 30
<211> LENGTH: 182
<212> TYPE: PRT
<213> ORGANISM: Escherichia coli

<400> SEQUENCE: 30

Met Gln Thr Glu His Val Ile Leu Leu Asn Ala Gln Gly Val Pro Thr
 1               5                  10                  15

Gly Thr Leu Glu Lys Tyr Ala Ala His Thr Ala Asp Thr Arg Leu His
            20                  25                  30

Leu Ala Phe Ser Ser Trp Leu Phe Asn Ala Lys Gly Gln Leu Leu Val
        35                  40                  45

Thr Arg Arg Ala Leu Ser Lys Lys Ala Trp Pro Gly Val Trp Thr Asn
    50                  55                  60

Ser Val Cys Gly His Pro Gln Leu Gly Glu Ser Asn Glu Asp Ala Val
65                  70                  75                  80

Ile Arg Arg Cys Arg Tyr Glu Leu Gly Val Glu Ile Thr Pro Pro Glu
                85                  90                  95

Ser Ile Tyr Pro Asp Phe Arg Tyr Arg Ala Thr Asp Pro Ser Gly Ile
            100                 105                 110

Val Glu Asn Glu Val Cys Pro Val Phe Ala Ala Arg Thr Thr Ser Ala
        115                 120                 125

Leu Gln Ile Asn Asp Asp Glu Val Met Asp Tyr Gln Trp Cys Asp Leu
    130                 135                 140

Ala Asp Val Leu His Gly Ile Asp Ala Thr Pro Trp Ala Phe Ser Pro
145                 150                 155                 160

Trp Met Val Met Gln Ala Thr Asn Arg Glu Ala Arg Lys Arg Leu Ser
                165                 170                 175

Ala Phe Thr Gln Leu Lys
            180
```

<210> SEQ ID NO 31
<211> LENGTH: 867
<212> TYPE: DNA
<213> ORGANISM: Saccharomyces cerevisiae

<400> SEQUENCE: 31

```
atgactgccg acaacaatag tatgccccat ggtgcagtat ctagttacgc caaattagtg     60

caaaaccaaa cacctgaaga cattttggaa gagtttcctg aaattattcc attacaacaa    120

agacctaata cccgatctag tgagacgtca aatgacgaaa gcggagaaac atgtttttct    180

ggtcatgatg aggagcaaat taagttaatg aatgaaaatt gtattgtttt ggattgggac    240

gataatgcta ttggtgccgg taccaagaaa gtttgtcatt taatggaaaa tattgaaaag    300

ggtttactac atcgtgcatt ctccgtcttt attttcaatg aacaaggtga attactttta    360

caacaaagag ccactgaaaa aataactttc cctgatcttt ggactaacac atgctgctct    420

catccactat gtattgatga cgaattaggt ttgaagggta agctagacga taagattaag    480

ggcgctatta ctgcggcggt gagaaaacta gatcatgaat taggtattcc agaagatgaa    540

actaagacaa ggggtaagtt tcacttttta aacagaatcc attacatggc accaagcaat    600

gaaccatggg gtgaacatga aattgattac atcctatttt ataagatcaa cgctaaagaa    660

aacttgactg tcaacccaaa cgtcaatgaa gttagagact tcaaatgggt ttcaccaaat    720

gatttgaaaa ctatgtttgc tgacccaagt tacaagttta cgccttggtt taagattatt    780

tgcgagaatt acttattcaa ctggtgggag caattagatg acctttctga agtggaaaat    840

gacaggcaaa ttcatagaat gctataa                                        867
```

<210> SEQ ID NO 32
<211> LENGTH: 288
<212> TYPE: PRT
<213> ORGANISM: Saccharomyces cerevisiae

<400> SEQUENCE: 32

```
Met Thr Ala Asp Asn Asn Ser Met Pro His Gly Ala Val Ser Ser Tyr
1               5                   10                  15

Ala Lys Leu Val Gln Asn Gln Thr Pro Glu Asp Ile Leu Glu Glu Phe
            20                  25                  30

Pro Glu Ile Ile Pro Leu Gln Gln Arg Pro Asn Thr Arg Ser Ser Glu
        35                  40                  45

Thr Ser Asn Asp Glu Ser Gly Glu Thr Cys Phe Ser Gly His Asp Glu
    50                  55                  60

Glu Gln Ile Lys Leu Met Asn Glu Asn Cys Ile Val Leu Asp Trp Asp
65                  70                  75                  80

Asp Asn Ala Ile Gly Ala Gly Thr Lys Lys Val Cys His Leu Met Glu
                85                  90                  95

Asn Ile Glu Lys Gly Leu Leu His Arg Ala Phe Ser Val Phe Ile Phe
            100                 105                 110

Asn Glu Gln Gly Glu Leu Leu Leu Gln Gln Arg Ala Thr Glu Lys Ile
        115                 120                 125

Thr Phe Pro Asp Leu Trp Thr Asn Thr Cys Cys Ser His Pro Leu Cys
    130                 135                 140

Ile Asp Asp Glu Leu Gly Leu Lys Gly Lys Leu Asp Asp Lys Ile Lys
145                 150                 155                 160

Gly Ala Ile Thr Ala Ala Val Arg Lys Leu Asp His Glu Leu Gly Ile
                165                 170                 175

Pro Glu Asp Glu Thr Lys Thr Arg Gly Lys Phe His Phe Leu Asn Arg
```

```
            180                 185                 190

Ile His Tyr Met Ala Pro Ser Asn Glu Pro Trp Gly Glu His Glu Ile
        195                 200                 205

Asp Tyr Ile Leu Phe Tyr Lys Ile Asn Ala Lys Glu Asn Leu Thr Val
    210                 215                 220

Asn Pro Asn Val Asn Glu Val Arg Asp Phe Lys Trp Val Ser Pro Asn
225                 230                 235                 240

Asp Leu Lys Thr Met Phe Ala Asp Pro Ser Tyr Lys Phe Thr Pro Trp
                245                 250                 255

Phe Lys Ile Ile Cys Glu Asn Tyr Leu Phe Asn Trp Trp Glu Gln Leu
            260                 265                 270

Asp Asp Leu Ser Glu Val Glu Asn Asp Arg Gln Ile His Arg Met Leu
        275                 280                 285


<210> SEQ ID NO 33
<211> LENGTH: 966
<212> TYPE: DNA
<213> ORGANISM: Citrus sinensis

<400> SEQUENCE: 33

atggttattg ctgaggttcc taagcttgcc tcagctgctg agtatttctt taaaatgggg      60

gtggaaggaa agaggttccg tcccacggtt ttattgctga tggcaacagc tctgaatgtg     120

cgagtacctg aacctctaca tgatggagta gaagatgctt cggcgactga actacgtaca     180

aggcaacaat gtatagctga gattacggag atgatccatg tagcaagcct tcttcatgat     240

gatgtcttgg atgatgcaga taccaggcgt ggtattggtt cattgaattt tgtaatgggc     300

aataagttag ctgtattagc gggtgatttt cttctttccc gtgcttgtgt tgcccttgcc     360

tctttgaaaa acacagaggt tgtgacgtta ctggcaaccg ttgtagagca tcttgttact     420

ggtgaaacca tgcaaatgac aacatcatct gaccaacgtt gtagcatgga ttattatatg     480

caaaaaacat actacaagac cgcatcatta atctcaaaca gctgcaaggc aattgccctt     540

cttgctggac aaacagccga agtggcaata ttagcttttg attatggaaa gaatctgggt     600

ctggcatatc aattaatcga cgatgttctc gatttcactg gcacatcagc ctctcttgga     660

aagggttctt tatctgacat ccggcatgga atcataacag ctccaatatt gtttgccatg     720

gaagagttcc ctcagttacg cacagtagtt gagcaaggct tcgaggattc ctcaaatgtt     780

gatattgccc ttgagtacct tgggaagagt cgagggatac aaaagacaag agaactggcc     840

gtgaagcatg ctaatcttgc tgcagctgcg attgattctc tacctgaaaa caatgatgag     900

gatgttacaa agtcaaggcg tgcactttta gatctcactc atagagtcat cacaagaaat     960

aaataa                                                                966


<210> SEQ ID NO 34
<211> LENGTH: 321
<212> TYPE: PRT
<213> ORGANISM: Citrus sinensis

<400> SEQUENCE: 34

Met Val Ile Ala Glu Val Pro Lys Leu Ala Ser Ala Ala Glu Tyr Phe
 1               5                  10                  15

Phe Lys Met Gly Val Glu Gly Lys Arg Phe Arg Pro Thr Val Leu Leu
            20                  25                  30

Leu Met Ala Thr Ala Leu Asn Val Arg Val Pro Glu Pro Leu His Asp
        35                  40                  45

Gly Val Glu Asp Ala Ser Ala Thr Glu Leu Arg Thr Arg Gln Gln Cys
```

-continued

```
    50                  55                  60

Ile Ala Glu Ile Thr Glu Met Ile His Val Ala Ser Leu Leu His Asp
65                  70                  75                  80

Asp Val Leu Asp Asp Ala Asp Thr Arg Arg Gly Ile Gly Ser Leu Asn
                85                  90                  95

Phe Val Met Gly Asn Lys Leu Ala Val Leu Ala Gly Asp Phe Leu Leu
            100                 105                 110

Ser Arg Ala Cys Val Ala Leu Ala Ser Leu Lys Asn Thr Glu Val Val
        115                 120                 125

Thr Leu Leu Ala Thr Val Val Glu His Leu Val Thr Gly Glu Thr Met
    130                 135                 140

Gln Met Thr Thr Ser Ser Asp Gln Arg Cys Ser Met Asp Tyr Tyr Met
145                 150                 155                 160

Gln Lys Thr Tyr Tyr Lys Thr Ala Ser Leu Ile Ser Asn Ser Cys Lys
                165                 170                 175

Ala Ile Ala Leu Leu Ala Gly Gln Thr Ala Glu Val Ala Ile Leu Ala
            180                 185                 190

Phe Asp Tyr Gly Lys Asn Leu Gly Leu Ala Tyr Gln Leu Ile Asp Asp
        195                 200                 205

Val Leu Asp Phe Thr Gly Thr Ser Ala Ser Leu Gly Lys Gly Ser Leu
    210                 215                 220

Ser Asp Ile Arg His Gly Ile Ile Thr Ala Pro Ile Leu Phe Ala Met
225                 230                 235                 240

Glu Glu Phe Pro Gln Leu Arg Thr Val Val Glu Gln Gly Phe Glu Asp
                245                 250                 255

Ser Ser Asn Val Asp Ile Ala Leu Glu Tyr Leu Gly Lys Ser Arg Gly
            260                 265                 270

Ile Gln Lys Thr Arg Glu Leu Ala Val Lys His Ala Asn Leu Ala Ala
        275                 280                 285

Ala Ala Ile Asp Ser Leu Pro Glu Asn Asn Asp Glu Asp Val Thr Lys
    290                 295                 300

Ser Arg Arg Ala Leu Leu Asp Leu Thr His Arg Val Ile Thr Arg Asn
305                 310                 315                 320

Lys
```

<210> SEQ ID NO 35
<211> LENGTH: 1269
<212> TYPE: DNA
<213> ORGANISM: Arabidopsis thaliana

<400> SEQUENCE: 35

```
atgttattca cgaggagtgt tgctcggatt tcttctaagt ttctgagaaa ccgtagcttc      60

tatggctcct ctcaatctct cgcctctcat cggttcgcaa tcattcccga tcagggtcac     120

tcttgttctg actctccaca caagggttac gtttgcagaa caacttattc attgaaatct     180

ccggtttttg gtggatttag tcatcaactc tatcaccaga gtagctcctt ggttgaggag     240

gagcttgacc cattttcgct tgttgccgat gagctgtcac ttcttagtaa taagttgaga     300

gagatggtac ttgccgaggt tccaaagctt gcctctgctg ctgagtactt cttcaaaagg     360

ggtgtgcaag gaaaacagtt tcgttcaact attttgctgc tgatggcgac agctctggat     420

gtacgagttc cagaagcatt gattggggaa tcaacagata tagtcacatc agaattacgc     480

gtaaggcaac ggggtattgc tgaaatcact gaaatgatac acgtcgcaag tctactgcac     540

gatgatgtct tggatgatgc cgatacaagg cgtggtgttg gttccttaaa tgttgtaatg     600
```

```
ggtaacaaga tgtcggtatt agcaggagac ttcttgctct cccgggcttg tggggctctc    660

gctgctttaa agaacacaga ggttgtagca ttacttgcaa ctgctgtaga acatcttgtt    720

accggtgaaa ccatggagat aactagttca accgagcagc gttatagtat ggactactac    780

atgcagaaga catattataa gacagcatcg ctaatctcta acagctgcaa agctgttgcc    840

gttctcactg gacaaacagc agaagttgcc gtgttagctt ttgagtatgg gaggaatctg    900

ggtttagcat tccaattaat agacgacatt cttgatttca cgggcacatc tgcctctctc    960

ggaaagggat cgttgtcaga tattcgccat ggagtcataa cagccccaat cctctttgcc   1020

atggaagagt ttcctcaact acgcgaagtt gttgatcaag ttgaaaaaga tcctaggaat   1080

gttgacattg ctttagagta tcttgggaag agcaagggaa tacagagggc aagagaatta   1140

gccatggaac atgcgaatct agcagcagct gcaatcgggt ctctacctga aacagacaat   1200

gaagatgtca aaagatcgag gcgggcactt attgacttga cccatagagt catcaccaga   1260

aacaagtga                                                           1269


<210> SEQ ID NO 36
<211> LENGTH: 422
<212> TYPE: PRT
<213> ORGANISM: Arabidopsis thaliana

<400> SEQUENCE: 36

Met Leu Phe Thr Arg Ser Val Ala Arg Ile Ser Ser Lys Phe Leu Arg
 1               5                  10                  15

Asn Arg Ser Phe Tyr Gly Ser Ser Gln Ser Leu Ala Ser His Arg Phe
            20                  25                  30

Ala Ile Ile Pro Asp Gln Gly His Ser Cys Ser Asp Ser Pro His Lys
        35                  40                  45

Gly Tyr Val Cys Arg Thr Thr Tyr Ser Leu Lys Ser Pro Val Phe Gly
    50                  55                  60

Gly Phe Ser His Gln Leu Tyr His Gln Ser Ser Ser Leu Val Glu Glu
65                  70                  75                  80

Glu Leu Asp Pro Phe Ser Leu Val Ala Asp Glu Leu Ser Leu Leu Ser
                85                  90                  95

Asn Lys Leu Arg Glu Met Val Leu Ala Glu Val Pro Lys Leu Ala Ser
            100                 105                 110

Ala Ala Glu Tyr Phe Phe Lys Arg Gly Val Gln Gly Lys Gln Phe Arg
        115                 120                 125

Ser Thr Ile Leu Leu Leu Met Ala Thr Ala Leu Asn Val Arg Val Pro
    130                 135                 140

Glu Ala Leu Ile Gly Glu Ser Thr Asp Ile Val Thr Ser Glu Leu Arg
145                 150                 155                 160

Val Arg Gln Arg Gly Ile Ala Glu Ile Thr Glu Met Ile His Val Ala
                165                 170                 175

Ser Leu Leu His Asp Asp Val Leu Asp Asp Ala Asp Thr Arg Arg Gly
            180                 185                 190

Val Gly Ser Leu Asn Val Val Met Gly Asn Lys Met Ser Val Leu Ala
        195                 200                 205

Gly Asp Phe Leu Leu Ser Arg Ala Cys Gly Ala Leu Ala Ala Leu Lys
    210                 215                 220

Asn Thr Glu Val Val Ala Leu Leu Ala Thr Ala Val Glu His Leu Val
225                 230                 235                 240

Thr Gly Glu Thr Met Glu Ile Thr Ser Ser Thr Glu Gln Arg Tyr Ser
                245                 250                 255
```

```
Met Asp Tyr Tyr Met Gln Lys Thr Tyr Tyr Lys Thr Ala Ser Leu Ile
            260                 265                 270

Ser Asn Ser Cys Lys Ala Val Ala Val Leu Thr Gly Gln Thr Ala Glu
        275                 280                 285

Val Ala Val Leu Ala Phe Glu Tyr Gly Arg Asn Leu Gly Leu Ala Phe
    290                 295                 300

Gln Leu Ile Asp Asp Ile Leu Asp Phe Thr Gly Thr Ser Ala Ser Leu
305                 310                 315                 320

Gly Lys Gly Ser Leu Ser Asp Ile Arg His Gly Val Ile Thr Ala Pro
                325                 330                 335

Ile Leu Phe Ala Met Glu Glu Phe Pro Gln Leu Arg Glu Val Val Asp
            340                 345                 350

Gln Val Glu Lys Asp Pro Arg Asn Val Asp Ile Ala Leu Glu Tyr Leu
        355                 360                 365

Gly Lys Ser Lys Gly Ile Gln Arg Ala Arg Glu Leu Ala Met Glu His
    370                 375                 380

Ala Asn Leu Ala Ala Ala Ala Ile Gly Ser Leu Pro Glu Thr Asp Asn
385                 390                 395                 400

Glu Asp Val Lys Arg Ser Arg Arg Ala Leu Ile Asp Leu Thr His Arg
                405                 410                 415

Val Ile Thr Arg Asn Lys
            420
```

```
<210> SEQ ID NO 37
<211> LENGTH: 1704
<212> TYPE: DNA
<213> ORGANISM: Ocimum basilicum

<400> SEQUENCE: 37

atgtcttgtg cacggatcac cgtaacattg ccgtatcgct ccgcaaaaac atcaattcaa      60

cggggaatta cgcattaccc cgcccttata cgcccacgct tctctgcttg cacgcctttg     120

gcatcggcga tgcctctaag ttcaactcct ctcatcaacg gggataactc tcagcgtaaa     180

aacacacgtc aacacatgga ggagagcagc agcaagagga gagaatatct gctggaggaa     240

acgacgcgaa aactgcagag aaacgacacc gaatcggtgg agaaactcaa gcttatcgac     300

aacatccaac agttgggaat cggctactat tttgaggacg ccatcaacgc cgtactccgc     360

tcgcctttct ccaccggaga agaagacctc ttcaccgctg ctctgcgctt ccgcttgctc     420

cgccacaacg gcatcgaaat cagccctgaa atattcctaa aattcaagga cgagagggga     480

aaattcgacg aatcggacac gctagggtta ctgagcttgt acgaagcgtc aaatttgggg     540

gttgcaggag aagaaatatt ggaggaggct atggagtttg cggaggctcg cctgagacgg     600

tcgctgtcag agccggcggc gccgcttcat ggtgaggtgg cgcaagcgct agatgtgccg     660

aggcatctga gaatggcgag gttggaagcg agacgattca tcgagcagta tggtaaacag     720

agcgatcatg atggagatct tttggagctg gcaattttgg attataatca agttcaggct     780

caacaccaat ccgaactcac tgaaataatc aggtggtgga aggagctcgg tttggtggat     840

aagttgagtt ttgggcgaga cagaccattg gagtgctttt tgtggaccgt ggggctcctc     900

ccagagccca agtattcgag cgttagaata gagttggcga aagccatctc tattctctta     960

gtgatcgatg atattttcga tacctatgga gagatggatg acctcatcct cttcaccgat    1020

gcaattcgaa gatgggatct tgaagcaatg gaggggctcc ctgagtacat gaaaatatgc    1080

tacatggcgt tgtacaatac caccaatgaa gtatgctaca aagtgctcag ggatactgga    1140

cggattgtcc tccttaacct caaatctacg tggatagaca tgattgaagg tttcatggag    1200
```

-continued

```
gaagcaaaat ggttcaatgg tggaagtgca ccaaaattgg aagagtatat agagaatgga   1260

gtgtccacgg caggagcata catggctttt gcacacatct tctttctcat aggagaaggt   1320

gttacacacc aaaattccca actcttcacc caaaaaccct accccaaggt cttctccgcc   1380

gccggccgca ttcttcgcct ctgggatgat ctcggaaccg ccaaggaaga gcaagagcga   1440

ggagatctgg cttcgtgcgt gcagttattt atgaaagaga agtcgttgac ggaagaggag   1500

gcaagaagtc gcattttgga agagataaaa ggattatgga gggatctgaa tggggaactg   1560

gtctacaaca agaatttgcc gttatccata atcaaagtcg cacttaacat ggcgagagct   1620

tctcaagttg tgtacaagca cgatcaagac acttattttt caagcgtaga caattatgtg   1680

gatgccctct tcttcactca ataa                                          1704
```

<210> SEQ ID NO 38
<211> LENGTH: 567
<212> TYPE: PRT
<213> ORGANISM: Ocimum basilicum

<400> SEQUENCE: 38

```
Met Ser Cys Ala Arg Ile Thr Val Thr Leu Pro Tyr Arg Ser Ala Lys
 1               5                  10                  15

Thr Ser Ile Gln Arg Gly Ile Thr His Tyr Pro Ala Leu Ile Arg Pro
            20                  25                  30

Arg Phe Ser Ala Cys Thr Pro Leu Ala Ser Ala Met Pro Leu Ser Ser
        35                  40                  45

Thr Pro Leu Ile Asn Gly Asp Asn Ser Gln Arg Lys Asn Thr Arg Gln
    50                  55                  60

His Met Glu Glu Ser Ser Ser Lys Arg Arg Glu Tyr Leu Leu Glu Glu
65                  70                  75                  80

Thr Thr Arg Lys Leu Gln Arg Asn Asp Thr Glu Ser Val Glu Lys Leu
                85                  90                  95

Lys Leu Ile Asp Asn Ile Gln Gln Leu Gly Ile Gly Tyr Tyr Phe Glu
            100                 105                 110

Asp Ala Ile Asn Ala Val Leu Arg Ser Pro Phe Ser Thr Gly Glu Glu
        115                 120                 125

Asp Leu Phe Thr Ala Ala Leu Arg Phe Arg Leu Leu Arg His Asn Gly
    130                 135                 140

Ile Glu Ile Ser Pro Glu Ile Phe Leu Lys Phe Lys Asp Glu Arg Gly
145                 150                 155                 160

Lys Phe Asp Glu Ser Asp Thr Leu Gly Leu Leu Ser Leu Tyr Glu Ala
                165                 170                 175

Ser Asn Leu Gly Val Ala Gly Glu Glu Ile Leu Glu Glu Ala Met Glu
            180                 185                 190

Phe Ala Glu Ala Arg Leu Arg Arg Ser Leu Ser Glu Pro Ala Ala Pro
        195                 200                 205

Leu His Gly Glu Val Ala Gln Ala Leu Asp Val Pro Arg His Leu Arg
    210                 215                 220

Met Ala Arg Leu Glu Ala Arg Arg Phe Ile Glu Gln Tyr Gly Lys Gln
225                 230                 235                 240

Ser Asp His Asp Gly Asp Leu Leu Glu Leu Ala Ile Leu Asp Tyr Asn
                245                 250                 255

Gln Val Gln Ala Gln His Gln Ser Glu Leu Thr Glu Ile Ile Arg Trp
            260                 265                 270

Trp Lys Glu Leu Gly Leu Val Asp Lys Leu Ser Phe Gly Arg Asp Arg
        275                 280                 285
```

```
Pro Leu Glu Cys Phe Leu Trp Thr Val Gly Leu Leu Pro Glu Pro Lys
    290                 295                 300

Tyr Ser Ser Val Arg Ile Glu Leu Ala Lys Ala Ile Ser Ile Leu Leu
305                 310                 315                 320

Val Ile Asp Asp Ile Phe Asp Thr Tyr Gly Glu Met Asp Asp Leu Ile
                325                 330                 335

Leu Phe Thr Asp Ala Ile Arg Arg Trp Asp Leu Glu Ala Met Glu Gly
            340                 345                 350

Leu Pro Glu Tyr Met Lys Ile Cys Tyr Met Ala Leu Tyr Asn Thr Thr
        355                 360                 365

Asn Glu Val Cys Tyr Lys Val Leu Arg Asp Thr Gly Arg Ile Val Leu
    370                 375                 380

Leu Asn Leu Lys Ser Thr Trp Ile Asp Met Ile Glu Gly Phe Met Glu
385                 390                 395                 400

Glu Ala Lys Trp Phe Asn Gly Gly Ser Ala Pro Lys Leu Glu Glu Tyr
                405                 410                 415

Ile Glu Asn Gly Val Ser Thr Ala Gly Ala Tyr Met Ala Phe Ala His
            420                 425                 430

Ile Phe Phe Leu Ile Gly Glu Gly Val Thr His Gln Asn Ser Gln Leu
        435                 440                 445

Phe Thr Gln Lys Pro Tyr Pro Lys Val Phe Ser Ala Ala Gly Arg Ile
    450                 455                 460

Leu Arg Leu Trp Asp Asp Leu Gly Thr Ala Lys Glu Glu Gln Glu Arg
465                 470                 475                 480

Gly Asp Leu Ala Ser Cys Val Gln Leu Phe Met Lys Glu Lys Ser Leu
                485                 490                 495

Thr Glu Glu Glu Ala Arg Ser Arg Ile Leu Glu Glu Ile Lys Gly Leu
            500                 505                 510

Trp Arg Asp Leu Asn Gly Glu Leu Val Tyr Asn Lys Asn Leu Pro Leu
        515                 520                 525

Ser Ile Ile Lys Val Ala Leu Asn Met Ala Arg Ala Ser Gln Val Val
    530                 535                 540

Tyr Lys His Asp Gln Asp Thr Tyr Phe Ser Ser Val Asp Asn Tyr Val
545                 550                 555                 560

Asp Ala Leu Phe Phe Thr Gln
                565
```

<210> SEQ ID NO 39
<211> LENGTH: 1812
<212> TYPE: DNA
<213> ORGANISM: Cinnamomum tenuipile

<400> SEQUENCE: 39

```
atggcattgc aaatgattgc tccatttcta tcctccttcc taccaaatcc cagacacagc      60

ctcgcagccc atggcctcac acaccagaaa tgtgtctcaa agcacatttc atgctcaacc     120

actacaccaa cctactcaac cacagttcca agaagatcag ggaactacaa gcccagcatc     180

tgggactatg attttgtgca gtcactagga agtggctaca aggtagaggc acatggaaca     240

cgtgtgaaga agttgaagga ggttgtaaag catttgttga aagaaacaga tagttctttg     300

gcccaaatag aactgattga caaactacgt cgtctaggtc taaggtggct cttcaaaaat     360

gagattaagc aagtgctata cacgatatca tcagacaaca ccagcataga aatgaggaaa     420

gatcttcatg cagtatcaac tcgatttaga cttcttagac aacatgggta caaggtctcc     480

acagatgttt tcaacgactt caaagatgaa aagggttgtt tcaagccaag cctttcaatg     540
```

```
gacataaagg gaatgttgag cttgtatgag gcttcacacc ttgcctttca aggggagact    600

gtgttggatg aggcaagagc tttcgtaagc acacatctca tggatatcaa ggagaacata    660

gacccaatcc ttcataaaaa agtggagcat gctttggata tgcctttgca ttggaggtta    720

gaaaaattag aggctaggtg gtacatggac atatacatga gggaagaagg catgaattct    780

tctttacttg aattggccat gcttcatttc aacattgtgc aaacaacatt ccaaacaaat    840

ttaaagagtt tgagcaggtg gtggaaagat ttgggtcttg gagagcagtt gagcttcact    900

agagacaggt tggtggaatg tttcttttgg gccgccgcaa tgacacctga gccacaattt    960

ggacgttgcc aggaagtcgt agcgaaagtt gctcaactca taataataat tgacgatatc   1020

tatgacgtgt atggtacggt ggatgagcta gaacttttta ctaatgcgat tgatagatgg   1080

gatcttgagg caatggagca gcttcctgaa tatatgaaga cctgtttctt agctttatac   1140

aacagtatta atgaaatagg ttatgacatt ttgaaagagg aagggcgcaa tgtcatacca   1200

taccttagaa atacgtggac agaattgtgt aaagccttct tagtggaggc caaatggtat   1260

agtagtggat atacaccaac gcttgaggag tatctgcaaa cctcatggat ttcgattgga   1320

agtctaccca tgcaaacata cgtttttgct ctacttggga aaaatctagc accggagagt   1380

agtgattttg ctgagaagat ctcggatatc ttacgattgg gaggaatgat gattcgactt   1440

ccggatgatt tgggaacttc aacggatgaa ctaaagagag gtgatgttcc aaaatccatt   1500

cagtgttaca tgcatgaagc aggtgttaca gaggatgttg ctcgcgacca cataatgggt   1560

ctatttcaag agacatggaa aaaactcaat gaataccttg tggaaagttc tcttccccat   1620

gcctttatcg atcatgctat gaatcttgga cgtgtctcct attgcactta caaacatgga   1680

gatggattta gtgatggatt tggagatcct ggcagtcaag agaaaaagat gttcatgtct   1740

ttatttgctg aacccttca agttgatgaa gccaagggta tttcatttta tgttgatggt   1800

ggatctgcct aa                                                       1812
```

<210> SEQ ID NO 40
<211> LENGTH: 603
<212> TYPE: PRT
<213> ORGANISM: Cinnamomum tenuipile

<400> SEQUENCE: 40

```
Met Ala Leu Gln Met Ile Ala Pro Phe Pro Ser Ser Phe Leu Pro Asn
 1               5                  10                  15

Pro Arg His Arg Leu Ala Ala His Gly Leu Thr His Gln Lys Cys Val
            20                  25                  30

Ser Lys His Ile Ser Cys Ser Thr Thr Thr Pro Thr Tyr Ser Thr Thr
        35                  40                  45

Val Pro Arg Arg Ser Gly Asn Tyr Lys Pro Ser Ile Trp Asp Tyr Asp
    50                  55                  60

Phe Val Gln Ser Leu Gly Ser Gly Tyr Lys Val Glu Ala His Gly Thr
65                  70                  75                  80

Arg Val Lys Lys Leu Lys Glu Val Val Lys His Leu Leu Lys Glu Thr
                85                  90                  95

Asp Ser Ser Leu Ala Gln Ile Glu Leu Ile Asp Lys Leu Arg Arg Leu
            100                 105                 110

Gly Leu Arg Trp Leu Phe Lys Asn Glu Ile Lys Gln Val Leu Tyr Thr
        115                 120                 125

Ile Ser Ser Asp Asn Thr Ser Ile Glu Met Arg Lys Asp Leu His Ala
    130                 135                 140
```

-continued

```
Val Ser Thr Arg Phe Arg Leu Leu Arg Gln His Gly Tyr Lys Val Ser
145                 150                 155                 160

Thr Asp Val Phe Asn Asp Phe Lys Asp Glu Lys Gly Cys Phe Lys Pro
                165                 170                 175

Ser Leu Ser Met Asp Ile Lys Gly Met Leu Ser Leu Tyr Glu Ala Ser
            180                 185                 190

His Leu Ala Phe Gln Gly Glu Thr Val Leu Asp Glu Ala Arg Ala Phe
        195                 200                 205

Val Ser Thr His Leu Met Asp Ile Lys Glu Asn Ile Asp Pro Ile Leu
    210                 215                 220

His Lys Lys Val Glu His Ala Leu Asp Met Pro Leu His Trp Arg Leu
225                 230                 235                 240

Glu Lys Leu Glu Ala Arg Trp Tyr Met Asp Ile Tyr Met Arg Glu Glu
                245                 250                 255

Gly Met Asn Ser Ser Leu Leu Glu Leu Ala Met Leu His Phe Asn Ile
            260                 265                 270

Val Gln Thr Thr Phe Gln Thr Asn Leu Lys Ser Leu Ser Arg Trp Trp
        275                 280                 285

Lys Asp Leu Gly Leu Gly Glu Gln Leu Ser Phe Thr Arg Asp Arg Leu
    290                 295                 300

Val Glu Cys Phe Phe Trp Ala Ala Ala Met Thr Pro Glu Pro Gln Phe
305                 310                 315                 320

Gly Arg Cys Gln Glu Ala Val Ala Lys Val Ala Gln Leu Ile Ile Ile
                325                 330                 335

Ile Asp Asp Ile Tyr Asp Val Tyr Gly Thr Val Asp Glu Leu Glu Leu
            340                 345                 350

Phe Thr Asn Ala Ile Asp Arg Trp Asp Leu Glu Ala Met Glu Gln Leu
        355                 360                 365

Pro Glu Tyr Met Lys Thr Cys Phe Leu Ala Leu Tyr Asn Ser Ile Asn
    370                 375                 380

Glu Ile Gly Tyr Glu Ile Leu Lys Glu Glu Gly Arg Asn Val Ile Pro
385                 390                 395                 400

Tyr Leu Arg Asn Thr Trp Thr Glu Leu Cys Lys Ala Phe Leu Val Glu
                405                 410                 415

Ala Lys Trp Tyr Ser Ser Gly Cys Thr Pro Thr Leu Glu Glu Tyr Leu
            420                 425                 430

Gln Thr Ser Trp Ile Ser Ile Gly Ser Leu Pro Met Gln Thr Tyr Val
        435                 440                 445

Phe Ala Leu Leu Gly Lys Asn Leu Ala Pro Glu Ser Ser Asp Phe Ala
    450                 455                 460

Glu Lys Ile Ser Asp Ile Leu Arg Leu Gly Gly Met Met Ile Arg Leu
465                 470                 475                 480

Pro Asp Asp Leu Gly Thr Ser Thr Asp Glu Leu Lys Arg Gly Asp Val
                485                 490                 495

Pro Lys Ser Ile Gln Cys Tyr Met His Glu Ala Gly Val Thr Glu Asp
            500                 505                 510

Val Ala Arg Asp His Ile Met Gly Leu Phe Gln Glu Thr Trp Lys Lys
        515                 520                 525

Leu Asn Glu Tyr Leu Val Glu Ser Ser Leu Pro His Ala Phe Ile Asp
    530                 535                 540

His Ala Met Asn Leu Gly Arg Val Ser Tyr Cys Thr Tyr Lys His Gly
545                 550                 555                 560

Asp Gly Phe Ser Asp Gly Phe Gly Asp Pro Gly Ser Gln Glu Lys Lys
                565                 570                 575
```

```
Met Phe Met Ser Leu Phe Ala Glu Pro Leu Gln Val Asp Glu Ala Lys
            580                 585                 590

Gly Ile Ser Phe Tyr Val Asp Gly Gly Ser Ala
        595                 600


<210> SEQ ID NO 41
<211> LENGTH: 1197
<212> TYPE: DNA
<213> ORGANISM: Saccharomyces cerevisiae

<400> SEQUENCE: 41

atgtctcaga acgtttacat tgtatcgact gccagaaccc caattggttc attccagggt      60

tctctatcct ccaagacagc agtggaattg ggtgctgttg ctttaaaagg cgccttggct     120

aaggttccag aattggatgc atccaaggat tttgacgaaa ttatttttgg taacgttctt     180

tctgccaatt tgggccaagc tccggccaga caagttgctt tggctgccgg tttgagtaat     240

catatcgttg caagcacagt taacaaggtc tgtgcatccg ctatgaaggc aatcattttg     300

ggtgctcaat ccatcaaatg tggtaatgct gatgttgtcg tagctggtgg ttgtgaatct     360

atgactaacg caccatacta catgccagca gcccgtgcgg gtgccaaatt tggccaaact     420

gttcttgttg atggtgtcga aagagatggg ttgaacgatg cgtacgatgg tctagccatg     480

ggtgtacacg cagaaaagtg tgcccgtgat tgggatatta ctagagaaca acaagacaat     540

tttgccatcg aatcctacca aaaatctcaa aaatctcaaa aggaaggtaa attcgacaat     600

gaaattgtac ctgttaccat taagggattt agaggtaagc ctgatactca agtcacgaag     660

gacgaggaac ctgctagatt acacgttgaa aaattgagat ctgcaaggac tgttttccaa     720

aaagaaaacg gtactgttac tgccgctaac gcttctccaa tcaacgatgg tgctgcagcc     780

gtcatcttgg tttccgaaaa agttttgaag gaaaagaatt tgaagccttt ggctattatc     840

aaaggttggg gtgaggccgc tcatcaacca gctgatttta catgggctcc atctcttgca     900

gttccaaagg ctttgaaaca tgctggcatc gaagacatca attctgttga ttactttgaa     960

ttcaatgaag ccttttcggt tgtcggtttg gtgaacacta agattttgaa gctagaccca    1020

tctaaggtta atgtatatgg tggtgctgtt gctctaggtc acccattggg ttgttctggt    1080

gctagagtgg ttgttacact gctatccatc ttacagcaag aaggaggtaa gatcggtgtt    1140

gccgccattt gtaatggtgg tggtggtgct tcctctattg tcattgaaaa gatatga       1197


<210> SEQ ID NO 42
<211> LENGTH: 398
<212> TYPE: PRT
<213> ORGANISM: Saccharomyces cerevisiae

<400> SEQUENCE: 42

Met Ser Gln Asn Val Tyr Ile Val Ser Thr Ala Arg Thr Pro Ile Gly
 1               5                  10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Ala Gly Leu Ser Asn
65                  70                  75                  80

His Ile Val Ala Ser Thr Val Asn Lys Val Cys Ala Ser Ala Met Lys
                85                  90                  95
```

```
Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
        275                 280                 285

Gln Pro Ala Asp Phe Thr Trp Ala Pro Ser Leu Ala Val Pro Lys Ala
    290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Val Thr Leu Leu
        355                 360                 365

Ser Ile Leu Gln Gln Glu Gly Gly Lys Ile Gly Val Ala Ala Ile Cys
    370                 375                 380

Asn Gly Gly Gly Gly Ala Ser Ser Ile Val Ile Glu Lys Ile
385                 390                 395


<210> SEQ ID NO 43
<211> LENGTH: 1200
<212> TYPE: DNA
<213> ORGANISM: Saccharomyces cerevisiae

<400> SEQUENCE: 43

atgtctaccg gtcttccctc cgtctacatc gtttctgccg ccagaacccc tgtggggtcc      60

ttccttggtc agctttccag cctctctgct gttcagctcg gtgcccatgc catcaagtct     120

gccgttgacc gcgttcccga aatcaaggcc gaggatgttg aggaggtctt ctttggcaat     180

gtcctctctg ctggtgtcgg tcaggctcct gcccgccagt gcgccctgaa ggccggtctc     240

tcgaacaagg tggttgccac caccgtcaac aaggtgtgcg cttccggcat gaaggccatc     300

atccttggcg cccagaccat catgactggc aatgcagaca tcgttgtcgc tggcggcacc     360

gagagcatgt ccaacgtccc ccactatatg cagaacctcc gcactggtgt caagtacggc     420
```

-continued

```
gacggcggcc ttgtcgacgg tatccagtcc gacggtctcc gtgatgcata tggcaaggag    480

ctcatgggtg ttcaggccga gctctgcgcc aaggaccatg aactgagccg tgaggcccag    540

gacgagtatg ccatcaactc gtaccagaag gcccaggccg ccaccgaggc tggtctgttc    600

aaggagattg cacctatcga ggtcccgggt ggccgcggca agcctgccat caagattgac    660

cgcgatgagg aggtcaagaa cctcaacatc gagaagctca agtccgcccg taccgtcttc    720

caggccaagg acggtaccgt cactgctccc aacgcctccc ccatcaacga tggcgccgct    780

gccgttgttc ttgtctccga ggctaagctc aaggagcttg gtatcaagcc catcgccaag    840

atccttggct ggggcgatgc tgctcacgag cctgagcgct tcacaactgc cccggctctt    900

gccattccca aggccatcaa gcatgccggt atcaaggagg aggacgttga cttctacgag    960

atcaatgagg ctttctctgt tgttgccctt gccaacatga aaatccttgg cctcgagccc   1020

gagaaggtca acgtctatgg tggctccgtt gccatcggcc accctcttgg ctgctccggt   1080

gctcgtgttg tcactaccct cacctccgtc ttggctgaga agaaggccag gattggctgc   1140

gctggtatct gcaacggtgg cggtggtgct tctgccatcg ttatcgaaaa cttgcagtaa   1200


<210> SEQ ID NO 44
<211> LENGTH: 399
<212> TYPE: PRT
<213> ORGANISM: Saccharomyces cerevisiae

<400> SEQUENCE: 44

Met Ser Thr Gly Leu Pro Ser Val Tyr Ile Val Ser Ala Ala Arg Thr
 1               5                  10                  15

Pro Val Gly Ser Phe Leu Gly Gln Leu Ser Ser Leu Ser Ala Val Gln
            20                  25                  30

Leu Gly Ala His Ala Ile Lys Ser Ala Val Asp Arg Val Pro Glu Ile
        35                  40                  45

Lys Ala Glu Asp Val Glu Glu Val Phe Phe Gly Asn Val Leu Ser Ala
    50                  55                  60

Gly Val Gly Gln Ala Pro Ala Arg Gln Cys Ala Leu Lys Ala Gly Leu
65                  70                  75                  80

Ser Asn Lys Val Val Ala Thr Thr Val Asn Lys Val Cys Ala Ser Gly
                85                  90                  95

Met Lys Ala Ile Ile Leu Gly Ala Gln Thr Ile Met Thr Gly Asn Ala
            100                 105                 110

Asp Ile Val Val Ala Gly Gly Thr Glu Ser Met Ser Asn Val Pro His
        115                 120                 125

Tyr Met Gln Asn Leu Arg Thr Gly Val Lys Tyr Gly Asp Gly Gly Leu
    130                 135                 140

Val Asp Gly Ile Gln Ser Asp Gly Leu Arg Asp Ala Tyr Gly Lys Glu
145                 150                 155                 160

Leu Met Gly Val Gln Ala Glu Leu Cys Ala Lys Asp His Glu Leu Ser
                165                 170                 175

Arg Glu Ala Gln Asp Glu Tyr Ala Ile Asn Ser Tyr Gln Lys Ala Gln
            180                 185                 190

Ala Ala Thr Glu Ala Gly Leu Phe Lys Glu Ile Ala Pro Ile Glu Val
        195                 200                 205

Pro Gly Gly Arg Gly Lys Pro Ala Ile Lys Ile Asp Arg Asp Glu Glu
    210                 215                 220

Val Lys Asn Leu Asn Ile Glu Lys Leu Lys Ser Ala Arg Thr Val Phe
225                 230                 235                 240

Gln Ala Lys Asp Gly Thr Val Thr Ala Pro Asn Ala Ser Pro Ile Asn
```

-continued

```
                245                 250                 255

Asp Gly Ala Ala Ala Val Val Leu Val Ser Glu Ala Lys Leu Lys Glu
            260                 265                 270

Leu Gly Ile Lys Pro Ile Ala Lys Ile Leu Gly Trp Gly Asp Ala Ala
        275                 280                 285

His Glu Pro Glu Arg Phe Thr Thr Ala Pro Ala Leu Ala Ile Pro Lys
    290                 295                 300

Ala Ile Lys His Ala Gly Ile Lys Glu Glu Asp Val Asp Phe Tyr Glu
305                 310                 315                 320

Ile Asn Glu Ala Phe Ser Val Val Ala Leu Ala Asn Met Lys Ile Leu
                325                 330                 335

Gly Leu Glu Pro Glu Lys Val Asn Val Tyr Gly Gly Ser Val Ala Ile
            340                 345                 350

Gly His Pro Leu Gly Cys Ser Gly Ala Arg Val Val Thr Thr Leu Thr
        355                 360                 365

Ser Val Leu Ala Glu Lys Lys Ala Arg Ile Gly Cys Ala Gly Ile Cys
    370                 375                 380

Asn Gly Gly Gly Gly Ala Ser Ala Ile Val Ile Glu Asn Leu Gln
385                 390                 395


<210> SEQ ID NO 45
<211> LENGTH: 1476
<212> TYPE: DNA
<213> ORGANISM: Saccharomyces cerevisiae

<400> SEQUENCE: 45

atgaaactct caactaaact ttgttggtgt ggtattaaag gaagacttag gccgcaaaag      60

caacaacaat tacacaatac aaacttgcaa atgactgaac taaaaaaaca aaagaccgct     120

gaacaaaaaa ccagacctca aaatgtcggt attaaaggta tccaaattta catcccaact     180

caatgtgtca accaatctga gctagagaaa tttgatggcg tttctcaagg taaatacaca     240

attggtctgg gccaaaccaa catgtctttt gtcaatgaca gagaagatat ctactcgatg     300

tccctaactg ttttgtctaa gttgatcaag agttacaaca tcgacaccaa caaaattggt     360

agattagaag tcggtactga aactctgatt gacaagtcca agtctgtcaa gtctgtcttg     420

atgcaattgt ttggtgaaaa cactgacgtc gaaggtattg acacgcttaa tgcctgttac     480

ggtggtacca acgcgttgtt caactctttg aactggattg aatctaacgc atgggatggt     540

agagacgcca ttgtagtttg cggtgatatt gccatctacg ataagggtgc cgcaagacca     600

accggtggtg ccggtactgt tgctatgtgg atcggtcctg atgctccaat tgtatttgac     660

tctgtaagag cttcttacat ggaacacgcc tacgattttt acaagccaga tttcaccagc     720

gaatatcctt acgtcgatgg tcatttttca ttaacttgtt acgtcaaggc tcttgatcaa     780

gtttacaaga gttattccaa gaaggctatt tctaaagggt tggttagcga tcccgctggt     840

tcggatgctt tgaacgtttt gaaatatttc gactacaacg ttttccatgt tccaacctgt     900

aaattggtca caaaatcata cggtagatta ctatataacg atttcagagc caatcctcaa     960

ttgttcccag aagttgacgc cgaattagct actcgcgatt atgacgaatc tttaaccgat    1020

aagaacattg aaaaaacttt tgttaatgtt gctaagccat tccacaaaga gagagttgcc    1080

caatctttga ttgttccaac aaacacaggt aacatgtaca ccgcatctgt ttatgccgcc    1140

tttgcatctc tattaaacta tgttggatct gacgacttac aaggcaagcg tgttggttta    1200

ttttcttacg gttccggttt agctgcatct ctatattctt gcaaaattgt tggtgacgtc    1260

caacatatta tcaaggaatt agatattact aacaaattag ccaagagaat caccgaaact    1320
```

```
ccaaaggatt acgaagctgc catcgaattg agagaaaatg cccatttgaa gaagaacttc   1380

aaacctcaag gttccattga gcatttgcaa agtggtgttt actacttgac caacatcgat   1440

gacaaattta gaagatctta cgatgttaaa aaataa                             1476


<210> SEQ ID NO 46
<211> LENGTH: 491
<212> TYPE: PRT
<213> ORGANISM: Saccharomyces cerevisiae

<400> SEQUENCE: 46

Met Lys Leu Ser Thr Lys Leu Cys Trp Cys Gly Ile Lys Gly Arg Leu
1               5                   10                  15

Arg Pro Gln Lys Gln Gln Gln Leu His Asn Thr Asn Leu Gln Met Thr
            20                  25                  30

Glu Leu Lys Lys Gln Lys Thr Ala Glu Gln Lys Thr Arg Pro Gln Asn
        35                  40                  45

Val Gly Ile Lys Gly Ile Gln Ile Tyr Ile Pro Thr Gln Cys Val Asn
    50                  55                  60

Gln Ser Glu Leu Glu Lys Phe Asp Gly Val Ser Gln Gly Lys Tyr Thr
65                  70                  75                  80

Ile Gly Leu Gly Gln Thr Asn Met Ser Phe Val Asn Asp Arg Glu Asp
                85                  90                  95

Ile Tyr Ser Met Ser Leu Thr Val Leu Ser Lys Leu Ile Lys Ser Tyr
            100                 105                 110

Asn Ile Asp Thr Asn Lys Ile Gly Arg Leu Glu Val Gly Thr Glu Thr
        115                 120                 125

Leu Ile Asp Lys Ser Lys Ser Val Lys Ser Val Leu Met Gln Leu Phe
    130                 135                 140

Gly Glu Asn Thr Asp Val Glu Gly Ile Asp Thr Leu Asn Ala Cys Tyr
145                 150                 155                 160

Gly Gly Thr Asn Ala Leu Phe Asn Ser Leu Asn Trp Ile Glu Ser Asn
                165                 170                 175

Ala Trp Asp Gly Arg Asp Ala Ile Val Val Cys Gly Asp Ile Ala Ile
            180                 185                 190

Tyr Asp Lys Gly Ala Ala Arg Pro Thr Gly Gly Ala Gly Thr Val Ala
        195                 200                 205

Met Trp Ile Gly Pro Asp Ala Pro Ile Val Phe Asp Ser Val Arg Ala
    210                 215                 220

Ser Tyr Met Glu His Ala Tyr Asp Phe Tyr Lys Pro Asp Phe Thr Ser
225                 230                 235                 240

Glu Tyr Pro Tyr Val Asp Gly His Phe Ser Leu Thr Cys Tyr Val Lys
                245                 250                 255

Ala Leu Asp Gln Val Tyr Lys Ser Tyr Ser Lys Lys Ala Ile Ser Lys
            260                 265                 270

Gly Leu Val Ser Asp Pro Ala Gly Ser Asp Ala Leu Asn Val Leu Lys
        275                 280                 285

Tyr Phe Asp Tyr Asn Val Phe His Val Pro Thr Cys Lys Leu Val Thr
    290                 295                 300

Lys Ser Tyr Gly Arg Leu Leu Tyr Asn Asp Phe Arg Ala Asn Pro Gln
305                 310                 315                 320

Leu Phe Pro Glu Val Asp Ala Glu Leu Ala Thr Arg Asp Tyr Asp Glu
                325                 330                 335

Ser Leu Thr Asp Lys Asn Ile Glu Lys Thr Phe Val Asn Val Ala Lys
            340                 345                 350
```

```
Pro Phe His Lys Glu Arg Val Ala Gln Ser Leu Ile Val Pro Thr Asn
        355                 360                 365

Thr Gly Asn Met Tyr Thr Ala Ser Val Tyr Ala Ala Phe Ala Ser Leu
    370                 375                 380

Leu Asn Tyr Val Gly Ser Asp Asp Leu Gln Gly Lys Arg Val Gly Leu
385                 390                 395                 400

Phe Ser Tyr Gly Ser Gly Leu Ala Ala Ser Leu Tyr Ser Cys Lys Ile
                405                 410                 415

Val Gly Asp Val Gln His Ile Ile Lys Glu Leu Asp Ile Thr Asn Lys
            420                 425                 430

Leu Ala Lys Arg Ile Thr Glu Thr Pro Lys Asp Tyr Glu Ala Ala Ile
        435                 440                 445

Glu Leu Arg Glu Asn Ala His Leu Lys Lys Asn Phe Lys Pro Gln Gly
    450                 455                 460

Ser Ile Glu His Leu Gln Ser Gly Val Tyr Tyr Leu Thr Asn Ile Asp
465                 470                 475                 480

Asp Lys Phe Arg Arg Ser Tyr Asp Val Lys Lys
                485                 490


<210> SEQ ID NO 47
<211> LENGTH: 1167
<212> TYPE: DNA
<213> ORGANISM: Staphylococcus aureus

<400> SEQUENCE: 47

atgacaatag gtatcgacaa aataaacttt tacgttccaa agtactatgt agacatggct     60

aaattagcag aagcacgcca agtagaccca aacaaatttt taattggaat tggtcaaact    120

gaaatggctg ttagtcctgt aaaccaagac atcgtttcaa tgggcgctaa cgctgctaag    180

gacattataa cagacgaaga taaaaagaaa attggtatgg taattgtggc aactgaatca    240

gcagttgatg ctgctaaagc agccgctgtt caaattcaca acttattagg tattcaacct    300

tttgcacgtt gctttgaaat gaaagaagct tgttatgctg caacaccagc aattcaatta    360

gctaaagatt atttagcaac tagaccgaat gaaaaagtat tagttattgc tacagataca    420

gcacgttatg gattgaattc aggcggcgag ccaacacaag gtgctggcgc agttgcgatg    480

gttattgcac ataatccaag cattttggca ttaaatgaag atgctgttgc ttacactgaa    540

gacgtttatg atttctggcg tccaactgga cataaatatc cattagttga tggtgcatta    600

tctaaagatg cttatatccg ctcattccaa caaagctgga atgaatacgc aaaacgtcaa    660

ggtaagtcgc tagctgactt cgcatctcta tgcttccatg ttccatttac aaaaaatggt    720

aaaaaggcat tagagtcaat cattgataac gctgatgaaa caactcaaga gcgtttacgt    780

tcaggatatg aagatgctgt agattataac cgttatgtcg gtaatattta tactggatca    840

ttatatttaa gcctaatatc attacttgaa aatcgtgatt tacaagctgg tgaaacaatc    900

ggtttattca gttatggctc aggttcagtt ggtgaatttt atagtgcgac attagttgaa    960

ggctacaaag atcatttaga tcaagctgca cataaagcat tattaaataa ccgtactgaa   1020

gtatctgttg atgcatatga aacattcttc aaacgttttg atgacgttga atttgacgaa   1080

gaacaagatg ctgttcatga agatcgtcat attttctact tatcaaatat tgaaaataac   1140

gttcgcgaat atcacagacc agagtaa                                       1167


<210> SEQ ID NO 48
<211> LENGTH: 388
<212> TYPE: PRT
```

<213> ORGANISM: Staphylococcus aureus

<400> SEQUENCE: 48

```
Met Thr Ile Gly Ile Asp Lys Ile Asn Phe Tyr Val Pro Lys Tyr Tyr
 1               5                  10                  15

Val Asp Met Ala Lys Leu Ala Glu Ala Arg Gln Val Asp Pro Asn Lys
            20                  25                  30

Phe Leu Ile Gly Ile Gly Gln Thr Glu Met Ala Val Ser Pro Val Asn
        35                  40                  45

Gln Asp Ile Val Ser Met Gly Ala Asn Ala Ala Lys Asp Ile Ile Thr
    50                  55                  60

Asp Glu Asp Lys Lys Lys Ile Gly Met Val Ile Val Ala Thr Glu Ser
65                  70                  75                  80

Ala Val Asp Ala Ala Lys Ala Ala Ala Val Gln Ile His Asn Leu Leu
                85                  90                  95

Gly Ile Gln Pro Phe Ala Arg Cys Phe Glu Met Lys Glu Ala Cys Tyr
            100                 105                 110

Ala Ala Thr Pro Ala Ile Gln Leu Ala Lys Asp Tyr Leu Ala Thr Arg
        115                 120                 125

Pro Asn Glu Lys Val Leu Val Ile Ala Thr Asp Thr Ala Arg Tyr Gly
    130                 135                 140

Leu Asn Ser Gly Gly Glu Pro Thr Gln Gly Ala Gly Ala Val Ala Met
145                 150                 155                 160

Val Ile Ala His Asn Pro Ser Ile Leu Ala Leu Asn Glu Asp Ala Val
                165                 170                 175

Ala Tyr Thr Glu Asp Val Tyr Asp Phe Trp Arg Pro Thr Gly His Lys
            180                 185                 190

Tyr Pro Leu Val Asp Gly Ala Leu Ser Lys Asp Ala Tyr Ile Arg Ser
        195                 200                 205

Phe Gln Gln Ser Trp Asn Glu Tyr Ala Lys Arg Gln Gly Lys Ser Leu
    210                 215                 220

Ala Asp Phe Ala Ser Leu Cys Phe His Val Pro Phe Thr Lys Met Gly
225                 230                 235                 240

Lys Lys Ala Leu Glu Ser Ile Ile Asp Asn Ala Asp Glu Thr Thr Gln
                245                 250                 255

Glu Arg Leu Arg Ser Gly Tyr Glu Asp Ala Val Asp Tyr Asn Arg Tyr
            260                 265                 270

Val Gly Asn Ile Tyr Thr Gly Ser Leu Tyr Leu Ser Leu Ile Ser Leu
        275                 280                 285

Leu Glu Asn Arg Asp Leu Gln Ala Gly Glu Thr Ile Gly Leu Phe Ser
    290                 295                 300

Tyr Gly Ser Gly Ser Val Gly Glu Phe Tyr Ser Ala Thr Leu Val Glu
305                 310                 315                 320

Gly Tyr Lys Asp His Leu Asp Gln Ala Ala His Lys Ala Leu Leu Asn
                325                 330                 335

Asn Arg Thr Glu Val Ser Val Asp Ala Tyr Glu Thr Phe Phe Lys Arg
            340                 345                 350

Phe Asp Asp Val Glu Phe Asp Glu Glu Gln Asp Ala Val His Glu Asp
        355                 360                 365

Arg His Ile Phe Tyr Leu Ser Asn Ile Glu Asn Asn Val Arg Glu Tyr
    370                 375                 380

His Arg Pro Glu
385
```

<210> SEQ ID NO 49
<211> LENGTH: 3165
<212> TYPE: DNA
<213> ORGANISM: Saccharomyces cerevisiae

<400> SEQUENCE: 49
atgccgccgc tattcaaggg actgaaacag atggcaaagc caattgccta tgtttcaaga 60
ttttcggcga aacgaccaat tcatataata ctttttttctc taatcatatc cgcattcgct 120
tatctatccg tcattcagta ttacttcaat ggttggcaac tagattcaaa tagtgttttt 180
gaaactgctc caaataaaga ctccaacact ctatttcaag aatgttccca ttactacaga 240
gattcctctc tagatggttg ggtatcaatc accgcgcatg aagctagtga gttaccagcc 300
ccacaccatt actatctatt aaacctgaac ttcaatagtc ctaatgaaac tgactccatt 360
ccagaactag ctaacacggt tttgagaaa gataatacaa aatatattct gcaagaagat 420
ctcagtgttt ccaaagaaat ttcttctact gatggaacga aatggaggtt aagaagtgac 480
agaaaaagtc ttttcgacgt aaagacgtta gcatattctc tctacgatgt attttcagaa 540
aatgtaaccc aagcagaccc gtttgacgtc cttattatgg ttactgccta cctaatgatg 600
ttctacacca tattcggcct cttcaatgac atgaggaaga ccgggtcaaa tttttggttg 660
agcgcctcta cagtggtcaa ttctgcatca tcacttttct tagcattgta tgtcacccaa 720
tgtattctag gcaaagaagt ttccgcatta actcttttg aaggtttgcc tttcattgta 780
gttgttgttg gtttcaagca caaaatcaag attgcccagt atgccctgga gaaatttgaa 840
agagtcggtt tatctaaaag gattactacc gatgaaatcg tttttgaatc cgtgagcgaa 900
gagggtggtc gtttgattca agaccatttg ctttgtattt ttgcctttat cggatgctct 960
atgtatgctc accaattgaa gactttgaca aacttctgca tattatcagc atttatccta 1020
atttttgaat tgattttaac tcctacattt tattctgcta tcttagcgct tagactggaa 1080
atgaatgtta tccacagatc tactattatc aagcaaacat tagaagaaga cggtgttgtt 1140
ccatctacag caagaatcat ttctaaagca gaaaagaaat ccgtatcttc tttcttaaat 1200
ctcagtgtgg ttgtcattat catgaaactc tctgtcatac tgttgtttgt cttcatcaac 1260
ttttataact ttggtgcaaa ttgggtcaat gatgccttca attcattgta cttcgataag 1320
gaacgtgttt ctctaccaga ttttattacc tcgaatgcct ctgaaaactt taaagagcaa 1380
gctattgtta gtgtcacccc attattatat tacaaaccca ttaagtccta ccaacgcatt 1440
gaggatatgg ttcttctatt gcttcgtaat gtcagtgttg ccattcgtga taggttcgtc 1500
agtaaattag ttctttccgc cttagtatgc agtgctgtca tcaatgtgta tttattgaat 1560
gctgctagaa ttcataccag ttatactgca gaccaattgg tgaaaactga agtcaccaag 1620
aagtctttta ctgctcctgt acaaaaggct tctacaccag ttttaaccaa taaaacagtc 1680
atttctggat cgaaagtcaa aagtttatca tctgcgcaat cgagctcatc aggaccttca 1740
tcatctagtg aggaagatga ttcccgcgat attgaaagct tggataagaa aatacgtcct 1800
ttagaagaat tagaagcatt attaagtagt ggaaatacaa aacaattgaa gaacaaagag 1860
gtcgctgcct tggttattca cggtaagtta cctttgtacg ctttggagaa aaaattaggt 1920
gatactacga gagcggttgc ggtacgtagg aaggctcttt caattttggc agaagctcct 1980
gtattagcat ctgatcgttt accatataaa aattatgact acgaccgcgt atttggcgct 2040
tgttgtgaaa atgttatagg ttacatgcct ttgcccgttg gtgttatagg ccccttggtt 2100
atcgatggta catcttatca tataccaatg gcaactacag agggttgttt ggtagcttct 2160
gccatgcgtg gctgtaaggc aatcaatgct ggcggtggtg caacaactgt tttaactaag 2220

-continued

```
gatggtatga caagaggccc agtagtccgt ttcccaactt tgaaaagatc tggtgcctgt   2280

aagatatggt tagactcaga agagggacaa aacgcaatta aaaaagcttt taactctaca   2340

tcaagatttg cacgtctgca acatattcaa acttgtctag caggagattt actcttcatg   2400

agatttagaa caactactgg tgacgcaatg ggtatgaata tgatttctaa aggtgtcgaa   2460

tactcattaa agcaaatggt agaagagtat ggctgggaag atatggaggt tgtctccgtt   2520

tctggtaact actgtaccga caaaaaacca gctgccatca actggatcga aggtcgtggt   2580

aagagtgtcg tcgcagaagc tactattcct ggtgatgttg tcagaaaagt gttaaaaagt   2640

gatgtttccg cattggttga gttgaacatt gctaagaatt tggttggatc tgcaatggct   2700

gggtctgttg gtggatttaa cgcacatgca gctaatttag tgacagctgt tttcttggca   2760

ttaggacaag atcctgcaca aaatgttgaa agttccaact gtataacatt gatgaaagaa   2820

gtggacggtg atttgagaat ttccgtatcc atgccatcca tcgaagtagg taccatcggt   2880

ggtggtactg ttctagaacc acaaggtgcc atgttggact tattaggtgt aagaggcccg   2940

catgctaccg ctcctggtac caacgcacgt caattagcaa gaatagttgc ctgtgccgtc   3000

ttggcaggtg aattatcctt atgtgctgcc ctagcagccg gccatttggt tcaaagtcat   3060

atgacccaca acaggaaacc tgctgaacca acaaaaccta acaatttgga cgccactgat   3120

ataaatcgtt tgaaagatgg gtccgtcacc tgcattaaat cctaa                   3165
```

<210> SEQ ID NO 50
<211> LENGTH: 1054
<212> TYPE: PRT
<213> ORGANISM: Saccharomyces cerevisiae

<400> SEQUENCE: 50

```
Met Pro Pro Leu Phe Lys Gly Leu Lys Gln Met Ala Lys Pro Ile Ala
1               5                   10                  15

Tyr Val Ser Arg Phe Ser Ala Lys Arg Pro Ile His Ile Ile Leu Phe
            20                  25                  30

Ser Leu Ile Ile Ser Ala Phe Ala Tyr Leu Ser Val Ile Gln Tyr Tyr
        35                  40                  45

Phe Asn Gly Trp Gln Leu Asp Ser Asn Ser Val Phe Glu Thr Ala Pro
    50                  55                  60

Asn Lys Asp Ser Asn Thr Leu Phe Gln Glu Cys Ser His Tyr Tyr Arg
65                  70                  75                  80

Asp Ser Ser Leu Asp Gly Trp Val Ser Ile Thr Ala His Glu Ala Ser
                85                  90                  95

Glu Leu Pro Ala Pro His His Tyr Tyr Leu Leu Asn Leu Asn Phe Asn
            100                 105                 110

Ser Pro Asn Glu Thr Asp Ser Ile Pro Glu Leu Ala Asn Thr Val Phe
        115                 120                 125

Glu Lys Asp Asn Thr Lys Tyr Ile Leu Gln Glu Asp Leu Ser Val Ser
    130                 135                 140

Lys Glu Ile Ser Ser Thr Asp Gly Thr Lys Trp Arg Leu Arg Ser Asp
145                 150                 155                 160

Arg Lys Ser Leu Phe Asp Val Lys Thr Leu Ala Tyr Ser Leu Tyr Asp
                165                 170                 175

Val Phe Ser Glu Asn Val Thr Gln Ala Asp Pro Phe Asp Val Leu Ile
            180                 185                 190

Met Val Thr Ala Tyr Leu Met Met Phe Tyr Thr Ile Phe Gly Leu Phe
        195                 200                 205
```

-continued

```
Asn Asp Met Arg Lys Thr Gly Ser Asn Phe Trp Leu Ser Ala Ser Thr
    210                 215                 220

Val Val Asn Ser Ala Ser Ser Leu Phe Leu Ala Leu Tyr Val Thr Gln
225                 230                 235                 240

Cys Ile Leu Gly Lys Glu Val Ser Ala Leu Thr Leu Phe Glu Gly Leu
                245                 250                 255

Pro Phe Ile Val Val Val Val Gly Phe Lys His Lys Ile Lys Ile Ala
            260                 265                 270

Gln Tyr Ala Leu Glu Lys Phe Glu Arg Val Gly Leu Ser Lys Arg Ile
        275                 280                 285

Thr Thr Asp Glu Ile Val Phe Glu Ser Val Ser Glu Glu Gly Gly Arg
    290                 295                 300

Leu Ile Gln Asp His Leu Leu Cys Ile Phe Ala Phe Ile Gly Cys Ser
305                 310                 315                 320

Met Tyr Ala His Gln Leu Lys Thr Leu Thr Asn Phe Cys Ile Leu Ser
                325                 330                 335

Ala Phe Ile Leu Ile Phe Glu Leu Ile Leu Thr Pro Thr Phe Tyr Ser
            340                 345                 350

Ala Ile Leu Ala Leu Arg Leu Glu Met Asn Val Ile His Arg Ser Thr
        355                 360                 365

Ile Ile Lys Gln Thr Leu Glu Glu Asp Gly Val Val Pro Ser Thr Ala
    370                 375                 380

Arg Ile Ile Ser Lys Ala Glu Lys Lys Ser Val Ser Ser Phe Leu Asn
385                 390                 395                 400

Leu Ser Val Val Val Ile Ile Met Lys Leu Ser Val Ile Leu Leu Phe
                405                 410                 415

Val Phe Ile Asn Phe Tyr Asn Phe Gly Ala Asn Trp Val Asn Asp Ala
            420                 425                 430

Phe Asn Ser Leu Tyr Phe Asp Lys Glu Arg Val Ser Leu Pro Asp Phe
        435                 440                 445

Ile Thr Ser Asn Ala Ser Glu Asn Phe Lys Glu Gln Ala Ile Val Ser
    450                 455                 460

Val Thr Pro Leu Leu Tyr Tyr Lys Pro Ile Lys Ser Tyr Gln Arg Ile
465                 470                 475                 480

Glu Asp Met Val Leu Leu Leu Leu Arg Asn Val Ser Val Ala Ile Arg
                485                 490                 495

Asp Arg Phe Val Ser Lys Leu Val Leu Ser Ala Leu Val Cys Ser Ala
            500                 505                 510

Val Ile Asn Val Tyr Leu Leu Asn Ala Ala Arg Ile His Thr Ser Tyr
        515                 520                 525

Thr Ala Asp Gln Leu Val Lys Thr Glu Val Thr Lys Lys Ser Phe Thr
    530                 535                 540

Ala Pro Val Gln Lys Ala Ser Thr Pro Val Leu Thr Asn Lys Thr Val
545                 550                 555                 560

Ile Ser Gly Ser Lys Val Lys Ser Leu Ser Ser Ala Gln Ser Ser Ser
                565                 570                 575

Ser Gly Pro Ser Ser Ser Ser Glu Glu Asp Asp Ser Arg Asp Ile Glu
            580                 585                 590

Ser Leu Asp Lys Lys Ile Arg Pro Leu Glu Glu Leu Glu Ala Leu Leu
        595                 600                 605

Ser Ser Gly Asn Thr Lys Gln Leu Lys Asn Lys Glu Val Ala Ala Leu
    610                 615                 620

Val Ile His Gly Lys Leu Pro Leu Tyr Ala Leu Glu Lys Lys Leu Gly
625                 630                 635                 640
```

```
Asp Thr Thr Arg Ala Val Ala Val Arg Arg Lys Ala Leu Ser Ile Leu
                645                 650                 655

Ala Glu Ala Pro Val Leu Ala Ser Asp Arg Leu Pro Tyr Lys Asn Tyr
            660                 665                 670

Asp Tyr Asp Arg Val Phe Gly Ala Cys Cys Glu Asn Val Ile Gly Tyr
        675                 680                 685

Met Pro Leu Pro Val Gly Val Ile Gly Pro Leu Val Ile Asp Gly Thr
    690                 695                 700

Ser Tyr His Ile Pro Met Ala Thr Thr Glu Gly Cys Leu Val Ala Ser
705                 710                 715                 720

Ala Met Arg Gly Cys Lys Ala Ile Asn Ala Gly Gly Gly Ala Thr Thr
                725                 730                 735

Val Leu Thr Lys Asp Gly Met Thr Arg Gly Pro Val Val Arg Phe Pro
            740                 745                 750

Thr Leu Lys Arg Ser Gly Ala Cys Lys Ile Trp Leu Asp Ser Glu Glu
        755                 760                 765

Gly Gln Asn Ala Ile Lys Lys Ala Phe Asn Ser Thr Ser Arg Phe Ala
    770                 775                 780

Arg Leu Gln His Ile Gln Thr Cys Leu Ala Gly Asp Leu Leu Phe Met
785                 790                 795                 800

Arg Phe Arg Thr Thr Thr Gly Asp Ala Met Gly Met Asn Met Ile Ser
                805                 810                 815

Lys Gly Val Glu Tyr Ser Leu Lys Gln Met Val Glu Glu Tyr Gly Trp
            820                 825                 830

Glu Asp Met Glu Val Val Ser Val Ser Gly Asn Tyr Cys Thr Asp Lys
        835                 840                 845

Lys Pro Ala Ala Ile Asn Trp Ile Glu Gly Arg Gly Lys Ser Val Val
    850                 855                 860

Ala Glu Ala Thr Ile Pro Gly Asp Val Val Arg Lys Val Leu Lys Ser
865                 870                 875                 880

Asp Val Ser Ala Leu Val Glu Leu Asn Ile Ala Lys Asn Leu Val Gly
                885                 890                 895

Ser Ala Met Ala Gly Ser Val Gly Gly Phe Asn Ala His Ala Ala Asn
            900                 905                 910

Leu Val Thr Ala Val Phe Leu Ala Leu Gly Gln Asp Pro Ala Gln Asn
        915                 920                 925

Val Glu Ser Ser Asn Cys Ile Thr Leu Met Lys Glu Val Asp Gly Asp
    930                 935                 940

Leu Arg Ile Ser Val Ser Met Pro Ser Ile Glu Val Gly Thr Ile Gly
945                 950                 955                 960

Gly Gly Thr Val Leu Glu Pro Gln Gly Ala Met Leu Asp Leu Leu Gly
                965                 970                 975

Val Arg Gly Pro His Ala Thr Ala Pro Gly Thr Asn Ala Arg Gln Leu
            980                 985                 990

Ala Arg Ile Val Ala Cys Ala Val Leu Ala Gly Glu Leu Ser Leu Cys
        995                 1000                1005

Ala Ala Leu Ala Ala Gly His Leu Val Gln Ser His Met Thr His Asn
    1010                1015                1020

Arg Lys Pro Ala Glu Pro Thr Lys Pro Asn Asn Leu Asp Ala Thr Asp
1025                1030                1035                1040

Ile Asn Arg Leu Lys Asp Gly Ser Val Thr Cys Ile Lys Ser
                1045                1050
```

<210> SEQ ID NO 51
<211> LENGTH: 1278
<212> TYPE: DNA
<213> ORGANISM: Staphylococcus aureus

<400> SEQUENCE: 51
atgcaaagtt tagataagaa tttccgacat ttatctcgtc aacaaaagtt acaacaattg 60
gtagataagc aatggttatc agaagatcaa ttcgacattt tattgaatca tccattaatt 120
gatgaggaag tagcaaatag tttaattgaa aatgtcatcg cgcaaggtgc attacccgtt 180
ggattattac cgaatatcat tgtggacgat aaggcatatg ttgtacctat gatggtggaa 240
gagccttcag ttgtcgctgc agctagttat ggtgcaaagc tagtgaatca gactggcgga 300
tttaaaacgg tatcttctga acgtattatg ataggtcaaa tcgtctttga tggcgttgac 360
gatactgaaa aattatcagc agacattaaa gctttagaaa agcaaattca taaaattgcg 420
gatgaggcat atccttctat taaagcgcgt ggtggtggtt accaacgtat agctattgat 480
acatttcctg agcaacagtt actatcttta aaagtatttg ttgatacgaa agatgctatg 540
ggcgctaata tgcttaatac gattttagag gccataactg catttttaaa aaatgaatct 600
ccacaaagcg acattttaat gagtatttta tccaatcatg caacagcgtc cgttgttaaa 660
gttcaaggcg aaattgacgt taaagattta gcaaggggcg agagaactgg agaagaggtt 720
gccaaacgaa tggaacgtgc ttctgtattg gcacaagttg atattcatcg tgctgcaaca 780
cataataaag gtgttatgaa tggcatacat gccgttgttt tagcaacagg aaatgatacg 840
cgtggtgcag aagcaagtgc gcatgcatac gcgagtcgtg acggacagta tcgtggtatt 900
gcaacatgga gatacgatca aaaacgtcaa cgtttaattg gtacaataga agtgcctatg 960
acattggcaa tcgttggcgg tggtacaaaa gtattaccaa ttgctaaagc ttctttagaa 1020
ttgctaaatg tagattcagc acaagaatta ggtcatgtag ttgctgccgt tggtttagca 1080
cagaactttg cagcatgtcg cgcgctcgtt tccgaaggta tccagcaagg ccatatgagc 1140
ttgcaatata aatctttagc tattgttgta ggtgcaaaag gtgatgaaat tgcgcaagta 1200
gctgaagcat tgaagcaaga accccgtgcg aatacacaag tagctgaacg cattttacaa 1260
gaaattagac aacaatag 1278

<210> SEQ ID NO 52
<211> LENGTH: 425
<212> TYPE: PRT
<213> ORGANISM: Staphylococcus aureus

<400> SEQUENCE: 52

Met Gln Ser Leu Asp Lys Asn Phe Arg His Leu Ser Arg Gln Gln Lys
1 5 10 15

Leu Gln Gln Leu Val Asp Lys Gln Trp Leu Ser Glu Asp Gln Phe Asp
20 25 30

Ile Leu Leu Asn His Pro Leu Ile Asp Glu Glu Val Ala Asn Ser Leu
35 40 45

Ile Glu Asn Val Ile Ala Gln Gly Ala Leu Pro Val Gly Leu Leu Pro
50 55 60

Asn Ile Ile Val Asp Asp Lys Ala Tyr Val Val Pro Met Met Val Glu
65 70 75 80

Glu Pro Ser Val Val Ala Ala Ala Ser Tyr Gly Ala Lys Leu Val Asn
85 90 95

Gln Thr Gly Gly Phe Lys Thr Val Ser Ser Glu Arg Ile Met Ile Gly
100 105 110

```
Gln Ile Val Phe Asp Gly Val Asp Asp Thr Glu Lys Leu Ser Ala Asp
        115                 120                 125

Ile Lys Ala Leu Glu Lys Gln Ile His Lys Ile Ala Asp Glu Ala Tyr
    130                 135                 140

Pro Ser Ile Lys Ala Arg Gly Gly Gly Tyr Gln Arg Ile Ala Ile Asp
145                 150                 155                 160

Thr Phe Pro Glu Gln Gln Leu Leu Ser Leu Lys Val Phe Val Asp Thr
                165                 170                 175

Lys Asp Ala Met Gly Ala Asn Met Leu Asn Thr Ile Leu Glu Ala Ile
            180                 185                 190

Thr Ala Phe Leu Lys Asn Glu Ser Pro Gln Ser Asp Ile Leu Met Ser
        195                 200                 205

Ile Leu Ser Asn His Ala Thr Ala Ser Val Val Lys Val Gln Gly Glu
    210                 215                 220

Ile Asp Val Lys Asp Leu Ala Arg Gly Glu Arg Thr Gly Glu Glu Val
225                 230                 235                 240

Ala Lys Arg Met Glu Arg Ala Ser Val Leu Ala Gln Val Asp Ile His
                245                 250                 255

Arg Ala Ala Thr His Asn Lys Gly Val Met Asn Gly Ile His Ala Val
            260                 265                 270

Val Leu Ala Thr Gly Asn Asp Thr Arg Gly Ala Glu Ala Ser Ala His
        275                 280                 285

Ala Tyr Ala Ser Arg Asp Gly Gln Tyr Arg Gly Ile Ala Thr Trp Arg
    290                 295                 300

Tyr Asp Gln Lys Arg Gln Arg Leu Ile Gly Thr Ile Glu Val Pro Met
305                 310                 315                 320

Thr Leu Ala Ile Val Gly Gly Gly Thr Lys Val Leu Pro Ile Ala Lys
                325                 330                 335

Ala Ser Leu Glu Leu Leu Asn Val Asp Ser Ala Gln Glu Leu Gly His
            340                 345                 350

Val Val Ala Ala Val Gly Leu Ala Gln Asn Phe Ala Ala Cys Arg Ala
        355                 360                 365

Leu Val Ser Glu Gly Ile Gln Gln Gly His Met Ser Leu Gln Tyr Lys
    370                 375                 380

Ser Leu Ala Ile Val Val Gly Ala Lys Gly Asp Glu Ile Ala Gln Val
385                 390                 395                 400

Ala Glu Ala Leu Lys Gln Glu Pro Arg Ala Asn Thr Gln Val Ala Glu
                405                 410                 415

Arg Ile Leu Gln Glu Ile Arg Gln Gln
            420                 425
```

<210> SEQ ID NO 53
<211> LENGTH: 1332
<212> TYPE: DNA
<213> ORGANISM: Saccharomyces cerevisiae

<400> SEQUENCE: 53

```
atgtcattac cgttcttaac ttctgcaccg ggaaaggtta ttatttttgg tgaacactct      60

gctgtgtaca acaagcctgc cgtcgctgct agtgtgtctg cgttgagaac ctacctgcta     120

ataagcgagt catctgcacc agatactatt gaattggact tcccggacat tagctttaat     180

cataagtggt ccatcaatga tttcaatgcc atcaccgagg atcaagtaaa ctcccaaaaa     240

ttggccaagg ctcaacaagc caccgatggc ttgtctcagg aactcgttag tcttttggat     300

ccgttgttag ctcaactatc cgaatccttc cactaccatg cagcgttttg tttcctgtat     360
```

-continued

```
atgtttgttt gcctatgccc ccatgccaag aatattaagt tttctttaaa gtctacttta    420

cccatcggtg ctgggttggg ctcaagcgcc tctatttctg tatcactggc cttagctatg    480

gcctacttgg gggggttaat aggatctaat gacttggaaa agctgtcaga aaacgataag    540

catatagtga atcaatgggc cttcataggt gaaaagtgta ttcacggtac cccttcagga    600

atagataacg ctgtggccac ttatggtaat gccctgctat ttgaaaaaga ctcacataat    660

ggaacaataa acacaaacaa ttttaagttc ttagatgatt tcccagccat tccaatgatc    720

ctaacctata ctagaattcc aaggtctaca aaagatcttg ttgctcgcgt tcgtgtgttg    780

gtcaccgaga aatttcctga agttatgaag ccaattctag atgccatggg tgaatgtgcc    840

ctacaaggct tagagatcat gactaagtta agtaaatgta aaggcaccga tgacgaggct    900

gtagaaacta ataatgaact gtatgaacaa ctattggaat tgataagaat aaatcatgga    960

ctgcttgtct caatcggtgt ttctcatcct ggattagaac ttattaaaaa tctgagcgat   1020

gatttgagaa ttggctccac aaaacttacc ggtgctggtg gcggcggttg ctctttgact   1080

ttgttacgaa gagacattac tcaagagcaa attgacagct tcaaaaagaa attgcaagat   1140

gattttagtt acgagacatt tgaaacagac ttgggtggga ctggctgctg tttgttaagc   1200

gcaaaaaatt tgaataaaga tcttaaaatc aaatccctag tattccaatt atttgaaaat   1260

aaaactacca caaagcaaca aattgacgat ctattattgc caggaaacac gaatttacca   1320

tggacttcat aa                                                         1332
```

<210> SEQ ID NO 54
<211> LENGTH: 443
<212> TYPE: PRT
<213> ORGANISM: Saccharomyces cerevisiae

<400> SEQUENCE: 54

```
Met Ser Leu Pro Phe Leu Thr Ser Ala Pro Gly Lys Val Ile Ile Phe
 1               5                  10                  15

Gly Glu His Ser Ala Val Tyr Asn Lys Pro Ala Val Ala Ala Ser Val
            20                  25                  30

Ser Ala Leu Arg Thr Tyr Leu Leu Ile Ser Glu Ser Ser Ala Pro Asp
        35                  40                  45

Thr Ile Glu Leu Asp Phe Pro Asp Ile Ser Phe Asn His Lys Trp Ser
    50                  55                  60

Ile Asn Asp Phe Asn Ala Ile Thr Glu Asp Gln Val Asn Ser Gln Lys
65                  70                  75                  80

Leu Ala Lys Ala Gln Gln Ala Thr Asp Gly Leu Ser Gln Glu Leu Val
                85                  90                  95

Ser Leu Leu Asp Pro Leu Leu Ala Gln Leu Ser Glu Ser Phe His Tyr
            100                 105                 110

His Ala Ala Phe Cys Phe Leu Tyr Met Phe Val Cys Leu Cys Pro His
        115                 120                 125

Ala Lys Asn Ile Lys Phe Ser Leu Lys Ser Thr Leu Pro Ile Gly Ala
    130                 135                 140

Gly Leu Gly Ser Ser Ala Ser Ile Ser Val Ser Leu Ala Leu Ala Met
145                 150                 155                 160

Ala Tyr Leu Gly Gly Leu Ile Gly Ser Asn Asp Leu Glu Lys Leu Ser
                165                 170                 175

Glu Asn Asp Lys His Ile Val Asn Gln Trp Ala Phe Ile Gly Glu Lys
            180                 185                 190

Cys Ile His Gly Thr Pro Ser Gly Ile Asp Asn Ala Val Ala Thr Tyr
        195                 200                 205
```

```
Gly Asn Ala Leu Leu Phe Glu Lys Asp Ser His Asn Gly Thr Ile Asn
    210                 215                 220

Thr Asn Asn Phe Lys Phe Leu Asp Asp Phe Pro Ala Ile Pro Met Ile
225                 230                 235                 240

Leu Thr Tyr Thr Arg Ile Pro Arg Ser Thr Lys Asp Leu Val Ala Arg
                245                 250                 255

Val Arg Val Leu Val Thr Glu Lys Phe Pro Glu Val Met Lys Pro Ile
            260                 265                 270

Leu Asp Ala Met Gly Glu Cys Ala Leu Gln Gly Leu Glu Ile Met Thr
        275                 280                 285

Lys Leu Ser Lys Cys Lys Gly Thr Asp Asp Glu Ala Val Glu Thr Asn
    290                 295                 300

Asn Glu Leu Tyr Glu Gln Leu Leu Glu Leu Ile Arg Ile Asn His Gly
305                 310                 315                 320

Leu Leu Val Ser Ile Gly Val Ser His Pro Gly Leu Glu Leu Ile Lys
                325                 330                 335

Asn Leu Ser Asp Asp Leu Arg Ile Gly Ser Thr Lys Leu Thr Gly Ala
            340                 345                 350

Gly Gly Gly Gly Cys Ser Leu Thr Leu Leu Arg Arg Asp Ile Thr Gln
        355                 360                 365

Glu Gln Ile Asp Ser Phe Lys Lys Lys Leu Gln Asp Asp Phe Ser Tyr
    370                 375                 380

Glu Thr Phe Glu Thr Asp Leu Gly Gly Thr Gly Cys Cys Leu Leu Ser
385                 390                 395                 400

Ala Lys Asn Leu Asn Lys Asp Leu Lys Ile Lys Ser Leu Val Phe Gln
                405                 410                 415

Leu Phe Glu Asn Lys Thr Thr Thr Lys Gln Gln Ile Asp Asp Leu Leu
            420                 425                 430

Leu Pro Gly Asn Thr Asn Leu Pro Trp Thr Ser
        435                 440
```

<210> SEQ ID NO 55
<211> LENGTH: 839
<212> TYPE: DNA
<213> ORGANISM: Staphylococcus aureus

<400> SEQUENCE: 55

```
atgcagtacc gtttaacgca ggtaaaatca aagttttaat agaagcctta gagagcggga      60

actattcgtc tattaaaagc gatgtttacg atggtatgtt atatgatgcg cctgaccatc     120

ttaagtcttt ggtgaaccgt tttgtagaat taaataatat tacagagccg ctagcagtaa     180

cgatccaaac gaatttacca ccatcacgtg gattaggatc gagtgcagct gtcgcggttg     240

cttttgttcg tgcaagttat gattttttag ggaaatcatt aacgaaagaa gaactcattg     300

aaaaggctaa ttgggcagag caaattgcac atggtaaacc aagtggtatt gatacgcaaa     360

cgattgtatc aggcaaacca gtttggttcc aaaaaggtca tgctgaaaca ttgaaaacgt     420

taagtttaga cggctatatg gttgttattg atactggtgt gaaaggttca acaagacaag     480

cggtagaaga tgttcataaa ctttgtgagg atcctcagta catgtcacat gtaaaacata     540

tcggtaagtt agttttacgt gcgagtgatg tgattgaaca tcataacttt gaagccctag     600

cggatatttt taatgaatgt catgcggatt taaaggcgtt gacagttagt catgataaaa     660

tagaacaatt aatgaaaatt ggtaaagaaa atggtgcgat tgctggaaaa cttactggtg     720

ctggtcgtgg tggaagtatg ttattgcttg ccaaagattt accaacagcg aaaaatattg     780
```

tgaaagctgt agaaaaagct ggtgcagcac atacatggat tgagaattta ggaggttaa 839

<210> SEQ ID NO 56
<211> LENGTH: 279
<212> TYPE: PRT
<213> ORGANISM: Staphylococcus aureus

<400> SEQUENCE: 56

```
Met Ala Val Pro Phe Asn Ala Gly Lys Ile Lys Val Leu Ile Glu Ala
 1               5                  10                  15

Leu Glu Ser Gly Asn Tyr Ser Ser Ile Lys Ser Asp Val Tyr Asp Gly
            20                  25                  30

Met Leu Tyr Asp Ala Pro Asp His Leu Lys Ser Leu Val Asn Arg Phe
        35                  40                  45

Val Glu Leu Asn Asn Ile Thr Glu Pro Leu Ala Val Thr Ile Gln Thr
    50                  55                  60

Asn Leu Pro Pro Ser Arg Gly Leu Gly Ser Ser Ala Ala Val Ala Val
65                  70                  75                  80

Ala Phe Val Arg Ala Ser Tyr Asp Phe Leu Gly Lys Ser Leu Thr Lys
                85                  90                  95

Glu Glu Leu Ile Glu Lys Ala Asn Trp Ala Glu Gln Ile Ala His Gly
            100                 105                 110

Lys Pro Ser Gly Ile Asp Thr Gln Thr Ile Val Ser Gly Lys Pro Val
        115                 120                 125

Trp Phe Gln Lys Gly His Ala Glu Thr Leu Lys Thr Leu Ser Leu Asp
    130                 135                 140

Gly Tyr Met Val Val Ile Asp Thr Gly Val Lys Gly Ser Thr Arg Gln
145                 150                 155                 160

Ala Val Glu Asp Val His Lys Leu Cys Glu Asp Pro Gln Tyr Met Ser
                165                 170                 175

His Val Lys His Ile Gly Lys Leu Val Leu Arg Ala Ser Asp Val Ile
            180                 185                 190

Glu His His Asn Phe Glu Ala Leu Ala Asp Ile Phe Asn Glu Cys His
        195                 200                 205

Ala Asp Leu Lys Ala Leu Thr Val Ser His Asp Lys Ile Glu Gln Leu
    210                 215                 220

Met Lys Ile Gly Lys Glu Asn Gly Ala Ile Ala Gly Lys Leu Thr Gly
225                 230                 235                 240

Ala Gly Arg Gly Gly Ser Met Leu Leu Leu Ala Lys Asp Leu Pro Thr
                245                 250                 255

Ala Lys Asn Ile Val Lys Ala Val Glu Lys Ala Gly Ala Ala His Thr
            260                 265                 270

Trp Ile Glu Asn Leu Gly Gly
        275
```

<210> SEQ ID NO 57
<211> LENGTH: 1356
<212> TYPE: DNA
<213> ORGANISM: Saccharomyces cerevisiae

<400> SEQUENCE: 57
atgtcagagt tgagagcctt cagtgcccca gggaaagcgt tactagctgg tggatattta 60
gttttagata caaaatatga agcatttgta gtcggattat cggcaagaat gcatgctgta 120
gcccatcctt acggttcatt gcaagggtct gataagtttg aagtgcgtgt gaaaagtaaa 180
caatttaaag atggggagtg gctgtaccat ataagtccta aaagtggctt cattcctgtt 240

```
tcgataggcg gatctaagaa ccctttcatt gaaaaagtta tcgctaacgt atttagctac    300

tttaaaccta acatggacga ctactgcaat agaaacttgt tcgttattga tattttctct    360

gatgatgcct accattctca ggaggatagc gttaccgaac atcgtggcaa cagaagattg    420

agttttcatt cgcacagaat tgaagaagtt cccaaaacag ggctgggctc ctcggcaggt    480

ttagtcacag ttttaactac agctttggcc tcctttttg tatcggacct ggaaaataat     540

gtagacaaat atagagaagt tattcataat ttagcacaag ttgctcattg tcaagctcag    600

ggtaaaattg gaagcgggtt tgatgtagcg gcggcagcat atggatctat cagatataga    660

agattcccac ccgcattaat ctctaatttg ccagatattg gaagtgctac ttacggcagt    720

aaactggcgc atttggttga tgaagaagac tggaatatta cgattaaaag taaccattta    780

ccttcgggat taactttatg gatgggcgat attaagaatg gttcagaaac agtaaaactg    840

gtccagaagg taaaaaattg gtatgattcg catatgccag aaagcttgaa aatatataca    900

gaactcgatc atgcaaattc tagatttatg gatggactat ctaaactaga tcgcttacac    960

gagactcatg acgattacag cgatcagata tttgagtctc ttgagaggaa tgactgtacc   1020

tgtcaaaagt atcctgaaat cacagaagtt agagatgcag ttgccacaat tagacgttcc   1080

tttagaaaaa taactaaaga atctggtgcc gatatcgaac ctcccgtaca aactagctta   1140

ttggatgatt gccagacctt aaaaggagtt cttacttgct taatacctgg tgctggtggt   1200

tatgacgcca ttgcagtgat tactaagcaa gatgttgatc ttagggctca aaccgctaat   1260

gacaaaagat tttctaaggt tcaatggctg gatgtaactc aggctgactg gggtgttagg   1320

aaagaaaaag atccggaaac ttatcttgat aaataa                             1356
```

<210> SEQ ID NO 58
<211> LENGTH: 451
<212> TYPE: PRT
<213> ORGANISM: Saccharomyces cerevisiae

<400> SEQUENCE: 58

```
Met Ser Glu Leu Arg Ala Phe Ser Ala Pro Gly Lys Ala Leu Leu Ala
1               5                   10                  15

Gly Gly Tyr Leu Val Leu Asp Thr Lys Tyr Glu Ala Phe Val Val Gly
            20                  25                  30

Leu Ser Ala Arg Met His Ala Val Ala His Pro Tyr Gly Ser Leu Gln
        35                  40                  45

Gly Ser Asp Lys Phe Glu Val Arg Val Lys Ser Lys Gln Phe Lys Asp
    50                  55                  60

Gly Glu Trp Leu Tyr His Ile Ser Pro Lys Ser Gly Phe Ile Pro Val
65                  70                  75                  80

Ser Ile Gly Gly Ser Lys Asn Pro Phe Ile Glu Lys Val Ile Ala Asn
                85                  90                  95

Val Phe Ser Tyr Phe Lys Pro Asn Met Asp Asp Tyr Cys Asn Arg Asn
            100                 105                 110

Leu Phe Val Ile Asp Ile Phe Ser Asp Asp Ala Tyr His Ser Gln Glu
        115                 120                 125

Asp Ser Val Thr Glu His Arg Gly Asn Arg Arg Leu Ser Phe His Ser
    130                 135                 140

His Arg Ile Glu Glu Val Pro Lys Thr Gly Leu Gly Ser Ser Ala Gly
145                 150                 155                 160

Leu Val Thr Val Leu Thr Thr Ala Leu Ala Ser Phe Phe Val Ser Asp
                165                 170                 175

Leu Glu Asn Asn Val Asp Lys Tyr Arg Glu Val Ile His Asn Leu Ala
```

```
            180                 185                 190

Gln Val Ala His Cys Gln Ala Gln Gly Lys Ile Gly Ser Gly Phe Asp
        195                 200                 205

Val Ala Ala Ala Ala Tyr Gly Ser Ile Arg Tyr Arg Arg Phe Pro Pro
    210                 215                 220

Ala Leu Ile Ser Asn Leu Pro Asp Ile Gly Ser Ala Thr Tyr Gly Ser
225                 230                 235                 240

Lys Leu Ala His Leu Val Asp Glu Glu Asp Trp Asn Ile Thr Ile Lys
                245                 250                 255

Ser Asn His Leu Pro Ser Gly Leu Thr Leu Trp Met Gly Asp Ile Lys
            260                 265                 270

Asn Gly Ser Glu Thr Val Lys Leu Val Gln Lys Val Lys Asn Trp Tyr
        275                 280                 285

Asp Ser His Met Pro Glu Ser Leu Lys Ile Tyr Thr Glu Leu Asp His
    290                 295                 300

Ala Asn Ser Arg Phe Met Asp Gly Leu Ser Lys Leu Asp Arg Leu His
305                 310                 315                 320

Glu Thr His Asp Asp Tyr Ser Asp Gln Ile Phe Glu Ser Leu Glu Arg
                325                 330                 335

Asn Asp Cys Thr Cys Gln Lys Tyr Pro Glu Ile Thr Glu Val Arg Asp
            340                 345                 350

Ala Val Ala Thr Ile Arg Arg Ser Phe Arg Lys Ile Thr Lys Glu Ser
        355                 360                 365

Gly Ala Asp Ile Glu Pro Pro Val Gln Thr Ser Leu Leu Asp Asp Cys
    370                 375                 380

Gln Thr Leu Lys Gly Val Leu Thr Cys Leu Ile Pro Gly Ala Gly Gly
385                 390                 395                 400

Tyr Asp Ala Ile Ala Val Ile Thr Lys Gln Asp Val Asp Leu Arg Ala
                405                 410                 415

Gln Thr Ala Asn Asp Lys Arg Phe Ser Lys Val Gln Trp Leu Asp Val
            420                 425                 430

Thr Gln Ala Asp Trp Gly Val Arg Lys Glu Lys Asp Pro Glu Thr Tyr
        435                 440                 445

Leu Asp Lys
    450


<210> SEQ ID NO 59
<211> LENGTH: 1077
<212> TYPE: DNA
<213> ORGANISM: Staphylococcus aureus

<400> SEQUENCE: 59

atgattcagg tcaaagcacc cggaaaactt tatattgctg gagaatatgc tgtaacagaa     60

ccaggatata aatctgtact tattgcgtta gatcgttttg taactgctac tattgaagaa    120

gcagaccaat ataaaggtac cattcattca aaagcattac atcataaccc agttacattt    180

agtagagatg aagatagtat tgtcatttca gatccacatg cagcaaaaca attaaattat    240

gtggtcacag ctattgaaat atttgaacaa tacgcgaaaa gttgcgatat agcgatgaag    300

cattttcatc tgactattga tagtaattta gatgattcaa atggtcataa atatggatta    360

ggttcaagtg cagcagtact tgtgtcagtt ataaaagtat taaatgaatt ttatgatatg    420

aagttatcta atttatacat ttataaacta gcagtgattg caaatatgaa gttacaaagt    480

ttaagttcat gcggagatat tgctgtgagt gtatatagtg gatggttagc gtatagtact    540

tttgatcatg aatgggttaa gcatcaaatt gaagatacta cggttgaaga agttttaatc    600
```

```
aaaaactggc ctggattgca catcgaacca ttacaagcac ctgaaaatat ggaagtactt    660

atcggttgga ctggctcacc ggcgtcatca ccacactttg ttagcgaagt gaaacgtttg    720

aaatcagatc cttcatttta cggtgacttc ttagaagatt cacatcgttg tgttgaaaag    780

cttattcatg cttttaaaac aaataacatt aaaggtgtgc aaaagatggt gcgtcagaat    840

cgtacaatta ttcaacgtat ggataaagaa gctacagttg atatagaaac tgaaaagcta    900

aaatatttgt gtgatattgc tgaaaagtat cacggtgcat ctaaaacatc aggcgctggt    960

ggtggagact gtggtattac aattatcaat aaagatgtag ataaagaaaa aatttatgat   1020

gaatggacaa aacatggtat taaaccatta aaatttaata tttatcatgg gcaataa      1077
```

```
<210> SEQ ID NO 60
<211> LENGTH: 358
<212> TYPE: PRT
<213> ORGANISM: Staphylococcus aureus

<400> SEQUENCE: 60

Met Ile Gln Val Lys Ala Pro Gly Lys Leu Tyr Ile Ala Gly Glu Tyr
 1               5                  10                  15

Ala Val Thr Glu Pro Gly Tyr Lys Ser Val Leu Ile Ala Leu Asp Arg
            20                  25                  30

Phe Val Thr Ala Thr Ile Glu Glu Ala Asp Gln Tyr Lys Gly Thr Ile
        35                  40                  45

His Ser Lys Ala Leu His His Asn Pro Val Thr Phe Ser Arg Asp Glu
    50                  55                  60

Asp Ser Ile Val Ile Ser Asp Pro His Ala Ala Lys Gln Leu Asn Tyr
65                  70                  75                  80

Val Val Thr Ala Ile Glu Ile Phe Glu Gln Tyr Ala Lys Ser Cys Asp
                85                  90                  95

Ile Ala Met Lys His Phe His Leu Thr Ile Asp Ser Asn Leu Asp Asp
            100                 105                 110

Ser Asn Gly His Lys Tyr Gly Leu Gly Ser Ser Ala Ala Val Leu Val
        115                 120                 125

Ser Val Ile Lys Val Leu Asn Glu Phe Tyr Asp Met Lys Leu Ser Asn
    130                 135                 140

Leu Tyr Ile Tyr Lys Leu Ala Val Ile Ala Asn Met Lys Leu Gln Ser
145                 150                 155                 160

Leu Ser Ser Cys Gly Asp Ile Ala Val Ser Val Tyr Ser Gly Trp Leu
                165                 170                 175

Ala Tyr Ser Thr Phe Asp His Glu Trp Val Lys His Gln Ile Glu Asp
            180                 185                 190

Thr Thr Val Glu Glu Val Leu Ile Lys Asn Trp Pro Gly Leu His Ile
        195                 200                 205

Glu Pro Leu Gln Ala Pro Glu Asn Met Glu Val Leu Ile Gly Trp Thr
    210                 215                 220

Gly Ser Pro Ala Ser Ser Pro His Phe Val Ser Glu Val Lys Arg Leu
225                 230                 235                 240

Lys Ser Asp Pro Ser Phe Tyr Gly Asp Phe Leu Glu Asp Ser His Arg
                245                 250                 255

Cys Val Glu Lys Leu Ile His Ala Phe Lys Thr Asn Asn Ile Lys Gly
            260                 265                 270

Val Gln Lys Met Val Arg Gln Asn Arg Thr Ile Ile Gln Arg Met Asp
        275                 280                 285

Lys Glu Ala Thr Val Asp Ile Glu Thr Glu Lys Leu Lys Tyr Leu Cys
```

```
    290                 295                 300

Asp Ile Ala Glu Lys Tyr His Gly Ala Ser Lys Thr Ser Gly Ala Gly
305                 310                 315                 320

Gly Gly Asp Cys Gly Ile Thr Ile Ile Asn Lys Asp Val Asp Lys Glu
                325                 330                 335

Lys Ile Tyr Asp Glu Trp Thr Lys His Gly Ile Lys Pro Leu Lys Phe
            340                 345                 350

Asn Ile Tyr His Gly Gln
        355
```

<210> SEQ ID NO 61
<211> LENGTH: 1191
<212> TYPE: DNA
<213> ORGANISM: Saccharomyces cerevisiae

<400> SEQUENCE: 61

```
atgaccgttt acacagcatc cgttaccgca cccgtcaaca tcgcaaccct taagtattgg      60

gggaaaaggg acacgaagtt gaatctgccc accaattcgt ccatatcagt gactttatcg     120

caagatgacc tcagaacgtt gacctctgcg gctactgcac ctgagtttga acgcgacact     180

ttgtggttaa atggagaacc acacagcatc gacaatgaaa gaactcaaaa ttgtctgcgc     240

gacctacgcc aattaagaaa ggaaatggaa tcgaaggacg cctcattgcc cacattatct     300

caatggaaac tccacattgt ctccgaaaat aactttccta cagcagctgg tttagcttcc     360

tccgctgctg gctttgctgc attggtctct gcaattgcta agttatacca attaccacag     420

tcaacttcag aaatatctag aatagcaaga aaggggtctg gttcagcttg tagatcgttg     480

tttggcggat acgtggcctg ggaaatggga aaagctgaag atggtcatga ttccatggca     540

gtacaaatcg cagacagctc tgactggcct cagatgaaag cttgtgtcct agttgtcagc     600

gatattaaaa aggatgtgag ttccactcag ggtatgcaat tgaccgtggc aacctccgaa     660

ctatttaaag aaagaattga acatgtcgta ccaaagagat ttgaagtcat gcgtaaagcc     720

attgttgaaa aagatttcgc cacctttgca aaggaaacaa tgatggattc caactctttc     780

catgccacat gtttggactc tttccctcca atattctaca tgaatgacac ttccaagcgt     840

atcatcagtt ggtgccacac cattaatcag ttttacggag aaacaatcgt tgcatacacg     900

tttgatgcag gtccaaatgc tgtgttgtac tacttagctg aaaatgagtc gaaactcttt     960

gcatttatct ataaattgtt tggctctgtt cctggatggg acaagaaatt tactactgag    1020

cagcttgagg ctttcaacca tcaatttgaa tcatctaact ttactgcacg tgaattggat    1080

cttgagttgc aaaaggatgt tgccagagtg attttaactc aagtcggttc aggcccacaa    1140

gaaacaaacg aatctttgat tgacgcaaag actggtctac caaaggaata a             1191
```

<210> SEQ ID NO 62
<211> LENGTH: 396
<212> TYPE: PRT
<213> ORGANISM: Saccharomyces cerevisiae

<400> SEQUENCE: 62

```
Met Thr Val Tyr Thr Ala Ser Val Thr Ala Pro Val Asn Ile Ala Thr
 1               5                  10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Ala Thr Ala Pro Glu Phe Glu Arg Asp Thr Leu Trp Leu Asn
```

```
    50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110

Pro Thr Ala Ala Gly Leu Ala Ser Ser Ala Ala Gly Phe Ala Ala Leu
        115                 120                 125

Val Ser Ala Ile Ala Lys Leu Tyr Gln Leu Pro Gln Ser Thr Ser Glu
    130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
        195                 200                 205

Thr Gln Gly Met Gln Leu Thr Val Ala Thr Ser Glu Leu Phe Lys Glu
    210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270

Tyr Met Asn Asp Thr Ser Lys Arg Ile Ile Ser Trp Cys His Thr Ile
        275                 280                 285

Asn Gln Phe Tyr Gly Glu Thr Ile Val Ala Tyr Thr Phe Asp Ala Gly
    290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
        355                 360                 365

Arg Val Ile Leu Thr Gln Val Gly Ser Gly Pro Gln Glu Thr Asn Glu
    370                 375                 380

Ser Leu Ile Asp Ala Lys Thr Gly Leu Pro Lys Glu
385                 390                 395


<210> SEQ ID NO 63
<211> LENGTH: 984
<212> TYPE: DNA
<213> ORGANISM: Staphylococcus aureus

<400> SEQUENCE: 63

ttgattaaaa gtggcaaagc acgtgcacat acgaatattg cacttataaa atattggggt      60

aaaaaagatg aagcactaat cattccaatg aataatagca tatctgttac attagaaaaa     120

ttttacactg aaacgaaagt cacttttaac gaccagttaa cacaggatca attttggttg     180

aatggtgaaa aggttagtgg caaagaatta gagaaaattt caaaatatat ggatattgtc     240
```

```
agaaatagag ctggcatcga ttggtatgct gaaattgaaa gcgacaattt tgtaccaaca    300

gcagcagggt tggcttcatc agcaagcgca tatgcagctt tagcagcagc ttgtaatcaa    360

gcactagact tgcagctgtc agataaggat ttatcgagat tggcgcgaat tggttcgggt    420

tctgcgtcgc gtagtattta tggtggattt gcagaatggg aaaaagggta taatgatgag    480

acgtcatatg ccgttccact tgaatcgaat cattttgaag atgaccttgc catgatattt    540

gttgtgatta atcaacattc taaaaaggta cctagtcgat atggtatgtc gttgacacga    600

aacacatcaa ggttttatca atattggtta gatcatattg atgaagattt agctgaagca    660

aaagcagcga ttcaagacaa agattttaaa cgccttggtg aagtaattga agaaaatggt    720

ttacgtatgc atgccacgaa tctgggatca acaccgccgt tcacttatct tgtgcaagaa    780

agttatgatg tcatggcgct cgttcacgaa tgccgagaag cgggatatcc gtgttatttt    840

acgatggatg cgggtcctaa tgtgaaaata cttgtagaaa agaaaaacaa gcaacagatt    900

atagataaat tattaacaca gtttgataat aaccaaatta ttgatagtga cattattgcc    960

acaggaattg aaataattga gtaa                                           984
```

<210> SEQ ID NO 64
<211> LENGTH: 327
<212> TYPE: PRT
<213> ORGANISM: Staphylococcus aureus

<400> SEQUENCE: 64

```
Met Ile Lys Ser Gly Lys Ala Arg Ala His Thr Asn Ile Ala Leu Ile
 1               5                  10                  15

Lys Tyr Trp Gly Lys Lys Asp Glu Ala Leu Ile Ile Pro Met Asn Asn
            20                  25                  30

Ser Ile Ser Val Thr Leu Glu Lys Phe Tyr Thr Glu Thr Lys Val Thr
        35                  40                  45

Phe Asn Asp Gln Leu Thr Gln Asp Gln Phe Trp Leu Asn Gly Glu Lys
    50                  55                  60

Val Ser Gly Lys Glu Leu Glu Lys Ile Ser Lys Tyr Met Asp Ile Val
65                  70                  75                  80

Arg Asn Arg Ala Gly Ile Asp Trp Tyr Ala Glu Ile Glu Ser Asp Asn
                85                  90                  95

Phe Val Pro Thr Ala Ala Gly Leu Ala Ser Ser Ala Ser Ala Tyr Ala
            100                 105                 110

Ala Leu Ala Ala Ala Cys Asn Gln Ala Leu Asp Leu Gln Leu Ser Asp
        115                 120                 125

Lys Asp Leu Ser Arg Leu Ala Arg Ile Gly Ser Gly Ser Ala Ser Arg
    130                 135                 140

Ser Ile Tyr Gly Gly Phe Ala Glu Trp Glu Lys Gly Tyr Asn Asp Glu
145                 150                 155                 160

Thr Ser Tyr Ala Val Pro Leu Glu Ser Asn His Phe Glu Asp Asp Leu
                165                 170                 175

Ala Met Ile Phe Val Val Ile Asn Gln His Ser Lys Lys Val Pro Ser
            180                 185                 190

Arg Tyr Gly Met Ser Leu Thr Arg Asn Thr Ser Arg Phe Tyr Gln Tyr
        195                 200                 205

Trp Leu Asp His Ile Asp Glu Asp Leu Ala Glu Ala Lys Ala Ala Ile
    210                 215                 220

Gln Asp Lys Asp Phe Lys Arg Leu Gly Glu Val Ile Glu Glu Asn Gly
225                 230                 235                 240
```

```
Leu Arg Met His Ala Thr Asn Leu Gly Ser Thr Pro Pro Phe Thr Tyr
                245                 250                 255

Leu Val Gln Glu Ser Tyr Asp Val Met Ala Leu Val His Glu Cys Arg
            260                 265                 270

Glu Ala Gly Tyr Pro Cys Tyr Phe Thr Met Asp Ala Gly Pro Asn Val
        275                 280                 285

Lys Ile Leu Val Glu Lys Lys Asn Lys Gln Gln Ile Ile Asp Lys Leu
    290                 295                 300

Leu Thr Gln Phe Asp Asn Asn Gln Ile Ile Asp Ser Asp Ile Ile Ala
305                 310                 315                 320

Thr Gly Ile Glu Ile Ile Glu
                325
```

<210> SEQ ID NO 65
<211> LENGTH: 1182
<212> TYPE: DNA
<213> ORGANISM: Saccharomyces cerevisiae

<400> SEQUENCE: 65

```
atgttgcaga gacattcctt gaagttgggg aaattctcca tcagaacact cgctactggt      60

gccccattag atgcatccaa actaaaaatt actagaaacc caaatccatc caagccaaga     120

ccaaatgaag aattagtgtt cggccagaca ttcaccgatc atatgttgac cattccttgg     180

tcagccaaag aagggtgggg cactccacac atcaagcctt acggtaatct ttctcttgac     240

ccatctgctt gtgtattcca ttatgcattt gaattatttg aaggtttgaa agcctacaga     300

actcctcaaa atactatcac catgttccgt ccggataaga acatggcccg tatgaacaag     360

tctgccgcta gaatttgttt gccaactttc gaatctgaag aattgatcaa acttaccggg     420

aaattgatcg aacaagataa acacttggtt cctcaaggta atggttactc attatacatc     480

agaccaacaa tgattggtac atccaagggt ttaggtgttg gcactccctc cgaggctctt     540

ctttatgtta ttacttctcc agtcggtcct tattataaga ctggtttcaa agccgtacgt     600

cttgaagcaa cagactatgc tacaagagct tggccaggtg gtgttggcga caaaaaattg     660

ggtgctaact atgccccatg catcttacct caactacaag ctgccaaaag agggtaccaa     720

caaaatctat ggttgttcgg cccagaaaag aacatcactg aggttggtac tatgaacgtg     780

ttcttcgttt tcctcaacaa agtcactggc aagaaggaat tggttaccgc tccattagat     840

ggtaccattt tagaaggtgt taccagagac tctgttttaa cattggctcg tgacaaacta     900

gatcctcaag aatgggacat caacgagcgt tattacacta ttactgaagt cgccactaga     960

gcaaaacaag gtgaactatt agaagccttc ggttctggta ctgctgctgt cgtttcacct    1020

atcaaggaaa ttggctggaa caacgaagat attcatgttc cactattgcc tggtgaacaa    1080

tgtggtgcat tgaccaagca agttgctcaa tggattgctg atatccaata cggtagagtc    1140

aattatggta actggtcaaa aactgttgcc gacttgaact aa                       1182
```

<210> SEQ ID NO 66
<211> LENGTH: 393
<212> TYPE: PRT
<213> ORGANISM: Saccharomyces cerevisiae

<400> SEQUENCE: 66

```
Met Leu Gln Arg His Ser Leu Lys Leu Gly Lys Phe Ser Ile Arg Thr
 1               5                  10                  15

Leu Ala Thr Gly Ala Pro Leu Asp Ala Ser Lys Leu Lys Ile Thr Arg
            20                  25                  30
```

-continued

```
Asn Pro Asn Pro Ser Lys Pro Arg Pro Asn Glu Glu Leu Val Phe Gly
        35                  40                  45

Gln Thr Phe Thr Asp His Met Leu Thr Ile Pro Trp Ser Ala Lys Glu
    50                  55                  60

Gly Trp Gly Thr Pro His Ile Lys Pro Tyr Gly Asn Leu Ser Leu Asp
65                  70                  75                  80

Pro Ser Ala Cys Val Phe His Tyr Ala Phe Glu Leu Phe Glu Gly Leu
                85                  90                  95

Lys Ala Tyr Arg Thr Pro Gln Asn Thr Ile Thr Met Phe Arg Pro Asp
            100                 105                 110

Lys Asn Met Ala Arg Met Asn Lys Ser Ala Ala Arg Ile Cys Leu Pro
        115                 120                 125

Thr Phe Glu Ser Glu Glu Leu Ile Lys Leu Thr Gly Lys Leu Ile Glu
    130                 135                 140

Gln Asp Lys His Leu Val Pro Gln Gly Asn Gly Tyr Ser Leu Tyr Ile
145                 150                 155                 160

Arg Pro Thr Met Ile Gly Thr Ser Lys Gly Leu Gly Val Gly Thr Pro
                165                 170                 175

Ser Glu Ala Leu Leu Tyr Val Ile Thr Ser Pro Val Gly Pro Tyr Tyr
            180                 185                 190

Lys Thr Gly Phe Lys Ala Val Arg Leu Glu Ala Thr Asp Tyr Ala Thr
        195                 200                 205

Arg Ala Trp Pro Gly Gly Val Gly Asp Lys Lys Leu Gly Ala Asn Tyr
    210                 215                 220

Ala Pro Cys Ile Leu Pro Gln Leu Gln Ala Ala Lys Arg Gly Tyr Gln
225                 230                 235                 240

Gln Asn Leu Trp Leu Phe Gly Pro Glu Lys Asn Ile Thr Glu Val Gly
                245                 250                 255

Thr Met Asn Val Phe Phe Val Phe Leu Asn Lys Val Thr Gly Lys Lys
            260                 265                 270

Glu Leu Val Thr Ala Pro Leu Asp Gly Thr Ile Leu Glu Gly Val Thr
        275                 280                 285

Arg Asp Ser Val Leu Thr Leu Ala Arg Asp Lys Leu Asp Pro Gln Glu
    290                 295                 300

Trp Asp Ile Asn Glu Arg Tyr Tyr Thr Ile Thr Glu Val Ala Thr Arg
305                 310                 315                 320

Ala Lys Gln Gly Glu Leu Leu Glu Ala Phe Gly Ser Gly Thr Ala Ala
                325                 330                 335

Val Val Ser Pro Ile Lys Glu Ile Gly Trp Asn Asn Glu Asp Ile His
            340                 345                 350

Val Pro Leu Leu Pro Gly Glu Gln Cys Gly Ala Leu Thr Lys Gln Val
        355                 360                 365

Ala Gln Trp Ile Ala Asp Ile Gln Tyr Gly Arg Val Asn Tyr Gly Asn
    370                 375                 380

Trp Ser Lys Thr Val Ala Asp Leu Asn
385                 390
```

<210> SEQ ID NO 67
<211> LENGTH: 930
<212> TYPE: DNA
<213> ORGANISM: Escherichia coli

<400> SEQUENCE: 67

```
atgaccacga agaaagctga ttacatttgg ttcaatgggg agatggttcg ctgggaagac      60

gcgaaggtgc atgtgatgtc gcacgcgctg cactatggca cttcggtttt tgaaggcatc     120
```

```
cgttgctacg actcgcacaa aggaccggtt gtattccgcc atcgtgagca tatgcagcgt    180

ctgcatgact ccgccaaaat ctatcgcttc ccggtttcgc agagcattga tgagctgatg    240

gaagcttgtc gtgacgtgat ccgcaaaaac aatctcacca gcgcctatat ccgtccgctg    300

atcttcgtcg gtgatgttgg catgggagta aacccgccag cgggatactc aaccgacgtg    360

attatcgctg ctttcccgtg gggagcgtat ctgggcgcag aagcgctgga gcaggggatc    420

gatgcgatgg tttcctcctg gaaccgcgca gcaccaaaca ccatcccgac ggcggcaaaa    480

gccggtggta actacctctc ttccctgctg gtgggtagcg aagcgcgccg ccacggttat    540

caggaaggta tcgcgctgga tgtgaacggt tatatctctg aaggcgcagg cgaaaacctg    600

tttgaagtga aagatggtgt gctgttcacc ccaccgttca cctcctccgc gctgccgggt    660

attacccgtg atgccatcat caaactggcg aaagagctgg gaattgaagt acgtgagcag    720

gtgctgtcgc gcgaatccct gtacctggcg gatgaagtgt ttatgtccgg tacggcggca    780

gaaatcacgc cagtgcgcag cgtagacggt attcaggttg gcgaaggccg ttgtggcccg    840

gttaccaaac gcattcagca agccttcttc ggcctcttca ctggcgaaac cgaagataaa    900

tggggctggt tagatcaagt taatcaataa                                      930


<210> SEQ ID NO 68
<211> LENGTH: 309
<212> TYPE: PRT
<213> ORGANISM: Escherichia coli

<400> SEQUENCE: 68

Met Thr Thr Lys Lys Ala Asp Tyr Ile Trp Phe Asn Gly Glu Met Val
 1               5                  10                  15

Arg Trp Glu Asp Ala Lys Val His Val Met Ser His Ala Leu His Tyr
            20                  25                  30

Gly Thr Ser Val Phe Glu Gly Ile Arg Cys Tyr Asp Ser His Lys Gly
        35                  40                  45

Pro Val Val Phe Arg His Arg Glu His Met Gln Arg Leu His Asp Ser
    50                  55                  60

Ala Lys Ile Tyr Arg Phe Pro Val Ser Gln Ser Ile Asp Glu Leu Met
65                  70                  75                  80

Glu Ala Cys Arg Asp Val Ile Arg Lys Asn Asn Leu Thr Ser Ala Tyr
                85                  90                  95

Ile Arg Pro Leu Ile Phe Val Gly Asp Val Gly Met Gly Val Asn Pro
            100                 105                 110

Pro Ala Gly Tyr Ser Thr Asp Val Ile Ile Ala Ala Phe Pro Trp Gly
        115                 120                 125

Ala Tyr Leu Gly Ala Glu Ala Leu Glu Gln Gly Ile Asp Ala Met Val
    130                 135                 140

Ser Ser Trp Asn Arg Ala Ala Pro Asn Thr Ile Pro Thr Ala Ala Lys
145                 150                 155                 160

Ala Gly Gly Asn Tyr Leu Ser Ser Leu Leu Val Gly Ser Glu Ala Arg
                165                 170                 175

Arg His Gly Tyr Gln Glu Gly Ile Ala Leu Asp Val Asn Gly Tyr Ile
            180                 185                 190

Ser Glu Gly Ala Gly Glu Asn Leu Phe Glu Val Lys Asp Gly Val Leu
        195                 200                 205

Phe Thr Pro Pro Phe Thr Ser Ser Ala Leu Pro Gly Ile Thr Arg Asp
    210                 215                 220

Ala Ile Ile Lys Leu Ala Lys Glu Leu Gly Ile Glu Val Arg Glu Gln
```

-continued

```
225                 230                 235                 240

Val Leu Ser Arg Glu Ser Leu Tyr Leu Ala Asp Glu Val Phe Met Ser
                245                 250                 255

Gly Thr Ala Ala Glu Ile Thr Pro Val Arg Ser Val Asp Gly Ile Gln
            260                 265                 270

Val Gly Glu Gly Arg Cys Gly Pro Val Thr Lys Arg Ile Gln Gln Ala
        275                 280                 285

Phe Phe Gly Leu Phe Thr Gly Glu Thr Glu Asp Lys Trp Gly Trp Leu
    290                 295                 300

Asp Gln Val Asn Gln
305


<210> SEQ ID NO 69
<211> LENGTH: 984
<212> TYPE: DNA
<213> ORGANISM: Bacillus subtilis

<400> SEQUENCE: 69

atgtcagtaa tgtcatatat tgatgcaatc aatttggcga tgaaagaaga aatggaacga      60

gattctcgcg ttttcgtcct tggggaagat gtaggaagaa aaggcggtgt gtttaaagcg     120

acagcgggac tctatgaaca atttggggaa gagcgcgtta tggatacgcc gcttgctgaa     180

tctgcaatcg caggagtcgg tatcggagcg gcaatgtacg gaatgagacc gattgctgaa     240

atgcagtttg ctgatttcat tatgccggca gtcaaccaaa ttatttctga agcggctaaa     300

atccgctacc gcagcaacaa tgactggagc tgtccgattg tcgtcagagc gccatacggc     360

ggaggcgtgc acggagccct gtatcattct caatcagtcg aagcaatttt cgccaaccag     420

cccggactga aaattgtcat gccatcaaca ccatatgacg cgaaagggct cttaaaagcc     480

gcagttcgtg acgaagaccc cgtgctgttt tttgagcaca agcgggcata ccgtctgata     540

aagggcgagg ttccggctga tgattatgtc ctgccaatcg gcaaggcgga cgtaaaaagg     600

gaaggcgacg acatcacagt gatcacatac ggcctgtgtg tccacttcgc cttacaagct     660

gcagaacgtc tcgaaaaaga tggcatttca gcgcatgtgg tggatttaag aacagtttac     720

ccgcttgata aagaagccat catcgaagct gcgtccaaaa ctggaaaggt tcttttggtc     780

acagaagata caaaagaagg cagcatcatg agcgaagtag ccgcaattat atccgagcat     840

tgtctgttcg acttagacgc gccgatcaaa cggcttgcag gtcctgatat tccggctatg     900

ccttatgcgc cgacaatgga aaaatacttt atggtcaacc ctgataaagt ggaagcggcg     960

atgagagaat tagcggagtt ttaa                                            984


<210> SEQ ID NO 70
<211> LENGTH: 327
<212> TYPE: PRT
<213> ORGANISM: Bacillus subtilis

<400> SEQUENCE: 70

Met Ser Val Met Ser Tyr Ile Asp Ala Ile Asn Leu Ala Met Lys Glu
 1               5                  10                  15

Glu Met Glu Arg Asp Ser Arg Val Phe Val Leu Gly Glu Asp Val Gly
            20                  25                  30

Arg Lys Gly Gly Val Phe Lys Ala Thr Ala Gly Leu Tyr Glu Gln Phe
        35                  40                  45

Gly Glu Glu Arg Val Met Asp Thr Pro Leu Ala Glu Ser Ala Ile Ala
    50                  55                  60

Gly Val Gly Ile Gly Ala Ala Met Tyr Gly Met Arg Pro Ile Ala Glu
```

```
65                  70                  75                  80

Met Gln Phe Ala Asp Phe Ile Met Pro Ala Val Asn Gln Ile Ile Ser
                85                  90                  95

Glu Ala Ala Lys Ile Arg Tyr Arg Ser Asn Asn Asp Trp Ser Cys Pro
            100                 105                 110

Ile Val Val Arg Ala Pro Tyr Gly Gly Gly Val His Gly Ala Leu Tyr
        115                 120                 125

His Ser Gln Ser Val Glu Ala Ile Phe Ala Asn Gln Pro Gly Leu Lys
    130                 135                 140

Ile Val Met Pro Ser Thr Pro Tyr Asp Ala Lys Gly Leu Leu Lys Ala
145                 150                 155                 160

Ala Val Arg Asp Glu Asp Pro Val Leu Phe Phe Glu His Lys Arg Ala
                165                 170                 175

Tyr Arg Leu Ile Lys Gly Glu Val Pro Ala Asp Asp Tyr Val Leu Pro
            180                 185                 190

Ile Gly Lys Ala Asp Val Lys Arg Glu Gly Asp Asp Ile Thr Val Ile
        195                 200                 205

Thr Tyr Gly Leu Cys Val His Phe Ala Leu Gln Ala Ala Glu Arg Leu
    210                 215                 220

Glu Lys Asp Gly Ile Ser Ala His Val Val Asp Leu Arg Thr Val Tyr
225                 230                 235                 240

Pro Leu Asp Lys Glu Ala Ile Ile Glu Ala Ala Ser Lys Thr Gly Lys
                245                 250                 255

Val Leu Leu Val Thr Glu Asp Thr Lys Glu Gly Ser Ile Met Ser Glu
            260                 265                 270

Val Ala Ala Ile Ile Ser Glu His Cys Leu Phe Asp Leu Asp Ala Pro
        275                 280                 285

Ile Lys Arg Leu Ala Gly Pro Asp Ile Pro Ala Met Pro Tyr Ala Pro
    290                 295                 300

Thr Met Glu Lys Tyr Phe Met Val Asn Pro Asp Lys Val Glu Ala Ala
305                 310                 315                 320

Met Arg Glu Leu Ala Glu Phe
                325


<210> SEQ ID NO 71
<211> LENGTH: 984
<212> TYPE: DNA
<213> ORGANISM: Bacillus subtilis

<400> SEQUENCE: 71

atgtcagtaa tgtcatatat tgatgcaatc aatttggcga tgaaagaaga aatggaacga      60

gattctcgcg ttttcgtcct tggggaagat gtaggaagaa aaggcggtgt gtttaaagcg     120

acagcgggac tctatgaaca atttggggaa gagcgcgtta tggatacgcc gcttgctgaa     180

tctgcaatcg caggagtcgg tatcggagcg gcaatgtacg gaatgagacc gattgctgaa     240

atgcagtttg ctgatttcat tatgccggca gtcaaccaaa ttatttctga agcggctaaa     300

atccgctacc gcagcaacaa tgactggagc tgtccgattg tcgtcagagc gccatacggc     360

ggaggcgtgc acggagccct gtatcattct caatcagtcg aagcaatttt cgccaaccag     420

cccggactga aaattgtcat gccatcaaca ccatatgacg cgaaagggct cttaaaagcc     480

gcagttcgtg acgaagaccc cgtgctgttt tttgagcaca agcgggcata ccgtctgata     540

aagggcgagg ttccggctga tgattatgtc ctgccaatcg gcaaggcgga cgtaaaaagg     600

gaaggcgacg acatcacagt gatcacatac ggcctgtgtg tccacttcgc cttacaagct     660
```

-continued

```
gcagaacgtc tcgaaaaaga tggcatttca gcgcatgtgg tggatttaag aacagtttac    720

ccgcttgata aagaagccat catcgaagct gcgtccaaaa ctggaaaggt tcttttggtc    780

acagaagata caaaagaagg cagcatcatg agcgaagtag ccgcaattat atccgagcat    840

tgtctgttcg acttagacgc gccgatcaaa cggcttgcag gtcctgatat tccggctatg    900

ccttatgcgc cgacaatgga aaaatacttt atggtcaacc ctgataaagt ggaagcggcg    960

atgagagaat tagcggagtt ttaa                                           984
```

```
<210> SEQ ID NO 72
<211> LENGTH: 327
<212> TYPE: PRT
<213> ORGANISM: Bacillus subtilis

<400> SEQUENCE: 72

Met Ser Val Met Ser Tyr Ile Asp Ala Ile Asn Leu Ala Met Lys Glu
 1               5                  10                  15

Glu Met Glu Arg Asp Ser Arg Val Phe Val Leu Gly Glu Asp Val Gly
            20                  25                  30

Arg Lys Gly Gly Val Phe Lys Ala Thr Ala Gly Leu Tyr Glu Gln Phe
        35                  40                  45

Gly Glu Glu Arg Val Met Asp Thr Pro Leu Ala Glu Ser Ala Ile Ala
    50                  55                  60

Gly Val Gly Ile Gly Ala Ala Met Tyr Gly Met Arg Pro Ile Ala Glu
65                  70                  75                  80

Met Gln Phe Ala Asp Phe Ile Met Pro Ala Val Asn Gln Ile Ile Ser
                85                  90                  95

Glu Ala Ala Lys Ile Arg Tyr Arg Ser Asn Asn Asp Trp Ser Cys Pro
            100                 105                 110

Ile Val Val Arg Ala Pro Tyr Gly Gly Gly Val His Gly Ala Leu Tyr
        115                 120                 125

His Ser Gln Ser Val Glu Ala Ile Phe Ala Asn Gln Pro Gly Leu Lys
    130                 135                 140

Ile Val Met Pro Ser Thr Pro Tyr Asp Ala Lys Gly Leu Leu Lys Ala
145                 150                 155                 160

Ala Val Arg Asp Glu Asp Pro Val Leu Phe Phe Glu His Lys Arg Ala
                165                 170                 175

Tyr Arg Leu Ile Lys Gly Glu Val Pro Ala Asp Asp Tyr Val Leu Pro
            180                 185                 190

Ile Gly Lys Ala Asp Val Lys Arg Glu Gly Asp Asp Ile Thr Val Ile
        195                 200                 205

Thr Tyr Gly Leu Cys Val His Phe Ala Leu Gln Ala Ala Glu Arg Leu
    210                 215                 220

Glu Lys Asp Gly Ile Ser Ala His Val Val Asp Leu Arg Thr Val Tyr
225                 230                 235                 240

Pro Leu Asp Lys Glu Ala Ile Ile Glu Ala Ala Ser Lys Thr Gly Lys
                245                 250                 255

Val Leu Leu Val Thr Glu Asp Thr Lys Glu Gly Ser Ile Met Ser Glu
            260                 265                 270

Val Ala Ala Ile Ile Ser Glu His Cys Leu Phe Asp Leu Asp Ala Pro
        275                 280                 285

Ile Lys Arg Leu Ala Gly Pro Asp Ile Pro Ala Met Pro Tyr Ala Pro
    290                 295                 300

Thr Met Glu Lys Tyr Phe Met Val Asn Pro Asp Lys Val Glu Ala Ala
305                 310                 315                 320
```

Met Arg Glu Leu Ala Glu Phe
325

<210> SEQ ID NO 73
<211> LENGTH: 1374
<212> TYPE: DNA
<213> ORGANISM: Bacillus subtilis

<400> SEQUENCE: 73
atggcaactg agtatgacgt agtcattctg ggcggcggta ccggcggtta tgttgcggcc 60
atcagagccg ctcagctcgg cttaaaaaca gccgttgtgg aaaaggaaaa actcggggga 120
acatgtctgc ataaaggctg tatcccgagt aaagcgctgc ttagaagcgc agaggtatac 180
cggacagctc gtgaagccga tcaattcgga gtggaaacgg ctggcgtgtc cctcaacttt 240
gaaaaagtgc agcagcgtaa gcaagccgtt gttgataagc ttgcagcggg tgtaaatcat 300
ttaatgaaaa aaggaaaaat tgacgtgtac accggatatg gacgtatcct tggaccgtca 360
atcttctctc cgctgccggg aacaatttct gttgagcggg gaaatggcga agaaaatgac 420
atgctgatcc cgaaacaagt gatcattgca acaggatcaa gaccgagaat gcttccgggt 480
cttgaagtgg acggtaagtc tgtactgact tcagatgagg cgctccaaat ggaggagctg 540
ccacagtcaa tcatcattgt cggcggaggg gttatcggta tcgaatgggc gtctatgctt 600
catgattttg gcgttaaggt aacggttatt gaatacgcgg atcgcatatt gccgactgaa 660
gatctagaga tttcaaaaga aatggaaagt cttcttaaga aaaaaggcat ccagttcata 720
acaggggcaa aagtgctgcc tgacacaatg acaaaaacat cagacgatat cagcatacaa 780
gcggaaaaag acggagaaac cgttacctat tctgctgaga aaatgcttgt ttccatcggc 840
agacaggcaa atatcgaagg catcggccta gagaacaccg atattgttac tgaaaatggc 900
atgatttcag tcaatgaaag ctgccaaacg aaggaatctc atatttatgc aatcggagac 960
gtaatcggtg gcctgcagtt agctcacgtt gcttcacatg agggaattat tgctgttgag 1020
cattttgcag gtctcaatcc gcatccgctt gatccgacgc ttgtgccgaa gtgcatttac 1080
tcaagccctg aagctgccag tgtcggctta accgaagacg aagcaaaggc gaacgggcat 1140
aatgtcaaaa tcggcaagtt cccatttatg gcgattggaa aagcgcttgt atacggtgaa 1200
agcgacggtt ttgtcaaaat cgtggctgac cgagatacag atgatattct cggcgttcat 1260
atgattggcc cgcatgtcac cgacatgatt tctgaagcgg gtcttgccaa agtgctggac 1320
gcaacaccgt gggaggtcgg gcaaacgatt tcacccgcat ccaacgcttt ctga 1374

<210> SEQ ID NO 74
<211> LENGTH: 457
<212> TYPE: PRT
<213> ORGANISM: Bacillus subtilis

<400> SEQUENCE: 74

Met Ala Thr Glu Tyr Asp Val Val Ile Leu Gly Gly Gly Thr Gly Gly
1 5 10 15

Tyr Val Ala Ala Ile Arg Ala Ala Gln Leu Gly Leu Lys Thr Ala Val
20 25 30

Val Glu Lys Glu Lys Leu Gly Gly Thr Cys Leu His Lys Gly Cys Ile
35 40 45

Pro Ser Lys Ala Leu Leu Arg Ser Ala Glu Val Tyr Arg Thr Ala Arg
50 55 60

Glu Ala Asp Gln Phe Gly Val Glu Thr Ala Gly Val Ser Leu Asn Phe
65 70 75 80

```
Glu Lys Val Gln Gln Arg Lys Gln Ala Val Val Asp Lys Leu Ala Ala
                85                  90                  95

Gly Val Asn His Leu Met Lys Lys Gly Lys Ile Asp Val Tyr Thr Gly
            100                 105                 110

Tyr Gly Arg Ile Leu Gly Pro Ser Ile Phe Ser Pro Leu Pro Gly Thr
        115                 120                 125

Ile Ser Val Glu Arg Gly Asn Gly Glu Glu Asn Asp Met Leu Ile Pro
    130                 135                 140

Lys Gln Val Ile Ile Ala Thr Gly Ser Arg Pro Arg Met Leu Pro Gly
145                 150                 155                 160

Leu Glu Val Asp Gly Lys Ser Val Leu Thr Ser Asp Glu Ala Leu Gln
                165                 170                 175

Met Glu Glu Leu Pro Gln Ser Ile Ile Ile Val Gly Gly Gly Val Ile
            180                 185                 190

Gly Ile Glu Trp Ala Ser Met Leu His Asp Phe Gly Val Lys Val Thr
        195                 200                 205

Val Ile Glu Tyr Ala Asp Arg Ile Leu Pro Thr Glu Asp Leu Glu Ile
    210                 215                 220

Ser Lys Glu Met Glu Ser Leu Leu Lys Lys Lys Gly Ile Gln Phe Ile
225                 230                 235                 240

Thr Gly Ala Lys Val Leu Pro Asp Thr Met Thr Lys Thr Ser Asp Asp
                245                 250                 255

Ile Ser Ile Gln Ala Glu Lys Asp Gly Glu Thr Val Thr Tyr Ser Ala
            260                 265                 270

Glu Lys Met Leu Val Ser Ile Gly Arg Gln Ala Asn Ile Glu Gly Ile
        275                 280                 285

Gly Leu Glu Asn Thr Asp Ile Val Thr Glu Asn Gly Met Ile Ser Val
    290                 295                 300

Asn Glu Ser Cys Gln Thr Lys Glu Ser His Ile Tyr Ala Ile Gly Asp
305                 310                 315                 320

Val Ile Gly Gly Leu Gln Leu Ala His Val Ala Ser His Glu Gly Ile
                325                 330                 335

Ile Ala Val Glu His Phe Ala Gly Leu Asn Pro His Pro Leu Asp Pro
            340                 345                 350

Thr Leu Val Pro Lys Cys Ile Tyr Ser Ser Pro Glu Ala Ala Ser Val
        355                 360                 365

Gly Leu Thr Glu Asp Glu Ala Lys Ala Asn Gly His Asn Val Lys Ile
    370                 375                 380

Gly Lys Phe Pro Phe Met Ala Ile Gly Lys Ala Leu Val Tyr Gly Glu
385                 390                 395                 400

Ser Asp Gly Phe Val Lys Ile Val Ala Asp Arg Asp Thr Asp Asp Ile
                405                 410                 415

Leu Gly Val His Met Ile Gly Pro His Val Thr Asp Met Ile Ser Glu
            420                 425                 430

Ala Gly Leu Ala Lys Val Leu Asp Ala Thr Pro Trp Glu Val Gly Gln
        435                 440                 445

Thr Ile Ser Pro Ala Ser Asn Ala Phe
    450                 455
```

<210> SEQ ID NO 75
<211> LENGTH: 1269
<212> TYPE: DNA
<213> ORGANISM: Pseudomonas entomophila

<400> SEQUENCE: 75

```
atgggcacgc acgtcatcaa gatgccggac attggcgaag gcatcgcgca ggtcgagttg      60
gtggaatggt tcgtcaaggt cggcgatgtg atcgccgagg accaggtggt ggccgatgtc     120
atgaccgaca aggccactgt ggaaatccct tcgccggtca gcggcaaggt gctggccctg     180
ggtggccagc cgggtgaagt gatggcggtc ggcagcgagc tgatccgcat cgaggtcgaa     240
ggcagcggca accatgtcga cacgccgcag accaagccgg ccgagcctgc acctgcgccg     300
gtcaaagccg aagccaagcc cgaggcgcgc ctcgaagcgc aaccgcaggc aagcaccagc     360
cataccgccg cccccatcgt gccgcgtgag gcccacgaca aaccactggc ctcccctgcc     420
gtgcgcaagc gcgccctgga cgccgggatc gagctgcgct acgtgcatgg cagcggcccg     480
gccgggcgca tcctgcatga agacctcgac gccttcatca gcaagccgca gaccagcgcc     540
ggccaggcgc cgggcggtta cggcaagcgc accgacagcg agcaggtgcc ggtgatcggc     600
ctgcgccgca agatcgccca gcgcatgcag gacgccaagc gccgtgtcgc ccacttcagc     660
tacgtcgagg aaatcgacgt caccaacctg gaagccctgc gccagcagct caacgccaag     720
catggcgaca gccgcggcaa gctgaccctg ctgccgttcc tggtgcgcgc catggtcgtc     780
gccctgcgcg atttcccgca gatcaacgcc acctacgatg acgaagccca ggtcatcacc     840
cgccacggcg cggtgcatgt gggcatcgcc acccaaggcg acaacggcct gatggtaccg     900
gtactgcgcc acgccgaagc cggcagcctg tggagcaatg ccagcgagat cgcccgcgtc     960
gcccatgccg cgcgcaacaa caaggccacc cgcgaagaac tgtccggctc gaccatcacc    1020
ttgaccagcc tcggcgcgct gggtggcatc gtcagcaccc cggtggtcaa caccccggaa    1080
gtggcgatcg tcggcgtcaa ccgcatggtc gagcggccga tggtgatcga cggccagatc    1140
gtcgtgcgca agatgatgaa cctgtccagc tcgttcgacc accgcgtggt cgacggcatg    1200
gacgccgccc tgttcatcca ggccgtgcgc ggcctgctgg aacagcctgc ctgcctgttc    1260
gtggagtga                                                            1269
```

<210> SEQ ID NO 76
<211> LENGTH: 422
<212> TYPE: PRT
<213> ORGANISM: Pseudomonas entomophila

<400> SEQUENCE: 76

```
Met Gly Thr His Val Ile Lys Met Pro Asp Ile Gly Glu Gly Ile Ala
1               5                   10                  15

Gln Val Glu Leu Val Glu Trp Phe Val Lys Val Gly Asp Val Ile Ala
            20                  25                  30

Glu Asp Gln Val Val Ala Asp Val Met Thr Asp Lys Ala Thr Val Glu
        35                  40                  45

Ile Pro Ser Pro Val Ser Gly Lys Val Leu Ala Leu Gly Gly Gln Pro
    50                  55                  60

Gly Glu Val Met Ala Val Gly Ser Glu Leu Ile Arg Ile Glu Val Glu
65                  70                  75                  80

Gly Ser Gly Asn His Val Asp Thr Pro Gln Thr Lys Pro Ala Glu Pro
                85                  90                  95

Ala Pro Ala Pro Val Lys Ala Glu Ala Lys Pro Glu Ala Arg Leu Glu
            100                 105                 110

Ala Gln Pro Gln Ala Ser Thr Ser His Thr Ala Ala Pro Ile Val Pro
        115                 120                 125

Arg Glu Ala His Asp Lys Pro Leu Ala Ser Pro Ala Val Arg Lys Arg
    130                 135                 140

Ala Leu Asp Ala Gly Ile Glu Leu Arg Tyr Val His Gly Ser Gly Pro
```

145 150 155 160

Ala Gly Arg Ile Leu His Glu Asp Leu Asp Ala Phe Ile Ser Lys Pro
165 170 175

Gln Thr Ser Ala Gly Gln Ala Pro Gly Gly Tyr Gly Lys Arg Thr Asp
180 185 190

Ser Glu Gln Val Pro Val Ile Gly Leu Arg Arg Lys Ile Ala Gln Arg
195 200 205

Met Gln Asp Ala Lys Arg Arg Val Ala His Phe Ser Tyr Val Glu Glu
210 215 220

Ile Asp Val Thr Asn Leu Glu Ala Leu Arg Gln Gln Leu Asn Ala Lys
225 230 235 240

His Gly Asp Ser Arg Gly Lys Leu Thr Leu Leu Pro Phe Leu Val Arg
245 250 255

Ala Met Val Val Ala Leu Arg Asp Phe Pro Gln Ile Asn Ala Thr Tyr
260 265 270

Asp Asp Glu Ala Gln Val Ile Thr Arg His Gly Ala Val His Val Gly
275 280 285

Ile Ala Thr Gln Gly Asp Asn Gly Leu Met Val Pro Val Leu Arg His
290 295 300

Ala Glu Ala Gly Ser Leu Trp Ser Asn Ala Ser Glu Ile Ala Arg Val
305 310 315 320

Ala His Ala Ala Arg Asn Asn Lys Ala Thr Arg Glu Glu Leu Ser Gly
325 330 335

Ser Thr Ile Thr Leu Thr Ser Leu Gly Ala Leu Gly Gly Ile Val Ser
340 345 350

Thr Pro Val Val Asn Thr Pro Glu Val Ala Ile Val Gly Val Asn Arg
355 360 365

Met Val Glu Arg Pro Met Val Ile Asp Gly Gln Ile Val Val Arg Lys
370 375 380

Met Met Asn Leu Ser Ser Ser Phe Asp His Arg Val Val Asp Gly Met
385 390 395 400

Asp Ala Ala Leu Phe Ile Gln Ala Val Arg Gly Leu Leu Glu Gln Pro
405 410 415

Ala Cys Leu Phe Val Glu
420

<210> SEQ ID NO 77
<211> LENGTH: 1059
<212> TYPE: DNA
<213> ORGANISM: Arabidopsis thaliana

<400> SEQUENCE: 77
atggcggctc ttttaggcag atcctgccgg aaactgagtt ttccgagctt gagtcacgga 60
gctaggaggg tatcgacgga aactggaaaa ccattgaatc tatactctgc tattaatcaa 120
gcgcttcaca tcgctttgga caccgatcct cggtcttatg tctttgggga agacgttggc 180
tttggtggag tctttcgctg tacaacaggt ttagctgaac gattcgggaa aaaccgtgtc 240
ttcaatactc ctctttgtga gcagggcatt gttggatttg gcattggtct agcagcaatg 300
ggtaatcgag caattgtaga gattcagttt gcagattata tatatcctgc ttttgatcag 360
attgttaatg aagctgcaaa gttcagatac cgaagtggta accaattcaa ctgtggagga 420
cttacgataa gagcaccata tggagcagtt ggtcatggtg gacattacca ttcacaatcc 480
cctgaagctt tcttttgcca tgtccctggt attaaggttg ttatccctcg gagtccacga 540
gaagcaaagg gactgttgtt gtcatgtatc cgtgatccaa atcccgttgt tttcttcgaa 600

```
ccaaagtggc tgtatcgtca agcagtagaa gaagtccctg agcatgacta tatgatacct    660

ttatcagaag cagaggttat aagagaaggc aatgacatta cactggttgg atggggagct    720

cagcttaccg ttatggaaca agcttgtctg gacgcggaaa aggaaggaat atcatgtgaa    780

ctgatagatc tcaagacact gcttccttgg gacaaagaaa ccgttgaggc ttcagttaaa    840

aagactggca gacttcttat aagccatgaa gctcctgtaa caggaggttt tggagcagag    900

atctctgcaa caattctgga acgttgcttt ttgaagttag aagctccagt aagcagagtt    960

tgtggtctgg atactccatt tcctcttgtg tttgaaccat tctacatgcc caccaagaac   1020

aagatattgg atgcaatcaa atcgactgtg aattactag                          1059


<210> SEQ ID NO 78
<211> LENGTH: 352
<212> TYPE: PRT
<213> ORGANISM: Arabidopsis thaliana

<400> SEQUENCE: 78

Met Ala Ala Leu Leu Gly Arg Ser Cys Arg Lys Leu Ser Phe Pro Ser
 1               5                  10                  15

Leu Ser His Gly Ala Arg Arg Val Ser Thr Glu Thr Gly Lys Pro Leu
            20                  25                  30

Asn Leu Tyr Ser Ala Ile Asn Gln Ala Leu His Ile Ala Leu Asp Thr
        35                  40                  45

Asp Pro Arg Ser Tyr Val Phe Gly Glu Asp Val Gly Phe Gly Gly Val
    50                  55                  60

Phe Arg Cys Thr Thr Gly Leu Ala Glu Arg Phe Gly Lys Asn Arg Val
65                  70                  75                  80

Phe Asn Thr Pro Leu Cys Glu Gln Gly Ile Val Gly Phe Gly Ile Gly
                85                  90                  95

Leu Ala Ala Met Gly Asn Arg Ala Ile Val Glu Ile Gln Phe Ala Asp
            100                 105                 110

Tyr Ile Tyr Pro Ala Phe Asp Gln Ile Val Asn Glu Ala Ala Lys Phe
        115                 120                 125

Arg Tyr Arg Ser Gly Asn Gln Phe Asn Cys Gly Gly Leu Thr Ile Arg
    130                 135                 140

Ala Pro Tyr Gly Ala Val Gly His Gly Gly His Tyr His Ser Gln Ser
145                 150                 155                 160

Pro Glu Ala Phe Phe Cys His Val Pro Gly Ile Lys Val Val Ile Pro
                165                 170                 175

Arg Ser Pro Arg Glu Ala Lys Gly Leu Leu Leu Ser Cys Ile Arg Asp
            180                 185                 190

Pro Asn Pro Val Val Phe Phe Glu Pro Lys Trp Leu Tyr Arg Gln Ala
        195                 200                 205

Val Glu Glu Val Pro Glu His Asp Tyr Met Ile Pro Leu Ser Glu Ala
    210                 215                 220

Glu Val Ile Arg Glu Gly Asn Asp Ile Thr Leu Val Gly Trp Gly Ala
225                 230                 235                 240

Gln Leu Thr Val Met Glu Gln Ala Cys Leu Asp Ala Glu Lys Glu Gly
                245                 250                 255

Ile Ser Cys Glu Leu Ile Asp Leu Lys Thr Leu Leu Pro Trp Asp Lys
            260                 265                 270

Glu Thr Val Glu Ala Ser Val Lys Lys Thr Gly Arg Leu Leu Ile Ser
        275                 280                 285

His Glu Ala Pro Val Thr Gly Gly Phe Gly Ala Glu Ile Ser Ala Thr
```

```
    290                 295                 300

Ile Leu Glu Arg Cys Phe Leu Lys Leu Glu Ala Pro Val Ser Arg Val
305                 310                 315                 320

Cys Gly Leu Asp Thr Pro Phe Pro Leu Val Phe Glu Pro Phe Tyr Met
                325                 330                 335

Pro Thr Lys Asn Lys Ile Leu Asp Ala Ile Lys Ser Thr Val Asn Tyr
            340                 345                 350
```

<210> SEQ ID NO 79
<211> LENGTH: 1419
<212> TYPE: DNA
<213> ORGANISM: Arabidopsis thaliana

<400> SEQUENCE: 79

```
atggctctgc atttgagatc ttctttttca tcaaaatcga ctttactcaa tattctcaga     60

cacaacctcg gtttcggttc taggagccac gtgactcggc atatccgcca aatcctacca    120

catgaccccc cgcttcgagg ttcacagaat ccaattagcc gtctctgtaa taccatggcg    180

gagccagaga cactctctag ttttgttcag cacgaatacg ccaacaatca tcaggtaatg    240

gactttccag gaggaaaggt agctttcaca cctgagattc aattcatatc agaatctgat    300

aaagagcgtg ttccttgcta ccgtgttctt gatgacaatg gccaacttat caccaacagc    360

cagtttgttc aggttagcga ggaggttgcg gtgaagatat atagcgatat ggttactctt    420

caaattatgg ataacatatt ctacgaagct caaagacaag gcagactttc cttttacgct    480

actgcaatcg gtgaagaggc cattaatatt gcatcagctg ctgctctcac tcctcaagat    540

gttatctttc ctcagtacag agagcctggt gttctactat ggcgtggttt cacgcttcaa    600

gaatttgcaa accagtgttt tgggaacaaa tctgattatg gaaaaggcag gcagatgccc    660

gtccactatg gctctaacaa gctcaattat tttaccgttt ctgcaaccat tgctacgcag    720

ttaccaaacg cggttggtgc tgcttattcc ttaaagatgg acaagaagga tgcatgtgcg    780

gtcacatatt ttggcgatgg tggcacgagt gagggagatt tccatgctgc tttgaatatt    840

gcagcagtta tggaagctcc tgttttattt atttgccgga acaatggatg ggccatcagt    900

actcccacct cagatcagtt ccgaagtgat ggtgtagtgg tcaaaggccg tgcttatgga    960

attcgaagta tacgtgtgga tggaaatgat gcacttgcca tgtacagtgc ggtacatact   1020

gctcgcgaaa tggcaattag agaacagagg ccaatcttga ttgaggcctt aacataccgt   1080

gtaggacacc attcaacatc agatgattcc actaggtacc gctctgcagg tgagatagag   1140

tggtggaaca aagcaagaaa cccactgtct aggtttagga catggattga aagtaatggc   1200

tggtggagtg ataaaacgga atcggatctg agaagcagaa tcaaaaaaga gatgttagaa   1260

gcgctccggg ttgcagagaa gactgagaaa ccgaatctgc agaacatgtt ctcagatgtc   1320

tacgatgttc ctccatctaa cctcagggaa caagaacttc tggtgaggca gacgatcaat   1380

agtcacccac aagattaccc atcagatgtg cctctttag                          1419
```

<210> SEQ ID NO 80
<211> LENGTH: 472
<212> TYPE: PRT
<213> ORGANISM: Arabidopsis thaliana

<400> SEQUENCE: 80

```
Met Ala Leu His Leu Arg Ser Ser Phe Ser Ser Lys Ser Thr Leu Leu
 1               5                  10                  15

Asn Ile Leu Arg His Asn Leu Gly Phe Gly Ser Arg Ser His Val Thr
            20                  25                  30
```

```
Arg His Ile Arg Gln Ile Leu Pro His Asp Pro Pro Leu Arg Gly Ser
        35                  40                  45

Gln Asn Pro Ile Ser Arg Leu Cys Asn Thr Met Ala Glu Pro Glu Thr
    50                  55                  60

Leu Ser Ser Phe Val Gln His Glu Tyr Ala Asn Asn His Gln Val Met
65                  70                  75                  80

Asp Phe Pro Gly Gly Lys Val Ala Phe Thr Pro Glu Ile Gln Phe Ile
                85                  90                  95

Ser Glu Ser Asp Lys Glu Arg Val Pro Cys Tyr Arg Val Leu Asp Asp
            100                 105                 110

Asn Gly Gln Leu Ile Thr Asn Ser Gln Phe Val Gln Val Ser Glu Glu
        115                 120                 125

Val Ala Val Lys Ile Tyr Ser Asp Met Val Thr Leu Gln Ile Met Asp
    130                 135                 140

Asn Ile Phe Tyr Glu Ala Gln Arg Gln Gly Arg Leu Ser Phe Tyr Ala
145                 150                 155                 160

Thr Ala Ile Gly Glu Glu Ala Ile Asn Ile Ala Ser Ala Ala Ala Leu
                165                 170                 175

Thr Pro Gln Asp Val Ile Phe Pro Gln Tyr Arg Glu Pro Gly Val Leu
            180                 185                 190

Leu Trp Arg Gly Phe Thr Leu Gln Glu Phe Ala Asn Gln Cys Phe Gly
        195                 200                 205

Asn Lys Ser Asp Tyr Gly Lys Gly Arg Gln Met Pro Val His Tyr Gly
    210                 215                 220

Ser Asn Lys Leu Asn Tyr Phe Thr Val Ser Ala Thr Ile Ala Thr Gln
225                 230                 235                 240

Leu Pro Asn Ala Val Gly Ala Ala Tyr Ser Leu Lys Met Asp Lys Lys
                245                 250                 255

Asp Ala Cys Ala Val Thr Tyr Phe Gly Asp Gly Gly Thr Ser Glu Gly
            260                 265                 270

Asp Phe His Ala Ala Leu Asn Ile Ala Ala Val Met Glu Ala Pro Val
        275                 280                 285

Leu Phe Ile Cys Arg Asn Asn Gly Trp Ala Ile Ser Thr Pro Thr Ser
    290                 295                 300

Asp Gln Phe Arg Ser Asp Gly Val Val Val Lys Gly Arg Ala Tyr Gly
305                 310                 315                 320

Ile Arg Ser Ile Arg Val Asp Gly Asn Asp Ala Leu Ala Met Tyr Ser
                325                 330                 335

Ala Val His Thr Ala Arg Glu Met Ala Ile Arg Glu Gln Arg Pro Ile
            340                 345                 350

Leu Ile Glu Ala Leu Thr Tyr Arg Val Gly His His Ser Thr Ser Asp
        355                 360                 365

Asp Ser Thr Arg Tyr Arg Ser Ala Gly Glu Ile Glu Trp Trp Asn Lys
    370                 375                 380

Ala Arg Asn Pro Leu Ser Arg Phe Arg Thr Trp Ile Glu Ser Asn Gly
385                 390                 395                 400

Trp Trp Ser Asp Lys Thr Glu Ser Asp Leu Arg Ser Arg Ile Lys Lys
                405                 410                 415

Glu Met Leu Glu Ala Leu Arg Val Ala Glu Lys Thr Glu Lys Pro Asn
            420                 425                 430

Leu Gln Asn Met Phe Ser Asp Val Tyr Asp Val Pro Pro Ser Asn Leu
        435                 440                 445

Arg Glu Gln Glu Leu Leu Val Arg Gln Thr Ile Asn Ser His Pro Gln
```

450 455 460

Asp Tyr Pro Ser Asp Val Pro Leu
465 470

<210> SEQ ID NO 81
<211> LENGTH: 1872
<212> TYPE: DNA
<213> ORGANISM: Arabidopsis thaliana

<400> SEQUENCE: 81
atgcaatcag ctatggcgct ttcgttctcc cagacgtcgt ttacaagacc aaaccacgtg 60
ctcggatcat ctggttctgt tttctctacg cccagaagtc tccggttctg cggactccgg 120
cgggaagcgt ttggtttctc aacgtcgaat cagttggcta ttcgcagtaa ccgaatccaa 180
tttctaagta ggaagtcatt ccaagtctcc gcttctgctt caagtaatgg taatggcgct 240
ccaccgaaat ctttcgatta cgatttgatc atcatcggag ctggagttgg tggccacgga 300
gctgctttgc acgccgttga aaagggactt aaaacagcca ttattgaagg agatgttgtt 360
ggagggactt gtgttaacag aggatgtgtg ccttctaaag ctcttcttgc tgttagtggt 420
cgaatgcggg aacttcagaa cgaacatcac atgaagtcct ttggtctcca ggtttcagct 480
gctggatatg atcgtcaggg tgtggcagat catgctaata atctggctac caaaatacga 540
aacaatctga ccaattcaat gaaggcaatt ggtgttgaca tattgactgg atttggcagt 600
gttctgggtc cacaaaaggt taaatatggg aaggacaata ttattactgc aaaagatata 660
atcattgcca ctggatctgt gccgtttgtc cctaaaggaa ttgaagttga tggaaagact 720
gtgatcacca gtgaccatgc tttgaaatta gagtctgtcc ctgagtggat tgcaattgta 780
ggaagtggtt atattggtct tgagttcagt gatgtttaca cagctcttgg aagtgaggta 840
acttttatag aagcactgga tcagctaatg cctggatttg atcctgagat cagtaagcta 900
gctcagaggg ttttgataaa tccaagaaag attgactatc atactggagt ctttgcaagc 960
aaaattactc cggcaaggga tggaaaacca gttctgattg agcttattga tgccaaaacc 1020
aaggaaccta aggatacttt ggaggtagat gctgctctta ttgctactgg gagagctcca 1080
ttcaccaatg gacttggctt ggaaaatgtc aatgttgtga cgcagagagg tttcatacca 1140
gttgatgagc gaatgcgtgt gatcgatgga aaggggactc tggttccgaa cttgtactgc 1200
attggtgatg ccaatggtaa attgatgctt gcacatgcag ccagtgccca aggaatttct 1260
gtggtcgagc aagtcagcgg cagagatcat gtgcttaatc atcttagcat cccagctgct 1320
tgctttactc atcctgaaat cagcatggtg ggattaacag agcctcaagc aaaagaaaaa 1380
ggcgagaagg aaggatttaa agttagtgtt gtcaagacaa gtttcaaggc taacacaaag 1440
gccctagctg aaaatgaagg agaaggaata gctaagatga tataccgacc tgacaatggt 1500
gaaatcttag gagttcatat atttggactg catgcagctg accttatcca tgaagcttct 1560
aatgcgattg ctctaggaac gcgtattcag gacataaaat tggcagttca tgcacatcca 1620
acactctctg aggtcctcga cgaactgttc aaagcagcca aggttgaaag tcatgctacg 1680
acaaggacag gagatgcaaa gataaagcta aacacgaacc aggaagatcg aaaaggaaga 1740
agaagaggag gagatgatga gaaacaacct tccgtaagta aagacttgaa agatatatct 1800
acaaggcctt cttctttctt tgagaatatt tctgttggag tcttgtctct gctttcactt 1860
atatttgttt aa 1872

<210> SEQ ID NO 82
<211> LENGTH: 623

```
<212> TYPE: PRT
<213> ORGANISM: Arabidopsis thaliana

<400> SEQUENCE: 82

Met Gln Ser Ala Met Ala Leu Ser Phe Ser Gln Thr Ser Phe Thr Arg
 1               5                  10                  15

Pro Asn His Val Leu Gly Ser Ser Gly Ser Val Phe Ser Thr Pro Arg
            20                  25                  30

Ser Leu Arg Phe Cys Gly Leu Arg Arg Glu Ala Phe Gly Phe Ser Thr
        35                  40                  45

Ser Asn Gln Leu Ala Ile Arg Ser Asn Arg Ile Gln Phe Leu Ser Arg
    50                  55                  60

Lys Ser Phe Gln Val Ser Ala Ser Ala Ser Ser Asn Gly Asn Gly Ala
65                  70                  75                  80

Pro Pro Lys Ser Phe Asp Tyr Asp Leu Ile Ile Ile Gly Ala Gly Val
                85                  90                  95

Gly Gly His Gly Ala Ala Leu His Ala Val Glu Lys Gly Leu Lys Thr
            100                 105                 110

Ala Ile Ile Glu Gly Asp Val Val Gly Gly Thr Cys Val Asn Arg Gly
        115                 120                 125

Cys Val Pro Ser Lys Ala Leu Leu Ala Val Ser Gly Arg Met Arg Glu
    130                 135                 140

Leu Gln Asn Glu His His Met Lys Ser Phe Gly Leu Gln Val Ser Ala
145                 150                 155                 160

Ala Gly Tyr Asp Arg Gln Gly Val Ala Asp His Ala Asn Asn Leu Ala
                165                 170                 175

Thr Lys Ile Arg Asn Asn Leu Thr Asn Ser Met Lys Ala Ile Gly Val
            180                 185                 190

Asp Ile Leu Thr Gly Phe Gly Ser Val Leu Gly Pro Gln Lys Val Lys
        195                 200                 205

Tyr Gly Lys Asp Asn Ile Ile Thr Ala Lys Asp Ile Ile Ile Ala Thr
    210                 215                 220

Gly Ser Val Pro Phe Val Pro Lys Gly Ile Glu Val Asp Gly Lys Thr
225                 230                 235                 240

Val Ile Thr Ser Asp His Ala Leu Lys Leu Glu Ser Val Pro Glu Trp
                245                 250                 255

Ile Ala Ile Val Gly Ser Gly Tyr Ile Gly Leu Glu Phe Ser Asp Val
            260                 265                 270

Tyr Thr Ala Leu Gly Ser Glu Val Thr Phe Ile Glu Ala Leu Asp Gln
        275                 280                 285

Leu Met Pro Gly Phe Asp Pro Glu Ile Ser Lys Leu Ala Gln Arg Val
    290                 295                 300

Leu Ile Asn Pro Arg Lys Ile Asp Tyr His Thr Gly Val Phe Ala Ser
305                 310                 315                 320

Lys Ile Thr Pro Ala Arg Asp Gly Lys Pro Val Leu Ile Glu Leu Ile
                325                 330                 335

Asp Ala Lys Thr Lys Glu Pro Lys Asp Thr Leu Glu Val Asp Ala Ala
            340                 345                 350

Leu Ile Ala Thr Gly Arg Ala Pro Phe Thr Asn Gly Leu Gly Leu Glu
        355                 360                 365

Asn Val Asn Val Val Thr Gln Arg Gly Phe Ile Pro Val Asp Glu Arg
    370                 375                 380

Met Arg Val Ile Asp Gly Lys Gly Thr Leu Val Pro Asn Leu Tyr Cys
385                 390                 395                 400
```

```
Ile Gly Asp Ala Asn Gly Lys Leu Met Leu Ala His Ala Ala Ser Ala
                405                 410                 415

Gln Gly Ile Ser Val Val Glu Gln Val Ser Gly Arg Asp His Val Leu
            420                 425                 430

Asn His Leu Ser Ile Pro Ala Ala Cys Phe Thr His Pro Glu Ile Ser
        435                 440                 445

Met Val Gly Leu Thr Glu Pro Gln Ala Lys Glu Lys Gly Glu Lys Glu
    450                 455                 460

Gly Phe Lys Val Ser Val Val Lys Thr Ser Phe Lys Ala Asn Thr Lys
465                 470                 475                 480

Ala Leu Ala Glu Asn Glu Gly Glu Gly Ile Ala Lys Met Ile Tyr Arg
                485                 490                 495

Pro Asp Asn Gly Glu Ile Leu Gly Val His Ile Phe Gly Leu His Ala
            500                 505                 510

Ala Asp Leu Ile His Glu Ala Ser Asn Ala Ile Ala Leu Gly Thr Arg
        515                 520                 525

Ile Gln Asp Ile Lys Leu Ala Val His Ala His Pro Thr Leu Ser Glu
    530                 535                 540

Val Leu Asp Glu Leu Phe Lys Ala Ala Lys Val Glu Ser His Ala Thr
545                 550                 555                 560

Thr Arg Thr Gly Asp Ala Lys Ile Lys Leu Asn Thr Asn Gln Glu Asp
                565                 570                 575

Arg Lys Gly Arg Arg Arg Gly Gly Asp Asp Glu Lys Gln Pro Ser Val
            580                 585                 590

Ser Lys Asp Leu Lys Asp Ile Ser Thr Arg Pro Ser Ser Phe Phe Glu
        595                 600                 605

Asn Ile Ser Val Gly Val Leu Ser Leu Leu Ser Leu Ile Phe Val
    610                 615                 620
```

<210> SEQ ID NO 83
<211> LENGTH: 1119
<212> TYPE: DNA
<213> ORGANISM: Ralstonia eutropha

<400> SEQUENCE: 83

```
atgagaatct tcaagctgcc cgacctgggc gaaggcctgc aggaggccga gatcgtgacc     60

tggcacgtca agaccggcga caccgtggcc gctgaccagc cgctgctgtc ggtggagacg    120

gccaaggcca tcgtggaaat cccgtcgccc tatgcaggca ccatcgccaa gctgtttgcg    180

cagcccggcg atatcgtcca cctgggcgcg ccgctggtcg gcgtcgaggg tgcgggcgag    240

gatgccgacg ccggcaccgt ggtgggctcg gtccaggtcg gcacgcacgt ggtcaatgaa    300

gccgcgcccg cgggctccgc ggcacccgcc gcggccatgg ccgcccgcgt caaggccacg    360

ccggcggtgc gcgcgctggc gcgccggctc ggggtggacc tggcaatggc cacggcatcg    420

ggccccgagg gcgtcgtcac cgccgccgac gtggagcggg tagccagcac gctggccgaa    480

ctgggcacgc cggaacagct gcgcggcgtg cgccgggcga tggcgcagaa catggcgcgt    540

gcacaagccg aagtggccgc cgccaccgtg atggacgacg ccgacatcca cgcctggcag    600

cccggcgccg atgtcaccat ccggctggtg cgcgccctgg tggccggctg ccgcgccgaa    660

cccggcctca atgcctggta cgaaggccag accgcccgcc gccacgtact gaagaagatc    720

gacgtcggca tcgcggccga cctgcccgaa ggcctgttcg tgccggtgct gcgcgacgtc    780

ggcaaccgcg atgccgcaga cctgcgccac ggcctggacc gcatgcgcgc cgacatccgc    840

gcgcgcacca tcgcgccgga ggagatgcgc ggcaacacca tcacgctgtc caacttcggc    900
```

```
atgatcgcgg ggcgctatgc cgcgccaatc gtggtgccgc cgaccgtggc aatcctgggt    960

gcggggcgcg tgcgcgagga agtggtagca gccggcggcg tgccggcggt gcaccgggtg   1020

atgccgctga gcctgacctt tgaccatcgc gtggtgacgg gtggggaggc ggcgcggttt   1080

ctggcggcgg tgattgcgga tctggagatg gcggtgtag                          1119


<210> SEQ ID NO 84
<211> LENGTH: 372
<212> TYPE: PRT
<213> ORGANISM: Ralstonia eutropha

<400> SEQUENCE: 84

Met Arg Ile Phe Lys Leu Pro Asp Leu Gly Glu Gly Leu Gln Glu Ala
 1               5                  10                  15

Glu Ile Val Thr Trp His Val Lys Thr Gly Asp Thr Val Ala Ala Asp
            20                  25                  30

Gln Pro Leu Leu Ser Val Glu Thr Ala Lys Ala Ile Val Glu Ile Pro
        35                  40                  45

Ser Pro Tyr Ala Gly Thr Ile Ala Lys Leu Phe Ala Gln Pro Gly Asp
    50                  55                  60

Ile Val His Leu Gly Ala Pro Leu Val Gly Val Glu Gly Ala Gly Glu
65                  70                  75                  80

Asp Ala Asp Ala Gly Thr Val Val Gly Ser Val Gln Val Gly Thr His
                85                  90                  95

Val Val Asn Glu Ala Ala Pro Ala Gly Ser Ala Ala Pro Ala Ala Ala
            100                 105                 110

Met Ala Ala Arg Val Lys Ala Thr Pro Ala Val Arg Ala Leu Ala Arg
        115                 120                 125

Arg Leu Gly Val Asp Leu Ala Met Ala Thr Ala Ser Gly Pro Glu Gly
    130                 135                 140

Val Val Thr Ala Ala Asp Val Glu Arg Val Ala Ser Thr Leu Ala Glu
145                 150                 155                 160

Leu Gly Thr Pro Glu Gln Leu Arg Gly Val Arg Arg Ala Met Ala Gln
                165                 170                 175

Asn Met Ala Arg Ala Gln Ala Glu Val Ala Ala Ala Thr Val Met Asp
            180                 185                 190

Asp Ala Asp Ile His Ala Trp Gln Pro Gly Ala Asp Val Thr Ile Arg
        195                 200                 205

Leu Val Arg Ala Leu Val Ala Gly Cys Arg Ala Glu Pro Gly Leu Asn
    210                 215                 220

Ala Trp Tyr Glu Gly Gln Thr Ala Arg Arg His Val Leu Lys Lys Ile
225                 230                 235                 240

Asp Val Gly Ile Ala Ala Asp Leu Pro Glu Gly Leu Phe Val Pro Val
                245                 250                 255

Leu Arg Asp Val Gly Asn Arg Asp Ala Ala Asp Leu Arg His Gly Leu
            260                 265                 270

Asp Arg Met Arg Ala Asp Ile Arg Ala Arg Thr Ile Ala Pro Glu Glu
        275                 280                 285

Met Arg Gly Asn Thr Ile Thr Leu Ser Asn Phe Gly Met Ile Ala Gly
    290                 295                 300

Arg Tyr Ala Ala Pro Ile Val Val Pro Pro Thr Val Ala Ile Leu Gly
305                 310                 315                 320

Ala Gly Arg Val Arg Glu Glu Val Val Ala Ala Gly Gly Val Pro Ala
                325                 330                 335

Val His Arg Val Met Pro Leu Ser Leu Thr Phe Asp His Arg Val Val
```

```
            340                 345                 350

Thr Gly Gly Glu Ala Ala Arg Phe Leu Ala Ala Val Ile Ala Asp Leu
        355                 360                 365

Glu Met Ala Val
    370
```

<210> SEQ ID NO 85
<211> LENGTH: 1158
<212> TYPE: DNA
<213> ORGANISM: Rhodobacter sphaeroides

<400> SEQUENCE: 85

```
atgtttcacg ctccgatgac cttcgacctc ggcgaggaga tcgccgccct ccgcgagacc      60

gtccatgcct gggcgcagga gcgggtgaag cccatggccg cccggatcga ccgcgagaac     120

gtcttcccgg ccgagctctg gcgcgagatg ggcgagctcg ggcttctggg catcacggtc     180

cccgaggaat tcggcggctc ggacatgggc tatctcgccc atacggtcgc cgtggaggag     240

gtggcgcgcg cctcggcctc ggtctcgctc agctacgggg cgcattccaa cctctgcgtg     300

aaccagatcc gcctgaacgg cagccctgag cagaaggcgc gctatctgcc gaagctcgtc     360

tcgggcgagc atgtgggggc gctcgccatg tccgaggcgg gcgcgggctc ggacgtggtg     420

tcgatgaagc tcaaggccga gaagcggaac ggctactatg tcctcaacgg cacgaaatac     480

tggatcacca acgggccgga tgcggatgtt ctggtggtct atgccaagac cgaccctgag     540

gcgggcgcga agggcatcac tgccttcctg atcgaaaagt cgatgacggg cttctcgacc     600

tcgccgcact tcgacaaggt ggggatgcgc ggctcgaaca cgggcgagct gatcttcgag     660

aattgcgagg tgccgttcga gaatgtcctc gggcaggacg gcaagggggt gcgcgtcctc     720

atgtcggggc tcgattacga gcgcgtggtg ctgtcgggga tcggcacggg gatcatggcg     780

gcctgcctcg acgaggtggt gccctactgc cagagccgcc agcagttcgg tcagccgatc     840

ggaaacttcc agctgatgca gggcaagctc gccgacatgt atgtcgcgct gaacacggcg     900

cgggcctatg tctacgagac ggcgcgcgcc tgcgatgcgg ggcgggtgac gcgcgcggat     960

gcggcgggct gcgtgctcta tgcctcggag caggcgatgg tgcaggcgca tcaggcggtg    1020

caggcgctcg gcggcgcggg cttcctgaac gattccgtcg tgagccggct cttccgcgat    1080

gcgaagctga tggagatcgg ggcgggaact tccgagatcc gccggatgct catcggccgc    1140

gaacttatgg cgggctga                                                  1158
```

<210> SEQ ID NO 86
<211> LENGTH: 385
<212> TYPE: PRT
<213> ORGANISM: Rhodobacter sphaeroides

<400> SEQUENCE: 86

```
Met Phe His Ala Pro Met Thr Phe Asp Leu Gly Glu Glu Ile Ala Ala
 1               5                  10                  15

Leu Arg Glu Thr Val His Ala Trp Ala Gln Glu Arg Val Lys Pro Met
            20                  25                  30

Ala Ala Arg Ile Asp Arg Glu Asn Val Phe Pro Ala Glu Leu Trp Arg
        35                  40                  45

Glu Met Gly Glu Leu Gly Leu Leu Gly Ile Thr Val Pro Glu Glu Phe
    50                  55                  60

Gly Gly Ser Asp Met Gly Tyr Leu Ala His Thr Val Ala Val Glu Glu
65                  70                  75                  80

Val Ala Arg Ala Ser Ala Ser Val Ser Leu Ser Tyr Gly Ala His Ser
```

-continued

```
                85                  90                  95

Asn Leu Cys Val Asn Gln Ile Arg Leu Asn Gly Ser Pro Glu Gln Lys
            100                 105                 110

Ala Arg Tyr Leu Pro Lys Leu Val Ser Gly Glu His Val Gly Ala Leu
        115                 120                 125

Ala Met Ser Glu Ala Gly Ala Gly Ser Asp Val Val Ser Met Lys Leu
    130                 135                 140

Lys Ala Glu Lys Arg Asn Gly Tyr Tyr Val Leu Asn Gly Thr Lys Tyr
145                 150                 155                 160

Trp Ile Thr Asn Gly Pro Asp Ala Asp Val Leu Val Val Tyr Ala Lys
                165                 170                 175

Thr Asp Pro Glu Ala Gly Ala Lys Gly Ile Thr Ala Phe Leu Ile Glu
            180                 185                 190

Lys Ser Met Thr Gly Phe Ser Thr Ser Pro His Phe Asp Lys Val Gly
        195                 200                 205

Met Arg Gly Ser Asn Thr Gly Glu Leu Ile Phe Glu Asn Cys Glu Val
    210                 215                 220

Pro Phe Glu Asn Val Leu Gly Gln Asp Gly Lys Gly Val Arg Val Leu
225                 230                 235                 240

Met Ser Gly Leu Asp Tyr Glu Arg Val Val Leu Ser Gly Ile Gly Thr
                245                 250                 255

Gly Ile Met Ala Ala Cys Leu Asp Glu Val Val Pro Tyr Cys Gln Ser
            260                 265                 270

Arg Gln Gln Phe Gly Gln Pro Ile Gly Asn Phe Gln Leu Met Gln Gly
        275                 280                 285

Lys Leu Ala Asp Met Tyr Val Ala Leu Asn Thr Ala Arg Ala Tyr Val
    290                 295                 300

Tyr Glu Thr Ala Arg Ala Cys Asp Ala Gly Arg Val Thr Arg Ala Asp
305                 310                 315                 320

Ala Ala Gly Cys Val Leu Tyr Ala Ser Glu Gln Ala Met Val Gln Ala
                325                 330                 335

His Gln Ala Val Gln Ala Leu Gly Gly Ala Gly Phe Leu Asn Asp Ser
            340                 345                 350

Val Val Ser Arg Leu Phe Arg Asp Ala Lys Leu Met Glu Ile Gly Ala
        355                 360                 365

Gly Thr Ser Glu Ile Arg Arg Met Leu Ile Gly Arg Glu Leu Met Ala
    370                 375                 380

Gly
385
```

<210> SEQ ID NO 87
<211> LENGTH: 1275
<212> TYPE: DNA
<213> ORGANISM: Pseudomonas putida

<400> SEQUENCE: 87

```
atgacggtga ccctgctgac gtattcgcgg gcatgcccgc tcccacaggg ggcggggccg      60

gatcccaagc tatggtgtaa cccaatttca agaacaagaa ggtgccccag catgcattac     120

ccctccctga acttcgccct gggcgagacc atcgacatgc tccgcgacca ggtgcgcacc     180

ttcgtcgccg ctgaactggc cccaagggcc gcgcagatcg accacgacaa cctgttcccc     240

gccgacatgt ggcgcaagtt cggtgacatg ggcctgctgg gcatcaccgt accggaagag     300

tacggcggcg ctggcctggg ctacctggcc catgtggtgt cgatggaaga gatcagccgt     360

ggctccgcct cggtggcgct gtcctacggc gcccattcca acctgtgcgt caaccagatc     420
```

```
aaccgcaacg gcacccacga gcagaagctc aagtacctgc ccaagctgat cagcggcgag    480

cacatcggcg ccttggccat gagcgagccc aatgccggtt ccgacgtggt gtcgatgaag    540

ctgcgcgcag aaaaacgcgg cgatcactac gtgctcaacg gcagcaagac ctggatcacc    600

aacggtcccg acgccaacac ctacgtgatt tacgccaaga ccgacctgga caagggtgcg    660

cacggcatca ccgcgttcat cgtcgagcgc gactggaaag gcttcagccg cagcaacaag    720

ttcgacaagc tgggcatgcg cgggtccaac acctgcgagt tgttcttcga tggcgtggaa    780

gtgccggcag agaacattct gggccagctc aacggcggcg tgcgcgtcct tatgagcggc    840

ctggactacg aacgtgtggt gctgtccggc ggcccgaccg gcatcatgca aagctgcatg    900

gacctggtgg tgccgtatat ccacgaccgc aagcaattcg gccagagcat cggcgagttc    960

cagctgatcc agggcaagat tgccgacatg tacacccagc tcaatgccag ccgcgcctac   1020

ctgtatgccg tggctcaggc gtgcgaccgt ggcgaaacca cccgcaagga cgctgccggc   1080

gtgatcctgt acaccgccga gcgtgccacg caaatggccc tggaggcgat ccagattctt   1140

ggcggcaacg gctatatcaa cgaattcccg gctggccgcc tgttgcgcga cgccaagctg   1200

tacgaaatcg gtgccggcac cagtgaaatc cgccggatgc tgatcggccg cgaactgttc   1260

aacgaaaccc gctga                                                    1275


<210> SEQ ID NO 88
<211> LENGTH: 424
<212> TYPE: PRT
<213> ORGANISM: Pseudomonas putida

<400> SEQUENCE: 88

Met Thr Val Thr Leu Leu Thr Tyr Ser Arg Ala Cys Pro Leu Pro Gln
1               5                   10                  15

Gly Ala Gly Pro Asp Pro Lys Leu Trp Cys Asn Pro Ile Ser Arg Thr
            20                  25                  30

Arg Arg Cys Pro Ser Met His Tyr Pro Ser Leu Asn Phe Ala Leu Gly
        35                  40                  45

Glu Thr Ile Asp Met Leu Arg Asp Gln Val Arg Thr Phe Val Ala Ala
    50                  55                  60

Glu Leu Ala Pro Arg Ala Ala Gln Ile Asp His Asp Asn Leu Phe Pro
65                  70                  75                  80

Ala Asp Met Trp Arg Lys Phe Gly Asp Met Gly Leu Leu Gly Ile Thr
                85                  90                  95

Val Pro Glu Glu Tyr Gly Gly Ala Gly Leu Gly Tyr Leu Ala His Val
            100                 105                 110

Val Ser Met Glu Glu Ile Ser Arg Gly Ser Ala Ser Val Ala Leu Ser
        115                 120                 125

Tyr Gly Ala His Ser Asn Leu Cys Val Asn Gln Ile Asn Arg Asn Gly
    130                 135                 140

Thr His Glu Gln Lys Leu Lys Tyr Leu Pro Lys Leu Ile Ser Gly Glu
145                 150                 155                 160

His Ile Gly Ala Leu Ala Met Ser Glu Pro Asn Ala Gly Ser Asp Val
                165                 170                 175

Val Ser Met Lys Leu Arg Ala Glu Lys Arg Gly Asp His Tyr Val Leu
            180                 185                 190

Asn Gly Ser Lys Thr Trp Ile Thr Asn Gly Pro Asp Ala Asn Thr Tyr
        195                 200                 205

Val Ile Tyr Ala Lys Thr Asp Leu Asp Lys Gly Ala His Gly Ile Thr
    210                 215                 220
```

```
Ala Phe Ile Val Glu Arg Asp Trp Lys Gly Phe Ser Arg Ser Asn Lys
225                 230                 235                 240

Phe Asp Lys Leu Gly Met Arg Gly Ser Asn Thr Cys Glu Leu Phe Phe
                245                 250                 255

Asp Gly Val Glu Val Pro Ala Glu Asn Ile Leu Gly Gln Leu Asn Gly
            260                 265                 270

Gly Val Arg Val Leu Met Ser Gly Leu Asp Tyr Glu Arg Val Val Leu
        275                 280                 285

Ser Gly Gly Pro Thr Gly Ile Met Gln Ser Cys Met Asp Leu Val Val
    290                 295                 300

Pro Tyr Ile His Asp Arg Lys Gln Phe Gly Gln Ser Ile Gly Glu Phe
305                 310                 315                 320

Gln Leu Ile Gln Gly Lys Ile Ala Asp Met Tyr Thr Gln Leu Asn Ala
                325                 330                 335

Ser Arg Ala Tyr Leu Tyr Ala Val Ala Gln Ala Cys Asp Arg Gly Glu
            340                 345                 350

Thr Thr Arg Lys Asp Ala Ala Gly Val Ile Leu Tyr Thr Ala Glu Arg
        355                 360                 365

Ala Thr Gln Met Ala Leu Glu Ala Ile Gln Ile Leu Gly Gly Asn Gly
    370                 375                 380

Tyr Ile Asn Glu Phe Pro Ala Gly Arg Leu Leu Arg Asp Ala Lys Leu
385                 390                 395                 400

Tyr Glu Ile Gly Ala Gly Thr Ser Glu Ile Arg Arg Met Leu Ile Gly
                405                 410                 415

Arg Glu Leu Phe Asn Glu Thr Arg
            420
```

<210> SEQ ID NO 89
<211> LENGTH: 2100
<212> TYPE: DNA
<213> ORGANISM: Dictyostelium discoideum

<400> SEQUENCE: 89

```
atgtttagtt taggaaaatt ggttaaaaaa gatgcttttt tttatagata tataacaaat     60

gttaataaag atttaaaaat taaaccaatt acaaagatat taattgcaaa tagaggtgaa    120

attgcatgtc gtgtaatgag aacagcaaaa tcaaaaggtg taaaaaccgt agcagtttat    180

agtgaagcag ataagaattc attacatgtt tcaatggcag atgagagtta tttaattgga    240

ccagcagcag ccaaagagag ttatttatgt ggaaataaga tcatagatgt agcaaagaga    300

tctggagcac aagcaattca tccaggttat ggtttcttat cagagaattc agattttgct    360

gatctctgtg agagagaagg tatcattttc attggaccac catcagatgc aatcaaagca    420

atgggtagca aaagtgcctc aaaggatatt atgatcaaag ctggcgtacc aaccatccca    480

ggttaccacg gtgaagatca gtcaatgagt gtgttgaaga gtgaggctgc aaagattggc    540

tatccagtat tgattaaagc tgttatgggt ggtggtggta aaggtatgag aatcgttgag    600

agagaggagg atttagagga cggtgttgag tcctcaaaga gagaggccac cgcatccttt    660

ggtgattcta gagttttggt agaaaagtat ttagttcatc caagacatgt ggagattcaa    720

gttttcgccg atagacatgg taattgtgtt cacctctttg agagagattg tagtgtacaa    780

agacgtcatc aaaagattat cgaagaggca ccagctccac atctctctga ggagcttaga    840

aagaaaatgg gtgatgctgc agttgccgcc gccaaggctg taggttacgt tggtgctggt    900

accgtagaat tcattttatc cgctgataat agcttcttct ttatggagat gaatacccgt    960
```

-continued

```
cttcaagtgg agcatccaat cactgaaatg atcaccaaac aagatttagt agaatggcaa   1020

ttgaaggtag ccgaatccca aacactccca atggagcaag aacaattgaa gattcatggt   1080

cactctttcg aagctcgtat ctacgcagag aatccagata gtgatttctt accaggtaca   1140

ggtaaattag cacatctttc aacaccaaca ccatccgata ctttacgtgt tgaaactggt   1200

gtacgtcaag gcgatgaagt tagcgtttac tatgatccaa tgattgccaa attggtggta   1260

tgggatcaag atagagagaa ggcattaaga tatttaagaa atgctctcga cgagtaccat   1320

atcattggtc tcaatacaaa catctctttc cttaagagat tatcaactca tccttcattt   1380

atggctggtg aagttgaaac tggtttcatc ccaattcaca gagaatcctt aatggcccca   1440

caagctccaa tgtctgatga ttcattagca ttggctgcca caagtttact cttaaaagag   1500

atcactcaac aaaaatcaaa agaagatcca aactcacctt ggtcaagttt aggtggtttc   1560

cgtattaatc ataatttaaa aaaacaagtt aaattcaatc aaaaagataa taaagttgtt   1620

gttaatgttg aattcattgg tggtggtggt gctgctgcta atggtaaaca taactttaaa   1680

gtaactttag ataatggtaa tgtcgttgaa gttttagatg caaaattaaa tcaaaataat   1740

gaaactatta gtgctcatgt aaatggtaga ttctataata acattaaatc cgtcattgta   1800

aaggatactt taacaatctt taatgaaggt caacaatacc aattggatat tcctcaagat   1860

gttaaaccaa aaggtgctga tggtgtattg ggttctttag tttcaccaat gcctggaaaa   1920

atcactaaag ttatggtaaa tgttggtgac atggttaaaa agggtcaacc aatcttactc   1980

atggaagcaa tgaaaatgga acatactatt cgttctccaa tcgatggtaa agttgaatca   2040

ttaccttata atgttaatga aatcgttgag gataagaaaa ctttggctgt tattgtttaa   2100
```

<210> SEQ ID NO 90
<211> LENGTH: 699
<212> TYPE: PRT
<213> ORGANISM: Dictyostelium discoideum

<400> SEQUENCE: 90

```
Met Phe Ser Leu Gly Lys Leu Val Lys Lys Asp Ala Phe Phe Tyr Arg
 1               5                  10                  15

Tyr Ile Thr Asn Val Asn Lys Asp Leu Lys Ile Lys Pro Ile Thr Lys
            20                  25                  30

Ile Leu Ile Ala Asn Arg Gly Glu Ile Ala Cys Arg Val Met Arg Thr
        35                  40                  45

Ala Lys Ser Lys Gly Val Lys Thr Val Ala Val Tyr Ser Glu Ala Asp
    50                  55                  60

Lys Asn Ser Leu His Val Ser Met Ala Asp Glu Ser Tyr Leu Ile Gly
65                  70                  75                  80

Pro Ala Ala Ala Lys Glu Ser Tyr Leu Cys Gly Asn Lys Ile Ile Asp
                85                  90                  95

Val Ala Lys Arg Ser Gly Ala Gln Ala Ile His Pro Gly Tyr Gly Phe
            100                 105                 110

Leu Ser Glu Asn Ser Asp Phe Ala Asp Leu Cys Glu Arg Glu Gly Ile
        115                 120                 125

Ile Phe Ile Gly Pro Pro Ser Asp Ala Ile Lys Ala Met Gly Ser Lys
    130                 135                 140

Ser Ala Ser Lys Asp Ile Met Ile Lys Ala Gly Val Pro Thr Ile Pro
145                 150                 155                 160

Gly Tyr His Gly Glu Asp Gln Ser Met Ser Val Leu Lys Ser Glu Ala
                165                 170                 175

Ala Lys Ile Gly Tyr Pro Val Leu Ile Lys Ala Val Met Gly Gly Gly
```

-continued

```
            180                 185                 190

Gly Lys Gly Met Arg Ile Val Glu Arg Glu Glu Asp Leu Glu Asp Gly
        195                 200                 205

Val Glu Ser Ser Lys Arg Glu Ala Thr Ala Ser Phe Gly Asp Ser Arg
    210                 215                 220

Val Leu Val Glu Lys Tyr Leu Val His Pro Arg His Val Glu Ile Gln
225                 230                 235                 240

Val Phe Ala Asp Arg His Gly Asn Cys Val His Leu Phe Glu Arg Asp
                245                 250                 255

Cys Ser Val Gln Arg Arg His Gln Lys Ile Ile Glu Glu Ala Pro Ala
            260                 265                 270

Pro His Leu Ser Glu Glu Leu Arg Lys Lys Met Gly Asp Ala Ala Val
        275                 280                 285

Ala Ala Ala Lys Ala Val Gly Tyr Val Gly Ala Gly Thr Val Glu Phe
    290                 295                 300

Ile Leu Ser Ala Asp Asn Ser Phe Phe Phe Met Glu Met Asn Thr Arg
305                 310                 315                 320

Leu Gln Val Glu His Pro Ile Thr Glu Met Ile Thr Lys Gln Asp Leu
                325                 330                 335

Val Glu Trp Gln Leu Lys Val Ala Glu Ser Gln Thr Leu Pro Met Glu
            340                 345                 350

Gln Glu Gln Leu Lys Ile His Gly His Ser Phe Glu Ala Arg Ile Tyr
        355                 360                 365

Ala Glu Asn Pro Asp Ser Asp Phe Leu Pro Gly Thr Gly Lys Leu Ala
    370                 375                 380

His Leu Ser Thr Pro Thr Pro Ser Asp Thr Leu Arg Val Glu Thr Gly
385                 390                 395                 400

Val Arg Gln Gly Asp Glu Val Ser Val Tyr Tyr Asp Pro Met Ile Ala
                405                 410                 415

Lys Leu Val Val Trp Asp Gln Asp Arg Glu Lys Ala Leu Arg Tyr Leu
            420                 425                 430

Arg Asn Ala Leu Asp Glu Tyr His Ile Ile Gly Leu Asn Thr Asn Ile
        435                 440                 445

Ser Phe Leu Lys Arg Leu Ser Thr His Pro Ser Phe Met Ala Gly Glu
    450                 455                 460

Val Glu Thr Gly Phe Ile Pro Ile His Arg Glu Ser Leu Met Ala Pro
465                 470                 475                 480

Gln Ala Pro Met Ser Asp Asp Ser Leu Ala Leu Ala Ala Thr Ser Leu
                485                 490                 495

Leu Leu Lys Glu Ile Thr Gln Gln Lys Ser Lys Glu Asp Pro Asn Ser
            500                 505                 510

Pro Trp Ser Ser Leu Gly Gly Phe Arg Ile Asn His Asn Leu Lys Lys
        515                 520                 525

Gln Val Lys Phe Asn Gln Lys Asp Asn Lys Val Val Val Asn Val Glu
    530                 535                 540

Phe Ile Gly Gly Gly Gly Ala Ala Ala Asn Gly Lys His Asn Phe Lys
545                 550                 555                 560

Val Thr Leu Asp Asn Gly Asn Val Val Glu Val Leu Asp Ala Lys Leu
                565                 570                 575

Asn Gln Asn Asn Glu Thr Ile Ser Ala His Val Asn Gly Arg Phe Tyr
            580                 585                 590

Asn Asn Ile Lys Ser Val Ile Val Lys Asp Thr Leu Thr Ile Phe Asn
        595                 600                 605
```

-continued

```
Glu Gly Gln Gln Tyr Gln Leu Asp Ile Pro Gln Asp Val Lys Pro Lys
    610                 615                 620

Gly Ala Asp Gly Val Leu Gly Ser Leu Val Ser Pro Met Pro Gly Lys
625                 630                 635                 640

Ile Thr Lys Val Met Val Asn Val Gly Asp Met Val Lys Lys Gly Gln
                645                 650                 655

Pro Ile Leu Leu Met Glu Ala Met Lys Met Glu His Thr Ile Arg Ser
            660                 665                 670

Pro Ile Asp Gly Lys Val Glu Ser Leu Pro Tyr Asn Val Asn Glu Ile
        675                 680                 685

Val Glu Asp Lys Lys Thr Leu Ala Val Ile Val
    690                 695
```

<210> SEQ ID NO 91
<211> LENGTH: 1767
<212> TYPE: DNA
<213> ORGANISM: Dictyostelium discoideum

<400> SEQUENCE: 91

```
atgttaaaat caatttcatt attaaaaaat aatcaaatat tattaaaaaa tataattaat     60

aatggtagaa ttataaataa tgttggtgaa aaattatcat caaaatcatt attaaaaatt    120

aattattcat catcaacaac tgatagaaca tttaatattt tagatggtac aattgataag    180

aattcagcag aatataaaga taatttaatt aatatgaatt caacattaaa acaattaaaa    240

gaaaatattg aaaagattaa attaggtggt ggtgaaaaat taaatcaaaa gaatatttca    300

cgtggaaagt tattagtacg tgaacgtatt gaagcattga ttgatgttgg atcaccattt    360

ttagagtttt ctcaattggc aggttgggga atgtatggta aggaggaggt tgcagcaggt    420

ggtatcatca caggtattgg taaaattcat ggtgttgaat gtgttattgt cgcaaatgac    480

tcaaccgtga agggaggtac ctactttcca atcactgtta aaaagcattt acgtgcacaa    540

gagattgccc aagagaataa tttaccatgt atttatttag tcgatagcgg tggtgcaaat    600

ttgccacgtc aagctgacgt gttcccagat cgtgaccatt ttggaagaat cttcttcaat    660

caagctaata tgtctgcaaa acgtattcca caaattgccg ttgtcatggg ttcatgtacc    720

gccggtggtg catacgtgcc agccatggct gacgaatcgg ttattgtcaa gggcaccggc    780

actatcttct tgggtggtcc accattggtc aaggctgcaa ctggtgagat tgtaacaagc    840

gaggagttgg gtggtgccga cctccattgt cgtacctctg gtgtcaccga tcattatgct    900

cgtgacgatg ccgaggccat cgccatcact cgtcgtatcg tgtccaattt aaatagaaag    960

aaacaaccat caccagtgat cactgaaacc gaggagccac tctatccaac tagtgaattg   1020

gctggtatcg taccaagtga tttaaagaag aatttcgata ttcgtaaggt tatcgcacgt   1080

ttagtcgatg gtagtagatt cgatgaattc aaagaactct atggcacaac tttaatttgt   1140

ggttttgcac gtgtacatgg tatgccagtt ggtatcatcg ccaacaacgg tattctcttt   1200

agtgaaagtg ccgtcaaggg tgcccatttc attgaacttt gcaatcaaag aggtatcccc   1260

ttagtcttcc ttcaaaacat cactggtttc atggttggta aaacttatga atctaaaggt   1320

atagccaagg atggcgctaa aatggtcatg gctgttgcca ccgccaaagt tccaaagatt   1380

acaatgatca ttggtggtag ttttggtgct ggtaattatg gtatgtgtgg tcgttcctac   1440

agtccacgtt tcctttacat gtggccaaat gctaaaatct ctgttatggg tggagaacaa   1500

gctgcctctg ttttagctca aattcaaaag gataacatgg caaaagaaaa taaacaatgg   1560

tcaccagaag aagaaaatac tttcaaaaaa ccaatctctg ataaattcga agaagaaggt   1620
```

-continued tcaatctatt acagttcagc tcgttgttgg gatgatggtg ttatcgatcc acaagattct 1680
cgtaaagtta tcgctttaag tttaagtgct tgtatgaatc aaccaattaa tccaccatct 1740
gatggttttg gtgttttcag aatgtaa 1767

<210> SEQ ID NO 92
<211> LENGTH: 588
<212> TYPE: PRT
<213> ORGANISM: Dictyostelium discoideum

<400> SEQUENCE: 92

Met Leu Lys Ser Ile Ser Leu Leu Lys Asn Asn Gln Ile Leu Leu Lys
1 5 10 15

Asn Ile Ile Asn Asn Gly Arg Ile Ile Asn Asn Val Gly Glu Lys Leu
20 25 30

Ser Ser Lys Ser Leu Leu Lys Ile Asn Tyr Ser Ser Ser Thr Thr Asp
35 40 45

Arg Thr Phe Asn Ile Leu Asp Gly Thr Ile Asp Lys Asn Ser Ala Glu
50 55 60

Tyr Lys Asp Asn Leu Ile Asn Met Asn Ser Thr Leu Lys Gln Leu Lys
65 70 75 80

Glu Asn Ile Glu Lys Ile Lys Leu Gly Gly Gly Glu Lys Leu Asn Gln
85 90 95

Lys Asn Ile Ser Arg Gly Lys Leu Leu Val Arg Glu Arg Ile Glu Ala
100 105 110

Leu Ile Asp Val Gly Ser Pro Phe Leu Glu Phe Ser Gln Leu Ala Gly
115 120 125

Trp Gly Met Tyr Gly Lys Glu Glu Val Ala Ala Gly Gly Ile Ile Thr
130 135 140

Gly Ile Gly Lys Ile His Gly Val Glu Cys Val Ile Val Ala Asn Asp
145 150 155 160

Ser Thr Val Lys Gly Gly Thr Tyr Phe Pro Ile Thr Val Lys Lys His
165 170 175

Leu Arg Ala Gln Glu Ile Ala Gln Glu Asn Asn Leu Pro Cys Ile Tyr
180 185 190

Leu Val Asp Ser Gly Gly Ala Asn Leu Pro Arg Gln Ala Asp Val Phe
195 200 205

Pro Asp Arg Asp His Phe Gly Arg Ile Phe Phe Asn Gln Ala Asn Met
210 215 220

Ser Ala Lys Arg Ile Pro Gln Ile Ala Val Val Met Gly Ser Cys Thr
225 230 235 240

Ala Gly Gly Ala Tyr Val Pro Ala Met Ala Asp Glu Ser Val Ile Val
245 250 255

Lys Gly Thr Gly Thr Ile Phe Leu Gly Gly Pro Pro Leu Val Lys Ala
260 265 270

Ala Thr Gly Glu Ile Val Thr Ser Glu Glu Leu Gly Gly Ala Asp Leu
275 280 285

His Cys Arg Thr Ser Gly Val Thr Asp His Tyr Ala Arg Asp Asp Ala
290 295 300

Glu Ala Ile Ala Ile Thr Arg Arg Ile Val Ser Asn Leu Asn Arg Lys
305 310 315 320

Lys Gln Pro Ser Pro Val Ile Thr Glu Thr Glu Glu Pro Leu Tyr Pro
325 330 335

Thr Ser Glu Leu Ala Gly Ile Val Pro Ser Asp Leu Lys Lys Asn Phe
340 345 350

```
Asp Ile Arg Lys Val Ile Ala Arg Leu Val Asp Gly Ser Arg Phe Asp
        355                 360                 365

Glu Phe Lys Glu Leu Tyr Gly Thr Thr Leu Ile Cys Gly Phe Ala Arg
    370                 375                 380

Val His Gly Met Pro Val Gly Ile Ile Ala Asn Asn Gly Ile Leu Phe
385                 390                 395                 400

Ser Glu Ser Ala Val Lys Gly Ala His Phe Ile Glu Leu Cys Asn Gln
                405                 410                 415

Arg Gly Ile Pro Leu Val Phe Leu Gln Asn Ile Thr Gly Phe Met Val
            420                 425                 430

Gly Lys Thr Tyr Glu Ser Lys Gly Ile Ala Lys Asp Gly Ala Lys Met
        435                 440                 445

Val Met Ala Val Ala Thr Ala Lys Val Pro Lys Ile Thr Met Ile Ile
    450                 455                 460

Gly Gly Ser Phe Gly Ala Gly Asn Tyr Gly Met Cys Gly Arg Ser Tyr
465                 470                 475                 480

Ser Pro Arg Phe Leu Tyr Met Trp Pro Asn Ala Lys Ile Ser Val Met
                485                 490                 495

Gly Gly Glu Gln Ala Ala Ser Val Leu Ala Gln Ile Gln Lys Asp Asn
            500                 505                 510

Met Ala Lys Glu Asn Lys Gln Trp Ser Pro Glu Glu Glu Asn Thr Phe
        515                 520                 525

Lys Lys Pro Ile Ser Asp Lys Phe Glu Glu Glu Gly Ser Ile Tyr Tyr
    530                 535                 540

Ser Ser Ala Arg Cys Trp Asp Asp Gly Val Ile Asp Pro Gln Asp Ser
545                 550                 555                 560

Arg Lys Val Ile Ala Leu Ser Leu Ser Ala Cys Met Asn Gln Pro Ile
                565                 570                 575

Asn Pro Pro Ser Asp Gly Phe Gly Val Phe Arg Met
            580                 585
```

<210> SEQ ID NO 93
<211> LENGTH: 2178
<212> TYPE: DNA
<213> ORGANISM: Homo sapiens

<400> SEQUENCE: 93

```
atggcggcgg cctctgcggt gtcggtgctg ctggtggcgg cggagaggaa ccggtggcat      60

cgtctcccga gcctgctcct gccgccgagg acatgggtgt ggaggcaaag aaccatgaag     120

tacacaacag ccacaggaag aaacattacc aaggtcctca ttgcaaacag aggagaaatt     180

gcctgcaggg tgatgcgcac agccaaaaaa ctgggtgtac agactgtggc ggtttatagt     240

gaggctgaca gaaattccat gcatgtagat atggcagatg aagcatattc catcggcccc     300

gctccctccc agcagagcta cctatctatg gagaaaatca ttcaagtggc caagacctct     360

gctgcacagg ctatccatcc aggatgcggt tttctctcag aaaacatgga atttgctgaa     420

ctttgtaagc aagaaggaat tatttttata ggccctcctc catctgcaat tagagacatg     480

ggtataaaga gcacatccaa atccataatg gctgctgctg gagtacctgt tgtggagggt     540

tatcatggtg aggaccaatc agaccagtgc ctgaaggaac acgccaggag aattggctat     600

cctgtcatga ttaaagccgt ccggggtgga ggaggaaaag gaatgaggat tgttagatca     660

gaacaagaat ttcaagaaca gttagagtca gcacggagag aagctaagaa gtctttcaat     720

gatgatgcta tgctgatcga gaagtttgta gacacaccga ggcatgtaga agtccaggtg     780

tttggtgatc accatggcaa tgctgtgtac ttgtttgaaa gagactgtag tgtgcagagg     840
```

```
cgacatcaga agatcattga ggaggcccca gcgcctggta ttaaatctga agtaagaaaa    900

aagctgggag aagctgcagt cagagctgct aaagctgtaa attatgttgg agcagggact    960

gtggagttta ttatggactc aaaacataat ttctgtttca tggagatgaa tacaaggctg   1020

caagtggaac atcctgttac tgagatgatc acaggaactg acttggtgga gtggcagctt   1080

agaattgcag caggagagaa gattcctttg agccaggaag aaataactct gcagggccat   1140

gccttcgaag ctagaatata tgcagaagat cctagcaata acttcatgcc tgtggcaggc   1200

ccattagtgc acctctctac tcctcgagca gacccttcca ccaggattga aactggagta   1260

cggcaaggag acgaagtttc cgtgcattat gaccccatga ttgcgaagct ggtcgtgtgg   1320

gcagcagatc gccaggcggc attgacaaaa ctgaggtaca gccttcgtca gtacaatatt   1380

gttggactgc acaccaacat tgacttctta ctcaacctgt ctggccaccc agagtttgaa   1440

gctgggaacg tgcacactga tttcatccct caacaccaca aacagttgtt gctcagtcgg   1500

aaggctgcag ccaaagagtc tttatgccag gcagccctgg gtctcatcct caaggagaaa   1560

gccatgaccg acactttcac tcttcaggca catgatcaat tctctccatt ttcgtctagc   1620

agtggaagaa gactgaatat ctcgtatacc agaaacatga ctcttaaaga tggtaaaaac   1680

aatgtagcca tagctgtaac gtataaccat gatgggtctt atagcatgca gattgaagat   1740

aaaactttcc aagtccttgg taatctttac agcgagggag actgcactta cctgaaatgt   1800

tctgttaatg gagttgctag taaagcgaag ctgattatcc tggaaaacac tatttaccta   1860

ttttccaagg aaggaagtat tgagattgac attccagtcc ccaaatactt atcttctgtg   1920

agctcacaag aaactcaggg cggcccctta gctcctatga ctggaaccat tgaaaaggtg   1980

tttgtcaaag ctggagacaa agtgaaagcg ggagattccc tcatggttat gatcgccatg   2040

aagatggagc ataccataaa gtctccaaag gatggcacag taaagaaagt gttctacaga   2100

gaaggtgctc aggccaacag acacactcct ttagtcgagt ttgaggagga agaatcagac   2160

aaaagggaat cggaataa                                                 2178
```

<210> SEQ ID NO 94
<211> LENGTH: 725
<212> TYPE: PRT
<213> ORGANISM: Homo sapiens

<400> SEQUENCE: 94

```
Met Ala Ala Ala Ser Ala Val Ser Val Leu Leu Val Ala Ala Glu Arg
 1               5                  10                  15

Asn Arg Trp His Arg Leu Pro Ser Leu Leu Leu Pro Pro Arg Thr Trp
            20                  25                  30

Val Trp Arg Gln Arg Thr Met Lys Tyr Thr Thr Ala Thr Gly Arg Asn
        35                  40                  45

Ile Thr Lys Val Leu Ile Ala Asn Arg Gly Glu Ile Ala Cys Arg Val
    50                  55                  60

Met Arg Thr Ala Lys Lys Leu Gly Val Gln Thr Val Ala Val Tyr Ser
65                  70                  75                  80

Glu Ala Asp Arg Asn Ser Met His Val Asp Met Ala Asp Glu Ala Tyr
                85                  90                  95

Ser Ile Gly Pro Ala Pro Ser Gln Gln Ser Tyr Leu Ser Met Glu Lys
            100                 105                 110

Ile Ile Gln Val Ala Lys Thr Ser Ala Ala Gln Ala Ile His Pro Gly
        115                 120                 125

Cys Gly Phe Leu Ser Glu Asn Met Glu Phe Ala Glu Leu Cys Lys Gln
```

130 135 140

Glu Gly Ile Ile Phe Ile Gly Pro Pro Pro Ser Ala Ile Arg Asp Met
145 150 155 160

Gly Ile Lys Ser Thr Ser Lys Ser Ile Met Ala Ala Ala Gly Val Pro
165 170 175

Val Val Glu Gly Tyr His Gly Glu Asp Gln Ser Asp Gln Cys Leu Lys
180 185 190

Glu His Ala Arg Arg Ile Gly Tyr Pro Val Met Ile Lys Ala Val Arg
195 200 205

Gly Gly Gly Gly Lys Gly Met Arg Ile Val Arg Ser Glu Gln Glu Phe
210 215 220

Gln Glu Gln Leu Glu Ser Ala Arg Arg Glu Ala Lys Lys Ser Phe Asn
225 230 235 240

Asp Asp Ala Met Leu Ile Glu Lys Phe Val Asp Thr Pro Arg His Val
245 250 255

Glu Val Gln Val Phe Gly Asp His His Gly Asn Ala Val Tyr Leu Phe
260 265 270

Glu Arg Asp Cys Ser Val Gln Arg Arg His Gln Lys Ile Ile Glu Glu
275 280 285

Ala Pro Ala Pro Gly Ile Lys Ser Glu Val Arg Lys Lys Leu Gly Glu
290 295 300

Ala Ala Val Arg Ala Ala Lys Ala Val Asn Tyr Val Gly Ala Gly Thr
305 310 315 320

Val Glu Phe Ile Met Asp Ser Lys His Asn Phe Cys Phe Met Glu Met
325 330 335

Asn Thr Arg Leu Gln Val Glu His Pro Val Thr Glu Met Ile Thr Gly
340 345 350

Thr Asp Leu Val Glu Trp Gln Leu Arg Ile Ala Ala Gly Glu Lys Ile
355 360 365

Pro Leu Ser Gln Glu Glu Ile Thr Leu Gln Gly His Ala Phe Glu Ala
370 375 380

Arg Ile Tyr Ala Glu Asp Pro Ser Asn Asn Phe Met Pro Val Ala Gly
385 390 395 400

Pro Leu Val His Leu Ser Thr Pro Arg Ala Asp Pro Ser Thr Arg Ile
405 410 415

Glu Thr Gly Val Arg Gln Gly Asp Glu Val Ser Val His Tyr Asp Pro
420 425 430

Met Ile Ala Lys Leu Val Val Trp Ala Ala Asp Arg Gln Ala Ala Leu
435 440 445

Thr Lys Leu Arg Tyr Ser Leu Arg Gln Tyr Asn Ile Val Gly Leu His
450 455 460

Thr Asn Ile Asp Phe Leu Leu Asn Leu Ser Gly His Pro Glu Phe Glu
465 470 475 480

Ala Gly Asn Val His Thr Asp Phe Ile Pro Gln His His Lys Gln Leu
485 490 495

Leu Leu Ser Arg Lys Ala Ala Ala Lys Glu Ser Leu Cys Gln Ala Ala
500 505 510

Leu Gly Leu Ile Leu Lys Glu Lys Ala Met Thr Asp Thr Phe Thr Leu
515 520 525

Gln Ala His Asp Gln Phe Ser Pro Phe Ser Ser Ser Ser Gly Arg Arg
530 535 540

Leu Asn Ile Ser Tyr Thr Arg Asn Met Thr Leu Lys Asp Gly Lys Asn
545 550 555 560

```
Asn Val Ala Ile Ala Val Thr Tyr Asn His Asp Gly Ser Tyr Ser Met
                565                 570                 575

Gln Ile Glu Asp Lys Thr Phe Gln Val Leu Gly Asn Leu Tyr Ser Glu
            580                 585                 590

Gly Asp Cys Thr Tyr Leu Lys Cys Ser Val Asn Gly Val Ala Ser Lys
        595                 600                 605

Ala Lys Leu Ile Ile Leu Glu Asn Thr Ile Tyr Leu Phe Ser Lys Glu
    610                 615                 620

Gly Ser Ile Glu Ile Asp Ile Pro Val Pro Lys Tyr Leu Ser Ser Val
625                 630                 635                 640

Ser Ser Gln Glu Thr Gln Gly Gly Pro Leu Ala Pro Met Thr Gly Thr
                645                 650                 655

Ile Glu Lys Val Phe Val Lys Ala Gly Asp Lys Val Lys Ala Gly Asp
            660                 665                 670

Ser Leu Met Val Met Ile Ala Met Lys Met Glu His Thr Ile Lys Ser
        675                 680                 685

Pro Lys Asp Gly Thr Val Lys Lys Val Phe Tyr Arg Glu Gly Ala Gln
    690                 695                 700

Ala Asn Arg His Thr Pro Leu Val Glu Phe Glu Glu Glu Glu Ser Asp
705                 710                 715                 720

Lys Arg Glu Ser Glu
                725


<210> SEQ ID NO 95
<211> LENGTH: 1692
<212> TYPE: DNA
<213> ORGANISM: Dictyostelium discoideum

<400> SEQUENCE: 95

atgtgggccg tcctgaggtt agccctgcgg ccgtgtgccc gcgcctctcc cgccgggccg      60

cgcgcctatc acggggactc ggtggcctcg ctgggcaccc agccggactt gggctctgcc     120

ctctaccagg agaactacaa gcagatgaaa gcactagtaa atcagctcca tgaacgagtg     180

gagcatataa aactaggagg tggtgagaaa gcccgagcac ttcacatatc aagaggaaaa     240

ctattgccca gagaaagaat tgacaatctc atagacccag ggtctccatt tctggaatta     300

tcccagtttg caggttacca gttatatgac aatgaggagg tgccaggagg tggcattatt     360

acaggcattg gaagagtatc aggagtagaa tgcatgatta ttgccaatga tgccaccgtc     420

aaaggaggtg cctactaccc agtgactgtg aaaaaacaat tacgggccca agaaattgcc     480

atgcaaaaca ggctcccctg catctactta gttgattcgg gaggagcata cttacctcga     540

caagcagatg tgtttccaga tcgagaccac tttggccgta cattctataa tcaggcaatt     600

atgtcttcta aaaatattgc acagatcgca gtggtcatgg gctcctgcac cgcaggagga     660

gcctatgtgc ctgccatggc tgatgaaaac atcattgtac gcaagcaggg taccattttc     720

ttggcaggac ccccccttggt taaagcggca actggggaag aagtatctgc tgaggatctt     780

ggaggtgctg atcttcattg cagaaagtct ggagtaagtg accactgggc tttggatgat     840

catcatgccc ttcacttaac taggaaggtt gtgaggaatc taaattatca gaagaaattg     900

gatgtcacca ttgaaccttc tgaagagcct ttatttcctg ctgatgaatt gtatggaata     960

gttggtgcta accttaagag gagctttgat gtccgagagg tcattgctag aatcgtggat    1020

ggaagcagat tcactgagtt caaagccttt tatggagaca cattagttac aggatttgct    1080

cgaatatttg ggtacccagt aggtatcgtt ggaaacaacg gagttctctt ttctgaatct    1140

gcaaaaaagg gtactcactt tgtccagtta tgctgccaaa gaaatattcc tctgctgttc    1200
```

```
cttcaaaaca ttactggatt tatggttggt agagagtatg aagctgaagg aattgccaag   1260

gatggtgcca agatggtggc cgctgtggcc tgtgcccaag tgcctaagat aaccctcatc   1320

attgggggct cctatggagc cggaaactat gggatgtgtg gcagagcata tagcccaaga   1380

tttctctaca tttggccaaa tgctcgtatc tcagtgatgg gaggagagca ggcagccaat   1440

gtgttggcca cgataacaaa ggaccaaaga gcccgggaag gaaagcagtt ctccagtgct   1500

gatgaagcgg ctttaaaaga gcccatcatt aagaagtttg aagaggaagg aaaccccttac   1560

tattccagcg caagggtatg ggatgatggg atcattgatc cagcagacac cagactggtc   1620

ttgggtctca gttttagtgc agccctcaac gcaccaatag agaagactga cttcggtatc   1680

ttcaggatgt aa                                                        1692
```

<210> SEQ ID NO 96
<211> LENGTH: 563
<212> TYPE: PRT
<213> ORGANISM: Dictyostelium discoideum

<400> SEQUENCE: 96

```
Met Trp Ala Val Leu Arg Leu Ala Leu Arg Pro Cys Ala Arg Ala Ser
 1               5                  10                  15

Pro Ala Gly Pro Arg Ala Tyr His Gly Asp Ser Val Ala Ser Leu Gly
            20                  25                  30

Thr Gln Pro Asp Leu Gly Ser Ala Leu Tyr Gln Glu Asn Tyr Lys Gln
        35                  40                  45

Met Lys Ala Leu Val Asn Gln Leu His Glu Arg Val Glu His Ile Lys
    50                  55                  60

Leu Gly Gly Gly Glu Lys Ala Arg Ala Leu His Ile Ser Arg Gly Lys
65                  70                  75                  80

Leu Leu Pro Arg Glu Arg Ile Asp Asn Leu Ile Asp Pro Gly Ser Pro
                85                  90                  95

Phe Leu Glu Leu Ser Gln Phe Ala Gly Tyr Gln Leu Tyr Asp Asn Glu
            100                 105                 110

Glu Val Pro Gly Gly Gly Ile Ile Thr Gly Ile Gly Arg Val Ser Gly
        115                 120                 125

Val Glu Cys Met Ile Ile Ala Asn Asp Ala Thr Val Lys Gly Gly Ala
    130                 135                 140

Tyr Tyr Pro Val Thr Val Lys Lys Gln Leu Arg Ala Gln Glu Ile Ala
145                 150                 155                 160

Met Gln Asn Arg Leu Pro Cys Ile Tyr Leu Val Asp Ser Gly Gly Ala
                165                 170                 175

Tyr Leu Pro Arg Gln Ala Asp Val Phe Pro Asp Arg Asp His Phe Gly
            180                 185                 190

Arg Thr Phe Tyr Asn Gln Ala Ile Met Ser Ser Lys Asn Ile Ala Gln
        195                 200                 205

Ile Ala Val Val Met Gly Ser Cys Thr Ala Gly Gly Ala Tyr Val Pro
    210                 215                 220

Ala Met Ala Asp Glu Asn Ile Ile Val Arg Lys Gln Gly Thr Ile Phe
225                 230                 235                 240

Leu Ala Gly Pro Pro Leu Val Lys Ala Ala Thr Gly Glu Glu Val Ser
                245                 250                 255

Ala Glu Asp Leu Gly Gly Ala Asp Leu His Cys Arg Lys Ser Gly Val
            260                 265                 270

Ser Asp His Trp Ala Leu Asp Asp His His Ala Leu His Leu Thr Arg
        275                 280                 285
```

```
Lys Val Val Arg Asn Leu Asn Tyr Gln Lys Lys Leu Asp Val Thr Ile
    290                 295                 300

Glu Pro Ser Glu Glu Pro Leu Phe Pro Ala Asp Glu Leu Tyr Gly Ile
305                 310                 315                 320

Val Gly Ala Asn Leu Lys Arg Ser Phe Asp Val Arg Glu Val Ile Ala
                325                 330                 335

Arg Ile Val Asp Gly Ser Arg Phe Thr Glu Phe Lys Ala Phe Tyr Gly
            340                 345                 350

Asp Thr Leu Val Thr Gly Phe Ala Arg Ile Phe Gly Tyr Pro Val Gly
        355                 360                 365

Ile Val Gly Asn Asn Gly Val Leu Phe Ser Glu Ser Ala Lys Lys Gly
    370                 375                 380

Thr His Phe Val Gln Leu Cys Cys Gln Arg Asn Ile Pro Leu Leu Phe
385                 390                 395                 400

Leu Gln Asn Ile Thr Gly Phe Met Val Gly Arg Glu Tyr Glu Ala Glu
                405                 410                 415

Gly Ile Ala Lys Asp Gly Ala Lys Met Val Ala Ala Val Ala Cys Ala
            420                 425                 430

Gln Val Pro Lys Ile Thr Leu Ile Ile Gly Gly Ser Tyr Gly Ala Gly
        435                 440                 445

Asn Tyr Gly Met Cys Gly Arg Ala Tyr Ser Pro Arg Phe Leu Tyr Ile
    450                 455                 460

Trp Pro Asn Ala Arg Ile Ser Val Met Gly Gly Glu Gln Ala Ala Asn
465                 470                 475                 480

Val Leu Ala Thr Ile Thr Lys Asp Gln Arg Ala Arg Glu Gly Lys Gln
                485                 490                 495

Phe Ser Ser Ala Asp Glu Ala Ala Leu Lys Glu Pro Ile Ile Lys Lys
            500                 505                 510

Phe Glu Glu Glu Gly Asn Pro Tyr Tyr Ser Ser Ala Arg Val Trp Asp
        515                 520                 525

Asp Gly Ile Ile Asp Pro Ala Asp Thr Arg Leu Val Leu Gly Leu Ser
    530                 535                 540

Phe Ser Ala Ala Leu Asn Ala Pro Ile Glu Lys Thr Asp Phe Gly Ile
545                 550                 555                 560

Phe Arg Met

<210> SEQ ID NO 97
<211> LENGTH: 1020
<212> TYPE: DNA
<213> ORGANISM: Homo sapiens

<400> SEQUENCE: 97

atggcggccg cggtggcggc ggcacctggg gccttgggat ccctgcatgc tggcggcgcc      60

cgcctggtgg ccgcttgcag tgcgtggctc tgcccggggt tgaggctgcc cggctcgttg     120

gcaggccggc gagcgggccc ggcgatctgg gcccagggct gggtacctgc ggccgggggt     180

cccgccccga aaaggggcta cagctctgag atgaagacgg aggacgagct gcgggtgcgg     240

cacctggagg aggagaaccg aggaattgtg gtgcttggaa taaacagagc ttatggcaaa     300

aattcactca gtaaaaatct tataaaaatg ctatcaaaag ctgtggatgc tttgaaatct     360

gataagaaag tacggaccat aataatcagg agtgaagtcc cagggatatt ctgtgctggt     420

gctgacctta aggaaagagc caaaatgagt tccagtgaag ttggtccttt tgtctccaaa     480

ataagagcag tgattaacga tattgctaat cttccagtac caacaattgc agcaatagat     540
```

```
ggactcgctt taggtggtgg tcttgaactg gctttagcct gtgatatacg agtagcagct    600

tcctctgcaa aaatgggcct ggttgaaaca aaattggcga ttattcctgg tggagggggg    660

acacagcgat tgccacgcgc cattggaatg tccctggcca aggagctcat attctctgcg    720

cgagtcctcg atggcaaaga agccaaagca gtgggcttaa tcagccacgt tctggaacag    780

aaccaggagg gagacgcggc ctacaggaag gccttggacc tggcgagaga gtttttacct    840

cagggacctg ttgcaatgag agtggcaaaa ttagcaatta atcaagggat ggaggtcgat    900

ttagtaacag ggttagccat agaagaagct tgttatgctc agaccattcc aacaaaagac    960

agacttgaag gtcttcttgc ttttaaagag aaaaggcccc ctcgctataa aggagaataa   1020


<210> SEQ ID NO 98
<211> LENGTH: 339
<212> TYPE: PRT
<213> ORGANISM: Homo sapiens

<400> SEQUENCE: 98

Met Ala Ala Ala Val Ala Ala Ala Pro Gly Ala Leu Gly Ser Leu His
1               5                   10                  15

Ala Gly Gly Ala Arg Leu Val Ala Ala Cys Ser Ala Trp Leu Cys Pro
            20                  25                  30

Gly Leu Arg Leu Pro Gly Ser Leu Ala Gly Arg Arg Ala Gly Pro Ala
        35                  40                  45

Ile Trp Ala Gln Gly Trp Val Pro Ala Ala Gly Gly Pro Ala Pro Lys
    50                  55                  60

Arg Gly Tyr Ser Ser Glu Met Lys Thr Glu Asp Glu Leu Arg Val Arg
65                  70                  75                  80

His Leu Glu Glu Glu Asn Arg Gly Ile Val Val Leu Gly Ile Asn Arg
                85                  90                  95

Ala Tyr Gly Lys Asn Ser Leu Ser Lys Asn Leu Ile Lys Met Leu Ser
            100                 105                 110

Lys Ala Val Asp Ala Leu Lys Ser Asp Lys Lys Val Arg Thr Ile Ile
        115                 120                 125

Ile Arg Ser Glu Val Pro Gly Ile Phe Cys Ala Gly Ala Asp Leu Lys
    130                 135                 140

Glu Arg Ala Lys Met Ser Ser Ser Glu Val Gly Pro Phe Val Ser Lys
145                 150                 155                 160

Ile Arg Ala Val Ile Asn Asp Ile Ala Asn Leu Pro Val Pro Thr Ile
                165                 170                 175

Ala Ala Ile Asp Gly Leu Ala Leu Gly Gly Gly Leu Glu Leu Ala Leu
            180                 185                 190

Ala Cys Asp Ile Arg Val Ala Ala Ser Ser Ala Lys Met Gly Leu Val
        195                 200                 205

Glu Thr Lys Leu Ala Ile Ile Pro Gly Gly Gly Gly Thr Gln Arg Leu
    210                 215                 220

Pro Arg Ala Ile Gly Met Ser Leu Ala Lys Glu Leu Ile Phe Ser Ala
225                 230                 235                 240

Arg Val Leu Asp Gly Lys Glu Ala Lys Ala Val Gly Leu Ile Ser His
                245                 250                 255

Val Leu Glu Gln Asn Gln Glu Gly Asp Ala Ala Tyr Arg Lys Ala Leu
            260                 265                 270

Asp Leu Ala Arg Glu Phe Leu Pro Gln Gly Pro Val Ala Met Arg Val
        275                 280                 285

Ala Lys Leu Ala Ile Asn Gln Gly Met Glu Val Asp Leu Val Thr Gly
    290                 295                 300
```

-continued

Leu Ala Ile Glu Glu Ala Cys Tyr Ala Gln Thr Ile Pro Thr Lys Asp
305 310 315 320

Arg Leu Glu Gly Leu Leu Ala Phe Lys Glu Lys Arg Pro Pro Arg Tyr
325 330 335

Lys Gly Glu

<210> SEQ ID NO 99
<211> LENGTH: 576
<212> TYPE: DNA
<213> ORGANISM: Drosophila persimilis

<400> SEQUENCE: 99
atgtccaccg aggaaaccag cgagtttgtg tcgaatctac gaaacctgtt cattagcatt 60
gaacaattgc cgatgcccgt aatcgccgca ttggatggcg ctgctttggg tggtggtctg 120
gaaatggctc tggcatgcga tatacgcacg gcagcttcaa ataccaaaat gggtctggta 180
gagactcgac tggccataat ccctggcgcc gggggcactc agcgactccc ccgcattctc 240
tctccctcgc tggcgaagga acttattttc actgcccgag tcttggatgg aagtgtggcc 300
aaggagctgg gtctggtcag ccatgttgta agccagaacg aaaaaaatga tgctgcctac 360
cagcaggccc taaagctcgc cgaggaaatc ctccccaacg gtccagtggg tgtgcgaatg 420
gccaaactgg ctattgacaa gggcatgcag gtcgacctaa gcacgggcta ctccattgaa 480
gaggtctgct atgctcaggt gatacccaca aaggaccgcc tggagggact cgccgcgttt 540
gccgagaaac gcaagcccgt ctacaaggga gagtaa 576

<210> SEQ ID NO 100
<211> LENGTH: 191
<212> TYPE: PRT
<213> ORGANISM: Drosophila persimilis

<400> SEQUENCE: 100

Met Ser Thr Glu Glu Thr Ser Glu Phe Val Ser Asn Leu Arg Asn Leu
1 5 10 15

Phe Ile Ser Ile Glu Gln Leu Pro Met Pro Val Ile Ala Ala Leu Asp
20 25 30

Gly Ala Ala Leu Gly Gly Gly Leu Glu Met Ala Leu Ala Cys Asp Ile
35 40 45

Arg Thr Ala Ala Ser Asn Thr Lys Met Gly Leu Val Glu Thr Arg Leu
50 55 60

Ala Ile Ile Pro Gly Ala Gly Gly Thr Gln Arg Leu Pro Arg Ile Leu
65 70 75 80

Ser Pro Ser Leu Ala Lys Glu Leu Ile Phe Thr Ala Arg Val Leu Asp
85 90 95

Gly Ser Val Ala Lys Glu Leu Gly Leu Val Ser His Val Val Ser Gln
100 105 110

Asn Glu Lys Asn Asp Ala Ala Tyr Gln Gln Ala Leu Lys Leu Ala Glu
115 120 125

Glu Ile Leu Pro Asn Gly Pro Val Gly Val Arg Met Ala Lys Leu Ala
130 135 140

Ile Asp Lys Gly Met Gln Val Asp Leu Ser Thr Gly Tyr Ser Ile Glu
145 150 155 160

Glu Val Cys Tyr Ala Gln Val Ile Pro Thr Lys Asp Arg Leu Glu Gly
165 170 175

Leu Ala Ala Phe Ala Glu Lys Arg Lys Pro Val Tyr Lys Gly Glu
180 185 190

<210> SEQ ID NO 101
<211> LENGTH: 1509
<212> TYPE: DNA
<213> ORGANISM: Saccharomyces cerevisiae

<400> SEQUENCE: 101
atggttttaa ccaataaaac agtcatttct ggatcgaaag tcaaaagttt atcatctgcg 60
caatcgagct catcaggacc ttcatcatct agtgaggaag atgattcccg cgatattgaa 120
agcttggata agaaaatacg tcctttagaa gaattagaag cattattaag tagtggaaat 180
acaaaacaat tgaagaacaa agaggtcgct gccttggtta ttcacggtaa gttacctttg 240
tacgctttgg agaaaaaatt aggtgatact acgagagcgg ttgcggtacg taggaaggct 300
ctttcaattt tggcagaagc tcctgtatta gcatctgatc gtttaccata taaaaattat 360
gactacgacc gcgtatttgg cgcttgttgt gaaaatgtta taggttacat gcctttgccc 420
gttggtgtta taggcccctt ggttatcgat ggtacatctt atcatatacc aatggcaact 480
acagagggtt gtttggtagc ttctgccatg cgtggctgta aggcaatcaa tgctggcggt 540
ggtgcaacaa ctgttttaac taaggatggt atgacaagag gcccagtagt ccgtttccca 600
actttgaaaa gatctggtgc ctgtaagata tggttagact cagaagaggg acaaaacgca 660
attaaaaaag cttttaactc tacatcaaga tttgcacgtc tgcaacatat tcaaacttgt 720
ctagcaggag atttactctt catgagattt agaacaacta ctggtgacgc aatgggtatg 780
aatatgattt ctaaaggtgt cgaatactca ttaaagcaaa tggtagaaga gtatggctgg 840
gaagatatgg aggttgtctc cgtttctggt aactactgta ccgacaaaaa accagctgcc 900
atcaactgga tcgaaggtcg tggtaagagt gtcgtcgcag aagctactat tcctggtgat 960
gttgtcagaa aagtgttaaa aagtgatgtt tccgcattgg ttgagttgaa cattgctaag 1020
aatttggttg gatctgcaat ggctgggtct gttggtggat ttaacgcaca tgcagctaat 1080
ttagtgacag ctgttttctt ggcattagga caagatcctg cacaaaatgt tgaaagttcc 1140
aactgtataa cattgatgaa agaagtggac ggtgatttga gaatttccgt atccatgcca 1200
tccatcgaag taggtaccat cggtggtggt actgttctag aaccacaagg tgccatgttg 1260
gacttattag gtgtaagagg cccgcatgct accgctcctg gtaccaacgc acgtcaatta 1320
gcaagaatag ttgcctgtgc cgtcttggca ggtgaattat ccttatgtgc tgccctagca 1380
gccggccatt tggttcaaag tcatatgacc cacaacagga aacctgctga accaacaaaa 1440
cctaacaatt tggacgccac tgatataaat cgtttgaaag atgggtccgt cacctgcatt 1500
aaatcctaa 1509

<210> SEQ ID NO 102
<211> LENGTH: 502
<212> TYPE: PRT
<213> ORGANISM: Saccharomyces cerevisiae

<400> SEQUENCE: 102

Met Val Leu Thr Asn Lys Thr Val Ile Ser Gly Ser Lys Val Lys Ser
1 5 10 15

Leu Ser Ser Ala Gln Ser Ser Ser Ser Gly Pro Ser Ser Ser Ser Glu
20 25 30

Glu Asp Asp Ser Arg Asp Ile Glu Ser Leu Asp Lys Lys Ile Arg Pro
35 40 45

Leu Glu Glu Leu Glu Ala Leu Leu Ser Ser Gly Asn Thr Lys Gln Leu
50 55 60

-continued

```
Lys Asn Lys Glu Val Ala Ala Leu Val Ile His Gly Lys Leu Pro Leu
65                  70                  75                  80

Tyr Ala Leu Glu Lys Lys Leu Gly Asp Thr Thr Arg Ala Val Ala Val
                85                  90                  95

Arg Arg Lys Ala Leu Ser Ile Leu Ala Glu Ala Pro Val Leu Ala Ser
            100                 105                 110

Asp Arg Leu Pro Tyr Lys Asn Tyr Asp Tyr Asp Arg Val Phe Gly Ala
        115                 120                 125

Cys Cys Glu Asn Val Ile Gly Tyr Met Pro Leu Pro Val Gly Val Ile
    130                 135                 140

Gly Pro Leu Val Ile Asp Gly Thr Ser Tyr His Ile Pro Met Ala Thr
145                 150                 155                 160

Thr Glu Gly Cys Leu Val Ala Ser Ala Met Arg Gly Cys Lys Ala Ile
                165                 170                 175

Asn Ala Gly Gly Gly Ala Thr Thr Val Leu Thr Lys Asp Gly Met Thr
            180                 185                 190

Arg Gly Pro Val Val Arg Phe Pro Thr Leu Lys Arg Ser Gly Ala Cys
        195                 200                 205

Lys Ile Trp Leu Asp Ser Glu Glu Gly Gln Asn Ala Ile Lys Lys Ala
    210                 215                 220

Phe Asn Ser Thr Ser Arg Phe Ala Arg Leu Gln His Ile Gln Thr Cys
225                 230                 235                 240

Leu Ala Gly Asp Leu Leu Phe Met Arg Phe Arg Thr Thr Thr Gly Asp
                245                 250                 255

Ala Met Gly Met Asn Met Ile Ser Lys Gly Val Glu Tyr Ser Leu Lys
            260                 265                 270

Gln Met Val Glu Glu Tyr Gly Trp Glu Asp Met Glu Val Val Ser Val
        275                 280                 285

Ser Gly Asn Tyr Cys Thr Asp Lys Lys Pro Ala Ala Ile Asn Trp Ile
    290                 295                 300

Glu Gly Arg Gly Lys Ser Val Val Ala Glu Ala Thr Ile Pro Gly Asp
305                 310                 315                 320

Val Val Arg Lys Val Leu Lys Ser Asp Val Ser Ala Leu Val Glu Leu
                325                 330                 335

Asn Ile Ala Lys Asn Leu Val Gly Ser Ala Met Ala Gly Ser Val Gly
            340                 345                 350

Gly Phe Asn Ala His Ala Ala Asn Leu Val Thr Ala Val Phe Leu Ala
        355                 360                 365

Leu Gly Gln Asp Pro Ala Gln Asn Val Glu Ser Ser Asn Cys Ile Thr
    370                 375                 380

Leu Met Lys Glu Val Asp Gly Asp Leu Arg Ile Ser Val Ser Met Pro
385                 390                 395                 400

Ser Ile Glu Val Gly Thr Ile Gly Gly Gly Thr Val Leu Glu Pro Gln
                405                 410                 415

Gly Ala Met Leu Asp Leu Leu Gly Val Arg Gly Pro His Ala Thr Ala
            420                 425                 430

Pro Gly Thr Asn Ala Arg Gln Leu Ala Arg Ile Val Ala Cys Ala Val
        435                 440                 445

Leu Ala Gly Glu Leu Ser Leu Cys Ala Ala Leu Ala Ala Gly His Leu
    450                 455                 460

Val Gln Ser His Met Thr His Asn Arg Lys Pro Ala Glu Pro Thr Lys
465                 470                 475                 480

Pro Asn Asn Leu Asp Ala Thr Asp Ile Asn Arg Leu Lys Asp Gly Ser
```

```
                485                 490                 495

Val Thr Cys Ile Lys Ser
            500


<210> SEQ ID NO 103
<211> LENGTH: 1059
<212> TYPE: DNA
<213> ORGANISM: Saccharomyces cerevisiae

<400> SEQUENCE: 103

atggcttcag aaaaagaaat taggagagag agattcttga acgttttccc taaattagta      60

gaggaattga acgcatcgct tttggcttac ggtatgccta aggaagcatg tgactggtat     120

gcccactcat tgaactacaa cactccaggc ggtaagctaa atagaggttt gtccgttgtg     180

gacacgtatg ctattctctc caacaagacc gttgaacaat tggggcaaga agaatacgaa     240

aaggttgcca ttctaggttg gtgcattgag ttgttgcagg cttacttctt ggtcgccgat     300

gatatgatgg acaagtccat taccagaaga ggccaaccat gttggtacaa ggttcctgaa     360

gttggggaaa ttgccatcaa tgacgcattc atgttagagg ctgctatcta caagcttttg     420

aaatctcact tcagaaacga aaaatactac atagatatca ccgaattgtt ccatgaggtc     480

accttccaaa ccgaattggg ccaattgatg gacttaatca ctgcacctga agacaaagtc     540

gacttgagta agttctccct aaagaagcac tccttcatag ttactttcaa gactgcttac     600

tattctttct acttgcctgt cgcattggcc atgtacgttg ccggtatcac ggatgaaaag     660

gatttgaaac aagccagaga tgtcttgatt ccattgggtg aatacttcca aattcaagat     720

gactacttag actgcttcgg taccccagaa cagatcggta agatcggtac agatatccaa     780

gataacaaat gttcttgggt aatcaacaag gcattggaac ttgcttccgc agaacaaaga     840

aagactttag acgaaaatta cggtaagaag gactcagtcg cagaagccaa atgcaaaaag     900

attttcaatg acttgaaaat tgaacagcta taccacgaat atgaagagtc tattgccaag     960

gatttgaagg ccaaaatttc tcaggtcgat gagtctcgtg gcttcaaagc tgatgtctta    1020

actgcgttct tgaacaaagt ttacaagaga agcaaatag                           1059


<210> SEQ ID NO 104
<211> LENGTH: 352
<212> TYPE: PRT
<213> ORGANISM: Saccharomyces cerevisiae

<400> SEQUENCE: 104

Met Ala Ser Glu Lys Glu Ile Arg Arg Glu Arg Phe Leu Asn Val Phe
 1               5                  10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
        115                 120                 125
```

```
Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350
```

<210> SEQ ID NO 105
<211> LENGTH: 1059
<212> TYPE: DNA
<213> ORGANISM: Saccharomyces cerevisiae

<400> SEQUENCE: 105

```
atggcttcag aaaaagaaat taggagagag agattcttga acgttttccc taaattagta      60

gaggaattga acgcatcgct tttggcttac ggtatgccta aggaagcatg tgactggtat     120

gcccactcat tgaactacaa cactccaggc ggtaagctaa atagaggttt gtccgttgtg     180

gacacgtatg ctattctctc caacaagacc gttgaacaat tggggcaaga agaatacgaa     240

aaggttgcca ttctaggttg gtgcattgag ttgttgcagg cttacttctt ggtcgccgat     300

gatatgatgg acaagtccat taccagaaga ggccaaccat gttggtacaa ggttcctgaa     360

gttggggaaa ttgccatcaa tgacgcattc atgttagagg ctgctatcta caagcttttg     420

aaatctcact tcagaaacga aaaatactac atagatatca ccgaattgtt ccatgaggtc     480

accttccaaa ccgaattggg ccaattgatg gacttaatca ctgcacctga agacaaagtc     540

gacttgagta agttctccct aaagaagcac tccttcatag ttactttcga aactgcttac     600

tattctttct acttgcctgt cgcattggcc atgtacgttg ccggtatcac ggatgaaaag     660

gatttgaaac aagccagaga tgtcttgatt ccattgggtg aatacttcca aattcaagat     720

gactacttag actgcttcgg taccccagaa cagatcggta agatcggtac agatatccaa     780

gataacaaat gttcttgggt aatcaacaag gcattggaac ttgcttccgc agaacaaaga     840

aagactttag acgaaaatta cggtaagaag gactcagtcg cagaagccaa atgcaaaaag     900
```

```
attttcaatg acttgaaaat tgaacagcta taccacgaat atgaagagtc tattgccaag    960

gatttgaagg ccaaaatttc tcaggtcgat gagtctcgtg gcttcaaagc tgatgtctta   1020

actgcgttct tgaacaaagt ttacaagaga agcaaatag                          1059


<210> SEQ ID NO 106
<211> LENGTH: 352
<212> TYPE: PRT
<213> ORGANISM: Saccharomyces cerevisiae

<400> SEQUENCE: 106

Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Glu Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350
```

<210> SEQ ID NO 107
<211> LENGTH: 1059
<212> TYPE: DNA
<213> ORGANISM: Saccharomyces cerevisiae

<400> SEQUENCE: 107
atggcttcag aaaaagaaat taggagagag agattcttga acgttttccc taaattagta 60
gaggaattga acgcatcgct tttggcttac ggtatgccta aggaagcatg tgactggtat 120
gcccactcat tgaactacaa cactccaggc ggtaagctaa atagaggttt gtccgttgtg 180
gacacgtatg ctattctctc caacaagacc gttgaacaat tggggcaaga agaatacgaa 240
aaggttgcca ttctaggttg gtgcattgag ttgttgcagg cttacttctt ggtcgccgat 300
gatatgatgg acaagtccat taccagaaga ggccaaccat gttggtacaa ggttcctgaa 360
gttggggaaa ttgccatcaa tgacgcattc atgttagagg ctgctatcta caagcttttg 420
aaatctcact tcagaaacga aaaatactac atagatatca ccgaattgtt ccatgaggtc 480
accttccaaa ccgaattggg ccaattgatg gacttaatca ctgcacctga agacaaagtc 540
gacttgagta agttctccct aaagaagcac tccttcatag ttactttcag aactgcttac 600
tattctttct acttgcctgt cgcattggcc atgtacgttg ccggtatcac ggatgaaaag 660
gatttgaaac aagccagaga tgtcttgatt ccattgggtg aatacttcca aattcaagat 720
gactacttag actgcttcgg taccccagaa cagatcggta agatcggtac agatatccaa 780
gataacaaat gttcttgggt aatcaacaag gcattggaac ttgcttccgc agaacaaaga 840
aagactttag acgaaaatta cggtaagaag gactcagtcg cagaagccaa atgcaaaaag 900
attttcaatg acttgaaaat tgaacagcta taccacgaat atgaagagtc tattgccaag 960
gatttgaagg ccaaaatttc tcaggtcgat gagtctcgtg gcttcaaagc tgatgtctta 1020
actgcgttct tgaacaaagt ttacaagaga agcaaatag 1059

<210> SEQ ID NO 108
<211> LENGTH: 352
<212> TYPE: PRT
<213> ORGANISM: Saccharomyces cerevisiae

<400> SEQUENCE: 108

Met Ala Ser Glu Lys Glu Ile Arg Arg Glu Arg Phe Leu Asn Val Phe
1 5 10 15

Pro Lys Leu Val Glu Glu Leu Asn Ala Ser Leu Leu Ala Tyr Gly Met
20 25 30

Pro Lys Glu Ala Cys Asp Trp Tyr Ala His Ser Leu Asn Tyr Asn Thr
35 40 45

Pro Gly Gly Lys Leu Asn Arg Gly Leu Ser Val Val Asp Thr Tyr Ala
50 55 60

Ile Leu Ser Asn Lys Thr Val Glu Gln Leu Gly Gln Glu Glu Tyr Glu
65 70 75 80

Lys Val Ala Ile Leu Gly Trp Cys Ile Glu Leu Leu Gln Ala Tyr Phe
85 90 95

Leu Val Ala Asp Asp Met Met Asp Lys Ser Ile Thr Arg Arg Gly Gln
100 105 110

Pro Cys Trp Tyr Lys Val Pro Glu Val Gly Glu Ile Ala Ile Asn Asp
115 120 125

Ala Phe Met Leu Glu Ala Ala Ile Tyr Lys Leu Leu Lys Ser His Phe
130 135 140

-continued

```
Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Arg Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350
```

<210> SEQ ID NO 109
<211> LENGTH: 1812
<212> TYPE: DNA
<213> ORGANISM: Cinnamomum tenuipile

<400> SEQUENCE: 109

```
atggcattgc aaatgattgc tccatttcta tcctccttcc tcccaaatcc cagacacagc     60

ctcgcagccc atggcctcac acaccagaaa tgtgtctcaa agcacatttc atgctccacc    120

actacaccaa cctactcaac cacagttcca agaagatcag ggaactacaa gcccagcatc    180

tgggactatg attttgtgca gtcactagga agtggctaca aggtagaggc acatggaaca    240

cgtgtgaaga agttgaagga agttgtaaag catttgttga aagaaacaga tagttctttg    300

gcccaaatag aactgattga caaactccgt cgtctaggtc taaggtggct cttcaaaaat    360

gagattaagc aagtgctata cacgatatca tcagacaaca ccagcataga aatgaggaaa    420

gatcttcatg cagtatcaac tcgatttaga cttcttagac aacatgggta caaggtctcc    480

acagatgttt tcaacgactt caaagatgaa aagggttgtt tcaagccaag cctttcaatg    540

gacataaagg gaatgttgag cttgtatgaa gcttcacacc ttgcctttca aggggagact    600

gtgttggatg aggcaagagc tttcgtaagc acacatctca tggatatcaa ggagaacata    660

gacccaatcc ttcataaaaa agtagagcat gctttggata tgcctttgca ttggaggtta    720

gaaaaattag aggctaggtg gtacatggac atatatatga gggaagaagg catgaattct    780

tctttacttg aattggccat gcttcatttc aacattgtgc aaacaacatt ccaaacaaat    840

ttaaagagtt tgtcaaggtg gtggaaagat ttgggtcttg gagagcagtt gagcttcact    900

agagacaggt tggtggaatg tttcttttgg gccgccgcaa tgacacctga gccacaattt    960

ggacgttgcc aggaagttgt agcgaaagtt gctcaactca taataataat tgacgatatc   1020
```

```
tatgacgtgt atggtacggt ggatgagcta gaacttttta ctaatgcgat tgatagatgg   1080

gatcttgagg caatggagca acttcctgaa tatatgaaga cctgtttctt agctttatac   1140

aacagtatta atgaaatagg ttatgacatt ttgaaagagg aagggcgcaa tgtcatacca   1200

taccttagaa atacgtggac agaattgtgt aaagcattct tagtggaggc caaatggtat   1260

agtagtggat atacaccaac gcttgaggag tatctgcaaa cctcatggat ttcgattgga   1320

agtctaccca tgcaaacata tgtttttgct ctacttggga aaaatctagc accggagagt   1380

agtgattttg ctgagaagat ctcggatatc ttacgattgg gaggaatgat gattcgactt   1440

ccggatgatt tgggaacttc aacggatgaa ctaaagagag gtgatgttcc aaaatccatt   1500

cagtgttaca tgcatgaagc aggtgttaca gaggatgttg ctcgcgacca cataatgggt   1560

ctatttcaag agacatggaa aaaactcaat gaataccttg tggaaagttc tcttccccat   1620

gcctttatcg atcatgctat gaatcttgga cgtgtctcct attgcactta caaacatgga   1680

gatggattta gtgatggatt tggagatcct ggcagtcaag agaaaaagat gttcatgtct   1740

ttatttgctg aacccttca agttgatgaa gccaagggta tttcatttta tgttgatggt   1800

ggatctgcct ga                                                       1812
```

```
<210> SEQ ID NO 110
<211> LENGTH: 603
<212> TYPE: PRT
<213> ORGANISM: Cinnamomum tenuipile

<400> SEQUENCE: 110

Met Ala Leu Gln Met Ile Ala Pro Phe Leu Ser Ser Phe Leu Pro Asn
1               5                   10                  15

Pro Arg His Ser Leu Ala Ala His Gly Leu Thr His Gln Lys Cys Val
            20                  25                  30

Ser Lys His Ile Ser Cys Ser Thr Thr Thr Pro Thr Tyr Ser Thr Thr
        35                  40                  45

Val Pro Arg Arg Ser Gly Asn Tyr Lys Pro Ser Ile Trp Asp Tyr Asp
    50                  55                  60

Phe Val Gln Ser Leu Gly Ser Gly Tyr Lys Val Glu Ala His Gly Thr
65                  70                  75                  80

Arg Val Lys Lys Leu Lys Glu Val Val Lys His Leu Leu Lys Glu Thr
                85                  90                  95

Asp Ser Ser Leu Ala Gln Ile Glu Leu Ile Asp Lys Leu Arg Arg Leu
            100                 105                 110

Gly Leu Arg Trp Leu Phe Lys Asn Glu Ile Lys Gln Val Leu Tyr Thr
        115                 120                 125

Ile Ser Ser Asp Asn Thr Ser Ile Glu Met Arg Lys Asp Leu His Ala
    130                 135                 140

Val Ser Thr Arg Phe Arg Leu Leu Arg Gln His Gly Tyr Lys Val Ser
145                 150                 155                 160

Thr Asp Val Phe Asn Asp Phe Lys Asp Glu Lys Gly Cys Phe Lys Pro
                165                 170                 175

Ser Leu Ser Met Asp Ile Lys Gly Met Leu Ser Leu Tyr Glu Ala Ser
            180                 185                 190

His Leu Ala Phe Gln Gly Glu Thr Val Leu Asp Glu Ala Arg Ala Phe
        195                 200                 205

Val Ser Thr His Leu Met Asp Ile Lys Glu Asn Ile Asp Pro Ile Leu
    210                 215                 220

His Lys Lys Val Glu His Ala Leu Asp Met Pro Leu His Trp Arg Leu
```

```
225                 230                 235                 240

Glu Lys Leu Glu Ala Arg Trp Tyr Met Asp Ile Tyr Met Arg Glu Glu
                245                 250                 255

Gly Met Asn Ser Ser Leu Leu Glu Leu Ala Met Leu His Phe Asn Ile
            260                 265                 270

Val Gln Thr Thr Phe Gln Thr Asn Leu Lys Ser Leu Ser Arg Trp Trp
        275                 280                 285

Lys Asp Leu Gly Leu Gly Glu Gln Leu Ser Phe Thr Arg Asp Arg Leu
    290                 295                 300

Val Glu Cys Phe Phe Trp Ala Ala Ala Met Thr Pro Glu Pro Gln Phe
305                 310                 315                 320

Gly Arg Cys Gln Glu Val Val Ala Lys Val Ala Gln Leu Ile Ile Ile
                325                 330                 335

Ile Asp Asp Ile Tyr Asp Val Tyr Gly Thr Val Asp Glu Leu Glu Leu
            340                 345                 350

Phe Thr Asn Ala Ile Asp Arg Trp Asp Leu Glu Ala Met Glu Gln Leu
        355                 360                 365

Pro Glu Tyr Met Lys Thr Cys Phe Leu Ala Leu Tyr Asn Ser Ile Asn
    370                 375                 380

Glu Ile Gly Tyr Asp Ile Leu Lys Glu Glu Gly Arg Asn Val Ile Pro
385                 390                 395                 400

Tyr Leu Arg Asn Thr Trp Thr Glu Leu Cys Lys Ala Phe Leu Val Glu
                405                 410                 415

Ala Lys Trp Tyr Ser Ser Gly Tyr Thr Pro Thr Leu Glu Glu Tyr Leu
            420                 425                 430

Gln Thr Ser Trp Ile Ser Ile Gly Ser Leu Pro Met Gln Thr Tyr Val
        435                 440                 445

Phe Ala Leu Leu Gly Lys Asn Leu Ala Pro Glu Ser Ser Asp Phe Ala
    450                 455                 460

Glu Lys Ile Ser Asp Ile Leu Arg Leu Gly Gly Met Met Ile Arg Leu
465                 470                 475                 480

Pro Asp Asp Leu Gly Thr Ser Thr Asp Glu Leu Lys Arg Gly Asp Val
                485                 490                 495

Pro Lys Ser Ile Gln Cys Tyr Met His Glu Ala Gly Val Thr Glu Asp
            500                 505                 510

Val Ala Arg Asp His Ile Met Gly Leu Phe Gln Glu Thr Trp Lys Lys
        515                 520                 525

Leu Asn Glu Tyr Leu Val Glu Ser Ser Leu Pro His Ala Phe Ile Asp
    530                 535                 540

His Ala Met Asn Leu Gly Arg Val Ser Tyr Cys Thr Tyr Lys His Gly
545                 550                 555                 560

Asp Gly Phe Ser Asp Gly Phe Gly Asp Pro Gly Ser Gln Glu Lys Lys
                565                 570                 575

Met Phe Met Ser Leu Phe Ala Glu Pro Leu Gln Val Asp Glu Ala Lys
            580                 585                 590

Gly Ile Ser Phe Tyr Val Asp Gly Gly Ser Ala
        595                 600
```

<210> SEQ ID NO 111
<211> LENGTH: 1260
<212> TYPE: DNA
<213> ORGANISM: Musa acuminata

<400> SEQUENCE: 111

```
atgagcttcg ctgtgaccag aacaagccgg tctttggtca ctccatgcgg ggtcacgccg     60
```

acgggctcgc tcggcctctc cgccatcgac cgggtgcccg gcctcaggca tatggtgcgg 120
tcgctacacg tgttcaggca aggccgggag ccggccagga tcatcaggga agcactgtcg 180
aaggcgctgg tgaagtacta ccccttcgcg gggcggttcg tggacgatcc cgagggcggc 240
ggcgaggttc gtgtcgcttg cactggcgag ggcgcttggt tcgtcgaggc caaggcggac 300
tgcagcttgg aggacgtgaa gtacctcgat ctcccgctca tgatccctga ggacgcgctc 360
ctgcccaagc cctgcccggg actgaacccc ctcgacctcc ctctcatgct gcaggtgaca 420
gagttcgtgg gcggcggatt cgtggtcggc ctcatctccg tccataccat cgccgacggc 480
ctcggcgtcg tccagttcat caacgccgtc gccgagatcg cccgtggcct gccgaagccc 540
accgtggagc ctgcatggtc ccgggaggtc atacccaacc cacctaagct gcctcccggt 600
ggcccgcccg tgttcccctc cttcaagctg ctccacgcca ccgtcgacct atcccctgac 660
cacatcgatc acgtcaagtc ccgacacttg gagctcaccg gccagcgctg ctctaccttc 720
gacgtcgcca tcgccaacct gtggcagtcc cgcacgcgcg ccatcaacct ggacccaggc 780
gtcgacgtgc acgtgtgctt cttcgccaac actcgccacc tgttgcgcca ggtcgtcctc 840
ctgccccccg aggatggcta ctacggcaac tgcttctacc cggtgaccgc caccgcccca 900
agcggcagga tcgcatcggc cgagctcatc gatgtcgtca gcatcatcag ggacgccaag 960
tcgaggctgc cgggcgagtt cgccaagtgg gctgccgggg atttcaagga cgacccttac 1020
gagctcagct tcacgtacaa ctcgctgttc gtgtcggact ggacccggct cggcttcctc 1080
gacgtcgact acggctgggg caagcccctc cacgttatac cgttcgcgta cttggacatc 1140
atggcggtcg gcatcatcgg ggcgccgccg gcgccgcaaa aggggactcg ggtgatggcg 1200
cagtgcgtcg agaaggagca catgcaggcg ttcctggaag agatgaaagg cttcgcttaa 1260

<210> SEQ ID NO 112
<211> LENGTH: 419
<212> TYPE: PRT
<213> ORGANISM: Musa acuminata

<400> SEQUENCE: 112

Met Ser Phe Ala Val Thr Arg Thr Ser Arg Ser Leu Val Thr Pro Cys
1 5 10 15

Gly Val Thr Pro Thr Gly Ser Leu Gly Leu Ser Ala Ile Asp Arg Val
20 25 30

Pro Gly Leu Arg His Met Val Arg Ser Leu His Val Phe Arg Gln Gly
35 40 45

Arg Glu Pro Ala Arg Ile Ile Arg Glu Ala Leu Ser Lys Ala Leu Val
50 55 60

Lys Tyr Tyr Pro Phe Ala Gly Arg Phe Val Asp Asp Pro Glu Gly Gly
65 70 75 80

Gly Glu Val Arg Val Ala Cys Thr Gly Glu Gly Ala Trp Phe Val Glu
85 90 95

Ala Lys Ala Asp Cys Ser Leu Glu Asp Val Lys Tyr Leu Asp Leu Pro
100 105 110

Leu Met Ile Pro Glu Asp Ala Leu Leu Pro Lys Pro Cys Pro Gly Leu
115 120 125

Asn Pro Leu Asp Leu Pro Leu Met Leu Gln Val Thr Glu Phe Val Gly
130 135 140

Gly Gly Phe Val Val Gly Leu Ile Ser Val His Thr Ile Ala Asp Gly
145 150 155 160

Leu Gly Val Val Gln Phe Ile Asn Ala Val Ala Glu Ile Ala Arg Gly

```
                165                 170                 175

Leu Pro Lys Pro Thr Val Glu Pro Ala Trp Ser Arg Glu Val Ile Pro
            180                 185                 190

Asn Pro Pro Lys Leu Pro Pro Gly Gly Pro Pro Val Phe Pro Ser Phe
        195                 200                 205

Lys Leu Leu His Ala Thr Val Asp Leu Ser Pro Asp His Ile Asp His
    210                 215                 220

Val Lys Ser Arg His Leu Glu Leu Thr Gly Gln Arg Cys Ser Thr Phe
225                 230                 235                 240

Asp Val Ala Ile Ala Asn Leu Trp Gln Ser Arg Thr Arg Ala Ile Asn
                245                 250                 255

Leu Asp Pro Gly Val Asp Val His Val Cys Phe Phe Ala Asn Thr Arg
            260                 265                 270

His Leu Leu Arg Gln Val Val Leu Leu Pro Pro Glu Asp Gly Tyr Tyr
        275                 280                 285

Gly Asn Cys Phe Tyr Pro Val Thr Ala Thr Ala Pro Ser Gly Arg Ile
    290                 295                 300

Ala Ser Ala Glu Leu Ile Asp Val Val Ser Ile Ile Arg Asp Ala Lys
305                 310                 315                 320

Ser Arg Leu Pro Gly Glu Phe Ala Lys Trp Ala Ala Gly Asp Phe Lys
                325                 330                 335

Asp Asp Pro Tyr Glu Leu Ser Phe Thr Tyr Asn Ser Leu Phe Val Ser
            340                 345                 350

Asp Trp Thr Arg Leu Gly Phe Leu Asp Val Asp Tyr Gly Trp Gly Lys
        355                 360                 365

Pro Leu His Val Ile Pro Phe Ala Tyr Leu Asp Ile Met Ala Val Gly
    370                 375                 380

Ile Ile Gly Ala Pro Pro Ala Pro Gln Lys Gly Thr Arg Val Met Ala
385                 390                 395                 400

Gln Cys Val Glu Lys Glu His Met Gln Ala Phe Leu Glu Glu Met Lys
                405                 410                 415

Gly Phe Ala
```

<210> SEQ ID NO 113
<211> LENGTH: 1359
<212> TYPE: DNA
<213> ORGANISM: Fragaria xananassa

<400> SEQUENCE: 113

```
atggagaaaa ttgaggtcag tataaattcc aaacacacca tcaaaccatc aacttcctct     60

acaccacttc agccttacaa gcttaccctc ctggaccagc tcactcctcc ggcgtatgtc    120

cccatcgtgt tcttctaccc cattactgac catgacttca atcttcctca aaccctagct    180

gacttaagac aagccctttc ggagactctc actttgtact atccactctc tggaagggtc    240

aaaaacaacc tatacatcga tgattttgaa gaaggtgtcc cataccttga ggctcgagtg    300

aattgtgaca tgactgattt tctaaggctt cggaaaatcg agtgccttaa tgagtttgtt    360

ccaataaaac catttagtat ggaagcaata tctgatgagc gttacccctt gcttggagtt    420

caagtcaacg ttttcgattc tggaatagca atcggtgtct ccgtctctca caagctcatc    480

gatggaggaa cggcagactg ttttctcaag tcctggggtg ctgtttttcg agggtgtcgt    540

gaaaatatca tacatcctag tctctctgaa gcagcattgc ttttcccacc gagagatgac    600

ttgcctgaaa agtatgtcga tcagatggaa gcgttatggt ttgccggaaa aaaagttgct    660

acaaggagat ttgtatttgg tgtgaaagcc atatcttcaa ttcaagatga agcgaagagc    720
```

```
gagtccgtgc ccaagccatc acgagttcat gccgtcactg gttttctctg gaaacatcta     780

atcgctgctt ctcgggcact aacatcaggt actacttcaa caagactttc tatagcggcc     840

caggcagtga acttaagaac acggatgaac atggagacag tgttggataa tgccactgga     900

aacttgttct ggtgggcaca ggccatacta gagctaagtc atacaacacc agagatcagt     960

gatcttaagc tgtgtgactt ggttaacttg ctcaatggat ctgtcaaaca atgtaacggt    1020

gattactttg agactttcaa gggtaaagag ggatatggaa gaatgtgcga gtatctagat    1080

tttcagagga ctatgagttc tatggaacca gcaccggata tttatttatt ctcgagctgg    1140

actaattttt tcaacccact tgattttgga tgggggagga catcatggat tggagttgca    1200

ggaaaaattg aatctgcaag ttgcaagttc ataatattag ttccaacaca atgcggttct    1260

ggaattgaag cgtgggtgaa tctagaagaa gagaaaatgg ctatgctaga acaagatccc    1320

cattttctag cgttagcatc tccaaagacc ttaatttaa                           1359


<210> SEQ ID NO 114
<211> LENGTH: 452
<212> TYPE: PRT
<213> ORGANISM: Fragaria xananassa

<400> SEQUENCE: 114

Met Glu Lys Ile Glu Val Ser Ile Asn Ser Lys His Thr Ile Lys Pro
1               5                   10                  15

Ser Thr Ser Ser Thr Pro Leu Gln Pro Tyr Lys Leu Thr Leu Leu Asp
            20                  25                  30

Gln Leu Thr Pro Pro Ala Tyr Val Pro Ile Val Phe Phe Tyr Pro Ile
        35                  40                  45

Thr Asp His Asp Phe Asn Leu Pro Gln Thr Leu Ala Asp Leu Arg Gln
    50                  55                  60

Ala Leu Ser Glu Thr Leu Thr Leu Tyr Tyr Pro Leu Ser Gly Arg Val
65                  70                  75                  80

Lys Asn Asn Leu Tyr Ile Asp Asp Phe Glu Glu Gly Val Pro Tyr Leu
                85                  90                  95

Glu Ala Arg Val Asn Cys Asp Met Thr Asp Phe Leu Arg Leu Arg Lys
            100                 105                 110

Ile Glu Cys Leu Asn Glu Phe Val Pro Ile Lys Pro Phe Ser Met Glu
        115                 120                 125

Ala Ile Ser Asp Glu Arg Tyr Pro Leu Leu Gly Val Gln Val Asn Val
    130                 135                 140

Phe Asp Ser Gly Ile Ala Ile Gly Val Ser Val Ser His Lys Leu Ile
145                 150                 155                 160

Asp Gly Gly Thr Ala Asp Cys Phe Leu Lys Ser Trp Gly Ala Val Phe
                165                 170                 175

Arg Gly Cys Arg Glu Asn Ile Ile His Pro Ser Leu Ser Glu Ala Ala
            180                 185                 190

Leu Leu Phe Pro Pro Arg Asp Asp Leu Pro Glu Lys Tyr Val Asp Gln
        195                 200                 205

Met Glu Ala Leu Trp Phe Ala Gly Lys Lys Val Ala Thr Arg Arg Phe
    210                 215                 220

Val Phe Gly Val Lys Ala Ile Ser Ser Ile Gln Asp Glu Ala Lys Ser
225                 230                 235                 240

Glu Ser Val Pro Lys Pro Ser Arg Val His Ala Val Thr Gly Phe Leu
                245                 250                 255

Trp Lys His Leu Ile Ala Ala Ser Arg Ala Leu Thr Ser Gly Thr Thr
```

```
            260                 265                 270

Ser Thr Arg Leu Ser Ile Ala Ala Gln Ala Val Asn Leu Arg Thr Arg
        275                 280                 285

Met Asn Met Glu Thr Val Leu Asp Asn Ala Thr Gly Asn Leu Phe Trp
    290                 295                 300

Trp Ala Gln Ala Ile Leu Glu Leu Ser His Thr Thr Pro Glu Ile Ser
305                 310                 315                 320

Asp Leu Lys Leu Cys Asp Leu Val Asn Leu Leu Asn Gly Ser Val Lys
                325                 330                 335

Gln Cys Asn Gly Asp Tyr Phe Glu Thr Phe Lys Gly Lys Glu Gly Tyr
            340                 345                 350

Gly Arg Met Cys Glu Tyr Leu Asp Phe Gln Arg Thr Met Ser Ser Met
        355                 360                 365

Glu Pro Ala Pro Asp Ile Tyr Leu Phe Ser Ser Trp Thr Asn Phe Phe
    370                 375                 380

Asn Pro Leu Asp Phe Gly Trp Gly Arg Thr Ser Trp Ile Gly Val Ala
385                 390                 395                 400

Gly Lys Ile Glu Ser Ala Ser Cys Lys Phe Ile Ile Leu Val Pro Thr
                405                 410                 415

Gln Cys Gly Ser Gly Ile Glu Ala Trp Val Asn Leu Glu Glu Glu Lys
            420                 425                 430

Met Ala Met Leu Glu Gln Asp Pro His Phe Leu Ala Leu Ala Ser Pro
        435                 440                 445

Lys Thr Leu Ile
    450


<210> SEQ ID NO 115
<211> LENGTH: 1374
<212> TYPE: DNA
<213> ORGANISM: Rosa hybrida

<400> SEQUENCE: 115

atggagaaaa ttgaggtcag tattatttcc cgagacacca ttaaaccatc agctgcttcc      60

tcttcactac acccttacaa gctttccatc atcgatcagt tcactcccac aacgtatttc     120

ccagttatat tcttctaccc cattactgac cgtgtcttca atcttcctca aaccttaacc     180

gacttgaaaa acactgtttc ccaggctctc actttgtacc atccactctc cgggaggata     240

aaaaacaacc tatacattga tgatttcgaa gcaggcatcc cctaccttga ggcccgagtg     300

aattttcaca tgattgattt tctaaggctt ccgaaaatcg agtggctaaa tgagtttgtt     360

ccaatggctc catatcgcaa ggaaacaata tctgagtttc ttcccttgct tggaattcaa     420

gtaaacattt tcgactctgg aatagcaatt ggtgtctctt tctctcacaa gatcaacgat     480

ggccaaacgg caagctgttt tctcaagtcc tgggttgcta tttttcgtgg gtatcgtaac     540

aaaatcatac atcctaatct ctctcaagct gcattacttt tgccatcgag ggatgacttg     600

cctgaaaagt acgtagctat gatggaaagg atgtggtttg gcgagaaaaa agttgttaca     660

aggagatttg tatttgatgc gaaagccata tccgcacttc aagatgaagg gaagagcgaa     720

tacgtgccca agccatcacg tgttcaggcc ctcactggtt ttctctggaa acatcaactc     780

gctgcttctc gggcattatc atcaggtact tcaacaagat tttccgtagc atcacagaca     840

gtgaacttaa ggtcaaaaat gaacatgaaa acgacgttgg acaatgccat tggtaatatc     900

tttttgtggg cttcggcacg gctagatcta aatgatacag caccagggag cagtgatctt     960

aagttgtgtg acttggttaa cttactcaat gaatctatca aagaatttaa cagtgattac    1020
```

```
ttggagattt tgaagggtaa agagggatat ggaggcatgt gtgatttgct agatttcatg   1080

gaagaaggga gttttgtaga accagcacca gagttttatt cattctcaag ctggactaga   1140

ttttttgacc aagttgattt tggatggggg aggccatctt gggttggatt ctcggggaga   1200

gttgaaacta gaaatttcac aatattcgtt gaaacacaat gcgatgacgg aattgatgcg   1260

tgggtgactg tagatgaaaa acaaatggct atgctagaac aagatccaca gtttttagca   1320

tttgcatctc caaacccccg aatttcaata gcctcttcag ttggtatgga ttaa         1374


<210> SEQ ID NO 116
<211> LENGTH: 457
<212> TYPE: PRT
<213> ORGANISM: Rosa hybrida

<400> SEQUENCE: 116

Met Glu Lys Ile Glu Val Ser Ile Ile Ser Arg Asp Thr Ile Lys Pro
 1               5                  10                  15

Ser Ala Ala Ser Ser Ser Leu His Pro Tyr Lys Leu Ser Ile Ile Asp
            20                  25                  30

Gln Phe Thr Pro Thr Thr Tyr Phe Pro Val Ile Phe Phe Tyr Pro Ile
        35                  40                  45

Thr Asp Arg Val Phe Asn Leu Pro Gln Thr Leu Thr Asp Leu Lys Asn
    50                  55                  60

Thr Val Ser Gln Ala Leu Thr Leu Tyr His Pro Leu Ser Gly Arg Ile
65                  70                  75                  80

Lys Asn Asn Leu Tyr Ile Asp Asp Phe Glu Ala Gly Ile Pro Tyr Leu
                85                  90                  95

Glu Ala Arg Val Asn Phe His Met Ile Asp Phe Leu Arg Leu Pro Lys
            100                 105                 110

Ile Glu Trp Leu Asn Glu Phe Val Pro Met Ala Pro Tyr Arg Lys Glu
        115                 120                 125

Thr Ile Ser Glu Phe Leu Pro Leu Leu Gly Ile Gln Val Asn Ile Phe
    130                 135                 140

Asp Ser Gly Ile Ala Ile Gly Val Ser Phe Ser His Lys Ile Asn Asp
145                 150                 155                 160

Gly Gln Thr Ala Ser Cys Phe Leu Lys Ser Trp Val Ala Ile Phe Arg
                165                 170                 175

Gly Tyr Arg Asn Lys Ile Ile His Pro Asn Leu Ser Gln Ala Ala Leu
            180                 185                 190

Leu Leu Pro Ser Arg Asp Asp Leu Pro Glu Lys Tyr Val Ala Met Met
        195                 200                 205

Glu Arg Met Trp Phe Gly Glu Lys Lys Val Val Thr Arg Arg Phe Val
    210                 215                 220

Phe Asp Ala Lys Ala Ile Ser Ala Leu Gln Asp Glu Gly Lys Ser Glu
225                 230                 235                 240

Tyr Val Pro Lys Pro Ser Arg Val Gln Ala Leu Thr Gly Phe Leu Trp
                245                 250                 255

Lys His Gln Leu Ala Ala Ser Arg Ala Leu Ser Ser Gly Thr Ser Thr
            260                 265                 270

Arg Phe Ser Val Ala Ser Gln Thr Val Asn Leu Arg Ser Lys Met Asn
        275                 280                 285

Met Lys Thr Thr Leu Asp Asn Ala Ile Gly Asn Ile Phe Leu Trp Ala
    290                 295                 300

Ser Ala Arg Leu Asp Leu Asn Asp Thr Ala Pro Gly Ser Ser Asp Leu
305                 310                 315                 320
```

```
Lys Leu Cys Asp Leu Val Asn Leu Leu Asn Glu Ser Ile Lys Glu Phe
                325                 330                 335

Asn Ser Asp Tyr Leu Glu Ile Leu Lys Gly Lys Glu Gly Tyr Gly Gly
            340                 345                 350

Met Cys Asp Leu Leu Asp Phe Met Glu Glu Gly Ser Phe Val Glu Pro
        355                 360                 365

Ala Pro Glu Phe Tyr Ser Phe Ser Ser Trp Thr Arg Phe Phe Asp Gln
    370                 375                 380

Val Asp Phe Gly Trp Gly Arg Pro Ser Trp Val Gly Phe Ser Gly Arg
385                 390                 395                 400

Val Glu Thr Arg Asn Phe Thr Ile Phe Val Glu Thr Gln Cys Asp Asp
                405                 410                 415

Gly Ile Asp Ala Trp Val Thr Val Asp Glu Lys Gln Met Ala Met Leu
            420                 425                 430

Glu Gln Asp Pro Gln Phe Leu Ala Phe Ala Ser Pro Asn Pro Arg Ile
        435                 440                 445

Ser Ile Ala Ser Ser Val Gly Met Asp
    450                 455
```

<210> SEQ ID NO 117
<211> LENGTH: 1812
<212> TYPE: DNA
<213> ORGANISM: Perilla frutescens

<400> SEQUENCE: 117

```
atgtctagca ttagccagaa ggtggtaatc ggcctaaaca aggcagcagc taataataat     60

ctccaaaact tggataggag aggttttaag acgcggtgtg tctcttctag taaggccgca    120

tcttgcctgc gtgcttcttg ctccttacaa ctagatgtta agccggttca agagggccga    180

cgcagtggaa actaccaacc ttctatttgg gatttcaact acgttcaatc tctcaacact    240

ccctataagg aagagaggta tttgacaagg catgctgaat tgattgtgca agtgaaaccg    300

ttgctggaga aaaaaatgga ggctgctcaa cagttggagt tgattgatga cttgaacaat    360

ctcggattgt cttatttttt tcaagaccgt attaagcaga ttttaagttt tatatatgac    420

gagaaccaat gtttccacag taatattaat gatcaagcag agaaaaggga tttgtatttc    480

acagctcttg gattcagaat tctcagacaa catggttttg atgtctctca agaagtattt    540

gattgtttca agaacgacag tggcagtgat tttaaggcaa gccttagtga caataccaaa    600

ggattgttac aactatacga ggcatctttc ctagtgagag aaggtgaaga cacactggag    660

caagctagac aattcgccac caaatttctg cggagaaaac ttgatgaaat tgacgacaat    720

catctattat catgcattca ccattctttg gagatcccac ttcactggag aattcaaagg    780

ctggaggcaa gatggttctt agatgcttac gcgacgaggc acgacatgaa tccagtcatt    840

cttgagctcg ccaagctcga tttcaatatt attcaagcaa cacaccaaga agaactcaag    900

gatgtctcaa ggtggtggca gaatacacgg ctggctgaga aactcccatt tgtgagggat    960

aggcttgtag aaagctactt ttgggccatt gcgctgtttg agcctcatca atatggatat   1020

cagagaagag tggcagccaa gattattact ctagcaacat ctatcgatga tgtttacgat   1080

atctatggta ccttagatga actgcagtta tttacagaca actttcgaag atgggatact   1140

gaatcactag gcagacttcc atatagcatg caattatttt atatggtaat ccacaacttt   1200

gtttctgagc tggcatacga aattctcaaa gagaagggtt tcatcgttat cccatattta   1260

cagagatcgt gggtagatct ggcggaatca tttttaaaag aagcaaattg gtactacagt   1320

ggatatacac caagcctgga agaatatatc gacaacggca gcatttcaat tggggcagtt   1380
```

```
gcagtattat cccaagttta tttcacatta gcaaactcca tagagaaacc taagatcgag   1440

agcatgtaca aataccatca cattcttcgc ctttccggat tgctcgtaag gcttcatgat   1500

gatctaggaa catcactgtt tgagaagaag agaggcgacg tgccgaaagc agtggagatt   1560

tgcatgaagg aaagaaatgt taccgaggaa gaggcggaag aacacgtgaa atatctgatt   1620

cgggaggcgt ggaaggagat gaacacagcg acgacggcag ccggttgtcc gtttatggat   1680

gagttgaatg tggccgcagc taatctcgga agagcggcgc agtttgtgta tctcgacgga   1740

gatggtcatg gcgtgcaaca ctctaaaatt catcaacaga tgggaggcct aatgttcgag   1800

ccatatgtct ga                                                       1812


<210> SEQ ID NO 118
<211> LENGTH: 603
<212> TYPE: PRT
<213> ORGANISM: Perilla frutescens

<400> SEQUENCE: 118

Met Ser Ser Ile Ser Gln Lys Val Val Ile Gly Leu Asn Lys Ala Ala
 1               5                  10                  15

Ala Asn Asn Asn Leu Gln Asn Leu Asp Arg Arg Gly Phe Lys Thr Arg
            20                  25                  30

Cys Val Ser Ser Ser Lys Ala Ala Ser Cys Leu Arg Ala Ser Cys Ser
        35                  40                  45

Leu Gln Leu Asp Val Lys Pro Val Gln Glu Gly Arg Arg Ser Gly Asn
    50                  55                  60

Tyr Gln Pro Ser Ile Trp Asp Phe Asn Tyr Val Gln Ser Leu Asn Thr
65                  70                  75                  80

Pro Tyr Lys Glu Glu Arg Tyr Leu Thr Arg His Ala Glu Leu Ile Val
                85                  90                  95

Gln Val Lys Pro Leu Leu Glu Lys Lys Met Glu Ala Ala Gln Gln Leu
            100                 105                 110

Glu Leu Ile Asp Asp Leu Asn Asn Leu Gly Leu Ser Tyr Phe Phe Gln
        115                 120                 125

Asp Arg Ile Lys Gln Ile Leu Ser Phe Ile Tyr Asp Glu Asn Gln Cys
    130                 135                 140

Phe His Ser Asn Ile Asn Asp Gln Ala Glu Lys Arg Asp Leu Tyr Phe
145                 150                 155                 160

Thr Ala Leu Gly Phe Arg Ile Leu Arg Gln His Gly Phe Asp Val Ser
                165                 170                 175

Gln Glu Val Phe Asp Cys Phe Lys Asn Asp Ser Gly Ser Asp Phe Lys
            180                 185                 190

Ala Ser Leu Ser Asp Asn Thr Lys Gly Leu Leu Gln Leu Tyr Glu Ala
        195                 200                 205

Ser Phe Leu Val Arg Glu Gly Glu Asp Thr Leu Glu Gln Ala Arg Gln
    210                 215                 220

Phe Ala Thr Lys Phe Leu Arg Arg Lys Leu Asp Glu Ile Asp Asp Asn
225                 230                 235                 240

His Leu Leu Ser Cys Ile His His Ser Leu Glu Ile Pro Leu His Trp
                245                 250                 255

Arg Ile Gln Arg Leu Glu Ala Arg Trp Phe Leu Asp Ala Tyr Ala Thr
            260                 265                 270

Arg His Asp Met Asn Pro Val Ile Leu Glu Leu Ala Lys Leu Asp Phe
        275                 280                 285

Asn Ile Ile Gln Ala Thr His Gln Glu Glu Leu Lys Asp Val Ser Arg
```

```
    290                 295                 300

Trp Trp Gln Asn Thr Arg Leu Ala Glu Lys Leu Pro Phe Val Arg Asp
305                 310                 315                 320

Arg Leu Val Glu Ser Tyr Phe Trp Ala Ile Ala Leu Phe Glu Pro His
                325                 330                 335

Gln Tyr Gly Tyr Gln Arg Arg Val Ala Ala Lys Ile Ile Thr Leu Ala
            340                 345                 350

Thr Ser Ile Asp Asp Val Tyr Asp Ile Tyr Gly Thr Leu Asp Glu Leu
        355                 360                 365

Gln Leu Phe Thr Asp Asn Phe Arg Arg Trp Asp Thr Glu Ser Leu Gly
    370                 375                 380

Arg Leu Pro Tyr Ser Met Gln Leu Phe Tyr Met Val Ile His Asn Phe
385                 390                 395                 400

Val Ser Glu Leu Ala Tyr Glu Ile Leu Lys Glu Lys Gly Phe Ile Val
                405                 410                 415

Ile Pro Tyr Leu Gln Arg Ser Trp Val Asp Leu Ala Glu Ser Phe Leu
            420                 425                 430

Lys Glu Ala Asn Trp Tyr Tyr Ser Gly Tyr Thr Pro Ser Leu Glu Glu
        435                 440                 445

Tyr Ile Asp Asn Gly Ser Ile Ser Ile Gly Ala Val Ala Val Leu Ser
    450                 455                 460

Gln Val Tyr Phe Thr Leu Ala Asn Ser Ile Glu Lys Pro Lys Ile Glu
465                 470                 475                 480

Ser Met Tyr Lys Tyr His His Ile Leu Arg Leu Ser Gly Leu Leu Val
                485                 490                 495

Arg Leu His Asp Asp Leu Gly Thr Ser Leu Phe Glu Lys Lys Arg Gly
            500                 505                 510

Asp Val Pro Lys Ala Val Glu Ile Cys Met Lys Glu Arg Asn Val Thr
        515                 520                 525

Glu Glu Glu Ala Glu Glu His Val Lys Tyr Leu Ile Arg Glu Ala Trp
    530                 535                 540

Lys Glu Met Asn Thr Ala Thr Thr Ala Ala Gly Cys Pro Phe Met Asp
545                 550                 555                 560

Glu Leu Asn Val Ala Ala Ala Asn Leu Gly Arg Ala Ala Gln Phe Val
                565                 570                 575

Tyr Leu Asp Gly Asp Gly His Gly Val Gln His Ser Lys Ile His Gln
            580                 585                 590

Gln Met Gly Gly Leu Met Phe Glu Pro Tyr Val
        595                 600
```

<210> SEQ ID NO 119
<211> LENGTH: 1812
<212> TYPE: DNA
<213> ORGANISM: Perilla citriodora

<400> SEQUENCE: 119

```
atgtctagca ttagccagaa ggtggtaatc ggcctaaaca aggcagcagc taataataat     60

ctccaaaact tggataggag aggttttaag acgcggtgtg tctcttctag taaggccgca    120

tcttgcctgc gtgcttcttg ctccttacaa ctagatgtta agccggttca agagggccga    180

cgcagtggaa actaccaacc ttccatttgg gatttcaact acgttcaatc tctcaacact    240

ccctataagg aagagaggta tttgacaagg catgctgaat tgattgtgca agtgaaaccg    300

ttgctggaga aaaaaatgga gcctgctcaa cagttggagt tgattgatga cttgaacaat    360

ctcggattgt cttatttttt tcaagaccgt attaagcaga ttttaagttt tatatatgac    420
```

```
gagaaccaat gtttccacag taatattaat gatcaagcag agaaaaggga tttgtatttc    480

acagctcttg gattcagact tctcagacaa catggttttg atgtctctca agaagtattt    540

gattgtttca agaacgacaa tggcagtgat tttaaggcaa gccttagtga caataccaaa    600

ggattgttac aactatacga ggcatctttc ctagtgagag aaggtgaaga tacactggag    660

caagctagac aattcgccac caaatttctg cggagaaaac ttgatgaaat tgacgacaat    720

catctattat catgcattca ccattctttg gagatcccac ttcactggag aattcaaagg    780

ctggaggcaa gatggttctt agatgcttac gcgacgaggc acgacatgaa tccagtcatt    840

cttgagctcg ccaagctcga tttcaatatt attcaagcaa cacaccaaga agaactcaag    900

gatgtctcaa ggtggtggca gaatacacgg ttggctgaga aactcccatt tgtgagggat    960

aggcttgtag aaagctactt ttgggccatt gcgctgtttg agcctcatca atatggatat   1020

cagagaagag tggcagccaa gattattact ctagcaacat ctatcgatga tgtttacgat   1080

atctatggta ccttagatga actgcagtta tttacagaca actttcgaag atgggatact   1140

gaatcactag gcagacttcc atatagcatg caattatttt atatggtaat ccacaacttt   1200

gtttctgagc tggcatacga aattctcaaa gagaagggtt tcatcgttat cccatattta   1260

cagagatcgt gggtagatct ggcggaatca tttttaaaag aagcaaattg gtactacagt   1320

ggatatacac caagcctgga agaatatatc gacaacggca gcatttcaat tggggcagtt   1380

gcagtattat cccaagttta tttcacatta gcaaactcca tagagaaacc taagatcgag   1440

agcatgtaca aataccatca cattcttcgc ctttccggat tgctcgtaag gcttcatgat   1500

gatctaggaa catcactgtt tgagaagaag agaggcgacg tgccgaaagc agtggagatt   1560

tgcatgaagg aaagaaatgt taccgaggaa gaggcagaag aacacgtgaa atatctgatt   1620

cgggaggcgt ggaaggagat gaacacagcg acgacggcag ccggttgtcc gtttatggat   1680

gagttgaatg tggccgcagc taatctcgga agagcggcgc agtttgtgta tctcgacgga   1740

gatggtcatg gcgtgcaaca ctctaaaatt catcaacaga tgggaggcct aatgttcgag   1800

ccatatgtct ga                                                        1812
```

<210> SEQ ID NO 120
<211> LENGTH: 603
<212> TYPE: PRT
<213> ORGANISM: Perilla citriodora

<400> SEQUENCE: 120

```
Met Ser Ser Ile Ser Gln Lys Val Val Ile Gly Leu Asn Lys Ala Ala
 1               5                  10                  15

Ala Asn Asn Asn Leu Gln Asn Leu Asp Arg Arg Gly Phe Lys Thr Arg
            20                  25                  30

Cys Val Ser Ser Ser Lys Ala Ala Ser Cys Leu Arg Ala Ser Cys Ser
        35                  40                  45

Leu Gln Leu Asp Val Lys Pro Val Gln Glu Gly Arg Arg Ser Gly Asn
    50                  55                  60

Tyr Gln Pro Ser Ile Trp Asp Phe Asn Tyr Val Gln Ser Leu Asn Thr
65                  70                  75                  80

Pro Tyr Lys Glu Glu Arg Tyr Leu Thr Arg His Ala Glu Leu Ile Val
                85                  90                  95

Gln Val Lys Pro Leu Leu Glu Lys Lys Met Glu Pro Ala Gln Gln Leu
            100                 105                 110

Glu Leu Ile Asp Asp Leu Asn Asn Leu Gly Leu Ser Tyr Phe Phe Gln
        115                 120                 125
```

```
Asp Arg Ile Lys Gln Ile Leu Ser Phe Ile Tyr Asp Glu Asn Gln Cys
    130                 135                 140

Phe His Ser Asn Ile Asn Asp Gln Ala Glu Lys Arg Asp Leu Tyr Phe
145                 150                 155                 160

Thr Ala Leu Gly Phe Arg Leu Leu Arg Gln His Gly Phe Asp Val Ser
                165                 170                 175

Gln Glu Val Phe Asp Cys Phe Lys Asn Asp Asn Gly Ser Asp Phe Lys
            180                 185                 190

Ala Ser Leu Ser Asp Asn Thr Lys Gly Leu Leu Gln Leu Tyr Glu Ala
        195                 200                 205

Ser Phe Leu Val Arg Glu Gly Glu Asp Thr Leu Glu Gln Ala Arg Gln
    210                 215                 220

Phe Ala Thr Lys Phe Leu Arg Arg Lys Leu Asp Glu Ile Asp Asp Asn
225                 230                 235                 240

His Leu Leu Ser Cys Ile His His Ser Leu Glu Ile Pro Leu His Trp
                245                 250                 255

Arg Ile Gln Arg Leu Glu Ala Arg Trp Phe Leu Asp Ala Tyr Ala Thr
            260                 265                 270

Arg His Asp Met Asn Pro Val Ile Leu Glu Leu Ala Lys Leu Asp Phe
        275                 280                 285

Asn Ile Ile Gln Ala Thr His Gln Glu Glu Leu Lys Asp Val Ser Arg
    290                 295                 300

Trp Trp Gln Asn Thr Arg Leu Ala Glu Lys Leu Pro Phe Val Arg Asp
305                 310                 315                 320

Arg Leu Val Glu Ser Tyr Phe Trp Ala Ile Ala Leu Phe Glu Pro His
                325                 330                 335

Gln Tyr Gly Tyr Gln Arg Arg Val Ala Ala Lys Ile Ile Thr Leu Ala
            340                 345                 350

Thr Ser Ile Asp Asp Val Tyr Asp Ile Tyr Gly Thr Leu Asp Glu Leu
        355                 360                 365

Gln Leu Phe Thr Asp Asn Phe Arg Arg Trp Asp Thr Glu Ser Leu Gly
    370                 375                 380

Arg Leu Pro Tyr Ser Met Gln Leu Phe Tyr Met Val Ile His Asn Phe
385                 390                 395                 400

Val Ser Glu Leu Ala Tyr Glu Ile Leu Lys Glu Lys Gly Phe Ile Val
                405                 410                 415

Ile Pro Tyr Leu Gln Arg Ser Trp Val Asp Leu Ala Glu Ser Phe Leu
            420                 425                 430

Lys Glu Ala Asn Trp Tyr Tyr Ser Gly Tyr Thr Pro Ser Leu Glu Glu
        435                 440                 445

Tyr Ile Asp Asn Gly Ser Ile Ser Ile Gly Ala Val Ala Val Leu Ser
    450                 455                 460

Gln Val Tyr Phe Thr Leu Ala Asn Ser Ile Glu Lys Pro Lys Ile Glu
465                 470                 475                 480

Ser Met Tyr Lys Tyr His His Ile Leu Arg Leu Ser Gly Leu Leu Val
                485                 490                 495

Arg Leu His Asp Asp Leu Gly Thr Ser Leu Phe Glu Lys Lys Arg Gly
            500                 505                 510

Asp Val Pro Lys Ala Val Glu Ile Cys Met Lys Glu Arg Asn Val Thr
        515                 520                 525

Glu Glu Glu Ala Glu Glu His Val Lys Tyr Leu Ile Arg Glu Ala Trp
    530                 535                 540

Lys Glu Met Asn Thr Ala Thr Thr Ala Ala Gly Cys Pro Phe Met Asp
```

-continued

```
545                 550                 555                 560

Glu Leu Asn Val Ala Ala Ala Asn Leu Gly Arg Ala Ala Gln Phe Val
                565                 570                 575

Tyr Leu Asp Gly Asp Gly His Gly Val Gln His Ser Lys Ile His Gln
            580                 585                 590

Gln Met Gly Gly Leu Met Phe Glu Pro Tyr Val
        595                 600
```

<210> SEQ ID NO 121
<211> LENGTH: 1812
<212> TYPE: DNA
<213> ORGANISM: Perilla citriodora

<400> SEQUENCE: 121

```
atgtctagca ttagccagaa ggtggtaatc ggcctaaaca aggcagcagc taataataat     60

ctccaaaact tggataggag aggttttaag acgcggtgtg tctcttctag taaggccgca    120

tcttgcctgc gtgcttcttg ctccttacaa ctagatgtta agccggttca agagggccga    180

cgcagtggaa actaccaacc ttccatttgg gatttcaact acgttcaatc tctcaacact    240

ccctataagg aagagaggta tttgacaagg catgctgaat tgattgtgca agtgaaaccg    300

ttgctggaga aaaaaatgga gcctgctcaa cagttggagt tgattgatga cttgaacaat    360

ctcggattgt cttatttttt tcaagaccgt attaagcaga ttttaagttt tatatatgac    420

gagaaccaat gtttccacag taatattaat gatcaagcag agaaaaggga tttgtatttc    480

acagctcttg gattcagact tctcagacaa catggttttg atgtctctca agaagtattt    540

gattgtttca agaacgacaa tggcagtgat tttaaggcaa gccttagtga caataccaaa    600

ggattgttac aactatacga ggcatctttc ctagtgagag aaggtgaaga tacactggag    660

caagctagac aattcgccac caaatttctg cggagaaaac ttgatgaaat tgacgacaat    720

catctattat catgcattca ccattctttg gagatcccac ttcactggag aattcaaagg    780

ctggaggcaa gatggttctt agatgcttac gcgacgaggc acgacatgaa tccagtcatt    840

cttgagctcg ccaagctcga tttcaatatt attcaagcaa cacaccaaga agaactcaag    900

gatgtctcaa ggtggtggca gaatacacgg ttggctgaga aactcccatt tgtgagggat    960

aggcttgtag aaagctactt ttgggccatt gcgctgtttg agcctcatca atatggatat   1020

cagagaagag tggcagccaa gattattact ctagcaacat ctatcgatga tgtttacgat   1080

atctatggta ccttagatga actgcagtta tttacagaca actttcgaag atgggatact   1140

gaatcactag gcagacttcc atatagcatg caattatttt atatggtaat ccacaacttt   1200

gtttctgagc tggcatacga aattctcaaa gagaagggtt tcatcgttat cccatattta   1260

cagagatcgt gggtagatct ggcggaatca tttttaaaag aagcaaattg gtactacagt   1320

ggatatacac caagcctgga agaatatatc gacaacggca gcatttcaat tggggcagtt   1380

gcagtattat cccaagttta tttcacatta gcaaactcca tagagaaacc taagatcgag   1440

agcatgtaca aataccatca cattcttcgc ctttccggat tgctcgtaag gcttcatgat   1500

gatctaggaa catcactgtt tgagaagaag agaggcgacg tgccgaaagc agtggagatt   1560

tgcatgaagg aaagaaatgt taccgaggaa gaggcagaag aacacgtgaa atatctgatt   1620

cgggaggcgt ggaaggagat gaacacagcg acgacggcag ccggttgtcc gtttatggat   1680

gagttgaatg tggccgcagc taatctcgga agagcggcgc agtttgtgta tctcgacgga   1740

gatggtcatg gcgtgcaaca ctctaaaatt catcaacaga tgggaggcct aatgttcgag   1800

ccatatgtct ga                                                       1812
```

<210> SEQ ID NO 122
<211> LENGTH: 603
<212> TYPE: PRT
<213> ORGANISM: Perilla citriodora

<400> SEQUENCE: 122

```
Met Ser Ser Ile Ser Gln Lys Val Val Ile Gly Leu Asn Lys Ala Ala
 1               5                  10                  15

Ala Asn Asn Asn Leu Gln Asn Leu Asp Arg Arg Gly Phe Lys Thr Arg
            20                  25                  30

Cys Val Ser Ser Ser Lys Ala Ala Ser Cys Leu Arg Ala Ser Cys Ser
        35                  40                  45

Leu Gln Leu Asp Val Lys Pro Val Gln Glu Gly Arg Arg Ser Gly Asn
    50                  55                  60

Tyr Gln Pro Ser Ile Trp Asp Phe Asn Tyr Val Gln Ser Leu Asn Thr
65                  70                  75                  80

Pro Tyr Lys Glu Glu Arg Tyr Leu Thr Arg His Ala Glu Leu Ile Val
                85                  90                  95

Gln Val Lys Pro Leu Leu Glu Lys Lys Met Glu Pro Ala Gln Gln Leu
            100                 105                 110

Glu Leu Ile Asp Asp Leu Asn Asn Leu Gly Leu Ser Tyr Phe Phe Gln
        115                 120                 125

Asp Arg Ile Lys Gln Ile Leu Ser Phe Ile Tyr Asp Glu Asn Gln Cys
    130                 135                 140

Phe His Ser Asn Ile Asn Asp Gln Ala Glu Lys Arg Asp Leu Tyr Phe
145                 150                 155                 160

Thr Ala Leu Gly Phe Arg Leu Leu Arg Gln His Gly Phe Asp Val Ser
                165                 170                 175

Gln Glu Val Phe Asp Cys Phe Lys Asn Asp Asn Gly Ser Asp Phe Lys
            180                 185                 190

Ala Ser Leu Ser Asp Asn Thr Lys Gly Leu Leu Gln Leu Tyr Glu Ala
        195                 200                 205

Ser Phe Leu Val Arg Glu Gly Glu Asp Thr Leu Glu Gln Ala Arg Gln
    210                 215                 220

Phe Ala Thr Lys Phe Leu Arg Arg Lys Leu Asp Glu Ile Asp Asp Asn
225                 230                 235                 240

His Leu Leu Ser Cys Ile His His Ser Leu Glu Ile Pro Leu His Trp
                245                 250                 255

Arg Ile Gln Arg Leu Glu Ala Arg Trp Phe Leu Asp Ala Tyr Ala Thr
            260                 265                 270

Arg His Asp Met Asn Pro Val Ile Leu Glu Leu Ala Lys Leu Asp Phe
        275                 280                 285

Asn Ile Ile Gln Ala Thr His Gln Glu Glu Leu Lys Asp Val Ser Arg
    290                 295                 300

Trp Trp Gln Asn Thr Arg Leu Ala Glu Lys Leu Pro Phe Val Arg Asp
305                 310                 315                 320

Arg Leu Val Glu Ser Tyr Phe Trp Ala Ile Ala Leu Phe Glu Pro His
                325                 330                 335

Gln Tyr Gly Tyr Gln Arg Arg Val Ala Ala Lys Ile Ile Thr Leu Ala
            340                 345                 350

Thr Ser Ile Asp Asp Val Tyr Asp Ile Tyr Gly Thr Leu Asp Glu Leu
        355                 360                 365

Gln Leu Phe Thr Asp Asn Phe Arg Arg Trp Asp Thr Glu Ser Leu Gly
    370                 375                 380
```

```
Arg Leu Pro Tyr Ser Met Gln Leu Phe Tyr Met Val Ile His Asn Phe
385                 390                 395                 400

Val Ser Glu Leu Ala Tyr Glu Ile Leu Lys Glu Lys Gly Phe Ile Val
                405                 410                 415

Ile Pro Tyr Leu Gln Arg Ser Trp Val Asp Leu Ala Glu Ser Phe Leu
            420                 425                 430

Lys Glu Ala Asn Trp Tyr Tyr Ser Gly Tyr Thr Pro Ser Leu Glu Glu
        435                 440                 445

Tyr Ile Asp Asn Gly Ser Ile Ser Ile Gly Ala Val Ala Val Leu Ser
    450                 455                 460

Gln Val Tyr Phe Thr Leu Ala Asn Ser Ile Glu Lys Pro Lys Ile Glu
465                 470                 475                 480

Ser Met Tyr Lys Tyr His His Ile Leu Arg Leu Ser Gly Leu Leu Val
                485                 490                 495

Arg Leu His Asp Asp Leu Gly Thr Ser Leu Phe Glu Lys Lys Arg Gly
            500                 505                 510

Asp Val Pro Lys Ala Val Glu Ile Cys Met Lys Glu Arg Asn Val Thr
        515                 520                 525

Glu Glu Glu Ala Glu Glu His Val Lys Tyr Leu Ile Arg Glu Ala Trp
    530                 535                 540

Lys Glu Met Asn Thr Ala Thr Thr Ala Ala Gly Cys Pro Phe Met Asp
545                 550                 555                 560

Glu Leu Asn Val Ala Ala Ala Asn Leu Gly Arg Ala Ala Gln Phe Val
                565                 570                 575

Tyr Leu Asp Gly Asp Gly His Gly Val Gln His Ser Lys Ile His Gln
            580                 585                 590

Gln Met Gly Gly Leu Met Phe Glu Pro Tyr Val
        595                 600
```

```
<210> SEQ ID NO 123
<211> LENGTH: 1812
<212> TYPE: DNA
<213> ORGANISM: Perilla citriodora

<400> SEQUENCE: 123

atgtctagca ttagccagaa ggtggtaatc ggcctaaaca aggcagcagc taataataat     60

ctccaaaact tggataggag aggttttaag acgcggtgtg tctcttctag taaggccgca    120

tcttgcctgc gtgcttcttg ctccttacaa ctagatgtta agccggttca agagggccga    180

cgcagtggaa actaccaacc ttccatttgg gatttcaact acgttcaatc tctcaacact    240

ccctataagg aagagaggta tttgacaagg catgctgaat tgattgtgca agtgaaaccg    300

ttgctggaga aaaaaatgga gcctgctcaa cagttggagt tgattgatga cttgaacaat    360

ctcggattgt cttatttttt tcaagaccgt attaagcaga ttttaagttt tatatatgac    420

gagaaccaat gtttccacag taatattaat gatcaagcag agaaaaggga tttgtatttc    480

acagctcttg gattcagact tctcagacaa catggttttg atgtctctca agaagtattt    540

gattgtttca agaacgacaa tggcagtgat tttaaggcaa gccttagtga caataccaaa    600

ggattgttac aactatacga ggcatctttc ctagtgagag aaggtgaaga tacactggag    660

caagctagac aattcgccac caaatttctg cggagaaaac ttgatgaaat tgacgacaat    720

catctattat catgcattca ccattctttg gagatcccac ttcactggag aattcaaagg    780

ctggaggcaa gatggttctt agatgcttac gcgacgaggc acgacatgaa tccagtcatt    840

cttgagctcg ccaagctcga tttcaatatt attcaagcaa cacaccaaga agaactcaag    900
```

```
gatgtctcaa ggtggtggca gaatacacgg ttggctgaga aactcccatt tgtgagggat    960

aggcttgtag aaagctactt ttgggccatt gcgctgtttg agcctcatca atatggatat   1020

cagagaagag tggcagccaa gattattact ctagcaacat ctatcgatga tgtttacgat   1080

atctatggta ccttagatga actgcagtta tttacagaca actttcgaag atgggatact   1140

gaatcactag gcagacttcc atatagcatg caattatttt atatggtaat ccacaacttt   1200

gtttctgagc tggcatacga aattctcaaa gagaagggtt tcatcgttat cccatattta   1260

cagagatcgt gggtagatct ggcggaatca tttttaaaag aagcaaattg gtactacagt   1320

ggatatacac caagcctgga agaatatatc gacaacggca gcatttcaat tggggcagtt   1380

gcagtattat cccaagttta tttcacatta gcaaactcca tagagaaacc taagatcgag   1440

agcatgtaca aataccatca cattcttcgc ctttccggat tgctcgtaag gcttcatgat   1500

gatctaggaa catcactgtt tgagaagaag agaggcgacg tgccgaaagc agtggagatt   1560

tgcatgaagg aaagaaatgt taccgaggaa gaggcagaag aacacgtgaa atatctgatt   1620

cgggaggcgt ggaaggagat gaacacagcg acgacggcag ccggttgtcc gtttatggat   1680

gagttgaatg tggccgcagc taatctcgga agagcggcgc agtttgtgta tctcgacgga   1740

gatggtcatg gcgtgcaaca ctctaaaatt catcaacaga tgggaggcct aatgttcgag   1800

ccatatgtct ga                                                       1812


<210> SEQ ID NO 124
<211> LENGTH: 603
<212> TYPE: PRT
<213> ORGANISM: Perilla citriodora

<400> SEQUENCE: 124

Met Ser Ser Ile Ser Gln Lys Val Val Ile Gly Leu Asn Lys Ala Ala
1               5                   10                  15

Ala Asn Asn Asn Leu Gln Asn Leu Asp Arg Arg Gly Phe Lys Thr Arg
            20                  25                  30

Cys Val Ser Ser Ser Lys Ala Ala Ser Cys Leu Arg Ala Ser Cys Ser
        35                  40                  45

Leu Gln Leu Asp Val Lys Pro Val Gln Glu Gly Arg Arg Ser Gly Asn
    50                  55                  60

Tyr Gln Pro Ser Ile Trp Asp Phe Asn Tyr Val Gln Ser Leu Asn Thr
65                  70                  75                  80

Pro Tyr Lys Glu Glu Arg Tyr Leu Thr Arg His Ala Glu Leu Ile Val
                85                  90                  95

Gln Val Lys Pro Leu Leu Glu Lys Lys Met Glu Pro Ala Gln Gln Leu
            100                 105                 110

Glu Leu Ile Asp Asp Leu Asn Asn Leu Gly Leu Ser Tyr Phe Phe Gln
        115                 120                 125

Asp Arg Ile Lys Gln Ile Leu Ser Phe Ile Tyr Asp Glu Asn Gln Cys
    130                 135                 140

Phe His Ser Asn Ile Asn Asp Gln Ala Glu Lys Arg Asp Leu Tyr Phe
145                 150                 155                 160

Thr Ala Leu Gly Phe Arg Leu Leu Arg Gln His Gly Phe Asp Val Ser
                165                 170                 175

Gln Glu Val Phe Asp Cys Phe Lys Asn Asp Asn Gly Ser Asp Phe Lys
            180                 185                 190

Ala Ser Leu Ser Asp Asn Thr Lys Gly Leu Leu Gln Leu Tyr Glu Ala
        195                 200                 205
```

```
Ser Phe Leu Val Arg Glu Gly Glu Asp Thr Leu Glu Gln Ala Arg Gln
    210                 215                 220

Phe Ala Thr Lys Phe Leu Arg Arg Lys Leu Asp Glu Ile Asp Asp Asn
225                 230                 235                 240

His Leu Leu Ser Cys Ile His His Ser Leu Glu Ile Pro Leu His Trp
                245                 250                 255

Arg Ile Gln Arg Leu Glu Ala Arg Trp Phe Leu Asp Ala Tyr Ala Thr
            260                 265                 270

Arg His Asp Met Asn Pro Val Ile Leu Glu Leu Ala Lys Leu Asp Phe
        275                 280                 285

Asn Ile Ile Gln Ala Thr His Gln Glu Glu Leu Lys Asp Val Ser Arg
    290                 295                 300

Trp Trp Gln Asn Thr Arg Leu Ala Glu Lys Leu Pro Phe Val Arg Asp
305                 310                 315                 320

Arg Leu Val Glu Ser Tyr Phe Trp Ala Ile Ala Leu Phe Glu Pro His
                325                 330                 335

Gln Tyr Gly Tyr Gln Arg Arg Val Ala Ala Lys Ile Ile Thr Leu Ala
            340                 345                 350

Thr Ser Ile Asp Asp Val Tyr Asp Ile Tyr Gly Thr Leu Asp Glu Leu
        355                 360                 365

Gln Leu Phe Thr Asp Asn Phe Arg Arg Trp Asp Thr Glu Ser Leu Gly
    370                 375                 380

Arg Leu Pro Tyr Ser Met Gln Leu Phe Tyr Met Val Ile His Asn Phe
385                 390                 395                 400

Val Ser Glu Leu Ala Tyr Glu Ile Leu Lys Glu Lys Gly Phe Ile Val
                405                 410                 415

Ile Pro Tyr Leu Gln Arg Ser Trp Val Asp Leu Ala Glu Ser Phe Leu
            420                 425                 430

Lys Glu Ala Asn Trp Tyr Tyr Ser Gly Tyr Thr Pro Ser Leu Glu Glu
        435                 440                 445

Tyr Ile Asp Asn Gly Ser Ile Ser Ile Gly Ala Val Ala Val Leu Ser
    450                 455                 460

Gln Val Tyr Phe Thr Leu Ala Asn Ser Ile Glu Lys Pro Lys Ile Glu
465                 470                 475                 480

Ser Met Tyr Lys Tyr His His Ile Leu Arg Leu Ser Gly Leu Leu Val
                485                 490                 495

Arg Leu His Asp Asp Leu Gly Thr Ser Leu Phe Glu Lys Lys Arg Gly
            500                 505                 510

Asp Val Pro Lys Ala Val Glu Ile Cys Met Lys Glu Arg Asn Val Thr
        515                 520                 525

Glu Glu Glu Ala Glu Glu His Val Lys Tyr Leu Ile Arg Glu Ala Trp
    530                 535                 540

Lys Glu Met Asn Thr Ala Thr Thr Ala Ala Gly Cys Pro Phe Met Asp
545                 550                 555                 560

Glu Leu Asn Val Ala Ala Ala Asn Leu Gly Arg Ala Ala Gln Phe Val
                565                 570                 575

Tyr Leu Asp Gly Asp Gly His Gly Val Gln His Ser Lys Ile His Gln
            580                 585                 590

Gln Met Gly Gly Leu Met Phe Glu Pro Tyr Val
        595                 600
```

<210> SEQ ID NO 125
<211> LENGTH: 1812
<212> TYPE: DNA
<213> ORGANISM: Cinnamomum tenuipile

<400> SEQUENCE: 125

```
atggcattgc aaatgattgc tccatttcta tcctccttcc tcccaaatcc cagacacagc     60
ctcgcagccc atggcctcac acaccagaaa tgtgtctcaa agcacatttc atgctccacc    120
actacaccaa cctactcaac cacagttcca agaagatcag ggaactacaa gcccagcatc    180
tgggactatg attttgtgca gtcactagga agtggctaca aggtagaggc acatggaaca    240
cgtgtgaaga agttgaagga agttgtaaag catttgttga aagaaacaga tagttctttg    300
gcccaaatag aactgattga caaactccgt cgtctaggtc taaggtggct cttcaaaaat    360
gagattaagc aagtgctata cacgatatca tcagacaaca ccagcataga aatgaggaaa    420
gatcttcatg cagtatcaac tcgatttaga cttcttagac aacatgggta caaggtctcc    480
acagatgttt tcaacgactt caaagatgaa aagggttgtt tcaagccaag cctttcaatg    540
gacataaagg gaatgttgag cttgtatgaa gcttcacacc ttgcctttca aggggagact    600
gtgttggatg aggcaagagc tttcgtaagc acacatctca tggatatcaa ggagaacata    660
gacccaatcc ttcataaaaa agtagagcat gctttggata tgcctttgca ttggaggtta    720
gaaaaattag aggctaggtg gtacatggac atatatatga gggaagaagg catgaattct    780
tctttacttg aattggccat gcttcatttc aacattgtgc aaacaacatt ccaaacaaat    840
ttaaagagtt tgtcaaggtg gtggaaagat ttgggtcttg gagagcagtt gagcttcact    900
agagacaggt tggtggaatg tttcttttgg gccgccgcaa tgacacctga gccacaattt    960
ggacgttgcc aggaagttgt agcgaaagtt gctcaactca taataataat tgacgatatc   1020
tatgacgtgt atggtacggt ggatgagcta gaacttttta ctaatgcgat tgatagatgg   1080
gatcttgagg caatggagca acttcctgaa tatatgaaga cctgtttctt agctttatac   1140
aacagtatta atgaaatagg ttatgacatt ttgaaagagg aagggcgcaa tgtcatacca   1200
taccttagaa atacgtggac agaattgtgt aaagcattct tagtggaggc caaatggtat   1260
agtagtggat atacaccaac gcttgaggag tatctgcaaa cctcatggat ttcgattgga   1320
agtctaccca tgcaaacata tgtttttgct ctacttggga aaaatctagc accggagagt   1380
agtgattttg ctgagaagat ctcggatatc ttacgattgg gaggaatgat gattcgactt   1440
ccggatgatt tgggaacttc aacggatgaa ctaaagagag gtgatgttcc aaaatccatt   1500
cagtgttaca tgcatgaagc aggtgttaca gaggatgttg ctcgcgacca cataatgggt   1560
ctatttcaag agacatggaa aaaactcaat gaataccttg tggaaagttc tcttccccat   1620
gcctttatcg atcatgctat gaatcttgga cgtgtctcct attgcactta caaacatgga   1680
gatggattta gtgatggatt tggagatcct ggcagtcaag agaaaaagat gttcatgtct   1740
ttatttgctg aaccccttca agttgatgaa gccaagggta tttcatttta tgttgatggt   1800
ggatctgcct ga                                                        1812
```

<210> SEQ ID NO 126
<211> LENGTH: 603
<212> TYPE: PRT
<213> ORGANISM: Cinnamomum tenuipile

<400> SEQUENCE: 126

```
Met Ala Leu Gln Met Ile Ala Pro Phe Leu Ser Ser Phe Leu Pro Asn
1               5                   10                  15

Pro Arg His Ser Leu Ala Ala His Gly Leu Thr His Gln Lys Cys Val
            20                  25                  30

Ser Lys His Ile Ser Cys Ser Thr Thr Thr Pro Thr Tyr Ser Thr Thr
```

-continued

```
        35                  40                  45

Val Pro Arg Arg Ser Gly Asn Tyr Lys Pro Ser Ile Trp Asp Tyr Asp
    50                  55                  60

Phe Val Gln Ser Leu Gly Ser Gly Tyr Lys Val Glu Ala His Gly Thr
65                  70                  75                  80

Arg Val Lys Lys Leu Lys Glu Val Val Lys His Leu Leu Lys Glu Thr
                85                  90                  95

Asp Ser Ser Leu Ala Gln Ile Glu Leu Ile Asp Lys Leu Arg Arg Leu
            100                 105                 110

Gly Leu Arg Trp Leu Phe Lys Asn Glu Ile Lys Gln Val Leu Tyr Thr
        115                 120                 125

Ile Ser Ser Asp Asn Thr Ser Ile Glu Met Arg Lys Asp Leu His Ala
    130                 135                 140

Val Ser Thr Arg Phe Arg Leu Leu Arg Gln His Gly Tyr Lys Val Ser
145                 150                 155                 160

Thr Asp Val Phe Asn Asp Phe Lys Asp Glu Lys Gly Cys Phe Lys Pro
                165                 170                 175

Ser Leu Ser Met Asp Ile Lys Gly Met Leu Ser Leu Tyr Glu Ala Ser
            180                 185                 190

His Leu Ala Phe Gln Gly Glu Thr Val Leu Asp Glu Ala Arg Ala Phe
        195                 200                 205

Val Ser Thr His Leu Met Asp Ile Lys Glu Asn Ile Asp Pro Ile Leu
    210                 215                 220

His Lys Lys Val Glu His Ala Leu Asp Met Pro Leu His Trp Arg Leu
225                 230                 235                 240

Glu Lys Leu Glu Ala Arg Trp Tyr Met Asp Ile Tyr Met Arg Glu Glu
                245                 250                 255

Gly Met Asn Ser Ser Leu Leu Glu Leu Ala Met Leu His Phe Asn Ile
            260                 265                 270

Val Gln Thr Thr Phe Gln Thr Asn Leu Lys Ser Leu Ser Arg Trp Trp
        275                 280                 285

Lys Asp Leu Gly Leu Gly Glu Gln Leu Ser Phe Thr Arg Asp Arg Leu
    290                 295                 300

Val Glu Cys Phe Phe Trp Ala Ala Ala Met Thr Pro Glu Pro Gln Phe
305                 310                 315                 320

Gly Arg Cys Gln Glu Val Val Ala Lys Val Ala Gln Leu Ile Ile Ile
                325                 330                 335

Ile Asp Asp Ile Tyr Asp Val Tyr Gly Thr Val Asp Glu Leu Glu Leu
            340                 345                 350

Phe Thr Asn Ala Ile Asp Arg Trp Asp Leu Glu Ala Met Glu Gln Leu
        355                 360                 365

Pro Glu Tyr Met Lys Thr Cys Phe Leu Ala Leu Tyr Asn Ser Ile Asn
    370                 375                 380

Glu Ile Gly Tyr Asp Ile Leu Lys Glu Glu Gly Arg Asn Val Ile Pro
385                 390                 395                 400

Tyr Leu Arg Asn Thr Trp Thr Glu Leu Cys Lys Ala Phe Leu Val Glu
                405                 410                 415

Ala Lys Trp Tyr Ser Ser Gly Tyr Thr Pro Thr Leu Glu Glu Tyr Leu
            420                 425                 430

Gln Thr Ser Trp Ile Ser Ile Gly Ser Leu Pro Met Gln Thr Tyr Val
        435                 440                 445

Phe Ala Leu Leu Gly Lys Asn Leu Ala Pro Glu Ser Ser Asp Phe Ala
    450                 455                 460
```

```
Glu Lys Ile Ser Asp Ile Leu Arg Leu Gly Gly Met Met Ile Arg Leu
465                 470                 475                 480

Pro Asp Asp Leu Gly Thr Ser Thr Asp Glu Leu Lys Arg Gly Asp Val
                485                 490                 495

Pro Lys Ser Ile Gln Cys Tyr Met His Glu Ala Gly Val Thr Glu Asp
            500                 505                 510

Val Ala Arg Asp His Ile Met Gly Leu Phe Gln Glu Thr Trp Lys Lys
        515                 520                 525

Leu Asn Glu Tyr Leu Val Glu Ser Ser Leu Pro His Ala Phe Ile Asp
    530                 535                 540

His Ala Met Asn Leu Gly Arg Val Ser Tyr Cys Thr Tyr Lys His Gly
545                 550                 555                 560

Asp Gly Phe Ser Asp Gly Phe Gly Asp Pro Gly Ser Gln Glu Lys Lys
                565                 570                 575

Met Phe Met Ser Leu Phe Ala Glu Pro Leu Gln Val Asp Glu Ala Lys
            580                 585                 590

Gly Ile Ser Phe Tyr Val Asp Gly Gly Ser Ala
        595                 600


<210> SEQ ID NO 127
<211> LENGTH: 1704
<212> TYPE: DNA
<213> ORGANISM: Ocimum basilicum

<400> SEQUENCE: 127

atgtcttgtg cacggatcac cgtaacattg ccgtatcgct ccgcaaaaac atcaattcaa     60

cggggaatta cgcattaccc cgcccttata cgcccacgct tctctgcttg cacgcctttg    120

gcatcggcga tgcctctaag ttcaactcct ctcatcaacg gggataactc tcagcgtaaa    180

aacacacgtc aacacatgga ggagagcagc agcaagagga gagaatatct gctggaggaa    240

acgacgcgaa aactgcagag aaacgacacc gaatcggtgg agaaactcaa gcttatcgac    300

aacatccaac agttgggaat cggctactat tttgaggacg ccatcaacgc cgtactccgc    360

tcgcctttct ccaccggaga agaagacctc ttcaccgctg ctctgcgctt ccgcttgctc    420

cgccacaacg gcatcgaaat cagccctgaa atattcctaa aattcaagga cgagagggga    480

aaattcgacg aatcggacac gctagggtta ctgagcttgt acgaagcgtc aaatttgggg    540

gttgcaggag aagaaatatt ggaggaggct atggagtttg cggaggctcg cctgagacgg    600

tcgctgtcag agccggcggc gccgcttcat ggtgaggtgg cgcaagcgct agatgtgccg    660

aggcatctga gaatggcgag gttggaagcg agacgattca tcgagcagta tggtaaacag    720

agcgatcatg atggagatct tttggagctg gcaattttgg attataatca agttcaggct    780

caacaccaat ccgaactcac tgaaataatc aggtggtgga aggagctcgg tttggtggat    840

aagttgagtt ttgggcgaga cagaccattg gagtgctttt tgtggaccgt ggggctcctc    900

ccagagccca agtattcgag cgttagaata gagttggcga aagccatctc tattctctta    960

gtgatcgatg atattttcga tacctatgga gagatggatg acctcatcct cttcaccgat   1020

gcaattcgaa gatgggatct tgaagcaatg gaggggctcc ctgagtacat gaaaatatgc   1080

tacatggcgt tgtacaatac caccaatgaa gtatgctaca aagtgctcag ggatactgga   1140

cggattgtcc tccttaacct caaatctacg tggatagaca tgattgaagg tttcatggag   1200

gaagcaaaat ggttcaatgg tggaagtgca ccaaaattgg aagagtatat agagaatgga   1260

gtgtccacgg caggagcata catggctttt gcacacatct tctttctcat aggagaaggt   1320

gttacacacc aaaattccca actcttcacc caaaaaccct accccaaggt cttctccgcc   1380
```

```
gccggccgca ttcttcgcct ctgggatgat ctcggaaccg ccaaggaaga gcaagagcga   1440

ggagatctgg cttcgtgcgt gcagttattt atgaaagaga agtcgttgac ggaagaggag   1500

gcaagaagtc gcattttgga agagataaaa ggattatgga gggatctgaa tggggaactg   1560

gtctacaaca agaatttgcc gttatccata atcaaagtcg cacttaacat ggcgagagct   1620

tctcaagttg tgtacaagca cgatcaagac acttattttt caagcgtaga caattatgtg   1680

gatgccctct tcttcactca ataa                                          1704


<210> SEQ ID NO 128
<211> LENGTH: 567
<212> TYPE: PRT
<213> ORGANISM: Ocimum basilicum

<400> SEQUENCE: 128

Met Ser Cys Ala Arg Ile Thr Val Thr Leu Pro Tyr Arg Ser Ala Lys
 1               5                  10                  15

Thr Ser Ile Gln Arg Gly Ile Thr His Tyr Pro Ala Leu Ile Arg Pro
            20                  25                  30

Arg Phe Ser Ala Cys Thr Pro Leu Ala Ser Ala Met Pro Leu Ser Ser
        35                  40                  45

Thr Pro Leu Ile Asn Gly Asp Asn Ser Gln Arg Lys Asn Thr Arg Gln
    50                  55                  60

His Met Glu Glu Ser Ser Ser Lys Arg Arg Glu Tyr Leu Leu Glu Glu
65                  70                  75                  80

Thr Thr Arg Lys Leu Gln Arg Asn Asp Thr Glu Ser Val Glu Lys Leu
                85                  90                  95

Lys Leu Ile Asp Asn Ile Gln Gln Leu Gly Ile Gly Tyr Tyr Phe Glu
            100                 105                 110

Asp Ala Ile Asn Ala Val Leu Arg Ser Pro Phe Ser Thr Gly Glu Glu
        115                 120                 125

Asp Leu Phe Thr Ala Ala Leu Arg Phe Arg Leu Leu Arg His Asn Gly
    130                 135                 140

Ile Glu Ile Ser Pro Glu Ile Phe Leu Lys Phe Lys Asp Glu Arg Gly
145                 150                 155                 160

Lys Phe Asp Glu Ser Asp Thr Leu Gly Leu Leu Ser Leu Tyr Glu Ala
                165                 170                 175

Ser Asn Leu Gly Val Ala Gly Glu Glu Ile Leu Glu Glu Ala Met Glu
            180                 185                 190

Phe Ala Glu Ala Arg Leu Arg Arg Ser Leu Ser Glu Pro Ala Ala Pro
        195                 200                 205

Leu His Gly Glu Val Ala Gln Ala Leu Asp Val Pro Arg His Leu Arg
    210                 215                 220

Met Ala Arg Leu Glu Ala Arg Arg Phe Ile Glu Gln Tyr Gly Lys Gln
225                 230                 235                 240

Ser Asp His Asp Gly Asp Leu Leu Glu Leu Ala Ile Leu Asp Tyr Asn
                245                 250                 255

Gln Val Gln Ala Gln His Gln Ser Glu Leu Thr Glu Ile Ile Arg Trp
            260                 265                 270

Trp Lys Glu Leu Gly Leu Val Asp Lys Leu Ser Phe Gly Arg Asp Arg
        275                 280                 285

Pro Leu Glu Cys Phe Leu Trp Thr Val Gly Leu Leu Pro Glu Pro Lys
    290                 295                 300

Tyr Ser Ser Val Arg Ile Glu Leu Ala Lys Ala Ile Ser Ile Leu Leu
305                 310                 315                 320
```

```
Val Ile Asp Asp Ile Phe Asp Thr Tyr Gly Glu Met Asp Asp Leu Ile
                325                 330                 335

Leu Phe Thr Asp Ala Ile Arg Arg Trp Asp Leu Glu Ala Met Glu Gly
            340                 345                 350

Leu Pro Glu Tyr Met Lys Ile Cys Tyr Met Ala Leu Tyr Asn Thr Thr
        355                 360                 365

Asn Glu Val Cys Tyr Lys Val Leu Arg Asp Thr Gly Arg Ile Val Leu
    370                 375                 380

Leu Asn Leu Lys Ser Thr Trp Ile Asp Met Ile Glu Gly Phe Met Glu
385                 390                 395                 400

Glu Ala Lys Trp Phe Asn Gly Gly Ser Ala Pro Lys Leu Glu Glu Tyr
                405                 410                 415

Ile Glu Asn Gly Val Ser Thr Ala Gly Ala Tyr Met Ala Phe Ala His
            420                 425                 430

Ile Phe Phe Leu Ile Gly Glu Gly Val Thr His Gln Asn Ser Gln Leu
        435                 440                 445

Phe Thr Gln Lys Pro Tyr Pro Lys Val Phe Ser Ala Ala Gly Arg Ile
    450                 455                 460

Leu Arg Leu Trp Asp Asp Leu Gly Thr Ala Lys Glu Glu Gln Glu Arg
465                 470                 475                 480

Gly Asp Leu Ala Ser Cys Val Gln Leu Phe Met Lys Glu Lys Ser Leu
                485                 490                 495

Thr Glu Glu Glu Ala Arg Ser Arg Ile Leu Glu Glu Ile Lys Gly Leu
            500                 505                 510

Trp Arg Asp Leu Asn Gly Glu Leu Val Tyr Asn Lys Asn Leu Pro Leu
        515                 520                 525

Ser Ile Ile Lys Val Ala Leu Asn Met Ala Arg Ala Ser Gln Val Val
    530                 535                 540

Tyr Lys His Asp Gln Asp Thr Tyr Phe Ser Ser Val Asp Asn Tyr Val
545                 550                 555                 560

Asp Ala Leu Phe Phe Thr Gln
                565


<210> SEQ ID NO 129
<211> LENGTH: 1812
<212> TYPE: DNA
<213> ORGANISM: Perilla frutescens

<400> SEQUENCE: 129

atgtctagca ttagccagaa ggtggtaatc ggcctaaaca aggcagcagc taataataat      60

ctccaaaact tggataggag aggttttaag acgcggtgtg tctcttctag taaggccgca     120

tcttgcctgc gtgcttcttg ctccttacaa ctagatgtta agccggttca agagggccga     180

cgcagtggaa actaccaacc ttctatttgg gatttcaact acgttcaatc tctcaacact     240

ccctataagg aagagaggta tttgacaagg catgctgaat tgattgtgca agtgaaaccg     300

ttgctggaga aaaaaatgga ggctgctcaa cagttggagt tgattgatga cttgaacaat     360

ctcggattgt cttatttttt tcaagaccgt attaagcaga ttttaagttt tatatatgac     420

gagaaccaat gtttccacag taatattaat gatcaagcag agaaaaggga tttgtatttc     480

acagctcttg gattcagaat tctcagacaa catggttttg atgtctctca agaagtattt     540

gattgtttca agaacgacag tggcagtgat tttaaggcaa gccttagtga caataccaaa     600

ggattgttac aactatacga ggcatctttc ctagtgagag aaggtgaaga cacactggag     660

caagctagac aattcgccac caaatttctg cggagaaaac ttgatgaaat tgacgacaat     720
```

-continued

```
catctattat catgcattca ccattctttg gagatcccac ttcactggag aattcaaagg    780

ctggaggcaa gatggttctt agatgcttac gcgacgaggc acgacatgaa tccagtcatt    840

cttgagctcg ccaagctcga tttcaatatt attcaagcaa cacaccaaga agaactcaag    900

gatgtctcaa ggtggtggca gaatacacgg ctggctgaga aactcccatt tgtgagggat    960

aggcttgtag aaagctactt ttgggccatt gcgctgtttg agcctcatca atatggatat   1020

cagagaagag tggcagccaa gattattact ctagcaacat ctatcgatga tgtttacgat   1080

atctatggta ccttagatga actgcagtta tttacagaca actttcgaag atgggatact   1140

gaatcactag gcagacttcc atatagcatg caattatttt atatggtaat ccacaacttt   1200

gtttctgagc tggcatacga aattctcaaa gagaagggtt tcatcgttat cccatattta   1260

cagagatcgt gggtagatct ggcggaatca tttttaaaag aagcaaattg gtactacagt   1320

ggatatacac caagcctgga agaatatatc gacaacggca gcatttcaat tggggcagtt   1380

gcagtattat cccaagttta tttcacatta gcaaactcca tagagaaacc taagatcgag   1440

agcatgtaca aataccatca cattcttcgc ctttccggat tgctcgtaag gcttcatgat   1500

gatctaggaa catcactgtt tgagaagaag agaggcgacg tgccgaaagc agtggagatt   1560

tgcatgaagg aaagaaatgt taccgaggaa gaggcggaag aacacgtgaa atatctgatt   1620

cgggaggcgt ggaaggagat gaacacagcg acgacggcag ccggttgtcc gtttatggat   1680

gagttgaatg tggccgcagc taatctcgga agagcggcgc agtttgtgta tctcgacgga   1740

gatggtcatg gcgtgcaaca ctctaaaatt catcaacaga tgggaggcct aatgttcgag   1800

ccatatgtct ga                                                        1812
```

```
<210> SEQ ID NO 130
<211> LENGTH: 603
<212> TYPE: PRT
<213> ORGANISM: Perilla frutescens

<400> SEQUENCE: 130

Met Ser Ser Ile Ser Gln Lys Val Val Ile Gly Leu Asn Lys Ala Ala
 1               5                  10                  15

Ala Asn Asn Asn Leu Gln Asn Leu Asp Arg Arg Gly Phe Lys Thr Arg
            20                  25                  30

Cys Val Ser Ser Ser Lys Ala Ala Ser Cys Leu Arg Ala Ser Cys Ser
        35                  40                  45

Leu Gln Leu Asp Val Lys Pro Val Gln Glu Gly Arg Arg Ser Gly Asn
    50                  55                  60

Tyr Gln Pro Ser Ile Trp Asp Phe Asn Tyr Val Gln Ser Leu Asn Thr
65                  70                  75                  80

Pro Tyr Lys Glu Glu Arg Tyr Leu Thr Arg His Ala Glu Leu Ile Val
                85                  90                  95

Gln Val Lys Pro Leu Leu Glu Lys Lys Met Glu Ala Ala Gln Gln Leu
            100                 105                 110

Glu Leu Ile Asp Asp Leu Asn Asn Leu Gly Leu Ser Tyr Phe Phe Gln
        115                 120                 125

Asp Arg Ile Lys Gln Ile Leu Ser Phe Ile Tyr Asp Glu Asn Gln Cys
    130                 135                 140

Phe His Ser Asn Ile Asn Asp Gln Ala Glu Lys Arg Asp Leu Tyr Phe
145                 150                 155                 160

Thr Ala Leu Gly Phe Arg Ile Leu Arg Gln His Gly Phe Asp Val Ser
                165                 170                 175
```

-continued

```
Gln Glu Val Phe Asp Cys Phe Lys Asn Asp Ser Gly Ser Asp Phe Lys
            180                 185                 190

Ala Ser Leu Ser Asp Asn Thr Lys Gly Leu Leu Gln Leu Tyr Glu Ala
        195                 200                 205

Ser Phe Leu Val Arg Glu Gly Glu Asp Thr Leu Glu Gln Ala Arg Gln
    210                 215                 220

Phe Ala Thr Lys Phe Leu Arg Arg Lys Leu Asp Glu Ile Asp Asp Asn
225                 230                 235                 240

His Leu Leu Ser Cys Ile His His Ser Leu Glu Ile Pro Leu His Trp
                245                 250                 255

Arg Ile Gln Arg Leu Glu Ala Arg Trp Phe Leu Asp Ala Tyr Ala Thr
            260                 265                 270

Arg His Asp Met Asn Pro Val Ile Leu Glu Leu Ala Lys Leu Asp Phe
        275                 280                 285

Asn Ile Ile Gln Ala Thr His Gln Glu Glu Leu Lys Asp Val Ser Arg
    290                 295                 300

Trp Trp Gln Asn Thr Arg Leu Ala Glu Lys Leu Pro Phe Val Arg Asp
305                 310                 315                 320

Arg Leu Val Glu Ser Tyr Phe Trp Ala Ile Ala Leu Phe Glu Pro His
                325                 330                 335

Gln Tyr Gly Tyr Gln Arg Arg Val Ala Ala Lys Ile Ile Thr Leu Ala
            340                 345                 350

Thr Ser Ile Asp Asp Val Tyr Asp Ile Tyr Gly Thr Leu Asp Glu Leu
        355                 360                 365

Gln Leu Phe Thr Asp Asn Phe Arg Arg Trp Asp Thr Glu Ser Leu Gly
    370                 375                 380

Arg Leu Pro Tyr Ser Met Gln Leu Phe Tyr Met Val Ile His Asn Phe
385                 390                 395                 400

Val Ser Glu Leu Ala Tyr Glu Ile Leu Lys Glu Lys Gly Phe Ile Val
                405                 410                 415

Ile Pro Tyr Leu Gln Arg Ser Trp Val Asp Leu Ala Glu Ser Phe Leu
            420                 425                 430

Lys Glu Ala Asn Trp Tyr Tyr Ser Gly Tyr Thr Pro Ser Leu Glu Glu
        435                 440                 445

Tyr Ile Asp Asn Gly Ser Ile Ser Ile Gly Ala Val Ala Val Leu Ser
    450                 455                 460

Gln Val Tyr Phe Thr Leu Ala Asn Ser Ile Glu Lys Pro Lys Ile Glu
465                 470                 475                 480

Ser Met Tyr Lys Tyr His His Ile Leu Arg Leu Ser Gly Leu Leu Val
                485                 490                 495

Arg Leu His Asp Asp Leu Gly Thr Ser Leu Phe Glu Lys Lys Arg Gly
            500                 505                 510

Asp Val Pro Lys Ala Val Glu Ile Cys Met Lys Glu Arg Asn Val Thr
        515                 520                 525

Glu Glu Glu Ala Glu Glu His Val Lys Tyr Leu Ile Arg Glu Ala Trp
    530                 535                 540

Lys Glu Met Asn Thr Ala Thr Thr Ala Ala Gly Cys Pro Phe Met Asp
545                 550                 555                 560

Glu Leu Asn Val Ala Ala Ala Asn Leu Gly Arg Ala Ala Gln Phe Val
                565                 570                 575

Tyr Leu Asp Gly Asp Gly His Gly Val Gln His Ser Lys Ile His Gln
            580                 585                 590

Gln Met Gly Gly Leu Met Phe Glu Pro Tyr Val
        595                 600
```

<210> SEQ ID NO 131
<211> LENGTH: 21
<212> TYPE: DNA
<213> ORGANISM: Artificial Sequence
<220> FEATURE:
<223> OTHER INFORMATION: Primer

<400> SEQUENCE: 131
tctagaacta gtggatcccc c 21

<210> SEQ ID NO 132
<211> LENGTH: 20
<212> TYPE: DNA
<213> ORGANISM: Artificial Sequence
<220> FEATURE:
<223> OTHER INFORMATION: Primer

<400> SEQUENCE: 132
atatcgaatt cctgcagccc 20

<210> SEQ ID NO 133
<211> LENGTH: 51
<212> TYPE: DNA
<213> ORGANISM: Artificial Sequence
<220> FEATURE:
<223> OTHER INFORMATION: Primer

<400> SEQUENCE: 133
ctagaactag tggatccccc atgactgccg acaacaatag tatgccccat g 51

<210> SEQ ID NO 134
<211> LENGTH: 56
<212> TYPE: DNA
<213> ORGANISM: Artificial Sequence
<220> FEATURE:
<223> OTHER INFORMATION: Primer

<400> SEQUENCE: 134
atatcgaatt cctgcagccc ttatagcatt ctatgaattt gcctgtcatt ttccac 56

<210> SEQ ID NO 135
<211> LENGTH: 50
<212> TYPE: DNA
<213> ORGANISM: Artificial Sequence
<220> FEATURE:
<223> OTHER INFORMATION: Primer

<400> SEQUENCE: 135
ctagaactag tggatccccc atggcttcag aaaaagaaat taggagagag 50

<210> SEQ ID NO 136
<211> LENGTH: 51
<212> TYPE: DNA
<213> ORGANISM: Artificial Sequence
<220> FEATURE:
<223> OTHER INFORMATION: Primer

<400> SEQUENCE: 136
atatcgaatt cctgcagccc ttatttgctt ctcttgtaaa ctttgttcaa g 51

<210> SEQ ID NO 137
<211> LENGTH: 55
<212> TYPE: DNA
<213> ORGANISM: Artificial Sequence
<220> FEATURE:
<223> OTHER INFORMATION: Primer

<400> SEQUENCE: 137
ctagaactag tggatccccc atgccgccgc tattcaaggg actgaaacag atggc 55

<210> SEQ ID NO 138
<211> LENGTH: 54
<212> TYPE: DNA
<213> ORGANISM: Artificial Sequence
<220> FEATURE:
<223> OTHER INFORMATION: Primer

<400> SEQUENCE: 138
atatcgaatt cctgcagccc ttaggattta atgcaggtga cggacccatc tttc 54

<210> SEQ ID NO 139
<211> LENGTH: 55
<212> TYPE: DNA
<213> ORGANISM: Artificial Sequence
<220> FEATURE:
<223> OTHER INFORMATION: Primer

<400> SEQUENCE: 139
ctagaactag tggatccccc atgccagttt taaccaataa aacagtcatt tctgg 55

<210> SEQ ID NO 140
<211> LENGTH: 45
<212> TYPE: DNA
<213> ORGANISM: Artificial Sequence
<220> FEATURE:
<223> OTHER INFORMATION: Primer

<400> SEQUENCE: 140
tctagaacta gtggatcccc catggctttg cagatgatag caccg 45

<210> SEQ ID NO 141
<211> LENGTH: 42
<212> TYPE: DNA
<213> ORGANISM: Artificial Sequence
<220> FEATURE:
<223> OTHER INFORMATION: Primer

<400> SEQUENCE: 141
atatcgaatt cctgcagccc ttaagcgcta cctccgtcta cg 42

<210> SEQ ID NO 142
<211> LENGTH: 47
<212> TYPE: DNA
<213> ORGANISM: Artificial Sequence
<220> FEATURE:
<223> OTHER INFORMATION: Primer

<400> SEQUENCE: 142
tctagaacta gtggatcccc catgagaagg tccggaaatt ataaacc 47

<210> SEQ ID NO 143
<211> LENGTH: 47
<212> TYPE: DNA
<213> ORGANISM: Artificial Sequence
<220> FEATURE:
<223> OTHER INFORMATION: Primer

<400> SEQUENCE: 143
tctagaacta gtggatcccc catgtcaacg accgttccga gaaggtc 47

<210> SEQ ID NO 144
<211> LENGTH: 47

<212> TYPE: DNA
<213> ORGANISM: Artificial Sequence
<220> FEATURE:
<223> OTHER INFORMATION: Primer

<400> SEQUENCE: 144
tctagaacta gtggatcccc catgtcaacg accgttccga gaaggtc 47

<210> SEQ ID NO 145
<211> LENGTH: 33
<212> TYPE: DNA
<213> ORGANISM: Artificial Sequence
<220> FEATURE:
<223> OTHER INFORMATION: Primer

<400> SEQUENCE: 145
cttcatagtt actttcagaa ctgcttacta ttc 33

<210> SEQ ID NO 146
<211> LENGTH: 33
<212> TYPE: DNA
<213> ORGANISM: Artificial Sequence
<220> FEATURE:
<223> OTHER INFORMATION: Primer

<400> SEQUENCE: 146
gaatagtaag cagttctgaa agtaactatg aag 33

<210> SEQ ID NO 147
<211> LENGTH: 33
<212> TYPE: DNA
<213> ORGANISM: Artificial Sequence
<220> FEATURE:
<223> OTHER INFORMATION: Primer

<400> SEQUENCE: 147
gaatagtaag cagttctgaa agtaactatg aag 33

<210> SEQ ID NO 148
<211> LENGTH: 50
<212> TYPE: DNA
<213> ORGANISM: Artificial Sequence
<220> FEATURE:
<223> OTHER INFORMATION: Primer

<400> SEQUENCE: 148
tctagaacta gtggatcccc catggagaaa attgaggtca gtattatttc 50

<210> SEQ ID NO 149
<211> LENGTH: 49
<212> TYPE: DNA
<213> ORGANISM: Artificial Sequence
<220> FEATURE:
<223> OTHER INFORMATION: Primer

<400> SEQUENCE: 149
atatcgaatt cctgcagccc ttaatccata ccaactgaag aggctattg 49

<210> SEQ ID NO 150
<211> LENGTH: 50
<212> TYPE: DNA
<213> ORGANISM: Artificial Sequence
<220> FEATURE:
<223> OTHER INFORMATION: Primer

<400> SEQUENCE: 150
tctagaacta gtggatcccc catggagaaa attgaggtca gtataaattc 50

<210> SEQ ID NO 151
<211> LENGTH: 48
<212> TYPE: DNA
<213> ORGANISM: Artificial Sequence
<220> FEATURE:
<223> OTHER INFORMATION: Primer

<400> SEQUENCE: 151
atatcgaatt cctgcagccc ttaaattaag gtctttggag atgctaac 48

<210> SEQ ID NO 152
<211> LENGTH: 47
<212> TYPE: DNA
<213> ORGANISM: Artificial Sequence
<220> FEATURE:
<223> OTHER INFORMATION: Primer

<400> SEQUENCE: 152
tctagaacta gtggatcccc catgagcttc gctgtgacca gaacaag 47

<210> SEQ ID NO 153
<211> LENGTH: 47
<212> TYPE: DNA
<213> ORGANISM: Artificial Sequence
<220> FEATURE:
<223> OTHER INFORMATION: Primer

<400> SEQUENCE: 153
atatcgaatt cctgcagccc ttaagcgaag cctttcatct cttccag 47

<210> SEQ ID NO 154
<211> LENGTH: 3165
<212> TYPE: DNA
<213> ORGANISM: Saccharomyces cerevisiae

<400> SEQUENCE: 154
atgccgccgc tattcaaggg actgaaacag atggcaaagc caattgccta tgtttcaaga 60
ttttcggcga aacgaccaat tcatataata ctttttctc taatcatatc cgcattcgct 120
tatctatccg tcattcagta ttacttcaat ggttggcaac tagattcaaa tagtgttttt 180
gaaactgctc caaataaaga ctccaacact ctatttcaag aatgttccca ttactacaga 240
gattcctctc tagatggttg ggtatcaatc accgcgcatg aagctagtga gttaccagcc 300
ccacaccatt actatctatt aaacctgaac ttcaatagtc ctaatgaaac tgactccatt 360
ccagaactag ctaacacggt tttgagaaa gataatacaa aatatattct gcaagaagat 420
ctcagtgttt ccaaagaaat ttcttctact gatggaacga aatggaggtt aagaagtgac 480
agaaaaagtc ttttcgacgt aaagacgtta gcatattctc tctacgatgt attttcagaa 540
aatgtaaccc aagcagaccc gtttgacgtc cttattatgg ttactgccta cctaatgatg 600
ttctacacca tattcggcct cttcaatgac atgaggaaga ccgggtcaaa tttttggttg 660
agcgcctcta cagtggtcaa ttctgcatca tcacttttct tagcattgta tgtcacccaa 720
tgtattctag gcaaagaagt ttccgcatta actctttttg aaggtttgcc tttcattgta 780
gttgttgttg gtttcaagca caaaatcaag attgcccagt atgccctgga gaaatttgaa 840
agagtcggtt tatctaaaag gattactacc gatgaaatcg tttttgaatc cgtgagcgaa 900
gagggtggtc gtttgattca agaccatttg ctttgtattt ttgcctttat cggatgctct 960
atgtatgctc accaattgaa gactttgaca aacttctgca tattatcagc atttatccta 1020
atttttgaat tgattttaac tcctacattt tattctgcta tcttagcgct tagactggaa 1080

```
atgaatgtta tccacagatc tactattatc aagcaaacat tagaagaaga cggtgttgtt   1140
ccatctacag caagaatcat ttctaaagca gaaaagaaat ccgtatcttc tttcttaaat   1200
ctcagtgtgg ttgtcattat catgaaactc tctgtcatac tgttgtttgt cttcatcaac   1260
ttttataact ttggtgcaaa ttgggtcaat gatgccttca attcattgta cttcgataag   1320
gaacgtgttt ctctaccaga ttttattacc tcgaatgcct ctgaaaactt taaagagcaa   1380
gctattgtta gtgtcacccc attattatat tacaaaccca ttaagtccta ccaacgcatt   1440
gaggatatgg ttcttctatt gcttcgtaat gtcagtgttg ccattcgtga taggttcgtc   1500
agtaaattag ttctttccgc cttagtatgc agtgctgtca tcaatgtgta tttattgaat   1560
gctgctagaa ttcataccag ttatactgca gaccaattgg tgaaaactga agtcaccaag   1620
aagtctttta ctgctcctgt acaaaaggct tctacaccag ttttaaccaa taaaacagtc   1680
atttctggat cgaaagtcaa aagtttatca tctgcgcaat cgagctcatc aggaccttca   1740
tcatctagtg aggaagatga ttcccgcgat attgaaagct tggataagaa aatacgtcct   1800
ttagaagaat tagaagcatt attaagtagt ggaaatacaa aacaattgaa gaacaaagag   1860
gtcgctgcct tggttattca cggtaagtta cctttgtacg ctttggagaa aaaattaggt   1920
gatactacga gagcggttgc ggtacgtagg aaggctcttt caattttggc agaagctcct   1980
gtattagcat ctgatcgttt accatataaa aattatgact acgaccgcgt atttggcgct   2040
tgttgtgaaa atgttatagg ttacatgcct ttgcccgttg gtgttatagg ccccttggtt   2100
atcgatggta catcttatca tataccaatg gcaactacag agggttgttt ggtagcttct   2160
gccatgcgtg gctgtaaggc aatcaatgct ggcggtggtg caacaactgt tttaactaag   2220
gatggtatga caagaggccc agtagtccgt ttcccaactt tgaaaagatc tggtgcctgt   2280
aagatatggt tagactcaga agagggacaa aacgcaatta aaaaagcttt taactctaca   2340
tcaagatttg cacgtctgca acatattcaa acttgtctag caggagattt actcttcatg   2400
agatttagaa caactactgg tgacgcaatg ggtatgaata tgatttctaa aggtgtcgaa   2460
tactcattaa agcaaatggt agaagagtat ggctgggaag atatggaggt tgtctccgtt   2520
tctggtaact actgtaccga caaaaaacca gctgccatca actggatcga aggtcgtggt   2580
aagagtgtcg tcgcagaagc tactattcct ggtgatgttg tcagaaaagt gttaaaaagt   2640
gatgtttccg cattggttga gttgaacatt gctaagaatt tggttggatc tgcaatggct   2700
gggtctgttg gtggatttaa cgcacatgca gctaatttag tgacagctgt tttcttggca   2760
ttaggacaag atcctgcaca aaatgttgaa agttccaact gtataacatt gatgaaagaa   2820
gtggacggtg atttgagaat ttccgtatcc atgccatcca tcgaagtagg taccatcggt   2880
ggtggtactg ttctagaacc acaaggtgcc atgttggact tattaggtgt aagaggcccg   2940
catgctaccg ctcctggtac caacgcacgt caattagcaa gaatagttgc ctgtgccgtc   3000
ttggcaggtg aattatcctt atgtgctgcc ctagcagccg gccatttggt tcaaagtcat   3060
atgacccaca acaggaaacc tgctgaacca acaaaaccta acaatttgga cgccactgat   3120
ataaatcgtt tgaaagatgg gtccgtcacc tgcattaaat cctaa                   3165
```

<210> SEQ ID NO 155
<211> LENGTH: 1054
<212> TYPE: PRT
<213> ORGANISM: Saccharomyces cerevisiae

<400> SEQUENCE: 155

Met Pro Pro Leu Phe Lys Gly Leu Lys Gln Met Ala Lys Pro Ile Ala

-continued

```
1               5                   10                  15

Tyr Val Ser Arg Phe Ser Ala Lys Arg Pro Ile His Ile Ile Leu Phe
            20                  25                  30

Ser Leu Ile Ile Ser Ala Phe Ala Tyr Leu Ser Val Ile Gln Tyr Tyr
        35                  40                  45

Phe Asn Gly Trp Gln Leu Asp Ser Asn Ser Val Phe Glu Thr Ala Pro
    50                  55                  60

Asn Lys Asp Ser Asn Thr Leu Phe Gln Glu Cys Ser His Tyr Tyr Arg
65                  70                  75                  80

Asp Ser Ser Leu Asp Gly Trp Val Ser Ile Thr Ala His Glu Ala Ser
                85                  90                  95

Glu Leu Pro Ala Pro His His Tyr Tyr Leu Leu Asn Leu Asn Phe Asn
            100                 105                 110

Ser Pro Asn Glu Thr Asp Ser Ile Pro Glu Leu Ala Asn Thr Val Phe
        115                 120                 125

Glu Lys Asp Asn Thr Lys Tyr Ile Leu Gln Glu Asp Leu Ser Val Ser
    130                 135                 140

Lys Glu Ile Ser Ser Thr Asp Gly Thr Lys Trp Arg Leu Arg Ser Asp
145                 150                 155                 160

Arg Lys Ser Leu Phe Asp Val Lys Thr Leu Ala Tyr Ser Leu Tyr Asp
                165                 170                 175

Val Phe Ser Glu Asn Val Thr Gln Ala Asp Pro Phe Asp Val Leu Ile
            180                 185                 190

Met Val Thr Ala Tyr Leu Met Met Phe Tyr Thr Ile Phe Gly Leu Phe
        195                 200                 205

Asn Asp Met Arg Lys Thr Gly Ser Asn Phe Trp Leu Ser Ala Ser Thr
    210                 215                 220

Val Val Asn Ser Ala Ser Ser Leu Phe Leu Ala Leu Tyr Val Thr Gln
225                 230                 235                 240

Cys Ile Leu Gly Lys Glu Val Ser Ala Leu Thr Leu Phe Glu Gly Leu
                245                 250                 255

Pro Phe Ile Val Val Val Val Gly Phe Lys His Lys Ile Lys Ile Ala
            260                 265                 270

Gln Tyr Ala Leu Glu Lys Phe Glu Arg Val Gly Leu Ser Lys Arg Ile
        275                 280                 285

Thr Thr Asp Glu Ile Val Phe Glu Ser Val Ser Glu Glu Gly Gly Arg
    290                 295                 300

Leu Ile Gln Asp His Leu Leu Cys Ile Phe Ala Phe Ile Gly Cys Ser
305                 310                 315                 320

Met Tyr Ala His Gln Leu Lys Thr Leu Thr Asn Phe Cys Ile Leu Ser
                325                 330                 335

Ala Phe Ile Leu Ile Phe Glu Leu Ile Leu Thr Pro Thr Phe Tyr Ser
            340                 345                 350

Ala Ile Leu Ala Leu Arg Leu Glu Met Asn Val Ile His Arg Ser Thr
        355                 360                 365

Ile Ile Lys Gln Thr Leu Glu Glu Asp Gly Val Val Pro Ser Thr Ala
    370                 375                 380

Arg Ile Ile Ser Lys Ala Glu Lys Lys Ser Val Ser Ser Phe Leu Asn
385                 390                 395                 400

Leu Ser Val Val Val Ile Ile Met Lys Leu Ser Val Ile Leu Leu Phe
                405                 410                 415

Val Phe Ile Asn Phe Tyr Asn Phe Gly Ala Asn Trp Val Asn Asp Ala
            420                 425                 430
```

```
Phe Asn Ser Leu Tyr Phe Asp Lys Glu Arg Val Ser Leu Pro Asp Phe
        435                 440                 445

Ile Thr Ser Asn Ala Ser Glu Asn Phe Lys Glu Gln Ala Ile Val Ser
    450                 455                 460

Val Thr Pro Leu Leu Tyr Tyr Lys Pro Ile Lys Ser Tyr Gln Arg Ile
465                 470                 475                 480

Glu Asp Met Val Leu Leu Leu Leu Arg Asn Val Ser Val Ala Ile Arg
                485                 490                 495

Asp Arg Phe Val Ser Lys Leu Val Leu Ser Ala Leu Val Cys Ser Ala
            500                 505                 510

Val Ile Asn Val Tyr Leu Leu Asn Ala Ala Arg Ile His Thr Ser Tyr
        515                 520                 525

Thr Ala Asp Gln Leu Val Lys Thr Glu Val Thr Lys Lys Ser Phe Thr
    530                 535                 540

Ala Pro Val Gln Lys Ala Ser Thr Pro Val Leu Thr Asn Lys Thr Val
545                 550                 555                 560

Ile Ser Gly Ser Lys Val Lys Ser Leu Ser Ser Ala Gln Ser Ser Ser
                565                 570                 575

Ser Gly Pro Ser Ser Ser Ser Glu Glu Asp Asp Ser Arg Asp Ile Glu
            580                 585                 590

Ser Leu Asp Lys Lys Ile Arg Pro Leu Glu Glu Leu Glu Ala Leu Leu
        595                 600                 605

Ser Ser Gly Asn Thr Lys Gln Leu Lys Asn Lys Glu Val Ala Ala Leu
    610                 615                 620

Val Ile His Gly Lys Leu Pro Leu Tyr Ala Leu Glu Lys Lys Leu Gly
625                 630                 635                 640

Asp Thr Thr Arg Ala Val Ala Val Arg Arg Lys Ala Leu Ser Ile Leu
                645                 650                 655

Ala Glu Ala Pro Val Leu Ala Ser Asp Arg Leu Pro Tyr Lys Asn Tyr
            660                 665                 670

Asp Tyr Asp Arg Val Phe Gly Ala Cys Cys Glu Asn Val Ile Gly Tyr
        675                 680                 685

Met Pro Leu Pro Val Gly Val Ile Gly Pro Leu Val Ile Asp Gly Thr
    690                 695                 700

Ser Tyr His Ile Pro Met Ala Thr Thr Glu Gly Cys Leu Val Ala Ser
705                 710                 715                 720

Ala Met Arg Gly Cys Lys Ala Ile Asn Ala Gly Gly Gly Ala Thr Thr
                725                 730                 735

Val Leu Thr Lys Asp Gly Met Thr Arg Gly Pro Val Val Arg Phe Pro
            740                 745                 750

Thr Leu Lys Arg Ser Gly Ala Cys Lys Ile Trp Leu Asp Ser Glu Glu
        755                 760                 765

Gly Gln Asn Ala Ile Lys Lys Ala Phe Asn Ser Thr Ser Arg Phe Ala
    770                 775                 780

Arg Leu Gln His Ile Gln Thr Cys Leu Ala Gly Asp Leu Leu Phe Met
785                 790                 795                 800

Arg Phe Arg Thr Thr Thr Gly Asp Ala Met Gly Met Asn Met Ile Ser
                805                 810                 815

Lys Gly Val Glu Tyr Ser Leu Lys Gln Met Val Glu Glu Tyr Gly Trp
            820                 825                 830

Glu Asp Met Glu Val Val Ser Val Ser Gly Asn Tyr Cys Thr Asp Lys
        835                 840                 845

Lys Pro Ala Ala Ile Asn Trp Ile Glu Gly Arg Gly Lys Ser Val Val
    850                 855                 860
```

```
Ala Glu Ala Thr Ile Pro Gly Asp Val Val Arg Lys Val Leu Lys Ser
865                 870                 875                 880

Asp Val Ser Ala Leu Val Glu Leu Asn Ile Ala Lys Asn Leu Val Gly
                885                 890                 895

Ser Ala Met Ala Gly Ser Val Gly Gly Phe Asn Ala His Ala Ala Asn
            900                 905                 910

Leu Val Thr Ala Val Phe Leu Ala Leu Gly Gln Asp Pro Ala Gln Asn
        915                 920                 925

Val Glu Ser Ser Asn Cys Ile Thr Leu Met Lys Glu Val Asp Gly Asp
    930                 935                 940

Leu Arg Ile Ser Val Ser Met Pro Ser Ile Glu Val Gly Thr Ile Gly
945                 950                 955                 960

Gly Gly Thr Val Leu Glu Pro Gln Gly Ala Met Leu Asp Leu Leu Gly
                965                 970                 975

Val Arg Gly Pro His Ala Thr Ala Pro Gly Thr Asn Ala Arg Gln Leu
            980                 985                 990

Ala Arg Ile Val Ala Cys Ala Val Leu Ala Gly Glu Leu Ser Leu Cys
        995                 1000                1005

Ala Ala Leu Ala Ala Gly His Leu Val Gln Ser His Met Thr His Asn
    1010                1015                1020

Arg Lys Pro Ala Glu Pro Thr Lys Pro Asn Asn Leu Asp Ala Thr Asp
1025                1030                1035                1040

Ile Asn Arg Leu Lys Asp Gly Ser Val Thr Cys Ile Lys Ser
                1045                1050
```

<210> SEQ ID NO 156
<211> LENGTH: 1059
<212> TYPE: DNA
<213> ORGANISM: Saccharomyces cerevisiae

<400> SEQUENCE: 156

```
atggcttcag aaaaagaaat taggagagag agattcttga acgttttccc taaattagta     60

gaggaattga acgcatcgct tttggcttac ggtatgccta aggaagcatg tgactggtat    120

gcccactcat tgaactacaa cactccaggc ggtaagctaa atagaggttt gtccgttgtg    180

gacacgtatg ctattctctc caacaagacc gttgaacaat tggggcaaga agaatacgaa    240

aaggttgcca ttctaggttg gtgcattgag ttgttgcagg cttacttctt ggtcgccgat    300

gatatgatgg acaagtccat taccagaaga ggccaaccat gttggtacaa ggttcctgaa    360

gttggggaaa ttgccatcaa tgacgcattc atgttagagg ctgctatcta caagcttttg    420

aaatctcact tcagaaacga aaaatactac atagatatca ccgaattgtt ccatgaggtc    480

accttccaaa ccgaattggg ccaattgatg gacttaatca ctgcacctga agacaaagtc    540

gacttgagta agttctccct aaagaagcac tccttcatag ttactttcaa gactgcttac    600

tattctttct acttgcctgt cgcattggcc atgtacgttg ccggtatcac ggatgaaaag    660

gatttgaaac aagccagaga tgtcttgatt ccattgggtg aatacttcca aattcaagat    720

gactacttag actgcttcgg taccccagaa cagatcggta agatcggtac agatatccaa    780

gataacaaat gttcttgggt aatcaacaag gcattggaac ttgcttccgc agaacaaaga    840

aagactttag acgaaaatta cggtaagaag gactcagtcg cagaagccaa atgcaaaaag    900

attttcaatg acttgaaaat tgaacagcta taccacgaat atgaagagtc tattgccaag    960

gatttgaagg ccaaaatttc tcaggtcgat gagtctcgtg gcttcaaagc tgatgtctta   1020

actgcgttct tgaacaaagt ttacaagaga agcaaatag                          1059
```

<210> SEQ ID NO 157
<211> LENGTH: 352
<212> TYPE: PRT
<213> ORGANISM: Saccharomyces cerevisiae

<400> SEQUENCE: 157

```
Met Ala Ser Glu Lys Glu Ile Arg Arg Glu Arg Phe Leu Asn Val Phe
 1               5                  10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350
```

<210> SEQ ID NO 158
<211> LENGTH: 867
<212> TYPE: DNA
<213> ORGANISM: Saccharomyces cerevisiae

<400> SEQUENCE: 158

```
atgactgccg acaacaatag tatgccccat ggtgcagtat ctagttacgc caaattagtg     60
caaaaccaaa cacctgaaga cattttggaa gagtttcctg aaattattcc attacaacaa    120
agacctaata cccgatctag tgagacgtca aatgacgaaa gcggagaaac atgtttttct    180
ggtcatgatg aggagcaaat taagttaatg aatgaaaatt gtattgtttt ggattgggac    240
gataatgcta ttggtgccgg taccaagaaa gtttgtcatt taatggaaaa tattgaaaag    300
ggtttactac atcgtgcatt ctccgtcttt attttcaatg aacaaggtga attactttta    360
caacaaagag ccactgaaaa aataactttc cctgatcttt ggactaacac atgctgctct    420
catccactat gtattgatga cgaattaggt ttgaagggta agctagacga taagattaag    480
ggcgctatta ctgcggcggt gagaaaacta gatcatgaat taggtattcc agaagatgaa    540
actaagacaa ggggtaagtt tcacttttta aacagaatcc attacatggc accaagcaat    600
gaaccatggg gtgaacatga aattgattac atcctatttt ataagatcaa cgctaaagaa    660
aacttgactg tcaacccaaa cgtcaatgaa gttagagact tcaaatgggt ttcaccaaat    720
gatttgaaaa ctatgtttgc tgacccaagt tacaagttta cgccttggtt taagattatt    780
tgcgagaatt acttattcaa ctggtgggag caattagatg acctttctga agtggaaaat    840
gacaggcaaa ttcatagaat gctataa                                        867
```

<210> SEQ ID NO 159
<211> LENGTH: 288
<212> TYPE: PRT
<213> ORGANISM: Saccharomyces cerevisiae

<400> SEQUENCE: 159

```
Met Thr Ala Asp Asn Asn Ser Met Pro His Gly Ala Val Ser Ser Tyr
1               5                   10                  15

Ala Lys Leu Val Gln Asn Gln Thr Pro Glu Asp Ile Leu Glu Glu Phe
            20                  25                  30

Pro Glu Ile Ile Pro Leu Gln Gln Arg Pro Asn Thr Arg Ser Ser Glu
        35                  40                  45

Thr Ser Asn Asp Glu Ser Gly Glu Thr Cys Phe Ser Gly His Asp Glu
    50                  55                  60

Glu Gln Ile Lys Leu Met Asn Glu Asn Cys Ile Val Leu Asp Trp Asp
65                  70                  75                  80

Asp Asn Ala Ile Gly Ala Gly Thr Lys Lys Val Cys His Leu Met Glu
                85                  90                  95

Asn Ile Glu Lys Gly Leu Leu His Arg Ala Phe Ser Val Phe Ile Phe
            100                 105                 110

Asn Glu Gln Gly Glu Leu Leu Leu Gln Gln Arg Ala Thr Glu Lys Ile
        115                 120                 125

Thr Phe Pro Asp Leu Trp Thr Asn Thr Cys Cys Ser His Pro Leu Cys
    130                 135                 140

Ile Asp Asp Glu Leu Gly Leu Lys Gly Lys Leu Asp Asp Lys Ile Lys
145                 150                 155                 160

Gly Ala Ile Thr Ala Ala Val Arg Lys Leu Asp His Glu Leu Gly Ile
                165                 170                 175

Pro Glu Asp Glu Thr Lys Thr Arg Gly Lys Phe His Phe Leu Asn Arg
            180                 185                 190

Ile His Tyr Met Ala Pro Ser Asn Glu Pro Trp Gly Glu His Glu Ile
        195                 200                 205
```

```
Asp Tyr Ile Leu Phe Tyr Lys Ile Asn Ala Lys Glu Asn Leu Thr Val
    210                 215                 220

Asn Pro Asn Val Asn Glu Val Arg Asp Phe Lys Trp Val Ser Pro Asn
225                 230                 235                 240

Asp Leu Lys Thr Met Phe Ala Asp Pro Ser Tyr Lys Phe Thr Pro Trp
                245                 250                 255

Phe Lys Ile Ile Cys Glu Asn Tyr Leu Phe Asn Trp Trp Glu Gln Leu
            260                 265                 270

Asp Asp Leu Ser Glu Val Glu Asn Asp Arg Gln Ile His Arg Met Leu
        275                 280                 285


<210> SEQ ID NO 160
<211> LENGTH: 1812
<212> TYPE: DNA
<213> ORGANISM: Cinnamomum tenuipile

<400> SEQUENCE: 160

atggctttgc agatgatagc accgtttctg tcttctttct taccaaaccc cagacattct      60

ttggcggctc atggtttgac gcatcaaaaa tgtgtcagta aacacatctc ttgttcgact     120

actaccccaa catactcaac gaccgttccg agaaggtccg gaaattataa accatccatt     180

tgggattatg attttgtcca gtcattaggc agtggttaca aggtagaagc tcacggtaca     240

agggttaaaa agctgaaaga agttgtgaaa catttgctaa aagaaacaga ttcaagccta     300

gctcaaatcg aattgattga caaacttcgt cgtttaggtt taagatggtt gtttaagaac     360

gagataaaac aagtcctgta cacaatatca tctgataata caagtattga aatgagaaag     420

gacttgcacg ctgtcagtac gagatttcgt ttattgcgtc aacatggcta taaagtctca     480

actgatgtat tcaatgattt taaagacgaa aagggatgct ttaagccttc attaagtatg     540

gacataaagg gtatgttgtc tctttatgaa gctagtcacc tagcattcca aggagaaacg     600

gtattggatg aagccagggc atttgtttca actcacttaa tggatataaa agaaaatata     660

gatcccatat tgcataaaaa ggttgaacat gccttggata tgccacttca ttggagactt     720

gaaaaattag aggcaaggtg gtatatggac atctacatga gggaagaagg tatgaactca     780

agtttattgg aacttgcaat gctacatttc aacattgtac aaactacttt tcagacaaat     840

cttaagtccc ttagtagatg gtggaaggac ttagggttgg gggaacaact aagtttcacg     900

agagacagac ttgttgaatg ttttttctgg gcagccgcta tgactcctga accacaattt     960

ggtagatgcc aagaagtagt agccaaagtc gctcaattga tcatcataat tgatgacatc    1020

tacgatgtat atggtaccgt agatgagttg gaattgttta ctaatgcaat tgatcgttgg    1080

gatctagaag ctatggagca gctgccagaa tacatgaaga cgtgcttttt ggctttgtat    1140

aattcaatca atgaaattgg atatgatatc ttaaaggagg agggcaggaa tgtcattccc    1200

tacttacgta acacttggac tgaattatgc aaagcttttc tagttgaagc aaaatggtac    1260

agtagcggat atacacctac gctagaagaa tatttgcaga cgtcgtggat tagtataggt    1320

tctttgccta tgcagacata tgtttttgct ctattgggca agaacttggc tcccgaatcc    1380

tccgatttcg ctgagaaaat tagtgatatt ttaagattgg gcggaatgat gatacgttta    1440

cctgatgatc ttggtacttc gacggacgaa ctaaaacgtg gagacgttcc aaaatccatc    1500

caatgttaca tgcacgaagc tggtgtcact gaggatgtag ctagggacca tattatggga    1560

ctgttccaag aaacttggaa gaaattaaac gaatacttag ttgaatcttc cttgcctcat    1620

gcgtttatag accacgctat gaatctaggg agagtctcat actgtacata caaacacggc    1680

gatggtttct cggacggttt cggtgaccca ggtagccagg aaaagaagat gttcatgtcc    1740
```

```
ttatttgccg aacctcttca agtagatgaa gctaaaggta tatcctttta cgtagacgga   1800

ggtagcgctt aa                                                        1812


<210> SEQ ID NO 161
<211> LENGTH: 603
<212> TYPE: PRT
<213> ORGANISM: Cinnamomum tenuipile

<400> SEQUENCE: 161

Met Ala Leu Gln Met Ile Ala Pro Phe Leu Ser Ser Phe Leu Pro Asn
 1               5                  10                  15

Pro Arg His Ser Leu Ala Ala His Gly Leu Thr His Gln Lys Cys Val
            20                  25                  30

Ser Lys His Ile Ser Cys Ser Thr Thr Thr Pro Thr Tyr Ser Thr Thr
        35                  40                  45

Val Pro Arg Arg Ser Gly Asn Tyr Lys Pro Ser Ile Trp Asp Tyr Asp
    50                  55                  60

Phe Val Gln Ser Leu Gly Ser Gly Tyr Lys Val Glu Ala His Gly Thr
65                  70                  75                  80

Arg Val Lys Lys Leu Lys Glu Val Val Lys His Leu Leu Lys Glu Thr
                85                  90                  95

Asp Ser Ser Leu Ala Gln Ile Glu Leu Ile Asp Lys Leu Arg Arg Leu
            100                 105                 110

Gly Leu Arg Trp Leu Phe Lys Asn Glu Ile Lys Gln Val Leu Tyr Thr
        115                 120                 125

Ile Ser Ser Asp Asn Thr Ser Ile Glu Met Arg Lys Asp Leu His Ala
    130                 135                 140

Val Ser Thr Arg Phe Arg Leu Leu Arg Gln His Gly Tyr Lys Val Ser
145                 150                 155                 160

Thr Asp Val Phe Asn Asp Phe Lys Asp Glu Lys Gly Cys Phe Lys Pro
                165                 170                 175

Ser Leu Ser Met Asp Ile Lys Gly Met Leu Ser Leu Tyr Glu Ala Ser
            180                 185                 190

His Leu Ala Phe Gln Gly Glu Thr Val Leu Asp Glu Ala Arg Ala Phe
        195                 200                 205

Val Ser Thr His Leu Met Asp Ile Lys Glu Asn Ile Asp Pro Ile Leu
    210                 215                 220

His Lys Lys Val Glu His Ala Leu Asp Met Pro Leu His Trp Arg Leu
225                 230                 235                 240

Glu Lys Leu Glu Ala Arg Trp Tyr Met Asp Ile Tyr Met Arg Glu Glu
                245                 250                 255

Gly Met Asn Ser Ser Leu Leu Glu Leu Ala Met Leu His Phe Asn Ile
            260                 265                 270

Val Gln Thr Thr Phe Gln Thr Asn Leu Lys Ser Leu Ser Arg Trp Trp
        275                 280                 285

Lys Asp Leu Gly Leu Gly Glu Gln Leu Ser Phe Thr Arg Asp Arg Leu
    290                 295                 300

Val Glu Cys Phe Phe Trp Ala Ala Ala Met Thr Pro Glu Pro Gln Phe
305                 310                 315                 320

Gly Arg Cys Gln Glu Val Val Ala Lys Val Ala Gln Leu Ile Ile Ile
                325                 330                 335

Ile Asp Asp Ile Tyr Asp Val Tyr Gly Thr Val Asp Glu Leu Glu Leu
            340                 345                 350

Phe Thr Asn Ala Ile Asp Arg Trp Asp Leu Glu Ala Met Glu Gln Leu
```

-continued

```
        355                 360                 365

Pro Glu Tyr Met Lys Thr Cys Phe Leu Ala Leu Tyr Asn Ser Ile Asn
    370                 375                 380

Glu Ile Gly Tyr Asp Ile Leu Lys Glu Glu Gly Arg Asn Val Ile Pro
385                 390                 395                 400

Tyr Leu Arg Asn Thr Trp Thr Glu Leu Cys Lys Ala Phe Leu Val Glu
                405                 410                 415

Ala Lys Trp Tyr Ser Ser Gly Tyr Thr Pro Thr Leu Glu Glu Tyr Leu
            420                 425                 430

Gln Thr Ser Trp Ile Ser Ile Gly Ser Leu Pro Met Gln Thr Tyr Val
        435                 440                 445

Phe Ala Leu Leu Gly Lys Asn Leu Ala Pro Glu Ser Ser Asp Phe Ala
    450                 455                 460

Glu Lys Ile Ser Asp Ile Leu Arg Leu Gly Gly Met Met Ile Arg Leu
465                 470                 475                 480

Pro Asp Asp Leu Gly Thr Ser Thr Asp Glu Leu Lys Arg Gly Asp Val
                485                 490                 495

Pro Lys Ser Ile Gln Cys Tyr Met His Glu Ala Gly Val Thr Glu Asp
            500                 505                 510

Val Ala Arg Asp His Ile Met Gly Leu Phe Gln Glu Thr Trp Lys Lys
        515                 520                 525

Leu Asn Glu Tyr Leu Val Glu Ser Ser Leu Pro His Ala Phe Ile Asp
    530                 535                 540

His Ala Met Asn Leu Gly Arg Val Ser Tyr Cys Thr Tyr Lys His Gly
545                 550                 555                 560

Asp Gly Phe Ser Asp Gly Phe Gly Asp Pro Gly Ser Gln Glu Lys Lys
                565                 570                 575

Met Phe Met Ser Leu Phe Ala Glu Pro Leu Gln Val Asp Glu Ala Lys
            580                 585                 590

Gly Ile Ser Phe Tyr Val Asp Gly Gly Ser Ala
        595                 600
```

DIMETHYLOCTANE AS AN ADVANCED BIOFUEL

RELATED APPLICATIONS

This application is a 35 USC §371 National Stage application of International Application No. PCT/US2008/083436 filed Nov. 13, 2008, now pending; which claims the benefit under 35 USC §119(e) to U.S. Application Ser. No. 60/987,683 filed Nov. 13, 2007, now expired. The disclosure of each of the prior applications is considered part of and is incorporated by reference in the disclosure of this application.

TECHNICAL FIELD

This invention describes genes, metabolic pathways, microbial strains and methods to biologically produce dimethyloctane from renewable feedstocks and compositions of dimethyloctane for use as an advanced biofuel.

BACKGROUND ART

Some oxygenate fuels produced by fermentation, like ethanol, have lower energy density than gasoline and absorb water, a property that prevents such fuels from being distributed with gasoline in existing pipelines. These fuels must be transported separately by rail or trucks to "splash" blending terminals, increasing the cost of blended fuels. Dimethyloctane has higher energy content than ethanol and because it does not absorb water, can be distributed on existing pipelines, avoiding additional transportation costs. Dimethyloctane can be useful as a neat fuel or fuel additive for gasoline, diesel, kerosene and jet fuels. Its relatively low volatility also minimizes environmental impacts.

SUMMARY OF THE INVENTION

In one aspect, the invention is directed to a recombinant microorganism. The recombinant microorganism is comprised of a biosynthetic pathway capable of converting a carbon source to geraniol or a geraniol derivative. At least one component (gene, gene product, enzyme) of the pathway is exogenous to the recombinant microorganism.

In one embodiment of this aspect, the biosynthetic pathway is encoded by at least one nucleic acid sequence encoding a polypeptide that catalyzes the conversion of a substrate to a product. The product is one of a) D-glyceraldehyde-3-phosphate and pyruvate to 1-deoxy-D-xylulose-5-phosphate; b) 1-deoxy-D-xylulose-5-phosphate to 2-methyl-D-erythritol-4-phosphate; c) 2-methyl-D-erythritol-4-phosphate to 4-(cytidine-5-diphospho)-2-C-methyl-D-erythritol; d) 4-(cytidine-5-diphospho)-2-C-methyl-D-erythritol to 2-phospho-4-(cytidine-5-diphospho)-2-C-methyl-D-erythritol; e) 2-phospho-4-(cytidine-5-diphospho)-2-C-methyl-D-erythritol to 2-C-methyl-D-erythritol-2,4-cyclodiphosphate; f) 2-C-methyl-D-erythritol-2,4-cyclodiphosphate to 1-hydroxy-2-methyl-2-(E)-butenyl-4-diphosphate; g) 1-hydroxy-2-methyl-2-(E)-butenyl-4-diphosphate to isopentenyl diphosphate; h) isopentenyl diphosphate to dimethylallyl diphosphate; and i) dimethylallyl diphosphate and isopentenyl diphosphate to geranyl diphosphate.

In one embodiment of this aspect, the biosynthetic pathway is encoded by at least one nucleic acid sequence encoding a polypeptide that catalyzes the conversion of a substrate to a product. The product is one of: a) 2 acetyl-CoA to acetoacetyl-CoA; b) acetoacetyl-CoA and acetyl-CoA to 3-hydroxy-3-methyl-glutaryl-CoA; c) 3-hydroxy-3-methylglutaryl-CoA to mevalonate; d) Mevalonate to mevalonate-5-phosphate; e) mevalonate-5-phosphate to mevalonte-5-diphosphate; f) mevalonte-5-diphosphate to isopentenyl diphosphate; g) isopentenyl diphosphate to dimethylallyl diphosphate; and h) dimethylallyl diphosphate and isopentenyl diphosphate to geranyl diphosphate.

In one embodiment of this aspect, the biosynthetic pathway is encoded by at least one nucleic acid sequence encoding a polypeptide that catalyzes the conversion of a substrate to a product. The product is one of: a) L-leucine to 4-methyl-2-oxopentanoate; b) 4-methyl-2-oxopentanoate to isovaleryl-CoA; c) isovaleryl-CoA to 3-methylcrotonyl-CoA; d) 3-methylcrotonyl-CoA to 3-methylglutaconyl-CoA; e) 3-methylglutaconyl-CoA to 3-hydroxy-3-methylglutaryl-CoA; f) 3-hydroxy-3-methylglutaryl-CoA to mevalonate; g) mevalonate to mevalonate-5-phosphate; h) mevalonate-5-phosphate to mevalonte-5-diphosphate; i) mevalonte-5-diphosphate to isopentenyl diphosphate; j) isopentenyl diphosphate to dimethylallyl diphosphate; and k) dimethylallyl diphosphate and isopentenyl diphosphate to geranyl diphosphate.

In one embodiment of this aspect, the biosynthetic pathway is encoded by at least one nucleic acid sequence encoding a polypeptide that catalyzes the conversion of a substrate to a product selected from the group consisting of: a) D-glyceraldehyde-3-phosphate and pyruvate to 1-deoxy-D-xylulose-5-phosphate; b) 1-deoxy-D-xylulose-5-phosphate to 2-methyl-D-erythritol-4-phosphate; c) 2-methyl-D-erythritol-4-phosphate to 4-(cytidine-5-diphospho)-2-C-methyl-D-erythritol; d) 4-(cytidine-5-diphospho)-2-C-methyl-D-erythritol to 2-phospho-4-(cytidine-5-diphospho)-2-C-methyl-D-erythritol; e) 2-phospho-4-(cytidine-5-diphospho)-2-C-methyl-D-erythritol to 2-C-methyl-D-erythritol-2,4-cyclodiphosphate; f) 2-C-methyl-D-erythritol-2,4-cyclodiphosphate to 1-hydroxy-2-methyl-2-(E)-butenyl-4-diphosphate; g) 1-hydroxy-2-methyl-2-(E)-butenyl-4-diphosphate to isopentenyl diphosphate; h) 2 acetyl-CoA to acetoacetyl-CoA; i) acetoacetyl-CoA and acetyl-CoA to 3-hydroxy-3-methyl-glutaryl-CoA; j) L-leucine to 4-methyl-2-oxopentanoate; k) 4-methyl-2-oxopentanoate to isovaleryl-CoA; 1) isovaleryl-CoA to 3-methylcrotonyl-CoA; m) 3-methylcrotonyl-CoA to 3-methylglutaconyl-CoA; n) 3-methylglutaconyl-CoA to 3-hydroxy-3-methylglutaryl-CoA; o) 3-hydroxy-3-methylglutaryl-CoA to mevalonate; p) mevalonate to mevalonate-5-phosphate; q) mevalonate-5-phosphate to mevalonte-5-diphosphate; r) mevalonte-5-diphosphate to isopentenyl diphosphate; s) isopentenyl diphosphate to dimethylallyl diphosphate; and t) dimethylallyl diphosphate and isopentenyl diphosphate to geranyl diphosphate.

In some embodiments of this aspect, the geraniol derivative in the recombinant microorganisms of the above embodiments is geranyl acetate. In some embodiments, the recombinant microorganism further comprises a nucleic acid sequence encoding a polypeptide that catalyzes the conversion of geranyl diphosphate to geraniol. In some embodiments, the recombinant microorganism further comprises a nucleic acid sequence encoding a polypeptide that catalyzes the conversion of geranyl diphosphate into an acyclic monoterpene. In some embodiments, the acyclic monoterpene is beta-myrcene and/or (E)-beta-ocimene and the polypeptide is ocimene synthase.

In some embodiments of this aspect, the recombinant microorganism is further capable of converting geraniol or a geraniol derivative, to geranyl acetate and comprises a nucleic acid sequence encoding geraniol acetyltransferase.

In some embodiments of this aspect, the microorganism is an archaea, a bacterium, a yeast, a fungus, a thraustochytrid, or a photosynthetic microorganism. In some embodiments, the bacterium is one of *Escherichia coli, Corynebacterium glutamicum, Pseudomonas putida, Bacillus subtilis, Rhodopseudomonas palustris, Rhodobacter sphaeroides, Micrococcus luteus, Streptomyces coelicolor, Streptomyces griseus, Lactobacillus fermentum, Lactococcus lactis, Lactobacillus bulgaricus, Acetobacter xylinum, Streptococcus lactis, Bacillus stearothermophilus, Propionibacter shermanii, Streptococcus thermophilus, Deinococcus radiodurans, Delftia acidovorans, Enterococcus faecium, Pseudomonas mendocina*, or *Serratia marcescens.*

In some embodiments, the yeast is one of *Saccharomyces cerevisiae, Saccharomyces carlsbergensis, Kluyveromyces lactis, Kluyveromyces marxianus, Yarrowia lipolytica, Debaryomyces hansenii, Ashbya gossypii, Zygosaccharomyces rouxii, Zygosaccharomyces bailiff, Brettanomyces bruxellensis, Schizosaccharomyces pombe, Rhodotorula glutinis, Pichia stipitis, Pichia pastoris, Candida tropicalis, Candida utilis* and *Candida guilliermondii.*

In some embodiments, the fungus is one of *Aspergillus niger, Aspergillus oryzae, Neurospora crassa, Penicillium chrysogenum* and *Fusarium venenatum.*

In some embodiments, the photosynthetic microorganism is one of *Anabaena* sp., *Chlamydomonas reinhardtii, Chlorella* sp., *Cyclotella* sp., *Gloeobacter violaceus, Nannochloropsis* sp., *Nodularia* sp., *Nostoc* sp., *Prochlorococcus* sp., *Synechococcus* sp., *Oscillatoria* sp., *Arthrospira* sp., *Lyngbya* sp., *Dunaliella* sp., and *Synechocystis* sp.

In some embodiments of the above, the carbon source is any one or more of carboxylic acids, alcohols, sugar alcohols, aldehydes, amino acids, carbohydrates, saturated or unsaturated fatty acids, ketones, peptides, proteins, lignocellulosic material, carbon dioxide, and coal. In some embodiments, the carboxylic acid is succinic acid, lactic acid, or acetic acid. In some embodiments, the carbohydrate is a monosaccharide, a disaccharide, an oligosaccharide, and a polysaccharide. In some embodiments, the carbon source is lignocellulosic material. In some embodiments, the carbon source is carbon dioxide. In some embodiments, the carbon source is coal.

In another aspect, the invention is directed to a synthetic artificial chromosome. The synthetic artificial chromosome comprises one or more nucleic acid sequences encoding at least one peptide. The peptide can be any one of a) 1-deoxy-xylulose 5-phosphate synthase; b) 1-deoxy-D-xylulose-5-phosphate reductoisomerase; c) 4-diphosphocytidyl-2-C-methyl-D-erythritol synthase; d) 4-diphosphocytidyl-2-C-methyl-D-erythritol kinase; e) 2-C-methyl-D-erythritol-2,4-cyclodiphosphate synthase; f) 1-hydroxy-2-methyl-2-(E)-butenyl-4-diphosphate synthase; g) 1-hydroxy-2-methyl-2-(E)-butenyl-4-diphosphate reductase; h) isopentenyl diphosphate isomerase; i) geranyl diphosphate synthase; and j) geraniol synthase.

In another aspect, the invention is directed to a synthetic artificial chromosome. The synthetic artificial chromosome comprises one or more nucleic acid sequences encoding at least one peptide. The peptide can be any one of a) acetyl-CoA acetyltransferase; b) 3-hydroxy-3-methyl-glutaryl-CoA synthase; c) 3-hydroxy-3-methyl-glutaryl-CoA reductase; d) mevalonate kinase; e) phosphomevalonate kinase; f) mevalonate-5-diphosphate decarboxylase; g) isopentenyl diphosphate isomerase; h) geranyl diphosphate synthase; and i) geraniol synthase.

In another aspect, the invention is directed to a synthetic artificial chromosome. The synthetic artificial chromosome comprises one or more nucleic acid sequences encoding at least one peptide. The peptide can be any one of a) branched chain aminotransferase or leucine aminotransferase; b) 2-oxoisovalerate dehydrogenase; c) isovaleryl-CoA dehydrogenase; d) 3-methylcrotonyl-CoA carboxylase; e) 3-methylglutaconyl-CoA hydratase; f) 3-hydroxy-3-methyl-glutaryl-CoA reductase; g) mevalonate kinase; h) phosphomevalonate kinase; i) mevalonate-5-diphosphate decarboxylase; j) isopentenyl diphosphate isomerase; k) geranyl diphosphate synthase; and l) geraniol synthase.

In another aspect, the invention is directed to a synthetic artificial chromosome comprising one or more nucleic acid sequences encoding at least one peptide. The peptide can be any one of a) 1-deoxy-xylulose 5-phosphate synthase; b) 1-deoxy-D-xylulose-5-phosphate reductoisomerase; c) 4-diphosphocytidyl-2-C-methyl-D-erythritol synthase; d) 4-diphosphocytidyl-2-C-methyl-D-erythritol kinase; e) 2-C-methyl-D-erythritol-2,4-cyclodiphosphate synthase; f) 1-hydroxy-2-methyl-2-(E)-butenyl-4-diphosphate synthase; g) 1-hydroxy-2-methyl-2-(E)-butenyl-4-diphosphate reductase; h) acetyl-CoA acetyltransferase; i) 3-hydroxy-3-methyl-glutaryl-CoA synthase; j) branched chain aminotransferase or leucine aminotransferase; k) 2-oxoisovalerate dehydrogenase; l) isovaleryl-CoA dehydrogenase; m) 3-methylcrotonyl-CoA carboxylase; n) 3-methylglutaconyl-CoA hydratase; o) 3-hydroxy-3-methyl-glutaryl-CoA reductase; p) mevalonate kinase; q) phosphomevalonate kinase; r) mevalonate-5-diphosphate decarboxylase; s) isopentenyl diphosphate isomerase; t) geranyl diphosphate synthase; and u) geraniol synthase.

In some embodiments of the prior four aspects, the synthetic artificial chromosome further comprises a nucleic acid sequence encoding a geraniol acetyltransferase. Some embodiments provide for a recombinant microorganism comprising a biosynthetic pathway capable of converting a carbon source to geraniol or a geraniol derivative; and comprising the artificial chromosome of any one of preceding four aspects. In some embodiments, the microorganism is an archaea, a bacterium, a yeast, a fungus, a thraustochytrid or a photosynthetic microorganism. In some embodiments, the bacterium is one of *Escherichia coli, Corynebacterium glutamicum, Pseudomonas putida, Bacillus subtilis, Rhodopseudomonas palustris, Rhodobacter sphaeroides, Micrococcus luteus, Streptomyces coelicolor, Streptomyces griseus, Lactobacillus fermentum, Lactococcus lactis, Lactobacillus bulgaricus, Acetobacter xylinum, Streptococcus lactis, Bacillus stearothermophilus, Propionibacter shermanii, Streptococcus thermophilus, Deinococcus radiodurans, Delftia acidovorans, Enterococcus faecium, Pseudomonas mendocina*, and *Serratia marcescens.*

In some embodiments, the yeast is one of *Saccharomyces cerevisiae, Saccharomyces carlsbergensis, Kluyveromyces lactis, Kluyveromyces marxianus, Yarrowia lipolytica, Debaryomyces hansenii, Ashbya gossypii, Zygosaccharomyces rouxii, Zygosaccharomyces bailiff, Brettanomyces bruxellensis, Schizosaccharomyces pombe Pichia stipitis, Pichia pastoris, Candida tropicalis, Candida utilis, Candida guilliermondii*, and *Rhodotorula glutinis.*

In some embodiments, the fungus is one of *Aspergillus niger, Aspergillus oryzae Neurospora crassa*, and *Penicillium chrysogenum* and *Fusarium venenatum*. In some embodiments, the microorganism is *Schizochytrium* sp. and *Thraustochytrium* sp. In some embodiments, the photosynthetic microorganism is one of *Anabaena, Nostoc, Synechocystis, Synechococcus, Oscillatoria, Arthrospira, Lyngbya, Prochlorococcus, Nodularia, Gloeobacter, Chlamydomonas reinhardtii, Chlorella, Dunaliella, Nannochloropsis*, and *Cyclotella.*

In some embodiments, the carbon source is one or more of carboxylic acids, alcohols, sugar alcohols, aldehydes, amino acids, carbohydrates, saturated or unsaturated fatty acids, ketones, peptides, proteins, lignocellulosic material, carbon dioxide, and coal. In some embodiments, the carboxylic acid is succinic acid, lactic acid, or acetic acid. In some embodiments, the carbohydrate is a monosaccharide, a disaccharide, an oligosaccharide, or a polysaccharide. In some embodiments, the carbon source is lignocellulosic material. In some embodiments, the carbon source is carbon dioxide. In some embodiments, the carbon source is coal.

In another aspect, the invention is directed to a method for metabolizing a carbon source to geraniol or a geraniol derivative. The method comprises the following steps. First, a culture medium comprising the carbon source is provided. The culture medium is contacted with the microorganism of any one of the preceding embodiments and aspects. The microorganism produces spent culture medium from the culture medium by metabolizing the carbon source to geraniol or the geraniol derivative. Lastly, the geraniol or the geraniol derivative is recovered from the spent culture medium.

In some embodiments of the above aspect, there is a further step of converting geraniol or the geraniol derivative to a product is 2,6-dimethyloctane, a 2,6-dimethyloctane derivative, or an isomer thereof.

In some embodiments, the conversion step comprises the following two steps: a) hydrogenating the geraniol or the geraniol derivative, wherein hydrogenation comprises the step of contacting geraniol or the geraniol derivative with hydrogen gas and a catalyst, which result in the formation of 2,6-dimethyloctane; and b) recovering the 2,6-dimethyloctane.

In some embodiments, the conversion step comprises either one of the following two steps: a) transformation of the geraniol —OH group into a leaving group followed by treatment with a hydride source; or b) dehydration of the geraniol —OH group with an acid and elevated temperature followed by hydrogenation of any unsaturated bond, wherein hydrogenation comprises contacting the unsaturated bond with hydrogen gas and catalyst.

In another aspect, the invention is directed to a composition comprising a compound of the formula I and/or II:

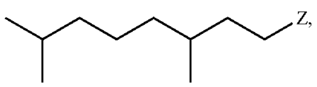

(I)

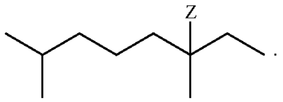

(II)

Z is either, H, O—R, or O—C(═O)R. R is H or optionally substituted alkyl, alkenyl, alkynyl or arylalkyl; or stereoisomers thereof, wherein the compound comprises a fraction of modern carbon ($f_M$ $^{14}C$) of at least about 1.003. In an embodiment of this aspect, Z is H.

In another aspect, the invention is directed to a composition comprising a compound of the formula I and/or II:

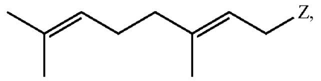

(I)

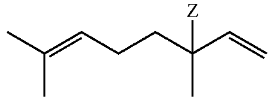

;

(II)

Z is either H, O—R, or O—C(═O)R. R is H or optionally substituted alkyl, alkenyl, alkynyl or arylalkyl; or stereoisomers thereof, wherein the compound comprises a fraction of modern carbon ($f_M$ $^{14}C$) of at least about 1.003. In an embodiment of this aspect, Z is H.

In another aspect, the invention is directed to a composition comprising a compound of the formula I, II, III, or any combination thereof:

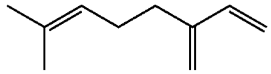

, (I)

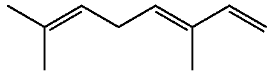

;

(II)

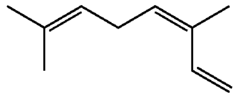

;

(III)

The compound comprises a fraction of modern carbon ($f_M$ $^{14}C$) of at least about 1.003.

In another aspect, the invention is directed to a fuel composition comprising the compound of the preceding three aspects. In some embodiments, the compound is a finished fuel. In some embodiments, the composition further comprises a petroleum fuel. In some embodiments, the petroleum fuel is one of gasoline, diesel, jet fuel, and heating oil. In some embodiments, the composition further comprises a biofuel. In some embodiments, the biofuel is ethanol or biodiesel.

In some embodiments, the compound comprises approximately 100% of the composition. In some embodiments, the compound is 1-5% of the weight of the composition. In some embodiments, the compound is 1-5% of the volume of the composition. In some embodiments, the compound is any one of 5-10%, 10-30%, or 25-40% of the weight of the composition. In some embodiments, the compound is any one of 5-10%, 10-30%, or 25-40% of the volume of the composition.

In some embodiments, the compound is 1% of the weight of the composition. In some embodiments, the compound is 1% of the volume of the composition. In some embodiments, the compound is less than 10% by volume. In some embodiments, the compound is less than 5% by volume. In some embodiments, the compound is less than 2% by volume.

In some embodiments, the compound is a bio-crude.

In another aspect, the invention is directed to a fuel additive composition comprising dimethyloctane.

In another aspect, the invention is directed to a fuel composition comprising a fuel and a fuel additive.

DETAILED DESCRIPTION OF THE INVENTION

The invention described herein relates to a recombinant microorganism capable of metabolizing a variety of carbon sources to geraniol or a geraniol derivative, which are preferably converted to 2,6-dimethyloctane and derivatives thereof. The invention also describes fuel compositions containing dimethyloctane and methods of using such compositions. In a preferred embodiment, the dimethyloctane is 2,6-dimethyloctane.

Figure 4:
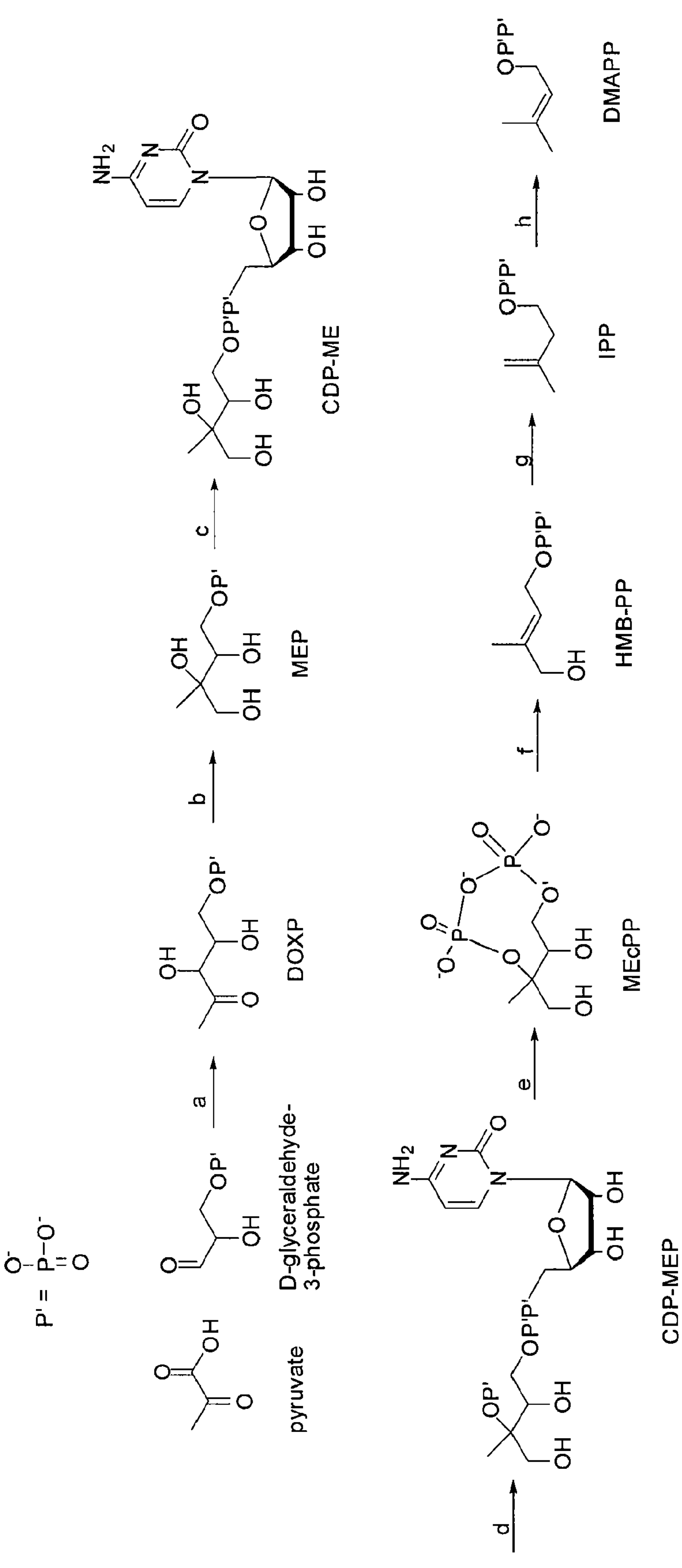
FIG. 4 depicts a schematic representation of the methylerythritol phosphate (MEP) pathway in the production of isopentenyl pyrophosphate (IPP) and dimethylallyl pyrophosphate (DMAPP).
Figure 6:
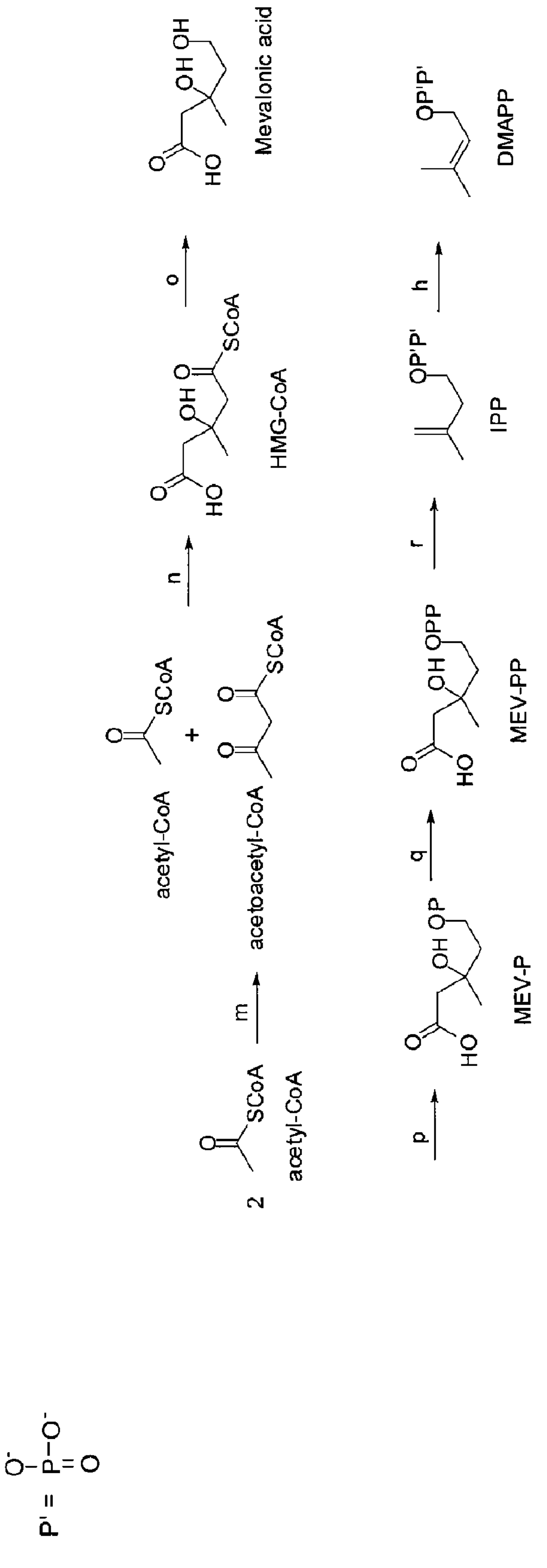
FIG. 6 depicts a schematic representation of the mevalonate (MEV) pathway in the production of isopentenyl pyrophosphate (IPP) and dimethylallyl pyrophosphate (DMAPP).

Many microorganisms use the mevalonate-dependent (MEV) pathway (MEV, see FIG. 6) or the methylerythritol phosphate pathway (MEP, see FIG. 4) for isoprenoid production. In particular, these two pathways lead to the formation of isopentenyl diphosphate and dimethylallyl pyrophosphate which serve as the basis for the biosynthesis of molecules used in a variety of important cellular processes. In particular, these intermediates are key to the formation of isoprenoids, a large and diverse class of compounds derived from five-carbon isoprene units. Over-expressing certain peptides and/or attenuating other genes in the MEP or MEV pathway increases the amount of key intermediates in the production of geraniol or geraniol derivatives, which subsequently can be converted to a dimethyloctane, such as 2,6-dimethyloctane.

Figure 5:
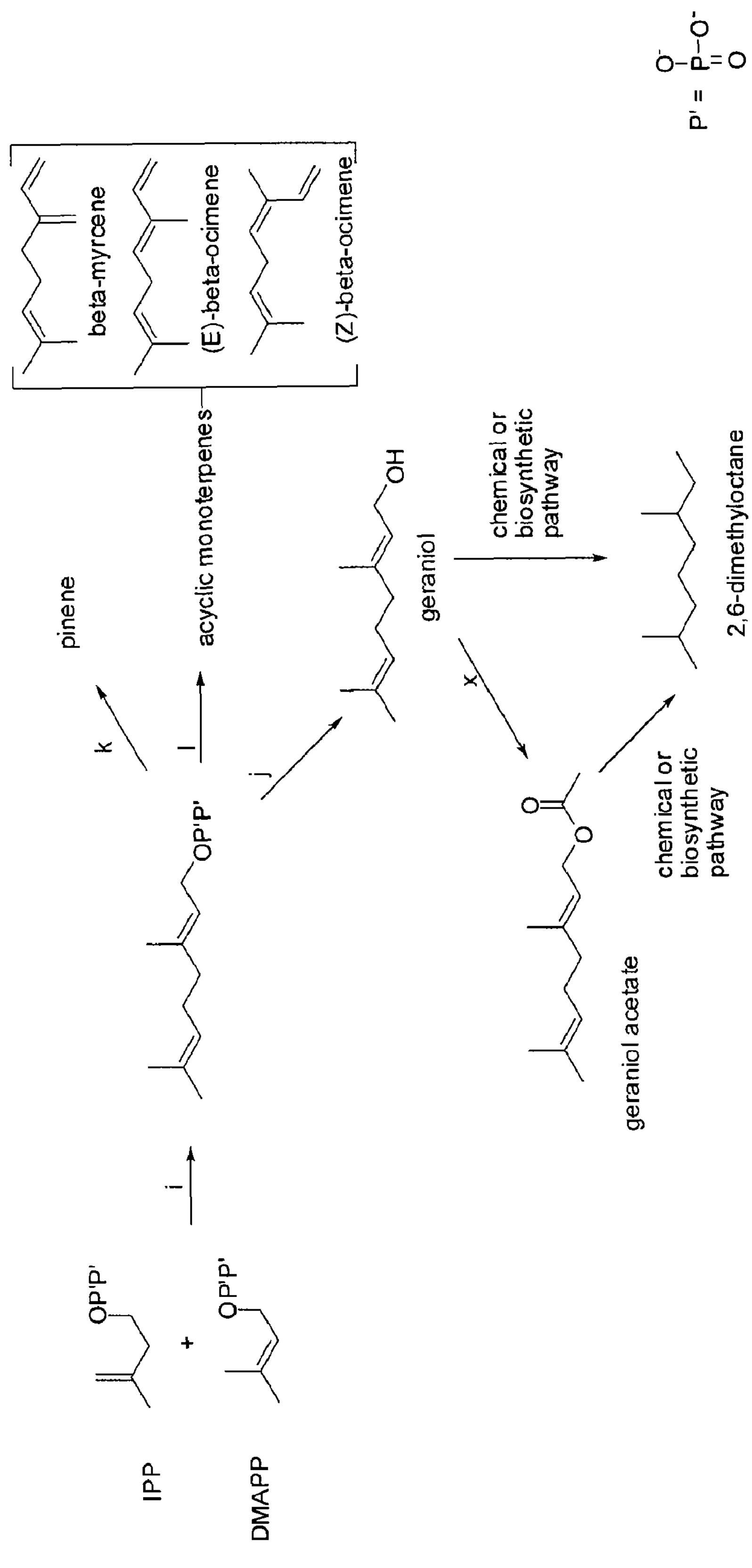
FIG. 5 depicts a schematic representation of preparation of geranyl diphosphate (GPP) from isopentenyl pyrophosphate (IPP) and dimethylallyl pyrophosphate (DMAPP), and possible subsequent pathways.

The MEP pathway is present in many bacteria and in the plastids of plants, but not in mammals. In this pathway, D-glyceraldehyde-3-phosphate and pyruvate are combined to yield 1-deoxy-D-xylylose 5-phosphate (DOXP). DOXP is then rearranged and reduced to generate 2-C-methyl-D-erythritol 4-phosphate (MEP). In the third reaction MEP is converted into 4-diphosphocytidyl-2-C-methylerythritol (CDP-ME), which is subsequently phosphorylated yielding 4-diphosphocytidyl-2C-methylerythritol 2-phosphate (CDP-MEP). This product is converted into 2-C-methyl-D-erythritol 2,4-cyclodiphosphate (MEcPP) and then reduced to 1-hydroxy-2-methyl-2-(E)-butenyl 4-diphosphate (HMB-PP). 2-C-methyl-D-erythritol-2,4-cyclodiphosphate is converted to isopentenyl diphosphate (IPP) by sequential reduction and dehydration reactions. In the final reaction of the pathway, IPP is isomerized by isopentenyl diphosphate isomerase to form dimethylallyl diphosphate (DMAPP). Both IPP and DMAPP then become the basic building blocks of polyisoprenoid biosynthesis. The conversion of DMAPP and IPP to geranyl diphosphate (GPP) is catalyzed by geranyl diphosphate synthase. Finally, the conversion of GPP to geraniol may be catalyzed by geraniol synthase (see FIG. 5). The overall stoichiometry for the conversion of glucose to geraniol by the MEP pathway is:

$$2\text{Glucose}+6\text{ATP}+4\text{NADPH}\rightarrow 1\text{Geraniol}+2CO_2+6\text{ADP}+1PPi;\ Y\text{max}=0.285\ \text{g/g}$$

The mevalonate pathway is an important cellular metabolic pathway present in all higher eukaryotes and many bacteria. In the mevalonate pathway (see FIG. 6), three molecules of acetyl-CoA are condensed, successively, to form 3-hydroxy-3-methylglutaryl-CoA (HMG-CoA), which is subsequently reduced to mevalonate by HMG-CoA reductase, the rate-limiting reaction in the pathway. Mevalonate is then phosphorylated and decarboxylated to form IPP, which is then isomerized to form DMAPP. The pathway for geraniol biosynthesis from IPP and DMAPP is similar to that described above for the MEP pathway (See FIG. 5).

The overall stoichiometry for the conversion of glucose to geraniol by the MEV pathway is:

$$3\text{Glucose}\rightarrow 1\text{Geraniol}+8CO_2+16\text{NADH}+1PPi\ \ Y\text{max}=0.428\ \text{g/g}$$

Figure 7:
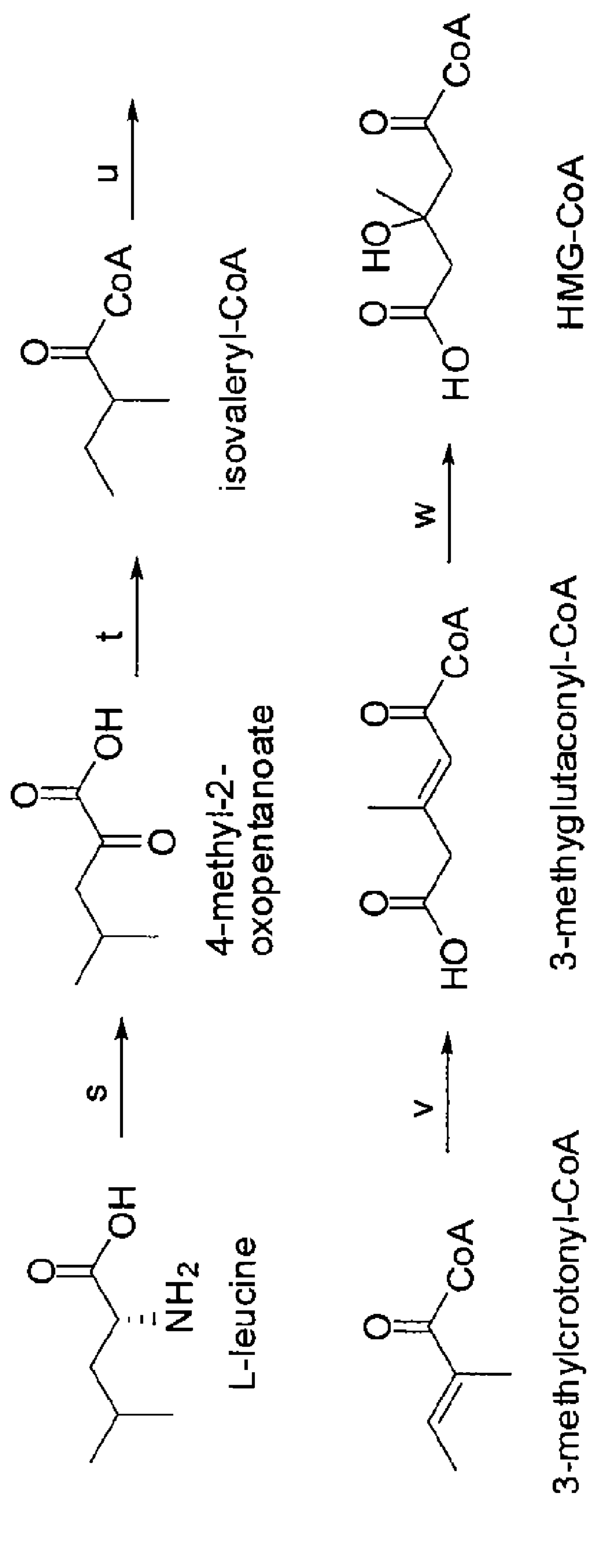
FIG. 7 depicts a schematic representation of a pathway from L-leucine to HMG-CoA.

In an alternative embodiment, the biosynthetic pathway involves a mevalonate related route (see FIG. 7), wherein the HMG-CoA intermediate is not preceded by the condensation of three molecules of acetyl CoA. Instead, a leucine molecule is transformed into 4-methyl-2-oxopentanoate by a branched chain aminotransferase or leucine aminotransferase, followed by conversion to isovaleryl-CoA by 2-oxoisovalerate dehydrogenase. This intermediate is reduced to 3-methylcrotonyl-CoA by isovaleryl-CoA dehydrogenase, and then converted to 3-methylglutaconyl-CoA by 3-methylcrotonyl-CoA carboxylase. Oxidation by 3-methylglutaconyl-CoA hydratase gives the HMG-CoA intermediate. The HMG-CoA intermediate continues along the MEV pathway (see FIG. 6), forming IPP, DMAPP and the subsequent products including geraniol and geraniol derivatives.

In one aspect, the invention provides a microorganism comprising a biosynthetic pathway capable of converting a carbon source to geraniol and geraniol derivatives, wherein at least one component of the pathway is exogenous to the recombinant microorganism. The enumerated pathway steps refer to steps illustrated in FIGS. 4-7 and have been included for the convenience of the reader.

In certain embodiments, the synthetic artificial chromosome described herein, further converts geraniol and/or stereoisomers thereof to geraniol acetate and comprises a nucleic acid sequence encoding geraniol acetyltransferase.

DEFINITIONS

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as C1-10 or as C1-C10 or C1-10. In certain embodiments, alkyl contains 1-10, 1-8, 1-6, 1-4, or 1-2 carbons.

As used herein, "hydrocarbyl residue" refers to a residue which contains only carbon and hydrogen. The residue may be aliphatic or aromatic, straight-chain, cyclic, branched, saturated or unsaturated, or any combination of these. The hydrocarbyl residue, when so stated however, may contain heteroatoms in addition to or instead of the carbon and hydrogen members of the hydrocarbyl group itself.

As used herein, "acyl" encompasses groups comprising an alkyl, alkenyl, alkynyl, aryl or arylalkyl radical attached at one of the two available valence positions of a carbonyl carbon atom.

"Aromatic" moiety or "aryl" moiety refers to a monocyclic or fused bicyclic moiety having the well-known characteristics of aromaticity; examples include phenyl and naphthyl. Similarly, "arylalkyl" refers to an aromatic ring system which is bonded to their attachment point through a linking group such as an alkylene. In certain embodiments, aryl is a 5-6 membered aromatic ring, optionally containing one or more heteroatoms selected from the group consisting of N, O, and S.

"Alkylene" as used herein refers to a divalent hydrocarbyl group; because it is divalent, it can link two other groups together. Typically it refers to $-(CH_2)_n-$ where n is 1-10, 1-8, 1-6, 1-4, or 1-2. The open valences need not be at opposite ends of a chain. Thus $-CH(Me)-$ and $-C(Me)_2-$ may also be referred to as alkylenes, as can a cyclic group such as cyclopropan-1,1-diyl.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Arylalkyl" refers to an aromatic ring system bonded to their attachment point through a linking group such as an alkylene, including substituted or unsubstituted, saturated or unsaturated, cyclic or acyclic linkers. Typically the linker is C1-C8 alkylene or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

In certain embodiments, optional substituents are selected from the group consisting of halo, =O, OR, $NR_2$, $NO_2$, and CN; wherein each R is independently H, C1-C6 alkyl, C2-C6 alkenyl, or C2-C6 alkynyl.

"Halo", as used herein includes fluoro, chloro, bromo and iodo. In certain embodiments, halo is fluoro or chloro.

"Attenuate" as used herein means to lessen the impact, activity or strength of something. A functional deletion of an enzyme can be used to attenuate an enzyme. A functional deletion is a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knock out mutation.

One of ordinary skill in the art will appreciate that there are many methods of attenuating enzyme activity. For example, attenuation can be accomplished by introducing amino acid sequence changes via altering the nucleic acid sequence, placing the gene under the control of a less active promoter, expressing interfering RNA, ribozymes or antisense sequences that targeting the gene of interest, or through any other technique known in the art.

"Carbon source" as used herein generally refers to a substrate or compound suitable to be used as a source of carbon for prokaryotic or simple eukaryotic cell growth. Carbon sources can be in various forms, including, but not limited to carboxylic acids (such as succinic acid, lactic acid, acetic acid), alcohols (e.g., ethanol), sugar alcohols (e.g., glycerol), aldehydes, amino acids, carbohydrates, saturated or unsaturated fatty acids, ketones, peptides, proteins, and mixtures thereof. Examples of carbohydrates include monosaccharides (such as glucose, galactose, xylose, arabinose, and fructose), disaccharides (such as sucrose and lactose), oligosaccharides, and polysaccharides (e.g., starch). Polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., Microb. Growth C1-Compd., [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., Arch. Microbiol. 153:485-489 (1990)). Hence it is contemplated that the source of carbon utilized in the present invention may encompass a wide variety of carbon containing substrates and will only be limited by the choice of organism. Lignocellulosic material, carbon dioxide ($CO_2$), and coal are also contemplated as suitable carbon sources.

"Culture medium" as used herein includes any medium which supports microorganism life (i.e. a microorganism that is actively metabolizing carbon). A culture medium usually contains a carbon source. The carbon source can be anything that can be utilized, with or without additional enzymes, by the microorganism for energy.

"Deletion" as used herein refers to the removal of one or more nucleotides from a nucleic acid molecule or one or more amino acids from a protein, the regions on either side being joined together.

"Detectable" as used herein refers to be capable of having an existence or presence ascertained.

"Dimethyloctane" refers to a hydrogen carbon of the formula $C_{10}H_{22}$, and the term includes stereoisomers thereof. Non-limiting examples of structural isomers of dimethyloctane include 2,2-dimethyloctane, 2,3-dimethyloctane, 2,4 dimethyloctane, 2,5-dimethyloctane, 2,7-dimethyloctane, 3,3-dimethyloctane, 3,4-dimethyloctane, 3,5-dimethyloctane, 3,6-dimethyloctane, 4,4-dimethyloctane, 4,5-dimethyloctane, and 4,6-dimethyloctane. In preferred embodiments, dimethyloctane refers to 2,6-dimethyloctane.

"Endogenous" as used herein in reference to a nucleic acid molecule and a particular cell or microorganism refers to a nucleic acid sequence or peptide that is in the cell and was not introduced into the cell using recombinant engineering techniques. For example, a gene that was present in the cell when the cell was originally isolated from nature. A gene is still considered endogenous if the control sequences, such as a promoter or enhancer sequences that activate transcription or translation have been altered through recombinant techniques.

"Enzyme Classification Numbers (EC)" as used herein are derived from the KEGG Ligand database, maintained by the Kyoto Encyclopedia of Genes and Genomics, sponsored in part by the University of Tokyo.

"Exogenous" as used herein with reference to a nucleic acid molecule and a particular cell refers to any nucleic acid molecule that does not originate from that particular cell as found in nature. Thus, a non-naturally-occurring nucleic acid molecule is considered to be exogenous to a cell once introduced into the cell. A nucleic acid molecule that is naturally-occurring also can be exogenous to a particular cell. For example, an entire coding sequence isolated from cell X is an exogenous nucleic acid with respect to cell Y once that coding sequence is introduced into cell Y, even if X and Y are the same cell type.

"Expression" as used herein refers to the process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

"Geraniol" as used herein refers to a chemical compound of the formula $C_{10}H_{18}O$, the structure

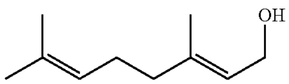

and the stereoisomers thereof.

"Geraniol derivative" refers to a derivative of geraniol, which includes but is not limited to geraniol acetate.

"Hydrocarbon" as used herein includes chemical compounds that containing the elements carbon (C) and hydrogen (H). Hydrocarbons consist of a carbon backbone and atoms of hydrogen attached to that backbone. Sometimes, the term is used as a shortened form of the term "aliphatic hydrocarbon." There are essentially three types of hydrocarbons: (1) aromatic hydrocarbons, which have at least one aromatic ring; (2) saturated hydrocarbons, also known as alkanes, which lack double, triple or aromatic bonds; and (3) unsaturated hydrocarbons, which have one or more double or triple bonds between carbon atoms. Alkenes are chemical compounds containing at least one double bond between carbon atoms and alkynes are chemical compounds containing at least one triple bond between carbon atoms.

"Isolated" as in "isolated" biological component (such as a nucleic acid molecule, protein, or cell) refers to the component that has been substantially separated or purified away from other biological components in which the component naturally occurs, such as other chromosomal and extrachromosomal DNA and RNA, and proteins. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

"Microorganism" as used herein includes prokaryotic and eukaryotic microbial species. The terms "microbial cells" and "microbes" are used interchangeably with the term microorganism.

"Myrcene" or "β-myrcene" as used herein refers to the acyclic monoterpene chemical compound $C_{10}H_{16}$, of the structure

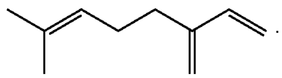

In certain embodiments, myrcene is formed from geranyl pyrophosphate. In certain embodiments, myrcene is formed from geraniol and is a geraniol derivative.

"Ocimene" or "β-ocimene" as used herein refers to the acyclic monoterpene chemical compound $C_{10}H_{16}$, of the structure:

(E)-β-ocimene

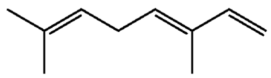

or (Z)-β-ocimene

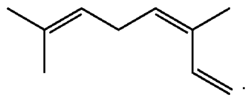

In certain embodiments, β-ocimene is formed from geranyl pyrophosphate. In certain embodiments, β-ocimene is formed from geraniol and is a geraniol derivative.

"Nucleic Acid Molecule" as used herein encompasses both RNA and DNA molecules including, without limitation, cDNA, genomic DNA and mRNA. Includes synthetic nucleic acid molecules, such as those that are chemically synthesized or recombinantly produced. The nucleic acid molecule can be double-stranded or single-stranded. Where single-stranded, the nucleic acid molecule can be the sense strand or the antisense strand. In addition, nucleic acid molecule can be circular or linear.

"Over-expressed" as used herein refers to when a gene is caused to be transcribed at an elevated rate compared to the endogenous transcription rate for that gene. In some examples, over-expression additionally includes an elevated rate of translation of the gene compared to the endogenous translation rate for that gene. Methods of testing for over-expression are well known in the art, for example transcribed RNA levels can be assessed using rtPCR and protein levels can be assessed using SDS page gel analysis.

"Purified" as used herein does not require absolute purity; rather, it is intended as a relative term.

"Recombinant" as used herein in reference to a recombinant nucleic acid molecule or protein is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or proteins, such as genetic engineering techniques. Recombinant is also used to describe nucleic acid molecules that have been artificially manipulated, but contain the same regulatory sequences and coding regions that are found in the organism from which the nucleic acid was isolated. A recombinant cell or microorganism is one that contains an exogenous nucleic acid molecule, such as a recombinant nucleic acid molecule.

"Spent medium" or "spent culture medium" as used herein refers to culture medium that has been used to support the growth of a microorganism.

"Stereoisomers" as used herein are isomeric molecules that have the same molecular formula and connectivity of bonded atoms, but which differ in the three dimensional orientations of their atoms in space. Non-limiting examples of stereoisomers are enantiomers, diastereomers, cis-trans isomers and conformers.

"Transformed or recombinant cell" as used herein refers to a cell into which a nucleic acid molecule has been introduced, such as an acyl-CoA synthase encoding nucleic acid molecule, for example by molecular biology techniques. Transformation encompasses all techniques by which a nucleic acid molecule can be introduced into such a cell, including, but not limited to, transfection with viral vectors, conjugation, transformation with plasmid vectors, and introduction of naked DNA by electroporation, lipofection, and particle gun acceleration.

"Fermentation conditions" referred to herein usually include temperature ranges, levels of aeration, and media selection, which when combined allow the microorganism to grow. Exemplary media include broths or gels. Generally, the medium includes a carbon source such as glucose, fructose, cellulose, or the like that can be metabolized by the microorganism directly, or enzymes can be used in the medium to facilitate metabolizing the carbon source. To determine if culture conditions permit product production, the microorganism can be cultured for 24, 36, or 48 hours and a sample can be obtained and analyzed. For example, the cells in the sample or the medium in which the cells were grown can be tested for the presence of the desired product.

"Vector" as used herein refers to a nucleic acid molecule as introduced into a cell, thereby producing a transformed cell. A vector can include nucleic acid sequences that permit it to replicate in the cell, such as an origin of replication. A vector can also include one or more selectable marker genes and other genetic elements known in the art.

"Finished fuel" is defined as a chemical compound or a mix of chemical compounds (produced through chemical, thermochemical or biological routes) that is in an adequate chemical and physical state to be used directly as a neat fuel or fuel additive in an engine. In many cases, but not always, the suitability of a finished fuel for use in an engine application is determined by a specification which describes the necessary physical and chemical properties that need to be met. Some examples of engines are: internal combustion engine, turbine, external combustion engine, boiler. Some examples of finished fuels include: diesel fuel to be used in a compression-ignited (diesel) internal combustion engine, jet fuel to be used in an aviation turbine, fuel oil to be used in a boiler to generate steam or in an external combustion engine, ethanol to be used in a flex-fuel engine. Examples of fuel specifications are ASTM standards, mainly used ion the US, and the EN standards, mainly used in Europe.

"Fuel additive" refers to a compound or composition that is used in combination with another fuel for a variety of reasons, which include but are not limited to complying with mandates on the use of biofuels, reducing the consumption of fossil fuel-derived products or enhancing the performance of a fuel or engine. For example, fuel additives can be used to alter the freezing/gelling point, cloud point, lubricity, viscosity, oxidative stability, ignition quality, octane level, and flash point. Additives can further function as antioxidants, demulsifiers, oxygenates and/or corrosion inhibitors. One of ordinary skill in the art will appreciate that dimethyloctane and dimethyloctane derivatives described herein can be mixed with one or more fuel or such fuel additives to reduce the dependence on fossil fuel-derived products and/or to impart a desired quality and specific additives are well known in the art. In addition, dimethyloctane and dimethyloctane derivatives can be used themselves as additives in blends with other fuels to impart a desired quality.

Non-limiting examples of additives to the fuel composition of the invention include: Hybrid compound blends such as combustion catalyst (organo-metallic compound which lowers the ignition point of fuel in the combustion chamber reducing the temperature burn from 1200 degrees to 800° F.), Burn rate modifier (increases the fuel burn time result in an approx. 30% increase of the available BTUs from the fuel), ethanol as an octane enhancer to reduce engine knock, biodiesel, polymerization (increases fuel ignition surface area resulting in increased power from ignition), Stabilizer/Demulsifier (prolongs life of fuel and prevents water vapor contamination), Corrosion inhibitor (prevents tank corrosion), Detergent agent (clean both gasoline and diesel engines with reduced pollution emissions), Catalyst additive (prolongs engine life and increases fuel economy), and Detergent (cleans engine); oxygenates, such as methanol, ethanol, isopropyl alcohol, n-butanol, gasoline grade t-butanol, methyl t-butyl ether, tertiary amyl methyl ether, tertiary hexyl methyl ether, ethyl tertiary butyl ether, tertiary amyl ethyl ether, and diisopropyl ether; antioxidants, such as, Butylated hydroxytoluene (BHT), 2,4-Dimethyl-6-tert-butylphenol, 2,6-Di-tert-butylphenol (2,6-DTBP), Phenylene diamine, and Ethylene diamine; antiknock agents, such as, Tetra-ethyl lead, Methylcyclopentadienyl manganese tricarbonyl (MMT), Ferrocene, and Iron pentacarbonyl, Toluene, isooctane; Lead scavengers (for leaded gasoline), such as, Tricresyl phosphate (TCP) (also an AW additive and EP additive), 1,2-Dibromoethane, and 1,2-Dichloroethane; and Fuel dyes, such as, Solvent Red 24, Solvent Red 26, Solvent Yellow 124, and Solvent Blue 35. Other additives include, Nitromethane (increases engine power, "nitro"), Acetone (vaporization additive, mainly used with methanol racing fuel to improve vaporisation at start up), Butyl rubber (as polyisobutylene succinimide, detergent to prevent fouling of diesel fuel injectors), Ferox (catalyst additive that increases fuel economy, cleans engine, lowers emission of pollutants, prolongs engine life), Ferrous picrate (improves combustion, increases mileage), Silicones (anti-foaming agents for diesel, damage oxygen sensors in gasoline engines), and Tetranitromethane (to increase cetane number of diesel fuel).

In certain embodiments, the invention provides for a fuel composition comprising dimethyloctane or a derivative thereof as described herein and one or more additives. In certain embodiments, the additives are at least 1-5%, 1-10%, 1-15%, 1-20%, 1-25%, 1-30%, 1-35%, 1-40%, 1-45%, 1-50%, 1-55%, 1-60%, 1-65%, 1-70%, 1-75%, 1-80%, 1-85%, 1-90%, 1-95%, or 1-100% of the weight of the composition. In certain embodiments, the additives comprise 1-5%, 1-10%, 1-15%, 1-20%, 1-25%, 1-30%, 1-35%, 1-40%, 1-45%, 1-50%, 1-55%, 1-60%, 1-65%, 1-70%, 1-75%, 1-80%, 1-85%, 1-90%, 1-95%, or 1-100% of the volume of the composition. In certain embodiments, the additives comprise 5-10%, 10-30%, or 25-40% of the weight of the composition. In certain embodiments, the additives comprise 5-10%, 10-30%, or 25-40% of the volume of the composition.

In certain embodiments, the additives are at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the weight of the composition.

In certain embodiments, the additives are at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the volume of the composition.

One of ordinary skill in the art will also appreciate that the dimethyloctane and dimethyloctane derivatives described herein are can be mixed with other fuels such as bio-diesel, various alcohols such as ethanol and butanol, and petroleum derived products such as gasoline. In certain embodiments, the conventional petroleum-based fuel is at least 10%, 20%, 30%, 40%, 50%, 60%, 75%, 85%, 95%, or 99% of the weight or volume of the composition.

Bio-crudes are biologically produced compounds or a mix of different biologically produced compounds that are used as a feedstock for petroleum refineries in replacement of, or in complement to, crude oil. In general, but not necessarily, these feedstocks have been pre-processed through biological, chemical, mechanical or thermal processes in order to be in a liquid state that is adequate for introduction in a petroleum refinery.

Microbial Hosts

Microbial hosts of the invention may be selected from but not limited to archaea, bacteria, cyanobacteria, fungi, yeasts, thraustochytrids and photosynthetic microorganisms. In certain embodiments, examples of criteria for selection of suitable microbial hosts include the following: intrinsic tolerance to desired product, high rate of glucose or alternative carbon substrate utilization, availability of genetic tools for gene manipulation, and the ability to generate stable chromosomal alterations. However, the present invention should not be interpreted to be limited by these criteria.

The microbial host used for geraniol or geraniol derivative production is preferably tolerant to geraniol or geraniol derivatives so that the yield is not limited by product toxicity. Suitable host strains with a tolerance for geraniol or geraniol derivatives may be identified by screening based on the intrinsic tolerance of the strain. The intrinsic tolerance of microbes to geraniol or geraniol derivatives may be measured by determining the concentration of geraniol or geraniol derivatives that is responsible for 50% inhibition of the growth rate ($IC_{50}$) when grown in a minimal culture medium. The $IC_{50}$ values may be determined using methods known in the art. For example, the microbes of interest may be grown in the presence of various amounts of geraniol or geraniol derivatives and the growth rate monitored by measuring the optical density. The doubling time may be calculated from the logarithmic part of the growth curve and used as a measure of the growth rate. The concentration of geraniol or of the geraniol derivative that produces 50% inhibition of growth may be determined from a graph of the percent inhibition of growth versus the concentration of geraniol or geraniol derivative. In some embodiments, the host strain should have an $IC_{50}$ for geraniol or geraniol derivative of greater than 0.5%. The $IC_{50}$ value can be similarly calculated for microbes in contact with compounds other than geraniol.

The ability to genetically modify the host is essential for the production of any recombinant microorganism. The mode of gene transfer technology may be by electroporation, conjugation, transduction or natural transformation. A broad range of host conjugative plasmids and drug resistance and nutritional markers are available. The cloning vectors are tailored to the host organisms based on the nature of antibiotic resistance markers that can function in that host.

In some embodiments, the microbial host also may be manipulated in order to inactivate competing pathways for carbon flow by deleting various genes. This may require the ability to direct chromosomal integration events. Additionally, the production host should be amenable to chemical mutagenesis so that mutations to improve intrinsic product, such as geraniol or geranyl acetate, tolerance may be obtained.

Microbial hosts of the invention may be selected from but not limited to archaea, bacteria, cyanobacteria, fungi, yeasts, thraustochytrids and photosynthetic microorganisms. Examples of suitable microbial hosts for use with the disclosed invention include, but are not limited to, members of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula*, and *Saccharomyces*. Examples of particular bacteria hosts include but are not limited to *Escherichia coli, Corynebacterium glutamicum, Pseudomonas putida, Bacillus subtilis, Rhodopseudomonas palustris, Rhodobacter sphaeroides, Micrococcus luteus, Streptomyces coelicolor, Streptomyces griseus, Lactobacillus fermentum, Lactococcus lactis, Lactobacillus bulgaricus, Acetobacter xylinum, Streptococcus lactis, Bacillus stearothermophilus, Propionibacter shermanii, Streptococcus thermophilus, Deinococcus radiodurans, Delftia acidovorans, Enterococcus faecium, Pseudomonas mendocina*, and *Serratia marcescens*. Examples of particular yeast hosts include but are not limited to *Saccharomyces cerevisiae, Saccharomyces carlsbergensis, Kluyveromyces lactis, Kluyveromyces marxianus, Yarrowia lipolytica, Debaryomyces hansenii, Ashbya gossypii, Zygosaccharomyces rouxii, Zygosaccharomyces bailiff, Brettanomyces bruxellensis, Schizosaccharomyces pombe, Rhodotorula glutinis, Pichia stipitis, Pichia pastoris, Candida tropicalis, Candida utilis* and *Candida guilliermondii*. Examples of particular fungal hosts include but are not limited to *Aspergillus niger, Aspergillus oryzae, Neurospora crassa, Fusarium venenatum* and *Penicillium chrysogenum*. Examples of particular photosynthetic microorganism hosts include but are not limited to *Anabaena* sp., *Chlamydomonas reinhardtii, Chlorella* sp., *Cyclotella* sp., *Gloeobacter violaceus, Nannochloropsis* sp., *Nodularia* sp., *Nostoc* sp., *Prochlorococcus* sp., *Synechococcus* sp., *Oscillatoria* sp., *Arthrospira* sp., *Lyngbya* sp., *Dunaliella* sp., and *Synechocys-*

*tis* sp. Examples of particular thraustochytrid hosts include but are not limited to *Schizochytrium* sp. and *Thraustochytrium* Sp.

Construction of Production Host

Recombinant organisms containing the necessary genes that will encode the enzymatic pathway for the conversion of a carbon source to geraniol or geranyl acetate may be constructed using techniques well known in the art. In the present invention, genes encoding the enzymes of one of the geraniol or geranyl acetate biosynthetic pathways of the invention may be isolated from various sources. Non-limiting examples of enzymes which are encoded in the present invention include 1-deoxy-xylulose 5-phosphate synthase (E.C. 2.2.1.7), 1-deoxy-D-xylulose-5-phosphate reductoisomerase (E.C. 1.1.1.267), 4-diphosphocytidyl-2-C-methyl-D-erythritol synthase (E.C. 2.7.7.60), 4-diphosphocytidyl-2-C-methyl-D-erythritol kinase (E.C. 2.7.1.148), 2-C-methyl-D-erythritol-2,4-cyclodiphosphate synthase (E.C. 4.6.1.12), 1-hydroxy-2-methyl-2-(E)-butenyl-4-diphosphate synthase (E.C. 1.17.4.3), 1-hydroxy-2-methyl-2-(E)-butenyl-4-diphosphate reductase (E.C. 1.17.1.2), isopentenyl diphosphate isomerase (E.C. 5.3.3.2), geranyl diphosphate synthase (E.C. 2.5.1.1), geraniol synthase (E.C. 4.2.3.-), geranyl diphosphate phosphatase, ocimene synthase (4.2.1.15), acetyl-CoA acetyltransferase (E.C. 2.3.1.9), 3-hydroxy-3-methyl-glutaryl-CoA synthase (E.C. 2.3.3.10), 3-hydroxy-3-methyl-glutaryl-CoA reductase (E.C. 1.1.1.34), mevalonate kinase (E.C. 2.7.1.36), phosphomevalonate kinase (E.C. 2.7.4.2), mevalonate-5-diphosphate decarboxylase (E.C. 4.1.1.33), branched chain aminotransferase (E.C. 2.6.1.42), leucine aminotransferase (2.6.1.6), 2-oxoisovalerate dehydrogenase (E.C. 1.2.1.25), isovaleryl-CoA dehydrogenase (E.C. 1.3.99.10), 3-methylcrotonyl-CoA carboxylase (E.C. 6.4.1.4) and 3-methylglutaconyl-CoA hydratase (E.C. 4.2.1.18). In addition, in some embodiments, the present invention includes genes that encode enzymes that catalyze or are part of the biosynthetic pathway in the conversion of geranyl diphosphate to geraniol, and/or geraniol to dimethyloctane.

A summary of the enzymes and the substrates and products of the reaction they catalyze is provided below:

| | SUBSTRATE | ENZYME | PRODUCT |
|---|---|---|---|
| a | D-glyceraldehyde-3-phosphate and pyruvate | 1-deoxy-xylulose 5-phosphate synthase (E.C. 2.2.1.7) | 1-deoxy-D-xylulose-5-phosphate (DOXP) |
| b | 1-deoxy-D-xylulose-5-phosphate (DOXP) | 1-deoxy-D-xylulose-5-phosphate reductoisomerase (E.C. 1.1.1.267) | 2-methyl-D-erythritol-4-phosphate (MEP) |
| c | 2-methyl-D-erythritol-4-phosphate (MEP) | 4-diphosphocytidyl-2-C-methyl-D-erythritol synthase (E.C. 2.7.7.60) | 4-(cytidine-5-diphospho)-2-C-methyl-D-erythritol (CDP-ME) |
| d | 4-(cytidine-5-diphospho)-2-C-methyl-D-erythritol (CDP-ME) | 4-diphosphocytidyl-2-C-methyl-D-erythritol kinase (E.C. 2.7.1.148) | 2-phospho-4-(cytidine-5-diphospho)-2-C-methyl-D-erythritol (CDP-MEP) |
| e | 2-phospho-4-(cytidine-5-diphospho)-2-C-methyl-D-erythritol (CDP-MEP) | 2-C-methyl-D-erythritol-2,4-cyclodiphosphate synthase (E.C. 4.6.1.12) | 2-C-methyl-D-erythritol-2,4-cyclodiphosphate (MEcPP) |
| f | 2-C-methyl-D-erythritol-2,4-cyclodiphosphate (MEcPP) | 1-hydroxy-2-methyl-2-(E)-butenyl-4-diphosphate synthase (E.C. 1.17.4.3) | 1-hydroxy-2-methyl-2-(E)-butenyl-4-diphosphate (HMB-PP) |
| g | 1-hydroxy-2-methyl-2-(E)-butenyl-4-diphosphate (HMB-PP) | 1-hydroxy-2-methyl-2-(E)-butenyl-4-diphosphate reductase (E.C. 1.17.1.2) | isopentenyl diphosphate (IPP) |
| h | isopentenyl diphosphate (IPP) | isopentenyl diphosphate isomerase (E.C. 5.3.3.2) | dimethylallyl diphosphate (DMAPP) |
| i | dimethylallyl diphosphate (DMAPP) and isopentenyl diphosphate (IPP) | geranyl diphosphate synthase (E.C. 2.5.1.1) | geranyl diphosphate (GPP) |
| j | geranyl diphosphate (GPP) | geraniol synthase (E.C. 4.2.3.—) | geraniol |
| k | geranyl diphosphate (GPP) | geranyl diphosphate phosphatase | pinene |
| l | geranyl diphosphate (GPP) | ocimene synthase (E.C. 4.2.1.15) | acyclic monoterpenes beta-myrcene (E)-beta-ocimene |
| m | 2 acetyl-CoA | acetyl-CoA acetyltransferase (E.C. 2.3.1.9) | acetoacetyl-CoA |
| n | acetoacetyl-CoA and acetyl-CoA | 3-hydroxy-3-methyl-glutaryl-CoA synthase (E.C. 2.3.3.10) | 3-hydroxy-3-methyl-glutaryl-CoA (HMG-CoA) |
| o | 3-hydroxy-3-methyl-glutaryl-CoA (HMG-CoA) | 3-hydroxy-3-methyl-glutaryl-CoA reductase (E.C. 1.1.1.34) | mevalonate (MEV) |
| p | mevalonate (MEV) | mevalonate kinase (E.C. 2.7.1.36) | mevalonate-5-phosphate (MEV-P) |
| q | mevalonate-5-phosphate (MEV-P) | phosphomevalonate kinase (E.C. 2.7.4.2) | mevalonate-5-diphosphate (MEV-PP) |
| r | mevalonte-5-diphosphate (MEV-PP) | mevalonate-5-diphosphate decarboxylase (E.C 4.1.1.33) | isopentenyl diphosphate (IPP) |
| s | L-leucine | branched chain aminotransferase (E.C. 2.6.1.42), or leucine aminotransferase (E.C. 2.6.1.6) | 4-methyl-2-oxopentanoate |
| t | 4-methyl-2-oxopentanoate | 2-oxoisovalerate dehydrogenase (E.C. 1.2.1.25) | isovaleryl-CoA |

-continued

| | SUBSTRATE | ENZYME | PRODUCT |
|---|---|---|---|
| u | isovaleryl-CoA | isovaleryl-CoA dehydrogenase (E.C. 1.3.99.10) | 3-methylcrotonyl-CoA is catalyzed |
| v | 3-methylcrotonyl-CoA | 3-methylcrotonyl-CoA carboxylase (E.C. 6.4.1.4) | 3-methylglutaconyl-CoA |
| w | 3-methylglutaconyl-CoA | 3-methylglutaconyl-CoA hydratase (E.C. 4.2.1.18) | 3-hydroxy-3-methylglutaryl-CoA (HMG-CoA) |
| x | geraniol | geraniol acetyltransferase | geraniol acetate |

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer-directed amplification methods such as polymerase chain reaction (U.S. Pat. No. 4,683,202) to obtain amounts of DNA suitable for transformation using appropriate vectors. Tools for codon optimization for expression in a heterologous host are readily available. Some tools for codon optimization are available based on the GC content of the host organism.

Once the relevant pathway genes are identified and isolated they may be transformed into suitable expression hosts by means well known in the art. Vectors or cassettes useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, TEF, CYC1, HIS3, GAL1, GAL10, ADH1, PGK, PHO5, GAPDH, ADC1, TRP1, URA3, LEU2, ENO, TPI, CUP1, FBA, GPD, and GPM (useful for expression in *Saccharomyces*); AOX1 (useful for expression in *Pichia*); and lac, ara, tet, trp, $IP_L$, $IP_R$, T7, tac, and trc (useful for expression in *Escherichia coli, Alcaligenes*, and *Pseudomonas*); the amy, apr, npr promoters and various phage promoters useful for expression in *Bacillus subtilis, Bacillus licheniformis*, and *Paenibacillus macerans*; nisA (useful for expression Gram-positive bacteria, Eichenbaum et al. Appl. Environ. Microbiol. 64(8):2763-2769 (1998)); and the synthetic P11 promoter (useful for expression in *Lactobacillus plantarum*, Rud et al., Microbiology 152:1011-1019 (2006)).

Termination control regions may also be derived from various genes native to the preferred hosts. Optionally, a termination site may be unnecessary.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in Gram-negative bacteria (Scott et al., Plasmid 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to effect gene replacement in a range of Gram-positive bacteria (Maguin et al., J. Bacteriol. 174(17):5633-5638 (1992)). Additionally, in vitro transposomes are available to create random mutations in a variety of genomes from commercial sources such as EPICENTRE®.

Culture Media and Conditions

Culture medium in the present invention contains suitable carbon source. In addition to an appropriate carbon source, culture medium typically contains suitable minerals, salts, cofactors, buffers and other components, known to those skilled in the art, suitable for the growth of the cultures and promotion of the enzymatic pathway necessary for geraniol production.

Typically cells are grown at a temperature in the range of 25° C. to 40° C. in an appropriate medium. Suitable growth media in the present invention are common commercially prepared media such as Luria Bertani (LB) broth, Sabouraud Dextrose (SD) broth or Yeast medium (YM) broth. Other defined or synthetic growth media may also be used, and the appropriate medium for growth of the particular microorganism will be known by one skilled in the art of microbiology or fermentation science. Suitable pH ranges for the fermentation are between pH 5.0 to pH 9.0. In some embodiments the initial pH is 6.0 to pH 8.0. Microorganism culture may be performed under aerobic, anaerobic, or microaerobic conditions.

Recovery and Conversion of Geraniol or Geranyl Acetate

Metabolic products of the recombinant microorganisms described herein are recovered from spent culture medium, preferably when the concentration of the product reaches a usable level. The concentration of geraniol and geranyl acetate in the spent culture media can be determined by a number of methods known in the art. For example, a high performance liquid chromatography (HPLC) with refractive index (RI) detection or alternatively gas chromatography (GC) methods are available.

Geraniol or geraniol derivative can be recovered by one or more techniques well known to a person having ordinary skill in the art. Non-limiting examples of techniques include liquid-liquid extraction, solid-phase extraction, filtration, fractional distillation, and chromatography. Recovery of other products such as dimethyloctane and dimethyloctane derivatives can be similarly carried out by these techniques.

Geraniol can be converted to dimethyloctane and/or stereoisomers thereof by enzymatic processes or chemical synthesis or a combination thereof. Structural isomers and stereoisomers of dimethyloctane can be formed by rearrangement of the carbons under conditions well known to those skilled in the art. In preferred embodiments, geraniol or a geraniol derivative is converted to 2,6-dimethyloctane.

Conversion of geraniol or a geraniol derivative to dimethyloctane or a dimethyloctane derivative product may be accomplished by chemical synthesis carried out by steps known to one skilled in the art. In certain embodiments, the method of the invention provides for the chemical conversion of geraniol or a geraniol derivative to 2,6-dimethyloctane comprising the steps of reduction of the alcohol to form the hydrocarbon intermediate, followed by hydrogenation of any unsaturated bonds. Reactions may take place in a variety of organic solvents or neat.

Reduction of the alcohol is carried out by steps known by one skilled in the art, and in certain embodiments involve forming a leaving group with the alcohol followed by displacement with a hydride source. For example, reaction of the alcohol with a tosyl-halide under basic conditions provides the tosylate ester which may be further reacted with a hydride source to give the hydrocarbon intermediate. Pyridine is a possible organic base and tosyl chloride is an example of a tosylating agent. An example of a hydride source is $LiAlH_4$, $NaBH_4$, or Raney nickel.

In other embodiments, reduction of the alcohol group of geraniol is accomplished by exposure of the alcohol to acid conditions and heat to form an unsaturated hydrocarbon, followed by hydrogenation to yield 2,6-dimethyloctane. $H_2SO_4$ or $H_3PO_4$ can be used as acid sources.

The unsaturated intermediate is reduced with $H_2$ and a catalyst. Hydrogenation of unsaturated bonds is carried out with heterogeneous or homogeneous catalysis. Heterogeneous or homogeneous hydrogenation catalysts is obtained from commercial sources. In certain embodiments, conditions for hydrogenation include treatment of double bonds with $H_2$ and a catalyst, wherein catalyst may contain Pt, Pd, Ni, Rh, or Ru; wherein each metal may optionally have chiral ligands. Other catalysts include Pd/C, Raney nickel, Wilkinson's catalyst, and $Ru(BINAP)Cl_2$. Reaction conditions such as time, heat and pressure may be varied to improve yield or selectivity.

In an alternative embodiment, geraniol is directly hydrogenated to 2,6-dimethyloctane using a hydrogenation catalyst discussed above and hydrogen gas. Reaction conditions such as time, heat and pressure may be varied to improve yield or selectivity. A non-limiting example of this process can be found in Example 13.

In yet another alternative embodiment, geraniol is converted to a geraniol acetate intermediate (see FIG. 5) before transformation to dimethyloctane. The conversion can occur in a biosynthetic manner as part of the metabolic process wherein geraniol acetyltransferase catalyzes the conversion of geraniol to geraniol acetate. In other embodiments, this step is accomplished by chemical synthesis, wherein a person having ordinary skill in the art acylates the alcohol to yield the acylated intermediate. A non-limiting example of the acylation reaction involves reacting the alcohol with the appropriate acyl halide or anhydride in the presence of base. In certain embodiments, the resulting geraniol acetate, generated by biosynthetic means, chemical means or a mixture thereof, is hydrogenated using a hydrogenation catalyst and hydrogen gas as described previously to give the 2,6-dimethyloctane.

Carbon Fingerprinting

Compositions that are derived from the biosynthetic methods described herein can be characterized by carbon fingerprinting, and their lack of impurities when compared to petroleum derived fuels. Carbon fingerprinting is valuable in distinguishing dimethyloctane derived by the biosynthetic methods described herein from other methods.

Biologically produced geraniol derivatives represent a new source of fuels, such as alcohols, diesel, and gasoline. These new fuels can be distinguished from fuels derived form petrochemical carbon on the basis of dual carbon-isotopic fingerprinting. Additionally, the specific source of biosourced carbon (e.g., glucose vs. glycerol) can be determined by dual carbon-isotopic fingerprinting (see U.S. Pat. No. 7,169,588, which is herein incorporated by reference in its entirety, in particular, see col. 4, line 31, to col. 6, line 8).

The geraniol derivatives and the associated biofuels, chemicals, and mixtures may be completely distinguished from their petrochemical derived counterparts on the basis of $^{14}C$ ($f_M$) and dual carbon-isotopic fingerprinting.

The geraniol derivatives described herein have utility in the production of biofuels and chemicals. The new geraniol derivative-based products provided by the instant invention additionally may be distinguished on the basis of dual carbon-isotopic fingerprinting from those materials derived solely from petrochemical sources. The ability to distinguish these products is beneficial in tracking these materials in commerce. For example, fuels or chemicals comprising both "new" and "old" carbon isotope profiles may be distinguished from fuels and chemicals made only of "old" materials. Thus, the instant materials may be followed in commerce or identified in commerce as a biofuel on the basis of their unique profile. In addition, other competing materials can be identified as being biologically derived or derived from a petrochemical source.

In a non-limiting example, a biofuel composition is made that includes a geraniol derivative having $\delta^{13}C$ of from about −10.9 to about −15.4, wherein the geraniol derivative accounts for at least about 85% of biosourced material (i.e., derived from a renewable resource such as cellulosic materials and sugars) in the composition. In other examples, the biofuel composition includes a geraniol derivative having the formula:

(I)

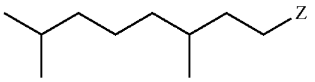

(II)

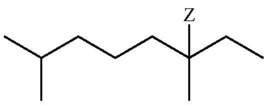

(III)

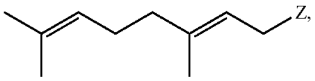

(IV)

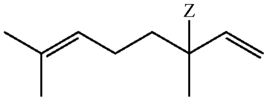
;

(V)

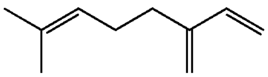
,

-continued (VI)

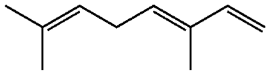

, or (VII)

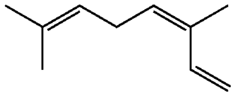

, wherein Z is H, O—R, or O—C(=O)R; R is H or an optionally substituted alkyl, such as a C1-C6 alkyl, an alkenyl, such as a C2-C6 alkenyl, an alkynyl, such as a C2-C6 alkynyl, or an arylalkyl, such as a C7-C12 arylalkyl; or stereoisomers thereof; wherein optional substituents are selected from the group consisting of halo, =O, OR, $NR_2$, $NO_2$, and CN; wherein each R is independently H, C1-C6 alkyl, C2-C6 alkenyl, or C2-C6 alkynyl. The geraniol derivative is additionally characterized as having a $\delta^{13}C$ of about −10.9 to about −15.4, and the geraniol derivative accounts for at least about 85% of biosourced material in the composition. In other non-limiting examples, the geraniol derivative in the biofuel composition is characterized by having a fraction of modern carbon ($f_M\ ^{14}C$) of at least about 1.003, 1.010, or 1.5.

Genes for Metabolic Pathways

Step a. The conversion of D-glyceraldehyde-3-phosphate and pyruvate to 1-deoxy-D-xylulose-5-phosphate (DOXP) is catalyzed by 1-deoxy-xylulose 5-phosphate synthase (E.C. 2.2.1.7), examples of which are found at SEQ ID NO:1 and 3. Other examples of sequences encoding this enzyme include but are not limited to, one or more genes that encode the following proteins (indicated below as GenPept accession numbers):

Q39UB1, Q74FC3, Q28WA7, Q9F1V2, Q2RYD6, Q3J1A8, Q16DV7, Q82ML4, Q9X7W3, Q5NN52, Q39RT4, Q74CB0, Q28W25, Q8VUR8, Q2RR29, Q3IYR6, Q16CP0, Q82 KW8, Q8CJP7, Q5NM38, Q6F7N5, Q8UHD7, Q0VMI4, Q2IPZ2, Q8YZ80, Q3M4F6, O67036, Q38854, Q5P228, Q81M54, Q731B7, Q818R9, Q635A7, Q5LH44, Q64Y02, Q9K971, Q6HDY8, Q65HJ2, Q5WF63, P54523, Q8A0C2, Q6G4D1, Q6G0D4, Q1LTI9, Q7VRH9, Q493G7, Q2KZ15, Q7WL37, Q7W7Q0, Q7VV87, Q89RW1, Q2YMF0, Q57ET1, Q8YFM2, Q8G292, P57536, Q8K9A1, Q1BLY7, Q62DU1, Q3JKA3, Q63JF4, Q393P4, Q2T7N5, Q13RX1, Q9PIH8, Q5HWF0, O78328, Q3AAN0, Q9A6M5, Q5L6H4, Q823V1, Q253R7, Q9PK62, Q9Z6J9, Q3KM28, Q8KFI9, O84335, Q1R1E5, Q7NUK5, Q97HD5, Q18B68, Q0TPD8, Q8XJE1, Q0SS05, Q894H0, Q487D3, Q6NGV3, Q8FPI2, Q8NPB2, Q4JVB5, Q11NY7, Q47BJ0, Q3Z8G9, Q3ZXC2, Q1IZP0, Q9RUB5, Q30Z99, Q24V05, Q6AJQ1, Q72CD3, Q8XE76, Q0TKM1, Q8FKB9, P77488, Q1RFC0, Q6D844, Q2JDD9, Q2A3D3, Q5NG39, Q8R639, Q75TB7, Q7NP63, Q5FUB1, Q7VNP7, Q4QKG6, P45205, Q2SA08, Q7VIJ7, Q1CUF6, Q9ZM94, O25121, Q5QVE8, Q1MRB3, Q6AFD5, Q72U01, Q8F153, Q92BZ0, Q71ZV7, Q8Y7C1, Q2W367, Q65TP4, Q11KE0, Q60AN1, Q1GZD7, Q2RIB9, P0A555, Q50000, Q73W57, Q8EWX7, P0A554, Q1D3G4, Q5FAI2, Q9JW13, Q9JXV7, Q82VD3, Q1QQ40, Q2YCH7, Q3JAD1, Q3SUZ1, Q5YTA2, Q2GC13, O22567, Q6MDK6, P57848, Q3A3Z6, Q3B5P3, Q4FN07, Q7N0J7, Q6LU07, Q12CQ9, Q7MSZ3, Q6A8V3, Q31AZ2, Q7VC14, Q7V7Q3, Q7V1G6, Q46L36, Q48NX0, Q9KGU7, Q4K5A5, Q3II09, Q3K660, Q88QG7, Q889Q1, Q4ZYU8, Q4FV64, Q1QE74, Q474C2, Q1LK34, Q8XX95, Q2 KBR2, Q1MKN4, Q985Y3, Q92RJ1, Q7UWB7, P26242, Q21UG7, Q2IRL7, Q6NB76, Q21A74, Q0S1H1, Q21F93, Q57SE2, Q5 PFR6, Q8Z8X3, Q8ZRD1, Q8EGR9, Q325I1, Q32JH8, Q83SG2, Q3Z4Y9, Q5LX42, Q1GCG4, Q2NV94, Q1GQK9, Q9RBN6, Q67NB6, Q2LUA7, Q8DL74, Q2JTX2, Q2JK64, Q9R6S7, Q8GAA0, Q7U6P6, Q3AXZ4, Q3AJP8, P73067, Q47NL9, Q9X291, Q72H81, Q5SMD7, Q8RAC5, Q3SKF1, Q30TC5, Q73LF4, O83796, Q83I20, Q83G46, Q9KTL3, Q5E6Z0, Q87RU0, Q8DFA3, Q7MN49, Q8D357, Q7M7Z0, Q8PJG7, Q3BRW8, Q4UW29, Q8P815, Q2P472, Q5H1A0, Q9PB95, Q87C03, Q1C4I9, Q8ZC45, Q1CL87, and Q66DV4.

Step b. The conversion of 1-deoxy-D-xylulose-5-phosphate (DOXP) to 2-methyl-D-erythritol-4-phosphate (MEP) is catalyzed by 1-deoxy-D-xylulose-5-phosphate reductoisomerase (E.C. 1.1.1.267), examples of which are found at SEQ ID NO:5 and SEQ ID NO:7. Other examples of sequences encoding this enzyme include but are not limited to, one or more genes that encode the following proteins (indicated below as GenPept accession numbers):

Q81N10, Q81B49, Q638M6, Q6HG59, Q81WL4, Q819Y3, Q636K5, Q6HEZ4, Q6FCG9, Q5PAI9, Q8YP49, O66722, Q9XFS9, Q5NZG9, Q732P8, Q5L9P6, Q64PY9, Q9KA69, Q65JJ3, Q5WFT4, O31753, Q8A684, Q8G7Y7, Q7VRE2, Q7WJ88, Q7WA54, Q7VYC4, Q89 KP9, P57329, Q8K9S7, Q62JD0, Q63T18, Q9PMV3, Q5HT65, Q9A709, Q5L651, Q823G9, Q9PKW8, Q9Z8J8, Q8KG43, O84074, Q7NVY8, Q97I58, Q8XJR1, Q895K5, Q485G4, Q6NGL1, Q8FP80, Q8NP10, Q4JV26, Q47F86, Q9RU84, Q6AP35, Q72DR3, Q8X8Y1, P45568, Q5FHA4, Q5HB55, Q6D8D9, Q5NEP6, Q8R622, Q5L0J6, Q74BW4, Q7NID1, Q5FPZ1, Q7VM27, Q4QM93, P44055, Q7VIT0, Q9ZML6, P56139, Q5QUF4, Q9AJD7, Q6AEY1, Q72U08, Q8F146, Q92C37, Q720A5, Q8Y7G4, Q65R75, Q9XES0, Q60BA4, P64013, Q7NC17, Q9CBU3, Q73VS1, Q8EWQ6, P64012, Q5F5X0, Q9JX33, Q9K1G8, Q82U01, Q5YS72, Q8W250, Q6MEL5, P57985, Q4FM64, Q7N8P3, Q6LN30, Q7MUW3, Q6A7K8, Q7VB62, Q7V6J8, Q7V0W0, Q48F65, Q9KGU6, Q4 KHH0, Q88 MH4, Q886N7, Q4ZWS2, Q4FRH9, Q8XZI5, Q92LP6, Q7URM5, Q6N5Q6, Q57T35, Q5PD59, Q8Z9A6, Q8ZRP3, Q8EGG9, Q83MD3, Q5LSU9, Q82K41, Q9KYS1, Q67PA9, Q8DK30, Q9RCT1, Q7U8C3, Q55663, Q9WZZ1, Q72KE2, Q5SJZ6, Q8RA28, Q73K78, O83610, Q83IC8, Q83GY8, Q9 KPV8, Q5E3E5, Q87ME3, Q8 DBF5, Q7MIG6, Q8D2G6, Q73GG3, Q7M9M7, Q5GTA4, Q8PML1, Q4USQ4, Q8PAV9, Q5H1E7, Q9PEI0, Q87EH9, Q8ZH62, Q667J3, and Q9X5F2.

Step c. The conversion of 2-methyl-D-erythritol-4-phosphate (MEP) to 4-(cytidine-5-diphospho)-2-C-methyl-D-erythritol (CDP-ME) is catalyzed by 4-diphosphocytidyl-2-C-methyl-D-erythritol synthase (E.C. 2.7.7.60), examples of which are found at SEQ ID NO:9 and SEQ ID NO:11. Other examples of sequences encoding this enzyme include but are not limited to, one or more genes that encode the following proteins (indicated below as GenPept accession numbers):

Q92F40, Q724H7, Q8YAB5, Q2YV76, Q5HJC5, P65176, P65177, Q6GK63, Q6GCM3, Q8NYI0, Q87LQ2, Q92CV0, Q720Y7, Q8Y832, Q2YV73, Q5HJC1, Q99WW8, Q7A7V0, Q6GK57, Q6GCL7, Q7A1W0, Q87Q30, Q8UFF4, Q2IQG8, A1USA2, Q6G3Z8, Q6G164, Q89LQ8, A5EIY9, A4YUQ7, Q2YPW1, Q57D18, Q8YHD8, Q8G0H4, A0RN28, Q9PM68, A1W1K9, Q5HSI4, Q9A7I5, Q310X3, Q6ARN9, Q72C30, A1VDX6, Q2NAE1, Q5FQD6, Q0BTD5, Q17WU1, Q7VFU3, Q1CU78, Q9ZM19, O25664, Q0C0N0, Q28Q60, Q1MR76, Q6ADI0, Q2W4Q8, Q0APQ6, Q11HV9, Q1QM99, Q3SSN8, Q2G708, A1B890, Q4FM31, Q2K8V5, Q1 MH21, Q98MX9, Q92Q90, Q08113, Q21YT7, Q2IW23, Q07MZ2, Q6N6M5, Q214R1, Q137C3, Q2RTS1, Q5LRN5,

Q1GGW9, Q1GTN0, Q30QG7, O83525, Q83NK3, Q83MX3, Q73G24, Q7MQW9, Q5GSM7, Q9RNZ1, Q6FAU1, Q8YLX9, Q3MAF5, O67343, P69834, Q5NYJ9, Q81VV5, Q73FC1, Q81J63, Q63HB4, Q5L917, Q64P77, Q9KGF8, Q6HPT2, Q65PD2, Q5WLT7, Q06755, Q8A0U8, Q8G7E2, Q494E8, Q7WCW3, Q7W5C9, Q7VZN2, P57495, Q8K9D6, Q62JI5, Q3JR99, Q63T70, Q39FB8, Q2SWT6, Q3A9N7, Q3AS33, Q824I4, Q9PJT1, Q9Z7X5, Q3KLN6, Q8KCU3, O84468, Q7NYL6, Q97EC9, Q8XHQ3, Q890M1, Q487E9, Q6NFC1, Q8FMI3, Q8NMB8, Q4JXJ7, Q47EL2, Q3ZAD7, Q3ZWE1, Q9RR90, Q8X7Y4, Q8FEJ5, Q46893, Q6D1B3, Q2J542, Q8R6H2, Q5L433, Q39ZL5, Q746Z9, Q7NGU6, Q7VLT5, Q4QMP4, O05029, Q2SKW7, Q5QUC3, Q88W46, Q72P59, Q8F7A0, Q65Q78, Q604M2, Q2RFM0, Q7TW54, Q9CCW6, Q743W5, P96864, Q5F829, Q9JTM3, Q9JYM4, Q82UR9, Q2Y751, Q3JCS9, Q5Z2R3, Q6MEE8, P57953, Q3A8C6, Q3B3A7, Q7N8K7, Q6LMT3, Q7MUQ9, Q6AAV8, Q31C80, Q7VDC7, Q7V647, Q7V2M1, Q46GW4, Q48F81, P57707, Q4 KHF4, Q3IDQ6, Q3 KH90, Q88MF7, Q886M1, Q4ZWQ6, Q4FR76, Q472F2, Q8XYW3, Q7UM15, Q3J2K9, Q57KJ4, Q5PEG1, Q2S210, Q8Z471, Q8ZMF6, Q8EBR2, Q31XA9, Q32CI3, Q7C093, Q3YYB5, Q2NVM4, Q2FK15, Q5HRJ7, Q8CQ77, Q4A0A8, Q3K093, Q8E4B4, Q8DYQ7, Q82GC8, Q9LOQ8, Q97QE5, Q8DPI2, Q67JP5, Q2LUS9, Q8DL91, Q2JUE5, Q5N3T2, Q31QF6, Q7U559, Q3AWK9, Q3ALY8, P74323, Q47LV0, Q9X1B3, Q72GN3, Q5SLX2, Q8R7S6, Q3SK38, Q9KUJ2, Q5E328, Q8DC60, Q7 MHQ4, Q8D223, Q8PLR8, Q3BUS8, Q4UTP4, Q8P9Z1, Q2P1L0, Q5GYK6, Q9PDT6, Q87DY4, Q8ZBP6, and Q66EC3

Step d. The conversion of 4-(cytidine-5-diphospho)-2-C-methyl-D-erythritol (CDP-ME) to 2-phospho-4-(cytidine-5-diphospho)-2-C-methyl-D-erythritol (CDP-MEP) is catalyzed by 4-diphosphocytidyl-2-C-methyl-D-erythritol kinase (E.C. 2.7.1.148), examples of which are found at SEQ ID NO:13 and SEQ ID NO:15. Other examples of sequences encoding this enzyme include but are not limited to, one or more genes that encode the following proteins (indicated below as GenPept accession numbers):

Q6F8J0, Q8UHP8, Q2IM67, Q5PB05, Q8YS61, Q3M3F2, O67060, O81014, Q5P725, Q81VZ6, Q73FG3, Q81JA2, Q63HI8, Q5LC56, Q64T40, Q9KGK0, Q6HPX2, Q65PH5, Q5WLV8, P37550, Q8AA41, Q6G4E4, Q6G0G3, Q8G6I4, Q492W0, Q7WNY5, Q7W182, Q7VUH0, Q89S79, Q2YMB5, Q57EW9, Q8YFI3, Q8G2D0, P57267, Q8K9X1, Q62FC4, Q3JW85, Q63XL7, Q39CU1, Q2T1B6, Q9PNJ0, Q5HU00, Q3AFM4, Q9A8L7, Q5L568, Q3AQY2, Q821×0, Q9PLC0, Q3KKN7, Q8KCC7, O84810, Q7NQS8, Q97F51, Q8XIA9, Q899A2, Q47Y90, Q6NIA1, Q8FQZ4, Q8NRY0, Q4JU24, Q479M3, Q3Z9E9, Q3ZZE5, Q9RR89, Q30ZH4, Q6AJL6, Q72BQ8, P62616, Q8FI04, P62615, Q3YSE4, Q5FHM5, Q5HBJ6, Q839U9, Q6D554, Q5NI19, Q8R6C8, Q5L3V4, Q39RQ7, Q74FE9, Q7NPF3, Q5FQP6, Q7VL54, Q4QL43, P45271, Q2SLA0, Q9ZJH3, O25984, Q5QV06, Q88Z91, Q38V25, Q6ADP2, Q72V75, Q8EZM8, Q92F77, Q724M3, Q8YAE1, Q2VYT6, Q65SB8, P56848, Q60A17, Q2RMC8, P65179, Q9CD51, Q741W1, P65178, Q5F9F6, Q9JUX8, Q9JZW4, Q82TQ3, Q2YBH5, Q3JDR0, Q3SPE5, Q5YPY8, Q2G7F1, Q8EU37, Q6MAT6, P57833, Q3A311, Q3B2S6, Q4FPG0, Q7N589, Q6LNB1, Q7MVU8, Q6AAD6, Q31B18, Q7VCH6, Q7V7W1, Q7V1E2, Q46L57, Q48MV8, P42805, Q4K691, Q3IK98, Q3K6W5, Q88PX5, Q888C5, Q4ZXX1, Q4FVB2, Q476F8, Q8Y2E0, Q986C6, Q92RM1, Q7UEV3, Q6NAZ1, Q2RXS7, Q3J5K7, Q57NN2, Q5PCR2, Q2S4Q4, Q8Z699, P30753, Q8EAR0, Q31ZQ1, Q32GZ9, Q83LD8, Q3Z0S6, Q5LX98, Q2NRS1, P93841, Q2FJE7, Q2YVV0, Q5HII1, P65180, P65181, Q6GJH6, Q6 GBZ3, P65182, Q5HRR0, Q8CQU6, Q4L3F2, Q49V04, Q3K3L9, Q8E7K5, Q8E245, Q820G3, Q9K3R6, Q8DS40, Q67JC2, Q2LUJ9, Q8DLJ1, Q2JQU4, Q2JLP6, Q5N2S7, Q31RH7, Q7U7D2, Q3AXF4, Q3AKD9, P72663, Q47SX2, Q9X1A3, Q72GN2, P83700, Q8R765, Q3SLR6, Q30TG0, Q73N18, O83386, Q83IA0, Q83FU3, Q9PPN9, Q9KQ23, Q5E6T6, Q87RN7, Q8DFF6, Q7MMZ0, Q8D2K6, Q73I23, Q5GTB0, Q8PNU1, Q3BX03, Q4URC0, Q8PC64, Q2NZW6, Q5GWR3, Q9PA75, Q87A21, Q8ZEY1, Q66AX8, and Q9X3W5.

Step e. The conversion of 2-phospho-4-(cytidine-5-diphospho)-2-C-methyl-D-erythritol (CDP-MEP) to 2-C-methyl-D-erythritol-2,4-cyclodiphosphate (MEcPP) is catalyzed by 2-C-methyl-D-erythritol-2,4-cyclodiphosphate synthase (E.C. 4.6.1.12), examples of which are found at SEQ ID NO:17 and SEQ ID NO:19. Other examples of sequences encoding this enzyme include but are not limited to, one or more genes that encode the following proteins (indicated below as GenPept accession numbers):

Q8UFF4, Q2IQG8, A1USA2, Q6G3Z8, Q6G164, Q89LQ8, A5EIY9, A4YUQ7, Q2YPW1, Q57D18, Q8YHD8, Q8G0H4, A0RN28, Q9PM68, A1W1K9, Q5HSI4, Q9A7I5, Q310X3, Q6ARN9, Q72C30, A1VDX6, Q2NAE1, Q5FQD6, Q0BTD5, Q9ZM19, O25664, Q0C0N0, Q28Q60, Q1MR76, Q6ADI0, Q2W4Q8, Q0APQ6, Q11HV9, Q1QM99, Q3SSN8, Q2G708, A1B890, Q4FM31, Q2K8V5, Q1 MH21, Q98MX9, Q92Q90, Q08113, Q21YT7, Q2IW23, Q07MZ2, Q6N6M5, Q214R1, Q137C3, Q2RTS1, Q5LRN5, Q1GGW9, Q1GTN0, Q30QG7, O83525, Q83NK3, Q83MX3, Q73G24, Q7MQW9, Q5GSM7, Q9RNZ1, Q6FAU4, Q5P993, Q2GIK8, Q8YQF0, Q3MC53, O67089, Q9CAK8, Q5NYK0, Q81VV4, Q73FC0, Q81J62, Q63HB3, Q5L8X2, Q64P34, Q9KGF7, Q6HPT1, Q65PD1, Q5WLT6, Q06756, Q8A0Y7, Q8G5L2, Q493M8, Q2KUX6, Q7WCW4, Q7W5D0, Q7VZN1, P57494, Q8K9D7, Q62JI6, Q3JRA0, Q63T71, Q39FB9, Q2SWT5, Q3A9N8, Q9M4W3, Q5L6S2, Q3APP2, Q824F7, Q9PJV8, Q9Z805, Q3KLR6, Q8KC25, O84441, Q7NYL5, Q97LX0, Q8XI08, Q899E9, Q487E8, Q6NFC2, Q8FMI4, Q8NMB9, Q4JXJ6, Q47EL1, Q3ZAD6, Q3ZWG5, Q9RXS6, P62618, Q8FEJ6, P62617, Q3YT02, Q2 GHV0, Q5FF92, Q5HC74, Q839V8, Q6D1B4, Q2J543, Q5NFU1, Q8R6E7, Q5L432, Q39ZL6, Q747A0, Q7NFH8, Q47956, Q4QMP5, P44815, Q2SKW6, Q5QUC4, Q72UP7, Q8F0A5, Q92F39, Q724H6, Q8YAB4, Q65Q79, Q604M1, Q2RFM1, P65184, Q7NC56, Q9CCW5, Q743W4, P65183, Q5F830, Q9JTM4, Q9JYM5, Q2GER2, Q82US7, Q2Y752, Q3JCS8, Q5Z2R2, P57954, Q3A8C7, Q3B2H9, Q7N8K6, Q6LMT4, P62368, P62369, Q7MXX0, Q6AAV7, Q319L1, Q48F85, P57708, Q4 KHF0, Q3IDQ5, Q3 KH86, Q88MF3, Q886L7, Q4ZWQ2, Q4FSB5, Q472F1, Q8XYW2, Q7UU80, Q3J2K8, Q57KJ5, Q5PEG2, Q2S211, Q8Z472, Q8ZMF7, Q8EBR3, Q31XA8, Q32CI4, P62619, Q3YYB6, Q2NVM3, Q82GC9, Q9L0Q7, Q67JP6, Q2LUT1, Q8DHC4, Q2JXJ4, Q2JNA9, Q5N549, Q31P19, P73426, Q47KT3, Q9WZB5, Q72HP8, Q8RQP5, Q8R7S8, Q3SK37, Q73KC6, Q9KUJ1, Q5E329, Q87LQ3, Q8DC59, Q7 MHQ5, Q8D224, Q8PLR7, Q3BUS7, Q4UTP5, Q8P9Z0, Q2P1L1, Q5GYK7, Q9PDT5, Q87DY3, Q8ZBP7, and Q66EC2.

Step f. The conversion of 2-C-methyl-D-erythritol-2,4-cyclodiphosphate (MEcPP) to 1-hydroxy-2-methyl-2-(E)-butenyl-4-diphosphate (HMB-PP) is catalyzed by 1-hydroxy-2-methyl-2-(E)-butenyl-4-diphosphate synthase (E.C. 1.17.4.3), examples of which are found at SEQ ID NO:21 and SEQ ID NO:23. Other examples of sequences encoding this enzyme include but are not limited to, one or more genes that encode the following proteins (indicated below as GenPept accession numbers):

Q82K43, Q9X7W2, Q82ML3, Q9KYR9, Q6FEM3, P58665, Q5PAJ1, P58666, O67496, Q5P7B3, Q81LV7, Q730Q8, Q818H8, Q634Q9, Q5L7W2, Q64N34, Q9 KD18, Q6HDN9, Q65HA9, Q5WHB2, P54482, Q8A4T0, Q6G1X4, Q6G104, Q8G7Y6, Q7WHN0, Q7W6P6, Q7VWL0, Q89VV9, Q57BA5, Q8YJ17, Q8FYT2, P57374, Q8K9P4, Q62JW4, Q63UT3, Q9PPM1, Q5HV95, Q9A9W0, Q5L669, Q823I7, Q9PKY3, Q9Z8H0, Q8KG23, O84060, Q7NS88, Q97I56, P58667, Q895K3, Q6NGL3, Q8FP82, Q8NP12, Q9RXC9, Q6AP32, Q72CD9, P62622, P62621, P62620, Q5FHA6, Q5HB57, Q6D276, Q5NH64, Q8RG40, Q5KX35, Q74D60, Q7NFA4, Q5FUR7, Q7VME2, P44667, Q7VI04, Q9ZLL0, O25342, Q5QYA9, Q6AEX9, Q72TR2, Q8F1H5, Q71ZM9, P58668, Q65R84, Q604Q5, Q7TXN6, Q7NBH3, Q9CBU5, Q73VS3, Q8EUI6, O33350, Q5F913, Q9JU34, Q9JZ40, Q82XV0, Q5YS74, Q6MD85, P57987, Q7N706, Q6LU49, Q7MVT7, Q6A7L2, Q7VBS7, Q7V7G9, Q7V215, P72241, Q9HXJ4, Q88PJ7, Q886Z0, P58669, Q98FG0, Q92L19, Q7UWC8, Q6NCF3, Q57L16, Q5PNI2, P58670, P58671, Q8EC32, Q83K43, Q5LQ99, Q67PA7, Q8DK70, Q5N3W3, Q7U712, P73672, Q9WZZ3, Q72H18, Q5SLI8, Q84GJ3, Q8RA30, Q73N90, O83460, Q83NE4, Q83N18, Q9KTX1, Q5E772, Q87S16, Q8DEZ8, Q7MNF1, Q8D1Y3, Q73IP1, Q7M8Z2, Q5GRK4, Q8PLJ8, Q8P9R7, Q5H0N8, Q9PAE3, Q87A73, P58672, Q667Z9, and Q5NR50.

Step g. The conversion of 1-hydroxy-2-methyl-2-(E)-butenyl-4-diphosphate (HMB-PP) to isopentenyl diphosphate (IPP) is catalyzed by 1-hydroxy-2-methyl-2-(E)-butenyl-4-diphosphate reductase (E.C. 1.17.1.2), examples of which are found at SEQ ID NO:25 and SEQ ID NO:27. Other examples of sequences encoding this enzyme include but are not limited to, one or more genes that encode the following proteins (indicated below as GenPept accession numbers):

Q89UU5, Q629Z7, Q63WH0, P0A5I1, P0A5I0, Q6N3G0, Q89QW7, Q62HM8, Q9ZFL0, P0A5I3, P0A5I2, Q6N1Y1, Q9RBJ0, P58673, Q5PAE7, P58674, O67625, Q5P224, Q81LU9, Q730P8, Q634Q0, Q64PU1, Q9 KD37, Q6HDN0, Q65H97, Q5WHC6, P54473, Q8A625, Q6G4C5, Q6G0C9, Q8G4L8, Q7WHF2, Q7W9B4, Q7VYS2, Q57EP6, Q8YFR1, Q8G257, P57247, Q8K9Z4, P94644, Q5HUR4, Q9A345, Q5L5D3, Q822D9, Q9PL59, Q9Z6P2, Q8KFN9, O84867, Q7NS59, Q97I09, P58675, Q895G2, Q6NI36, Q8FQP0, Q8NRM2, Q9RSG0, Q6AL80, Q72G08, P62625, P62624, P62623, Q5FFL5, Q5HB13, Q6D0C6, Q5NGK4, Q8R152, Q5KX24, Q749Y8, Q7NG74, Q5FUH7, Q7VPK4, P44976, Q7VJV5, P65186, P65185, Q5QZR7, Q6ADV0, Q72S57, Q8F3I3, Q71ZL9, P58676, Q65RQ4, Q607E5, Q9X781, Q73WH6, Q8EWR9, Q5FAF2, P65191, P65192, Q82WM1, Q5YQ94, Q6MC97, P57960, Q7N8W9, Q6LUK8, Q7MWK6, Q6AA89, Q7VDS2, Q7V4T7, Q7V329, Q9HVM7, P21864, Q88Q89, Q889E1, P58677, Q985W3, Q92RG2, Q7ULU1, Q57TL2, Q5PKI4, P58678, P58679, Q8EBI7, Q7UDT8, Q5LNJ7, Q82IE8, Q9FBM1, Q67QZ8, Q8DK29, Q5N249, Q7U9K4, Q55643, Q9X1F7, Q72G65, Q5SMC8, Q8RA76, Q73NQ6, O83558, Q83NB2, Q83MR9, Q9KU44, Q5E7N1, Q87S87, Q8DET0, Q7MNM5, Q8D2R2, Q73FQ1, Q7M8Y6, Q5GTN6, Q8PN17, Q8PBG4, Q5H2D9, P65193, P65194, P58680, Q66ES1, and Q5NP61.

Step h. The conversion of isopentenyl diphosphate (IPP) to dimethylallyl diphosphate (DMAPP) is catalyzed by isopentenyl diphosphate isomerase (E.C. 5.3.3.2), examples of which are found at SEQ ID NO:29 and SEQ ID NO:31. Other examples of sequences encoding this enzyme include but are not limited to, one or more genes that encode the following proteins (indicated below as GenPept accession numbers):

Q38929, Q5P011, Q1LZ95, O48964, Q39472, Q13907, Q4R4W5, O35586, P58044, O42641, Q7N1V4, Q5R8R6, O35760, Q10132, P15496, Q9YB30, Q8YNH4, Q3MAB0, Q42553, O27997, Q5NWG5, Q81SX4, Q73AZ6, Q81FS0, Q63DN3, Q6HL56, Q65I10, P50740, Q6MMK2, O51627, Q660I6, O48965, Q3AQM4, Q8KFR5, Q39471, Q39664, Q9RVE2, Q837E2, Q01335, Q9HHE4, Q9BXS1, Q9 KWF6, Q9CIF5, Q88WB6, Q38X74, Q92BX2, Q71ZT7, Q8Y7A5, Q8TT35, Q46CL4, Q58272, Q8TX99, Q8PW37, Q6M174, O26154, Q2RIU8, Q3IUB0, Q5YXN4, Q8EST0, Q8L114, Q3B213, Q7N0A6, Q6L1S1, Q9UZS9, Q8ZYF6, Q8U2H9, O58893, Q76CZ1, Q989L5, Q1RIK2, Q92HM7, Q4ULD7, Q9ZD90, Q68WS6, Q2YYY9, Q5HDL0, P65102, P99172, Q6GE88, Q6G6X4, P58052, Q8NV55, Q5HLP8, Q8CRB6, Q4L8K4, Q49ZS3, Q9 KWG2, Q8DUI9, P65103, P65104, Q5XCM6, P65105, Q48U28, Q97SH8, Q8DR48, P61615, P95997, Q96YW9, Q67NT4, Q8DJ26, Q5N019, P74287, Q9HLX2, Q97CC2, Q31EW3, Q87JH5, Q8 KP37, Q9 KWD1, Q9KK75, Q7X5H2, P60923, Q8FND7, Q8NN99, Q8XD58, Q8FE75, Q46822, Q6D3F5, Q5UX45, Q9HP40, Q6AC73, Q7VEU0, P72002, Q5YYB6, Q6LUX5, Q6A5Z1, P26173, Q9Z5D3, Q57K77, Q5PL31, Q8Z3X9, Q8ZM82, Q31WF1, Q32BV2, Q83MJ9, Q3YXY0, Q5LWT6, Q82MJ7, Q9X7Q6, and Q5E7U8.

Step i. The conversion of dimethylallyl diphosphate (DMAPP) and isopentenyl diphosphate (IPP) to geranyl diphosphate (GPP) is catalyzed by geranyl diphosphate synthase (E.C. 2.5.1.1), examples of which are found at SEQ ID NO:33 and SEQ ID NO:35. Other examples of sequences encoding this enzyme include but are not limited to, one or more genes that encode the following proteins (indicated below as GenPept accession numbers):

Q09152, P49351, O24241, Q43315, P49352, O24242, P49350, Q8WMY2, P08836, Q92235, O64905, P14324, P49349, P49353, Q920E5, Q92250, P05369, O14230, P08524, P34802, O04046, Q9LUD9, Q9SLG2, O22043, Q758K0, P56966, P80042, Q42698, Q92236, Q94ID7, O95749, Q9WTN0, P0A5H9, P0A5H8, P24322, Q6F596, Q9P885, Q43133, Q12051, P39464, P95999, Q58270, O26156, and Q53479.

Step j. The conversion of geranyl diphosphate (GPP) to geraniol may be catalyzed by geraniol synthase (E.C. 4.2.3.-), examples of which are found at SEQ ID NO:37 and SEQ ID NO:39. Other examples of sequences of genes encoding this enzyme include but are not limited to AF529266, AJ457070, and AY362553 (GenBank accession numbers).

Step k. The conversion of geranyl diphosphate (GPP) to pinene may be catalyzed by geranyl diphosphate phosphatase, which may be encoded by SEQ ID NO:35, or by other sequences such as: O24475, AY557744, YDR503C, YDR284C, and YDR481C (62 bases deleted 5' coding sequence) (GenBank accession numbers).

Step 1. The conversion of geranyl diphosphate (GPP) into acyclic monoterpenes, predominantly beta-myrcene and (E)-beta-ocimene is catalyzed by ocimene synthase (4.2.1.15) which may be encoded by, but is not limited to: AY195607, AM458362, AY575970, and AB110642 (GenBank accession numbers).

Step m. The conversion of 2 acetyl-CoA to acetoacetyl-CoA is catalyzed by acetyl-CoA acetyltransferase (E.C. 2.3.1.9), examples of which are found at SEQ ID NO:41 and SEQ ID NO:43. Other examples of sequences encoding this enzyme include, but are not limited to, one or more genes that encode the following proteins (indicated below as GenPept accession numbers):

P76461, P44873, Q9I2A8, Q12598, Q04677, Q8S4Y1, Q9FIK7, Q9BWD1, Q8CAY6, Q5XI22, P45369, Q9ZHI1, P24752, Q8HXY6, Q8QZT1, P66927, P46707, P66926, P54810, P14610, P14611, P17764, P50174, P10551, P45363, Q6L8K7, P41338, P07097, P45359, Q18AR0, Q2FJQ9, Q2G124, Q2YVF5, Q5HIU0, Q99WM3, Q7A7L2, Q6GJW4, Q6GCB8, Q8NY95, Q5HS07, Q8CQN7, P45855, P45362, P81347, and Q46939.

Step n. The conversion of acetoacetyl-CoA and acetyl-CoA to 3-hydroxy-3-methyl-glutaryl-CoA (HMG-CoA) is catalyzed by 3-hydroxy-3-methyl-glutaryl-CoA synthase (E.C. 2.3.3.10), examples of which are found at SEQ ID NO:45 and SEQ ID NO:47. Other exemplary sequences include, but are not limited to genes that encode the following proteins (indicated below as GenPept accession numbers):

P54961, P23228, P13704, Q01581, Q8JZK9, Q5R7Z9, P17425, P54870, Q2KIE6, P54868, P54869, O02734, P22791, P54873, P54871, P54872, P54874, and P54839.

Step o. The conversion of 3-hydroxy-3-methyl-glutaryl-CoA (HMG-CoA) to mevalonate (MEV) is catalyzed by 3-hydroxy-3-methyl-glutaryl-CoA reductase (E.C. 1.1.1.34), examples of which are found at SEQ ID NO:49 and SEQ ID NO:51. Other examples of sequences encoding this enzyme include, but are not limited to, one or more genes that encode the following proteins (indicated below as GenPept accession numbers):

P14891, P34135, O64966, P29057, A2X8W3, Q0DY59, P48020, P12683, P43256, Q9XEL8, P34136, O64967, P29058, P48022, Q41437, P12684, Q00583, Q9XHL5, Q41438, Q9YAS4, O76819, O28538, Q9Y7D2, Q0C8L9, P54960, P48021, Q03163, P00347, P14773, Q12577, Q59468, P04035, O24594, P09610, Q58116, O26662, Q01237, Q01559, Q12649, O74164, Q1W675, Q5R6N3, Q9V1R3, O59469, Q29512, P51639, P16237, Q10283, P16393, O08424, and P20715.

In a preferred embodiment, the membrane binding domain of HMG-CoA reductase is deleted to cause overexpression of a cytosolic form of the enzyme. This may be achieved, for example, by deleting the DNA sequence encoding amino acids 1-552 from the *S. cerevisiae* HMG1 gene.

Step p. The conversion of mevalonate (MEV) to mevalonate-5-phosphate (MEV-P) is catalyzed by mevalonate kinase (E.C. 2.7.1.36), examples of which are found at SEQ ID NO:53 and SEQ ID NO:55. Other examples of sequences encoding this enzyme include, but are not limited to, one or more genes that encode the following proteins (indicated below as GenPept accession numbers):

Q9Y946, P46086, O27995, Q5E9T8, Q03426, Q58487, Q50559, Q9R008, Q9V187, Q8U0F3, O59291, Q5JJC6, P17256, Q09780, and P07277.

Step q. The conversion of mevalonate-5-phosphate (MEV-P) to mevalonate-5-diphosphate (MEV-PP) is catalyzed by phosphomevalonate kinase (E.C. 2.7.4.2), examples of which are found at SEQ ID NO:57 and SEQ ID NO:59. Other examples of sequences encoding this enzyme include, but are not limited to, one or more genes that encode the following proteins (indicated below as GenPept accession numbers):

P24521, Q2KIU2, Q9VIT2, Q15126, Q9D1G2, and Q29081.

Step r. The conversion of mevalonte-5-diphosphate (MEV-PP) to isopentenyl diphosphate (IPP) is catalyzed by mevalonate-5-diphosphate decarboxylase (E.C. 4.1.1.33), examples of which are found at SEQ ID NO:61 and SEQ ID NO:63. Other examples of sequences encoding this enzyme include, but are not limited to, one or more genes that encode the following proteins (indicated below as GenPept accession numbers):

P53602, Q99JF5, Q62967, and P32377.

Step s. The conversion of L-leucine to 4-methyl-2-oxopentanoate is catalyzed by a branched chain aminotransferase (E.C. 2.6.1.42), or leucine aminotransferase (2.6.1.6), examples of which are found at SEQ ID NO:65 and SEQ ID NO:67. Other examples of sequences encoding this enzyme include, but are not limited to, one or more genes that encode the following proteins (indicated below as GenPept accession numbers):

Q9FYA6, P54688, Q9M401, P54690, A7SLW1, P38891, Q5EA40, O35855, O35854, O15382, Q5REP0, A9UZ24, Q9M439, P54687, P24288, Q9GKM4, Q93Y32, O14370, Q54N47, P47176, O32954, Q10399, P39576, O86505, Q5HIC1, P63512, P99138, Q6GJB4, Q6 GBT3, P63513, Q5HRJ8, Q8CQ78, Q9Y885, Q9LPM9, O31461, P54689, Q9ZJF1, O26004, O67733, P0AB82, P0AB81, P0AB80, P0A1A6, P0A1A5, O86428, O27481, P54691, O29329, Q92I26, Q4ULR3, O05970, Q1RIJ2, Q58414, Q9AKE5, P74921, and O19098.

Step t. The conversion of 4-methyl-2-oxopentanoate to isovaleryl-CoA is catalyzed by 2-oxoisovalerate dehydrogenase (E.C. 1.2.1.25), an example of which is SEQ ID NO:69, 71, 73, and 75, SEQ ID NO:77, 79, 81, and 83, and which may also be encoded by, but is not limited to, one or more genes that encode the following proteins (indicated below as GenPept accession numbers):

A8Z2F0 and Q11Q90.

Step u. The conversion of isovaleryl-CoA to 3-methylcrotonyl-CoA is catalyzed by isovaleryl-CoA dehydrogenase (E.C. 1.3.99.10), examples of which are found at SEQ ID NO:85 and SEQ ID NO:87. Other examples of sequences encoding this enzyme include, but are not limited to, one or more genes that encode the following proteins (indicated below as GenPept accession numbers):

Q9FS88, Q9FS87, Q9SWG0, Q3SZI8, P34275, P26440, Q9JHI5, Q5RBD5, and P12007.

Step v. The conversion of 3-methylcrotonyl-CoA to 3-methylglutaconyl-CoA is catalyzed by 3-methylcrotonyl-CoA carboxylase (E.C. 6.4.1.4), examples of which are found at SEQ ID NO:89, 91 and SEQ ID NO:93 and 95. Other examples of sequences encoding this enzyme include, but are not limited to, one or more genes that encode the following proteins (indicated below as GenPept accession numbers):

Q42523, Q54KE6, Q96RQ3, Q99MR8, Q2QMG2, Q42777, Q9LDD8, P34385, Q8T2J9, Q9V9A7, Q9HCC0, Q3ULD5, and Q5XIT9.

Step w. The conversion of 3-methylglutaconyl-CoA to 3-hydroxy-3-methylglutaryl-CoA (HMG-CoA) is catalyzed by 3-methylglutaconyl-CoA hydratase (E.C. 4.2.1.18), examples of which are found at SEQ ID NO:97 and SEQ ID NO:99. Other examples of sequences encoding this enzyme include, but are not limited to, one or more genes that encode the following proteins (indicated below as GenPept accession numbers):

Q54HG7, Q13825, and Q9JLZ3.

Step x. The conversion of geraniol to geraniol acetate is catalyzed by geraniol acetyltransferase (E.C. 2.3.1.-). The dash indicates that this enzyme has not yet been categorized.

Some of the claims below contain language relating to a pathway step, e.g., "(pathway step a)". The enumerated pathway steps refer to steps illustrated in FIGS. 4-7 and have been included for the convenience of the reader.

The following examples are offered to illustrate but not to limit the invention.

EXAMPLE 1

Strains

*Saccharomyces cerevisiae* BY4709 (MATa ade2delta::hisG his3delta200 leu2delta0 lys2delta0 met15delta0 trp1delta63 ura3delta0) (ATCC No. 200869) and BY4700 (MATa ura3delta0) (ATCC No. 200866) were obtained from ATCC (Manassas, Va.) and were maintained on Yeast Peptone Dextrose medium (YPD) at 30° C. *Pichia pastoris* CBS 704 was obtained from ATCC (No. 28485) and was maintained on YPD at 30° C. For plasmid selection in *S. cerevisiae* hosts, cells were grown on SD medium supplemented with appropriate amino acid dropout mixtures. Strains 7134 and 7565 were maintained on SD-ura to ensure maintenance of chromosomal integrations.

EXAMPLE 2

Plasmids and Cloning

A set of 31 yeast episomal expression plasmids was obtained from ATCC (No. 87669). Plasmids are named according a p4XX template, with the second number corresponding to replication origin (2μ=2, CEN/ARS=1) and the final number corresponding to nutritional marker (3=Histidine, 4=Tryptophan, 5=Leucine and 6=Uracil). In addition, plasmids may have either the ADH, GPD, TEF or CYC promoter driving expression. Genes of interest were cloned directly from yeast genomic DNA into expression vectors and sequenced (BATJ, San Diego). Cloning was carried out using the InFusion high-throughput cloning kit from Clontech (Mountain View, Calif.). Adaptor ends were created for each of the forward (TCTAGAACTAGTGGATCCCCC) (SEQ ID NO:131) and reverse (ATATCGAATTCCTGCAGCCC) (SEQ ID NO:132) primers to allow cloning into any of the vectors of the p4XX series digested with SmaI. DNA was transformed into yeast via electroporation, which was performed in 0.2 cm cuvettes at 1.2 mV. Following electroporation, 1M sorbitol was added and cells were incubated at 30° C. for 1 hr prior to plating on selective media.

EXAMPLE 3

Genes and Strain Construction

A truncated form of 3-hydroxy-3-methylglutaryl-coenzyme A reductase 1 (Genbank accession M22002) (HMGΔ552) (SEQ ID NO:101) was created based upon the work of Polakowski, Stahl and Lang (Appl Microbiol Biotechnol (1998) 49: 66-71). This construct eliminates the first 1656 nucleotides from *Saccharomyces cerevisiae* HMG1, creating a new 1509 bp sequence and a 509 amino acid protein. The deletion was constructed by overlap polymerase chain reaction (PCR) using primers specific for the 3' end and the 5' deletion. Briefly, full-length HMG1 was cloned from *S. cerevisiae* genomic DNA, sequence verified and used subsequently as a template for PCR to eliminate the initial 1656 nucleotides and introduce a new ATG start codon. After constructing the truncated HMG1 by PCR, this was cloned into a yeast expression plasmid (p423TEF), sequence verified, and used in subsequent experiments.

Native *S. cerevisiae* isopentenyl diphosphate isomerase (IDI1) (Genbank accession NC_001148) was amplified from yeast genomic DNA, sequence verified and cloned into p425TEF for subsequent expression.

Farnesyl diphosphate synthase (ERG20) (Genbank accession Z49442) (SEQ ID NO:103) was amplified from *S. cerevisiae* genomic DNA and cloned into p423TEF. A mutation was made in the sequence to convert the AAG codon, corresponding to lysine 197, to a GAA codon, encoding glutamate, by site-directed mutagenesis. This mutation was first described by Chambon et al. (Curr Genet (1990) 18:41-46) called erg20-2 (SEQ ID NO:105). Another mutation was made at the same position, converting the GAA codon to CGT, encoding arginine (Karst, et al. (2004) Cell Biol International, 28:193-197). All three forms of ERG20 were sequence verified and expressed from p423TEF.

The chromosomally encoded ERG20 was later replaced with both mutant forms, K197E and K197R (SEQ ID NO:107), to create strains 7134 and 7565, respectively. Integration constructs were made by amplifying the mutant form of ERG20 with *P. pastoris* URA3 overlapping primers, creating a fragment containing the mutant ERG20 flanked immediately downstream by a URA3 allele. The resulting fragments were transformed into BY4704, and ura+ prototrophs were selected. Integration was verified using gene specific primers for both URA3 and ERG20, and the resulting erg20 mutant strains were further verified by sequencing the newly integrated mutant allele.

A geraniol synthase from *Cinnamomum tenuipile* was synthesized (DNA2.0, Menlo Park, Calif.) based on published GerS sequence (Genbank accession AJ457070) (SEQ ID NO:109) (Yang, et al. (2005) Phytochemistry, 66:285-293) and codon optimized for expression in *S. cerevisiae*. Optimized CtGES has 75% identity to GerS at the nucleotide level, 100% identity at the amino acid level. Full-length CtGES was subcloned to p424TEF for expression in *S. cerevisiae*. Two DNA constructs were then created that eliminate unwanted plant plastidic targeting sequences: truncation 1 and truncation 3 (hereafter CtGES_trunc1 and CtGES_trunc3). ATG start sites were added to the DNA sequence immediately upstream of T136 and A151 to create the new truncated DNA sequences. All CtGES constructs were sequence verified and expressed from p424TEF.

EXAMPLE 4

Growth Conditions

Strains containing combinations of HMG, IDI and CtGES truncations were grown on SD plates with appropriate nutritional dropouts. Isolated colonies were picked from selective plates and grown in 3 mls of growth medium at 30° C. until culture was noticeably turbid, usually 24-48 hrs. Cells were then inoculated (1:100) into 25 mls of liquid medium in 250 ml baffled flasks. Both plastic and glass flasks were used with no discernable difference in production of geraniol. Cultures were then grown in a shaker at 30° C. with 250 rpm of shaking. Cultures were harvested after 24-72 hrs of growth.

EXAMPLE 5

Analytical Techniques

Samples were analyzed using gas chromatography (7890A Gas chromatograph, Agilent Technologies, USA) coupled with flame ionization (FID) for detection. Compounds were identified by comparison with the retention times for directly injected standard solutions. Compounds were also analyzed by GC coupled to mass spectrometry (5975C Inert MSD, Agilent Technologies, USA) for identification purposes by comparison with a spectral library (National Institute of Standards and Technology—NIST 2005). The instrument was interfaced with MSD ChemStation software (version E.02) for data recording and analysis.

A 15 m×250 um×0.25 um HP-Innowax column (Agilent, USA) was used for this purpose. The following conditions were employed for the GC run: 1.0 ul split injection, split 10:1, constant pressure of 9.6 psi, injector temperature of 250° C., detector temperature 250° C., temperature program of 70° C. with 2 min hold time, then 70-150° C. at 25° C./min and 150-170° C. at 10° C./min. A post run time of 2 min at 230° C. was included in the run cycle to condition the column and avoid any carry-over of sample constituents to the next run.

Quantification of compounds was accomplished using a standard mixture consisting of: nerol, geraniol, ocimene, citronellol, geranyl acetate, 3-methyl-3-butenol, 3-methyl-2-butenol, myrcene at ranges 1-1000 uM and internal standard linalool (50 uM), all prepared in 50% ethanol. Samples were mixed 1:1 with ethanol containing the internal standard, vortexed, filtered through a 0.2 um PVDF syringe filter. The limit of quantification (RSD<15%) by GC/FID is 2 uM and the calibration range is linear for the range 1-1000 uM. The limit of detection was estimated at 0.5 uM.

EXAMPLE 6

Production of Geraniol Transformed Strains 7134 and 7565

Figure 1:
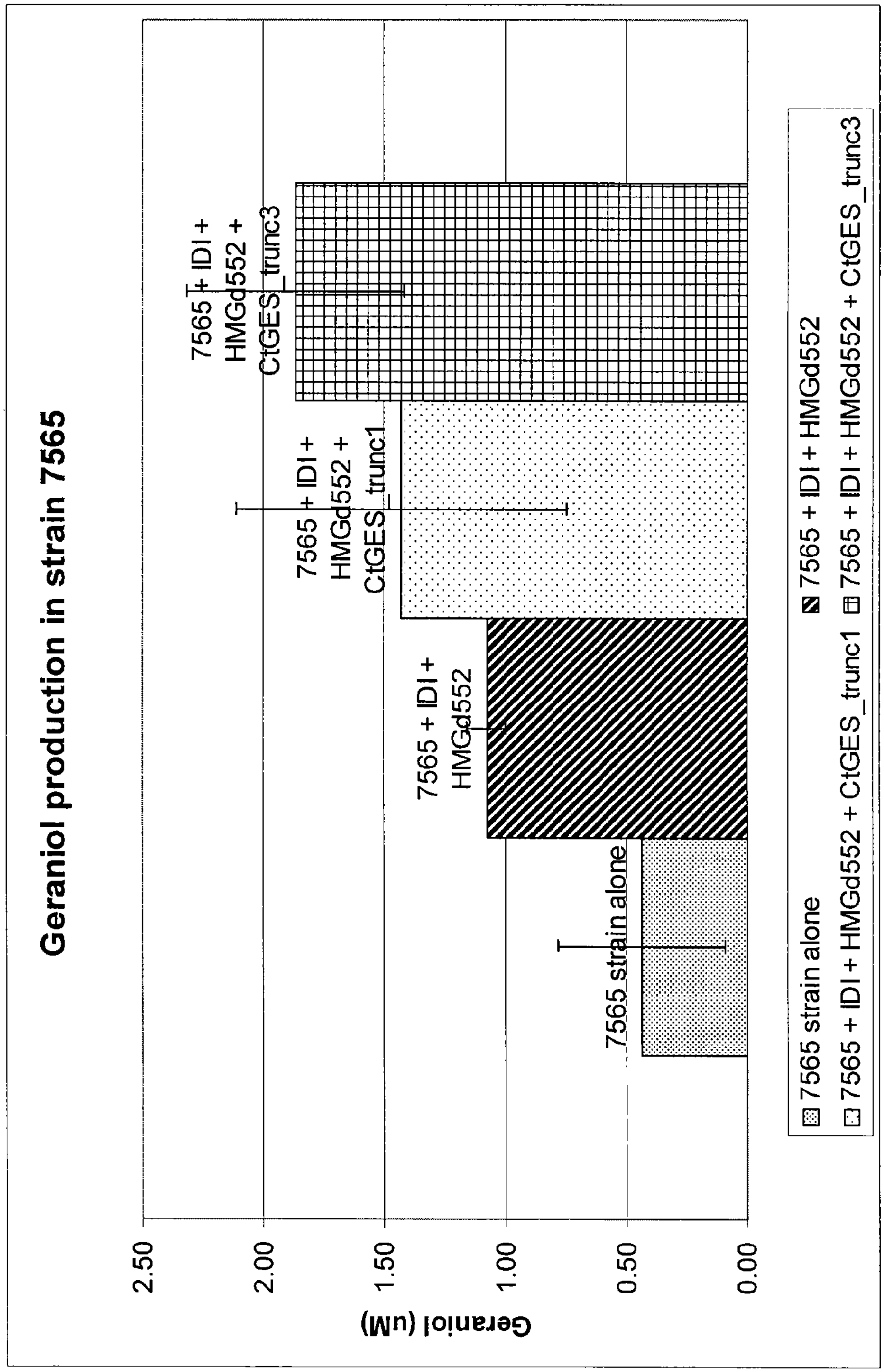
FIG. 1 depicts a graph summarizing geraniol production in strain 7565 expressing various genes.
Figure 2:
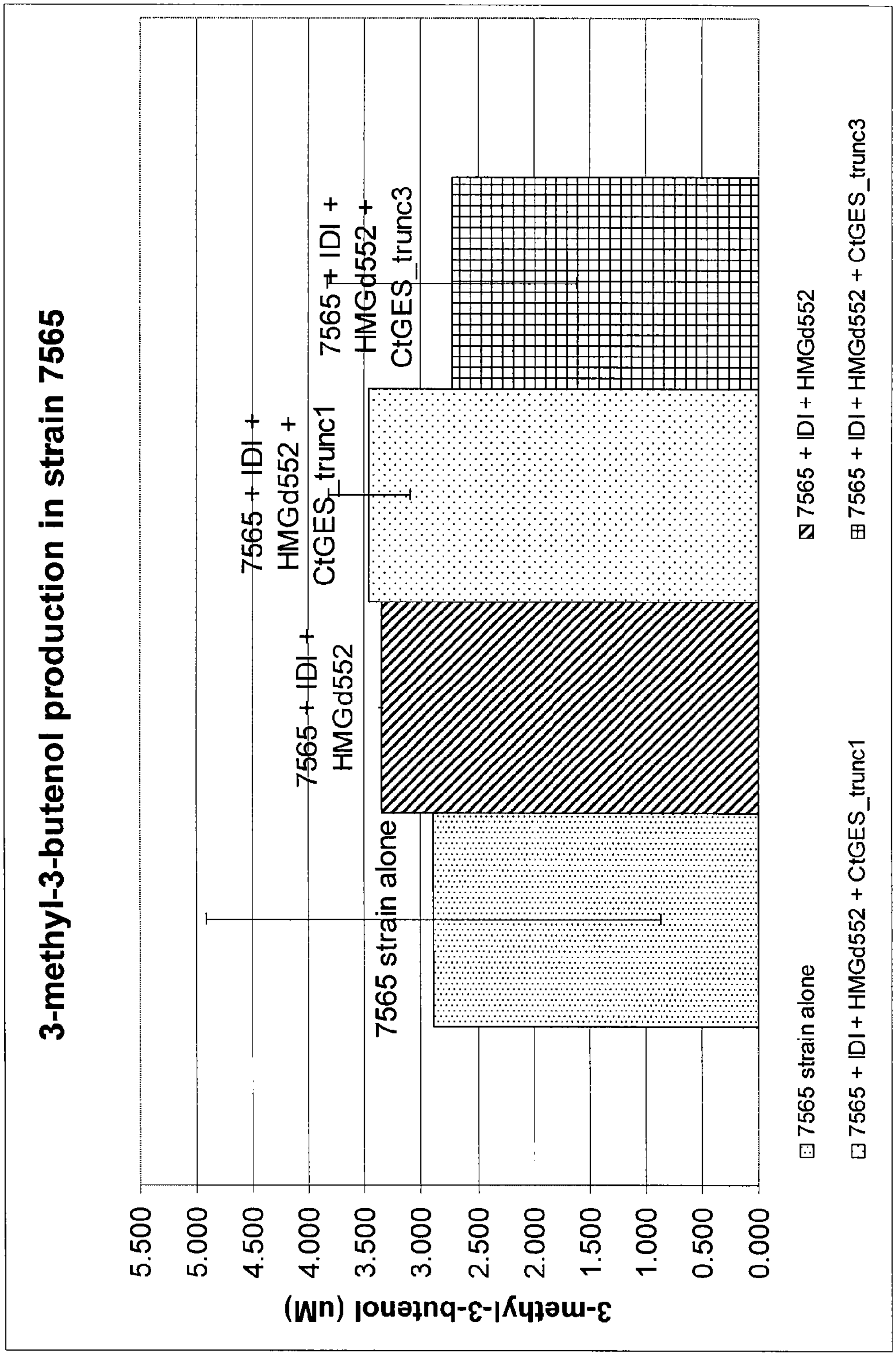
FIG. 2 depicts a graph summarizing 3-methyl-3-butenol production in strain 7565 expressing various genes.
Figure 3:
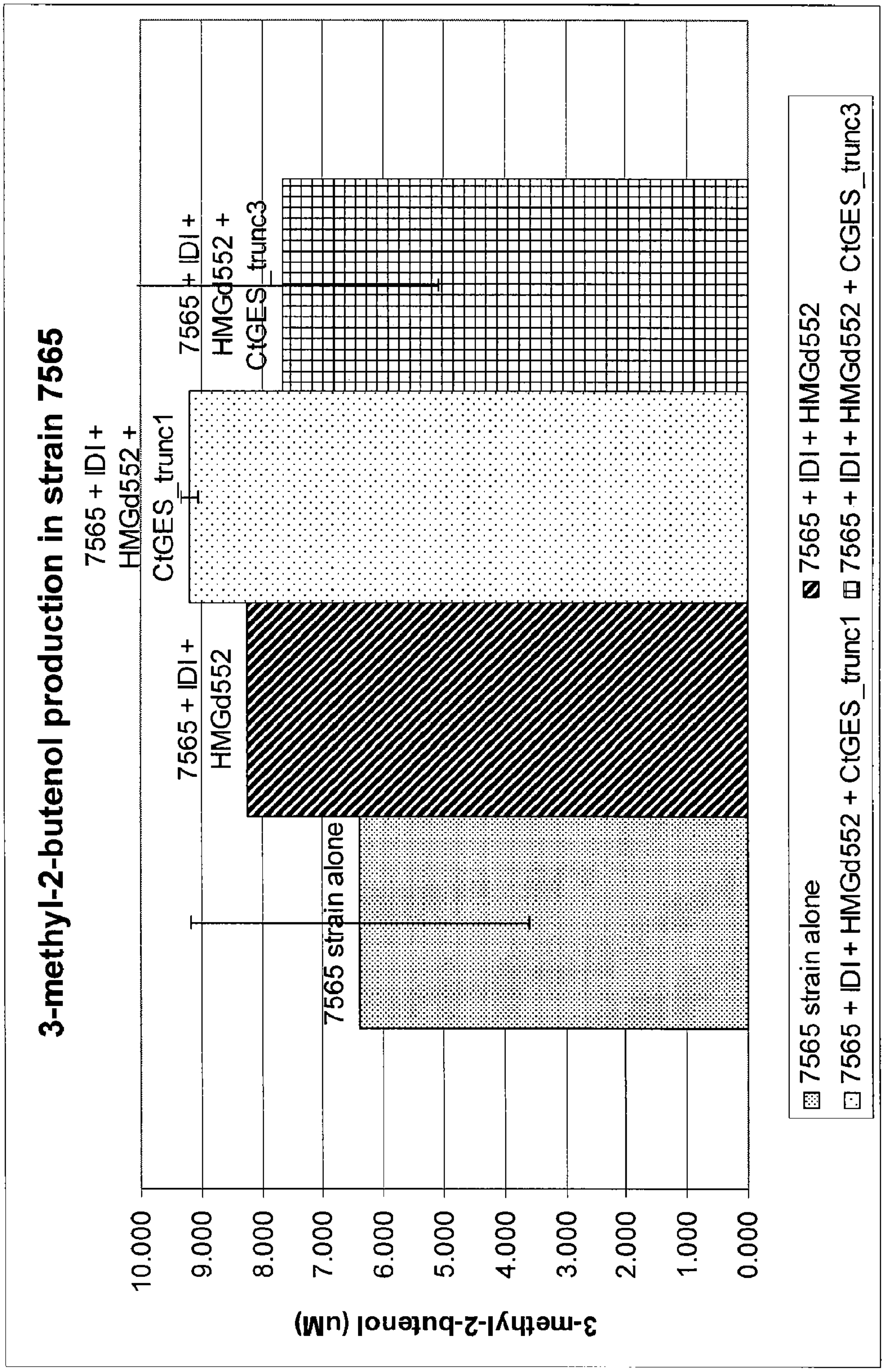
FIG. 3 depicts a graph summarizing 3-methyl-2-butenol production in strain 7565 expressing various genes.

Strain 7134 or 7565 without any plasmids produced traces of geraniol due to the presence of the chromosomally encoded mutant erg20 allele. Wild-type yeast strain BY4709 or BY4700 produced no detectable levels of geraniol as determined by GC/MS analysis. When strains 7134 or 7565 were transformed with IDI1 and the HMGΔ552 construct, and expressed episomally from the TEF promoter, a statistically significant increase in geraniol was observed. This background was further modified by the addition of CtGES. When the CtGES_trunc1 was expressed from a plasmid encoded TEF promoter, an increase in geraniol was observed, however it was not found to be statistically significant. When CtGES_trunc3 was used in place of CtGES_trunc1, a statistically significant increase in geraniol was observed. The level of geraniol reached 1.85±0.45 μM, compared to a background level of 1.08±0.08 μM after 48 hrs growth in strain 7565 (FIG. 1). Geraniol production in strains grown 24 hrs is significantly lower than strains grown for 48-72 hrs. Levels in 7134 were similar to those found in strain 7565 but not statistically significant, although production trends were identical. In all cases, geraniol was the main monoterpene product of the strains, without significant levels of related monoterpenoid side products like linalool, myrcene, ocimene and limonene. Extended incubation in the presence of yeast producing geraniol resulted in conversion of geraniol to citronellol by an unknown mechanism. Citronellol was not produced during initial production phases and was not observed in cultures not producing geraniol. In strain 7565, significant levels of 3-methyl-3-butenol and 3-methyl-2-butenol were detected as a consequence of the mutated erg20 allele (FIGS. 2 and 3). Neither of these compounds could be detected in the BY4704 background strain.

EXAMPLE 7

Preparation of Geraniol Acetate

Geraniol acetyltransferase is introduced into an expression vector that is functional in a recombinant microorganism expressing geraniol. The enzyme is expressed and it utilizes existing pools of acetyl-CoA as the acetyl group donor for the acetyltransferase reaction. Cells are grown in a medium that contains elevated levels of acetate, which then are imported into the cell. The acetate is transesterified to make the acetyl-CoA thioester using a native *Saccharomyces* enzyme such as acetyl-CoA synthase (ACS1, ACS2), and then incorporated into the geraniol acetate molecule.

EXAMPLE 8

Preparation of Geraniol Acetate

A cell line expressing a geraniol acetyltransferase is used to transform exogenously supplied geraniol to geraniol acetate in vivo. Several examples of acetyltransferases that can acetylate geraniol are known, and the primer sequences of a few (RhAAT, *Rosa hybrida* Accession no. AY850287 (SEQ ID NO:115); SAAT, *Fragaria xananassa* Accession no. AAG13130 (SEQ ID NO:113); BAAT, *Musa acuminata* Accession no. AX025506 (SEQ ID NO:111)) have been included as references for how to clone the genes into a suitable yeast expression plasmid.

EXAMPLE 9

Chemical Conversion of Geraniol Acetate to 2,6-Dimethyloctane

Using a combination of catalysts, geraniol acetate is converted to 2,6-dimethyloctane in a manner similar to that of conversion of geraniol to 2,6-dimethyloctane as described in Example 13.

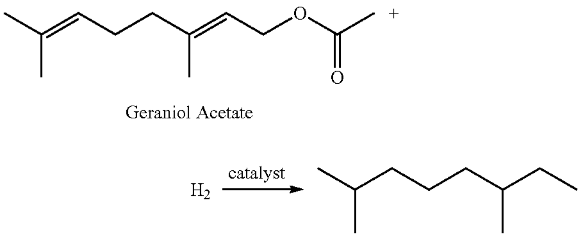

Geraniol Acetate 2,6-dimethyloctane

EXAMPLE 10

Primer Sequences

This example describes various cloning primers and mutation primers that may be used in the present invention. Capital letters indicate homology to vector sequence and lowercase indicate homology to target gene sequence.

| Cloning primers | | SEQ ID NO: |
|---|---|---|
| IDI_F | CTAGAACTAGTGGATCCCCCatgactgccgacaacaatagtatgccccatg | 133 |
| IDI_R | ATATCGAATTCCTGCAGCCCttatagcattctatgaatttgcctgtcattttccac | 134 |
| E20_F | CTAGAACTAGTGGATCCCCCatggcttcagaaaaagaaattaggagagag | 135 |
| E20_R | ATATCGAATTCCTGCAGCCCttatttgcttctcttgtaaactttgttcaag | 136 |
| HMG1_F | CTAGAACTAGTGGATCCCCCatgccgccgctattcaagggactgaaacagatggc | 137 |
| HMG1_R | ATATCGAATTCCTGCAGCCCttaggatttaatgcaggtgacggacccatctttc | 138 |
| HMG_552F | CTAGAACTAGTGGATCCCCCatgccagttttaaccaataaaacagtcatttctgg | 139 |
| CtGoptFLF | TCTAGAACTAGTGGATCCCCCatggctttgcagatgatagcaccg | 140 |
| CtGoptR | ATATCGAATTCCTGCAGCCCttaagcgctacctccgtctacg | 141 |
| CtGoptT1F | TCTAGAACTAGTGGATCCCCCatgagaaggtccggaaattataaacc | 142 |
| CtGoptT3F | TCTAGAACTAGTGGATCCCCCatgtcaacgaccgttccgagaaggtc | 143 |
| Mutation primers | | 144 |
| K197R_F | Cttcatagttactttcagaactgcttactattc | 145 |
| K197R_R | Gaatagtaagcagttctgaaagtaactatgaag | 146 |
| Acetyltransferases | | 147 |
| RHAAT_F | TCTAGAACTAGTGGATCCCCCatggagaaaattgaggtcagtattatttc | 148 |
| RHAAT_R | ATATCGAATTCCTGCAGCCCttaatccataccaactgaagaggctattg | 149 |
| SAAT_F | TCTAGAACTAGTGGATCCCCCatggagaaaattgaggtcagtataaattc | 150 |
| SAAT_R | ATATCGAATTCCTGCAGCCCttaaattaaggtctttggagatgctaac | 151 |
| BAAT_F | TCTAGAACTAGTGGATCCCCCatgagcttcgctgtgaccagaacaag | 152 |
| BAAT_R | ATATCGAATTCCTGCAGCCCttaagcgaagcctttcatctcttccag | 153 |

EXAMPLE 11

DNA/Protein Sequences

This example describes nucleotide sequences of ScHMG1, ScERG20, ScIDI1, and CtGESopt2; along with the amino acid sequences they encode.

ScHMG1_DNA (SEQ ID NO: 154)

atgccgccgctattcaagggactgaaacagatggcaaagccaattgcctatgtttcaagattttcggcgaaacgaccaattcatataat actttttttctctaatcatatccgcattcgcttatctatccgtcattcagtattacttcaatggttggcaactagattcaaatagtgtttttgaaact gctccaaataaagactccaacactctatttcaagaatgttcccattactacagagattcctctctagatggttgggtatcaatcaccgcgc atgaagctagtgagttaccagccccacaccattactatctattaaacctgaacttcaatagtcctaatgaaactgactccattccagaact agctaacacggtttttgagaaagataatacaaaatatattctgcaagaagatctcagtgtttccaaagaaatttcttctactgatggaacg aaatggaggttaagaagtgacagaaaaagtcttttcgacgtaaagacgttagcatattctctctacgatgtattttcagaaaatgtaaccc aagcagacccgtttgacgtccttattatggttactgcctacctaatgatgttctacaccatattcggcctcttcaatgacatgaggaagac cgggtcaaattttggttgagcgcctctacagtggtcaattctgcatcatcacttttcttagcattgtatgtcacccaatgtattctaggcaa agaagtttccgcattaactctttttgaaggtttgcctttcattgtagttgttgttggtttcaagcacaaaatcaagattgcccagtatgccctg gagaaatttgaaagagtcggtttatctaaaaggattactaccgatgaaatcgtttttgaatccgtgagcgaagagggtggtcgtttgatt -continued caagaccatttgctttgtatttttgcctttatcggatgctctatgtatgctcaccaattgaagactttgacaaacttctgcatattatcagcattt atcctaatttttgaattgattttaactcctacattttattctgctatcttagcgcttagactggaaatgaatgttatccacagatctactattatca agcaaacattagaagaagacggtgttgttccatctacagcaagaatcatttctaaagcagaaaagaaatccgtatcttctttcttaaatct cagtgtggttgtcattatcatgaaactctctgtcatactgttgtttgtcttcatcaacttttataactttggtgcaaattgggtcaatgatgcctt caattcattgtacttcgataaggaacgtgtttctctaccagattttattacctcgaatgcctctgaaaactttaaagagcaagctattgttagt gtcaccccattattatattacaaacccattaagtcctaccaacgcattgaggatatggttcttctattgcttcgtaatgtcagtgttgccattc gtgataggttcgtcagtaaattagttctttccgccttagtatgcagtgctgtcatcaatgtgtatttattgaatgctgctagaattcataccag ttatactgcagaccaattggtgaaaactgaagtcaccaagaagtcttttactgctcctgtacaaaaggcttctacaccagttttaaccaat aaaacagtcatttctggatcgaaagtcaaaagtttatcatctgcgcaatcgagctcatcaggaccttcatcatctagtgaggaagatgat tcccgcgatattgaaagcttggataagaaaatacgtcctttagaagaattagaagcattattaagtagtggaaatacaaaacaattgaag aacaaagaggtcgctgccttggttattcacggtaagttacctttgtacgctttggagaaaaaattaggtgatactacgagagcggttgc ggtacgtaggaaggctctttcaattttggcagaagctcctgtattagcatctgatcgtttaccatataaaaattatgactacgaccgcgtat ttggcgcttgttgtgaaaatgttataggttacatgcctttgcccgttggtgttataggccccttggttatcgatggtacatcttatcatatacc aatggcaactacagagggttgtttggtagcttctgccatgcgtggctgtaaggcaatcaatgctggcggtggtgcaacaactgttttaa ctaaggatggtatgacaagaggcccagtagtccgtttcccaactttgaaaagatctggtgcctgtaagatatggttagactcagaaga gggacaaaacgcaattaaaaaagcttttaactctacatcaagatttgcacgtctgcaacatattcaaacttgtctagcaggagatttactc ttcatgagatttagaacaactactggtgacgcaatgggtatgaatatgatttctaaaggtgtcgaatactcattaaagcaaatggtagaa gagtatggctgggaagatatggaggttgtctccgtttctggtaactactgtaccgacaaaaaaccagctgccatcaactggatcgaag gtcgtggtaagagtgtcgtcgcagaagctactattcctggtgatgttgtcagaaaagtgttaaaaagtgatgtttccgcattggttgagtt gaacattgctaagaatttggttggatctgcaatggctgggtctgttggtggatttaacgcacatgcagctaatttagtgacagctgttttct tggcattaggacaagatcctgcacaaaatgttgaaagttccaactgtataacattgatgaaagaagtggacggtgatttgagaatttcc gtatccatgccatccatcgaagtaggtaccatcggtggtggtactgttctagaaccacaaggtgccatgttggacttattaggtgtaag aggcccgcatgctaccgctcctggtaccaacgcacgtcaattagcaagaatagttgcctgtgccgtcttggcaggtgaattatccttat gtgctgccctagcagccggccatttggttcaaagtcatatgacccacaacaggaaacctgctgaaccaacaaaacctaacaatttgg acgccactgatataaatcgtttgaaagatgggtccgtcacctgcattaaatcctaa ScHMG1_prot (SEQ ID NO: 155)

MPPLFKGLKQMAKPIAYVSRFSAKRPIHIILFSLIISAFAYLSVIQYYFNGWQLDSNSV

FETAPNKDSNTLFQECSHYYRDSSLDGWVSITAHEASELPAPHHYYLLNLNFNSPNE

TDSIPELANTVFEKDNTKYILQEDLSVSKEISSTDGTKWRLRSDRKSLFDVKTLAYSL

YDVFSENVTQADPFDVLIMVTAYLMMFYTIFGLFNDMRKTGSNFWLSASTVVNSA

SSLFLALYVTQCILGKEVSALTLFEGLPFIVVVVGFKHKIKIAQYALEKFERVGLSKR

ITTDEIVFESVSEEGGRLIQDHLLCIFAFIGCSMYAHQLKTLTNFCILSAFILIFELILTP

TFYSAILALRLEMNVIHRSTIIKQTLEEDGVVPSTARIISKAEKKSVSSFLNLSVVVIIM

KLSVILLFVFINFYNFGANWVNDAFNSLYFDKERVSLPDFITSNASENFKEQAIVSVT

PLLYYKPIKSYQRIEDMVLLLLRNVSVAIRDRFVSKLVLSALVCSAVINVYLLNAARI

HTSYTADQLVKTEVTKKSFTAPVQKASTPVLTNKTVISGSKVKSLSSAQSSSSGPSSS

SEEDDSRDIESLDKKIRPLEELEALLSSGNTKQLKNKEVAALVIHGKLPLYALEKKL

GDTTRAVAVRRKALSILAEAPVLASDRLPYKNYDYDRVFGACCENVIGYMPLPVG

VIGPLVIDGTSYHIPMATTEGCLVASAMRGCKAINAGGGATTVLTKDGMTRGPVVR

FPTLKRSGACKIWLDSEEGQNAIKKAFNSTSRFARLQHIQTCLAGDLLFMRFRTTTG

DAMGMNMISKGVEYSLKQMVEEYGWEDMEVVSVSGNYCTDKKPAAINWIEGRG

-continued

KSVVAEATIPGDVVRKVLKSDVSALVELNIAKNLVGSAMAGSVGGFNAHAANLVT

AVFLALGQDPAQNVESSNCITLMKEVDGDLRISVSMPSIEVGTIGGGTVLEPQGAML

DLLGVRGPHATAPGTNARQLARIVACAVLAGELSLCAALAAGHLVQSHMTHNRKP

AEPTKPNNLDATDINRLKDGSVTCIKS

ScERG20_DNA (SEQ ID NO: 156)

atggcttcagaaaaagaaattaggagagagagattcttgaacgttttccctaaattagtagaggaattgaacgcatcgcttttggcttac ggtatgcctaaggaagcatgtgactggtatgcccactcattgaactacaacactccaggcggtaagctaaatagaggtttgtccgttgt ggacacgtatgctattctctccaacaagaccgttgaacaattggggcaagaagaatacgaaaaggttgccattctaggttggtgcattg agttgttgcaggcttacttcttggtcgccgatgatatgatggacaagtccattaccagaagaggccaaccatgttggtacaaggttcct gaagttggggaaattgccatcaatgacgcattcatgttagaggctgctatctacaagcttttgaaatctcacttcagaaacgaaaaatac tacatagatatcaccgaattgttccatgaggtcaccttccaaaccgaattgggccaattgatggacttaatcactgcacctgaagacaa agtcgacttgagtaagttctccctaaagaagcactccttcatagttactttcaagactgcttactattctttctacttgcctgtcgcattggcc atgtacgttgccggtatcacggatgaaaaggatttgaaacaagccagagatgtcttgattccattgggtgaatacttccaaattcaagat gactacttagactgcttcggtaccccagaacagatcggtaagatcggtacagatatccaagataacaaatgttcttgggtaatcaacaa ggcattggaacttgcttccgcagaacaaagaaagactttagacgaaaattacggtaagaaggactcagtcgcagaagccaaatgca aaaagattttcaatgacttgaaaattgaacagctataccacgaatatgaagagtctattgccaaggatttgaaggccaaaatttctcagg tcgatgagtctcgtggcttcaaagctgatgtcttaactgcgttcttgaacaaagtttacaagagaagcaaatag ScERG20_prot (SEQ ID NO: 157)

MASEKEIRRERFLNVFPKLVEELNASLLAYGMPKEACDWYAHSLNYNTPGGKLNR

GLSVVDTYAILSNKTVEQLGQEEYEKVAILGWCIELLQAYFLVADDMMDKSITRRG

QPCWYKVPEVGEIAINDAFMLEAAIYKLLKSHFRNEKYYIDITELFHEVTFQTELGQ

LMDLITAPEDKVDLSKFSLKKHSFIVTFKTAYYSFYLPVALAMYVAGITDEKDLKQ

ARDVLIPLGEYFQIQDDYLDCFGTPEQIGKIGTDIQDNKCSWVINKALELASAEQRK

TLDENYGKKDSVAEAKCKKIFNDLKIEQLYHEYEESIAKDLKAKISQVDESRGFKA

DVLTAFLNKVYKRSK

ScIDI1_DNA (SEQ ID NO: 158)

atgactgccgacaacaatagtatgccccatggtgcagtatctagttacgccaaattagtgcaaaaccaaacacctgaagacattttgga agagtttcctgaaattattccattacaacaaagacctaatacccgatctagtgagacgtcaaatgacgaaagcggagaaacatgtttttc tggtcatgatgaggagcaaattaagttaatgaatgaaaattgtattgttttggattgggacgataatgctattggtgccggtaccaagaa agtttgtcatttaatggaaaatattgaaaagggtttactacatcgtgcattctccgtctttattttcaatgaacaaggtgaattacttttacaac aaagagccactgaaaaaataactttccctgatctttggactaacacatgctgctctcatccactatgtattgatgacgaattaggtttgaa gggtaagctagacgataagattaagggcgctattactgcggcggtgagaaaactagatcatgaattaggtattccagaagatgaaac taagacaaggggtaagtttcacttttttaaacagaatccattacatggcaccaagcaatgaaccatggggtgaacatgaaattgattacat cctattttataagatcaacgctaaagaaaacttgactgtcaacccaaacgtcaatgaagttagagacttcaaatgggtttcaccaaatga tttgaaaactatgtttgctgacccaagttacaagtttacgccttggtttaagattatttgcgagaattacttattcaactggtgggagcaatt agatgacctttctgaagtggaaaatgacaggcaaattcatagaatgctataa ScIDI1_prot (SEQ ID NO: 159)

MTADNNSMPHGAVSSYAKLVQNQTPEDILEEFPEIIPLQQRPNTRSSETSNDESGETC

FSGHDEEQIKLMNENCIVLDWDDNAIGAGTKKVCHLMENIEKGLLHRAFSVFIFNE

QGELLLQQRATEKITFPDLWTNTCCSHPLCIDDELGLKGKLDDKIKGAITAAVRKLD

-continued

HELGIPEDETKTRGKFHFLNRIHYMAPSNEPWGEHEIDYILFYKINAKENLTVNPNV

NEVRDFKWVSPNDLKTMFADPSYKFTPWFKIICENYLFNWWEQLDDLSEVENDRQI

HRML

CtGESopt2_DNA (SEQ ID NO: 160)

atggctttgcagatgatagcaccgtttctgtcttctttcttaccaaaccccagacattctttggcggctcatggtttgacgcatcaaaaatg tgtcagtaaacacatctcttgttcgactactaccccaacatactcaacgaccgttccgagaaggtccggaaattataaaccatccatttg ggattatgattttgtccagtcattaggcagtggttacaaggtagaagctcacggtacaagggttaaaaagctgaaagaagttgtgaaac atttgctaaaagaaacagattcaagcctagctcaaatcgaattgattgacaaacttcgtcgtttaggtttaagatggttgtttaagaacga gataaaacaagtcctgtacacaatatcatctgataatacaagtattgaaatgagaaaggacttgcacgctgtcagtacgagatttcgttt attgcgtcaacatggctataaagtctcaactgatgtattcaatgattttaaagacgaaaagggatgctttaagccttcattaagtatggac ataaagggtatgttgtctctttatgaagctagtcacctagcattccaaggagaaacggtattggatgaagccagggcatttgtttcaact cacttaatggatataaaagaaaatatagatcccatattgcataaaaaggttgaacatgccttggatatgccacttcattggagacttgaaa aattagaggcaaggtggtatatggacatctacatgagggaagaaggtatgaactcaagtttattggaacttgcaatgctacatttcaac attgtacaaactacttttcagacaaatcttaagtcccttagtagatggtggaaggacttagggttgggggaacaactaagtttcacgaga gacagacttgttgaatgtttttttctgggcagccgctatgactcctgaaccacaatttggtagatgccaagaagtagtagccaaagtcgct caattgatcatcataattgatgacatctacgatgtatatggtaccgtagatgagttggaattgtttactaatgcaattgatcgttgggatcta gaagctatggagcagctgccagaatacatgaagacgtgctttttggctttgtataattcaatcaatgaaattggatatgatatcttaaagg aggagggcaggaatgtcattccctacttacgtaacacttggactgaattatgcaaagcttttctagttgaagcaaaatggtacagtagc ggatatacacctacgctagaagaatatttgcagacgtcgtggattagtataggttctttgcctatgcagacatatgtttttgctctattggg caagaacttggctcccgaatcctccgatttcgctgagaaaattagtgatattttaagattgggcggaatgatgatacgtttacctgatgat cttggtacttcgacggacgaactaaaacgtggagacgttccaaaatccatccaatgttacatgcacgaagctggtgtcactgaggatg tagctagggaccatattatgggactgttccaagaaacttggaagaaattaaacgaatacttagttgaatcttccttgcctcatgcgtttata gaccacgctatgaatctagggagagtctcatactgtacatacaaacacggcgatggtttctcggacggtttcggtgacccaggtagcc aggaaaagaagatgttcatgtccttatttgccgaacctcttcaagtagatgaagctaaaggtatatccttttacgtagacggaggtagcg cttaa CtGESopt2_prot (SEQ ID NO: 161)

MALQMIAPFLSSFLPNPRHSLAAHGLTHQKCVSKHISCSTTTPTYSTTVPRRSGNYK

PSIWDYDFVQSLGSGYKVEAHGTRVKKLKEVVKHLLKETDSSLAQIELIDKLRRLG

LRWLFKNEIKQVLYTISSDNTSIEMRKDLHAVSTRFRLLRQHGYKVSTDVFNDFKD

EKGCFKPSLSMDIKGMLSLYEASHLAFQGETVLDEARAFVSTHLMDIKENIDPILHK

KVEHALDMPLHWRLEKLEARWYMDIYMREEGMNSSLLELAMLHFNIVQTTFQTN

LKSLSRWWKDLGLGEQLSFTRDRLVECFFWAAAMTPEPQFGRCQEVVAKVAQLIII

IDDIYDVYGTVDELELFTNAIDRWDLEAMEQLPEYMKTCFLALYNSINEIGYDILKE

EGRNVIPYLRNTWTELCKAFLVEAKWYSSGYTPTLEEYLQTSWISIGSLPMQTYVFA

LLGKNLAPESSDFAEKISDILRLGGMMIRLPDDLGTSTDELKRGDVPKSIQCYMHEA

GVTEDVARDHIMGLFQETWKKLNEYLVESSLPHAFIDHAMNLGRVSYCTYKHGDG

FSDGFGDPGSQEKKMFMSLFAEPLQVDEAKGISFYVDGGSA

EXAMPLE 12

Chemical Conversion of Geraniol to 2,6-Dimethyloctane Via Octatriene

It was envisioned that geraniol could be converted to 2,6-dimethyloctane by first dehydrating geraniol to the octatriene and then hydrogenating the octatriene to 2,6-dimethyloctane.

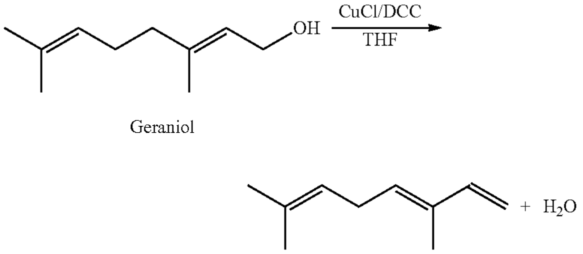

Geraniol

+ $H_2O$ (E)-3,7-dimethylocta-1,3,6-triene

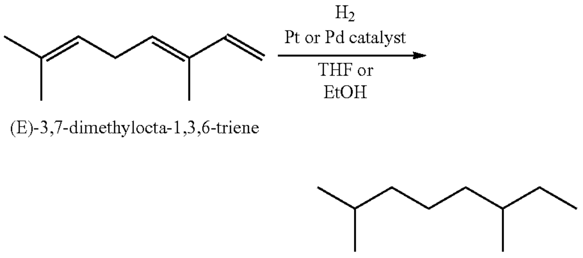

(E)-3,7-dimethylocta-1,3,6-triene 2,6-dimethyloctane

The dehydration step was successful. But it was observed that the triene is susceptible to polymerization before it could be hydrogenated.

EXAMPLE 13

Chemical Conversion of Geraniol to 2,6-Dimethyloctane Via Direct Hydrogenation An alternative strategy to convert geraniol to 2,3-dimethyloctane is direct hydrogenation of geraniol to 2,6-dimethyloctane.

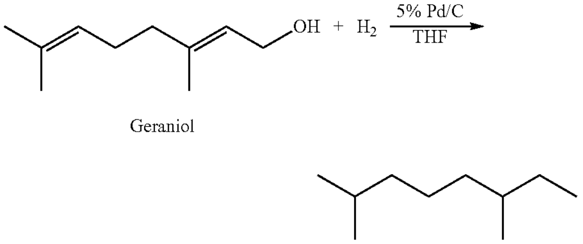

+ $H_2$

Geraniol 2,6-dimethyloctane

-continued

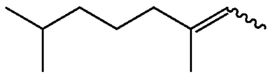

3,7-dimethyloct-2-ene

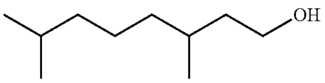

3,7-dimethyloctan-1-ol

The initial step in the sequence was the use of palladium on carbon (5.09 g, 5% Pd) to catalyze the hydrogenation of geraniol (184 g, 1.19 mol) in tetrahydrofuran (700 mL) at room temperature for 15 hours. Following the hydrogenation, the reaction mixture was filtered to remove the catalyst, and the filter cake was washed with hexane. The THF and hexane were removed by rotary evaporation. The reaction mixture was separated by vacuum distillation into two cuts; the alcohol product, 3,7-dimethyloctan-1-ol (50.51 g, 0.30 mol) plus a mixture of 3,7-dimethyloct-2-ene and 2,6-dimethyloctane (53.69 g). An ethereal product remained in the stillpot. The isolated octane/octene mixture was reduced with hydrogen gas in the presence of Pd/C (1.69 g, 5% Pd) to yield 2,6-dimethyloctane. The reduction was carried out neat, the only solvent present was a small volume of ethanol used to wash out the flask containing the starting material. The reaction was run in a Parr shaker for 20 hours. Following the hydrogenation the reaction was filtered, and the filter cake was washed with hexane. The crude reaction was concentrated by rotary evaporation. The dimethyloctane was isolated by vacuum distillation (83 to 86° C. at 70 mm Hg.) to yield 40 g (30% yield) of product. The product was identified by both NMR and GC/MS.

The yield of the desired 2,6-dimethyl octane can be improved by changing the catalyst and the reaction conditions. A combination of dehydration catalysts (e.g. zeolites, acidic ion exchange catalysts, sulfonated silica or alumina) and hydrogenation catalysts (e.g. Pd, Pt, Ru, Rh, Ni, NiO, CoO, $MoO_3$, $Al_2O_3$) could be used. The temperature (up to 400° C.) and hydrogen pressure (up to 5000 psi) can be optimized. The use of a flow reactor would increase the yield of the desired 2,6-dimethyloctane. Increasing the yield may also be accomplished by converting the 3,7-dimethyloctan-1-ol fraction to 2,6-dimethyloctane. This is accomplished by dehydration of the alcohol followed by hydrogenation of any double bond intermediates.

EXAMPLE 14

Fuel Properties of 2,6-Dimethyloctane

Tables 1 and 2 summarizes various fuel properties of 2,6-dimethyloctane.

TABLE 1

| Fuel Properties (1) | | | | | | | |
|---|---|---|---|---|---|---|---|
| Fuel tested | Description | Measured Cetane[3] N° | Implied Cetane N° | Pour ° C. | Cloud ° C. | CFPP[1] ° C. | Flash[4] ° F. |
| ULSD[2] | Reference fuel | 45.7 | — | −18 | −13 | −16 | 176 |
| ULSD w/ 10% DMO | | 46.3 | 51.7 | −18 | −13 | −17 | 150 |

[1]Cold Filter Plugging Point
[2]Ultra Low Sulfur Diesel
[3]ASTM Requirements for Cetane: >40
[4]ASTM Requirements for Flash Point: >100° F.

TABLE 2

| 2,6 Dimethyloctane Fuel Properties | | | | | | |
|---|---|---|---|---|---|---|
| Fuel tested | Description | RON[1] N° | MON N° | Measured Octane N° | Implied Octane N° | Measured RVP[3] psi |
| Regular 87 grade gasoline | Reference fuel | 91.4 | 80.3 | 87.2 | — | 11.6 |
| 2% DMO/98% Reg Gasoline | | 90.3 | 82.2 | 86.2 | 37.2 | 11.2 |
| 5% DMO/95% Reg Gasoline | | 88.8 | 80.9 | 84.8 | 39.2 | 10.9 |
| 10% DMO/90% Reg Gasoline | | 87.1 | 79.7 | 83.4 | 49.2 | 10.4 |

[1]Research Octane Number
2: Motor Octane Number
[3]Reid vapor pressure

EXAMPLE 15

Production of 2,6-Dimethyloctane Precursors in Photosynthetic Microbes

Eukaryotic microalgae are capable of producing various isoprenoid compounds (e.g., carotenoids, xanthophylls, sterols, phytic acid) and thus possess the enzymes necessary to convert $CO_2$ to geranyl-diphosphate. Certain chlorophytes (green algae) produce isoprenoids via the non-mevalonate (MEP) pathway both in the cytoplasm and chloroplasts, but in many algae (e.g., diatoms, chrysophytes) the mevalonate (MEV) pathway is used to produce isoprenoids in the cytoplasm while the MEP pathway is used to produce isoprenoids in the chloroplasts. Cyanobacteria produce isoprenoids primarily by the MEP pathway, although several enzymes of the MEV pathway have been observed in various species. As discussed in previous sections, increasing the activity of one or more enzymes in these pathways by introduction of heterologous genes that encode the various enzymes can lead to higher levels of geranyl-diphophate, the precursor of various monoterpenes which can subsequently be converted to various 2,6-dimethyloctane precursors (e.g, geraniol, linalool, nerol).

Glyceraldehyde-3-P is produced from $CO_2$ via photosynthesis in cyanobacterial cells and in the chloroplasts of eukaryotic microalgae and can subsequently be converted through glycolytic reactions to pyruvate. Thus, both precursors for the MEP pathway are produced from $CO_2$ during photosynthesis. Increasing the activity of the MEP pathway enzymes that produce geranyl-diphosphate via mutagenesis or by expression of heterologous genes would increase the amount of geranyl-diphosphate available for subsequent conversion to monoterpenes. In the case of using eukaryotic microalgae as host systems, modification of the genes so that the encoded enzymes contain plastid transit peptides would enable targeting of the enzymes to the chloroplasts. Concomitant reduction of the native enzymes involved in the synthesis of non-essential isoprenoids (e.g., carotenoids) would increase the amount of geranyl-diphosphate available for 2,6-dimethyloctane precursor production. Overexpression of the MEP pathway in the cytoplasm would also lead to enhanced 2,6-dimethyloctane precursor production.

Introduction of genes that encode enzymes of the MEV pathway should also lead to higher levels of monoterpene synthesis in eukaryotic microalgae and cyanobacteria. For eukaryotic microalgae, the encoded enzymes could be targeted to either the cytoplasm or the chloroplast. Acetyl-CoA, the initial substrate for the MEV pathway, is known to be produced both in plastids and in the cytoplasm. Cytoplasmic levels of acetyl-CoA could be enhanced by overexpression of ATP-citrate lyase or citrate lyase and acetyl-CoA synthetase. Plastidial levels of acetyl-CoA could be enhanced by overexpression of plastidial pyruvate dehydrogenase. Acetoacetyl-CoA synthetase activity could also be enhanced by introduction of heterologous genes in order to produce higher levels of substrate for HMG-CoA Synthase, one of the key MEV pathway enzymes.

To enable the production of monoterpenes in photosynthetic microbes, it is also necessary to add a gene that encodes an enzyme that catalyzes the complete dephosphorylation of geranyl-diphosphate. Examples of genes that can be used in this manner include geraniol synthase and linalool synthase (GenBank Accession numbers DQ234300 (SEQ ID NO:117), DQ234299 (SEQ ID NO:119), DQ234298 (SEQ ID NO:121), DQ088667 (SEQ ID NO:123), AJ457070 (SEQ ID NO:125), AY362553 (SEQ ID NO:127), DQ897973 (SEQ ID NO:129), and AAR11765 (same as AY362553)).

Below are some exemplary sequences. Lowercase letters indicate nucleotides, while uppercase letters indicate amino acid residues.

a) DXS(Accession # NP_414954)(*ecoli*)

SEQ ID NO: 1 atgagttttgatattgccaaatacccgaccctggcactggtcgactccacccaggagttacgactgttgccgaaagagagtttaccga aactctgcgacgaactgcgccgctatttactcgacagcgtgagccgttccagcgggcacttcgcctccgggctgggcacggtcgaa ctgaccgtggcgctgcactatgtctacaacaccccgtttgaccaattgatttgggatgtggggcatcaggcttatccgcataaaattttg accggacgccgcgacaaaatcggcaccatccgtcagaaaggcggtctgcacccgttcccgtggcgcggcgaaagcgaatatgac gtattaagcgtcgggcattcatcaacctccatcagtgccggaattggtattgcggttgctgccgaaaaagaaggcaaaaatcgccgc accgtctgtgtcattggcgatggcgcgattaccgcaggcatggcgtttgaagcgatgaatcacgcgggcgatatccgtcctgatatg ctggtgattctcaacgacaatgaaatgtcgatttccgaaaatgtcggcgcgctcaacaaccatctggcacagctgctttccggtaagct ttactcttcactgcgcgaaggcgggaaaaaagttttctctggcgtgccgccaattaaagagctgctcaaacgcaccgaagaacatatt aaaggcatggtagtgcctggcacgttgtttgaagagctgggctttaactacatcggcccggtggacggtcacgatgtgctggggctt atcaccacgctaaagaacatgcgcgacctgaaaggcccgcagttcctgcatatcatgaccaaaaaaggtcgtggttatgaaccggc agaaaaagacccgatcactttccacgccgtgcctaaatttgatccctccagcggttgtttgccgaaaagtagcggcggtttgccgagc tattcaaaaatctttggcgactggttgtgcgaaacggcagcgaaagacaacaagctgatggcgattactccggcgatgcgtgaaggt tccggcatggtcgagttttcacgtaaattcccggatcgctacttcgacgtggcaattgccgagcaacacgcggtgacctttgctgcgg gtctggcgattggtgggtacaaacccattgtcgcgatttactccactttcctgcaacgcgcctatgatcaggtgctgcatgacgtggcg attcaaaagcttccggtcctgttcgccatcgaccgcgcgggcattgttggtgctgacggtcaaacccatcagggtgcttttgatctctct tacctgcgctgcataccggaaatggtcattatgaccccgagcgatgaaaacgaatgtcgccagatgctctataccggctatcactata acgatggcccgtcagcggtgcgctacccgcgtggcaacgcggtcggcgtggaactgacgccgctggaaaaactaccaattggca aaggcattgtgaagcgtcgtggcgagaaactggcgatccttaactttggtacgctgatgccagaagcggcgaaagtcgccgaatcg ctgaacgccacgctggtcgatatgcgttttgtgaaaccgcttgatgaagcgttaattctggaaatggccgccagccatgaagcgctgg tcaccgtagaagaaaacgccattatgggcggcgcaggcagcggcgtgaacgaagtgctgatggcccatcgtaaaccagtacccgt gctgaacattggcctgccggacttctttattccgcaaggaactcaggaagaaatgcgcgccgaactcggcctcgatgccgctggtat ggaagccaaaatcaaggcctggctggcataa

SEQ ID NO: 2

MSFDIAKYPTLALVDSTQELRLLPKESLPKLCDELRRYLLDSVSRSSGHFASGLGTV

ELTVALHYVYNTPFDQLIWDVGHQAYPHKILTGRRDKIGTIRQKGGLHPFPWRGES

EYDVLSVGHSSTSISAGIGIAVAAEKEGKNRRTVCVIGDGAITAGMAFEAMNHAGDI

RPDMLVILNDNEMSISENVGALNNHLAQLLSGKLYSSLREGGKKVFSGVPPIKELLK

RTEEHIKGMVVPGTLFEELGFNYIGPVDGHDVLGLITTLKNMRDLKGPQFLHIMTK

KGRGYEPAEKDPITFHAVPKFDPSSGCLPKSSGGLPSYSKIFGDWLCETAAKDNKLM

AITPAMREGSGMVEFSRKFPDRYFDVAIAEQHAVTFAAGLAIGGYKPIVAIYSTFLQ

RAYDQVLHDVAIQKLPVLFAIDRAGIVGADGQTHQGAFDLSYLRCIPEMVIMTPSD

ENECRQMLYTGYHYNDGPSAVRYPRGNAVGVELTPLEKLPIGKGIVKRRGEKLAIL

NFGTLMPEAAKVAESLNATLVDMRFVKPLDEALILEMAASHEALVTVEENAIMGG

AGSGVNEVLMAHRKPVPVLNIGLPDFFIPQGTQEEMRAELGLDAAGMEAKIKAWLA (*Arabidopsis thaliana*): DXPS1; 1-deoxy-D-xylulose-5-phosphate synthase
DXS (Accession #NP_566686)(athal)

SEQ ID NO: 3 atgtcatatcaaacacagattaacaaattctctcaaatggctctctccgtatttgcctttccttcttacataaataggaatccttcactaaaat atcttaaaccttcttctatgtcttctacaaaatattcaaaagtaagagcaacaacattttcagagaaaggtgaatattattcaaacagacca -continued ccaactcctttattggacacaatcaaccatccaatgcacatgaaaaatctctccatcaaagaactcaaagttctttcggacgagttgaga tctgatgttatttttaatgtttcgaaaactggaggacacttgggttcgaatcttggtgttgttgagctcaccgtggcccttcattacatcttca atactcctcatgataagatcctttgggatgttggtcatcagtcttatcctcacaagattctaacgggaagaagaggaaagatgaagaca ataaggcagaccaatggcctctccggctacaccaagcgaagagagagtgagcatgactcttttggcaccgggcacagttcgaccac actatctgcaggcttagggatggctgtagggagggatttgaaggggatgaacaacagcgtggtttcggttataggcgatggtgctat gacagctggacaagcttatgaagcaatgaacaatgctggctacttacactccaacatgattgtgattctcaacgacaacaaacaagtat ctttgcctactgctaacttggatggaccaactcaacctgttggagctctgagctgtgctcttagtaggctgcaatctaattgtggaatgatt agagagactagttcaacactgtttgaagaacttggttttcactatgttggtccagttgatggacacaacatagatgatctggtctccattct tgaaacattaaagagcaccaaaaccataggaccggttcttatccatgtcgtgactgagaaaggtcgtggatatccttacgcagagaga gctgatgacaagtatcatgttttaaaatttgatccagaaacaggtaaacagttcaaaaatatttccaagactcagtcttacacttcctgtttt gtggaggccttgattgcagaagcagaggcagacaaagatattgttgccattcatgcagccatgggaggtggaaccatgttgaatctct tcgaaagccgctttcctacaaggtgtttcgatgtcggcatagcagaacaacatgcagttaccttcgctgctggtcttgcttgcgaagga cttaagccctttgtacaatctactcatctttcatgcaacgggcatatgatcaagttgtacatgatgttgatctacagaaactgcctgtgag atttgcaatagatagagcaggacttatgggagcagatggtccaacacattgtggagcatttgatgtgacgtttatggcatgtctaccaa acatgatagtaatggctccatctgatgaagcagagcttttttaacatggttgcaaccgctgcagctattgatgaccgtccttcttgctttcg atatcatagaggaaatggtattggtgtttcacttcctcctggtaacaaaggtgtccctcttcagattgggagaggtaggatactaaggga cggcgagagggttgcgcttttgggctatggatcagcggtgcaaagatgtttagaggctgcatctatgctaagcgaacgcggattaaa gataacagtagcggatgcaagattctgtaagccgttagatgttgctctcattcgtagcttagctaaatcacacgaggttttgatcacggtt gaagaaggttccattggaggatttggatcgcatgtggtacaatttcttgcacttgatggccttcttgatggaaagctc aaggtatatcga acatggatcaccaatggatcaactagctga

SEQ ID NO: 4

MSYQTQINKFSQMALSVFAFPSYINRNPSLKYLKPSSMSSTKYSKVRATTFSEKGEY

YSNRPPTPLLDTINHPMHMKNLSIKELKVLSDELRSDVIFNVSKTGGHLGSNLGVVE

LTVALHYIFNTPHDKILWDVGHQSYPHKILTGRRGKMKTIRQTNGLSGYTKRRESE

HDSFGTGHSSTTLSAGLGMAVGRDLKGMNNSVVSVIGDGAMTAGQAYEAMNNA

GYLHSNMIVILNDNKQVSLPTANLDGPTQPVGALSCALSRLQSNCGMIRETSSTLFE

ELGFHYVGPVDGHNIDDLVSILETLKSTKTIGPVLIHVVTEKGRGYPYAERADDKYH

VLKFDPETGKQFKNISKTQSYTSCFVEALIAEAEADKDIVAIHAAMGGGTMLNLFES

RFPTRCFDVGIAEQHAVTFAAGLACEGLKPFCTIYSSFMQRAYDQVVHDVDLQKLP

VRFAIDRAGLMGADGPTHCGAFDVTFMACLPNMIVMAPSDEAELFNMVATAAAID

DRPSCFRYHRGNGIGVSLPPGNKGVPLQIGRGRILRDGERVALLGYGSAVQRCLEA

ASMLSERGLKITVADARFCKPLDVALIRSLAKSHEVLITVEEGSIGGFGSHVVQFLAL

DGLLDGKLKVYRTWITNGSTS

*Escherichia coli* str. K12 substr. MG1655): 1-deoxy-D-xylulose 5-phosphate
reductoisomerase
b) DXR(Accession # NP_414715)(*ecoli*)

SEQ ID NO: 5 atgaagcaactcaccattctgggctcgaccggctcgattggttgcagcacgctggacgtggtgcgccataatcccgaacacttccgc gtagttgcgctggtggcaggcaaaaatgtcactcgcatggtagaacagtgcctggaattctctccccgctatgccgtaatggacgatg aagcgagtgcgaaacttcttaaaacgatgctacagcaacagggtagccgcaccgaagtcttaagtgggcaacaagccgcttgcgat atggcagcgcttgaggatgttgatcaggtgatggcagccattgttggcgctgctgggctgttacctacgcttgctgcgatccgcgcgg gtaaaaccattttgctggccaataaagaatcactggttacctgcggacgtctgtttatggacgccgtaaagcagagcaaagcgcaatt gttaccggtcgatagcgaacataacgccatttttcagagtttaccgcaacctatccagcataatctgggatacgctgaccttgagcaaa -continued atggcgtggtgtccattttacttaccgggtctggtggccctttccgtgagacgccattgcgcgatttggcaacaatgacgccggatcaa gcctgccgtcatccgaactggtcgatggggcgtaaaatttctgtcgattcggctaccatgatgaacaaaggtctggaatacattgaag cgcgttggctgtttaacgccagcgccagccagatggaagtgctgattcacccgcagtcagtgattcactcaatggtgcgctatcagg acggcagtgttctggcgcagctgggggaaccggatatgcgtacgccaattgcccacaccatggcatggccgaatcgcgtgaactct ggcgtgaagccgctcgattttgcaaactaagtgcgttgacatttgccgcaccggattatgatcgttatccatgcctg aaactggcgat ggaggcgttcgaacaaggccaggcagcgacgacagcattgaatgccgcaaacgaaatcaccgttgctgcttttcttgcgcaacaaa tccgctttacggatatcgctgcgttgaatttatccgtactggaaaaaatggatatgcgcgaaccacaatgtgtggacgatgtgttatctgt tgatgcgaacgcgcgtgaagtcgccagaaaagaggtgatgcgtctcgcaagctga

SEQ ID NO: 6

MKQLTILGSTGSIGCSTLDVVRHNPEHFRVVALVAGKNVTRMVEQCLEFSPRYAV

MDDEASAKLLKTMLQQQGSRTEVLSGQQAACDMAALEDVDQVMAAIVGAAGLL

PTLAAIRAGKTILLANKESLVTCGRLFMDAVKQSKAQLLPVDSEHNAIFQSLPQPIQ

HNLGYADLEQNGVVSILLTGSGGPFRETPLRDLATMTPDQACRHPNWSMGRKISVD

SATMMNKGLEYIEARWLFNASASQMEVLIHPQSVIHSMVRYQDGSVLAQLGEPDM

RTPIAHTMAWPNRVNSGVKPLDFCKLSALTFAAPDYDRYPCLKLAMEAFEQGQAA

TTALNAANEITVAAFLAQQIRFTDIAALNLSVLEKMDMREPQCVDDVLSVDANARE

VARKEVMRLAS (*Arabidopsis thaliana*): DXR (1-DEOXY-D-XYLULOSE 5-PHOSPHATE
REDUCTOISOMERASE)
DXR(Accession # NP_201085)(athal)

SEQ ID NO: 7 atgatgacattaaactcactatctccagctgaatccaaagctatttctttcttggatacctccaggttcaatccaatccctaaactctcaggt gggtttagtttgaggaggaggaatcaagggagaggttttggaaaaggtgttaagtgttcagtgaaagtgcagcagcaacaacaacct cctccagcatggcctgggagagctgtccctgaggcgcctcgtcaatcttgggatggaccaaaacccatctctatcgttggatctactg gttctattggcactcagacattggatattgtggctgagaatcctgacaaattcagagttgtggctctagctgctggttcgaatgttactcta cttgctgatcaggtaaggagatttaagcctgcattggttgctgttagaaacgagtcactgattaatgagcttaaagaggctttagctgatt tggactataaactcgagattattccaggagagcaaggagtgattgaggttgcccgacatcctgaagctgtaaccgttgttaccggaat agtaggttgtgcgggactaaagcctacggttgctgcaattgaagcaggaaaggacattgctcttgcaaacaaagagacattaatcgc aggtggtcctttcgtgcttccgcttgccaacaaacataatgtaaagattcttccggcagattcagaacattctgccatatttcagtgtattc aaggtttgcctgaaggcgctctgcgcaagataatcttgactgcatctggtggagcttttagggattggcctgtcgaaaagctaaagga agttaaagtagcggatgcgttgaagcatccaaactggaacatgggaaagaaaatcactgtggactctgctacgcttttcaacaagggt cttgaggtcattgaagcgcattatttgtttggagctgagtatgacgatatagagattgtcattcatccgcaaagtatcatacattccatgatt gaaacacaggattcatctgtgcttgctcaattgggttggcctgatatgcgtttaccgattctctacaccatgtcatggcccgatagagttc cttgttctgaagtaacttggccaagacttgacctttgcaaactcggttcattgactttcaagaaaccagacaatgtgaaatacccatccat ggatcttgcttatgctgctggacgagctggaggcacaatgactggagttctcagcgccgccaatgagaaagctgttgaaatgttcatt gatgaaaagataagctatttggatatcttcaaggttgtggaattaacatgcgataaacatcgaaacgagttggtaacatcaccgtctctt gaagagattgttcactatgacttgtgggcacgtgaatatgccgcgaatgtgcagctttcttctggtgctaggccagttcatgcatga

SEQ ID NO: 8

MMTLNSLSPAESKAISFLDTSRFNPIPKLSGGFSLRRRNQGRGFGKGVKCSVKVQQQ

QQPPPAWPGRAVPEAPRQSWDGPKPISIVGSTGSIGTQTLDIVAENPDKFRVVALAA

GSNVTLLADQVRRFKPALVAVRNESLINELKEALADLDYKLEIIPGEQGVIEVARHP

EAVTVVTGIVGCAGLKPTVAAIEAGKDIALANKETLIAGGPFVLPLANKHNVKILPA

DSEHSAIFQCIQGLPEGALRKIILTASGGAFRDWPVEKLKEVKVADALKHPNWNMG

KKITVDSATLFNKGLEVIEAHYLFGAEYDDIEIVIHPQSIIHSMIETQDSSVLAQLGWP

-continued

DMRLPILYTMSWPDRVPCSEVTWPRLDLCKLGSLTFKKPDNVKYPSMDLAYAAGR

AGGTMTGVLSAANEKAVEMFIDEKISYLDIFKVVELTCDKHRNELVTSPSLEEIVHY

DLWAREYAANVQLSSGARPVHA (*Escherichia coli* str. K12 substr. MG1655): 4-diphosphocytidyl-2C-methyl-D-erythritol synthase
c) IspD (Accession # NP_417227)(*ecoli*)

SEQ ID NO: 9 atggcaaccactcatttggatgtttgcgccgtggttccggcggccggatttggccgtcgaatgcaaacggaatgtcctaagcaatatct ctcaatcggtaatcaaaccattcttgaacactcggtgcatgcgctgctggcgcatccccgggtgaaacgtgtcgtcattgccataagtc ctggcgatagccgttttgcacaacttcctctggcgaatcatccgcaaatcaccgttgtagatggcggtgatgagcgtgccgattccgtg ctggcaggtctgaaagccgctggcgacgcgcagtgggtattggtgcatgacgccgctcgtccttgtttgcatcaggatgacctcgcg cgattgttggcgttgagcgaaaccagccgcacgggggggatcctcgccgcaccagtgcgcgatactatgaaacgtgccgaaccg ggcaaaaatgccattgctcataccgttgatcgcaacggcttatggcacgcgctgacgccgcaatttttccctcgtgagctgttacatga ctgtctgacgcgcgctctaaatgaaggcgcgactattaccgacgaagcctcggcgctggaatattgcggattccatcctcagttggtc gaaggccgtgcggataacattaaagtcacgcgcccggaagatttggcactggccgagttttacctcacccgaaccatccatcagga gaatacataa

SEQ ID NO: 10

MATTHLDVCAVVPAAGFGRRMQTECPKQYLSIGNQTILEHSVHALLAHPRVKRVVI

AISPGDSRFAQLPLANHPQITVVDGGDERADSVLAGLKAAGDAQWVLVHDAARPC

LHQDDLARLLALSETSRTGGILAAPVRDTMKRAEPGKNAIAHTVDRNGLWHALTP

QFFPRELLHDCLTRALNEGATITDEASALEYCGFHPQLVEGRADNIKVTRPEDLALA

EFYLTRTIHQENT (*Arabidopsis thaliana*): ISPD (2-C-METHYL-D-ERYTHRITOL 4-PHOSPHATE CYTIDYLTRANSFERASE)
IspD (Accession # NP_565286)(athal)

SEQ ID NO: 11 atggcgatgcttcagacgaatcttggcttcattacttctccgacatttctgtgtccgaagcttaaagtcaaattgaactcttatctgtggttta gctatcgttctcaagttcaaaaactggatttttcgaaaagggttaatagaagctacaaaagagatgctttattattgtcaatcaagtgttctt catcgactggatttgataatagcaatgttgttgtgaaggagaagagtgtatctgtgattcttttagctggaggtc aaggcaagagaatga aaatgagtatgccaaagcagtacataccacttcttggtcagccaattgctttgtatagctttttcacgttttcacgtatgcctgaagtgaag gaaattgtagttgtatgtgatcctttttttcagagacattttgaagaatacgaagaatcaattgatgttgatcttagattcgctattcctggca aagaaagacaagattctgtttacagtggacttcaggaaatcgatgtgaactctgagcttgtttgtatccacgactctgcccgaccattgg tgaatactgaagatgtcgagaaggtccttaaagatggttccgcggttggagcagctgtacttggtgttcctgctaaagctacaatcaaa gaggtcaattctgattcgcttgtggtgaaaactctcgacagaaaaaccctatgggaaatgcagacaccacaggtgatcaaaccagag ctattgaaaaagggtttcgagcttgtaaaaagtgaaggtctagaggtaacagatgacgtttcgattgttgaatacctcaagcatccagtt tatgtctctcaaggatcttatacaaacatcaaggttacaacacctgatgatttactgcttgctgagagaatcttgagcgaggactcatga

SEQ ID NO: 12

MAMLQTNLGFITSPTFLCPKLKVKLNSYLWFSYRSQVQKLDFSKRVNRSYKRDALL

LSIKCSSSTGFDNSNVVVKEKSVSVILLAGGQGKRMKMSMPKQYIPLLGQPIALYSF

FTFSRMPEVKEIVVVCDPFFRDIFEEYEESIDVDLRFAIPGKERQDSVYSGLQEIDVNS

ELVCIHDSARPLVNTEDVEKVLKDGSAVGAAVLGVPAKATIKEVNSDSLVVKTLDR

KTLWEMQTPQVIKPELLKKGFELVKSEGLEVTDDVSIVEYLKHPVYVSQGSYTNIK

VTTPDDLLLAERILSEDS (*Escherichia coli* str. K12 substr. MG1655): 4-diphosphocytidyl-2-C-methylerythritol kinase
d) IspE(Accession#NP_415726)(*ecoli*)

SEQ ID NO: 13

-continued atgcggacacagtggccctctccggcaaaacttaatctgtttttatacattaccggtcagcgtgcggatggttaccacacgctgcaaac gctgtttcagtttcttgattacggcgacaccatcagcattgagcttcgtgacgatggggatattcgtctgttaacgcccgttgaaggcgt ggaacatgaagataacctgatcgttcgcgcagcgcgattgttgatgaaaactgcggcagacagcgggcgtcttccgacgggaagc ggtgcgaatatcagcattgacaagcgtttgccgatgggcggcggtctcggcggtggttcatccaatgccgcgacggtcctggtggc attaaatcatctctggcaatgcgggctaagcatggatgagctggcggaaatggggctgacgctgggcgcagatgttcctgtctttgtt cgggggcatgccgcgtttgccgaaggcgttggtgaaatactaacgccggtggatccgccagagaagtggtatctggtggcgcacc ctggtgtaagtattccgactccggtgatttttaaagatcctgaactcccgcgcaatacgccaaaaaggtcaatagaaacgttgctaaaat gtgaattcagcaatgattgcgaggttatcgcaagaaaacgttttcgcgaggttgatgcggtgctttcctggctgttagaatacgccccgt cgcgcctgactgggacaggggcctgtgtctttgctgaatttgatacagagtctgaagcccgccaggtgctagagcaagccccggaa tggctcaatggctttgtggcgaaaggcgctaatctttccccattgcacagagccatgctttaa

SEQ ID NO: 14

MRTQWPSPAKLNLFLYITGQRADGYHTLQTLFQFLDYGDTISIELRDDGDIRLLTPV

EGVEHEDNLIVRAARLLMKTAADSGRLPTGSGANISIDKRLPMGGGLGGGSSNAAT

VLVALNHLWQCGLSMDELAEMGLTLGADVPVFVRGHAAFAEGVGEILTPVDPPEK

WYLVAHPGVSIPTPVIFKDPELPRNTPKRSIETLLKCEFSNDCEVIARKRFREVDAVL

SWLLEYAPSRLTGTGACVFAEFDTESEARQVLEQAPEWLNGFVAKGANLSPLHRA

ML (*Arabidopsis thaliana*): ATCDPMEK (PIGMENT DEFECTIVE 277); 4-(cytidine 5'-diphospho)-2-C-methyl-D-erythritol kinase
IspE(Accession# NP_180261)(athal)

SEQ ID NO: 15 atggcaacggcttctcctccatttatctcaactctcagcttcactcactcttctttcaaaacttcttcttcttcttcattttctccgaagcttcttc gacccctcttaagcttttccgtcaaagcttccagaaagcaagtagagatagtgtttgatcctgatgagaggcttaataagataggtgatg atgttgacaaagaagctcctttgtccaggcttaagctcttctcaccttgcaagatcaatgttttcttgaggatcaccggaaagcgagaag atgggtttcatgatttagcctctttgtttcatgtgattagcttaggagacactattaaattctcattgtcaccatcaaagtctaaagatcgtttg tctactaacgttcaaggagtccctgttgatgggagaaatctgattataaaagcacttaacctttacaggaagaaaactggtagtaacag attcttctggattcatttagataagaaggtgcctaccggggctggactcggtggtggaagtagtaatgctgcaactgcactctgggcg gcaaatgagctcaatggaggtcttgtcactgagaacgaactccaggattggtcaagtgaaattgggtcagatattcctttcttcttctcg catggagctgcctattgtaccgggagaggtgagattgtccaagaccttcctccaccttttcctcttgatcttccgatggtgctcataaagc cccgagaagcatgttccactgctgaagtttacaaacgtcttcgtttagatcagacgagcaatattaatcccttgacattactagagaatgt gaccagcaatggtgtgtctcaaagcatatgcgtaaacgatttggaaccgccagcgttttcagttcttccatctctaaaacgcttgaagca acggataatagcatctggacgtggggaatacgatgctgtgtttatgtctgggagtggaagcactattatcggtattggttcaccagatc ctcctcaatttatatatgatgatgaagaatacaagaacgtgttcttgtctgaagcaaactttatgacgcgtgaggctaatgaatggtacaa agaacctgcttctgcaaatgctactacctcatccgccgaatctcgcatggatttccaatga

SEQ ID NO: 16

MATASPPFISTLSFTHSSFKTSSSSSFSPKLLRPLLSFSVKASRKQVEIVFDPDERLNKI

GDDVDKEAPLSRLKLFSPCKINVFLRITGKREDGFHDLASLFHVISLGDTIKFSLSPSK

SKDRLSTNVQGVPVDGRNLIIKALNLYRKKTGSNRFFWIHLDKKVPTGAGLGGGSS

NAATALWAANELNGGLVTENELQDWSSEIGSDIPFFFSHGAAYCTGRGEIVQDLPPP

FPLDLPMVLIKPREACSTAEVYKRLRLDQTSNINPLTLLENVTSNGVSQSICVNDLEP

PAFSVLPSLKRLKQRIIASGRGEYDAVFMSGSGSTIIGIGSPDPPQFIYDDEEYKNVFL

SEANFMTREANEWYKEPASANATTSSAESRMDFQ (*Escherichia coli* str. K12 substr. MG1655): 2C-methyl-D-erythritol 2,4-cyclodiphosphate synthase
e)IspF(Accession# NP_417226)(*ecoli*)

-continued

SEQ ID NO: 17 atgcgaattggacacggttttgacgtacatgcctttggcggtgaaggcccaattatcattggtggcgtacgcattccttacgaaaaagg attgctggcgcattctgatggcgacgtggcgctccatgcgttgaccgatgcattgcttggcgcggcggcgctgggggatatcggca agctgttcccggataccgatccggcatttaaaggtgccgatagccgcgagctgctacgcgaagcctggcgtcgtattcaggcgaag ggttatacccttggcaacgtcgatgtcactatcatcgctcaggcaccgaagatgttgccgcacattccacaaatgcgcgtgtttattgcc gaagatctcggctgccatatggatgatgttaacgtgaaagccactactacggaaaaactgggatttaccggacgtggggaagggatt gcctgtgaagcggtggcgctactcattaaggcaacaaaatga

SEQ ID NO: 18

MRIGHGFDVHAFGGEGPIIIGGVRIPYEKGLLAHSDGDVALHALTDALLGAAALGDI

GKLFPDTDPAFKGADSRELLREAWRRIQAKGYTLGNVDVTIIAQAPKMLPHIPQMR

VFIAEDLGCHMDDVNVKATTTEKLGFTGRGEGIACEAVALLIKATK (*Arabidopsis thaliana*): ISPF (Homolog of E. coli ispF (isoprenoids F)); 2-C-methyl-D-erythritol 2,4-cyclodiphosphate synthase
IspF(Accession#NP_564819)(athal)

SEQ ID NO: 19 atggctacttcttctactcagcttctactgtcttcttcttctttgtttcactctcaaattaccaaaaagccattccttctcccggcgacgaagat cggcgtttggagaccgaagaagtctctctcgttatcatgtcgtccttcagcctcggtttcagctgcttcttccgccgtcgacgtcaatga atctgtgacttcagagaaaccaaccaaaacgcttccgtttcgaatcggtcatggtttcgatctacatcgtttagagccagggtatcctctg atcatcggtgggattgttattcctcatgatagaggctgcgaagctcactccgatgtggatgcaattttgggagcactaggccttccagat ataggtcagattttccctgactctgatcctaaatggaaaggagctgcttcttctgtattcatcaaagaagctgtgagactcatggacgag gcagggtatgagataggaaacctagacgcgacgttgattctccagagaccaaaaattagtccacacaaagagacaatccgatccaa tctgtccaagcttcttggagcagatccttctgtagtgaacttgaaagccaaaacacatgagaaagttgatagcctcggagaaaacaga agcatagcagctcacactgttattctcctcatgaagaaatag

SEQ ID NO: 20

MATSSTQLLLSSSSLFHSQITKKPFLLPATKIGVWRPKKSLSLSCRPSASVSAASSAV

DVNESVTSEKPTKTLPFRIGHGFDLHRLEPGYPLIIGGIVIPHDRGCEAHSDVDAILGA

LGLPDIGQIFPDSDPKWKGAASSVFIKEAVRLMDEAGYEIGNLDATLILQRPKISPHK

ETIRSNLSKLLGADPSVVNLKAKTHEKVDSLGENRSIAAHTVILLMKK

*Escherichia coli* str. K12 substr. MG1655): 1-hydroxy-2-methyl-2-(E)-butenyl 4-diphosphate synthase
f) IspG(Accession#NP_417010)(*ecoli*)

SEQ ID NO: 21 atgcataaccaggctccaattcaacgtagaaaatcaacacgtatttacgttgggaatgtgccgattggcgatggtgctcccatcgccgt acagtccatgaccaatacgcgtacgacagacgtcgaagcaacggtcaatcaaatcaaggcgctggaacgcgttggcgctgatatcg tccgtgtatccgtaccgacgatggacgcggcagaagcgttcaaactcatcaaacagcaggttaacgtgccgctggtggctgacatcc acttcgactatcgcattgcgctgaaagtagcggaatacggcgtcgattgtctgcgtattaaccctggcaatatcggtaatgaagagcgt attcgcatggtggttgactgtgcgcgcgataaaaacattccgatccgtattggcgttaacgccggatcgctggaaaaagatctgcaag aaaagtatggcgaaccgacgccgcaggcgttgctggaatctgccatgcgtcatgttgatcatctcgatcgcctgaacttcgatcagttc aaagtcagcgtgaaagcgtctgacgtcttcctcgctgttgagtcttatcgtttgctggcaaaacagatcgatcagccgttgcatctggg gatcaccgaagccggtggtgcgcgcagcggggcagtaaaatccgccattggtttaggtctgctgctgtctgaaggcatcggcgaca cgctgcgcgtatcgctggcggccgatccggtcgaagagatcaaagtcggtttcgatattttgaaatcgctgcgtatccgttcgcgagg gatcaacttcatcgcctgcccgacctgttcgcgtcaggaatttgatgttatcggtacggttaacgcgctggagcaacgcctggaagat atcatcactccgatggacgtttcgattatcggctgcgtggtgaatggcccaggtgaggcgctggtttctacactcggcgtcaccggcg gcaacaagaaaagcggcctctatgaagatggcgtgcgcaaagaccgtctggacaacaacgatatgatcgaccagctggaagcac gcattcgtgcgaaagccagtcagctggacgaagcgcgtcgaattgacgttcagcaggttgaaaaataa

SEQ ID NO: 22

MHNQAPIQRRKSTRIYVGNVPIGDGAPIAVQSMTNTRTTDVEATVNQIKALERVGA

-continued

DIVRVSVPTMDAAEAFKLIKQQVNVPLVADIHFDYRIALKVAEYGVDCLRINPGNIG

NEERIRMVVDCARDKNIPIRIGVNAGSLEKDLQEKYGEPTPQALLESAMRHVDHLD

RLNFDQFKVSVKASDVFLAVESYRLLAKQIDQPLHLGITEAGGARSGAVKSAIGLGL

LLSEGIGDTLRVSLAADPVEEIKVGFDILKSLRIRSRGINFIACPTCSRQEFDVIGTVNA

LEQRLEDIITPMDVSIIGCVVNGPGEALVSTLGVTGGNKKSGLYEDGVRKDRLDNN

DMIDQLEARIRAKASQLDEARRIDVQQVEK (*Arabidopsis thaliana*): GcpE (CHLOROPLAST BIOGENESIS 4)
IspG(Accession# NP_001119467)(athal)

SEQ ID NO: 23 atggcgactggagtattgccagctccggtttctgggatcaagataccggattcgaaagtcgggtttggtaaaagcatgaatcttgtgag aatttgtgatgttaggagtctaagatctgctaggagaagagtttcggttatccggaattcaaaccaaggctctgatttagctgagcttcaa cctgcatccgaaggaagccctctcttagtgccaagacagaaatattgtgaatcattgcataagacggtgagaaggaagactcgtactg ttatggttggaaatgtcgcccttggaagcgaacatccgataaggattcaaacgatgactacttcggatacaaaagatattactggaact gttgatgaggttatgagaatagcggataaaggagctgatattgtaaggataactgttcaagggaagaaagaggcggatgcgtgcttt gaaataaaagataaactcgttcagcttaattacaatataccgctggttgcagatattcattttgcccctactgtagccttacgagtcgctga atgctttgacaagatccgtgtcaacccaggaaattttgcggacaggcgggcccagtttgagacgatagattatacagaagatgaatat cagaaagaactccagcatatcgagcaggtcttcactcctttggttgagaaatgcaaaaagtacgggagagcaatgcgtattgggaca aatcatggaagtctttctgaccgtatcatgagctattacggggattctccccgaggaatggttgaatctgcgtttgagtttgcaagaatat gtcggaaattagactatcacaactttgttttctcaatgaaagcgagcaacccagtgatcatggtccaggcgtaccgtttacttgtggctg agatgtatgttcatggatgggattatcctttgcatttgggagttactgaggcaggagaaggcgaagatggacggatgaaatctgcgatt ggaattgggacgcttcttcaggacgggctcggtgacacaataagagtttcactgacggagccaccagaagaggagatagatccctg caggcgattggctaacctcgggacaaaagctgccaaacttcaacaaggcgttgcaccgtttgaagaaaagcataggcattactttgat tttcagcgtcggacgggtgatctacctgtacaaaaagagggagaagaggttgattacagaaatgtccttcaccgtgatggttctgttct gatgtcgatttctctggatcaactaaaggcacctgaactcctctacagatcactcgctacaaagcttgtcgtgggtatgccattcaagga tctggcaactgttgattcaatcttattaagagagctaccgcctgtagatgatcaagtggctcgtttggctctaaaacggttgattgatgtca gtatgggagttatagcacctttatcagagcaactaacaaagccattgcccaatgccatggttcttgtcaacctcaaggaactatctggtg gcgcttacaagcttctccctgaaggtacacgcttggttgtctctctacgaggcgatgagccttacgaggagcttgaaatactcaaaaac attgatgctactatgattctccatgatgtacctttcactgaagacaaagttagcagagtacatgcagctcggaggctattcgagttcttatc cgagaattcagttaactttcctgttattcatcacataaacttcccaaccggaatccacagagacgaattggtgattcatgcagggacatat gctggaggccttcttgtggatggactaggtgatggcgtaatgctcgaagcacctgaccaagattttgattttcttaggaatacttccttca acttattacaaggatgcagaatgcgtaacactaagacggaatatgtatcgtgcccgtcttgtggaagaacgcttttcgacttgcaagaa atcagcgccgagatccgagaaaagacttcccatttacctggcgtttcggttaaaactcaagactttcatacatgtttttcaagaaaaagtt ttcttctgtttttgaatgtaaacaaattgaataatggcgcagatcgcaatcatgggatgcattgtgaatggaccaggagaaatggcagat gctga

SEQ ID NO: 24

MATGVLPAPVSGIKIPDSKVGFGKSMNLVRICDVRSLRSARRRVSVIRNSNQGSDLA

ELQPASEGSPLLVPRQKYCESLHKTVRRKTRTVMVGNVALGSEHPIRIQTMTTSDTK

DITGTVDEVMRIADKGADIVRITVQGKKEADACFEIKDKLVQLNYNIPLVADIHFAP

TVALRVAECFDKIRVNPGNFADRRAQFETIDYTEDEYQKELQHIEQVFTPLVEKCKK

YGRAMRIGTNHGSLSDRIMSYYGDSPRGMVESAFEFARICRKLDYHNFVFSMKASN

PVIMVQAYRLLVAEMYVHGWDYPLHLGVTEAGEGEDGRMKSAIGIGTLLQDGLG

DTIRVSLTEPPEEEIDPCRRLANLGTKAAKLQQGVAPFEEKHRHYFDFQRRTGDLPV

-continued

QKEGEEVDYRNVLHRDGSVLMSISLDQLKAPELLYRSLATKLVVGMPFKDLATVD

SILLRELPPVDDQVARLALKRLIDVSMGVIAPLSEQLTKPLPNAMVLVNLKELSGGA

YKLLPEGTRLVVSLRGDEPYEELEILKNIDATMILHDVPFTEDKVSRVHAARRLFEF

LSENSVNFPVIHHINFPTGIHRDELVIHAGTYAGGLLVDGLGDGVMLEAPDQDFDFL

RNTSFNLLQGCRMRNTKTEYVSCPSCGRTLFDLQEISAEIREKTSHLPGVSVKTQDF

HTCFSRKSFLLFLNVNKLNNGADRNHGMHCEWTRRNGRC (*Escherichia coli* str. K12 substr. MG1655): 1-hydroxy-2-methyl-2-(E)-butenyl 4-diphosphate reductase, 4Fe-4S protein
g) IspH(Accession# NP_414570)(*ecoli*)

SEQ ID NO: 25 atgcagatcctgttggccaacccgcgtggtttttgtgccggggtagaccgcgctatcagcattgttgaaaacgcgctggccatttacg gcgcaccgatatatgtccgtcacgaagtggtacataaccgctatgtggtcgatagcttgcgtgagcgtggggctatctttattgagcag attagcgaagtaccggacggcgcgatcctgattttctccgcacacggtgtttctcaggcggtacgtaacgaagcaaaaagtcgcgatt tgacggtgtttgatgccacctgtccgctggtgaccaaagtgcatatggaagtcgcccgcgccagtcgccgtggcgaagaatctattct catcggtcacgccgggcacccggaagtggaagggacaatgggccagtacagtaacccggaaggggggaatgtatctggtcgaatc gccggacgatgtgtggaaactgacggtcaaaaacgaagagaagctctcctttatgacccagaccacgctgtcggtggatgacacgt ctgatgtgatcgacgcgctgcgtaaacgcttcccgaaaattgtcggtccgcgcaaagatgacatctgctacgccacgactaaccgtc aggaagcggtacgcgccctggcagaacaggcggaagttgtgttggtggtcggttcgaaaaactcctccaactccaaccgtctggcg gagctggcccagcgtatgggcaaacgcgcgtttttgattgacgatgcgaaagacatccaggaagagtgggtgaaagaggttaaatg cgtcggcgtgactgcgggcgcatcggctccggatattctggtgcagaatgtggtggcacgtttgcagcagctgggcggtggtgaag ccattccgctggaaggccgtgaagaaaacattgttttcgaagtgccgaaagagctgcgtgtcgatattcgtgaagtcgattaa

SEQ ID NO: 26

MQILLANPRGFCAGVDRAISIVENALAIYGAPIYVRHEVVHNRYVVDSLRERGAIFIE

QISEVPDGAILIFSAHGVSQAVRNEAKSRDLTVFDATCPLVTKVHMEVARASRRGEE

SILIGHAGHPEVEGTMGQYSNPEGGMYLVESPDDVWKLTVKNEEKLSFMTQTTLSV

DDTSDVIDALRKRFPKIVGPRKDDICYATTNRQEAVRALAEQAEVVLVVGSKNSSN

SNRLAELAQRMGKRAFLIDDAKDIQEEWVKEVKCVGVTAGASAPDILVQNVVARL

QQLGGGEAIPLEGREENIVFEVPKELRVDIREVD (*Arabidopsis thaliana*): CLB6 (CHLOROPLAST BIOGENESIS 6); 4-hydroxy-3-methylbut-2-en-1-yl diphosphate reductase
IspH(Accession#NP_567965)(athal)

SEQ ID NO: 27 atggctgttgcgctccaattcagccgattatgcgttcgaccggatactttcgtgcgggagaatcatctctctggatccggatctctccgc cgccggaaagctttatcagtccggtgctcgtctggcgatgagaacgctccttcgccatcggtggtgatggactccgatttcgacgcca aggtgttccgtaagaacttgacgagaagcgataattacaatcgtaaagggttcggtcataaggaggagacactcaagctcatgaatc gagagtacaccagtgatatattggagacactgaaaacaaatgggtatacttattcttggggagatgttactgtgaaactcgctaaagca tatggtttttgctggggtgttgagcgtgctgttcagattgcatatgaagcacgaaagcagtttccagaggagaggctttggattactaac gaaatcattcataacccgaccgtcaataagaggttggaagatatggatgttaaaattattccggttgaggattcaaagaaacagtttgat gtagtagagaaagatgatgtggttatccttcctgcgtttggagctggtgttgacgagatgtatgttcttaatgataaaaaggtgcaaattg ttgacacgacttgtccttgggtgacaaaggtctggaacacggttgagaagcacaagaaggggggaatacacatcagtaatccatggta aatataatcatgaagagacgattgcaactgcgtcttttgcaggaaagtacatcattgtaaagaacatgaaagaggcaaattacgtttgtg attacattctcggtggccaatacgatggatctagctccacaaaagaggagttcatggagaaattcaaatacgcaatttcgaagggtttc gatcccgacaatgaccttgtcaaagttggtattgcaaaccaaacaacgatgctaaagggagaaacagaggagatagaaagattactc gagacaacaatgatgcgcaagtatggagtggaaaatgtaagcggacatttcatcagcttcaacacaatatgcgacgctactcaagag cgacaagacgcaatctatgagctagtggaagagaagattgacctcatgctagtggttggcggatggaattcaagtaacacctctcac -continued cttcaggaaatctcagaggcacggggaatcccatcttactggatcgatagtgagaaacggataggacctgggaataaaatagcctat aagctccactatggagaactggtcgagaaggaaaactttctcccaaagggaccaataacaatcggtgtgacatcaggtgcatcaacc ccggataaggtcgtggaagatgctttggtgaaggtgttcgacattaaacgtgaagagttattgcagctggcttga

SEQ ID NO: 28

MAVALQFSRLCVRPDTFVRENHLSGSGSLRRRKALSVRCSSGDENAPSPSVVMDSD

FDAKVFRKNLTRSDNYNRKGFGHKEETLKLMNREYTSDILETLKTNGYTYSWGDV

TVKLAKAYGFCWGVERAVQIAYEARKQFPEERLWITNEIIHNPTVNKRLEDMDVKI

IPVEDSKKQFDVVEKDDVVILPAFGAGVDEMYVLNDKKVQIVDTTCPWVTKVWNT

VEKHKKGEYTSVIHGKYNHEETIATASFAGKYIIVKNMKEANYVCDYILGGQYDGS

SSTKEEFMEKFKYAISKGFDPDNDLVKVGIANQTTMLKGETEEIGRLLETTMMRKY

GVENVSGHFISFNTICDATQERQDAIYELVEEKIDLMLVVGGWNSSNTSHLQEISEA

RGIPSYWIDSEKRIGPGNKIAYKLHYGELVEKENFLPKGPITIGVTSGASTPDKVVED

ALVKVFDIKREELLQLA (*Escherichia coli* str. K12 substr. MG1655): isopentenyl diphosphate isomerase
h) IDI (Accession#NP_417365)(*ecoli*)

SEQ ID NO: 29 atgcaaacggaacacgtcattttattgaatgcacagggagttcccacgggtacgctggaaaagtatgccgcacacacggcagacac ccgcttacatctcgcgttctccagttggctgtttaatgccaaaggacaattattagttacccgccgcgcactgagcaaaaaagcatggc ctggcgtgtggactaactcggtttgtgggcacccacaactgggagaaagcaacgaagacgcagtgatccgccgttgccgttatgag cttggcgtggaaattacgcctcctgaatctatctatcctgactttcgctaccgcgccaccgatccgagtggcattgtggaaaatgaagt gtgtccggtatttgccgcacgcaccactagtgcgttacagatcaatgatgatgaagtgatggattatcaatggtgtgatttagcagatgt attacacggtattgatgccacgccgtgggcgttcagtccgtggatggtgatgcaggcgacaaatcgcgaagccagaaaacgattatc tgcatttacccagcttaaataa

SEQ ID NO: 30

MQTEHVILLNAQGVPTGTLEKYAAHTADTRLHLAFSSWLFNAKGQLLVTRRALSK

KAWPGVWTNSVCGHPQLGESNEDAVIRRCRYELGVEITPPESIYPDFRYRATDPSGI

VENEVCPVFAARTTSALQINDDEVMDYQWCDLADVLHGIDATPWAFSPWMVMQA

TNREARKRLSAFTQLK

IDI1 (*Saccharomyces cerevisiae*): Idi1p Chromosome XVI, NC_001148.3 (328728..327862)
Gene ID: 855986; Other Aliases: YPL117C, BOT2, LPH10; Other Designations:
Isopentenyl diphosphate:dimethylallyl diphosphate isomerase (IPP isomerase)
IDI (Accession# NP_015208)(scer)

SEQ ID NO: 31 atgactgccgacaacaatagtatgccccatggtgcagtatctagttacgccaaattagtgcaaaaccaaacacctgaagacattttgga agagtttcctgaaattattccattacaacaaagacctaatacccgatctagtgagacgtcaaatgacgaaagcggagaaacatgtttttc tggtcatgatgaggagcaaattaagttaatgaatgaaaattgtattgttttggattgggacgataatgctattggtgccggtaccaagaa agtttgtcatttaatggaaaatattgaaaagggtttactacatcgtgcattctccgtctttattttcaatgaacaaggtgaattacttttacaac aaagagccactgaaaaaataactttccctgatctttggactaacacatgctgctctcatccactatgtattgatgacgaattaggtttgaa gggtaagctagacgataagattaagggcgctattactgcggcggtgagaaaactagatcatgaattaggtattccagaagatgaaac taagacaaggggtaagtttcactttttaaacagaatccattacatggcaccaagcaatgaaccatggggtgaacatgaaattgattacat cctattttataagatcaacgctaaagaaaacttgactgtcaacccaaacgtcaatgaagttagagacttcaaatgggtttcaccaaatga tttgaaaactatgtttgctgacccaagttacaagtttacgccttggtttaagattatttgcgagaattacttattcaactggtgggagcaatt agatgacctttctgaagtggaaaatgacaggcaaattcatagaatgctataa

SEQ ID NO: 32

MTADNNSMPHGAVSSYAKLVQNQTPEDILEEFPEIIPLQQRPNTRSSETSNDESGETC

FSGHDEEQIKLMNENCIVLDWDDNAIGAGTKKVCHLMENIEKGLLHRAFSVFIFNE

-continued

QGELLLQQRATEKITFPDLWTNTCCSHPLCIDDELGLKGKLDDKIKGAITAAVRKLD

HELGIPEDETKTRGKFHFLNRIHYMAPSNEPWGEHEIDYILFYKINAKENLTVNPNV

NEVRDFKWVSPNDLKTMFADPSYKFTPWFKIICENYLFNWWEQLDDLSEVENDRQI

HRML geranyl diphosphate synthase [*Citrus sinensis*]
i)GPP synthase (Accession#CAC16851)(citsin)

SEQ ID NO: 33 atggttattgctgaggttcctaagcttgcctcagctgctgagtatttctttaaaatgggggtggaaggaaagaggttccgtcccacggttt tattgctgatggcaacagctctgaatgtgcgagtacctgaacctctacatgatggagtagaagatgcttcggcgactgaactacgtaca aggcaacaatgtatagctgagattacggagatgatccatgtagcaagccttcttcatgatgatgtcttggatgatgcagataccaggcg tggtattggttcattgaattttgtaatgggcaataagttagctgtattagcgggtgattttcttctttcccgtgcttgtgttgcccttgcctcttt gaaaaacacagaggttgtgacgttactggcaaccgttgtagagcatcttgttactggtgaaaccatgcaaatgacaacatcatctgacc aacgttgtagcatggattattatatgcaaaaaaacatactacaagaccgcatcattaatctcaaacagctgcaaggcaattgcccttcttg ctggacaaacagccgaagtggcaatattagcttttgattatggaaagaatctgggtctggcatatcaattaatcgacgatgttctcgattt cactggcacatcagcctctcttggaaagggttctttatctgacatccggcatggaatcataacagctccaatattgtttgccatggaaga gttccctcagttacgcacagtagttgagcaaggcttcgaggattcctcaaatgttgatattgcccttgagtaccttgggaagagtcgag ggatacaaaagacaagagaactggccgtgaagcatgctaatcttgctgcagctgcgattgattctctacctgaaaacaatgatgagga tgttacaaagtcaaggcgtgcacttttagatctcactcatagagtcatcacaagaaataaataa

SEQ ID NO: 34

MVIAEVPKLASAAEYFFKMGVEGKRFRPTVLLLMATALNVRVPEPLHDGVEDASA

TELRTRQQCIAEITEMIHVASLLHDDVLDDADTRRGIGSLNFVMGNKLAVLAGDFL

LSRACVALASLKNTEVVTLLATVVEHLVTGETMQMTTSSDQRCSMDYYMQKTYY

KTASLISNSCKAIALLAGQTAEVAILAFDYGKNLGLAYQLIDDVLDFTGTSASLGKG

SLSDIRHGIITAPILFAMEEFPQLRTVVEQGFEDSSNVDIALEYLGKSRGIQKTRELAV

KHANLAAAAIDSLPENNDEDVTKSRRALLDLTHRVITRNK (*Arabidopsis thaliana*): GPPS/GPS1 (GERANYLPYROPHOSPHATE SYNTHASE);
dimethylallyltranstransferase
GPP synthase (Accession# NM_001036406)(athal)

SEQ ID NO: 35 atgttattcacgaggagtgttgctcggatttcttctaagtttctgagaaaccgtagcttctatggctcctctcaatctctcgcctctcatcgg ttcgcaatcattcccgatcagggtcactcttgttctgactctccacacaagggttacgtttgcagaacaacttattcattgaaatctccggt ttttggtggatttagtcatcaactctatcaccagagtagctccttggttgaggaggagcttgacccattttcgcttgttgccgatgagctgt cacttcttagtaataagttgagagagatggtacttgccgaggttccaaagcttgcctctgctgctgagtacttcttcaaaaggggtgtgc aaggaaaacagtttcgttcaactattttgctgctgatggcgacagctctggatgtacgagttccagaagcattgattggggaatcaaca gatatagtcacatcagaattacgcgtaaggcaacggggtattgctgaaatcactgaaatgatacacgtcgcaagtctactgcacgatg atgtcttggatgatgccgatacaaggcgtggtgttggttccttaaatgttgtaatgggtaacaagatgtcggtattagcaggagacttctt gctctcccgggcttgtggggctctcgctgctttaaagaacacagaggttgtagcattacttgcaactgctgtagaacatcttgttaccgg tgaaaccatggagataactagttcaaccgagcagcgttatagtatggactactacatgcagaagacatattataagacagcatcgcta atctctaacagctgcaaagctgttgccgttctcactggacaaacagcagaagttgccgtgttagcttttgagtatgggaggaatctggg tttagcattccaattaatagacgacattcttgatttcacgggcacatctgcctctctcggaaagggatcgttgtcagatattcgccatgga gtcataacagccccaatcctctttgccatggaagagtttcctcaactacgcgaagttgttgatcaagttgaaaaagatcctaggaatgtt gacattgctttagagtatcttgggaagagcaagggaatacagagggcaagagaattagccatggaacatgcgaatctagcagcagc tgcaatcgggtctctacctgaaacagacaatgaagatgtcaaaagatcgaggcgggcacttattgacttgacccatagagtcatcacc agaaacaagtga

SEQ ID NO: 36

-continued

MLFTRSVARISSKFLRNRSFYGSSQSLASHRFAIIPDQGHSCSDSPHKGYVCRTTYSL

KSPVFGGFSHQLYHQSSSLVEEELDPFSLVADELSLLSNKLREMVLAEVPKLASAAE

YFFKRGVQGKQFRSTILLLMATALNVRVPEALIGESTDIVTSELRVRQRGIAEITEMI

HVASLLHDDVLDDADTRRGVGSLNVVMGNKMSVLAGDFLLSRACGALAALKNTE

VVALLATAVEHLVTGETMEITSSTEQRYSMDYYMQKTYYKTASLISNSCKAVAVL

TGQTAEVAVLAFEYGRNLGLAFQLIDDILDFTGTSASLGKGSLSDIRHGVITAPILFA

MEEFPQLREVVDQVEKDPRNVDIALEYLGKSKGIQRARELAMEHANLAAAAIGSLP

ETDNEDVKRSRRALIDLTHRVITRNK geraniol synthase [*Ocimum basilicum*]
j) GES (accession #AAR11765)(obas)

SEQ ID NO: 37 atgtcttgtgcacggatcaccgtaacattgccgtatcgctccgcaaaaacatcaattcaacggggaattacgcattaccccgcccttat acgcccacgcttctctgcttgcacgcctttggcatcggcgatgcctctaagttcaactcctctcatcaacggggataactctcagcgtaa aaacacacgtcaacacatggaggagagcagcagcaagaggagagaatatctgctggaggaaacgacgcgaaaactgcagagaa acgacaccgaatcggtggagaaactcaagcttatcgacaacatccaacagttgggaatcggctactattttgaggacgccatcaacg ccgtactccgctcgcctttctccaccggagaagaagacctcttcaccgctgctctgcgcttccgcttgctccgccacaacggcatcga aatcagccctgaaatattcctaaaattcaaggacgagaggggaaaattcgacgaatcggacacgctagggttactgagcttgtacga agcgtcaaatttgggggttgcaggagaagaaatattggaggaggctatggagtttgcggaggctcgcctgagacggtcgctgtcag agccggcggcgccgcttcatggtgaggtggcgcaagcgctagatgtgccgaggcatctgagaatggcgaggttggaagcgagac gattcatcgagcagtatggtaaacagagcgatcatgatggagatcttttggagctggcaattttggattataatcaagttcaggctcaac accaatccgaactcactgaaataatcaggtggtggaaggagctcggtttggtggataagttgagttttgggcgagacagaccattgg agtgctttttgtggaccgtggggctcctcccagagcccaagtattcgagcgttagaatagagttggcgaaagccatctctattctcttag tgatcgatgatattttcgatacctatggagagatggatgacctcatcctcttcaccgatgcaattcgaagatgggatcttgaagcaatgg aggggctccctgagtacatgaaaatatgctacatggcgttgtacaataccaccaatgaagtatgctacaaagtgctcagggatactgg acggattgtcctccttaacctcaaatctacgtggatagacatgattgaaggtttcatggaggaagcaaaatggttcaatggtggaagtg caccaaaattggaagagtatatagagaatggagtgtccacggcaggagcatacatggcttttgcacacatcttctttctcataggagaa ggtgttacacaccaaaattcccaactcttcacccaaaaaccctaccccaaggtcttctccgccgccggccgcattcttcgcctctggga tgatctcggaaccgccaaggaagagcaagagcgaggagatctggcttcgtgcgtgcagttatttatgaaagagaagtcgttgacgg aagaggaggcaagaagtcgcattttggaagagataaaaggattatggagggatctgaatggggaactggtctacaacaagaatttg ccgttatccataatcaaagtcgcacttaacatggcgagagcttctcaagttgtgtacaagcacgatcaagacacttatttttcaagcgta gacaattatgtggatgccctcttcttcactcaataa

SEQ ID NO: 38

MSCARITVTLPYRSAKTSIQRGITHYPALIRPRFSACTPLASAMPLSSTPLINGDNSQR

KNTRQHMEESSSKRREYLLEETTRKLQRNDTESVEKLKLIDNIQQLGIGYYFEDAIN

AVLRSPFSTGEEDLFTAALRFRLLRHNGIEISPEIFLKFKDERGKFDESDTLGLLSLYE

ASNLGVAGEEILEEAMEFAEARLRRSLSEPAAPLHGEVAQALDVPRHLRMARLEAR

RFIEQYGKQSDHDGDLLELAILDYNQVQAQHQSELTEIIRWWKELGLVDKLSFGRD

RPLECFLWTVGLLPEPKYSSVRIELAKAISILLVIDDIFDTYGEMDDLILFTDAIRRWD

LEAMEGLPEYMKICYMALYNTTNEVCYKVLRDTGRIVLLNLKSTWIDMIEGFMEE

AKWFNGGSAPKLEEYIENGVSTAGAYMAFAHIFFLIGEGVTHQNSQLFTQKPYPKV

FSAAGRILRLWDDLGTAKEEQERGDLASCVQLFMKEKSLTEEEARSRILEEIKGLWR

DLNGELVYNKNLPLSIIKVALNMARASQVVYKHDQDTYFSSVDNYVDALFFTQ geraniol synthase [*Cinnamomum tenuipile*]

-continued

GES (accession# CAD29734)(cinten)

SEQ ID NO: 39 atggcattgcaaatgattgctccatttctatcctccttcctaccaaatcccagacacagcctcgcagcccatggcctcacacaccagaa atgtgtctcaaagcacatttcatgctcaaccactacaccaacctactcaaccacagttccaagaagatcagggaactacaagcccagc atctgggactatgattttgtgcagtcactaggaagtggctacaaggtagaggcacatggaacacgtgtgaagaagttgaaggaggtt gtaaagcatttgttgaaagaaacagatagttctttggcccaaatagaactgattgacaaactacgtcgtctaggtctaaggtggctcttc aaaaatgagattaagcaagtgctatacacgatatcatcagacaacaccagcatagaaatgaggaaagatcttcatgcagtatcaactc gatttagacttcttagacaacatgggtacaaggtctccacagatgttttcaacgacttcaaagatgaaaagggttgtttcaagccaagcc tttcaatggacataaagggaatgttgagcttgtatgaggcttcacaccttgcctttcaaggggagactgtgttggatgaggcaagagct ttcgtaagcacacatctcatggatatcaaggagaacatagacccaatccttcataaaaaagtggagcatgctttggatatgcctttgcat tggaggttagaaaaattagaggctaggtggtacatggacatatacatgagggaagaaggcatgaattcttctttacttgaattggccat gcttcatttcaacattgtgcaaacaacattccaaacaaatttaaagagtttgagcaggtggtggaaagatttgggtcttggagagcagtt gagcttcactagagacaggttggtggaatgtttcttttgggccgccgcaatgacacctgagccacaatttggacgttgccaggaagtc gtagcgaaagttgctcaactcataataataattgacgatatctatgacgtgtatggtacggtggatgagctagaactttttactaatgcga ttgatagatgggatcttgaggcaatggagcagcttcctgaatatatgaagacctgtttcttagctttatacaacagtattaatgaaataggt tatgacattttgaaagaggaagggcgcaatgtcataccataccttagaaatacgtggacagaattgtgtaaagccttcttagtggaggc caaatggtatagtagtggatatacaccaacgcttgaggagtatctgcaaacctcatggatttcgattggaagtctacccatgcaaacat acgtttttgctctacttgggaaaaatctagcaccggagagtagtgattttgctgagaagatctcggatatcttacgattgggaggaatga tgattcgacttccggatgatttgggaacttcaacggatgaactaaagagaggtgatgttccaaaatccattcagtgttacatgcatgaag caggtgttacagaggatgttgctcgcgaccacataatgggtctatttcaagagacatggaaaaaactcaatgaataccttgtggaaagt tctcttccccatgcctttatcgatcatgctatgaatcttggacgtgtctcctattgcacttacaaacatggagatggatttagtgatggattt ggagatcctggcagtcaagagaaaaagatgttcatgtctttatttgctgaaccccttcaagttgatgaagccaagggtatttcattttatgt tgatggtggatctgcctaa

SEQ ID NO: 40

MALQMIAPFPSSFLPNPRHRLAAHGLTHQKCVSKHISCSTTTPTYSTTVPRRSGNYK

PSIWDYDFVQSLGSGYKVEAHGTRVKKLKEVVKHLLKETDSSLAQIELIDKLRRLG

LRWLFKNEIKQVLYTISSDNTSIEMRKDLHAVSTRFRLLRQHGYKVSTDVFNDFKD

EKGCFKPSLSMDIKGMLSLYEASHLAFQGETVLDEARAFVSTHLMDIKENIDPILHK

KVEHALDMPLHWRLEKLEARWYMDIYMREEGMNSSLLELAMLHFNIVQTTFQTN

LKSLSRWWKDLGLGEQLSFTRDRLVECFFWAAAMTPEPQFGRCQEAVAKVAQLIII

IDDIYDVYGTVDELELFTNAIDRWDLEAMEQLPEYMKTCFLALYNSINEIGYEILKE

EGRNVIPYLRNTWTELCKAFLVEAKWYSSGCTPTLEEYLQTSWISIGSLPMQTYVFA

LLGKNLAPESSDFAEKISDILRLGGMMIRLPDDLGTSTDELKRGDVPKSIQCYMHEA

GVTEDVARDHIMGLFQETWKKLNEYLVESSLPHAFIDHAMNLGRVSYCTYKHGDG

FSDGFGDPGSQEKKMFMSLFAEPLQVDEAKGISFYVDGGSA (*Saccharomyces cerevisiae*): Acetyl-CoA C-acetyltransferase (acetoacetyl-CoA thiolase)
m) erg10 (accession #NP_015297)(scer)

SEQ ID NO: 41 atgtctcagaacgtttacattgtatcgactgccagaaccccaattggttcattccagggttctctatcctccaagacagcagtggaattgg gtgctgttgctttaaaaggcgccttggctaaggttccagaattggatgcatccaaggattttgacgaaattatttttggtaacgttctttctg ccaatttgggccaagctccggccagacaagttgctttggctgccggtttgagtaatcatatcgttgcaagcacagttaacaaggtctgt gcatccgctatgaaggcaatcattttgggtgctcaatccatcaaatgtggtaatgctgatgttgtcgtagctggtggttgtgaatctatga ctaacgcaccatactacatgccagcagcccgtgcgggtgccaaatttggccaaactgttcttgttgatggtgtcgaaagagatgggtt gaacgatgcgtacgatggtctagccatgggtgtacacgcagaaaagtgtgcccgtgattgggatattactagagaacaacaagaca -continued attttgccatcgaatcctaccaaaaatctcaaaaatctcaaaaggaaggtaaattcgacaatgaaattgtacctgttaccattaagggatt tagaggtaagcctgatactcaagtcacgaaggacgaggaacctgctagattacacgttgaaaaattgagatctgcaaggactgttttc caaaaagaaaacggtactgttactgccgctaacgcttctccaatcaacgatggtgctgcagccgtcatcttggtttccgaaaaagttttg aaggaaaagaatttgaagcctttggctattatcaaaggttggggtgaggccgctcatcaaccagctgattttacatgggctccatctctt gcagttccaaaggctttgaaacatgctggcatcgaagacatcaattctgttgattactttgaattcaatgaagccttttcggttgtcggttt ggtgaacactaagattttgaagctagacccatctaaggttaatgtatatggtggtgctgttgctctaggtcacccattgggttgttctggt gctagagtggttgttacactgctatccatcttacagcaagaaggaggtaagatcggtgttgccgccatttgtaatggtggtggtggtgct tcctctattgtcattgaaaagatatga

SEQ ID NO: 42

MSQNVYIVSTARTPIGSFQGSLSSKTAVELGAVALKGALAKVPELDASKDFDEIIFG

NVLSANLGQAPARQVALAAGLSNHIVASTVNKVCASAMKAIILGAQSIKCGNADV

VVAGGCESMTNAPYYMPAARAGAKFGQTVLVDGVERDGLNDAYDGLAMGVHAE

KCARDWDITREQQDNFAIESYQKSQKSQKEGKFDNEIVPVTIKGFRGKPDTQVTKD

EEPARLHVEKLRSARTVFQKENGTVTAANASPINDGAAAVILVSEKVLKEKNLKPL

AIIKGWGEAAHQPADFTWAPSLAVPKALKHAGIEDINSVDYFEFNEAFSVVGLVNT

KILKLDPSKVNVYGGAVALGHPLGCSGARVVVTLLSILQQEGGKIGVAAICNGGGG

ASSIVIEKI (*Saccharomyces cerevisiae*): Acetyl-CoA C-acetyltransferase (acetoacetyl-CoA thiolase)
Thiolase (accession # XP_965702)(ncra)

SEQ ID NO: 43 atgtctaccggtcttccctccgtctacatcgtttctgccgccagaacccctgtggggtccttccttggtcagctttccagcctctctgctgt tcagctcggtgcccatgccatcaagtctgccgttgaccgcgttcccgaaatcaaggccgaggatgttgaggaggtcttctttggcaat gtcctctctgctggtgtcggtcaggctcctgcccgccagtgcgccctgaaggccggtctctcgaacaaggtggttgccaccaccgtc aacaaggtgtgcgcttccggcatgaaggccatcatccttggcgcccagaccatcatgactggcaatgcagacatcgttgtcgctggc ggcaccgagagcatgtccaacgtcccccactatatgcagaacctccgcactggtgtcaagtacggcgacggcggccttgtcgacg gtatccagtccgacggtctccgtgatgcatatggcaaggagctcatgggtgttcaggccgagctctgcgccaaggaccatgaactg agccgtgaggcccaggacgagtatgccatcaactcgtaccagaaggcccaggccgccaccgaggctggtctgttcaaggagattg cacctatcgaggtcccgggtggccgcggcaagcctgccatcaagattgaccgcgatgaggaggtcaagaacctcaacatcgagaa gctcaagtccgcccgtaccgtcttccaggccaaggacggtaccgtcactgctcccaacgcctcccccatcaacgatggcgccgctg ccgttgttcttgtctccgaggctaagctcaaggagcttggtatcaagcccatcgccaagatccttggctggggcgatgctgctcacga gcctgagcgcttcacaactgccccggctcttgccattcccaaggccatcaagcatgccggtatcaaggaggaggacgttgacttcta cgagatcaatgaggctttctctgttgttgcccttgccaacatgaaaatccttggcctcgagcccgagaaggtcaacgtctatggtggct ccgttgccatcggccaccctcttggctgctccggtgctcgtgttgtcactaccctcacctccgtcttggctgagaagaaggccaggatt ggctgcgctggtatctgcaacggtggcggtggtgcttctgccatcgttatcgaaaacttgcagtaa

SEQ ID NO: 44

MSTGLPSVYIVSAARTPVGSFLGQLSSLSAVQLGAHAIKSAVDRVPEIKAEDVEEVF

FGNVLSAGVGQAPARQCALKAGLSNKVVATTVNKVCASGMKAIILGAQTIMTGNA

DIVVAGGTESMSNVPHYMQNLRTGVKYGDGGLVDGIQSDGLRDAYGKELMGVQA

ELCAKDHELSREAQDEYAINSYQKAQAATEAGLFKEIAPIEVPGGRGKPAIKIDRDE

EVKNLNIEKLKSARTVFQAKDGTVTAPNASPINDGAAAVVLVSEAKLKELGIKPIAK

ILGWGDAAHEPERFTTAPALAIPKAIKHAGIKEEDVDFYEINEAFSVVALANMKILG

LEPEKVNVYGGSVAIGHPLGCSGARVVTTLTSVLAEKKARIGCAGICNGGGGASAI

VIENLQ

-continued (*Saccharomyces cerevisiae*): 3-hydroxy-3-methylglutaryl-CoA (HMG-CoA) synthase
n) erg13 (accession # NP_013580)(scer)

SEQ ID NO: 45 atgaaactctcaactaaactttgttggtgtggtattaaaggaagacttaggccgcaaaagcaacaacaattacacaatacaaacttgca aatgactgaactaaaaaaacaaaagaccgctgaacaaaaaaccagacctcaaaatgtcggtattaaaggtatccaaatttacatccca actcaatgtgtcaaccaatctgagctagagaaatttgatggcgtttctcaaggtaaatacacaattggtctgggccaaaccaacatgtct tttgtcaatgacagagaagatatctactcgatgtccctaactgttttgtctaagttgatcaagagttacaacatcgacaccaacaaaattg gtagattagaagtcggtactgaaactctgattgacaagtccaagtctgtcaagtctgtcttgatgcaattgtttggtgaaaacactgacgt cgaaggtattgacacgcttaatgcctgttacggtggtaccaacgcgttgttcaactctttgaactggattgaatctaacgcatgggatgg tagagacgccattgtagtttgcggtgatattgccatctacgataagggtgccgcaagaccaaccggtggtgccggtactgttgctatgt ggatcggtcctgatgctccaattgtatttgactctgtaagagcttcttacatggaacacgcctacgatttttacaagccagatttcaccag cgaatatccttacgtcgatggtcatttttcattaacttgttacgtcaaggctcttgatcaagtttacaagagttattccaagaaggctatttct aaagggttggttagcgatcccgctggttcggatgctttgaacgttttgaaatatttcgactacaacgttttccatgttccaacctgtaaatt ggtcacaaaatcatacggtagattactatataacgatttcagagccaatcctcaattgttcccagaagttgacgccgaattagctactcg cgattatgacgaatctttaaccgataagaacattgaaaaaacttttgttaatgttgctaagccattccacaaagagagagttgcccaatct ttgattgttccaacaaacacaggtaacatgtacaccgcatctgtttatgccgcctttgcatctctattaaactatgttggatctgacgactta caaggcaagcgtgttggtttattttcttacggttccggtttagctgcatctctatattcttgcaaaattgttggtgacgtccaacatattatca aggaattagatattactaacaaattagccaagagaatcaccgaaactccaaaggattacgaagctgccatcgaattgagagaaaatg cccatttgaagaagaacttcaaacctcaaggttccattgagcatttgcaaagtggtgtttactacttgaccaacatcgatgacaaatttag aagatcttacgatgttaaaaaataa

SEQ ID NO: 46

MKLSTKLCWCGIKGRLRPQKQQQLHNTNLQMTELKKQKTAEQKTRPQNVGIKGIQ

IYIPTQCVNQSELEKFDGVSQGKYTIGLGQTNMSFVNDREDIYSMSLTVLSKLIKSY

NIDTNKIGRLEVGTETLIDKSKSVKSVLMQLFGENTDVEGIDTLNACYGGTNALFNS

LNWIESNAWDGRDAIVVCGDIAIYDKGAARPTGGAGTVAMWIGPDAPIVFDSVRAS

YMEHAYDFYKPDFTSEYPYVDGHFSLTCYVKALDQVYKSYSKKAISKGLVSDPAG

SDALNVLKYFDYNVFHVPTCKLVTKSYGRLLYNDFRANPQLFPEVDAELATRDYD

ESLTDKNIEKTFVNVAKPFHKERVAQSLIVPTNTGNMYTASVYAAFASLLNYVGSD

DLQGKRVGLFSYGSGLAASLYSCKIVGDVQHIIKELDITNKLAKRITETPKDYEAAIE

LRENAHLKKNFKPQGSIEHLQSGVYYLTNIDDKFRRSYDVKK (*Staphylococcus aureus* subsp. *aureus* N315): 3-hydroxy-3-methylglutaryl CoA synthase
mvaS (accession # NP_375658)(saur)

SEQ ID NO: 47 atgacaataggtatcgacaaaataaacttttacgttccaaagtactatgtagacatggctaaattagcagaagcacgccaagtagaccc aaacaaatttttaattggaattggtcaaactgaaatggctgttagtcctgtaaaccaagacatcgtttcaatgggcgctaacgctgctaag gacattataacagacgaagataaaaagaaaattggtatggtaattgtggcaactgaatcagcagttgatgctgctaaagcagccgctg ttcaaattcacaacttattaggtattcaaccttttgcacgttgctttgaaatgaaagaagcttgttatgctgcaacaccagcaattcaattag ctaaagattatttagcaactagaccgaatgaaaaagtattagttattgctacagatacagcacgttatggattgaattcaggcggcgagc caacacaaggtgctggcgcagttgcgatggttattgcacataatccaagcattttggcattaaatgaagatgctgttgcttacactgaag acgtttatgatttctggcgtccaactggacataaatatccattagttgatggtgcattatctaaagatgcttatatccgctcattccaacaaa gctggaatgaatacgcaaaacgtcaaggtaagtcgctagctgacttcgcatctctatgcttccatgttccatttacaaaaatgggtaaaa aggcattagagtcaatcattgataacgctgatgaaacaactcaagagcgtttacgttcaggatatgaagatgctgtagattataaccgtt atgtcggtaatatttatactggatcattatatttaagcctaatatcattacttgaaaatcgtgatttacaagctggtgaaacaatcggtttattc agttatggctcaggttcagttggtgaattttatagtgcgacattagttgaaggctacaaagatcatttagatcaagctgcacataaagcat -continued tattaaataaccgtactgaagtatctgttgatgcatatgaaacattcttcaaacgttttgatgacgttgaatttgacgaagaacaagatgct gttcatgaagatcgtcatattttctacttatcaaatattgaaaataacgttcgcgaatatcacagaccagagtaa

SEQ ID NO: 48

MTIGIDKINFYVPKYYVDMAKLAEARQVDPNKFLIGIGQTEMAVSPVNQDIVSMGA

NAAKDIITDEDKKKIGMVIVATESAVDAAKAAAVQIHNLLGIQPFARCFEMKEACY

AATPAIQLAKDYLATRPNEKVLVIATDTARYGLNSGGEPTQGAGAVAMVIAHNPSI

LALNEDAVAYTEDVYDFWRPTGHKYPLVDGALSKDAYIRSFQQSWNEYAKRQGK

SLADFASLCFHVPFTKMGKKALESIIDNADETTQERLRSGYEDAVDYNRYVGNIYT

GSLYLSLISLLENRDLQAGETIGLFSYGSGSVGEFYSATLVEGYKDHLDQAAHKALL

NNRTEVSVDAYETFFKRFDDVEFDEEQDAVHEDRHIFYLSNIENNVREYHRPE (*Saccharomyces cerevisiae*): Hmg1p
Chromosome XIII, NC_001145.2 (118897 . . . 115733) Gene ID: 854900; Other Aliases:
YML075C; Other Designations: One of two isozymes of HMG-CoA reductase that
catalyzes the conversion
o) hmg1 (accession # NP_013636)(scer)

SEQ ID NO: 49 atgccgccgctattcaagggactgaaacagatggcaaagccaattgcctatgtttcaagattttcggcgaaacgaccaattcatataat actttttctctaatcatatccgcattcgcttatctatccgtcattcagtattacttcaatggttggcaactagattcaaatagtgtttttgaaact gctccaaataaagactccaacactctatttcaagaatgttcccattactacagagattcctctctagatggttgggtatcaatcaccgcgc atgaagctagtgagttaccagccccacaccattactatctattaaacctgaacttcaatagtcctaatgaaactgactccattccagaact agctaacacggtttttgagaaagataatacaaaatatattctgcaagaagatctcagtgtttccaaagaaatttcttctactgatggaacg aaatggaggttaagaagtgacagaaaaagtcttttcgacgtaaagacgttagcatattctctctacgatgtattttcagaaaatgtaaccc aagcagacccgtttgacgtccttattatggttactgcctacctaatgatgttctacaccatattcggcctcttcaatgacatgaggaagac cgggtcaaatttttggttgagcgcctctacagtggtcaattctgcatcatcacttttcttagcattgtatgtcacccaatgtattctaggcaa agaagtttccgcattaactcttttgaaggtttgcctttcattgtagttgttgttggtttcaagcacaaaatcaagattgcccagtatgccctg gagaaatttgaaagagtcggtttatctaaaaggattactaccgatgaaatcgtttttgaatccgtgagcgaagagggtggtcgtttgatt caagaccatttgctttgtatttttgcctttatcggatgctctatgtatgctcaccaattgaagactttgacaaacttctgcatattatcagcattt atcctaatttttgaattgattttaactcctacatttttattctgctatcttagcgcttagactggaaatgaatgttatccacagatctactattatca agcaaacattagaagaagacggtgttgttccatctacagcaagaatcatttctaaagcagaaaagaaatccgtatcttctttcttaaatct cagtgtggttgtcattatcatgaaactctctgtcatactgttgtttgtcttcatcaacttttataactttggtgcaaattgggtcaatgatgcctt caattcattgtacttcgataaggaacgtgtttctctaccagattttattacctcgaatgcctctgaaaactttaaagagcaagctattgttagt gtcaccccattattatattacaaacccattaagtcctaccaacgcattgaggatatggttcttctattgcttcgtaatgtcagtgttgccattc gtgataggttcgtcagtaaattagttctttccgccttagtatgcagtgctgtcatcaatgtgtatttattgaatgctgctagaattcataccag ttatactgcagaccaattggtgaaaactgaagtcaccaagaagtcttttactgctcctgtacaaaaggcttctacaccagttttaaccaat aaaacagtcatttctggatcgaaagtcaaaagtttatcatctgcgcaatcgagctcatcaggaccttcatcatctagtgaggaagatgat tcccgcgatattgaaagcttggataagaaaatacgtcctttagaagaattagaagcattattaagtagtggaaatacaaaacaattgaag aacaaagaggtcgctgccttggttattcacggtaagttacctttgtacgctttggagaaaaaattaggtgatactacgagagcggttgc ggtacgtaggaaggctctttcaattttggcagaagctcctgtattagcatctgatcgtttaccatataaaaattatgactacgaccgcgtat ttggcgcttgttgtgaaaatgttataggttacatgcctttgcccgttggtgttataggccccttggttatcgatggtacatcttatcatatacc aatggcaactacagagggttgtttggtagcttctgccatgcgtggctgtaaggcaatcaatgctggcggtggtgcaacaactgttttaa ctaaggatggtatgacaagaggcccagtagtccgtttcccaactttgaaaagatctggtgcctgtaagatatggttagactcagaaga gggacaaaacgcaattaaaaaagcttttaactctacatcaagatttgcacgtctgcaacatattcaaacttgtctagcaggagatttactc ttcatgagatttagaacaactactggtgacgcaatgggtatgaatatgatttctaaaggtgtcgaatactcattaaagcaaatggtagaa gagtatggctgggaagatatggaggttgtctccgtttctggtaactactgtaccgacaaaaaaccagctgccatcaactggatcgaag -continued gtcgtggtaagagtgtcgtcgcagaagctactattcctggtgatgttgtcagaaaagtgttaaaaagtgatgtttccgcattggttgagtt gaacattgctaagaatttggttggatctgcaatggctgggtctgttggtggatttaacgcacatgcagctaatttagtgacagctgttttct tggcattaggacaagatcctgcacaaaatgttgaaagttccaactgtataacattgatgaaagaagtggacggtgatttgagaatttcc gtatccatgccatccatcgaagtaggtaccatcggtggtggtactgttctagaaccacaaggtgccatgttggacttattaggtgtaag aggcccgcatgctaccgctcctggtaccaacgcacgtcaattagcaagaatagttgcctgtgccgtcttggcaggtgaattatccttat gtgctgccctagcagccggccatttggttcaaagtcatatgacccacaacaggaaacctgctgaaccaacaaaacctaacaatttgg acgccactgatataaatcgtttgaaagatgggtccgtcacctgcattaaatcctaa

SEQ ID NO: 50

MPPLFKGLKQMAKPIAYVSRFSAKRPIHIILFSLIISAFAYLSVIQYYFNGWQLDSNSV

FETAPNKDSNTLFQECSHYYRDSSLDGWVSITAHEASELPAPHHYYLLNLNFNSPNE

TDSIPELANTVFEKDNTKYILQEDLSVSKEISSTDGTKWRLRSDRKSLFDVKTLAYSL

YDVFSENVTQADPFDVLIMVTAYLMMFYTIFGLFNDMRKTGSNFWLSASTVVNSA

SSLFLALYVTQCILGKEVSALTLFEGLPFIVVVVGFKHKIKIAQYALEKFERVGLSKR

ITTDEIVFESVSEEGGRLIQDHLLCIFAFIGCSMYAHQLKTLTNFCILSAFILIFELILTP

TFYSAILALRLEMNVIHRSTIIKQTLEEDGVVPSTARIISKAEKKSVSSFLNLSVVVIIM

KLSVILLFVFINFYNFGANWVNDAFNSLYFDKERVSLPDFITSNASENFKEQAIVSVT

PLLYYKPIKSYQRIEDMVLLLLRNVSVAIRDRFVSKLVLSALVCSAVINVYLLNAARI

HTSYTADQLVKTEVTKKSFTAPVQKASTPVLTNKTVISGSKVKSLSSAQSSSSGPSSS

SEEDDSRDIESLDKKIRPLEELEALLSSGNTKQLKNKEVAALVIHGKLPLYALEKKL

GDTTRAVAVRRKALSILAEAPVLASDRLPYKNYDYDRVFGACCENVIGYMPLPVG

VIGPLVIDGTSYHIPMATTEGCLVASAMRGCKAINAGGGATTVLTKDGMTRGPVVR

FPTLKRSGACKIWLDSEEGQNAIKKAFNSTSRFARLQHIQTCLAGDLLFMRFRTTTG

DAMGMNMISKGVEYSLKQMVEEYGWEDMEVVSVSGNYCTDKKPAAINWIEGRG

KSVVAEATIPGDVVRKVLKSDVSALVELNIAKNLVGSAMAGSVGGFNAHAANLVT

AVFLALGQDPAQNVESSNCITLMKEVDGDLRISVSMPSIEVGTIGGGTVLEPQGAML

DLLGVRGPHATAPGTNARQLARIVACAVLAGELSLCAALAAGHLVQSHMTHNRKP

AEPTKPNNLDATDINRLKDGSVTCIKS mvaA (*Staphylococcus aureus* subsp. *aureus* N315): hydroxymethylglutaryl-CoA reductase
mvaA (accession # NP_375657)(saur)

SEQ ID NO: 51 atgcaaagtttagataagaatttccgacatttatctcgtcaacaaaagttacaacaattggtagataagcaatggttatcagaagatcaat tcgacattttattgaatcatccattaattgatgaggaagtagcaaatagtttaattgaaaatgtcatcgcgcaaggtgcattacccgttgga ttattaccgaatatcattgtggacgataaggcatatgttgtacctatgatggtggaagagccttcagttgtcgctgcagctagttatggtg caaagctagtgaatcagactggcggatttaaaacggtatcttctgaacgtattatgataggtcaaatcgtctttgatggcgttgacgata ctgaaaaattatcagcagacattaaagctttagaaaagcaaattcataaaattgcggatgaggcatatccttctattaaagcgcgtggtg gtggttaccaacgtatagctattgatacatttcctgagcaacagttactatctttaaaagtatttgttgatacgaaagatgctatgggcgct aatatgcttaatacgattttagaggccataactgcatttttaaaaaatgaatctccacaaagcgacattttaatgagtattttatccaatcatg caacagcgtccgttgttaaagttcaaggcgaaattgacgttaaagatttagcaagggggcgagagaactggagaagaggttgccaaa cgaatggaacgtgcttctgtattggcacaagttgatattcatcgtgctgcaacacataataaaggtgttatgaatggcatacatgccgtt gttttagcaacaggaaatgatacgcgtggtgcagaagcaagtgcgcatgcatacgcgagtcgtgacggacagtatcgtggtattgca acatggagatacgatcaaaaacgtcaacgtttaattggtacaatagaagtgcctatgacattggcaatcgttggcggtggtacaaaagt attaccaattgctaaagcttctttagaattgctaaatgtagattcagcacaagaattaggtcatgtagttgctgccgttggtttagcacaga -continued actttgcagcatgtcgcgcgctcgtttccgaaggtatccagcaaggccatatgagcttgcaatataaatctttagctattgttgtaggtgc aaaaggtgatgaaattgcgcaagtagctgaagcattgaagcaagaaccccgtgcgaatacacaagtagctgaacgcattttacaaga aattagacaacaatag

SEQ ID NO: 52

MQSLDKNFRHLSRQQKLQQLVDKQWLSEDQFDILLNHPLIDEEVANSLIENVIAQG

ALPVGLLPNIIVDDKAYVVPMMVEEPSVVAAASYGAKLVNQTGGFKTVSSERIMIG

QIVFDGVDDTEKLSADIKALEKQIHKIADEAYPSIKARGGGYQRIAIDTFPEQQLLSL

KVFVDTKDAMGANMLNTILEAITAFLKNESPQSDILMSILSNHATASVVKVQGEIDV

KDLARGERTGEEVAKRMERASVLAQVDIHRAATHNKGVMNGIHAVVLATGNDTR

GAEASAHAYASRDGQYRGIATWRYDQKRQRLIGTIEVPMTLAIVGGGTKVLPIAKA

SLELLNVDSAQELGHVVAAVGLAQNFAACRALVSEGIQQGHMSLQYKSLAIVVGA

KGDEIAQVAEALKQEPRANTQVAERILQEIRQQ

ERG12 (*Saccharomyces cerevisiae*): Erg12p Chromosome XIII, NC_001145.2 (684465 . . . 685796)
Gene ID: 855248; Other Aliases: YMR208W, RAR1; Other Designations:
Mevalonate kinase
p) erg12 (accession# NP_013935)(scer)

SEQ ID NO: 53 atgtcattaccgttcttaacttctgcaccgggaaaggttattatttttggtgaacactctgctgtgtacaacaagcctgccgtcgctgctag tgtgtctgcgttgagaacctacctgctaataagcgagtcatctgcaccagatactattgaattggacttcccggacattagctttaatcat aagtggtccatcaatgatttcaatgccatcaccgaggatcaagtaaactcccaaaaattggccaaggctcaacaagccaccgatggc ttgtctcaggaactcgttagtcttttggatccgttgttagctcaactatccgaatccttccactaccatgcagcgttttgtttcctgtatatgttt gtttgcctatgccccccatgccaagaatattaagtttttctttaaagtctactttacccatcggtgctgggttgggctcaagcgcctctatttct gtatcactggccttagctatggcctacttggggggggttaataggatctaatgacttggaaaagctgtcagaaaacgataagcatatagt gaatcaatgggccttcataggtgaaaagtgtattcacggtaccccttcaggaatagataacgctgtggccacttatggtaatgccctgc tatttgaaaaagactcacataatggaacaataaacacaaacaattttaagttcttagatgatttcccagccattccaatgatcctaacctat actagaattccaaggtctacaaaagatcttgttgctcgcgttcgtgtgttggtcaccgagaaatttcctgaagttatgaagccaattctag atgccatgggtgaatgtgccctacaaggcttagagatcatgactaagttaagtaaatgtaaaggcaccgatgacgaggctgtagaaa ctaataatgaactgtatgaacaactattggaattgataagaataaatcatggactgcttgtctcaatcggtgtttctcatcctggattagaa cttattaaaaatctgagcgatgatttgagaattggctccacaaaacttaccggtgctggtggcggcggttgctctttgactttgttacgaa gagacattactcaagagcaaattgacagcttcaaaaagaaattgcaagatgattttagttacgagacatttgaaacagacttgggtggg actggctgctgtttgttaagcgcaaaaaatttgaataaagatcttaaaatcaaatccctagtattccaattatttgaaaataaaactaccac aaagcaacaaattgacgatctattattgccaggaaacacgaatttaccatggacttcataa

SEQ ID NO: 54

MSLPFLTSAPGKVIIFGEHSAVYNKPAVAASVSALRTYLLISESSAPDTIELDFPDISF

NHKWSINDFNAITEDQVNSQKLAKAQQATDGLSQELVSLLDPLLAQLSESFHYHAA

FCFLYMFVCLCPHAKNIKFSLKSTLPIGAGLGSSASISVSLALAMAYLGGLIGSNDLE

KLSENDKHIVNQWAFIGEKCIHGTPSGIDNAVATYGNALLFEKDSHNGTINTNNFKF

LDDFPAIPMILTYTRIPRSTKDLVARVRVLVTEKFPEVMKPILDAMGECALQGLEIM

TKLSKCKGTDDEAVETNNELYEQLLELIRINHGLLVSIGVSHPGLELIKNLSDDLRIG

STKLTGAGGGGCSLTLLRRDITQEQIDSFKKKLQDDFSYETFETDLGGTGCCLLSAK

NLNKDLKIKSLVFQLFENKTTTKQQIDDLLLPGNTNLPWTS (*Staphylococcus aureus* subsp. *aureus* N315): mevalonate kinase
mvaK1 (accession # NP_373801)(saur)

SEQ ID NO: 55 atgcagtaccgtttaacgcaggtaaaatcaaagttttaatagaagccttagagagcgggaactattcgtctattaaaagcgatgtttacg atggtatgttatatgatgcgcctgaccatcttaagtctttggtgaaccgttttgtagaattaaataatattacagagccgctagcagtaacg -continued atccaaacgaatttaccaccatcacgtggattaggatcgagtgcagctgtcgcggttgcttttgttcgtgcaagttatgatttttaggga aatcattaacgaaagaagaactcattgaaaaggctaattgggcagagcaaattgcacatggtaaaccaagtggtattgatacgcaaac gattgtatcaggcaaaccagtttggttccaaaaaggtcatgctgaaacattgaaaacgttaagtttagacggctatatggttgttattgat actggtgtgaaaggttcaacaagacaagcggtagaagatgttcataaactttgtgaggatcctcagtacatgtcacatgtaaaacatat cggtaagttagttttacgtgcgagtgatgtgattgaacatcataactttgaagccctagcggatatttttaatgaatgtcatgcggatttaa aggcgttgacagttagtcatgataaaatagaacaattaatgaaaattggtaaagaaaatggtgcgattgctggaaaacttactggtgct ggtcgtggtggaagtatgttattgcttgccaaagatttaccaacagcgaaaaatattgtgaaagctgtagaaaaagctggtgcagcac atacatggattgagaatttaggaggttaa

SEQ ID NO: 56

MAVPFNAGKIKVLIEALESGNYSSIKSDVYDGMLYDAPDHLKSLVNRFVELNNITEP

LAVTIQTNLPPSRGLGSSAAVAVAFVRASYDFLGKSLTKEELIEKANWAEQIAHGKP

SGIDTQTIVSGKPVWFQKGHAETLKTLSLDGYMVVIDTGVKGSTRQAVEDVHKLCE

DPQYMSHVKHIGKLVLRASDVIEHHNFEALADIFNECHADLKALTVSHDKIEQLMK

IGKENGAIAGKLTGAGRGGSMLLLAKDLPTAKNIVKAVEKAGAAHTWIENLGG

ERG8 (*Saccharomyces cerevisiae*): Erg8p
Chromosome XIII, NC_001145.2 (712314 . . . 713669) Gene ID: 855260; Other Aliases: YMR220W; Other Designations: Phosphomevalonate kinase
q) erg8 (accession# NP_013947)(scer)

SEQ ID NO: 57 atgtcagagttgagagccttcagtgccccagggaaagcgttactagctggtggatatttagttttagatacaaaatatgaagcatttgta gtcggattatcggcaagaatgcatgctgtagcccatccttacggttcattgcaagggtctgataagtttgaagtgcgtgtgaaaagtaa acaatttaaagatggggagtggctgtaccatataagtcctaaaagtggcttcattcctgtttcgataggcggatctaagaaccctttcatt gaaaaagttatcgctaacgtatttagctactttaaacctaacatggacgactactgcaatagaaacttgttcgttattgatattttctctgatg atgcctaccattctcaggaggatagcgttaccgaacatcgtggcaacagaagattgagttttcattcgcacagaattgaagaagttccc aaaacagggctgggctcctcggcaggtttagtcacagttttaactacagctttggcctcctttttttgtatcggacctggaaaataatgtag acaaatatagagaagttattcataatttagcacaagttgctcattgtcaagctcagggtaaaattggaagcgggtttgatgtagcggcg gcagcatatggatctatcagatatagaagattcccacccgcattaatctctaatttgccagatattggaagtgctacttacggcagtaaa ctggcgcatttggttgatgaagaagactggaatattacgattaaaagtaaccatttaccttcgggattaactttatggatgggcgatatta agaatggttcagaaacagtaaaactggtccagaaggtaaaaaattggtatgattcgcatatgccagaaagcttgaaaatatatacaga actcgatcatgcaaattctagatttatggatggactatctaaactagatcgcttacacgagactcatgacgattacagcgatcagatattt gagtctcttgagaggaatgactgtacctgtcaaaagtatcctgaaatcacagaagttagagatgcagttgccacaattagacgttccttt agaaaaataactaaagaatctggtgccgatatcgaacctcccgtacaaactagcttattggatgattgccagaccttaaaaggagttctt acttgcttaatacctggtgctggtggttatgacgccattgcagtgattactaagcaagatgttgatcttagggctcaaaccgctaatgac aaaagattttctaaggttcaatggctggatgtaactcaggctgactggggtgttaggaaagaaaaagatccggaaacttatcttgataa ataa

SEQ ID NO: 58

MSELRAFSAPGKALLAGGYLVLDTKYEAFVVGLSARMHAVAHPYGSLQGSDKFEV

RVKSKQFKDGEWLYHISPKSGFIPVSIGGSKNPFIEKVIANVFSYFKPNMDDYCNRN

LFVIDIFSDDAYHSQEDSVTEHRGNRRLSFHSHRIEEVPKTGLGSSAGLVTVLTTALA

SFFVSDLENNVDKYREVIHNLAQVAHCQAQGKIGSGFDVAAAAYGSIRYRRFPPALI

SNLPDIGSATYGSKLAHLVDEEDWNITIKSNHLPSGLTLWMGDIKNGSETVKLVQK

VKNWYDSHMPESLKIYTELDHANSRFMDGLSKLDRLHETHDDYSDQIFESLERNDC

TCQKYPEITEVRDAVATIRRSFRKITKESGADIEPPVQTSLLDDCQTLKGVLTCLIPG

AGGYDAIAVITKQDVDLRAQTANDKRFSKVQWLDVTQADWGVRKEKDPETYLDK (*Staphylococcus aureus* subsp. *aureus* N315): phosphomevalonate kinase
mvaK2 (accession # NP_373803)(saur)

SEQ ID NO: 59 atgattcaggtcaaagcacccggaaaactttatattgctggagaatatgctgtaacagaaccaggatataaatctgtacttattgcgttag atcgttttgtaactgctactattgaagaagcagaccaatataaaggtaccattcattcaaaagcattacatcataacccagttacatttagt agagatgaagatagtattgtcatttcagatccacatgcagcaaaacaattaaattatgtggtcacagctattgaaatatttgaacaatacg cgaaaagttgcgatatagcgatgaagcattttcatctgactattgatagtaatttagatgattcaaatggtcataaatatggattaggttca agtgcagcagtacttgtgtcagttataaaagtattaaatgaattttatgatatgaagttatctaatttatacatttataaactagcagtgattgc aaatatgaagttacaaagtttaagttcatgcggagatattgctgtgagtgtatatagtggatggttagcgtatagtacttttgatcatgaat gggttaagcatcaaattgaagatactacggttgaagaagttttaatcaaaaactggcctggattgcacatcgaaccattacaagcacct gaaaatatggaagtacttatcggttggactggctcaccggcgtcatcaccacactttgttagcgaagtgaaacgtttgaaatcagatcct tcattttacggtgacttcttagaagattcacatcgttgtgttgaaaagcttattcatgcttttaaaacaaataacattaaaggtgtgcaaaag atggtgcgtcagaatcgtacaattattcaacgtatggataaagaagctacagttgatatagaaactgaaaagctaaaatatttgtgtgata ttgctgaaaagtatcacggtgcatctaaaacatcaggcgctggtggtggagactgtggtattacaattatcaataaagatgtagataaa gaaaaaatttatgatgaatggacaaaacatggtattaaaccattaaaatttaatatttatcatgggcaataa

SEQ ID NO: 60

MIQVKAPGKLYIAGEYAVTEPGYKSVLIALDRFVTATIEEADQYKGTIHSKALHHNP

VTFSRDEDSIVISDPHAAKQLNYVVTAIEIFEQYAKSCDIAMKHFHLTIDSNLDDSNG

HKYGLGSSAAVLVSVIKVLNEFYDMKLSNLYIYKLAVIANMKLQSLSSCGDIAVSV

YSGWLAYSTFDHEWVKHQIEDTTVEEVLIKNWPGLHIEPLQAPENMEVLIGWTGSP

ASSPHFVSEVKRLKSDPSFYGDFLEDSHRCVEKLIHAFKTNNIKGVQKMVRQNRTII

QRMDKEATVDIETEKLKYLCDIAEKYHGASKTSGAGGGDCGITIINKDVDKEKIYD

EWTKHGIKPLKFNIYHGQ

*Saccharomyces cerevisiae*): Mevalonate pyrophosphate decarboxylase
r) mvd1 (accession# NP_014441)(scer)

SEQ ID NO: 61 atgaccgtttacacagcatccgttaccgcacccgtcaacatcgcaacccttaagtattgggggaaaagggacacgaagttgaatctg cccaccaattcgtccatatcagtgactttatcgcaagatgacctcagaacgttgacctctgcggctactgcacctgagtttgaacgcga cactttgtggttaaatggagaaccacacagcatcgacaatgaaagaactcaaaattgtctgcgcgacctacgccaattaagaaagga aatggaatcgaaggacgcctcattgcccacattatctcaatggaaactccacattgtctccgaaaataactttcctacagcagctggttt agcttcctccgctgctggctttgctgcattggtctctgcaattgctaagttataccaattaccacagtcaacttcagaaatatctagaatag caagaaaggggtctggttcagcttgtagatcgttgtttggcggatacgtggcctgggaaatgggaaaagctgaagatggtcatgattc catggcagtacaaatcgcagacagctctgactggcctcagatgaaagcttgtgtcctagttgtcagcgatattaaaaaggatgtgagtt ccactcagggtatgcaattgaccgtggcaacctccgaactatttaaagaaagaattgaacatgtcgtaccaaagagatttgaagtcatg cgtaaagccattgttgaaaaagatttcgccacctttgcaaaggaaacaatgatggattccaactctttccatgccacatgtttggactcttt ccctccaatattctacatgaatgacacttccaagcgtatcatcagttggtgccacaccattaatcagttttacggagaaacaatcgttgca tacacgtttgatgcaggtccaaatgctgtgttgtactacttagctgaaaatgagtcgaaactctttgcatttatctataaattgtttggctctg ttcctggatgggacaagaaatttactactgagcagcttgaggctttcaaccatcaatttgaatcatctaactttactgcacgtgaattggat cttgagttgcaaaaggatgttgccagagtgattttaactcaagtcggttcaggcccacaagaaacaaacgaatctttgattgacgcaaa gactggtctaccaaaggaataa

SEQ ID NO: 62

MTVYTASVTAPVNIATLKYWGKRDTKLNLPTNSSISVTLSQDDLRTLTSAATAPEFE

RDTLWLNGEPHSIDNERTQNCLRDLRQLRKEMESKDASLPTLSQWKLHIVSENNFP

TAAGLASSAAGFAALVSAIAKLYQLPQSTSEISRIARKGSGSACRSLFGGYVAWEM

-continued

GKAEDGHDSMAVQIADSSDWPQMKACVLVVSDIKKDVSSTQGMQLTVATSELFKE

RIEHVVPKRFEVMRKAIVEKDFATFAKETMMDSNSFHATCLDSFPPIFYMNDTSKRI

ISWCHTINQFYGETIVAYTFDAGPNAVLYYLAENESKLFAFIYKLFGSVPGWDKKFT

TEQLEAFNHQFESSNFTARELDLELQKDVARVILTQVGSGPQETNESLIDAKTGLPKE

*Staphylococcus aureus* subsp. *aureus* N315): mevalonate diphosphate decarboxylase
mvaD (accession # NP_373802)(saur)

SEQ ID NO: 63 ttgattaaaagtggcaaagcacgtgcacatacgaatattgcacttataaaatattggggtaaaaaagatgaagcactaatcattccaatg aataatagcatatctgttacattagaaaaattttacactgaaacgaaagtcacttttaacgaccagttaacacaggatcaattttggttgaa tggtgaaaaggttagtggcaaagaattagagaaaatttcaaaatatatggatattgtcagaaatagagctggcatcgattggtatgctg aaattgaaagcgacaattttgtaccaacagcagcagggttggcttcatcagcaagcgcatatgcagctttagcagcagcttgtaatcaa gcactagacttgcagctgtcagataaggatttatcgagattggcgcgaattggttcgggttctgcgtcgcgtagtatttatggtggatttg cagaatgggaaaaagggtataatgatgagacgtcatatgccgttccacttgaatcgaatcattttgaagatgaccttgccatgatatttgt tgtgattaatcaacattctaaaaaggtacctagtcgatatggtatgtcgttgacacgaaacacatcaaggttttatcaatattggttagatc atattgatgaagatttagctgaagcaaaagcagcgattcaagacaaagattttaaacgccttggtgaagtaattgaagaaaatggtttac gtatgcatgccacgaatctgggatcaacaccgccgttcacttatcttgtgcaagaaagttatgatgtcatggcgctcgttcacgaatgcc gagaagcgggatatccgtgttattttacgatggatgcgggtcctaatgtgaaaatacttgtagaaaagaaaaacaagcaacagattata gataaattattaacacagtttgataataaccaaattattgatagtgacattattgccacaggaattgaaataattgagtaa

SEQ ID NO: 64

MIKSGKARAHTNIALIKYWGKKDEALIIPMNNSISVTLEKFYTETKVTFNDQLTQDQ

FWLNGEKVSGKELEKISKYMDIVRNRAGIDWYAEIESDNFVPTAAGLASSASAYAA

LAAACNQALDLQLSDKDLSRLARIGSGSASRSIYGGFAEWEKGYNDETSYAVPLES

NHFEDDLAMIFVVINQHSKKVPSRYGMSLTRNTSRFYQYWLDHIDEDLAEAKAAIQ

DKDFKRLGEVIEENGLRMHATNLGSTPPFTYLVQESYDVMALVHECREAGYPCYFT

MDAGPNVKILVEKKNKQQIIDKLLTQFDNNQIIDSDIIATGIEIIE

*Saccharomyces cerevisiae*): Bat1p
Chromosome VIII, NC_001140.5 (517531 . . . 518712)
Gene ID: 856615; Other Aliases: YHR208W, ECA39, TWT1; Other Designations:
Mitochondrial branched-chain amino acid
s) Bat1 (accession # NP_012078)(scer)

SEQ ID NO: 65 atgttgcagagacattccttgaagttggggaaattctccatcagaacactcgctactggtgccccattagatgcatccaaactaaaaatt actagaaacccaaatccatccaagccaagaccaaatgaagaattagtgttcggccagacattcaccgatcatatgttgaccattccttg gtcagccaaagaagggtggggcactccacacatcaagccttacggtaatctttctcttgacccatctgcttgtgtattccattatgcattt gaattatttgaaggtttgaaagcctacagaactcctcaaaatactatcaccatgttccgtccggataagaacatggcccgtatgaacaa gtctgccgctagaatttgtttgccaactttcgaatctgaagaattgatcaaacttaccgggaaattgatcgaacaagataaacacttggtt cctcaaggtaatggttactcattatacatcagaccaacaatgattggtacatccaagggtttaggtgttggcactccctccgaggctcttc tttatgttattacttctccagtcggtccttattataagactggtttcaaagccgtacgtcttgaagcaacagactatgctacaagagcttgg ccaggtggtgttggcgacaaaaaattgggtgctaactatgccccatgcatcttacctcaactacaagctgccaaaagagggtaccaa caaaatctatggttgttcggcccagaaaagaacatcactgaggttggtactatgaacgtgttcttcgttttcctcaacaaagtcactggca agaaggaattggttaccgctccattagatggtaccattttagaaggtgttaccagagactctgttttaacattggctcgtgacaaactaga tcctcaagaatgggacatcaacgagcgttattacactattactgaagtcgccactagagcaaaacaaggtgaactattagaagccttc ggttctggtactgctgctgtcgtttcacctatcaaggaaattggctggaacaacgaagatattcatgttccactattgcctggtgaacaat gtggtgcattgaccaagcaagttgctcaatggattgctgatatccaatacggtagagtcaattatggtaactggtcaaaaactgttgccg acttgaactaa

SEQ ID NO: 66

-continued

MLQRHSLKLGKFSIRTLATGAPLDASKLKITRNPNPSKPRPNEELVFGQTFTDHMLTI
PWSAKEGWGTPHIKPYGNLSLDPSACVFHYAFELFEGLKAYRTPQNTITMFRPDKN
MARMNKSAARICLPTFESEELIKLTGKLIEQDKHLVPQGNGYSLYIRPTMIGTSKGL
GVGTPSEALLYVITSPVGPYYKTGFKAVRLEATDYATRAWPGGVGDKKLGANYAP
CILPQLQAAKRGYQQNLWLFGPEKNITEVGTMNVFFVFLNKVTGKKELVTAPLDGT
ILEGVTRDSVLTLARDKLDPQEWDINERYYTITEVATRAKQGELLEAFGSGTAAVV
SPIKEIGWNNEDIHVPLLPGEQCGALTKQVAQWIADIQYGRVNYGNWSKTVADLN ilvE (accession # YP_026247)(*ecoli*)

SEQ ID NO: 67 atgaccacgaagaaagctgattacatttggttcaatggggagatggttcgctgggaagacgcgaaggtgcatgtgatgtcgcacgc
gctgcactatggcacttcggtttttgaaggcatccgttgctacgactcgcacaaaggaccggttgtattccgccatcgtgagcatatgc
agcgtctgcatgactccgccaaaatctatcgcttcccggtttcgcagagcattgatgagctgatggaagcttgtcgtgacgtgatccgc
aaaaacaatctcaccagcgcctatatccgtccgctgatcttcgtcggtgatgttggcatgggagtaaacccgccagcgggatactcaa
ccgacgtgattatcgctgctttcccgtggggagcgtatctgggcgcagaagcgctggagcaggggatcgatgcgatggtttcctcct
ggaaccgcgcagcaccaaacaccatcccgacggcggcaaaagccggtggtaactacctctcttccctgctggtgggtagcgaagc
gcgccgccacggttatcaggaaggtatcgcgctggatgtgaacggttatatctctgaaggcgcaggcgaaaacctgtttgaagtgaa
agatggtgtgctgttcaccccaccgttcacctcctccgcgctgccgggtattacccgtgatgccatcatcaaactggcgaaagagctg
ggaattgaagtacgtgagcaggtgctgtcgcgcgaatccctgtacctggcggatgaagtgtttatgtccggtacggcggcagaaatc
acgccagtgcgcagcgtagacggtattcaggttggcgaaggccgttgtggcccggttaccaaacgcattcagcaagccttcttcgg
cctcttcactggcgaaaccgaagataaatggggctggttagatcaagttaatcaataa

SEQ ID NO: 68

MTTKKADYIWFNGEMVRWEDAKVHVMSHALHYGTSVFEGIRCYDSHKGPVVFRH
REHMQRLHDSAKIYRFPVSQSIDELMEACRDVIRKNNLTSAYIRPLIFVGDVGMGVN
PPAGYSTDVIIAAFPWGAYLGAEALEQGIDAMVSSWNRAAPNTIPTAAKAGGNYLS
SLLVGSEARRHGYQEGIALDVNGYISEGAGENLFEVKDGVLFTPPFTSSALPGITRD
AIIKLAKELGIEVREQVLSRESLYLADEVFMSGTAAEITPVRSVDGIQVGEGRCGPVT
KRIQQAFFGLFTGETEDKWGWLDQVNQ branched chain dehydrogenase E1 beta subunit (accession # NP_390284)(bsub)

SEQ ID NO: 69 atgtcagtaatgtcatatattgatgcaatcaatttggcgatgaaagaagaaatggaacgagattctcgcgttttcgtccttggggaagat
gtaggaagaaaaggcggtgtgtttaaagcgacagcgggactctatgaacaatttggggaagagcgcgttatggatacgccgcttgc
tgaatctgcaatcgcaggagtcggtatcggagcggcaatgtacggaatgagaccgattgctgaaatgcagtttgctgatttcattatgc
cggcagtcaaccaaattatttctgaagcggctaaaatccgctaccgcagcaacaatgactggagctgtccgattgtcgtcagagcgc
catacggcggaggcgtgcacggagccctgtatcattctcaatcagtcgaagcaattttcgccaaccagcccggactgaaaattgtcat
gccatcaacaccatatgacgcgaaagggctcttaaaagccgcagttcgtgacgaagaccccgtgctgtttttttgagcacaagcgggc
ataccgtctgataaagggcgaggttccggctgatgattatgtcctgccaatcggcaaggcggacgtaaaaagggaaggcgacgac
atcacagtgatcacatacggcctgtgtgtccacttcgccttacaagctgcagaacgtctcgaaaaagatggcatttcagcgcatgtggt
ggatttaagaacagtttacccgcttgataaagaagccatcatcgaagctgcgtccaaaactggaaaggttcttttggtcacagaagata
caaaagaaggcagcatcatgagcgaagtagccgcaattatatccgagcattgtctgttcgacttagacgcgccgatcaaacggcttg
caggtcctgatattccggctatgccttatgcgccgacaatggaaaaatactttatggtcaaccctgataaagtggaagcggcgatgag
agaattagcggagttttaa

SEQ ID NO: 70

MSVMSYIDAINLAMKEEMERDSRVFVLGEDVGRKGGVFKATAGLYEQFGEERVM
DTPLAESAIAGVGIGAAMYGMRPIAEMQFADFIMPAVNQIISEAAKIRYRSNNDWSC

-continued

PIVVRAPYGGGVHGALYHSQSVEAIFANQPGLKIVMPSTPYDAKGLLKAAVRDEDP

VLFFEHKRAYRLIKGEVPADDYVLPIGKADVKREGDDITVITYGLCVHFALQAAER

LEKDGISAHVVDLRTVYPLDKEAIIEAASKTGKVLLVTEDTKEGSIMSEVAAIISEHC

LFDLDAPIKRLAGPDIPAMPYAPTMEKYFMVNPDKVEAAMRELAEF (*Bacillus subtilis* subsp. *subtilis* str. 168): branched-chain alpha-keto acid dehydrogenase E1 subunit (2-oxoisovalerate
branched chain dehydrogenase E1 alpha subunit (accession # NP_390284)(bsub)

SEQ ID NO: 71 atgtcagtaatgtcatatattgatgcaatcaatttggcgatgaaagaagaaatggaacgagattctcgcgttttcgtccttggggaagat gtaggaagaaaaggcggtgtgtttaaagcgacagcgggactctatgaacaatttggggaagagcgcgttatggatacgccgcttgc tgaatctgcaatcgcaggagtcggtatcggagcggcaatgtacggaatgagaccgattgctgaaatgcagtttgctgatttcattatgc cggcagtcaaccaaattatttctgaagcggctaaaatccgctaccgcagcaacaatgactggagctgtccgattgtcgtcagagcgc catacggcggaggcgtgcacggagccctgtatcattctcaatcagtcgaagcaattttcgccaaccagcccggactgaaaattgtcat gccatcaacaccatatgacgcgaaagggctcttaaaagccgcagttcgtgacgaagaccccgtgctgtttttgagcacaagcgggc ataccgtctgataaagggcgaggttccggctgatgattatgtcctgccaatcggcaaggcggacgtaaaaagggaaggcgacgac atcacagtgatcacatacggcctgtgtgtccacttcgccttacaagctgcagaacgtctcgaaaaagatggcatttcagcgcatgtggt ggatttaagaacagtttacccgcttgataaagaagccatcatcgaagctgcgtccaaaactggaaaggttcttttggtcacagaagata caaaagaaggcagcatcatgagcgaagtagccgcaattatatccgagcattgtctgttcgacttagacgcgccgatcaaacggcttg caggtcctgatattccggctatgccttatgcgccgacaatggaaaaatactttatggtcaaccctgataaagtggaagcggcgatgag agaattagcggagttttaa

SEQ ID NO: 72

MSVMSYIDAINLAMKEEMERDSRVFVLGEDVGRKGGVFKATAGLYEQFGEERVM

DTPLAESAIAGVGIGAAMYGMRPIAEMQFADFIMPAVNQIISEAAKIRYRSNNDWSC

PIVVRAPYGGGVHGALYHSQSVEAIFANQPGLKIVMPSTPYDAKGLLKAAVRDEDP

VLFFEHKRAYRLIKGEVPADDYVLPIGKADVKREGDDITVITYGLCVHFALQAAER

LEKDGISAHVVDLRTVYPLDKEAIIEAASKTGKVLLVTEDTKEGSIMSEVAAIISEHC

LFDLDAPIKRLAGPDIPAMPYAPTMEKYFMVNPDKVEAAMRELAEF (*Bacillus subtilis* subsp. *subtilis* str. 168): dihydrolipoamide dehydrogenase
Dihydrolipoamide dehydrogenase (accession # NP_390286)(bsub)

SEQ ID NO: 73 atggcaactgagtatgacgtagtcattctgggcggcggtaccggcggttatgttgcggccatcagagccgctcagctcggcttaaaa acagccgttgtggaaaaggaaaaactcgggggaacatgtctgcataaaggctgtatcccgagtaaagcgctgcttagaagcgcaga ggtataccggacagctcgtgaagccgatcaattcggagtggaaacggctggcgtgtccctcaactttgaaaaagtgcagcagcgta agcaagccgttgttgataagcttgcagcgggtgtaaatcatttaatgaaaaaggaaaaattgacgtgtacaccggatatggacgtatc cttggaccgtcaatcttctctccgctgccgggaacaatttctgttgagcggggaaatggcgaagaaaatgacatgctgatcccgaaac aagtgatcattgcaacaggatcaagaccgagaatgcttccgggtcttgaagtggacggtaagtctgtactgacttcagatgaggcgct ccaaatggaggagctgccacagtcaatcatcattgtcggcggaggggttatcggtatcgaatgggcgtctatgcttcatgattttggcg ttaaggtaacggttattgaatacgcggatcgcatattgccgactgaagatctagagatttcaaaagaaatggaaagtcttcttaagaaaa aaggcatccagttcataacaggggcaaaagtgctgcctgacacaatgacaaaaacatcagacgatatcagcatacaagcggaaaa agacggagaaaccgttacctattctgctgagaaaatgcttgtttccatcggcagacaggcaaatatcgaaggcatcggcctagagaa caccgatattgttactgaaaatggcatgatttcagtcaatgaaagctgccaaacgaaggaatctcatatttatgcaatcggagacgtaat cggtggcctgcagttagctcacgttgcttcacatgagggaattattgctgttgagcattttgcaggtctcaatccgcatccgcttgatccg acgcttgtgccgaagtgcatttactcaagccctgaagctgccagtgtcggcttaaccgaagacgaagcaaaggcgaacgggcataa tgtcaaaatcggcaagttcccatttatggcgattggaaaagcgcttgtatacggtgaaagcgacggttttgtcaaaatcgtggctgacc -continued gagatacagatgatattctcggcgttcatatgattggcccgcatgtcaccgacatgatttctgaagcgggtcttgccaaagtgctggac gcaacaccgtgggaggtcgggcaaacgatttcacccgcatccaacgctttctga

SEQ ID NO: 74

MATEYDVVILGGGTGGYVAAIRAAQLGLKTAVVEKEKLGGTCLHKGCIPSKALLR

SAEVYRTAREADQFGVETAGVSLNFEKVQQRKQAVVDKLAAGVNHLMKKGKIDV

YTGYGRILGPSIFSPLPGTISVERGNGEENDMLIPKQVIIATGSRPRMLPGLEVDGKSV

LTSDEALQMEELPQSIIIVGGGVIGIEWASMLHDFGVKVTVIEYADRILPTEDLEISKE

MESLLKKKGIQFITGAKVLPDTMTKTSDDISIQAEKDGETVTYSAEKMLVSIGRQAN

IEGIGLENTDIVTENGMISVNESCQTKESHIYAIGDVIGGLQLAHVASHEGIIAVEHFA

GLNPHPLDPTLVPKCIYSSPEAASVGLTEDEAKANGHNVKIGKFPFMAIGKALVYGE

SDGFVKIVADRDTDDILGVHMIGPHVTDMISEAGLAKVLDATPWEVGQTISPASNAF (*Pseudomonas entomophila* L48): branched-chain alpha-keto acid dehydrogenase subunit E2
2-methylpropanoyl-CoA:enzyme-N6-(dihydrolipoyl)lysine *S*-(2-methylpropanoyl)transferase (accession # YP_609357)(pento)

SEQ ID NO: 75 atgggcacgcacgtcatcaagatgccggacattggcgaaggcatcgcgcaggtcgagttggtggaatggttcgtcaaggtcggcg atgtgatcgccgaggaccaggtggtggccgatgtcatgaccgacaaggccactgtggaaatcccttcgccggtcagcggcaaggt gctggccctgggtggccagccgggtgaagtgatggcggtcggcagcgagctgatccgcatcgaggtcgaaggcagcggcaacc atgtcgacacgccgcagaccaagccggccgagcctgcacctgcgccggtcaaagccgaagccaagcccgaggcgcgcctcga agcgcaaccgcaggcaagcaccagccataccgccgcccccatcgtgccgcgtgaggcccacgacaaaccactggcctcccctg ccgtgcgcaagcgcgccctggacgccgggatcgagctgcgctacgtgcatggcagcggcccggccgggcgcatcctgcatgaa gacctcgacgccttcatcagcaagccgcagaccagcgccggccaggcgccgggcggttacggcaagcgcaccgacagcgagc aggtgccggtgatcggcctgcgccgcaagatcgcccagcgcatgcaggacgccaagcgccgtgtcgcccacttcagctacgtcg aggaaatcgacgtcaccaacctggaagccctgcgccagcagctcaacgccaagcatggcgacagccgcggcaagctgaccctg ctgccgttcctggtgcgcgccatggtcgtcgccctgcgcgatttcccgcagatcaacgccacctacgatgacgaagcccaggtcatc acccgccacggcgcggtgcatgtgggcatcgccacccaaggcgacaacggcctgatggtaccggtactgcgccacgccgaagc cggcagcctgtggagcaatgccagcgagatcgcccgcgtcgcccatgccgcgcgcaacaacaaggccacccgcgaagaactgt ccggctcgaccatcaccttgaccagcctcggcgcgctgggtggcatcgtcagcaccccggtggtcaacaccccggaagtggcgat cgtcggcgtcaaccgcatggtcgagcggccgatggtgatcgacggccagatcgtcgtgcgcaagatgatgaacctgtccagctcg ttcgaccaccgcgtggtcgacggcatggacgccgccctgttcatccaggccgtgcgcggcctgctggaacagcctgcctgcctgtt cgtggagtga

SEQ ID NO: 76

MGTHVIKMPDIGEGIAQVELVEWFVKVGDVIAEDQVVADVMTDKATVEIPSPVSG

KVLALGGQPGEVMAVGSELIRIEVEGSGNHVDTPQTKPAEPAPAPVKAEAKPEARL

EAQPQASTSHTAAPIVPREAHDKPLASPAVRKRALDAGIELRYVHGSGPAGRILHED

LDAFISKPQTSAGQAPGGYGKRTDSEQVPVIGLRRKIAQRMQDAKRRVAHFSYVEE

IDVTNLEALRQQLNAKHGDSRGKLTLLPFLVRAMVVALRDFPQINATYDDEAQVIT

RHGAVHVGIATQGDNGLMVPVLRHAEAGSLWSNASEIARVAHAARNNKATREELS

GSTITLTSLGALGGIVSTPVVNTPEVAIVGVNRMVERPMVIDGQIVVRKMMNLSSSF

DHRVVDGMDAALFIQAVRGLLEQPACLFVE (*Arabidopsis thaliana*): BCDH BETA1 (BRANCHED-CHAIN ALPHA-KETO ACID DECARBOXYLASE E1 BETA SUBUNIT);
branched chain dehydrogenase E1 beta subunit (accession # NP_175947)(athal)

SEQ ID NO: 77 atggcggctcttttaggcagatcctgccggaaactgagttttccgagcttgagtcacggagctaggagggtatcgacggaaactgga -continued aaaccattgaatctatactctgctattaatcaagcgcttcacatcgctttggacaccgatcctcggtcttatgtctttggggaagacgttgg ctttggtggagtctttcgctgtacaacaggtttagctgaacgattcgggaaaaaccgtgtcttcaatactcctctttgtgagcagggcatt gttggatttggcattggtctagcagcaatgggtaatcgagcaattgtagagattcagtttgcagattatatatatcctgcttttgatcagatt gttaatgaagctgcaaagttcagataccgaagtggtaaccaattcaactgtggaggacttacgataagagcaccatatggagcagttg gtcatggtggacattaccattcacaatcccctgaagctttcttttgccatgtccctggtattaaggttgttatccctcggagtccacgagaa gcaaagggactgttgttgtcatgtatccgtgatccaaatcccgttgttttcttcgaaccaaagtggctgtatcgtcaagcagtagaagaa gtccctgagcatgactatatgataccttttatcagaagcagaggttataagagaaggcaatgacattacactggttggatggggagctc agcttaccgttatggaacaagcttgtctggacgcggaaaaggaaggaatatcatgtgaactgatagatctcaagacactgcttccttgg gacaaagaaaccgttgaggcttcagttaaaaagactggcagacttcttataagccatgaagctcctgtaacaggaggttttggagcag agatctctgcaacaattctggaacgttgcttttttgaagttagaagctccagtaagcagagtttgtggtctggatactccatttcctcttgtgt ttgaaccattctacatgcccaccaagaacaagatattggatgcaatcaaatcgactgtgaattactag

SEQ ID NO: 78

MAALLGRSCRKLSFPSLSHGARRVSTETGKPLNLYSAINQALHIALDTDPRSYVFGE

DVGFGGVFRCTTGLAERFGKNRVFNTPLCEQGIVGFGIGLAAMGNRAIVEIQFADYI

YPAFDQIVNEAAKFRYRSGNQFNCGGLTIRAPYGAVGHGGHYHSQSPEAFFCHVPG

IKVVIPRSPREAKGLLLSCIRDPNPVVFFEPKWLYRQAVEEVPEHDYMIPLSEAEVIR

EGNDITLVGWGAQLTVMEQACLDAEKEGISCELIDLKTLLPWDKETVEASVKKTGR

LLISHEAPVTGGFGAEISATILERCFLKLEAPVSRVCGLDTPFPLVFEPFYMPTKNKIL

DAIKSTVNY (*Arabidopsis thaliana*): 2-oxoisovalerate dehydrogenase, putative/3-methyl-2-
oxobutanoate dehydrogenase
branched chain dehydrogenase E1 alpha subunit (accession # NP_568209)(athal)

SEQ ID NO: 79 atggctctgcatttgagatcttcttttcatcaaaatcgactttactcaatattctcagacacaacctcggtttcggttctaggagccacgtg actcggcatatccgccaaatcctaccacatgacccccgcttcgaggttcacagaatccaattagccgtctctgtaataccatggcgg agccagagacactctctagttttgttcagcacgaatacgccaacaatcatcaggtaatggactttccaggaggaaaggtagctttcaca cctgagattcaattcatatcagaatctgataaagagcgtgttccttgctaccgtgttcttgatgacaatggccaacttatcaccaacagcc agtttgttcaggttagcgaggaggttgcggtgaagatatatagcgatatggttactcttcaaattatggataacatattctacgaagctca aagacaaggcagactttccttttacgctactgcaatcggtgaagaggccattaatattgcatcagctgctgctctcactcctcaagatgtt atctttcctcagtacagagagcctggtgttctactatggcgtggtttcacgcttcaagaatttgcaaaccagtgttttgggaacaaatctg attatggaaaaggcaggcagatgcccgtccactatggctctaacaagctcaattattttaccgtttctgcaaccattgctacgcagttac caaacgcggttggtgctgcttattccttaaagatggacaagaaggatgcatgtgcggtcacatattttggcgatggtggcacgagtga gggagatttccatgctgctttgaatattgcagcagttatggaagctcctgttttatttatttgccggaacaatggatgggccatcagtactc ccacctcagatcagttccgaagtgatggtgtagtggtcaaaggccgtgcttatggaattcgaagtatacgtgtggatggaaatgatgc acttgccatgtacagtgcggtacatactgctcgcgaaatggcaattagagaacagaggccaatcttgattgaggccttaacataccgt gtaggacaccattcaacatcagatgattccactaggtaccgctctgcaggtgagatagagtggtggaacaaagcaagaaacccact gtctaggtttaggacatggattgaaagtaatggctggtggagtgataaaacggaatcggatctgagaagcagaatcaaaaaagagat gttagaagcgctccgggttgcagagaagactgagaaaccgaatctgcagaacatgttctcagatgtctacgatgttcctccatctaac ctcagggaacaagaacttctggtgaggcagacgatcaatagtcacccacaagattacccatcagatgtgcctctttag

SEQ ID NO: 80

MALHLRSSFSSKSTLLNILRHNLGFGSRSHVTRHIRQILPHDPPLRGSQNPISRLCNTM

AEPETLSSFVQHEYANNHQVMDFPGGKVAFTPEIQFISESDKERVPCYRVLDDNGQ

LITNSQFVQVSEEVAVKIYSDMVTLQIMDNIFYEAQRQGRLSFYATAIGEEAINIASA

AALTPQDVIFPQYREPGVLLWRGFTLQEFANQCFGNKSDYGKGRQMPVHYGSNKL

-continued

NYFTVSATIATQLPNAVGAAYSLKMDKKDACAVTYFGDGGTSEGDFHAALNIAAV

MEAPVLFICRNNGWAISTPTSDQFRSDGVVVKGRAYGIRSIRVDGNDALAMYSAVH

TAREMAIREQRPILIEALTYRVGHHSTSDDSTRYRSAGEIEWWNKARNPLSRFRTWI

ESNGWWSDKTESDLRSRIKKEMLEALRVAEKTEKPNLQNMFSDVYDVPPSNLREQ

ELLVRQTINSHPQDYPSDVPL (*Arabidopsis thaliana*): LPD1 (LIPOAMIDE DEHYDROGENASE 1)
lipoamide dehydrogenase (accession # NP_001078165)(athal)

SEQ ID NO: 81 atgcaatcagctatggcgctttcgttctcccagacgtcgtttacaagaccaaaccacgtgctcggatcatctggttctgttttctctacgc ccagaagtctccggttctgcggactccggcgggaagcgtttggtttctcaacgtcgaatcagttggctattcgcagtaaccgaatcca atttctaagtaggaagtcattccaagtctccgcttctgcttcaagtaatggtaatggcgctccaccgaaatctttcgattacgatttgatcat catcggagctggagttggtggccacggagctgctttgcacgccgttgaaaagggacttaaaacagccattattgaaggagatgttgtt ggagggacttgtgttaacagaggatgtgtgccttctaaagctcttcttgctgttagtggtcgaatgcgggaacttcagaacgaacatca catgaagtcctttggtctccaggtttcagctgctggatatgatcgtcagggtgtggcagatcatgctaataatctggctaccaaaatacg aaacaatctgaccaattcaatgaaggcaattggtgttgacatattgactggatttggcagtgttctgggtccacaaaaggttaaatatgg gaaggacaatattattactgcaaaagatataatcattgccactggatctgtgccgtttgtccctaaaggaattgaagttgatggaaagac tgtgatcaccagtgaccatgctttgaaattagagtctgtccctgagtggattgcaattgtaggaagtggttatattggtcttgagttcagtg atgtttacacagctcttggaagtgaggtaacttttatagaagcactggatcagctaatgcctggatttgatcctgagatcagtaagctag ctcagagggttttgataaatccaagaaagattgactatcatactggagtctttgcaagcaaaattactccggcaagggatgggaaacc agttctgattgagcttattgatgccaaaaccaaggaacctaaggatactttggaggtagatgctgctcttattgctactgggagagctcc attcaccaatggacttggcttggaaaatgtcaatgttgtgacgcagagaggtttcataccagttgatgagcgaatgcgtgtgatcgatg gaaaggggactctggttccgaacttgtactgcattggtgatgccaatggtaaattgatgcttgcacatgcagccagtgcccaaggaatt tctgtggtcgagcaagtcagcggcagagatcatgtgcttaatcatcttagcatcccagctgcttgctttactcatcctgaaatcagcatg gtgggattaacagagcctcaagcaaaagaaaaaggcgagaaggaaggatttaaagttagtgttgtcaagacaagtttcaaggctaac acaaaggccctagctgaaaatgaaggagaaggaatagctaagatgatataccgacctgacaatggtgaaatcttaggagttcatatat ttggactgcatgcagctgaccttatccatgaagcttctaatgcgattgctctaggaacgcgtattcaggacataaaattggcagttcatg cacatccaacactctctgaggtcctcgacgaactgttcaaagcagccaaggttgaaagtcatgctacgacaaggacaggagatgca aagataaagctaaacacgaaccaggaagatcgaaaaggaagaagaagaggaggagatgatgagaaacaaccttccgtaagtaaa gacttgaaagatatatctacaaggccttcttctttctttgagaatatttctgttggagtcttgtctctgctttcacttatatttgtttaa

SEQ ID NO: 82

MQSAMALSFSQTSFTRPNHVLGSSGSVFSTPRSLRFCGLRREAFGFSTSNQLAIRSNR

IQFLSRKSFQVSASASSNGNGAPPKSFDYDLIIIGAGVGGHGAALHAVEKGLKTAIIE

GDVVGGTCVNRGCVPSKALLAVSGRMRELQNEHHMKSFGLQVSAAGYDRQGVA

DHANNLATKIRNNLTNSMKAIGVDILTGFGSVLGPQKVKYGKDNIITAKDIIIATGSV

PFVPKGIEVDGKTVITSDHALKLESVPEWIAIVGSGYIGLEFSDVYTALGSEVTFIEAL

DQLMPGFDPEISKLAQRVLINPRKIDYHTGVFASKITPARDGKPVLIELIDAKTKEPK

DTLEVDAALIATGRAPFTNGLGLENVNVVTQRGFIPVDERMRVIDGKGTLVPNLYCI

GDANGKLMLAHAASAQGISVVEQVSGRDHVLNHLSIPAACFTHPEISMVGLTEPQA

KEKGEKEGFKVSVVKTSFKANTKALAENEGEGIAKMIYRPDNGEILGVHIFGLHAA

DLIHEASNAIALGTRIQDIKLAVHAHPTLSEVLDELFKAAKVESHATTRTGDAKIKL

NTNQEDRKGRRRGGDDEKQPSVSKDLKDISTRPSSFFENISVGVLSLLSLIFV (*Ralstonia eutropha* H16): branched-chain alpha-keto acid dehydrogenase subunit E2
2-methylpropanoyl-CoA: enzyme-N6-(dihydrolipoyl)lysine S-(2-

-continued methylpropanoyl)transferase (accession # YP_841747)(reutro)

SEQ ID NO: 83 atgagaatcttcaagctgcccgacctgggcgaaggcctgcaggaggccgagatcgtgacctggcacgtcaagaccggcgacacc gtggccgctgaccagccgctgctgtcggtggagacggccaaggccatcgtggaaatcccgtcgccctatgcaggcaccatcgcca agctgtttgcgcagcccggcgatatcgtccacctgggcgcgccgctggtcggcgtcgagggtgcgggcgaggatgccgacgccg gcaccgtggtgggctcggtccaggtcggcacgcacgtggtcaatgaagccgcgcccgcgggctccgcggcacccgccgcggc catggccgcccgcgtcaaggccacgccggcggtgcgcgcgctggcgcgccggctcggggtggacctggcaatggccacggca tcgggccccgagggcgtcgtcaccgccgccgacgtggagcgggtagccagcacgctggccgaactgggcacgccggaacagc tgcgcggcgtgcgccgggcgatggcgcagaacatggcgcgtgcacaagccgaagtggccgccgccaccgtgatggacgacgc cgacatccacgcctggcagcccggcgccgatgtcaccatccggctggtgcgcgccctggtggccggctgccgcgccgaacccg gcctcaatgcctggtacgaaggccagaccgcccgccgccacgtactgaagaagatcgacgtcggcatcgcggccgacctgcccg aaggcctgttcgtgccggtgctgcgcgacgtcggcaaccgcgatgccgcagacctgcgccacggcctggaccgcatgcgcgccg acatccgcgcgcgcaccatcgcgccggaggagatgcgcggcaacaccatcacgctgtccaacttcggcatgatcgcggggcgct atgccgcgccaatcgtggtgccgccgaccgtggcaatcctgggtgcggggcgcgtgcgcgaggaagtggtagcagccggcggc gtgccggcggtgcaccgggtgatgccgctgagcctgacctttgaccatcgcgtggtgacgggtggggaggcggcgcggtttctgg cggcggtgattgcggatctggagatggcggtgtag

SEQ ID NO: 84

MRIFKLPDLGEGLQEAEIVTWHVKTGDTVAADQPLLSVETAKAIVEIPSPYAGTIAK

LFAQPGDIVHLGAPLVGVEGAGEDADAGTVVGSVQVGTHVVNEAAPAGSAAPAA

AMAARVKATPAVRALARRLGVDLAMATASGPEGVVTAADVERVASTLAELGTPE

QLRGVRRAMAQNMARAQAEVAAATVMDDADIHAWQPGADVTIRLVRALVAGCR

AEPGLNAWYEGQTARRHVLKKIDVGIAADLPEGLFVPVLRDVGNRDAADLRHGLD

RMRADIRARTIAPEEMRGNTITLSNFGMIAGRYAAPIVVPPTVAILGAGRVREEVVA

AGGVPAVHRVMPLSLTFDHRVVTGGEAARFLAAVIADLEMAV (*Rhodobacter sphaeroides* 2.4.1): isovaleryl-CoA dehydrogenase
u) ivdH (accession #YP_352568)(rsph)

SEQ ID NO: 85 atgtttcacgctccgatgaccttcgacctcggcgaggagatcgccgccctccgcgagaccgtccatgcctgggcgcaggagcggg tgaagcccatggccgcccggatcgaccgcgagaacgtcttcccggccgagctctggcgcgagatgggcgagctcgggcttctgg gcatcacggtccccgaggaattcggcggctcggacatgggctatctcgcccatacggtcgccgtggaggaggtggcgcgcgcct cggcctcggtctcgctcagctacggggcgcattccaacctctgcgtgaaccagatccgcctgaacggcagccctgagcagaaggc gcgctatctgccgaagctcgtctcgggcgagcatgtgggggcgctcgccatgtccgaggcgggcgcgggctcggacgtggtgtc gatgaagctcaaggccgagaagcggaacggctactatgtcctcaacggcacgaaatactggatcaccaacgggccggatgcgga tgttctggtggtctatgccaagaccgaccctgaggcgggcgcgaagggcatcactgccttcctgatcgaaaagtcgatgacgggctt ctcgacctcgccgcacttcgacaaggtggggatgcgcggctcgaacacgggcgagctgatcttcgagaattgcgaggtgccgttc gagaatgtcctcgggcaggacggcaagggggtgcgcgtcctcatgtcggggctcgattacgagcgcgtggtgctgtcggggatc ggcacggggatcatggcggcctgcctcgacgaggtggtgccctactgccagagccgccagcagttcggtcagccgatcggaaac ttccagctgatgcagggcaagctcgccgacatgtatgtcgcgctgaacacggcgcgggcctatgtctacgagacggcgcgcgcct gcgatgcggggcgggtgacgcgcgcggatgcggcgggctgcgtgctctatgcctcggagcaggcgatggtgcaggcgcatcag gcggtgcaggcgctcggcggcgcgggcttcctgaacgattccgtcgtgagccggctcttccgcgatgcgaagctgatggagatcg gggcgggaacttccgagatccgccggatgctcatcggccgcgaacttatggcgggctga

SEQ ID NO: 86

MFHAPMTFDLGEEIAALRETVHAWAQERVKPMAARIDRENVFPAELWREMGELGL

LGITVPEEFGGSDMGYLAHTVAVEEVARASASVSLSYGAHSNLCVNQIRLNGSPEQ

-continued

KARYLPKLVSGEHVGALAMSEAGAGSDVVSMKLKAEKRNGYYVLNGTKYWITNG

PDADVLVVYAKTDPEAGAKGITAFLIEKSMTGFSTSPHFDKVGMRGSNTGELIFENC

EVPFENVLGQDGKGVRVLMSGLDYERVVLSGIGTGIMAACLDEVVPYCQSRQQFG

QPIGNFQLMQGKLADMYVALNTARAYVYETARACDAGRVTRADAAGCVLYASEQ

AMVQAHQAVQALGGAGFLNDSVVSRLFRDAKLMEIGAGTSEIRRMLIGRELMAG (*Pseudomonas putida* KT2440): acyl-CoA dehydrogenase domain-containing protein Ivd (accession #NP_746190)(pput)

SEQ ID NO: 87 atgacggtgaccctgctgacgtattcgcgggcatgcccgctcccacaggggggcggggccggatcccaagctatggtgtaacccaa tttcaagaacaagaaggtgccccagcatgcattacccctccctgaacttcgccctgggcgagaccatcgacatgctccgcgaccag gtgcgcaccttcgtcgccgctgaactggccccaagggccgcgcagatcgaccacgacaacctgttccccgccgacatgtggcgca agttcggtgacatgggcctgctgggcatcaccgtaccggaagagtacggcggcgctggcctgggctacctggcccatgtggtgtc gatggaagagatcagccgtggctccgcctcggtggcgctgtcctacggcgcccattccaacctgtgcgtcaaccagatcaaccgca acggcacccacgagcagaagctcaagtacctgcccaagctgatcagcggcgagcacatcggcgccttggccatgagcgagccca atgccggttccgacgtggtgtcgatgaagctgcgcgcagaaaaacgcggcgatcactacgtgctcaacggcagcaagacctggat caccaacggtcccgacgccaacacctacgtgatttacgccaagaccgacctggacaagggtgcgcacggcatcaccgcgttcatc gtcgagcgcgactggaaaggcttcagccgcagcaacaagttcgacaagctgggcatgcgcgggtccaacacctgcgagttgttctt cgatggcgtggaagtgccggcagagaacattctgggccagctcaacggcggcgtgcgcgtccttatgagcggcctggactacga acgtgtggtgctgtccggcggcccgaccggcatcatgcaaagctgcatggacctggtggtgccgtatatccacgaccgcaagcaat tcggccagagcatcggcgagttccagctgatccagggcaagattgccgacatgtacacccagctcaatgccagccgcgcctacctg tatgccgtggctcaggcgtgcgaccgtggcgaaaccacccgcaaggacgctgccggcgtgatcctgtacaccgccgagcgtgcc acgcaaatggccctggaggcgatccagattcttggcggcaacggctatatcaacgaattcccggctggccgcctgttgcgcgacgc caagctgtacgaaatcggtgccggcaccagtgaaatccgccggatgctgatcggccgcgaactgttcaacgaaacccgctga

SEQ ID NO: 88

MTVTLLTYSRACPLPQGAGPDPKLWCNPISRTRRCPSMHYPSLNFALGETIDMLRD

QVRTFVAAELAPRAAQIDHDNLFPADMWRKFGDMGLLGITVPEEYGGAGLGYLAH

VVSMEEISRGSASVALSYGAHSNLCVNQINRNGTHEQKLKYLPKLISGEHIGALAMS

EPNAGSDVVSMKLRAEKRGDHYVLNGSKTWITNGPDANTYVIYAKTDLDKGAHGI

TAFIVERDWKGFSRSNKFDKLGMRGSNTCELFFDGVEVPAENILGQLNGGVRVLMS

GLDYERVVLSGGPTGIMQSCMDLVVPYIHDRKQFGQSIGEFQLIQGKIADMYTQLN

ASRAYLYAVAQACDRGETTRKDAAGVILYTAERATQMALEAIQILGGNGYINEFPA

GRLLRDAKLYEIGAGTSEIRRMLIGRELFNETR (*Dictyostelium discoideum* AX4): 3-methylcrotonyl-CoA:carbon dioxide ligase alpha subunit v) mccA (accession # XP_637277)and mccB (accession # XP_645342)(ddisco)
mccA

SEQ ID NO: 89 atgtttagtttaggaaaattggttaaaaaagatgctttttttttatagatatataacaaatgttaataaagatttaaaaattaaaccaattacaaa gatattaattgcaaatagaggtgaaattgcatgtcgtgtaatgagaacagcaaaatcaaaaggtgtaaaaaccgtagcagtttatagtg aagcagataagaattcattacatgtttcaatggcagatgagagttatttaattggaccagcagcagccaaagagagttatttatgtggaa ataagatcatagatgtagcaaagagatctggagcacaagcaattcatccaggttatggtttcttatcagagaattcagattttgctgatct ctgtgagagagagaaggtatcattttcattggaccaccatcagatgcaatcaaagcaatgggtagcaaaagtgcctcaaaggatattatg atcaaagctggcgtaccaaccatcccaggttaccacggtgaagatcagtcaatgagtgtgttgaagagtgaggctgcaaagattggc tatccagtattgattaaagctgttatgggtggtggtggtaaaggtatgagaatcgttgagagagaggaggatttagaggacggtgttga gtcctcaaagagagaggccaccgcatcctttggtgattctagagttttggtagaaaagtatttagttcatccaagacatgtggagattca agttttcgccgatagacatggtaattgtgttcacctctttgagagagattgtagtgtacaaagacgtcatcaaaagattatcgaagaggc -continued accagctccacatctctctgaggagcttagaaagaaaatgggtgatgctgcagttgccgccgccaaggctgtaggttacgttggtgct ggtaccgtagaattcattttatccgctgataatagcttcttctttatggagatgaatacccgtcttcaagtggagcatccaatcactgaaat gatcaccaaacaagatttagtagaatggcaattgaaggtagccgaatcccaaacactcccaatggagcaagaacaattgaagattca tggtcactctttcgaagctcgtatctacgcagagaatccagatagtgatttcttaccaggtacaggtaaattagcacatctttcaacacca acaccatccgatactttacgtgttgaaactggtgtacgtcaaggcgatgaagttagcgtttactatgatccaatgattgccaaattggtg gtatgggatcaagatagagagaaggcattaagatatttaagaaatgctctcgacgagtaccatatcattggtctcaatacaaacatctct ttccttaagagattatcaactcatccttcatttatggctggtgaagttgaaactggtttcatcccaattcacagagaatccttaatggcccca caagctccaatgtctgatgattcattagcattggctgccacaagtttactcttaaaagagatcactcaacaaaaatcaaaagaagatcca aactcaccttggtcaagtttaggtggtttccgtattaatcataatttaaaaaaacaagttaaattcaatcaaaaagataataaagttgttgtta atgttgaattcattggtggtggtggtgctgctgctaatggtaaacataactttaaagtaactttagataatggtaatgtcgttgaagttttag atgcaaaattaaatcaaaataatgaaactattagtgctcatgtaaatggtagattctataataacattaaatccgtcattgtaaaggatactt taacaatctttaatgaaggtcaacaataccaattggatattcctcaagatgttaaaccaaaaggtgctgatggtgtattgggttctttagttt caccaatgcctggaaaaatcactaaagttatggtaaatgttggtgacatggttaaaaagggtcaaccaatcttactcatggaagcaatg aaaatggaacatactattcgttctccaatcgatggtaaagttgaatcattaccttataatgttaatgaaatcgttgaggataagaaaacttt ggctgttattgtttaa

SEQ ID NO: 90

MFSLGKLVKKDAFFYRYITNVNKDLKIKPITKILIANRGEIACRVMRTAKSKGVKTV

AVYSEADKNSLHVSMADESYLIGPAAAKESYLCGNKIIDVAKRSGAQAIHPGYGFL

SENSDFADLCEREGIIFIGPPSDAIKAMGSKSASKDIMIKAGVPTIPGYHGEDQSMSV

LKSEAAKIGYPVLIKAVMGGGGKGMRIVEREEDLEDGVESSKREATASFGDSRVLV

EKYLVHPRHVEIQVFADRHGNCVHLFERDCSVQRRHQKIIEEAPAPHLSEELRKKM

GDAAVAAAKAVGYVGAGTVEFILSADNSFFFMEMNTRLQVEHPITEMITKQDLVE

WQLKVAESQTLPMEQEQLKIHGHSFEARIYAENPDSDFLPGTGKLAHLSTPTPSDTL

RVETGVRQGDEVSVYYDPMIAKLVVWDQDREKALRYLRNALDEYHIIGLNTNISFL

KRLSTHPSFMAGEVETGFIPIHRESLMAPQAPMSDDSLALAATSLLLKEITQQKSKE

DPNSPWSSLGGFRINHNLKKQVKFNQKDNKVVVNVEFIGGGGAAANGKHNFKVTL

DNGNVVEVLDAKLNQNNETISAHVNGRFYNNIKSVIVKDTLTIFNEGQQYQLDIPQ

DVKPKGADGVLGSLVSPMPGKITKVMVNVGDMVKKGQPILLMEAMKMEHTIRSPI

DGKVESLPYNVNEIVEDKKTLAVIV

*Dictyostelium discoideum* AX4): 3-methylcrotonyl-CoA:carbon dioxide ligase beta subunit mccB

SEQ ID NO: 91 atgttaaaatcaatttcattattaaaaaataatcaaatattattaaaaaatataattaataatggtagaattataaataatgttggtgaaaaatt atcatcaaaatcattattaaaaattaattattcatcatcaacaactgatagaacatttaatattttagatggtacaattgataagaattcagca gaatataaagataatttaattaatatgaattcaacattaaaacaattaaaagaaaatattgaaaagattaaattaggtggtggtgaaaaatt aaatcaaaagaatatttcacgtggaaagttattagtacgtgaacgtattgaagcattgattgatgttggatcaccatttttagagttttctca attggcaggttggggaatgtatggtaaggaggaggttgcagcaggtggtatcatcacaggtattggtaaaattcatggtgttgaatgtg ttattgtcgcaaatgactcaaccgtgaagggaggtacctactttccaatcactgttaaaaagcatttacgtgcacaagagattgcccaag agaataatttaccatgtatttatttagtcgatagcggtggtgcaaatttgccacgtcaagctgacgtgttcccagatcgtgaccattttgga agaatcttcttcaatcaagctaatatgtctgcaaaacgtattccacaaattgccgttgtcatgggttcatgtaccgccggtggtgcatacg tgccagccatggctgacgaatcggttattgtcaagggcaccggcactatcttcttgggtggtccaccattggtcaaggctgcaactgg tgagattgtaacaagcgaggagttgggtggtgccgacctccattgtcgtacctctggtgtcaccgatcattatgctcgtgacgatgccg -continued aggccatcgccatcactcgtcgtatcgtgtccaatttaaatagaaagaaacaaccatcaccagtgatcactgaaaccgaggagccact ctatccaactagtgaattggctggtatcgtaccaagtgatttaaagaagaatttcgatattcgtaaggttatcgcacgtttagtcgatggta gtagattcgatgaattcaaagaactctatggcacaactttaatttgtggttttgcacgtgtacatggtatgccagttggtatcatcgccaac aacggtattctctttagtgaaagtgccgtcaagggtgcccatttcattgaactttgcaatcaaagaggtatccccttagtcttccttcaaaa catcactggtttcatggttggtaaaacttatgaatctaaaggtatagccaaggatggcgctaaaatggtcatggctgttgccaccgcca aagttccaaagattacaatgatcattggtggtagttttggtgctggtaattatggtatgtgtggtcgttcctacagtccacgtttcctttacat gtggccaaatgctaaaatctctgttatgggtggagaacaagctgcctctgttttagctcaaattcaaaaggataacatggcaaaagaaa ataaacaatggtcaccagaagaagaaaatactttcaaaaaaccaatctctgataaattcgaagaagaaggttcaatctattacagttca gctcgttgttgggatgatggtgttatcgatccacaagattctcgtaaagttatcgctttaagtttaagtgcttgtatgaatcaaccaattaat ccaccatctgatggttttggtgttttcagaatgtaa

SEQ ID NO: 92

MLKSISLLKNNQILLKNIINNGRIINNVGEKLSSKSLLKINYSSSTTDRTFNILDGTIDK

NSAEYKDNLINMNSTLKQLKENIEKIKLGGGEKLNQKNISRGKLLVRERIEALIDVG

SPFLEFSQLAGWGMYGKEEVAAGGIITGIGKIHGVECVIVANDSTVKGGTYFPITVK

KHLRAQEIAQENNLPCIYLVDSGGANLPRQADVFPDRDHFGRIFFNQANMSAKRIPQ

IAVVMGSCTAGGAYVPAMADESVIVKGTGTIFLGGPPLVKAATGEIVTSEELGGAD

LHCRTSGVTDHYARDDAEAIAITRRIVSNLNRKKQPSPVITETEEPLYPTSELAGIVPS

DLKKNFDIRKVIARLVDGSRFDEFKELYGTTLICGFARVHGMPVGIIANNGILFSESA

VKGAHFIELCNQRGIPLVFLQNITGFMVGKTYESKGIAKDGAKMVMAVATAKVPKI

TMIIGGSFGAGNYGMCGRSYSPRFLYMWPNAKISVMGGEQAASVLAQIQKDNMAK

ENKQWSPEEENTFKKPISDKFEEEGSIYYSSARCWDDGVIDPQDSRKVIALSLSACM

NQPINPPSDGFGVFRM (*Homo sapiens*): methylcrotonoyl-Coenzyme A carboxylase 1 (alpha)
mccA (accession # NP_064551)and mccB (accession # XP_645342)(hsap) mccA

SEQ ID NO: 93 atggcggcggcctctgcggtgtcggtgctgctggtggcggcggagaggaaccggtggcatcgtctcccgagcctgctcctgccgc cgaggacatgggtgtggaggcaaagaaccatgaagtacacaacagccacaggaagaaacattaccaaggtcctcattgcaaacag aggagaaattgcctgcagggtgatgcgcacagccaaaaaactgggtgtacagactgtggcggtttatagtgaggctgacagaaatt ccatgcatgtagatatggcagatgaagcatattccatcggccccgctccctcccagcagagctacctatctatggagaaaatcattcaa gtggccaagacctctgctgcacaggctatccatccaggatgcggttttctctcagaaaacatggaatttgctgaactttgtaagcaaga aggaattatttttataggccctcctccatctgcaattagagacatgggtataaagagcacatccaaatccataatggctgctgctggagt acctgttgtggagggttatcatggtgaggaccaatcagaccagtgcctgaaggaacacgccaggagaattggctatcctgtcatgatt aaagccgtccggggtggaggaggaaaaggaatgaggattgttagatcagaacaagaatttcaagaacagttagagtcagcacgga gagaagctaagaagtctttcaatgatgatgctatgctgatcgagaagtttgtagacacaccgaggcatgtagaagtccaggtgtttggt gatcaccatggcaatgctgtgtacttgtttgaaagagactgtagtgtgcagaggcgacatcagaagatcattgaggaggccccagcg cctggtattaaatctgaagtaagaaaaaagctgggagaagctgcagtcagagctgctaaagctgtaaattatgttggagcagggact gtggagtttattatggactcaaaacataatttctgtttcatggagatgaatacaaggctgcaagtggaacatcctgttactgagatgatca caggaactgacttggtggagtggcagcttagaattgcagcaggagagaagattcctttgagccaggaagaaataactctgcagggc catgccttcgaagctagaatatatgcagaagatcctagcaataacttcatgcctgtggcaggcccattagtgcacctctctactcctcga gcagacccttccaccaggattgaaactggagtacggcaaggagacgaagtttccgtgcattatgaccccatgattgcgaagctggtc gtgtgggcagcagatcgccaggcggcattgacaaaactgaggtacagccttcgtcagtacaatattgttggactgcacaccaacatt gacttcttactcaacctgtctggccacccagagtttgaagctgggaacgtgcacactgatttcatccctcaacaccacaaacagttgttg ctcagtcggaaggctgcagccaaagagtctttatgccaggcagccctgggtctcatcctcaaggagaaagccatgaccgacactttc -continued actcttcaggcacatgatcaattctctccattttcgtctagcagtggaagaagactgaatatctcgtataccagaaacatgactcttaaag atggtaaaaacaatgtagccatagctgtaacgtataaccatgatgggtcttatagcatgcagattgaagataaaactttccaagtccttg gtaatctttacagcgagggagactgcacttacctgaaatgttctgttaatggagttgctagtaaagcgaagctgattatcctggaaaaca ctatttacctattttccaaggaaggaagtattgagattgacattccagtccccaaatacttatcttctgtgagctcacaagaaactcaggg cggccccttagctcctatgactggaaccattgaaaaggtgtttgtcaaagctggagacaaagtgaaagcgggagattccctcatggtt atgatcgccatgaagatggagcataccataaagtctccaaaggatggcacagtaaagaaagtgttctacagagaaggtgctcaggc caacagacacactcctttagtcgagtttgaggaggaagaatcagacaaaagggaatcggaataa

SEQ ID NO: 94

MAAASAVSVLLVAAERNRWHRLPSLLLPPRTWVWRQRTMKYTTATGRNITKVLIA

NRGEIACRVMRTAKKLGVQTVAVYSEADRNSMHVDMADEAYSIGPAPSQQSYLS

MEKIIQVAKTSAAQAIHPGCGFLSENMEFAELCKQEGIIFIGPPPSAIRDMGIKSTSKSI

MAAAGVPVVEGYHGEDQSDQCLKEHARRIGYPVMIKAVRGGGGKGMRIVRSEQE

FQEQLESARREAKKSFNDDAMLIEKFVDTPRHVEVQVFGDHHGNAVYLFERDCSV

QRRHQKIIEEAPAPGIKSEVRKKLGEAAVRAAKAVNYVGAGTVEFIMDSKHNFCFM

EMNTRLQVEHPVTEMITGTDLVEWQLRIAAGEKIPLSQEEITLQGHAFEARIYAEDP

SNNFMPVAGPLVHLSTPRADPSTRIETGVRQGDEVSVHYDPMIAKLVVWAADRQA

ALTKLRYSLRQYNIVGLHTNIDFLLNLSGHPEFEAGNVHTDFIPQHHKQLLLSRKAA

AKESLCQAALGLILKEKAMTDTFTLQAHDQFSPFSSSSGRRLNISYTRNMTLKDGKN

NVAIAVTYNHDGSYSMQIEDKTFQVLGNLYSEGDCTYLKCSVNGVASKAKLIILEN

TIYLFSKEGSIEIDIPVPKYLSSVSSQETQGGPLAPMTGTIEKVFVKAGDKVKAGDSL

MVMIAMKMEHTIKSPKDGTVKKVFYREGAQANRHTPLVEFEEEESDKRESE (*Dictyostelium discoideum* AX4): 3-methylcrotonyl-CoA:carbon dioxide ligase beta subunit mccB

SEQ ID NO: 95 atgtgggccgtcctgaggttagccctgcggccgtgtgcccgcgcctctcccgccgggccgcgcgcctatcacggggactcggtgg cctcgctgggcacccagccggacttgggctctgccctctaccaggagaactacaagcagatgaaagcactagtaaatcagctccat gaacgagtggagcatataaaactaggaggtggtgagaaagcccgagcacttcacatatcaagaggaaaactattgcccagagaaa gaattgacaatctcatagacccagggtctccatttctggaattatcccagtttgcaggttaccagttatatgacaatgaggaggtgccag gaggtggcattattacaggcattggaagagtatcaggagtagaatgcatgattattgccaatgatgccaccgtcaaaggaggtgccta ctacccagtgactgtgaaaaaacaattacgggcccaagaaattgccatgcaaaacaggctcccctgcatctacttagttgattcggga ggagcatacttacctcgacaagcagatgtgtttccagatcgagaccactttggccgtacattctataatcaggcaattatgtcttctaaaa atattgcacagatcgcagtggtcatgggctcctgcaccgcaggaggagcctatgtgcctgccatggctgatgaaaacatcattgtac gcaagcagggtaccatttttcttggcaggaccccccttggttaaagcggcaactggggaagaagtatctgctgaggatcttggaggtg ctgatcttcattgcagaaagtctggagtaagtgaccactgggctttggatgatcatcatgcccttcacttaactaggaaggttgtgagga atctaaattatcagaagaaattggatgtcaccattgaaccttctgaagagcctttatttcctgctgatgaattgtatggaatagttggtgcta accttaagaggagctttgatgtccgagaggtcattgctagaatcgtggatggaagcagattcactgagttcaaagccttttatggagac acattagttacaggatttgctcgaatatttgggtacccagtaggtatcgttggaaacaacggagttctcttttctgaatctgcaaaaaagg gtactcactttgtccagttatgctgccaaagaaatattcctctgctgttccttcaaaacattactggatttatggttggtagagagtatgaag ctgaaggaattgccaaggatggtgccaagatggtggccgctgtggcctgtgcccaagtgcctaagataaccctcatcattgggggct cctatggagccggaaactatgggatgtgtggcagagcatatagcccaagatttctctacatttggccaaatgctcgtatctcagtgatg ggaggagagcaggcagccaatgtgttggccacgataacaaaggaccaaagagcccgggaaggaaagcagttctccagtgctgat gaagcggctttaaaagagcccatcattaagaagtttgaagaggaaggaaacccttactattccagcgcaagggtatgggatgatggg -continued atcattgatccagcagacaccagactggtcttgggtctcagttttagtgcagccctcaacgcaccaatagagaagactgacttcggtat cttcaggatgtaa

SEQ ID NO: 96

MWAVLRLALRPCARASPAGPRAYHGDSVASLGTQPDLGSALYQENYKQMKALVN

QLHERVEHIKLGGGEKARALHISRGKLLPRERIDNLIDPGSPFLELSQFAGYQLYDNE

EVPGGGIITGIGRVSGVECMIIANDATVKGGAYYPVTVKKQLRAQEIAMQNRLPCIY

LVDSGGAYLPRQADVFPDRDHFGRTFYNQAIMSSKNIAQIAVVMGSCTAGGAYVP

AMADENIIVRKQGTIFLAGPPLVKAATGEEVSAEDLGGADLHCRKSGVSDHWALD

DHHALHLTRKVVRNLNYQKKLDVTIEPSEEPLFPADELYGIVGANLKRSFDVREVIA

RIVDGSRFTEFKAFYGDTLVTGFARIFGYPVGIVGNNGVLFSESAKKGTHFVQLCCQ

RNIPLLFLQNITGFMVGREYEAEGIAKDGAKMVAAVACAQVPKITLIIGGSYGAGN

YGMCGRAYSPRFLYIWPNARISVMGGEQAANVLATITKDQRAREGKQFSSADEAA

LKEPIIKKFEEEGNPYYSSARVWDDGIIDPADTRLVLGLSFSAALNAPIEKTDFGIFRM (*Homo sapiens*): AU RNA binding protein/enoyl-Coenzyme A hydratase
w) enoyl-coA hydratase (accession # NP_001689) (hsap)

SEQ ID NO: 97 atggcggccgcggtggcggcggcacctggggccttgggatccctgcatgctggcggcgcccgcctggtggccgcttgcagtgcg tggctctgcccggggttgaggctgcccggctcgttggcaggccggcgagcgggcccggcgatctgggcccagggctgggtacct gcggccgggggtcccgccccgaaaaggggctacagctctgagatgaagacggaggacgagctgcgggtgcggcacctggagg aggagaaccgaggaattgtggtgcttggaataaacagagcttatggcaaaaattcactcagtaaaaatcttataaaaatgctatcaaaa gctgtggatgctttgaaatctgataagaaagtacggaccataataatcaggagtgaagtcccagggatattctgtgctggtgctgacct taaggaaagagccaaaatgagttccagtgaagttggtccttttgtctccaaaataagagcagtgattaacgatattgctaatcttccagta ccaacaattgcagcaatagatggactcgctttaggtggtggtcttgaactggctttagcctgtgatatacgagtagcagcttcctctgca aaaatgggcctggttgaaacaaaattggcgattattcctggtggagggggacacagcgattgccacgcgccattggaatgtccctg gccaaggagctcatattctctgcgcgagtcctcgatggcaaagaagccaaagcagtgggcttaatcagccacgttctggaacagaa ccaggagggagacgcggcctacaggaaggccttggacctggcgagagagtttttacctcagggacctgttgcaatgagagtggca aaattagcaattaatcaagggatggaggtcgatttagtaacagggttagccatagaagaagcttgttatgctcagaccattccaacaaa agacagacttgaaggtcttcttgcttttaaagagaaaaggcccccctcgctataaaggagaataa

SEQ ID NO: 98

MAAAVAAAPGALGSLHAGGARLVAACSAWLCPGLRLPGSLAGRRAGPAIWAQG

WVPAAGGPAPKRGYSSEMKTEDELRVRHLEEENRGIVVLGINRAYGKNSLSKNLIK

MLSKAVDALKSDKKVRTIIIRSEVPGIFCAGADLKERAKMSSSEVGPFVSKIRAVIND

IANLPVPTIAAIDGLALGGGLELALACDIRVAASSAKMGLVETKLAIIPGGGGTQRLP

RAIGMSLAKELIFSARVLDGKEAKAVGLISHVLEQNQEGDAAYRKALDLAREFLPQ

GPVAMRVAKLAINQGMEVDLVTGLAIEEACYAQTIPTKDRLEGLLAFKEKRPPRYK

GE (*Drosophila persimilis*): GL11030 gene product from transcript GL11030-RA
Enoyl-coA hydratase(accession # XP_002015424) (dper)

SEQ ID NO: 99 atgtccaccgaggaaaccagcgagtttgtgtcgaatctacgaaacctgttcattagcattgaacaattgccgatgcccgtaatcgccgc attggatggcgctgctttgggtggtggtctggaaatggctctggcatgcgatatacgcacggcagcttcaaataccaaaatgggtctg gtagagactcgactggccataatccctggcgccgggggcactcagcgactcccccgcattctctctccctcgctggcgaaggaactt attttcactgcccgagtcttggatggaagtgtggccaaggagctgggtctggtcagccatgttgtaagccagaacgaaaaaaatgatg ctgcctaccagcaggccctaaagctcgccgaggaaatcctccccaacggtccagtgggtgtgcgaatggccaaactggctattgac aagggcatgcaggtcgacctaagcacgggctactccattgaagaggtctgctatgctcaggtgatacccacaaaggaccgcctgga -continued gggactcgccgcgtttgccgagaaacgcaagcccgtctacaagggagagtaa

SEQ ID NO: 100

MSTEETSEFVSNLRNLFISIEQLPMPVIAALDGAALGGGLEMALACDIRTAASNTKM

GLVETRLAIIPGAGGTQRLPRILSPSLAKELIFTARVLDGSVAKELGLVSHVVSQNEK

NDAAYQQALKLAEEILPNGPVGVRMAKLAIDKGMQVDLSTGYSIEEVCYAQVIPTK

DRLEGLAAFAEKRKPVYKGE (*Saccharomyces cerevisiae*): Hmg1p
HMG552

SEQ ID NO: 101 atggttttaaccaataaaacagtcatttctggatcgaaagtcaaaagtttatcatctgcgcaatcgagctcatcaggaccttcatcatcta gtgaggaagatgattcccgcgatattgaaagcttggataagaaaatacgtcctttagaagaattagaagcattattaagtagtggaaat acaaaacaattgaagaacaaagaggtcgctgccttggttattcacggtaagttacctttgtacgctttggagaaaaaattaggtgatact acgagagcggttgcggtacgtaggaaggctctttcaattttggcagaagctcctgtattagcatctgatcgtttaccatataaaaattatg actacgaccgcgtatttggcgcttgttgtgaaaatgttataggttacatgcctttgcccgttggtgttataggccccttggttatcgatggt acatcttatcatataccaatggcaactacagagggttgtttggtagcttctgccatgcgtggctgtaaggcaatcaatgctggcggtggt gcaacaactgttttaactaaggatggtatgacaagaggcccagtagtccgtttcccaactttgaaaagatctggtgcctgtaagatatg gttagactcagaagagggacaaaacgcaattaaaaaagcttttaactctacatcaagatttgcacgtctgcaacatattcaaacttgtct agcaggagatttactcttcatgagatttagaacaactactggtgacgcaatgggtatgaatatgatttctaaaggtgtcgaatactcatta aagcaaatggtagaagagtatggctgggaagatatggaggttgtctccgtttctggtaactactgtaccgacaaaaaaccagctgcca tcaactggatcgaaggtcgtggtaagagtgtcgtcgcagaagctactattcctggtgatgttgtcagaaaagtgttaaaaagtgatgttt ccgcattggttgagttgaacattgctaagaatttggttggatctgcaatggctgggtctgttggtggatttaacgcacatgcagctaattt agtgacagctgttttcttggcattaggacaagatcctgcacaaaatgttgaaagttccaactgtataacattgatgaaagaagtggacg gtgatttgagaatttccgtatccatgccatccatcgaagtaggtaccatcggtggtggtactgttctagaaccacaaggtgccatgttgg acttattaggtgtaagaggcccgcatgctaccgctcctggtaccaacgcacgtcaattagcaagaatagttgcctgtgccgtcttggca ggtgaattatccttatgtgctgccctagcagccggccatttggttcaaagtcatatgacccacaacaggaaacctgctgaaccaacaa aacctaacaatttggacgccactgatataaatcgtttgaaagatgggtccgtcacctgcattaaatcctaa

SEQ ID NO: 102

MVLTNKTVISGSKVKSLSSAQSSSSGPSSSSEEDDSRDIESLDKKIRPLEELEALLSSG

NTKQLKNKEVAALVIHGKLPLYALEKKLGDTTRAVAVRRKALSILAEAPVLASDRL

PYKNYDYDRVFGACCENVIGYMPLPVGVIGPLVIDGTSYHIPMATTEGCLVASAMR

GCKAINAGGGATTVLTKDGMTRGPVVRFPTLKRSGACKIWLDSEEGQNAIKKAFNS

TSRFARLQHIQTCLAGDLLFMRFRTTTGDAMGMNMISKGVEYSLKQMVEEYGWE

DMEVVSVSGNYCTDKKPAAINWIEGRGKSVVAEATIPGDVVRKVLKSDVSALVEL

NIAKNLVGSAMAGSVGGFNAHAANLVTAVFLALGQDPAQNVESSNCITLMKEVDG

DLRISVSMPSIEVGTIGGGTVLEPQGAMLDLLGVRGPHATAPGTNARQLARIVACA

VLAGELSLCAALAAGHLVQSHMTHNRKPAEPTKPNNLDATDINRLKDGSVTCIKS erg20

SEQ ID NO: 103 atggcttcagaaaaagaaattaggagagagagattcttgaacgttttccctaaattagtagaggaattgaacgcatcgcttttggcttac ggtatgcctaaggaagcatgtgactggtatgcccactcattgaactacaacactccaggcggtaagctaaatagaggtttgtccgttgt ggacacgtatgctattctctccaacaagaccgttgaacaattggggcaagaagaatacgaaaaggttgccattctaggttggtgcattg agttgttgcaggcttacttcttggtcgccgatgatatgatggacaagtccattaccagaagaggccaaccatgttggtacaaggttcct gaagttggggaaattgccatcaatgacgcattcatgttagaggctgctatctacaagcttttgaaatctcacttcagaaacgaaaaatac tacatagatatcaccgaattgttccatgaggtcaccttccaaaccgaattgggccaattgatggacttaatcactgcacctgaagacaa -continued agtcgacttgagtaagttctccctaaagaagcactccttcatagttactttcaagactgcttactattctttctacttgcctgtcgcattggcc atgtacgttgccggtatcacggatgaaaaggatttgaaacaagccagagatgtcttgattccattgggtgaatacttccaaattcaagat gactacttagactgcttcggtaccccagaacagatcggtaagatcggtacagatatccaagataacaaatgttcttgggtaatcaacaa ggcattggaacttgcttccgcagaacaaagaaagactttagacgaaaattacggtaagaaggactcagtcgcagaagccaaatgca aaaagattttcaatgacttgaaaattgaacagctataccacgaatatgaagagtctattgccaaggatttgaaggccaaaatttctcagg tcgatgagtctcgtggcttcaaagctgatgtcttaactgcgttcttgaacaaagtttacaagagagaagcaaatag

SEQ ID NO: 104

MASEKEIRRERFLNVFPKLVEELNASLLAYGMPKEACDWYAHSLNYNTPGGKLNR

GLSVVDTYAILSNKTVEQLGQEEYEKVAILGWCIELLQAYFLVADDMMDKSITRRG

QPCWYKVPEVGEIAINDAFMLEAAIYKLLKSHFRNEKYYIDITELFHEVTFQTELGQ

LMDLITAPEDKVDLSKFSLKKHSFIVTFKTAYYSFYLPVALAMYVAGITDEKDLKQ

ARDVLIPLGEYFQIQDDYLDCFGTPEQIGKIGTDIQDNKCSWVINKALELASAEQRK

TLDENYGKKDSVAEAKCKKIFNDLKIEQLYHEYEESIAKDLKAKISQVDESRGFKA

DVLTAFLNKVYKRSK* erg20 K197E (erg20-2)

SEQ ID NO: 105 atggcttcagaaaaagaaattaggagagagagattcttgaacgttttccctaaattagtagaggaattgaacgcatcgcttttggcttac ggtatgcctaaggaagcatgtgactggtatgcccactcattgaactacaacactccaggcggtaagctaaatagaggtttgtccgttgt ggacacgtatgctattctctccaacaagaccgttgaacaattggggcaagaagaatacgaaaaggttgccattctaggttggtgcattg agttgttgcaggcttacttcttggtcgccgatgatatgatggacaagtccattaccagaagaggccaaccatgttggtacaaggttcct gaagttggggaaattgccatcaatgacgcattcatgttagaggctgctatctacaagcttttgaaatctcacttcagaaacgaaaaatac tacatagatatcaccgaattgttccatgaggtcaccttccaaaccgaattgggccaattgatggacttaatcactgcacctgaagacaa agtcgacttgagtaagttctccctaaagaagcactccttcatagttactttcgaaactgcttactattctttctacttgcctgtcgcattggcc atgtacgttgccggtatcacggatgaaaaggatttgaaacaagccagagatgtcttgattccattgggtgaatacttccaaattcaagat gactacttagactgcttcggtaccccagaacagatcggtaagatcggtacagatatccaagataacaaatgttcttgggtaatcaacaa ggcattggaacttgcttccgcagaacaaagaaagactttagacgaaaattacggtaagaaggactcagtcgcagaagccaaatgca aaaagattttcaatgacttgaaaattgaacagctataccacgaatatgaagagtctattgccaaggatttgaaggccaaaatttctcagg tcgatgagtctcgtggcttcaaagctgatgtcttaactgcgttcttgaacaaagtttacaagagagaagcaaatag

SEQ ID NO: 106

MASEKEIRRERFLNVFPKLVEELNASLLAYGMPKEACDWYAHSLNYNTPGGKLNR

GLSVVDTYAILSNKTVEQLGQEEYEKVAILGWCIELLQAYFLVADDMMDKSITRRG

QPCWYKVPEVGEIAINDAFMLEAAIYKLLKSHFRNEKYYIDITELFHEVTFQTELGQ

LMDLITAPEDKVDLSKFSLKKHSFIVTFETAYYSFYLPVALAMYVAGITDEKDLKQA

RDVLIPLGEYFQIQDDYLDCFGTPEQIGKIGTDIQDNKCSWVINKALELASAEQRKTL

DENYGKKDSVAEAKCKKIFNDLKIEQLYHEYEESIAKDLKAKISQVDESRGFKADV

LTAFLNKVYKRSK erg20 K197R

SEQ ID NO: 107 atggcttcagaaaaagaaattaggagagagagattcttgaacgttttccctaaattagtagaggaattgaacgcatcgcttttggcttac ggtatgcctaaggaagcatgtgactggtatgcccactcattgaactacaacactccaggcggtaagctaaatagaggtttgtccgttgt ggacacgtatgctattctctccaacaagaccgttgaacaattggggcaagaagaatacgaaaaggttgccattctaggttggtgcattg agttgttgcaggcttacttcttggtcgccgatgatatgatggacaagtccattaccagaagaggccaaccatgttggtacaaggttcct gaagttggggaaattgccatcaatgacgcattcatgttagaggctgctatctacaagcttttgaaatctcacttcagaaacgaaaaatac -continued tacatagatatcaccgaattgttccatgaggtcaccttccaaaccgaattgggccaattgatggacttaatcactgcacctgaagacaa agtcgacttgagtaagttctccctaaagaagcactccttcatagttactttcagaactgcttactattctttctacttgcctgtcgcattggcc atgtacgttgccggtatcacggatgaaaaggatttgaaacaagccagagatgtcttgattccattgggtgaatacttccaaattcaagat gactacttagactgcttcggtaccccagaacagatcggtaagatcggtacagatatccaagataacaaatgttcttgggtaatcaacaa ggcattggaacttgcttccgcagaacaaagaaagactttagacgaaaattacggtaagaaggactcagtcgcagaagccaaatgca aaaagattttcaatgacttgaaaattgaacagctataccacgaatatgaagagtctattgccaaggatttgaaggccaaaatttctcagg tcgatgagtctcgtggcttcaaagctgatgtcttaactgcgttcttgaacaaagtttacaagagaagcaaatag

SEQ ID NO: 108

MASEKEIRRERFLNVFPKLVEELNASLLAYGMPKEACDWYAHSLNYNTPGGKLNR

GLSVVDTYAILSNKTVEQLGQEEYEKVAILGWCIELLQAYFLVADDMMDKSITRRG

QPCWYKVPEVGEIAINDAFMLEAAIYKLLKSHFRNEKYYIDITELFHEVTFQTELGQ

LMDLITAPEDKVDLSKFSLKKHSFIVTFRTAYYSFYLPVALAMYVAGITDEKDLKQ

ARDVLIPLGEYFQIQDDYLDCFGTPEQIGKIGTDIQDNKCSWVINKALELASAEQRK

TLDENYGKKDSVAEAKCKKIFNDLKIEQLYHEYEESIAKDLKAKISQVDESRGFKA

DVLTAFLNKVYKRSK

GerS

SEQ ID NO: 109 atggcattgcaaatgattgctccatttctatcctccttcctcccaaatcccagacacagcctcgcagcccatggcctcacacaccagaa atgtgtctcaaagcacatttcatgctccaccactacaccaacctactcaaccacagttccaagaagatcagggaactacaagcccagc atctgggactatgattttgtgcagtcactaggaagtggctacaaggtagaggcacatggaacacgtgtgaagaagttgaaggaagtt gtaaagcatttgttgaaagaaacagatagttctttggcccaaatagaactgattgacaaactccgtcgtctaggtctaaggtggctcttc aaaaatgagattaagcaagtgctatacacgatatcatcagacaacaccagcatagaaatgaggaaagatcttcatgcagtatcaactc gatttagacttcttagacaacatgggtacaaggtctccacagatgttttcaacgacttcaaagatgaaaagggttgtttcaagccaagcc tttcaatggacataaagggaatgttgagcttgtatgaagcttcacaccttgcctttcaaggggagactgtgttggatgaggcaagagctt tcgtaagcacacatctcatggatatcaaggagaacatagacccaatccttcataaaaaagtagagcatgctttggatatgcctttgcatt ggaggttagaaaaattagaggctaggtggtacatggacatatatatgagggaagaaggcatgaattcttctttacttgaattggccatg cttcatttcaacattgtgcaaacaacattccaaacaaatttaaagagtttgtcaaggtggtggaaagatttgggtcttggagagcagttga gcttcactagagacaggttggtggaatgtttcttttgggccgccgcaatgacacctgagccacaatttggacgttgccaggaagttgta gcgaaagttgctcaactcataataataattgacgatatctatgacgtgtatggtacggtggatgagctagaacttttttactaatgcgattg atagatgggatcttgaggcaatggagcaacttcctgaatatatgaagacctgtttcttagctttatacaacagtattaatgaaataggttat gacattttgaaagaggaagggcgcaatgtcataccataccttagaaatacgtggacagaattgtgtaaagcattcttagtggaggcca aatggtatagtagtggatatacaccaacgcttgaggagtatctgcaaacctcatggatttcgattggaagtctacccatgcaaacatatg tttttgctctacttgggaaaaatctagcaccggagagtagtgattttgctgagaagatctcggatatcttacgattgggaggaatgatgat tcgacttccggatgatttgggaacttcaacggatgaactaaagagaggtgatgttccaaaatccattcagtgttacatgcatgaagcag gtgttacagaggatgttgctcgcgaccacataatgggtctatttcaagagacatggaaaaaactcaatgaataccttgtggaaagttctc ttccccatgcctttatcgatcatgctatgaatcttggacgtgtctcctattgcacttacaaacatggagatggatttagtgatggatttgga gatcctggcagtcaagagaaaaagatgttcatgtctttatttgctgaaccccttcaagttgatgaagccaagggtatttcattttatgttgat ggtggatctgcctga

SEQ ID NO: 110

MALQMIAPFLSSFLPNPRHSLAAHGLTHQKCVSKHISCSTTTPTYSTTVPRRSGNYK

PSIWDYDFVQSLGSGYKVEAHGTRVKKLKEVVKHLLKETDSSLAQIELIDKLRRLG

LRWLFKNEIKQVLYTISSDNTSIEMRKDLHAVSTRFRLLRQHGYKVSTDVFNDFKD

EKGCFKPSLSMDIKGMLSLYEASHLAFQGETVLDEARAFVSTHLMDIKENIDPILHK

-continued

KVEHALDMPLHWRLEKLEARWYMDIYMREEGMNSSLLELAMLHFNIVQTTFQTN
LKSLSRWWKDLGLGEQLSFTRDRLVECFFWAAAMTPEPQFGRCQEVVAKVAQLIII
IDDIYDVYGTVDELELFTNAIDRWDLEAMEQLPEYMKTCFLALYNSINEIGYDILKE
EGRNVIPYLRNTWTELCKAFLVEAKWYSSGYTPTLEEYLQTSWISIGSLPMQTYVFA
LLGKNLAPESSDFAEKISDILRLGGMMIRLPDDLGTSTDELKRGDVPKSIQCYMHEA
GVTEDVARDHIMGLFQETWKKLNEYLVESSLPHAFIDHAMNLGRVSYCTYKHGDG
FSDGFGDPGSQEKKMFMSLFAEPLQVDEAKGISFYVDGGSA

BAAT

SEQ ID NO: 111 atgagcttcgctgtgaccagaacaagccggtctttggtcactccatgcggggtcacgccgacgggctcgctcggcctctccgccatc
gaccgggtgcccggcctcaggcatatggtgcggtcgctacacgtgttcaggcaaggccgggagccggccaggatcatcagggaa
gcactgtcgaaggcgctggtgaagtactaccccttcgcggggcggttcgtggacgatcccgagggcggcggcgaggttcgtgtcg
cttgcactggcgagggcgcttggttcgtcgaggccaaggcggactgcagcttggaggacgtgaagtacctcgatctcccgctcatg
atccctgaggacgcgctcctgcccaagccctgcccgggactgaacccctcgacctccctctcatgctgcaggtgacagagttcgt
gggcggcggattcgtggtcggcctcatctccgtccataccatcgccgacggcctcggcgtcgtccagttcatcaacgccgtcgccg
agatcgcccgtggcctgccgaagcccaccgtggagcctgcatggtcccgggaggtcatacccaacccacctaagctgcctcccgg
tggcccgcccgtgttcccctccttcaagctgctccacgccaccgtcgacctatcccctgaccacatcgatcacgtcaagtcccgacac
ttggagctcaccggccagcgctgctctaccttcgacgtcgccatcgccaacctgtggcagtcccgcacgcgcgccatcaacctgga
cccaggcgtcgacgtgcacgtgtgcttcttcgccaacactcgccacctgttgcgccaggtcgtcctcctgccccccgaggatggcta
ctacggcaactgcttctacccggtgaccgccaccgccccaagcggcaggatcgcatcggccgagctcatcgatgtcgtcagcatca
tcagggacgccaagtcgaggctgccgggcgagttcgccaagtgggctgccggggatttcaaggacgaccccttacgagctcagctt
cacgtacaactcgctgttcgtgtcggactggacccggctcggcttcctcgacgtcgactacggctggggcaagcccctccacgttat
accgttcgcgtacttggacatcatggcggtcggcatcatcggggcgccgccggcgccgcaaaaggggactcgggtgatggcgca
gtgcgtcgagaaggagcacatgcaggcgttcctggaagagatgaaaggcttcgcttaa

SEQ ID NO: 112

MSFAVTRTSRSLVTPCGVTPTGSLGLSAIDRVPGLRHMVRSLHVFRQGREPARIIRE
ALSKALVKYYPFAGRFVDDPEGGGEVRVACTGEGAWFVEAKADCSLEDVKYLDL
PLMIPEDALLPKPCPGLNPLDLPLMLQVTEFVGGGFVVGLISVHTIADGLGVVQFIN
AVAEIARGLPKPTVEPAWSREVIPNPPKLPPGGPPVFPSFKLLHATVDLSPDHIDHVK
SRHLELTGQRCSTFDVAIANLWQSRTRAINLDPGVDVHVCFFANTRHLLRQVVLLP
PEDGYYGNCFYPVTATAPSGRIASAELIDVVSIIRDAKSRLPGEFAKWAAGDFKDDP
YELSFTYNSLFVSDWTRLGFLDVDYGWGKPLHVIPFAYLDIMAVGIIGAPPAPQKGT
RVMAQCVEKEHMQAFLEEMKGFA

SAAT

SEQ ID NO: 113 atggagaaaattgaggtcagtataaattccaaacacaccatcaaaccatcaacttcctctacaccacttcagccttacaagcttaccctc
ctggaccagctcactcctccggcgtatgtccccatcgtgttcttctaccccattactgaccatgacttcaatcttcctcaaaccctagctg
acttaagacaagccctttcggagactctcactttgtactatccactctctggaaagggtcaaaaacaacctatacatcgatgattttgaaga
aggtgtcccataccttgaggctcgagtgaattgtgacatgactgattttctaaggcttcggaaaatcgagtgccttaatgagtttgttcca
ataaaaccatttagtatggaagcaatatctgatgagcgttaccccttgcttggagttcaagtcaacgttttcgattctggaatagcaatcg
gtgtctccgtctctcacaagctcatcgatggaggaacggcagactgttttctcaagtcctggggtgctgtttttcgagggtgtcgtgaaa
atatcatacatcctagtctctctgaagcagcattgcttttcccaccgagagatgacttgcctgaaaagtatgtcgatcagatggaagcgtt
atggtttgccggaaaaaaagttgctacaaggagatttgtatttggtgtgaaagccatatcttcaattcaagatgaagcgaagagcgagt -continued ccgtgcccaagccatcacgagttcatgccgtcactggttttctctggaaacatctaatcgctgcttctcgggcactaacatcaggtacta cttcaacaagactttctatagcggcccaggcagtgaacttaagaacacggatgaacatggagacagtgttggataatgccactggaa acttgttctggtgggcacaggccatactagagctaagtcatacaacaccagagatcagtgatcttaagctgtgtgacttggttaacttgc tcaatggatctgtcaaacaatgtaacggtgattactttgagactttcaagggtaaagagggatatggaagaatgtgcgagtatctagatt ttcagaggactatgagttctatggaaccagcaccggatatttatttattctcgagctggactaatttttttcaacccacttgattttggatggg ggaggacatcatggattggagttgcaggaaaaaattgaatctgcaagttgcaagttcataatattagttccaacacaatgcggttctgga attgaagcgtgggtgaatctagaagaagagaaaatggctatgctagaacaagatccccattttctagcgttagcatctccaaagacctt aatttaa

SEQ ID NO: 114

MEKIEVSINSKHTIKPSTSSTPLQPYKLTLLDQLTPPAYVPIVFFYPITDHDFNLPQTLA

DLRQALSETLTLYYPLSGRVKNNLYIDDFEEGVPYLEARVNCDMTDFLRLRKIECL

NEFVPIKPFSMEAISDERYPLLGVQVNVFDSGIAIGVSVSHKLIDGGTADCFLKSWG

AVFRGCRENIIHPSLSEAALLFPPRDDLPEKYVDQMEALWFAGKKVATRRFVFGVK

AISSIQDEAKSESVPKPSRVHAVTGFLWKHLIAASRALTSGTTSTRLSIAAQAVNLRT

RMNMETVLDNATGNLFWWAQAILELSHTTPEISDLKLCDLVNLLNGSVKQCNGDY

FETFKGKEGYGRMCEYLDFQRTMSSMEPAPDIYLFSSWTNFFNPLDFGWGRTSWIG

VAGKIESASCKFIILVPTQCGSGIEAWVNLEEEKMAMLEQDPHFLALASPKTLI

RhAAT

SEQ ID NO: 115 atggagaaaattgaggtcagtattatttcccgagacaccattaaaccatcagctgcttcctcttcactacacccttacaagctttccatcat cgatcagttcactcccacaacgtatttcccagttatattcttctaccccattactgaccgtgtcttcaatcttcctcaaaccttaaccgacttg aaaaacactgtttcccaggctctcactttgtaccatccactctccgggaggataaaaaacaacctatacattgatgatttcgaagcaggc atcccctaccttgaggcccgagtgaattttcacatgattgattttctaaggcttccgaaaatcgagtggctaaatgagtttgttccaatgg ctccatatcgcaaggaaacaatatctgagtttcttcccttgcttggaattcaagtaaacattttcgactctggaatagcaattggtgtctcttt ctctcacaagatcaacgatggccaaacggcaagctgttttctcaagtcctgggttgctatttttcgtgggtatcgtaacaaaatcatacat cctaatctctctcaagctgcattacttttgccatcgagggatgacttgcctgaaaagtacgtagctatgatggaaaggatgtggtttggc gagaaaaaagttgttacaaggagatttgtatttgatgcgaaagccatatccgcacttcaagatgaagggaagagcgaatacgtgccc aagccatcacgtgttcaggccctcactggttttctctggaaacatcaactcgctgcttctcgggcattatcatcaggtacttcaacaagat tttccgtagcatcacagacagtgaacttaaggtcaaaaatgaacatgaaaacgacgttggacaatgccattggtaatatctttttgtggg cttcggcacggctagatctaaatgatacagcaccagggagcagtgatcttaagttgtgtgacttggttaacttactcaatgaatctatca aagaatttaacagtgattacttggagattttgaagggtaaagagggatatggaggcatgtgtgatttgctagatttcatggaagaaggg agttttgtagaaccagcaccagagttttattcattctcaagctggactagatttttttgaccaagttgattttggatgggggaggccatcttg ggttggattctcggggagagttgaaactagaaatttcacaatattcgttgaaacacaatgcgatgacggaattgatgcgtgggtgactg tagatgaaaaacaaatggctatgctagaacaagatccacagtttttagcatttgcatctccaaacccccgaatttcaatagcctcttcagt tggtatggattaa

SEQ ID NO: 116

MEKIEVSIISRDTIKPSAASSSLHPYKLSIIDQFTPTTYFPVIFFYPITDRVFNLPQTLTD

LKNTVSQALTLYHPLSGRIKNNLYIDDFEAGIPYLEARVNFHMIDFLRLPKIEWLNEF

VPMAPYRKETISEFLPLLGIQVNIFDSGIAIGVSFSHKINDGQTASCFLKSWVAIFRGY

RNKIIHPNLSQAALLLPSRDDLPEKYVAMMERMWFGEKKVVTRRFVFDAKAISALQ

DEGKSEYVPKPSRVQALTGFLWKHQLAASRALSSGTSTRFSVASQTVNLRSKMNM

KTTLDNAIGNIFLWASARLDLNDTAPGSSDLKLCDLVNLLNESIKEFNSDYLEILKG

-continued

KEGYGGMCDLLDFMEEGSFVEPAPEFYSFSSWTRFFDQVDFGWGRPSWVGFSGRV

ETRNFTIFVETQCDDGIDAWVTVDEKQMAMLEQDPQFLAFASPNPRISIASSVGMD

DQ234300

SEQ ID NO: 117 atgtctagcattagccagaaggtggtaatcggcctaaacaaggcagcagctaataataatctccaaaacttggataggagaggtttta agacgcggtgtgtctcttctagtaaggccgcatcttgcctgcgtgcttcttgctccttacaactagatgttaagccggttcaagagggcc gacgcagtggaaactaccaaccttctatttgggatttcaactacgttcaatctctcaacactccctataaggaagagaggtatttgacaa ggcatgctgaattgattgtgcaagtgaaaccgttgctggagaaaaaaatggaggctgctcaacagttggagttgattgatgacttgaa caatctcggattgtcttattttttcaagaccgtattaagcagattttaagttttatatatgacgagaaccaatgtttccacagtaatattaatg atcaagcagagaaaagggatttgtatttcacagctcttggattcagaattctcagacaacatggttttgatgtctctcaagaagtatttgat tgtttcaagaacgacagtggcagtgattttaaggcaagccttagtgacaataccaaaggattgttacaactatacgaggcatctttccta gtgagagaaggtgaagacacactggagcaagctagacaattcgccaccaaatttctgcggagaaaacttgatgaaattgacgacaa tcatctattatcatgcattcaccattctttggagatcccacttcactggagaattcaaaggctggaggcaagatggttcttagatgcttacg cgacgaggcacgacatgaatccagtcattcttgagctcgccaagctcgatttcaatattattcaagcaacacaccaagaagaactcaa ggatgtctcaaggtggtggcagaatacacggctggctgagaaactcccatttgtgagggataggcttgtagaaagctacttttgggcc attgcgctgtttgagcctcatcaatatggatatcagagaagagtggcagccaagattattactctagcaacatctatcgatgatgtttacg atatctatggtaccttagatgaactgcagttatttacagacaactttcgaagatgggatactgaatcactaggcagacttccatatagcat gcaattattttatatggtaatccacaactttgtttctgagctggcatacgaaattctcaaagagaagggtttcatcgttatcccatatttacag agatcgtgggtagatctggcggaatcattttttaaaagaagcaaattggtactacagtggatatacaccaagcctggaagaatatatcga caacggcagcatttcaattggggcagttgcagtattatcccaagtttatttcacattagcaaactccatagagaaacctaagatcgagag catgtacaaataccatcacattcttcgcctttccggattgctcgtaaggcttcatgatgatctaggaacatcactgtttgagaagaagaga ggcgacgtgccgaaagcagtggagatttgcatgaaggaaagaaatgttaccgaggaagaggcggaagaacacgtgaaatatctg attcgggaggcgtggaaggagatgaacacagcgacgacggcagccggttgtccgtttatggatgagttgaatgtggccgcagcta atctcggaagagcggcgcagtttgtgtatctcgacggagatggtcatggcgtgcaacactctaaaattcatcaacagatgggaggcc taatgttcgagccatatgtctga

SEQ ID NO: 118

MSSISQKVVIGLNKAAANNNLQNLDRRGFKTRCVSSSKAASCLRASCSLQLDVKPV

QEGRRSGNYQPSIWDFNYVQSLNTPYKEERYLTRHAELIVQVKPLLEKKMEAAQQL

ELIDDLNNLGLSYFFQDRIKQILSFIYDENQCFHSNINDQAEKRDLYFTALGFRILRQ

HGFDVSQEVFDCFKNDSGSDFKASLSDNTKGLLQLYEASFLVREGEDTLEQARQFA

TKFLRRKLDEIDDNHLLSCIHHSLEIPLHWRIQRLEARWFLDAYATRHDMNPVILEL

AKLDFNIIQATHQEELKDVSRWWQNTRLAEKLPFVRDRLVESYFWAIALFEPHQYG

YQRRVAAKIITLATSIDDVYDIYGTLDELQLFTDNFRRWDTESLGRLPYSMQLFYM

VIHNFVSELAYEILKEKGFIVIPYLQRSWVDLAESFLKEANWYYSGYTPSLEEYIDNG

SISIGAVAVLSQVYFTLANSIEKPKIESMYKYHHILRLSGLLVRLHDDLGTSLFEKKR

GDVPKAVEICMKERNVTEEEAEEHVKYLIREAWKEMNTATTAAGCPFMDELNVA

AANLGRAAQFVYLDGDGHGVQHSKIHQQMGGLMFEPYV

DQ234299

SEQ ID NO: 119 atgtctagcattagccagaaggtggtaatcggcctaaacaaggcagcagctaataataatctccaaaacttggataggagaggtttta agacgcggtgtgtctcttctagtaaggccgcatcttgcctgcgtgcttcttgctccttacaactagatgttaagccggttcaagagggcc gacgcagtggaaactaccaaccttccatttgggatttcaactacgttcaatctctcaacactccctataaggaagagaggtatttgacaa ggcatgctgaattgattgtgcaagtgaaaccgttgctggagaaaaaaatggagcctgctcaacagttggagttgattgatgacttgaa -continued caatctcggattgtcttatttttttcaagaccgtattaagcagattttaagttttatatatgacgagaaccaatgtttccacagtaatattaatg atcaagcagagaaaagggatttgtatttcacagctcttggattcagacttctcagacaacatggttttgatgtctctcaagaagtatttgat tgtttcaagaacgacaatggcagtgattttaaggcaagccttagtgacaataccaaaggattgttacaactatacgaggcatctttccta gtgagagaaggtgaagatacactggagcaagctagacaattcgccaccaaatttctgcggagaaaacttgatgaaattgacgacaat catctattatcatgcattcaccattctttggagatcccacttcactggagaattcaaaggctggaggcaagatggttcttagatgcttacg cgacgaggcacgacatgaatccagtcattcttgagctcgccaagctcgatttcaatattattcaagcaacacaccaagaagaactcaa ggatgtctcaaggtggtggcagaatacacggttggctgagaaactcccatttgtgagggataggcttgtagaaagctacttttgggcc attgcgctgtttgagcctcatcaatatggatatcagagaagagtggcagccaagattattactctagcaacatctatcgatgatgtttacg atatctatggtaccttagatgaactgcagttatttacagacaactttcgaagatgggatactgaatcactaggcagacttccatatagcat gcaattattttatatggtaatccacaactttgtttctgagctggcatacgaaattctcaaagagaagggtttcatcgttatcccatatttacag agatcgtgggtagatctggcggaatcattttaaaagaagcaaattggtactacagtggatatacaccaagcctggaagaatatatcga caacggcagcatttcaattggggcagttgcagtattatcccaagtttatttcacattagcaaactccatagagaaacctaagatcgagag catgtacaaataccatcacattcttcgcctttccggattgctcgtaaggcttcatgatgatctaggaacatcactgtttgagaagaagaga ggcgacgtgccgaaagcagtggagatttgcatgaaggaaagaaatgttaccgaggaagaggcagaagaacacgtgaaatatctga ttcgggaggcgtggaaggagatgaacacagcgacgacggcagccggttgtccgtttatggatgagttgaatgtggccgcagctaat ctcggaagagcggcgcagtttgtgtatctcgacggagatggtcatggcgtgcaacactctaaaattcatcaacagatgggaggccta atgttcgagccatatgtctga

SEQ ID NO: 120

MSSISQKVVIGLNKAAANNNLQNLDRRGFKTRCVSSSKAASCLRASCSLQLDVKPV

QEGRRSGNYQPSIWDFNYVQSLNTPYKEERYLTRHAELIVQVKPLLEKKMEPAQQL

ELIDDLNNLGLSYFFQDRIKQILSFIYDENQCFHSNINDQAEKRDLYFTALGFRLLRQ

HGFDVSQEVFDCFKNDNGSDFKASLSDNTKGLLQLYEASFLVREGEDTLEQARQFA

TKFLRRKLDEIDDNHLLSCIHHSLEIPLHWRIQRLEARWFLDAYATRHDMNPVILEL

AKLDFNIIQATHQEELKDVSRWWQNTRLAEKLPFVRDRLVESYFWAIALFEPHQYG

YQRRVAAKIITLATSIDDVYDIYGTLDELQLFTDNFRRWDTESLGRLPYSMQLFYM

VIHNFVSELAYEILKEKGFIVIPYLQRSWVDLAESFLKEANWYYSGYTPSLEEYIDNG

SISIGAVAVLSQVYFTLANSIEKPKIESMYKYHHILRLSGLLVRLHDDLGTSLFEKKR

GDVPKAVEICMKERNVTEEEAEEHVKYLIREAWKEMNTATTAAGCPFMDELNVA

AANLGRAAQFVYLDGDGHGVQHSKIHQQMGGLMFEPYV

DQ234298

SEQ ID NO: 121 atgtctagcattagccagaaggtggtaatcggcctaaacaaggcagcagctaataataatctccaaaacttggataggagaggtttta agacgcggtgtgtctcttctagtaaggccgcatcttgcctgcgtgcttcttgctccttacaactagatgttaagccggttcaagagggcc gacgcagtggaaactaccaaccttccatttgggatttcaactacgttcaatctctcaacactccctataaggaagagaggtatttgacaa ggcatgctgaattgattgtgcaagtgaaaccgttgctggagaaaaaaatggagcctgctcaacagttggagttgattgatgacttgaa caatctcggattgtcttatttttttcaagaccgtattaagcagattttaagttttatatatgacgagaaccaatgtttccacagtaatattaatg atcaagcagagaaaagggatttgtatttcacagctcttggattcagacttctcagacaacatggttttgatgtctctcaagaagtatttgat tgtttcaagaacgacaatggcagtgattttaaggcaagccttagtgacaataccaaaggattgttacaactatacgaggcatctttccta gtgagagaaggtgaagatacactggagcaagctagacaattcgccaccaaatttctgcggagaaaacttgatgaaattgacgacaat catctattatcatgcattcaccattctttggagatcccacttcactggagaattcaaaggctggaggcaagatggttcttagatgcttacg cgacgaggcacgacatgaatccagtcattcttgagctcgccaagctcgatttcaatattattcaagcaacacaccaagaagaactcaa ggatgtctcaaggtggtggcagaatacacggttggctgagaaactcccatttgtgagggataggcttgtagaaagctacttttgggcc -continued attgcgctgtttgagcctcatcaatatggatatcagagaagagtggcagccaagattattactctagcaacatctatcgatgatgtttacg atatctatggtaccttagatgaactgcagttatttacagacaactttcgaagatgggatactgaatcactaggcagacttccatatagcat gcaattattttatatggtaatccacaactttgtttctgagctggcatacgaaattctcaaagagaagggtttcatcgttatcccatatttacag agatcgtgggtagatctggcggaatcatttttaaaagaagcaaattggtactacagtggatatacaccaagcctggaagaatatatcga caacggcagcatttcaattggggcagttgcagtattatcccaagtttatttcacattagcaaactccatagagaaacctaagatcgagag catgtacaaataccatcacattcttcgcctttccggattgctcgtaaggcttcatgatgatctaggaacatcactgtttgagaagaagaga ggcgacgtgccgaaagcagtggagatttgcatgaaggaaagaaatgttaccgaggaagaggcagaagaacacgtgaaatatctga ttcgggaggcgtggaaggagatgaacacagcgacgacggcagccggttgtccgtttatggatgagttgaatgtggccgcagctaat ctcggaagagcggcgcagtttgtgtatctcgacggagatggtcatggcgtgcaacactctaaaattcatcaacagatgggaggccta atgttcgagccatatgtctga

SEQ ID NO: 122

MSSISQKVVIGLNKAAANNNLQNLDRRGFKTRCVSSSKAASCLRASCSLQLDVKPV

QEGRRSGNYQPSIWDFNYVQSLNTPYKEERYLTRHAELIVQVKPLLEKKMEPAQQL

ELIDDLNNLGLSYFFQDRIKQILSFIYDENQCFHSNINDQAEKRDLYFTALGFRLLRQ

HGFDVSQEVFDCFKNDNGSDFKASLSDNTKGLLQLYEASFLVREGEDTLEQARQFA

TKFLRRKLDEIDDNHLLSCIHHSLEIPLHWRIQRLEARWFLDAYATRHDMNPVILEL

AKLDFNIIQATHQEELKDVSRWWQNTRLAEKLPFVRDRLVESYFWAIALFEPHQYG

YQRRVAAKIITLATSIDDVYDIYGTLDELQLFTDNFRRWDTESLGRLPYSMQLFYM

VIHNFVSELAYEILKEKGFIVIPYLQRSWVDLAESFLKEANWYYSGYTPSLEEYIDNG

SISIGAVAVLSQVYFTLANSIEKPKIESMYKYHHILRLSGLLVRLHDDLGTSLFEKKR

GDVPKAVEICMKERNVTEEEAEEHVKYLIREAWKEMNTATTAAGCPFMDELNVA

AANLGRAAQFVYLDGDGHGVQHSKIHQQMGGLMFEPYV

DQ088667

SEQ ID NO: 123 atgtctagcattagccagaaggtggtaatcggcctaaacaaggcagcagctaataataatctccaaaacttggataggagaggtttta agacgcggtgtgtctcttctagtaaggccgcatcttgcctgcgtgcttcttgctccttacaactagatgttaagccggttcaagagggcc gacgcagtggaaactaccaaccttccatttgggatttcaactacgttcaatctctcaacactccctataaggaagagaggtatttgacaa ggcatgctgaattgattgtgcaagtgaaaccgttgctggagaaaaaaatggagcctgctcaacagttggagttgattgatgacttgaa caatctcggattgtcttatttttttcaagaccgtattaagcagattttaagttttatatatgacgagaaccaatgtttccacagtaatattaatg atcaagcagagaaaagggatttgtatttcacagctcttggattcagacttctcagacaacatggttttgatgtctctcaagaagtatttgat tgtttcaagaacgacaatggcagtgattttaaggcaagccttagtgacaataccaaaggattgttacaactatacgaggcatctttccta gtgagagaaggtgaagatacactggagcaagctagacaattcgccaccaaatttctgcggagaaaacttgatgaaattgacgacaat catctattatcatgcattcaccattctttggagatcccacttcactggagaattcaaaggctggaggcaagatggttcttagatgcttacg cgacgaggcacgacatgaatccagtcattcttgagctcgccaagctcgatttcaatattattcaagcaacacaccaagaagaactcaa ggatgtctcaaggtggtggcagaatacacggttggctgagaaactcccatttgtgagggataggcttgtagaaagctacttttgggcc attgcgctgtttgagcctcatcaatatggatatcagagaagagtggcagccaagattattactctagcaacatctatcgatgatgtttacg atatctatggtaccttagatgaactgcagttatttacagacaactttcgaagatgggatactgaatcactaggcagacttccatatagcat gcaattattttatatggtaatccacaactttgtttctgagctggcatacgaaattctcaaagagaagggtttcatcgttatcccatatttacag agatcgtgggtagatctggcggaatcatttttaaaagaagcaaattggtactacagtggatatacaccaagcctggaagaatatatcga caacggcagcatttcaattggggcagttgcagtattatcccaagtttatttcacattagcaaactccatagagaaacctaagatcgagag catgtacaaataccatcacattcttcgcctttccggattgctcgtaaggcttcatgatgatctaggaacatcactgtttgagaagaagaga ggcgacgtgccgaaagcagtggagatttgcatgaaggaaagaaatgttaccgaggaagaggcagaagaacacgtgaaatatctga -continued ttcgggaggcgtggaaggagatgaacacagcgacgacggcagccggttgtccgtttatggatgagttgaatgtggccgcagctaat ctcggaagagcggcgcagtttgtgtatctcgacggagatggtcatggcgtgcaacactctaaaattcatcaacagatgggaggccta atgttcgagccatatgtctga

SEQ ID NO: 124

MSSISQKVVIGLNKAAANNNLQNLDRRGFKTRCVSSSKAASCLRASCSLQLDVKPV

QEGRRSGNYQPSIWDFNYVQSLNTPYKEERYLTRHAELIVQVKPLLEKKMEPAQQL

ELIDDLNNLGLSYFFQDRIKQILSFIYDENQCFHSNINDQAEKRDLYFTALGFRLLRQ

HGFDVSQEVFDCFKNDNGSDFKASLSDNTKGLLQLYEASFLVREGEDTLEQARQFA

TKFLRRKLDEIDDNHLLSCIHHSLEIPLHWRIQRLEARWFLDAYATRHDMNPVILEL

AKLDFNIIQATHQEELKDVSRWWQNTRLAEKLPFVRDRLVESYFWAIALFEPHQYG

YQRRVAAKIITLATSIDDVYDIYGTLDELQLFTDNFRRWDTESLGRLPYSMQLFYM

VIHNFVSELAYEILKEKGFIVIPYLQRSWVDLAESFLKEANWYYSGYTPSLEEYIDNG

SISIGAVAVLSQVYFTLANSIEKPKIESMYKYHHILRLSGLLVRLHDDLGTSLFEKKR

GDVPKAVEICMKERNVTEEEAEEHVKYLIREAWKEMNTATTAAGCPFMDELNVA

AANLGRAAQFVYLDGDGHGVQHSKIHQQMGGLMFEPYV

AJ457070

SEQ ID NO: 125 atggcattgcaaatgattgctccatttctatcctccttcctcccaaatcccagacacagcctcgcagcccatggcctcacacaccagaa atgtgtctcaaagcacatttcatgctccaccactacaccaacctactcaaccacagttccaagaagatcagggaactacaagcccagc atctgggactatgattttgtgcagtcactaggaagtggctacaaggtagaggcacatggaacacgtgtgaagaagttgaaggaagtt gtaaagcatttgttgaaagaaacagatagttctttggcccaaatagaactgattgacaaactccgtcgtctaggtctaaggtggctcttc aaaaatgagattaagcaagtgctatacacgatatcatcagacaacaccagcatagaaatgaggaaagatcttcatgcagtatcaactc gatttagacttcttagacaacatgggtacaaggtctccacagatgttttcaacgacttcaaagatgaaaagggttgtttcaagccaagcc tttcaatggacataaagggaatgttgagcttgtatgaagcttcacaccttgcctttcaaggggagactgtgttggatgaggcaagagctt tcgtaagcacacatctcatggatatcaaggagaacatagacccaatccttcataaaaaagtagagcatgctttggatatgcctttgcatt ggaggttagaaaaattagaggctaggtggtacatggacatatatatgagggaagaaggcatgaattcttctttacttgaattggccatg cttcatttcaacattgtgcaaacaacattccaaacaaatttaaagagtttgtcaaggtggtggaaagatttgggtcttggagagcagttga gcttcactagagacaggttggtggaatgtttcttttgggccgccgcaatgacacctgagccacaatttggacgttgccaggaagttgta gcgaaagttgctcaactcataataataattgacgatatctatgacgtgtatggtacggtggatgagctagaactttttactaatgcgattg atagatgggatcttgaggcaatggagcaacttcctgaatatatgaagacctgtttcttagctttatacaacagtattaatgaaataggttat gacattttgaaagaggaagggcgcaatgtcataccataccttagaaatacgtggacagaattgtgtaaagcattcttagtggaggcca aatggtatagtagtggatatacaccaacgcttgaggagtatctgcaaacctcatggatttcgattggaagtctacccatgcaaacatatg tttttgctctacttgggaaaaatctagcaccggagagtagtgattttgctgagaagatctcggatatcttacgattgggaggaatgatgat tcgacttccggatgatttgggaacttcaacggatgaactaaagagaggtgatgttccaaaatccattcagtgttacatgcatgaagcag gtgttacagaggatgttgctcgcgaccacataatgggtctatttcaagagacatggaaaaaactcaatgaataccttgtggaaagttctc ttccccatgcctttatcgatcatgctatgaatcttggacgtgtctcctattgcacttacaaacatggagatggatttagtgatggatttgga gatcctggcagtcaagagaaaaagatgttcatgtctttatttgctgaaccccttcaagttgatgaagccaagggtatttcattttatgttgat ggtggatctgcctga

SEQ ID NO: 126

MALQMIAPFLSSFLPNPRHSLAAHGLTHQKCVSKHISCSTTTPTYSTTVPRRSGNYK

PSIWDYDFVQSLGSGYKVEAHGTRVKKLKEVVKHLLKETDSSLAQIELIDKLRRLG

LRWLFKNEIKQVLYTISSDNTSIEMRKDLHAVSTRFRLLRQHGYKVSTDVFNDFKD

EKGCFKPSLSMDIKGMLSLYEASHLAFQGETVLDEARAFVSTHLMDIKENIDPILHK

-continued

KVEHALDMPLHWRLEKLEARWYMDIYMREEGMNSSLLELAMLHFNIVQTTFQTN

LKSLSRWWKDLGLGEQLSFTRDRLVECFFWAAAMTPEPQFGRCQEVVAKVAQLIII

IDDIYDVYGTVDELELFTNAIDRWDLEAMEQLPEYMKTCFLALYNSINEIGYDILKE

EGRNVIPYLRNTWTELCKAFLVEAKWYSSGYTPTLEEYLQTSWISIGSLPMQTYVFA

LLGKNLAPESSDFAEKISDILRLGGMMIRLPDDLGTSTDELKRGDVPKSIQCYMHEA

GVTEDVARDHIMGLFQETWKKLNEYLVESSLPHAFIDHAMNLGRVSYCTYKHGDG

FSDGFGDPGSQEKKMFMSLFAEPLQVDEAKGISFYVDGGSA

AY362553

SEQ ID NO: 127 atgtcttgtgcacggatcaccgtaacattgccgtatcgctccgcaaaaacatcaattcaacggggaattacgcattaccccgcccttat acgcccacgcttctctgcttgcacgcctttggcatcggcgatgcctctaagttcaactcctctcatcaacggggataactctcagcgtaa aaacacacgtcaacacatggaggagagcagcagcaagaggagagaatatctgctggaggaaacgacgcgaaaactgcagagaa acgacaccgaatcggtggagaaactcaagcttatcgacaacatccaacagttgggaatcggctactattttgaggacgccatcaacg ccgtactccgctcgcctttctccaccggagaagaagacctcttcaccgctgctctgcgcttccgcttgctccgccacaacggcatcga aatcagccctgaaatattcctaaaattcaaggacgagaggggaaaattcgacgaatcggacacgctagggttactgagcttgtacga agcgtcaaatttgggggttgcaggagaagaaatattggaggaggctatggagtttgcggaggctcgcctgagacggtcgctgtcag agccggcggcgccgcttcatggtgaggtggcgcaagcgctagatgtgccgaggcatctgagaatggcgaggttggaagcgagac gattcatcgagcagtatggtaaacagagcgatcatgatggagatcttttggagctggcaattttggattataatcaagttcaggctcaac accaatccgaactcactgaaataatcaggtggtggaaggagctcggtttggtggataagttgagttttgggcgagacagaccattgg agtgctttttgtggaccgtggggctcctcccagagcccaagtattcgagcgttagaatagagttggcgaaagccatctctattctcttag tgatcgatgatattttcgatacctatggagagatggatgacctcatcctcttcaccgatgcaattcgaagatgggatcttgaagcaatgg aggggctccctgagtacatgaaaatatgctacatggcgttgtacaataccaccaatgaagtatgctacaaagtgctcagggatactgg acggattgtcctccttaacctcaaatctacgtggatagacatgattgaaggtttcatggaggaagcaaaatggttcaatggtggaagtg caccaaaattggaagagtatatagagaatggagtgtccacggcaggagcatacatggcttttgcacacatcttctttctcataggagaa ggtgttacacaccaaaattcccaactcttcacccaaaaaccctaccccaaggtcttctccgccgccggccgcattcttcgcctctggga tgatctcggaaccgccaaggaagagcaagagcgaggagatctggcttcgtgcgtgcagttatttatgaaagagaagtcgttgacgg aagaggaggcaagaagtcgcattttggaagagataaaaggattatggagggatctgaatggggaactggtctacaacaagaatttg ccgttatccataatcaaagtcgcacttaacatggcgagagcttctcaagttgtgtacaagcacgatcaagacacttatttttcaagcgta gacaattatgtggatgccctcttcttcactcaataa

SEQ ID NO: 128

MSCARITVTLPYRSAKTSIQRGITHYPALIRPRFSACTPLASAMPLSSTPLINGDNSQR

KNTRQHMEESSSKRREYLLEETTRKLQRNDTESVEKLKLIDNIQQLGIGYYFEDAIN

AVLRSPFSTGEEDLFTAALRFRLLRHNGIEISPEIFLKFKDERGKFDESDTLGLLSLYE

ASNLGVAGEEILEEAMEFAEARLRRSLSEPAAPLHGEVAQALDVPRHLRMARLEAR

RFIEQYGKQSDHDGDLLELAILDYNQVQAQHQSELTEIIRWWKELGLVDKLSFGRD

RPLECFLWTVGLLPEPKYSSVRIELAKAISILLVIDDIFDTYGEMDDLILFTDAIRRWD

LEAMEGLPEYMKICYMALYNTTNEVCYKVLRDTGRIVLLNLKSTWIDMIEGFMEE

AKWFNGGSAPKLEEYIENGVSTAGAYMAFAHIFFLIGEGVTHQNSQLFTQKPYPKV

FSAAGRILRLWDDLGTAKEEQERGDLASCVQLFMKEKSLTEEEARSRILEEIKGLWR

DLNGELVYNKNLPLSIIKVALNMARASQVVYKHDQDTYFSSVDNYVDALFFTQ

DQ897973

SEQ ID NO: 129 atgtctagcattagccagaaggtggtaatcggcctaaacaaggcagcagctaataataatctccaaaacttggataggagaggtttta -continued agacgcggtgtgtctcttctagtaaggccgcatcttgcctgcgtgcttcttgctccttacaactagatgttaagccggttcaagagggcc gacgcagtggaaactaccaaccttctatttgggatttcaactacgttcaatctctcaacactccctataaggaagagaggtatttgacaa ggcatgctgaattgattgtgcaagtgaaaccgttgctggagaaaaaaatggaggctgctcaacagttggagttgattgatgacttgaa caatctcggattgtcttattttttcaagaccgtattaagcagattttaagttttatatatgacgagaaccaatgtttccacagtaatattaatg atcaagcagagaaaagggatttgtatttcacagctcttggattcagaattctcagacaacatggttttgatgtctctcaagaagtatttgat tgtttcaagaacgacagtggcagtgattttaaggcaagccttagtgacaataccaaaggattgttacaactatacgaggcatctttccta gtgagagaaggtgaagacacactggagcaagctagacaattcgccaccaaatttctgcggagaaaacttgatgaaattgacgacaa tcatctattatcatgcattcaccattctttggagatcccacttcactggagaattcaaaggctggaggcaagatggttcttagatgcttacg cgacgaggcacgacatgaatccagtcattcttgagctcgccaagctcgatttcaatattattcaagcaacacaccaagaagaactcaa ggatgtctcaaggtggtggcagaatacacggctggctgagaaactcccatttgtgagggataggcttgtagaaagctacttttgggcc attgcgctgtttgagcctcatcaatatggatatcagagaagagtggcagccaagattattactctagcaacatctatcgatgatgtttacg atatctatggtaccttagatgaactgcagttatttacagacaactttcgaagatgggatactgaatcactaggcagacttccatatagcat gcaattattttatatggtaatccacaactttgtttctgagctggcatacgaaattctcaaagagaagggtttcatcgttatcccatatttacag agatcgtgggtagatctggcggaatcatttttaaaagaagcaaattggtactacagtggatatacaccaagcctggaagaatatatcga caacggcagcatttcaattggggcagttgcagtattatcccaagtttatttcacattagcaaactccatagagaaacctaagatcgagag catgtacaaataccatcacattcttcgcctttccggattgctcgtaaggcttcatgatgatctaggaacatcactgtttgagaagaagaga ggcgacgtgccgaaagcagtggagatttgcatgaaggaaagaaatgttaccgaggaagaggcggaagaacacgtgaaatatctg attcgggaggcgtggaaggagatgaacacagcgacgacggcagccggttgtccgtttatggatgagttgaatgtggccgcagcta atctcggaagagcggcgcagtttgtgtatctcgacggagatggtcatggcgtgcaacactctaaaattcatcaacagatgggaggcc taatgttcgagccatatgtctga

SEQ ID NO: 130

MSSISQKVVIGLNKAAANNNLQNLDRRGFKTRCVSSSKAASCLRASCSLQLDVKPV

QEGRRSGNYQPSIWDFNYVQSLNTPYKEERYLTRHAELIVQVKPLLEKKMEAAQQL

ELIDDLNNLGLSYFFQDRIKQILSFIYDENQCFHSNINDQAEKRDLYFTALGFRILRQ

HGFDVSQEVFDCFKNDSGSDFKASLSDNTKGLLQLYEASFLVREGEDTLEQARQFA

TKFLRRKLDEIDDNHLLSCIHHSLEIPLHWRIQRLEARWFLDAYATRHDMNPVILEL

AKLDFNIIQATHQEELKDVSRWWQNTRLAEKLPFVRDRLVESYFWAIALFEPHQYG

YQRRVAAKIITLATSIDDVYDIYGTLDELQLFTDNFRRWDTESLGRLPYSMQLFYM

VIHNFVSELAYEILKEKGFIVIPYLQRSWVDLAESFLKEANWYYSGYTPSLEEYIDNG

SISIGAVAVLSQVYFTLANSIEKPKIESMYKYHHILRLSGLLVRLHDDLGTSLFEKKR

GDVPKAVEICMKERNVTEEEAEEHVKYLIREAWKEMNTATTAAGCPFMDELNVA

AANLGRAAQFVYLDGDGHGVQHSKIHQQMGGLMFEPYV

The invention claimed is:

1. A method for producing a fuel or fuel additive, wherein said method comprises:

(i) providing a culture medium, wherein the culture medium comprises a carbon source;

(ii) contacting said culture medium with a recombinant microorganism comprising a biosynthetic pathway capable of converting a carbon source to geraniol acetate, wherein the recombinant microorganism comprises an exogenous gene encoding a geraniol acetyl transferase and at least one additional exogenous gene encoding an enzyme of the pathway;

(iii) recovering said geraniol acetate from the culture medium; and (iv) converting said geraniol acetate to said fuel or fuel additive.

2. The method of claim 1, wherein the at least one additional exogenous gene encodes an enzyme selected from the group consisting of:

a 1-deoxy-xylulose 5-phosphate synthase; a 1-deoxy-D-xylulose-5-phosphate reductoisomerase; a 4-diphosphocytidyl-2-C-methyl-D-erythritol synthase; a 4-diphosphocytidyl-2-C-methyl-D-erythritol kinase; a 2-C-methyl-D-erythritol-2,4-cyclodiphosphate synthase; a 1-hydroxy-2-methyl-2-(E)-butenyl-4-diphosphate synthase; a 1-hydroxy-2-methyl-2-(E)-butenyl-4-diphosphate reductase; an acetyl-CoA acetyltransferase; a 3-hydroxy-3-methyl-glutaryl-CoA synthase; a branched chain aminotransferase or leucine aminotransferase; a 2-oxoisovalerate dehydrogenase; an isovaleryl-CoA dehydrogenase; a 3-methylcrotonyl-CoA carboxylase; a 3-methylglutaconyl-CoA hydratase; a 3-hydroxy-3-methyl-glutaryl-CoA reductase; a mevalonate kinase; a phosphomevalonate kinase; a mevalonate-5-diphosphate decarboxylase; an isopentenyl diphosphate isomerase; a geranyl diphosphate synthase; and a geraniol synthase.

3. The method of claim 2, wherein at least one additional exogenous gene encodes a 3 hydroxy-3-methyl-glutaryl-CoA reductase.

4. The method of claim 3, wherein at least one additional exogenous gene encodes a truncated 3-hydroxy-3-methyl-glutaryl-CoA reductase.

5. The method of claim 2, wherein at least one additional exogenous gene encodes an isopentyl diphosphate isomerase.

6. The method of claim 2, wherein at least one additional exogenous gene encodes a geraniol synthase.

7. The method of claim 2, wherein the recombinant microorganism further comprises an exogenous gene encoding a mutant farnesyl pyrophosphate synthase.

8. The method of claim 7, wherein said microorganism comprises a gene replacement of an endogenous farnesyl pyrophosphatase synthase gene with a gene encoding a mutant farnesyl pyrophosphate synthase.

9. The method of claim 1, wherein the fuel or fuel additive is a dimethyloctane, or a derivative or isomer thereof.

10. The method of claim 9, wherein step (iv) comprises:

hydrogenating the geraniol acetate, wherein the hydrogenating comprises the step of contacting the geraniol acetate with hydrogen gas and a catalyst, which results in the formation of 2,6-dimethyloctane.

11. The method of claim 1, wherein the microorganism is an archaea, a bacterium, a yeast, a fungus, a thraustochytrid, or a photosynthetic microorganism.

12. The method of claim 1, where the carbon source is selected from the group consisting of carboxylic acids, alcohols, sugar alcohols, aldehydes, amino acids, carbohydrates, saturated or unsaturated fatty acids, ketones, peptides, proteins, lignocellulosic material, carbon dioxide, and coal.

13. A method for producing geraniol acetate, wherein said method comprises:

(i) providing a culture medium, wherein the culture medium comprises a carbon source;

(ii) contacting said culture medium with a recombinant microorganism comprising a biosynthetic pathway capable of converting a carbon source to geraniol acetate, wherein the recombinant microorganism comprises an exogenous gene encoding a geraniol acetyl transferase and at least one additional exogenous gene encoding an enzyme of the pathway; and (iii) recovering said geraniol acetate from the culture medium.

14. The method of claim 13, wherein the at least one additional exogenous gene encodes an enzyme selected from the group consisting of:

a 1-deoxy-xylulose 5-phosphate synthase; a 1-deoxy-D-xylulose-5-phosphate reductoisomerase; a 4-diphosphocytidyl-2-C-methyl-D-erythritol synthase; a 4-diphosphocytidyl-2-C-methyl-D-erythritol kinase; a 2-C-methyl-D-erythritol-2,4-cyclodiphosphate synthase; a 1-hydroxy-2-methyl-2-(E)-butenyl-4-diphosphate synthase; a 1-hydroxy-2-methyl-2-(E)-butenyl-4-diphosphate reductase; an acetyl-CoA acetyltransferase; a 3-hydroxy-3-methyl-glutaryl-CoA synthase; a branched chain aminotransferase or leucine aminotransferase; a 2-oxoisovalerate dehydrogenase; an isovaleryl-CoA dehydrogenase; a 3-methylcrotonyl-CoA carboxylase; a 3-methylglutaconyl-CoA hydratase; a 3-hydroxy-3-methyl-glutaryl-CoA reductase; a mevalonate kinase; a phosphomevalonate kinase; a mevalonate-5-diphosphate decarboxylase; an isopentenyl diphosphate isomerase; a geranyl diphosphate synthase; and a geraniol synthase.

* * * * *